(12) United States Patent
Cervin et al.

(10) Patent No.: US 9,909,144 B2
(45) Date of Patent: *Mar. 6, 2018

(54) COMPOSITIONS AND METHODS FOR PRODUCING ISOPRENE

(71) Applicants: Danisco US Inc., Palo Alto, CA (US); The Goodyear Tire & Rubber Company, Akron, OH (US)

(72) Inventors: Marguerite A. Cervin, Redwood City, CA (US); Gopal K. Chotani, Cupertino, CA (US); Frank J. Feher, Copley, OH (US); Richard La Duca, Pleasanton, CA (US); Joseph C. McAuliffe, Sunnyvale, CA (US); Andrei Miasnikov, Mountain View, CA (US); Caroline M. Peres, Palo Alto, CA (US); Aaron S. Puhala, Kent, OH (US); Karl J. Sanford, Cupertino, CA (US); Fernando Valle, Burlingame, CA (US); Gregory M. Whited, Belmont, CA (US)

(73) Assignees: Danisco US Inc., Palo Alto, CA (US); The Goodyear Tire & Rubber Company, Akron, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/987,681

(22) Filed: Jan. 4, 2016

(65) Prior Publication Data

US 2016/0281113 A1    Sep. 29, 2016

Related U.S. Application Data

(60) Continuation of application No. 13/600,132, filed on Aug. 30, 2012, now Pat. No. 9,260,727, which is a division of application No. 12/335,071, filed on Dec. 15, 2008, now Pat. No. 8,288,148.

(60) Provisional application No. 61/013,574, filed on Dec. 13, 2007.

(51) Int. Cl.

| | | |
|---|---|---|
| C12N 1/20 | (2006.01) |
| C12N 1/00 | (2006.01) |
| C12N 15/00 | (2006.01) |
| C12P 5/02 | (2006.01) |
| C07H 21/04 | (2006.01) |
| C12P 5/00 | (2006.01) |
| C12N 9/10 | (2006.01) |
| C12N 9/12 | (2006.01) |
| C12N 9/88 | (2006.01) |
| C12N 9/90 | (2006.01) |
| C12N 15/52 | (2006.01) |

(52) U.S. Cl.
CPC ............ *C12P 5/007* (2013.01); *C12N 9/1022* (2013.01); *C12N 9/1205* (2013.01); *C12N 9/1229* (2013.01); *C12N 9/88* (2013.01); *C12N 9/90* (2013.01); *C12N 15/52* (2013.01); *C12Y 203/01009* (2013.01); *C12Y 207/01036* (2013.01); *C12Y 401/01033* (2013.01); *C12Y 402/03027* (2013.01); *C12Y 503/03002* (2013.01); *Y02E 50/343* (2013.01)

(58) Field of Classification Search
None
See application file for complete search history.

(56) References Cited

U.S. PATENT DOCUMENTS

| | | | |
|---|---|---|---|
| 1,344,713 | A | 6/1920 | Peters |
| 3,686,349 | A | 8/1972 | Schliebs et al. |
| 4,570,029 | A | 2/1986 | Kulprathipanja et al. |
| 4,647,344 | A | 3/1987 | Linder et al. |
| 4,683,195 | A | 7/1987 | Mullis et al. |
| 4,683,202 | A | 7/1987 | Mullis |
| 4,703,007 | A | 10/1987 | Mulholland et al. |
| 4,846,872 | A | 7/1989 | Kamuro et al. |
| 4,965,188 | A | 10/1990 | Mullis et al. |
| 5,322,770 | A | 6/1994 | Gelfand |
| 5,349,126 | A | 9/1994 | Chappell et al. |
| 5,380,831 | A | 1/1995 | Adang et al. |
| 5,436,391 | A | 7/1995 | Fujimoto et al. |
| 5,545,816 | A | 8/1996 | Ausich et al. |
| 5,849,970 | A | 12/1998 | Fall et al. |
| 5,874,276 | A | 2/1999 | Fowler et al. |
| 6,022,725 | A | 2/2000 | Fowler et al. |
| 6,106,888 | A | 8/2000 | Dale et al. |
| 6,176,176 | B1 | 1/2001 | Dale et al. |
| 6,268,328 | B1 | 7/2001 | Mitchinson et al. |
| 6,270,739 | B1 | 8/2001 | Barnicki et al. |
| 6,294,653 | B1 | 9/2001 | Mayfield |
| 6,582,914 | B1 | 6/2003 | Caldwell et al. |
| 6,806,076 | B1 | 10/2004 | Miyake et al. |

(Continued)

FOREIGN PATENT DOCUMENTS

| | | |
|---|---|---|
| DE | 196 29 568 C1 | 1/1998 |
| EP | 0 215 594 A2 | 3/1987 |

(Continued)

OTHER PUBLICATIONS

Albrecht, M. et al. (Aug. 2000). "Novel Hydroxycarotenoids with Improved Antioxidative Properties Produced by Gene Combination in *Escherichia coli*," *Nature Biotechnology* 18:843-846.
Alexopoulos, C.J. (1962). Introductory Mycology, Wiley: New York, NY, pp. ix-x, (Table of Contents Only).
Allison, R. et al. (1986). "The Nucleotide Sequence of the Coding Region of Tobacco Etch Virus Genomic RNA: Evidence for the Synthesis of a Single Polyprotein," *Virology* 154:9-20.
Alper, H. et al. (2008). "Uncovering the Gene Knockout Landscape for Improved Lycopene Production in *E. coli*," *AppL Microbiol. Biotechnol.* 10 pages.
Alterthum, F. et al. (Aug. 1989). "Efficient Ethanol Production from Glucose, Lactose, and Xylose by Recombinant *Escherichia coli*," *Applied Environmental Microbiology* 55(8):1943-1948.
Altschul, S.F. et al. (1990). "Basic Local Alignment Search Tool," *J Mol. Biol.* 215:403-410.

(Continued)

*Primary Examiner* — Iqbal H Chowdhury
(74) *Attorney, Agent, or Firm* — Mintz Levin Cohn Ferris Glovsky and Popeo, P.C.

(57) ABSTRACT

The invention features methods for producing isoprene from cultured cells. The invention also provides compositions that include these cultured cells.

24 Claims, 172 Drawing Sheets

(56) References Cited

U.S. PATENT DOCUMENTS

| | | |
|---|---|---|
| 6,989,257 B2 | 1/2006 | Berry et al. |
| 6,998,471 B2 | 2/2006 | Hallahan et al. |
| 7,129,392 B2 | 10/2006 | Hahn et al. |
| 7,132,268 B2 | 11/2006 | Miyake et al. |
| 7,132,527 B2 | 11/2006 | Payne et al. |
| 7,172,886 B2 | 2/2007 | Keasling et al. |
| 7,183,089 B2 | 2/2007 | Keasling et al. |
| 7,208,298 B2 | 4/2007 | Miyake et al. |
| 7,241,587 B2 | 7/2007 | Dodge et al. |
| 7,262,041 B2 | 8/2007 | Baldwin et al. |
| 7,364,885 B2 | 4/2008 | Miyake et al. |
| 7,531,333 B2 | 5/2009 | Miyake et al. |
| 8,173,410 B2 | 5/2012 | Bott et al. |
| 8,288,148 B2 | 10/2012 | Cervin et al. |
| 8,709,785 B2 | 4/2014 | Cervin et al. |
| 9,260,727 B2 | 2/2016 | Cervin et al. |
| 2002/0095818 A1 | 7/2002 | Jain et al. |
| 2003/0033626 A1 | 2/2003 | Hahn et al. |
| 2004/0005678 A1 | 1/2004 | Kleasling et al. |
| 2004/0219629 A1 | 11/2004 | Cheng et al. |
| 2005/0287655 A1 | 12/2005 | Tabata et al. |
| 2006/0009647 A1 | 1/2006 | Yeates et al. |
| 2006/0020095 A1 | 1/2006 | Gandon-Pain |
| 2008/0038805 A1 | 2/2008 | Melis |
| 2008/0178354 A1 | 7/2008 | Chappell |
| 2009/0155874 A1 | 6/2009 | Clark et al. |
| 2009/0203102 A1 | 8/2009 | Cervin et al. |
| 2010/0003716 A1 | 1/2010 | Cervin et al. |
| 2010/0048964 A1 | 2/2010 | Calabria et al. |
| 2010/0086978 A1 | 4/2010 | Beck et al. |
| 2010/0113846 A1 | 5/2010 | McAuliffe et al. |
| 2010/0196982 A1 | 8/2010 | Anderson |
| 2011/0045563 A1 | 2/2011 | Melis |
| 2011/0076743 A1 | 3/2011 | Beck et al. |

FOREIGN PATENT DOCUMENTS

| | | |
|---|---|---|
| EP | 0 215 594 A3 | 3/1987 |
| EP | 0 215 594 B1 | 3/1987 |
| EP | 0 215 594 B2 | 3/1987 |
| EP | 0 238 023 A2 | 9/1987 |
| EP | 0 238 023 A3 | 9/1987 |
| EP | 0 238 023 B1 | 9/1987 |
| EP | 0 238 023 B2 | 9/1987 |
| EP | 0 244 234 A2 | 11/1987 |
| EP | 0 244 234 A3 | 11/1987 |
| EP | 0 244 234 B1 | 11/1987 |
| EP | 0 244 234 B2 | 11/1987 |
| EP | 1 118 855 A2 | 7/2001 |
| EP | 1 118 855 A3 | 7/2001 |
| JP | 2006-271379 A | 10/2006 |
| JP | 2008-035831 A | 2/2008 |
| JP | 2008-182950 A | 8/2008 |
| JP | 2009-207402 A | 9/2009 |
| KR | 2001-0084864 A | 9/2001 |
| RU | 2 197 461 C2 | 1/2003 |
| WO | WO-95/04134 | 2/1995 |
| WO | WO-96/35796 | 11/1996 |
| WO | WO-98/02550 A2 | 1/1998 |
| WO | WO-98/02550 A3 | 1/1998 |
| WO | WO-00/17327 A2 | 3/2000 |
| WO | WO-00/17327 A3 | 3/2000 |
| WO | WO-00/17327 A9 | 3/2000 |
| WO | WO-01/58839 A1 | 8/2001 |
| WO | WO-02/099095 A2 | 12/2002 |
| WO | WO-02/099095 A3 | 12/2002 |
| WO | WO-2004/033646 A2 | 4/2004 |
| WO | WO-2004/033646 A3 | 4/2004 |
| WO | WO-2004/111214 | 12/2004 |
| WO | WO-2005/001036 A2 | 1/2005 |
| WO | WO-2005/001036 C1 | 1/2005 |
| WO | WO-2005/007682 A2 | 1/2005 |
| WO | WO-2005/007682 A3 | 1/2005 |
| WO | WO-2005/078074 A2 | 8/2005 |
| WO | WO-2005/078074 A3 | 8/2005 |
| WO | WO-2006/063752 | 6/2006 |
| WO | WO-2006/085899 A2 | 8/2006 |
| WO | WO-2006/085899 A3 | 8/2006 |
| WO | WO-2007/018062 | 2/2007 |
| WO | WO-2007/136847 A2 | 11/2007 |
| WO | WO-2007/136847 A3 | 11/2007 |
| WO | WO-2007/140339 A2 | 12/2007 |
| WO | WO-2007/140339 A3 | 12/2007 |
| WO | WO-2007/140339 A8 | 12/2007 |
| WO | WO-2008/003078 A2 | 1/2008 |
| WO | WO-2008/003078 A3 | 1/2008 |
| WO | WO-2008/003078 A8 | 1/2008 |
| WO | WO-2008/137092 A2 | 11/2008 |
| WO | WO-2008/137092 A3 | 11/2008 |
| WO | WO-2008/153925 A2 | 12/2008 |
| WO | WO-2008/153925 A3 | 12/2008 |
| WO | WO-2008/153925 A9 | 12/2008 |
| WO | WO-2008/153934 A2 | 12/2008 |
| WO | WO-2008/153934 A3 | 12/2008 |
| WO | WO-2008/153935 A2 | 12/2008 |
| WO | WO-2008/153935 A3 | 12/2008 |
| WO | WO-2009/036067 A2 | 3/2009 |
| WO | WO-2009/036067 A3 | 3/2009 |
| WO | WO-2009/064910 A2 | 5/2009 |
| WO | WO-2009/064910 A3 | 5/2009 |
| WO | WO-2009/076676 A2 | 6/2009 |
| WO | WO-2009/076676 A3 | 6/2009 |
| WO | WO-2009/132220 A2 | 10/2009 |
| WO | WO-2009/132220 A3 | 10/2009 |
| WO | WO-2009/132220 A9 | 10/2009 |
| WO | WO-2010/003007 A2 | 1/2010 |
| WO | WO-2010/003007 A3 | 1/2010 |
| WO | WO-2010/005525 | 1/2010 |
| WO | WO-2010/031062 | 3/2010 |
| WO | WO-2010/031068 | 3/2010 |
| WO | WO-2010/031076 A2 | 3/2010 |
| WO | WO-2010/031076 A3 | 3/2010 |
| WO | WO-2010/031077 | 3/2010 |
| WO | WO-2010/031079 | 3/2010 |
| WO | WO-2010/078457 A2 | 7/2010 |
| WO | WO-2010/078457 A3 | 7/2010 |
| WO | WO-2010/124146 A2 | 10/2010 |
| WO | WO-2010/124146 A3 | 10/2010 |

OTHER PUBLICATIONS

Altschul, S.F. et al. (1996). "Local Alignment Statistics," Chapter 27 in Multiple Alignment and Phylogenetic Trees, American Press, Inc. 266:460-480.

Alves, R. et al. (Nov. 2000). "Effect of Overall Feedback Inhibition in Unbranched Biosynthetic Pathways," *Biophysical Journal* 79(5):2290-2304.

Anderson, M.S. et al. (Nov. 15, 1989). "Isopentenyl Diphosphate: Dimethylallyl Diphosphate Isomerase. An Improved Purification of the Enzyme and Isolation of the Gene from *Saccharomyces cerevisiae*," *J. Biol. Chem.* 264(32):19169-19175.

Andreassi, J.L. et al. (2004, e-pub. Dec. 4, 2004). "*Streptococcus pneumoniae* Isoprenoid Biosynthesis is Downregulated by Diphosphomevalonate: An Antimicrobial Target," *Biochemistry* 43(51):16461-16466.

Andreassi, J.L. et al. (2007, e-pub. Mar. 30, 2007). "Crystal Structure of the *Streptococcus pneumoniae* Mevalonate Kinase in Complex with Diphosphomevalonate," *Protein Science* 16:983-989.

Aon, J.C. et al. (Feb. 2008, e-pub. Dec. 14, 2007). "Suppressing Posttranslational Gluconoylation of Heterologous Proteins by Metabolic Engineering of *Escherichia coli*," *Applied and Environmental Microbiology* 74(4):950-958.

Arai, Y. et al. (2004). "Production of Polyhydroxybutyrate by Polycistronic Expression of Bacterial Genes in Tobacco Plastid," *Plant Cell Physiol.* 45(9):1176-1184.

Ashby, M.N. et al. (Aug. 5, 1990). "Elucidation of the Deficiency in Two Yeast Coenzyme Q Mutants: Characterization of the Structural Gene Encoding Hexaprenyl Pyrophosphate Synthetase," *The Journal of Biological Chemistry* 265(22):13157-13164.

Ausubel, F.M. et al. eds. (1987). Current Protocols in Molecular Biology, John Wiley and Sons, Inc., pp. 1-13, (Table of Contents Only).

(56) References Cited

OTHER PUBLICATIONS

Baba, T. et al. (Feb. 21, 2006). "Construction of *Escherichia coli* K-12 In-Frame, Single-Gene Knockout Mutants: The Keio Collection," *Molecular Systems Biology* pp. 1-11.

Ballas, N. et al. (1989). "Efficient Functioning of Plant Promoters and Poly(A) Sites in *Xenopus oocytes*," *Nucleic Acids Research* 17(19):7891-7903.

Barkovich, R. et al. (2001, e-pub. Dec. 1, 2000). "Metabolic Engineering of Isoprenoids," *Metabolic Engineering* 3:27-29.

Beaucage, S.L. et al. (1981). "Deoxynucleoside Phosphoramidites—A New Class of Key Intermediates for Deoxypolynucleotide Synthesis," *Tetrahedron Letters* 22(20):1859-1862.

Bellion, E. et al. (1993). "Methylamine Utilization in Yeast and Bacteria: Studies Using in vivo NMR," Chapter 32 in Microbial Growth $C_1$ Compounds, Muerrell, J.C. et al. eds, Intercept Ltd: Andover, UK, pp. 415-432.

Bennett, J.W. et al. eds. (1991). "Gene Cloning and Analysis," Chapter 3 in More Gene Manipulations in Fungi, Academic Press, San Diego, CA pp. 70-76.

Berman, H. et al. (2007, e-pub. Nov. 16, 2006). "The Worldwide Protein Data Bank (wwPDB): Ensuring a Single, Uniform Archive of PDB Data," *Nucleic Acids Research* 35:D301-D303.

Beytia, E. et al. (Oct. 25, 1970). "Purification and Mechanism of Action of Hog Liver Mevalonic Kinase," *The Journal of Biological Chemistry* 245(20):5450-5458.

Bock, R. et al. (2000). "Extranuclear Inheritance: Plastid Genetic: Manipulation of Plastid Genomes and Biotechnological Application," *Progress in Botany* 61:76-90.

Bock, R. (2001). "Transgenic Plastids in Basic Research and Plant Biotechnology," *J. Mol. Biol.* 312:425-438.

Bock, R. et al. (Jun. 2004). "Taming Plastids for a Green Future," *Trends in Biotechnology* 22(6):311-318.

Boel, E. et al. (1984). "Two Different Types of Intervening Sequences in the Glucoamylase Gene from *Aspergillus niger*," *The EMBO Journal* 3(7):1581-1585.

Bouvier, F. et al. (2005). "Biogenesis, Molecular Regulation and Function of Plant Isoprenoids," *Progress in Lipid Res.* 44:357-429.

Boynton, J.E. et al. (1993). "Chloroplast Transformation in *Chlamydomonas*," *Methods in Enzymology* 217(37):510.536.

Broun, P. et al. (Nov. 13, 1998). "Catalytic Plasticity of Fatty Acid Modification Enzymes Underlying Chemical Diversity of Plant Lipids," *Science* 282:1315-1317.

Brunger, A.T. et al. (1998). "*Crystallography & NMF? System*: A New Software Suite for Macromolecular Structure Determination," *Acta Cryst.* D54:905-921.

Bubunenko, M. et al. (Apr. 2007). "Essentiality of Ribosomal and Transcription Antitermination Proteins Analyzed by Systematic Gene Replacement in *Escherichia coli*," *Journal of Bacteriology* 189(7):2844-2853.

Campbell, E.I. et al. (1989). "Improved Transformation Efficiency of *Aspergillus niger* Using the Homologous *niaD* Gene for Nitrate Reductase," *Curr. Genet.* 16:53-56.

Campbell, J.W. et al. (Oct. 2001). "*Escherichia coli* FadR Positively Regulates Transcription of the *fabB* Fatty Acid Biosynthetic Gene," *J. Bacteriol.* 183(20):5982-5990.

Campos, N. et al. (2001). "*Escherichia coli* Engineering to Synthesize Isopentenyl Diphosphate and Dimethylallyl Diphosphate from Mevalonate: A Novel System for the Genetic Analysis of the 2-C-Methyl-D-Erythritol 4-Phospate Pathway for Isoprenoid Biosynthesis," *Biochem. J.* 353:59-67.

Cao, Q-N. et al. (2000). "Penicillopepsin-JT2, a Recombinant Enzyme from *Penicillium janthinellum* and the Contribution of a Hydrogen Bond in Subsite *S3* to *kcat*," *Protein Science* 9:991-1001.

Chamberlin, M. et al. (Oct. 17, 1970). "New RNA Polymerase from *Escherichia coli* Infected with Bacteriophage T7," *Nature* 228:227-231.

Champenoy, S. et al. (1998). "Expression of the Yeast Mevalonate Kinase Gene in Transgenic Tobacco," *Molecular Breeding* 4:291-300.

Chan, W. et al. (2007, e-pub. Apr. 10, 2007). "A Recombineering Based Approach for High-Throughput Conditional Knockout Targeting Vector Construction," *Nucleic Acids Research* 35(8):e64, 13 pages.

Chappell J. et al. (1995). Is the Reaction Catalyzed by 3-Hydroxy-3-Methylglutaryl-Coenzyme A Reductase a Rate-Limiting Step for Isoprenoid Biosynthesis in Plants?*Plant Physiology* (109):1337-1343.

Chemler, J.A. et al. (May 23, 2006). "Biosynthesis of Isoprenoids, Polyunsaturated Fatty Acids and Flavonoids in *Saccharomyces cerevisiae*," *Microbial Cell Factories* 5:20, 9 pages.

Chica, R.A. et al. (2005). "Semi-Rational Approaches to Engineering Enzyme Activity: Combining the Benefits of Directed Evolution and Rational Design," *Current Opinion in Biotechnology* 16:378-384.

Cho, H-J. et al. (1995). "Expression Pattern of Bacterial Polycistronic Genes in Tobacco Cells," *Journal of Fermentation and Bioengineering* 80(2):111-117.

Clarke, S. (1992). "Protein Isoprenylation and Methylation at Carboxyl-Terminal Cysteine Residues," *Annu. Rev. Biochem.* 61:355-386.

Clough, S.J. et al. (1998). "Floral Dip: A Simplified Method for *Agrobacterium-Mediated* Transformation of *Arabidopsis thaliana*," *The Plant Journal* 16(6):735-743.

Collaborative Computational Project, No. 4. (1994). "The *CCP4* Suite: Programs for Protein Crystallography," *Acta Cryst.* D50:760-763.

Cordier, H. et al. (1999). "Heterologous Expression in *Saccharomyces cerevisiae* of an *Arabidopsis thaliana* cDNA Encoding Mevalonate Diphosphate Decarboxylase," *Plant Molecular Biology* 39:953-967.

Crueger, W. et al. (1989). Biotechnology: A Textbook of Industrial Microbiology, Second Edition, Brock, T.D. ed., Sinauer Associates, Inc.: Sunderland, MA, pp. vii-x, (Table of Contents).

Cunningham, F.X. et al. (1998). "Genes and Enzymes of Carotenoid Biosynthesis in Plants," *Ann. Rev. Plant Physiol. Plant Mol. Biol.* 49:557-583.

Cunningham, F.X. et al. (Oct. 2000). "Evidence of a Role for LytB in the Nonmevalonate Pathway of Isoprenoid Biosynthesis," *Journal of Bacteriology* 182(20):5841-5848.

Dale, P.J. (1992). "Spread of Engineered Genes to Wild Relatives," *Plant PhysioL* 100:13-15.

Dale, G.E. et al. (2003). "The Protein as a Variable in Protein Crystallization," *Journal of Structural Biology* 142:88-97.

Daniell, H. (1997). "Transformation and Foreign Gene Expression in Plants Mediated by Microprojectile Bombardment," Chapter 35 in Methods in Molecular Biology, Recombinant Gene Expression Protocols, Tuan, R S. ed., Humana Press: Totowa, NJ, 62:463-489.

Daniell, H. et al. (Apr. 1998) "Containment of Herbicide Resistance Through Genetic Engineering of the Chloroplast Genome," *Nature Biotechnology* 16:345-348.

Datsenko, K.A. et al. (Jun. 6, 2000). "One-Step Inactivation of Chromosomal Genes in *Escherichia coli* K-12 Using PCR Products," *PNAS* 97(12):6640-6645.

Datta, S. et al. (2006). "A Set of Recombineering Plasmids for Gram-Negative Bacteria," *Gene* 379:109-115.

Datukishvili, N.T. et al. (2001). "Isolation and Purification of Protein Responsible for the Conversion of Dimethylallylpyrophosphate from Poplar Leaves into Isoprene," *Russian Journal of Plant Physiology* 48(2):222-225.

Davidson, S. (Oct.-Dec. 2003). "Light Factories," located at http://www.publish.csiro.au/?act=view_file&file_id=EC117p10.pdf>, last visited on Oct. 2, 2008.

Davis, I.W. et al. (2007). "MolProbity: All-Atom Contacts and Structure Validation for Proteins and Nucleic Acids," *Nucleic Acids Research* 35:W375-W383.

De Cosa, B. et al. (Jan. 2001). "Overexpression of the *Bt* cry2Aa2operon in Chloroplasts Leads to Formation of Insecticidal Crystals," *Nature Biotechnology* 19:71-74.

Del Campo, E. M. et al. (1997). "Plastid *ndhD* Gene of Barley, Sequence and Transcript Editing (Accesion No. Y12258) (PGR 97-090)," *Plant Physiol.* 114:747-749.

(56) References Cited

OTHER PUBLICATIONS

Della-Cioppa, G. et al. (1987). "Protein Trafficking in Plant Cells," *Plant Physiol.* 84:965-968.

Deppenmeier, U. et al. (2002). "The Genome of *Methanosarcina mazei*: Evidence for Lateral Gene Transfer Between Bacteria and Archaea," *J. Mol. Microbiol. Biotechnol.* 4(4):453461.

Deroles, S.C. et al. (1988). "Expression and Inheritance of Kanamycin Resistance in a Large Number of Transgenic Petunias Generated by *Agrobacterium*-Mediated Transformation," *Plant Molecular Biology* 11:355-364.

Dettmer, K. et al. (2000). "Stability of Reactive Low Boiling Hydrocarbons on Carbon Based Adsorbents Typically Used for Adsorptive Enrichment and Thermal Desorption," *Fresenius J. Anal. Chem.* 366:70-78.

Devereux, J. et al. (1984). "A Comprehensive Set of Sequence Analysis Programs for the VAX," *Nucleic Acids Research* 12(1):387-395.

Devos, D. et al. (2000). "Practical Limits of Function Prediction," *Proteins: Structure, Function, and Genetics* 41:98-107.

Dewick, P.M. et al. (2002, e-pub. Jan. 22, 2002). "The Biosynthesis of C5025 Terpenoid Compounds," *Nat. Prod. Rep.* 19:181-222.

Dhe-Paganon, S. et al. (1994). "Mechanism of Mevalonate Pyrophosphate Decarboxylase: Evidence for a Carbocationic Transition State," *Biochemistry* 33(45):13355-13362.

Dorsey, J.K. et al. (Sep. 25, 1968). "The Inhibition of Mevalonic Kinase by Geranyl and Farnesyl Pyrophosphates," *The Journal of Biological Chemistry* 243(18):4667-4670.

Doumith, M. et al. (2000, e-pub. Aug. 25, 2000). "Analysis of Genes Involved in 6-Deoxyhexose Biosynthesis and Transfer in *Saccharopolyspora elythraea*," *Mol. Gen Genet.* 264:477-485.

Dynan, W.S. et al. (Aug. 29, 1985). "Control of Eukaryotic Messenger RNA Synthesis by Sequence-Specific DNA-Binding Proteins," *Nature* 316:774-778.

Eisenreich, W. et al. (Sep. 1998). "The Deoxyxylulose Phosphate Pathway of Terpenoid Biosynthesis in Plants and Microorganisms," *Chemistry and Biology* 5(9):R221-R233.

Eisenreich, W. et al, (Feb. 2001). "Deoxyxylulose Phosphate Pathway to Terpenoids," *Trends in Plant Science* 6(2):78-84.

Elroy-Stein, 0. et al. (Aug. 1989). "Cap-Independent Translation of mRNA Conferred by Encephalomyocarditis Virus 5' Sequence Improves the Performance of the Vaccinia Virus/Bacteriophage T7 Hybrid Expression System," *PNAS USA* 86:6126-6130.

EMBL-EBI Accession No. AOPFK2, last updated on Mar. 2, 2010, located at <http://srs.ebi.ac.uk/srsbin/cgi-bin/wgetz?-e+[UNIPROT;AOPFK2_POPNI]+newid>, last visited on Jun. 2, 2010, 2 pages.

EMBL-EBI Accession No. A9PGR5, last updated on Mar. 2, 2010, located at <http://srs.ebi.ac.uk/srsbin/cgi-bin/wgetz?-e+[UNIPROT;A9PGR5_POPTR]+newid>, last visited on Jun. 2, 2010, 2 pages.

EMBL-EBI Accession No. AB198180, last updated May 10, 2005, located at <http://www.ebi.ac.uk/cgi-bin/dbfetch?db=embl&id=ab198180&Subm . . . >, last visited on Aug. 7, 2009, 2 pages.

EMBL-EBI Accession No. AY341431, last updated Apr. 16, 2005, located at <http://www.ebi.ac.uk/cgi-bin/dbfetch?db=embl&id=AY341431&Sub . . . >, last visited on Nov. 26, 2009, 2 pages.

Emsley, P. et al. (2004). "*Coot*: Model-Building Tools for Molecular Graphics," *Acta Crystallographica* D60:2126-2132.

Extended European Search Report dated Jun. 14, 2011, for EP Patent Application No. 08860589.4, filed on Dec. 15, 2008, 10 pages.

Fall, R. (Sep. 12, 2003). "Final Technical Report: DE-FG03-97ER20274, 'Microbial Production of Isoprene'," located at <http://www.osti.gov/bridge/product.biblio.jsp?query_id=1&page=0&osti_id=814920>, last visited on May 26, 2010, 4 pages.

Farmer, W.R. et al. (May 2000). "Improving Lycopene Production in *Escherichia coli* by Engineering Metabolic Control," *Nature Biotechnology* 18:533-537.

Feng, D-F. et al. (1987). "Progressive Sequence Alignment as a Prerequisite to Correct Phylogenetic Trees," *Journal of Molecular Evolution* 25:351-360.

Finkelstein, D.B. (1992). "Transformation," Chapter 6 in Biotechnology of Filamentous Fungi, Butterworth-Heinemann: Boston, MA, pp. 113-156.

Flores, S. et al. (Aug. 20, 2004, e-pub. Jul. 23, 2004). "Growth-Rate Recovery of *Escherichia coli* Cultures Carrying a Multicopy Plasmid, by Engineering of the Pentose-Phosphate Pathway," *Biotechnology and Bioengineering* 87(4):485-494.

Fu, Z. et al. (2008, e-pub. Feb. 27, 2008). "Biochemical and Structural Basis for Feedback Inhibition of Mevalonate Kinase and Isoprenoid Metabolism," *Biochemistry* 47:3715-3724.

Gallie, D.R. et al. (1989). "Eukaryotic Viral 5'-Leader Sequences Act as Translational Enhancers in Eukaryotes and Prokaryotes," in Molecular Biology of RNA, Cech, T.R. ed. Alan R. Liss, Inc: New York, NY, pp. 237-256.

Garret, T.A. et al. (May 15, 1998). "Accumulation of a Lipid A Precursor Lacking the 4'-Phosphate Following Inactivation of the *Escherichia coli IpxK* Gene," *The Journal of Biological Chemistry* 273(20):12457-12465.

GenBank Accession No. AB198180, last updated on May 10, 2005, located at <http://www.ncbi.nlm.nih.gov/nuccore/63108309>, last visited on Jun. 2, 2010, 2 pages.

GenBank Accession No. AJ294819.1, last updated Apr. 15, 2005, located at <http://www.ncbi.nlm.nih.gov/nuccore/AJ294819.1>, last visited on Dec. 7, 2011, 2 pages.

GenBank Accession No. AJ457070, last updated on Apr. 15, 2005, located at <http://www.ncbi.nlm.nih.gov/nuccore/38092202>, last visited on Jun. 2, 2010, 2 pages.

GenBank Accession No. AM410988.1, last updated Aug. 14, 2008, located at <http://www.ncbi.nlm.nih.gov/nuccore/AM410988.1>, last visited on Dec. 7, 2011, 2 pages.

GenBank Accession No. AY182241, last updated on May 4, 2004, located at <http://www.ncbi.nlm.nih.gov/nuccore/32265057>, last visited on Jun. 2, 2010, 2 pages.

GenBank Accession No. AY279379, last updated on Mar. 11, 2005, located at <http://www.ncbi.nlm.nih.gov/nuccore/30984014>, last visited on Jun. 2, 2010, 2 pages.

GenBank Accession No. AY316691, last updated on Feb. 15, 2005, located at <http://www.ncbi.nlm.nih.gov/nuccore/35187003>, last visited on Jun. 2, 2010, 2 pages.

GenBank Accession No. AY341431, last updated on Feb. 15, 2005, located at <http://www.ncbi.nlm.nih.gov/nuccore/33358228>, last visited on Jun. 2, 2010, 3 pages.

GenBank Accession No. EF147555.1, last updated Mar. 24, 2009, located at <http://www.ncbi.nlm.nih.gov/nuccore/EF147555.1>, last visited on Aug. 25, 2015, 2 pages.

GenBank Accession No. EF638224.1, last updated May 3, 2010, located at <http://www.ncbi.nlm.nih.gov/nuccore/EF638224.1>, last visited on Aug. 25, 2015, 2 pages.

GenBank Accession No. EU693027, last updated on May 27, 2008, located at <http://www.ncbi.nlm.nih.gov/nuccore/189017053>, last visited on Jun. 2, 2010, 2 pages.

GenBank Accession No. CAC35696, last updated Apr. 15, 2005, located at <http://www.ncbi.nlm.nih.gov/protein/CAC35696>, last visited on Apr. 6, 2011, 2 pages.

Geneseq Database Accession No. AFB74822, "Monoterpene synthetase protein SEQ ID No. 4." Retrieved from EBI accession No. GSP:AFB74822 (Apr. 19, 2007.).

Gerhardt, P. et al. eds. (1994). Manual of Methods for General and Molecular Bacteriology, American Society for Microbiology: Washington, D.C., p. v, (Table of Contents Only).

Goedegebuur, F. et al. (2002, e-pub. May 7, 2002). "Cloning and Relational Analysis of 15 Novel Fungal Endoglucanases from Family 12 Glycosyl Hydrolase," *Curr. Genet.* 41:89-98.

Goldschmidt-Clermont, M. (1991). "Transgenic Expression of Aminoglycoside Adenine Transferase in the Chloroplast: A Selectable Marker for Site-Directed Transformation of Chlamydomonas," *Nucleic Acids Res.* 19(15):4083-4089.

Goodwin, T.W. (1971). "Biosynthesis of Carotenoids and Plant Triterpenes: The Fifth CIBA Medal Lecture," *Biochem. J.* 123(3):293-329.

(56) References Cited

OTHER PUBLICATIONS

Gottschalk, G. (1986). Bacterial Metabolism Second Edition, Springer Verlag: New York, NY, pp. xi-xiii, (Table of Contents Only).

Grawert, T. et al. (2004, e-pub. Sep. 21, 2004). "IspH Protein of *Escherichia coli*: Studies on Iron-Sulfur Cluster Implementation and Catalysis," *Journal American Chemistry Society* 126:12847-12855.

Greenberg, J.P. et al. (1993). "Sub-Parts Per Billion Detection of Isoprene Using a Reduction Gas Detector with a Portable Gas Chromatograph," *Atmospheric Environment* 27A(16):2689-2692.

Grochowski, L.L. et al. (May 2006). "*Methanocaldococcus jannaschii* Uses a Modified Mevalonate Pathway for Biosynthesis of Isopentenyl Diphosphate," *Journal of Bacteriology* 188(9):3192-3198.

Guda, C. et al. (2000). "Stable Expression for a Biodegradable Protein-Based Polymer in Tobacco Chloroplasts," *Plant Cell Reports* 19:257-262.

Guerineau, F. et al. (1991). "Effect of Deletions in the Cauliflower Mosaic Virus Polyadenylation Sequence on the Choice of the Polyadenylation Sites in Tobacco Protoplasts," *Mol. Gen. Genet.* 226:141-144.

Guo, D-A. et al. (1995). "Developmental Regulation of Sterol Biosynthesis in *Zea mays*," *Lipids* 30(3):203-219.

Hahn, F.M. et al. (May 12, 1995). "Isolation of *Schizosaccharomyces pombe* Isopentenyl Diphosphate Isomerase in cDNA Clones by Complementation and Synthesis of the Enzyme in *Escherichia coli*," *The Journal of Biological Chemistry* 270(19):11298-11303.

Hahn, F.M. et al. (Feb. 1996). "Open Reading Frame 176 in the Photosynthesis Gene Cluster of *Rhodobacter capsulatus* Encodes *idi*, a Gene for Isopentenyl Diphosphate Isomerase," *Journal of Bacteriology* 178(3):619-624.

Hahn, F.M. et al. (Aug. 1999). "*Escherichia coli* Open Reading Frame 696 is *idi*, a Nonessential Gene Encoding Isopentenyl Diphosphate Isomerase," *Journal of Bacteriology* 181(15):4499-4504.

Hahn, F.M. et al. (Jan. 2001). "1-Deoxy D-Xylulose 5-Phosphate Synthase, the Gene Product of Open Reading Frame (ORF) 2816 and ORF 2895 in *Rhodobacter capsulatus*," *Journal of Bacteriology* 183(1):1-11.

Hamano, Y. et al. (2001). "Cloning of a Gene Cluster Encoding Enzymes Responsible for the Mevalonate Pathway from a Terpenoid-Antibiotic-Producing *Streptomyces* Strain," *Biosci. Biotechnol. Biochem.* 65(7):1627-1635.

Hamilton, C.M. et al. (Sep. 1989). "New Method for Generating Deletions and Gene Replacements in *Escherichia coli*," *Journal of Bacteriology* 171(9):4617-4622.

Hale, W.G. et al. (1991). The Harper Collins Dictionary of Biology, Ehrlich, E. ed., Harper Perennial: New York, NY, 2 pages.

Hanai, T. et al. (Dec. 2007). "Engineered Synthetic Pathway for Isopropanol Production in *Escherichia coli*," *Applied and Environmental Microbiology* 73(24):7814-7818.

Harker, M. et al. (1999). "Expression of Prokaryotic 1-Deoxy-D-Xylulose-5-Phosphatases in *Escherichia coli* Increases Carotenoid and Ubiquinone Biosynthesis," *FEBS Letters* 448:115-119.

Harkki, A. et al. (Jun. 1989). "A Novel Fungal Expression System: Secretion of Active Calf Chymosin from the Filamentous Fungus *Trichoderma reesei*," *Bio. Technol.*7:596-603.

Hedl, M. et al. (Apr. 2002). "*Enterococcus faecalis* Acetoacetyl-Coenzyme A Thiolase/3-Hydroxy-3-Methylglutaryl-Coenzyme A Reductase, a Dual-Function Protein of Isopentenyl Diphosphate Biosynthesis," *J. Bacteriol.* 184(8):2116-2122.

Hedl, M. et al. (Apr. 2004). "Class II 3-Hydroxy-3-Methylglutaryl Coenzyme A Reductases," *Journal of Bacteriology* 186(7):1927-1932.

Hellman, U. et al. (1995). "Improvement of an "In-Gel" Digestion Procedure for the Micropreparation of Internal Protein Fragments for Amino Acid Fragments for Amino Acid Sequencing," *Analytical Biochemistry* 224:451-455.

Herbers, K. et al. (Jun. 1996). "Manipulating Metabolic Partitioning in Transgenic Plants", *TIBTECH* 14:198-205.

Herz, S. et al. (Mar. 14, 2000). "Biosynthesis of Terpenoids: YgbB Protein Converts 4-Diphosphocytidyl-2C-Methyl-D-Erythritol 2-Phosphate to 2C-Methyl-D-Erythritol 2,4-Cyclodiphosphate," *Proc. Natl. Acad. Sci. USA* 97(6):2486-2490.

Higgins, D.G. et al. (1989). "Fast and Sensitive Multiple Sequence Alignments on a Microcomputer," *Cabios Communications* 5(2):151-153.

Hinson, D.D. et al. (1997). "Post-Translation Regulation of Mevalonate Kinase by Intermediates of the Cholesterol and Nonsterol Isoprene Biosynthetic Pathways," *Journal of Lipid Research* 38:2216-2223.

Hoeffler, J-F et al. (2002). "Isoprenoid Biosynthesis via the Methylerythritol Phosphate Pathway. Mechanistic Investigations of the 1-Deoxy-D-Xylulose 5-Phosphate Reductoisomerase," *Eur. J. Biochem.* 269:4446-4457.

Huang, K-X. et al. (1999). "Overexpression, Purification, and Characterization of the Thermostable Mevalonate Kinase from *Methanococcus jannaschii*," *Protein Expression and Purification* 17:33-40.

Hunter, B.K. (1985). "Formaldehyde Metabolism by *Escherichia coli*. Carbon and Solvent Deuterium Incorporation into Glycerol, 1,2-Propanediol, and 1,3-Propanediol," *Biochemistry* 24(15):4148-4155.

Hyatt, D.C. et al. (Mar. 27, 2007). "Structure of Limonene Synthase, A Simple Model for Terpenoid Cyclase Catalysis," *PNAS* 104(13):5360-5365.

Ilmen, M. et al. (Apr. 1997). "Regulation of Cellulase Gene Expression in the Filamentous Fungus *Trichoderma reesei*," *Appl. Environ. Microbiol.* 63(4):1298-1306.

Innis, M.A. et al. (Apr. 5, 1985). "Expression, Glycosylation, and Secretion of an *Aspergillus* Glucoamylase by *Saccharomyces cerevisiae*," *Science* 228:21-26.

International Search Report dated Jun. 18, 2009, for PCT Patent Application No. PCT/US08/86869, filed on Dec. 15, 2008, one page. (2.40).

International Search Report dated Dec. 8, 2009, for PCT Application No. PCT/US2009/041581, filed on Apr. 23, 2009, nine pages. (5.40).

International Search Report dated Dec. 30, 2010, for PCT Application No. PCT/US2010/032134, filed on Apr. 22, 2010, 15 pages. (15.40).

Jenkins, L.S. et al. (Jan. 1987). "Genetic and Molecular Characterization of the Genes Involved in Short-Chain Fatty Acid Degradation in *Escherichia coli*: The *ato* System," *Journal of Bacteriology* 169(1):42-52.

Jeong, S.-W. et al. (2004, e-pub. Jan. 21, 2004). "Dicistronic Expression of the Green Fluorescent Protein and Antibiotic Resistance Genes in the Plastid for Selection and Tracking of Plastid-Transformed Cells in Tobacco," *Plant Cell Rep* 22:747-751.

Jobling, S.A. et al. (Feb. 12, 1987). "Enhanced Translation of Chimaeric Messenger RNAs Containing a Plant Viral Untranslated Leader Sequence," *Nature* 235:622-625.

Jones, K.L. et al. (2000). "Low-Copy Plasmids Can Perform as Well as or Better Than High-Copy Plasmids for Metabolic Engineering of Bacteria," *Metabolic Engineering* 2:238-338.

Jones, E.Y. et al. (1991). "Methodology Employed for the Structure Determination of Tumour Necrosis Factor, a Case of High Non-Crystallographic Symmetry," *Acta Cryst* A47:753-770.

Joshi, C.P. (1987). "Putative Polyadenylation Signals in Nuclear Genes of Higher Plants: A Compilation and Analysis," *Nucleic Acid Research* 15(23):9627-9640.

Julsing, M.K. et al. (2007). "Functional Analysis of Genes Involved in the Biosynthesis of Isoprene in *Bacillus subtilis*," *Applied Microbiol. Biotechnol.* 75:1377-1384.

Kacian, D.L. et al. (Oct. 1972). "A Replicating RNA Molecule Suitable for a Detailed Analysis of Extracellular Evolution and Replication," *Proc. Natl. Acad. Sci. USA* 69(10):3038-3042.

Kajiwara, S. et al. (1997). "Expression of an Exogenous Isopentenyl Diphosphate Isomerase Gene Enhances Isoprenoid Biosynthesis in *Escherichia coli*," *Biochem. J.* 324:421-426.

(56) References Cited

OTHER PUBLICATIONS

Kampranis, S.C. et al. (Jun. 2007). "Rational Conversion of Substrate and Product Specificity in a *Salvia* Monoterpene Synthase: Structural Insights into the Evolution of Terpene Synthase Function," *The Plant Cell* 19:1994-2005.

Kaneda, K. et al. (Jan. 30, 2001). "An Unusual Isopentenyl Diphosphate Isomerase Found in the Mevalonate Pathway Gene Cluster from *Streptomyces* sp. Strain CL190," *PNAS* 98(3):932-937.

Karl, T. et al. (2003). "Dynamic Measurements of Partition Coefficients Using Proton-Transfer-Reaction Mass Spectrometry (PTR-MS)," *International Journal of Mass Spectrometry* 223-224:383-295.

Karlin, S. (Jun. 1993). "Applications and Statistics for Multiple High-Scoring Segments in Molecular Sequences," *Proc. Natl. Acad. ScL USA* 90:5873-5787.

Kavanagh, T.A. et al. (Jul. 1999). "Homeologous Plastid DNA Transformation in Tobacco is Mediated by Multiple Recombination Events," *Genetics* 52:1111-1122.

Keasling, J.D. (Mar. 29, 2004). "Genetic Tools for Metabolic Enzyme Production in *Escherichia coli,*" *presented at* NIGMS 2004 PSI Protein Production & Crystallization Workshop, Bethesda, MD, Mar. 29-31, 2004, located at <http://www-nmr.cabm/rutgers.edu/labdocuments/workshops/psi_ppcw_32904/ppcw_32904.html>, last visited on Jun. 4, 2010, 66 pages.

Keasling, J.D. (May 7, 2005). "Drugs from Bugs: Engineering Microorganisms to Produce New Drugs," *presented at* Engineering a Better World: *Our Environment, Our Health*, Berkeley, CA, May 7, 2005, 62 pages.

Keasling, J.D. (Sep. 23, 2007). "Engineering Microbes for Production of Low-Cost, Effective, Anti-Malarial Drugs," *presented at Enzyme Engineering XIX*, Harrison Hot Springs, British Columbia, Canada, Sep. 23-28, 2007, 152 pages.

Keegan, R.M. et al. (2007). "Automated Search-Model Discovery and Preparation for Structure Solution by Molecular Replacement," *Acta Crystallographica* D63:447-457.

Keeler, K.H. et al. (1996). "Movement of Crop Transgenes into Wild Plants," Chapter 20 in *Herbicide Resistant Crops: Agricultural, Environmental, Economic, Regulatory, and Technical Aspects*, Duke, S.O. ed., Lewis Publishers: Boca Raton, FL., pp. 303-330.

Kelly, J.M. et al. (1985). "Transformation of *Aspergillus niger* by the *amdS* Gene of *Aspergillus nidulans*," *The EMBO Journal* 4(2):475-479.

Khan, M.S. et al. (Sep. 1999). "Fluorescent Antibiotic Resistance Marker for Tracking Plastid Transformation in Higher Plants," *Nature Biotechnology* 17:910-914.

Kieser, T. eds. et al. (Jul. 2000). "Introduction of DNA into *Streptomyces*," Chapter 10 in *Practical Streptomyces Genetics*, pp. 229-252.

Kinghorn, J.R. et al. (1992). Applied Molecular Genetics of Filamentous Fungi, Blackie Academic Professional and Chapman and Hall: London, 3 pages, (Table of Contents Only).

Kisselev, L. (Jan. 2002). "Polypeptide Release Factors in Prokaryotes and Eukaryotes: Same Function, Different Structure," *Structure* 10:8-9.

Klein-Marcuschamer, D. et al. (2007, e-pub. Aug. 2, 2007). "Engineering Microbial Cell Factories for Biosynthesis of Isoprenoid Molecules: Beyond Lycopene," *TRENDS in Biotechnology* 25(9):417-424.

Klein-Marcuschamer, D. et al. (Feb. 19, 2008). "Assessing the Potential of Mutational Strategies to Elicit New Phenotypes in Industrial Strains," *Proc. Natl. Acad. Sci.* 105(7):2319-2324.

Koga, Y. et al. (Mar. 2007). "Biosynthesis of Ether-Type Polar Lipids in Archaea and Evolutionary Considerations," *Microbiology and Molecular Biology Reviews* 71(1):97-120.

Koksal, M. et al. (2010, e-pub. Jul. 17, 2010). "Structure of Isoprene Synthase Illuminates the Chemical Mechanism of Teragram Atmospheric Carbon Emission," *J. Mol. Biol.* pp. 1-11.

Kooter, J. M., et al. (Sep. 1999). "Listening to the Silent Genes: Transgene Silencing, Gene Regulation and Pathogen Control," *Trends in Plant Science* 4(9):340-347.

Kota, M. et al. (Mar. 1999). "Overexpression of the *Bacillus thuringiensis* (Bt) Cry2Aa2 Protein in Chloroplasts Confers Resistance to Plants Against Susceptible and Bt-Resistant Insects," *Proc. Natl. Acad. Sci. USA* 96:1840-1845.

Kozak, M. (Oct. 25, 1991). "Structural Features in Eukaryotic mRNAs That Modulate the Initiation of Translation," *The Journal of Biological Chemistry* 266(30):19867-19870.

Kozak, M. (1999). "Initiation of Translation in Prokaryotes and Eukaryotes," *Gene* 234:187-208.

Kreigler, M. (1990). Gene Transfer and Expression: A Laboratory Manual, W.H. Freeman and Company: New York, NY, pp. Vii-x, (Table of Contents Only.).

Kunkel, T. A. (Jan. 1985). "Rapid and Efficient Site-Specific Mutagenesis without Phenotypic Selection," *Proc. Natl. Acad. Sci. USA* 82:488-492.

Kuzma, J. et al. (1995). "Bacteria Produce the Volatile Hydrocarbon Isoprene," *Current Microbiology* 30:97-103.

Kuzuyama, T. et al. (1998). "Direct Formation of 2-C Methyl-D-Erythritol 4-Phosphate from 1-Deoxy-D-Xylulose 5-Phosphate by 1-Deoxy-D-Xylulose 5-Phosphate Reductoisomerase, a New Enzyme in the Non-Mevalonate Pathway to Isopentenyl Diphosphate," *Tetrahedron Letters* 39:4509-4512.

Kuzuyama, T. et al. (1998). "Fosmidomycin, a Specific Inhibitor of 1-Deoxy-D-Xylulose 5-Phosphate Reductoisomerase in the Nonmevalonate Pathway for Terpenoid Biosynthesis," *Tetrahedron Letters* 39:7913-7916.

Lange, B.M. et al. (Nov. 23, 1999). "Isopentenyl Diphosphate Biosynthesis via a Mevalonate-lndependent Pathway: Isopentenyl Monophosphate Kinase Catalyzes the Terminal Enzymatic Step," *PNAS* 96(24):13714-13719.

Lange, B.M. et al. (Sep. 2001). "Isoprenoid Biosynthesis. Metabolite Profiling of Peppermint Oil Gland Secretory Cells and Application to Herbicide Target Analysis," *Plant Physiology* 127:305-314.

Law, C.K. (1984). "Heat and Mass Transfer in Combustion: Fundamental Concepts and Analytical Techniques," *Progress in Energy and Combustion Science* 10:295-318.

Lehning, A. et al. (1999). "Isoprene Synthase Activity and Its Relation to Isoprene Emission in *Quercus robur* L. Leaves," *Plant, Cell and Environment* 22:495-504.

Lerner, C.G. et al. (1990). "Low Copy Number Plasmids for Regulated Low-Level Expression of Cloned Genes in *Escherichia coli* with Blue/White Insert Screening Capability," *Nucleic Acids Research* 18(15):4631.

Li, W. et al. (2010, e-pub. Nov. 1, 2009). "Non-Redundant Patent Sequence Databases with Value-Added Annotations at Two Levels," *Nucleic Acids Research* 38:D52-D56.

Lichtenthaler, H.K. et al. (1997). "Biosynthesis of Isoprenoids in Higher Plant Chloroplasts Proceeds via a Mevalonate-Independent Pathway," *FEBS Letters* 400:271-274.

Lichtenthaler, H.K. (1999). "The 1-Deoxy-D-Xylulose-5-Phosphate Pathway of Isoprenoid Biosynthesis in Plants," *Annu. Rev. Plant Physiol. Plant Mol. Biol.* 50:47-65.

Lin, X-M. et al. (2008, e-pub. Apr. 26, 2008). "Proteomic Analysis of Nalidixic Acid Resistance in *Escherichia coli*: Identification and Functional Characterization of Om Proteins," *Journal of Proteome Research* pp. A-G.

Lluch, M.A. et al. (2000). "Molecular Cloning and Expression Analysis of the Mevalonate Kinase Gene from *Arabidopsis thaliana*," *Plant Molecular Biology* 42:365-376.

Lois, L.M. et al. (Mar. 1998). "Cloning and Characterization of a Gene from *Escherichia coli* Encoding a Transketolase-Like Enzyme that Catalyzes the Synthesis of D-1-Deoxyxylulose 5-Phosphate, a Common Precursor for Isoprenoid, Thiamin, and Pyridoxol Biosynthesis," *Proc. Natl. Acad. Sci. USA* 95:2105-2110.

Loivamaki, M. et al. (Jun. 2007). "*Arabidopsis*, A Model to Study Biological Functions of Isoprene Emission?" *Plant Physiology* 144:1066-1078.

Lommel, S.A. et al. (1991). "Identification of the Maize Chlorotic Mottle Virus Capsid Protein Cistron and Characterization of its Subgenomic Messenger RNA," *Virology* 181:382-385.

(56) References Cited

OTHER PUBLICATIONS

Locker, J. et al. (2002). "Monoterpene Biosynthesis in Lemon (*Citrus Limon*). cDNA Isolation and Functional Analysis of Four Monoterpene Synthases," *European Journal of Biochemistry* 269:3160-3171.

Luli, G.W. et al. (Apr. 1990). "Comparison of Growth, Acetate Production, and Acetate Inhibition of *Escherichia coli* in Batch and Fed-Batch Fermentations," *Applied and Environmental Microbiology* 56(4):1004-1011.

Lottgen, H. et al. (Feb. 1, 2000). "Biosynthesis of Terpenoids: YchB Protein *Escherichia coli* Phosphorylates the 2-Hydroxy Group of 4-Diphosphocytidyl-2C-Methyl-D-Erythritol," *PNAS* 97(3):1062-1067.

Macejak, D.G. et al. (Sep. 5, 1991). "Internal Initiation of Translation Mediated by the 5' Leader of a Cellular mRNA," *Nature* 353:90-94.

Mahmoud, S.S. et al. (Jul. 17, 2001). "Metabolic Engineering of Essential Oil Yield and Composition in Mint by Altering Expression of Deoxyxylulose Phosphate Reductoisomerase and Menthofuran Synthase," *PNAS* 98(15):8915-8920.

Maldonado-Mendoza, I.E. et al. (1997). "Molecular Characterization of Three Differentially Expressed Members of the *Camptotheca acuminata* 3-Hydroxy-3-Methylglutaryl CoA Reductase (HMGR) Gene Family," *Plant Molecular Biology* 134:781-790.

Mann, V. et al. (Aug. 2000). "Metabolic Engineering of Astaxanthin Production in Tobacco Flowers," *Nature Biotechnology* 18:888-892.

Martin, V.J.J. et al. (Dec. 5, 2001). "The In Vivo Synthesis of Plant Sesquiterpenes by *Escherichia coli*," *Biotechnology and Bioengineering* 75(5):497-503.

Martin, V.J.J. et al. (Jul. 2003). "Engineering a Mevalonate Pathway in *Escherichia coli* for Production of Terpenoids," *Nature Biotechnology* 21(7):796-802.

Martin, W. et al. (May 14, 1998). "Gene Transfer to the Nucleus and the Evolution of Chloroplasts," *Nature* 393:162-165.

Mash Ego, M.R. et al. (2007, e-pub. Nov. 8, 2006). "Microbial Metabolomics: Past, Present and Future Methodologies," *Biotechnol. Lett.* 29:1-16.

Matsuoka, S. et al. (Feb. 25, 1991). "Variable Product Specificity of Microsomal Dehydrodolichyl Diphosphate Synthase from Rat Liver," *The Journal of Biological Chemistry* 266(6):3464-3468.

Matteucci, M.D. et al. (1981). "Synthesis of Deoxyoligonucleotides on a Polymer Support," *J. American Chemical Society* 103(11):3185-3191.

Matthews, P.D. et al. (2000). "Metabolic Engineering of Carotenoid Accumulation in *Escherichia coli* by Modulation of the Isoprenoid Precursor Pool with Expression of Deoxyxylulose Phosphate Synthase," *Appl Microbial Biotechnol* 53:396-400.

Maury, J. et al. (2005, e-pub. Jul. 5, 2005). "Microbial Isoprenoid Production: An Example of Green Chemistry through Metabolic Engineering," *Adv. Biochem. Engin/Biotechnol.* 100:19-51.

McPherson, A. (2004). "Introduction to Protein Crystallization," *Methods* 34:254-265.

Meinkoth, J. et al. (1984). "Hybridization of Nucleic Acids Immobilized on Solid Supports," *Analytical Biochemistry* 138:267-284.

Meyer, P. et al. (1996). "Homology-Dependent Gene Silencing in Plants," *Ann. Rev. Plant Physiol. Plant Mol. Biol.* 47:23-48.

Millen, R.S. et al. (Mar. 2001). "Many Parallel Losses of *infA* from Chloroplast DNA During Angiosperm Evolution with Multiple Independent Transfers to the Nucleus," *The Plant Cell* 13:645-658.

Miller, B. (2001). "Erstmalige Isolierung Eines Isoprenysthase-Gens and Heterologe Expression Des Aus Der Pappel Stammenden Gens Sowie Charakterisierung der Eingangsschritte des Mevalonat-unabhangigen Isoprenoidbiosyntheseweges aus dem Cyanobakterium Synechococcus leopoliensis," located at <http://kups.ub.uni-koeln.de/883/>, last visited on Jun. 23, 2011, English Translation included, 2 pages.

Miller, B. et al. (2001, e-pub. May 10, 2001). "First Isolation of an Isoprene Synthase Gene from Poplar and Successful Expression of the Gene in *Escherichia coli*," *Planta* 213:483-487.

Milne, P.J. et al. (1995). "Measurement of Vertical Distribution of Isoprene in Surface Seawater, its Chemical Fate, and its Emission from Several Phytoplankton Monocultures," *Marine Chemistry* 48:237-244.

Mo, H. et al. (2004). "Studies of the Isoprenoid-Mediated Inhibition of Mevalonate Synthesis Applied to Cancer Chemotherapy and Chemoprevention," *Exp. Biol. Med.* 229:567-585.

Mogen, B.D. et al. (Dec. 1990). "Upstream Sequences Other than AAUAAA are Required for Efficient Messenger RNA 3'-End Formation in Plants," *The Plant Cell* 2:1261-1272.

Monson, R.K. et al. (1992). "Relationships Among Isoprene Emission Rate, Photosynthesis, and Isoprene Synthase Activity as Influenced by Temperature," *Plant Physiol.* 98:1175-1180.

Munroe, D. et al. (1990). "Tales of Poly(A): a Review," *Gene* 91:151-158.

Murray, E.E. et al. (1989). "Codon Usage in Plant Genes," *Nucleic Acids Research* 17(2): 477-498.

Nakamura, C.E. et al. (2003). "Metabolic Engineering for the Microbial Production of 1,3-Propanediol," *Current Opinion in Biotechnology* 14:454-459.

Nanchen, A. et al. (Apr. 2008, e-pub. Jan. 25, 2008). "Cyclic AMP-Dependent Catabolite Repression is the Dominant Control Mechanism of Metabolic Fluxes Under Glucose Limitation in *Escherichia coli*," *Journal of Bacteriology* 190(7):2323-2330.

Nawrath, C. et al. (Dec. 1994). "Targeting of the Polyhydroxybutyrate Biosynthetic Pathway to the Plastids of *Arabidopsis thaliana* Results in High Levels of Polymer Accumulation," *Proc. Natl. Acad. Sci. USA* 91:12760-12764.

Needleman, S. B. et al. (1970). "A General Method Applicable to the Search for Similarities in the Amino Acid Sequence of Two Proteins," *J. MoL Biol.* 48:443-453.

Neidhardt, F.C. et al. (Sep. 1974). "Culture Medium for Enterobacteria," *J. Bacteriology* 119(3):736-747.

Neidhardt, F.C. et al. (1990). "Table 1. Overall Macromolecular Composition of an Average *E. coli* B/r Cell$^a$," in Chapter 1 in Physiology of the Bacterial Cell: A Molecular Approach, Sinauer Associates, Inc.: Sunderland, MA, pp. 4.

Nevalainen, K.M.H. et al. (1992). "The Molecular Biology of Trichoderma and Its Application to the Expression of Both Homologous and Heterologous Genes," Chapter 6 in Molecular Industrial Mycology, Systems and Applications for Filamentous Fungi, Leong, S.A. et al. eds., Marcel Dekker Inc.: New York, NY, pp. 129-148.

Newman, J.D. et al. (Nov. 5, 2006, e-pub. Jul. 28, 2006). "High-Level Production of Amorpha-4,11-Diene in a Two-Phase Partitioning Bioreactor of Metabolically Engineered *Escherichia coli*," *Biotechnology and Bioengineering* 95(4):684-691.

Newman, T. et al. (1994). "Genes Galore: A Summary of Methods for Accessing Results from Large-Scale Partial Sequencing of Anonymous *Arabidopsis* cDNA Clones," *Plant Physiology* 106:1241-1255.

Nielsen, K.M. et al. (1997). "Analysis and Developmental Profile of Carotenoid Pigments in Petals of Three Yellow Petunia Cultivars," *Scientia Horticulturae* 71:257-266.

Niinemets, O. et al. (Nov. 2002). "Stomatal Constraints May Affect Emission of Oxygenated Monoterpenoids from the Foliage of *Pinus pinea*," *Plant Physiology* 130:1371-1385.

Noronha, S.B. et al. (May 5, 2000). "Investigation of the TCA Cycle and the Glyoxylate Shunt in *Escherichia coli* BL21 and JM109 Using $^{13}$C-NMR/MS," *Biotechnology and Bioengineering* 68(3):316-327.

Nunberg, J.H. et al. (Nov. 1984). "Molecular Cloning and Characterization of the Glucoamylase Gene of *Aspergillus awamori*," *Mol. Cell. Biol.* 4(11):2306-2315.

Oh, M-K. et al. (Apr. 12, 2002). "Global Expression Profiling of Acetate-Grown *Escherichia coli*," *The Journal of Biological Chemistry* 277(15):13175-13183.

Ondrey, G. et al. (Oct. 2008). "Bio-Based Isoprene," *Chemical Engineering, Access Intelligence Association*, Rockville, MA, 115(1):14.

Oulmouden, A. et al. (1991). "Nucleotide Sequence of the *ERG12* Gene of *Saccharomyces cerevisiae* Encoding Mevalonate Kinase," *Curr. Genet.* 19:9-14.

(56) References Cited

OTHER PUBLICATIONS

Pachuk, C.J. et al. (2000). "Chain Reaction Cloning: A One-Step Method for Directional Ligation of Multiple DNA Fragments," *Gene* 243:19-25.
Pearson, W.R. et al. (Apr. 1988). "Improved Tools for Biological Sequence Comparison," *Proc. Natl. Acad. Sci. USA* 85:2444-2448.
Pegg, S.C.-H. et al. (2006). "Leveraging Enzyme Structure-Function Relationships for Functional Inference and Experimental Design: The Structure-Function Linkage Database," *Biochemistry* 45:2545-2555.
Penttila, M. et al. (1987). "A Versatile Transformation System for the Cellulolytic Filamentous Fungus *Trichoderma reesei*," *Gene* 61:155-164.
Perego, M. (1993). "Integrational Vectors for Genetic Manipulation in *Bacillus subtilis*," Chapter 42 in *Bacillus subtilis* and Other Gram-Positive Bacteria: Biochemistry, Physiology, and Molecular Genetics, Sonenshein et al. eds., American Society for Microbiology: Washington, D.C., pp. 615-624.
Phan, R.M. et al. (2001, e-pub. Sep. 13, 2001). "Synthesis of (S)-Isoprenoid Thiodiphosphates as Substrates and Inhibitors," *J. Org. Chem.* 66(20):6705-6710.
Phillips, T.A. et al. (Jul. 1984). "*lon* Gene Product of *Escherichia coli* is a Heat-Shock Protein," *Journal of Bacteriology* 159(1):283-287.
Phue, J-N. et al. (2004). "Transcription Levels of Key Metabolic Genes are the Cause for Different Glucose Utilization Pathways in *E. coli* B (BL21) and *E. coli* K (JM109)," *Journal of Biotechnology* 109:21-30.
Phue, J-N. et al. (2005, e-pub. Aug. 11, 2005). "Impact of Dissolved Oxygen Concentration on Acetate Accumulation and Physiology of *E. coli* BL21, Evaluating Transcription Levels of Key Genes at Different Dissolved Oxygen Conditions," *Metabolic Engineering* 7:353-363.
Pilloff, D. et al. (Feb. 14, 2003). "The Kinetic Mechanism of Phosphomevalonate Kinase," *The Journal of Biological Chemistry* 278(7):4510-4515.
Pitera, D.J. et al. (2007, e-pub. Nov. 23, 2006). "Balancing a Heterologous Mevalonate Pathway for Improved Isoprenoid Production in *Escherichia coli*," *Metabolic Engineering* 9:193-207.
Pommer, H. et al. (1975). "Industrial Synthesis of Terpene Compounds," *Pure and Applied Chemistry* 43(3-4):527-551.
Potter, D. et al. (Oct. 10, 1997). "Identification of Catalytic Residues in Human Mevalonate Kinase," *The Journal of Biological Chemistry* 272(41):25449-25454.
Pourquie, J. et al. (1988). "Scale Up of Cellulase Production and Utilization," in Biochemistry and Genetics of Cellulose Degradation, Aubert, J.-P. et al. eds., Academic Press: San Diego, CA, pp. 71-86.
Proudfoot, N. (Feb. 22, 1991). "Poly(A) Signals," *Cell* 64:671-674.
Ramos-Valdivia, A.G. et al. (1997). "Isopentenyl Diphosphate Isomerase: A Core Enzyme in Isoprenoid Biosynthesis: A Review of its Biochemistry and Function," *Natural Product Reports* 6:591-603.
Raschke, M. et al. (2004, e-pub. Oct. 28, 2004). "A High-Performance Liquid Chromatography Methods for the Analysis of Intermediates of the Deoxyxylulose Phosphate Pathway," *Analytical Biochemistry* 335:235-243.
Re, E.B. et al. (1995). "Co-Expression of Native and Introduced Genes Reveals Cryptic Regulation of HMG CoA Reductase Expression in *Arabidopsis*," *the Plant Journal* 7(5):771-784.
Reiling, K.K. et al. (Jul. 20, 2004, e-pub. Jun. 18, 2004). "Mono and Diterpene Production in *Escherichia coli*," *Biotechnology and Bioengineering* 87(2):200-212.
Rodrìguez-Concepcion, M. et al. (2000). "Genetic Evidence of Branching in the Isoprenoid Pathway for the Production of Isopentenyl Diphosphate and Dimethylallyl Diphosphate in *Escherichia coli.*," *FEBS Letters* 473:328-332.
Rodrìguez-Concepcion, M. et al. (Nov. 2002). "Elucidation of the Methylerythritol Phosphate Pathway for Isoprenoid Biosynthesis in Bacteria and Plastids. A Metabolic Milestone Achieved Through Genomics," *Plant Physiology* 130:1079-1089.
Rodriguez-Villalon, A. et al. (2008). "Carotenoid Accumulation in Bacteria with Enhanced Supply of Isoprenoid Precursors by Upregulation of Exogenous or Endogenous Pathways," *Journal of Biotechnology* 135:78-84.
Rohdich, F. et al. (Oct. 12, 1999). "Cytidine 5'-Triphosphate-Dependent Biosynthesis of Isoprenoids: YgbP Protein of *Escherichia coli* Catalyzes the Formation of 4-Diphosphocytidyl-2-C-Methylerythritol," *PNAS* 96(21):11758-11763.
Rohdich, F. et al. (Jun. 6, 2000). "Biosynthesis of Terpenoids: 4-Diphosphocytidyl-2C-Methyl-D-Erythritol Synthase of *Arabidopsis thaliana*," *PNAS* 97(12):6451-6456.
Rohmer, M. (1998). "Isoprenoid Biosynthesis Via the Mevalonate-Independent Route, a Novel Target for Antibacterial Drugs?" *Progress in Drug Research* 50:137-154.
Rohrich, R.C. et al. (2005, e-pub. Nov. 2, 2005). "Reconstitution of an Apicoplast-Localised Electron Transfer Pathway Involved in the Isoprenoid Biosynthesis of *Plasmodium falciparum*," *FEBS Letters* 579:6433-6438.
Rondon, M.R. et al. (May 1999). "Toward Functional Genomics in Bacteria: Analysis of Gene Expression in *Escherichia coli* from a Bacterial Artificial Chromosome Library of *Bacillus cereus*," *Proc. Natl. Acad. Sci. USA* 96:6451-6455.
Rosenfeld, J. et al. (1992). "In-Gel Digestion of Proteins for Internal Sequence Analysis After One- or Two-Dimensional Gel Electrophoresis," *Analytical Biochemistry* 203:173-179.
Rost, B. et al. (2004). "The PredictProtein Server," *Nucleic Acids Research* 32:W321-W326.
Sambrook, J. et al. (1989). Molecular Cloning: A Laboratory Manual, 2nd edition, Cold Spring Harbor Laboratory Press: New York, NY, pp. xi-xxxviii (Table of Contents Only).
Sanchez, C. et al. (Apr. 2002). "The Biosynthetic Gene Cluster for the Antitumor Rebeccamycin: Characterization and Generation of Indolocarbazole Derivatives," *Chemistry and Biology* 9(4):519-531.
Sander, R. (Apr. 8, 1999). Compilation of Henry's Law Constants for Inorganic and Organic Species of Potential Importance in Environmental Chemistry, 3:1-107.
Sanfacon, H. et al. (1991). "A Dissection of the Cauliflower Mosaic Virus Polyadenylation Signal," *Genes & Development* 5:141-149.
Sasaki, K. et al. (2005, e-pub. Apr. 7, 2005). "Gene Expression and Characterization of Isoprene Synthase from *Populus alba*," *FEBS Letters* 579:2514-2518.
Schneider, D. et al. (Jul. 9, 2002). "Genomic Comparisons Among *Escherichia coli* Strains B, K-12, and 0157:H7 Using IS Elements as Molecular Markers," *BMC Microbiology* 2:18, 8 pages.
Schnitzler, J.-P. et al. (2005, e-pub. Jul. 29, 2005). "Biochemical Properties of Isoprene Synthase in Poplar (*Populus x canescens*)," *Planta* 222(5):777-786.
Scholler, C. et al. (1997). "Volatile Metabolites from some Gram-Negative Bacteria," *Chemosphere* 35(7):1487-1495.
Scott, E. et al. (2007, e-pub. Mar. 27, 2007). "Biomass in the Manufacture of Industrial Products—The Use of Proteins and Amino Acids," *AppL Microbiol. Biotechnol.* 75:751-762.
Sen, S. et al. (2007). "Developments in Directed Evolution for Improving Enzyme Functions," *AppL Biochem. Biotechnol.* 143:212-223.
Serino, G. et al. (1997). "A Negative Selection Scheme Based on the Expression of Cytosine Deaminase in Plastids," *The Plant Journal* 12(3):697-701.
Sharkey, T.D. et al. (Feb. 1, 2005). "Supplemental data for: Evolution of the Isoprene Biosynthetic Pathway in Kudzu," *Plant Physiology* 137(2):700-712.
Sharkey, T.D. et al. (Feb. 2005). "Evolution of the Isoprene Biosynthetic Pathway in Kudzu," *Plant Physiology* 137:700-712.
Sheir-Neiss, G. et al. (Jul. 1984). "Characterization of the Secreted Cellulases of *Trichoderma reesei* Wild Type and Mutants During Controlled Fermentations," *Appl. Microbiol. Biotechnol.* 20(1):46-53.
Shelton, D. et al. (2004, e-pub. Nov. 26, 2004). "Isolation and Partial Characterization of a Putative Monoterpene Synthase from *Melaleuca alternifolia*," *Plant Physiology and Biochemistry* 42:875-882.

(56) References Cited

OTHER PUBLICATIONS

Shinozaki, K. et al. (1986). "The Complete Nucleotide Sequence of the Tobacco Chloroplast Genome: its Gene Organization and Expression," *The EMBO Journal* 5(9):2043-2049.

Shirk, M.C. et al. (2002, e-pub. Jul. 27, 2002). "Isoprene Formation in *Bacillus subtilis*: A Barometer of Central Carbon Assimilation in a Bioreactor?" *Biotechnol. Prog.* 18(5):1109-1115.

Silver, G.M. et al. (1991). "Enzymatic Synthesis of Isoprene from Dimethylallyl Diphosphate in Aspen Leaf Extracts," *Plant Physiol.* 97:1588-1591.

Silver, G.M. et al. (Jun. 2, 1995). "Characterization of Aspen Isoprene Synthase, an Enzyme Responsible for Leaf Isoprene Emission to the Atmosphere," *The Journal of Biological Chemistry* 270(22):13010-13016.

Sivy, T.L. et al. (2002). "Isoprene Synthase Activity Parallels Fluctuations of Isoprene Release During Growth of *Bacillus subtilis*," *Biochemical and Biophysical Research Communications* 294:71-75.

Siwko, M.E. et al. (2007, e-pub. Oct. 4, 2006). "Does Isoprene Protect Plant Membranes from Thermal Shock? A Molecular Dynamics Study," *Biochimica et Biophysica Acta* 1768:198-206.

Slabinski, L. et al. (2007). "The Challenge of Protein Structure Determination-Lessons from Structural Genomics," *Protein Science* 16:2472-2482.

Slater, S. et al. (Apr. 1992). "Production of Poly-(3-Hydroxybutyrate-Co-3-Hydroxyvalerate) in a Recombinant *Escherichia coli* Strain," *Applied and Environmental Microbiology* 58(4):1089-1094.

Slater, S. et al. (Oct. 1999). "Metabolic Engineering of *Arabidopsis* and *Brassica* for Poly(3-Hydroxybutyrate-co-3-Hydroxyvalerate) Copolymer Production," *Nature Biotechnology* 17:1011-1016.

Smit, A. et al. (2000). "Biosynthesis of Isoprenoids via Mevalonate in Archaea: The Lost Pathway," *Genome Research* 10:1468-1484.

Smith, T. et al. (1981). "Comparison of Biosequences." *Advances in Applied Mathematics* 2:482-489.

Sprenger, G.A. et al. (Nov. 1997). "Identification of a Thiamin-Dependent Synthase in *Escherichia coli* Required for the Formation of the 1-Deoxy-D-Xylulose 5-Phosphate Precursor to Isoprenoids, Thiamin, and Pyridoxol," *Proc. Natl. Acad. Sci. USA* 94:12857-12862.

Starks, C.M. et al. (Sep. 19, 1997). "Structural Basis for Cyclic Terpene Biosynthesis by Tobacco 5-Epi-Aristolochene Synthase," *Science* 277:1815-1820.

Staub, J. M. et al. (1995). "Expression of a Chimeric *uid* A Gene Indicates that Polycistronic mRNAs are Efficiently Translated in Tobacco Plastids," *The Plant Journal* 7(5):845-848.

Staub, J. M. et al. (Mar. 2000). "High-Yield Production of a Human Therapeutic Protein in Tobacco Chloroplast," *Nature Biotechnology* 18:333-338.

Steinbuchel, A. (2003). "Production of Rubber-Like Polymers by Microorganisms," *Current Opinion in Microbiology* 6:261-270.

Steller, I. et al. (1997). "An Algorithm for Automatic Indexing of Oscillation Images using Fourier Analysis," *Journal of Applied Crystallography* 30:1036.1040.

Stermer, B.A. et al. (1994). "Regulation of HMG-CoA Reductase Activity in Plants," *Journal of Lipid Research* 35:1133-1140.

Stevens, D.R. et al. (1997). "Genetic Engineering of Eukaryotic Algae: Progress and Prospects," *J. Phycol.* 33:713-722.

Sulter, G.J. et al. (1990). "Proliferation and Metabolic Significance of Peroxisomes in *Candida boidinii* During Growth on D-Alanine or Oleic Acid as the Sole Carbon Source," *Arch. Microbiol.* 153:485-489.

Sutherlin, A. et al. (Aug. 2002). "*Enterococcus faecalis* 3-Hydroxy-3-Methylglutaryl Coenzyme A Synthase, an Enzyme of Isopentenyl Diphosphate Biosynthesis," *Journal of Bacteriology* 184(15):4065-4070.

Takagi, M. et al. (Aug. 2000). "A Gene Cluster for the Mevalonate Pathway from *Streptomyces* sp. Strain CL190," *Journal of Bacteriology* 182(15):4153-4157.

Takahashi, S. et al. (Feb. 1999). "Purification, Characterization, and Cloning of a Eubacterial 3-Hydroxy-3-Methylglutaryl Coenzyme A Reductase, a Key Enzyme Involved in Biosynthesis of Terpenoids," *Journal of Bacteriology* 181(4):1256-1263.

Takara Bio Inc. (Feb. 2008). "Chaperon Plasmid Set," Cat. # 3340, pp. 1-8.

Teymouri, F. et al. (2005, e-pub. Feb. 24, 2005). "Optimization of the Ammonia Fiber Explosion (AFEX) Treatment Parameters for Enzymatic Hydrolysis of Corn Stover," *Bioresource Technology* 96:2014-2018.

Thomas, F. et al. (1988). "Expression of the *rpl23*, *rpl2* and *rps19* Genes in Spinach Chloroplasts," *Nucleic Acids Research* 16(6):2461-2472.

Thomason, L.C. et al. (2007, e-pub. Apr. 16, 2007). "Multicopy Plasmid Modification with Phage A Red Recombineering," *Plasmid* 58:148-158.

Thouvenot, B. et al. (2004). "The Strong Efficiency of the *Escherichia coli gapA* P1 Promoter Depends on a Complex Combination of Functional Determinants," *Biochem. J.* 383:371-382.

Timberlake, W.E. (1991). "Gene Cloning and Analysis" in Chapter 3 in More Gene Manipulations in Fungi, Bennett et al. eds., Academic Press: San Diego, CA, pp. 70-76.

Toriyama, K. et al. (1985). "Cell Suspension and Protoplast Culture in Rice," *Plant Science* 41:179-183.

Tsay, Y.H. et al. (Feb. 1991). "Cloning and Characterization of *ERG8*, an Essential Gene of *Saccharomyces cerevisiae* That Encodes Phosphomevalonate Kinase," *Molecular and Cellular Biology* 11(2):620-631.

Tsudsuki, T. (Apr. 24, 1988) "Direct submission, bases 1-155939", Data Processing Center, 1998, Aichi-Gakuin University, Aixhi, Japan, 12 pages.

UniProt Database Accession No. A2XGY9, located at <http://www.uniprot.org/uniprot/A2XGY9.txt>, last visited on Aug. 25, 2015, 2 pages.

UniProt Database Accession No. A5AR04, located at <http://www.uniprot.org/uniprot/A5AR04.txt, last visited on Aug. 25, 2015, 2 pages.

UniProt Database Accession No. A5B7V4, located at <http://www.uniprot.org/uniprot/A5B7V4.txt, last visited on Aug. 25, 2015, 2 pages.

UniProt Database Accession No. A5BKK1, located at < http://www.uniprot.org/uniprot/A5BKK1.txt>, last visited on Aug. 25, 2015, 2 pages.

UniProt Database Accession No. A5BLS5, located at < http://www.uniprot.org/uniprot/A5BLS5.txt, last visited on Aug. 25, 2015, 2 pages.

UniProt Database Accession No. A9PGR5, located at <http://www.uniprot.org/uniprot/A9PGR5.txt>, last visited on Aug. 25, 2015 1 page.

UniProt Database Accession No. B1 P189, last updated Jul. 27, 2011, located at <http://www.uniprotorgiobs/201109112CDIFX17BK.txt>, last visited on Sep. 11, 2011, 1 page.

UniProt Database Accession No. B3GEM8, located at <http://www.uniprot.org/uniprot/B3GEM8.txt>, last visited on Aug. 25, 2015, 1 page.

UniProt Database Accession No. B3TPQ7, located at < http://www.uniprot.org/uniprot/B3TPQ7.txt>, last visited Aug. 25, 2015, 2 pages.

UniProt Database Accession No. B7FLI6, last updated Jul. 27, 2011, located at <http://www.uniprotorg/jobs/20110911315BAXCRQU.txt>, last visited on Sep. 11, 2011, 1 page.

UniProt Database Accession No. B9HE95, located at <http://www.uniprot.org/uniprot/B9HE95.txt, last visited on Aug. 25, 2015, 2 pages.

UniProt Database Accession No. B9MXU1, last updated Jul. 27, 2011, located at < http://www.uniprotorg/jobs/201109112CDIFV8DIC.txt>, last visited on Sep. 11, 2011, 2 pages.

UniProt Database Accession No. B9PAP5, last updated Jul. 27, 2011, located at <http://www.uniprotorg/jobs/201109112CDIG1HNFH.txt>, last visited on Sep. 11, 2011, 2 pages.

(56) References Cited

OTHER PUBLICATIONS

UniProt Database Accession No. B9RPM0, located at < http://www.uniprot.org/uniprot/B9RPM0.txt>, last visited Aug. 25, 2015, 2 pages.
UniProt Database Accession No. B9T537, last updated Nov. 30, 2010, located at <http://www.uniprotorg/jobs/20110911315BB065GR.txt>, last visited on Sep. 11, 2011, 1 page.
UniProt Database Accession No. B9T825, located at <http://www.uniprot.org/uniprot/B9T825.txt>, last visited on Aug. 25, 2015, 2 pages.
UniProt Database Accession No. Q0PCI3, last updated Jul. 27, 2011, located at <http://www.uniprotorg/jobs/20110911315BAPL92C.txt>, last visited on Sep. 11, 2011, 1 page.
UniProt Database Accession No. Q0PCI4, last updated Jul. 27, 2011, located at <http://www.uniprotorg/jobs/20110911315BAQURQ8.txt>, last visited on Sep. 11, 2011, 1 page.
UniProt Database Accession No. Q50L36, located at <http://www.uniprot.org/uniprot/Q50L36.txt, last visited on Aug. 25, 2015, 2 pages.
UniProt Database Accession No. Q5SBP1, located at <http://www.uniprot.org/uniprot/Q5SBP1.txt, last visited on Aug. 25, 2015, 2 pages.
UniProt Database Accession No. Q5SBP2, located at <http://www.uniprot.org/uniprot/Q5SBP2.1xt>, last visited on Aug. 25, 2015, 2 pages.
UniProt Database Accession No. Q5SBP4, located at < http://www.uniprot.org/uniprot/Q5SBP4.txt>, last visited on Aug. 25, 2015, 2 pages.
UniProt Database Accession No. Q5UB07, located at < http://www.uniprot.org/uniprot/Q5UB07.txt>, last visited on Aug. 25, 2015, 3 pages.
UniProt Database Accession No. Q672F7, located at < http://www.uniprot.org/uniprot/Q672F7.txt>, last visited on Aug. 25, 2015, 2 pages.
UniProt Database Accession No. Q6EJ97, located at < http://www.uniprot.org/uniprot/Q6EJ97.txt>, last visited on Aug. 25, 2015, 2 pages.
UniProt Database Accession No. Q6PWU1, located at < http://www.uniprot.org/uniprot/Q6PWU2.txt>, last visited on Aug. 25, 2015, 2 pages.
UniProt Database Accession No. Q7Y1V1, located at < http://www.uniprot.org/uniprot/Q7Y1V1.txt>, last visited on Aug. 25, 2015, 1 page.
UniProt Database Accession No. Q941 H1, last updated Jul. 27, 2011, located at <http://www.uniprotorg/jobs/201109112CDIG6PW6Y.txt>, last visited on Sep. 11, 2011, 1 page.
UniProt Database Accession No. Q9AR86, located at < http://www.uniprotorg/uniprot/Q9AR86.txt>, last visited on Aug. 25, 2015 2 pages.
UniProt Database Accession No. Q9LIA1; Q84UU7, located at < http://www.uniprot.org/uniprot/Q9LIA1.txt>, last visited on Aug. 25, 2015, 3 pages.
UniProt Database Accession No. Q9LRZ6, located at < http://www.uniprot.org/uniprot/Q9LRZ6.txt>, last visited on Aug. 25, 2015, 3 pages.
UniProt Database Accession No. Q7XAS7, located at <http://www.uniprot.org/uniprot/Q7XAS7.txt>, last visited on Aug. 25, 2015, 2 pages.
UniProt Database Accession No. Q9FQ26, located at <http://www.uniprot.org/uniprot/Q9FQ26.txt>, last visited on Aug. 25, 2015, 1 page.
Vadali, R.V. et al. (2005, e-pub. Sep. 2, 2005). "Enhanced Lycopene Productivity by Manipulation of Carbon Flow to Isopentenyl Diphosphate in *Escherichia coli*," *Biotechnol. Prog.* 21(5):1558-1561.
Vagin, A. et al. (1997). "*MOLREP*: An Automated Program for Molecular Replacement," *Journal of Applied Crystallography* 30:1022-1025.
Vandamme, E.J. et al. (2002, e-pub. 2002). "Bioflavours and Fragrances via Fermentation and Biocatalysis," *Journal of Chemical Technology and Biotechnology* 77:1323-1332.
Van Den Hondel, C.A.M.J.J. et al. (1991). "Heterologous Gene Expression in Filamentous Fungi," Chapter 18 in More Gene Manipulations in Fungi, Bennett, J.W. et al. eds., Academic Press, Inc.: San Diego, CA, pp. 396-428.
Van De Walle, M. et al. (Jan. 5, 1998). "Proposed Mechanism of Acetate Accumulation in Two Recombinant *Escherichia coli* Strains During High Density Fermentation," *Biotechnology and Bioengineering* 57(1):71-78.
Van Hylckama, J.E.T. et al. (Apr. 2000). "Characterization of the Gene Cluster Involved in Isoprene Metabolism in *Rhodococcus* sp. Strain AD45," *Journal of Bacteriology* 182(7):1956-1963.
Vane, L.M. (2005, e-pub. Apr. 21, 2005). "A Review of Pervaporation for Product Recovery from Biomass Fermentation Processes," *Journal of Chemical Technology and Biotechnology* 80:603-629.
Velikova, V. et al. (2005). "Consequences of Inhibition of Isoprene Synthesis in *Phragmites australis* Leaves Exposed to Elevated Temperatures," *Agriculture, Ecosystems & Environment* 106:209-217.
Vidal, M. et al. (2006, e-pub. Nov. 23, 2005). "Evaluation of Lower Flammability Limits of Fuel-Air-Diluent Mixtures Using Calculated Adiabatic Flame Temperatures," *Journal of Hazardous Materials* 130:21-27.
Voss, S. et al. (1997). "Mutagenesis of a Flexible Loop in Streptavidin Leads to Higher Affinity for the *Strep-tag* II Peptide and Improved Performance in Recombinant Protein Purification," *Protein Engineering* 10(8):975-982.
Voynova, N.E. et al. (Jan. 2004). "*Staphylococcus aureus* Mevalonate Kinase: Isolation and Characterization of an Enzyme of the Isoprenoid Biosyntheitc Pathway," *Journal of Bacteriology* 186(1):61-67.
Wagner, W.P. et al. (Aug. 1999). "Three Distinct Phases of Isoprene Formation During Growth and Sporulation of *Bacillus subtilis,*" *Journal of Bacteriology* 181(15):4700-4703.
Wagner, W.P. et al. (Jan. 2000, e-pub. Nov. 18, 1999). "Isoprene Biosynthesis in *Bacillus subtilis* Via the Methylerythritol Phosphate Pathway," *J. Nat. Prod.* 63(1):37-40.
Wang, C-W. et al. (Jan. 20, 1999). "Engineered Isoprenoid Pathway Enhances Astaxanthin Production in *Escherichia coli,*" *Biotechnology and Bioengineering* 62(2):235-241.
Ward, M. et al. (Aug. 1993). "Use of *Aspergillus* Overproducing Mutants, Cured for Integrated Plasm id, to Overproduce Heterologous Proteins," *Appl. Microbiol. Biotechnol.* 39(6):738-743.
Weissermel, K. et al. (2003). Industrial Organic Chemistry, 4$^{th}$, Completely Revised Edition, translated by Lindley, C.R. et al., Wiley-VCH GmbH & Co. KGaA, Weinheim, Germany, pp. 117-222.
Whisstock, J.C. et al. (2003). "Prediction of Protein Function from Protein Sequence and Structure," *Quarterly Reviews of Biophysics* 36(3):307-340.
Whittington, D.A. et al. (Nov. 26, 2002). "Bornyl Diphosphate Synthase: Structure and Strategy for Carbocation Manipulation by a Terpenoid Cyclase," *PNAS* 99(24):15375-15380.
Wildermuth, M.C. et al. (1998). "Biochemical Characterization of Stromal and Thylakoid-Bound Isoforms of Isoprene Synthase in Willow Leaves," *Plant Physiology* 116:1111-1123.
Wilding, E.I. et al. (Aug. 2000). "Identification, Evolution, and Essentiality of the Mevalonate Pathway for Isopentenyl Diphosphate Biosynthesis in Gram-Positive Cocci," *Journal of Bacteriology* 182(15):4319-4327.
Wilkins, K. (1996). "Volatile Metabolites from Actinomycetes," *Chemosphere* 32(7):1427-1434.
Williams, D.C. et al. (1998). "Truncation of Limonene Synthase Preprotein Provides a Fully Active 'Pseudomature' Form of This Monoterpene Cyclase and Reveals the Function of the Amino-Terminal Arginine Pair," *Biochemistry* 37(35):12213-12220.
Wishart, M.J. et al. (Nov. 10, 1995). "A Single Mutation Converts a Novel Phosphotyrosine Binding Domain into a Dual-Specificity Phosphatase," *The Journal of Biological Chemistry* 270(45):26782-26785.

(56) References Cited

OTHER PUBLICATIONS

Withers, S.T. et al. (Oct. 2007, e-pub. Aug. 10, 2007). "Identification of Isopentenol Biosynthetic Genes from *Bacillus subtilis* by a Screening Method Based on Isoprenoid Precursor Toxicity," *Applied and Environmental Microbiology* 73(19):6277-6283.

Witkowski, A. et al. (1999, e-pub. Aug. 18, 1999). "Conversion of p-Ketoacyl Synthase to a Malonyl Decarboxylase by Replacement of the Active-Site Cysteine with Glutamine," *Biochemistry* 38(36):11643-11650.

Wolfertz, M. et al. (2003). "Biochemical Regulation of Isoprene Emission," *Plant, Cell and Environment* 26:1357-1364.

Wolfertz, M. et al. (Aug. 2004). "Rapid Regulation of the Methylerythritol 4-Phosphate Pathway During Isoprene Synthesis," *Plant Physiology* 135:1939-1945.

Wu, D.Y. et al. (1989). "The Ligation Amplification Reaction (LAR)-Amplification of Specific DNA Sequences Using Sequential Rounds of Template-Dependent Ligation," *Genomics* 4:560-569.

Xia, X-X. et al. (2008). "Comparison of the Extracellular Proteomes of *Escherichia coli* B and K-12 Strains During High Cell Density Cultivation," *Proteomics* 8:1-15.

Yamada, K. et al. (1989). "Production of Glycerol from Methanol by a Mutant Strain of *Candida boidinii* No. 2201," *Agric. Biol. Chem.* 53(2):541-543.

Yang, D. et al. (Mar. 15, 2002, published ahead of print Dec. 19, 2001). "Structure of the *Methanococcus jannaschii* Mevalonate Kinase, a Member of the GHMP Kinase Superfamily," *The Journal of Biological Chemistry* 277(11):9462-9467.

Ye, X. et al. (Jan. 14, 2000). "Engineering the Provitamin A ((3-Carotene) Biosynthetic Pathway into (Carotenoid-Free) Rice Endosperm," *Science* 287:303-305.

Yelton, M.M. et al. (Mar. 1984). "Transformation of *Aspergillus nidulans* by Using a *trpC* Plasmid," *Proc. Natl. Acad. Sci. USA* 81:1470-1474.

Yoon, S-H. et al. (2007, e-pub. May 15, 2007). "Increased /3-Carotene Production in Recombinant *Escherichia coli* Harboring an Engineered Isoprenoid Precursor Pathway with Mevalonate Addition," *Biotechnol. Prog.* 23(3):599-605.

Yoon, S-H. et al. (2009). "Combinatorial Expression of Bacterial Whole Mevalonate Pathway for the Production of I3-Carotene in *E. coli*," *Journal of Biotechnology* 140:218-226.

Zepeck, F. et al. (2005, e-pub. Oct. 14, 2005). "Biosynthesis of Isoprenoids. Purification and Properties of IspG Protein from *Escherichia coli*," *J. Org. Chem.* 70:9168-9174.

FIG. 1

1-
atgtgtgcgacctcttctcaatttactcagattaccgagcataattcccgtcgttccgcaaact
atcagccaaacctgtggaatttcgaattcctgcaatccctggagaacgacctgaaagtggaaaa
gctggaggagaaagcgaccaaactggaggaagaagttcgctgcatgatcaaccgtgtagacacc
cagccgctgtccctgctggagctgatcgacgatgtgcagcgcctgggtctgacctacaaatttg
aaaaagacatcattaaagccctggaaaacatcgtactgctggacgaaaacaaaaagaacaaatc
tgacctgcacgcaaccgctctgtctttccgtctgctgcgtcagcacggtttcgaggtttctcag
gatgtttttgagcgtttcaaggataaagaaggtggtttcagcggtgaactgaaaggtgacgtcc
aaggcctgctgagcctgtatgaagcgtcttacctgggtttcgagggtgagaacctgctggagga
ggcgcgtaccttttccatcacccacctgaagaacaacctgaaagaaggcattaataccaaggtt
gcagaacaagtgagccacgccctggaactgccatatcaccagcgtctgcaccgtctggaggcac
gttggttcctggataaatacgaaccgaaagaaccgcatcaccagctgctgctggagctggcgaa
gctggattttaacatggtacagaccctgcaccagaaagagctgcaagatctgtcccgctggtgg
accgagatgggcctggctagcaaactggattttgtacgcgaccgcctgatggaagtttatttct
gggcactgggtatggcgccagaccgcagtttggtgaatgtcgcaaagctgttactaaaatgtt
tggtctggtgacgatcatcgatgacgtgatgacgtttatggcactctggacgaactgcaactg
ttcaccgatgctgtagagcgctgggacgttaacgctattaacaccctgccggactatatgaaac
tgtgtttcctggcactgtacaacaccgttaacgacacgtcctattctattctgaaagagaaagg
tcataacaacctgtcctatctgacgaaaagctggcgtgaactgtgcaaagcctttctgcaagag
gcgaaatggtccaacaacaaaattatcccggctttctccaagtacctggaaaacgccagcgttt
cctcctccggtgtagcgctgctggcgccgtcttacttttcgtatgccagcagcaggaagacat
ctccgaccacgcgctgcgttccctgaccgacttccatggtctggtgcgttctagctgcgttatc
ttccgcctgtcaacgatctggccacctctgcggcggagctggaacgtggcgagactaccaatt
ctatcattagctacatgcacgaaaacgatggtaccagcgaggaacaggcccgcgaagaactgcg
taaactgatcgacgccgaatggaaaaagatgaatcgtgaacgcgttagcgactccaccctgctg
cctaaagcgttcatggaaatcgcagttaacatggcacgtgtttcccactgcacctaccagtatg
gcgatggtctgggtcgcccagactacgcgactgaaaaccgcatcaaactgctgctgattgaccc
tttccgattaaccagctgatgtatgtc
taactgcag
(SEQ ID NO:1)

FIG. 3A 1-
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaagcgaagcggcactgctctttaacaatttatcagacaatctgt
gtgggcactcgaccggaattatcgattaactttattattaaaaattaagaggtatatattaat
gtatcgattaaataaggaggaataaaccATGtgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacacccagccgctgtcctgctggagctgatcgacgatgtg
cagcgcctgggtctgacctacaaatttgaaaagacatcattaaagccctggaaaacatcgtac
tgctggacgaaaacaaaagaacaaatctgacctgcacgcaaccgctctgtctttccgtctgct
gcgtcagcacggtttcgaggtttctcaggatgttttgagcgtttcaggataaagaaggtggt
ttcagcggtgaactgaaaggtgacgtccaaggcctgctgagcctgtatgaagcgtcttacctgg
gtttcgagggtgagaacctgctggaggaggcgcgtaccttttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggatttttgta
cgcgaccgcctgatggaagtttatttctgggcactgggtatggcgccagacccgcagtttggtg
aatgtcgcaaagctgttactaaaatgtttggtctggtgacgatcatcgatgacgtgtatgacgt
ttatggcactctggacgaactgcaactgttcaccgatgctgtagagcgctgggacgttaacgct
attaacaccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggctttc
tccaagtacctggaaaacgccagcgtttcctcctccggtgtagcgctgctggcgccgtcttact
tttccgtatgccagcagcaggaagacatctccgaccacgcgctgcgttccctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccgaatggaaaagatgaatcg
tgaacgcgttagcgactccaccctgctgcctaaagcgttcatggaaatcgcagttaacatggca
cgtgtttccactgcacctaccagtatggcgatggtctgggtcgcccagactacgcgactgaaa
accgcatcaaactgctgctgattgacccttccgattaaccagctgatgtatgtcTAActgca
gctggtaccatatgggaattcgaagctttctagaacaaaaactcatctcagaagaggatctgaa
tagcgccgtcgaccatcatcatcatcattgagtttaaacggtctccagcttggctgttttg
gcggatgagagaagattttcagcctgatacagattaaatcagaacgcagaagcggtctgataaa
acagaatttgcctggcggcagtagcgcggtggtcccacctgaccccatgccgaactcagaagtg
aaacgccgtagcgccgatggtagtgtgggtctccccatgcgagagtagggaactgccaggcat
caaataaaacgaaaggctcagtcgaaagactgggcctttcgttttatctgttgtttgtcggtga
acgctctcctgagtaggacaaatccgccgggagcggatttgaacgttgcgaagcaacggcccgg

FIG. 3B

```
agggtggcgggcaggacgcccgccataaactgccaggcatcaaattaagcagaaggccatcctg
acggatggccttttttgcgtttctacaaactcttttttgtttatttttctaaatacattcaaatat
gtatccgctcatgagacaataaccctgataaatgcttcaataatattgaaaaaggaagagtatg
agtattcaacatttccgtgtcgcccttattccctttttttgcggcattttgccttcctgttttttg
ctcacccagaaacgctggtgaaagtaaaagatgctgaagatcagttgggtgcacgagtgggtta
catcgaactggatctcaacagcggtaagatccttgagagttttcgccccgaagaacgttttcca
atgatgagcacttttaaagttctgctatgtggcgcggtattatcccgtgttgacgccgggcaag
agcaactcggtcgccgcatacactattctcagaatgacttggttgagtactccagtcacaga
aaagcatcttacggatggcatgacagtaagagaattatgcagtgctgccataaccatgagtgat
aacactgcggccaacttacttctgacaacgatcggaggaccgaaggagctaaccgcttttttgc
acaacatgggggatcatgtaactcgccttgatcgttgggaaccggagctgaatgaagccatacc
aaacgacgagcgtgacaccacgatgcctgtagcaatggcaacaacgttgcgcaaactattaact
ggcgaactacttactctagcttccggcaacaattaatagactggatggaggcggataaagttg
caggaccacttctgcgctcggcccttccggctggctggtttattgctgataaatctggagccgg
tgagcgtgggtctcgcggtatcattgcagcactggggccagatggtaagccctcccgtatcgta
gttatctacacgacggggagtcaggcaactatggatgaacgaaatagacagatcgctgagatag
gtgcctcactgattaagcattggtaactgtcagaccaagtttactcatatatactttagattga
tttaaaacttcatttttaatttaaaaggatctaggtgaagatcctttttgataatctcatgacc
aaaatcccttaacgtgagttttcgttccactgagcgtcagaccccgtagaaaagatcaaaggat
cttcttgagatccttttttttctgcgcgtaatctgctgcttgcaaacaaaaaaaccaccgctacc
agcggtggtttgtttgccggatcaagagctaccaactctttttccgaaggtaactggcttcagc
agagcgcagataccaaatactgtccttctagtgtagccgtagttaggccaccacttcaagaact
ctgtagcaccgcctacatacctcgctctgctaatcctgttaccagtggctgctgccagtggcga
taagtcgtgtcttaccgggttggactcaagacgatagttaccggataaggcgcagcggtcgggc
tgaacggggggttcgtgcacacagcccagcttggagcgaacgacctacaccgaactgagatacc
tacagcgtgagctatgagaaagcgccacgcttcccgaagggagaaaggcggacaggtatccggt
aagcggcagggtcggaacaggagagcgcacgagggagcttccaggggaaacgcctggtatctt
tatagtcctgtcgggtttcgccacctctgacttgagcgtcgatttttgtgatgctcgtcagggg
ggcggagcctatggaaaaacgccagcaacgcggcctttttacggttcctggccttttgctggcc
ttttgctcacatgttctttcctgcgttatcccctgattctgtggataaccgtattaccgccttt
gagtgagctgataccgctcgccgcagccgaacgaccgagcgcagcgagtcagtgagcgaggaag
cggaagagcgcctgatgcggtattttctccttacgcatctgtgcggtatttcacaccgcatatg
gtgcactctcagtacaatctgctctgatgccgcatagttaagccagtatacactccgctatcgc
tacgtgactgggtcatggctgcgccccgacacccgccaacacccgctgacgcgccctgacgggc
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaacctttcgcggtatggcatgatagcgc
ccggaagagagtcaattcaggtggtgaatgtgaaaccagtaacgttatacgatgtcgcagagt
atgccggtgtctcttatcagaccgtttccgcgtggtgaaccaggccagccacgtttctgcgaa
aacgcgggaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct
```

FIG. 3C

Gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggcccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatcccgccgtcaaccaccat
caaacaggattttcgcctgctggggcaaaccagcgtggaccgcttgctgcaactctctcagggc
caggcggtgaagggcaatcagctgttgcccgtctcactggtgaaaagaaaaaccacctggcgc
ccaatacgcaaaccgcctctccccgcgcgttggccgattcattaatgcagctggcacgacaggt
ttcccgactggaaagcgggcagtgagcgcaacgcaattaatgtgagttagcgcgaattgatctg
(SEQ ID NO:2)

FIG. 5A

1-
ttctcatgtttgacagcttatcatcgataagctttaatgcggtagtttatcacagttaaattgc
taacgcagtcaggcaccgtgtatgaaatctaacaatgcgctcatcgtcatcctcggcaccgtca
ccctggatgctgtaggcataggcttggttatgccggtactgccgggcctcttgcgggatatccg
gatatagttcctcctttcagcaaaaaaccctcaagacccgtttagaggccccaaggggttatg
ctagttattgctcagcggtggcagcagccaactcagcttcctttcgggctttgttagcagccgg
atccctgcagttagacatacatcagctggttaatcgggaaagggtcaatcagcagcagtttgat
gcggttttcagtcgcgtagtctgggcgacccagaccatcgccatactggtaggtgcagtgggaa
acacgtgccatgttaactgcgatttccatgaacgcttaggcagcagggtggagtcgctaacgc
gttcacgattcatcttttccattcggcgtcgatcagtttacgcagttcttcgcgggcctgttc
ctcgctggtaccatcgttttcgtgcatgtagctaatgatagaattggtagtctcgccacgttcc
agctccgccgcagaggtggccagatcgttgcacaggcggaagataacgcagctagaacgcacca
gaccatggaagtcggtcagggaacgcagcgcgtggtcggagatgtcttcctgctgctggcatac
ggaaaagtaagacggcgccagcagcgctacaccggaggaggaaacgctggcgttttccaggtac
ttggagaaagccgggataattttgttgttggaccatttcgcctcttgcagaaaggctttgcaca
gttcacgccagcttttcgtcagataggacaggttgttatgacctttctctttcagaatagaata
ggacgtgtcgttaacggtgttgtacagtgccaggaaacacagtttcatatagtccggcagggtg
ttaatagcgttaacgtcccagcgctctacagcatcggtgaacagttgcagttcgtccagagtgc
cataaacgtcatacacgtcatcgatgatcgtcaccagaccaaacatttagtaacagctttgcg
acattcaccaaactgcgggtctggcgccatacccagtgcccagaaataaacttccatcaggcgg
tcgcgtacaaaatccagtttgctagccaggccatctcggtccaccagcgggacagatcttgca
gctctttctggtcagggtctgtaccatgttaaaatccagcttcgccagctccagcagcagctg
gtgatgcggttctttcggttcgtatttatccaggaaccaacgtgcctccagacggtgcagacgc
tggtgatatggcagttccagggcgtggctcacttgttctgcaaccttggtattaatgccttctt
tcaggttgttcttcaggtgggtgatggaaaaggtacgcgcctcctccagcaggttctcaccctc
gaaacccaggtaagacgcttcatacaggctcagcaggccttggacgtcacctttcagttcaccg
ctgaaaccaccttctttatccttgaaacgctcaaaaacatcctgagaaacctcgaaaccgtgct
gacgcagcagacggaaagacagagcggttgcgtgcaggtcagatttgttcttttttgttttcgtc
cagcagtacgatgttttccagggctttaatgatgtcttttttcaaatttgtaggtcagacccagg
cgctgcacatcgtcgatcagctccagcagggacagcggctgggtgtctacacggttgatcatgc
agcgaacttcttcctccagtttggtcgctttctcctccagcttttccactttcaggtcgttctc
cagggattgcaggaattcgaaattccacaggtttggctgatagtttgcggaacgacgggaatta
tgctcggtaatctgagtaaattgagaagaggtcgcacacatatgacgaccttcgatatggccgc
tgctgtgatgatgatgatgatgatgatgatgatgccatggtatatctccttcttaaagttaa
acaaaattatttctagagggaattgttatccgctcacaattcccctatagtgagtcgtattaa
tttcgcgggatcgagatctcgatcctctacgccggacgcatcgtggccggcatcaccggcgcca
caggtgcggttgctggcgcctatatcgccgacatcaccgatggggaagatcgggctcgccactt
cgggctcatgagcgcttgtttcggcgtgggtatggtggcaggccccgtggccgggggactgttg
ggcgccatctccttgcatgcaccattccttgcggcggcggtgctcaacggcctcaacctactac
tgggctgcttcctaatgcaggagtcgcataagggagagcgtcgagatcccggacaccatcgaat
ggcgcaaaaccttcgcggtatggcatgatagcgcccggaagagagtcaattcaggtggtgaa
tgtgaaaccagtaacgttatacgatgtcgcagagtatgccggtgtctcttatcagaccgtttcc
cgcgtggtgaaccaggccagccacgtttctgcgaaaacgcgggaaaaagtggaagcggcgatgg
cggagctgaattacattcccaaccgcgtggcacaacaactggcgggcaaacagtcgttgctgat
tggcgttgccacctccagtctggccctgcacgcgccgtcgcaaattgtcgcggcgattaaatct

FIG. 5B

```
cgcgccgatcaactgggtgccagcgtggtggtgtcgatggtagaacgaagcggcgtcgaagcct
gtaaagcggcggtgcacaatcttctcgcgcaacgcgtcagtgggctgatcattaactatccgct
ggatgaccaggatgccattgctgtggaagctgcctgcactaatgttccggcgttatttcttgat
gtctctgaccagacacccatcaacagtattattttctcccatgaagacggtacgcgactgggcg
tggagcatctggtcgcattgggtcaccagcaaatcgcgctgttagcgggcccattaagttctgt
ctcggcgcgtctgcgtctggctggctggcataaatatctcactcgcaatcaaattcagccgata
gcggaacgggaaggcgactggagtgccatgtccggttttcaacaaaccatgcaaatgctgaatg
agggcatcgttcccactgcgatgctggttgccaacgatcagatggcgctgggcgcaatgcgcgc
cattaccgagtccgggctgcgcgttggtgcggatatctcggtagtgggatacgacgataccgaa
gacagctcatgttatatcccgccgttaaccaccatcaaacaggattttcgcctgctggggcaaa
ccagcgtggaccgcttgctgcaactctctcagggccaggcggtgaagggcaatcagctgttgcc
cgtctcactggtgaaaagaaaaaccaccctggcgcccaatacgcaaaccgcctctcccgcgcg
ttggccgattcattaatgcagctggcacgacaggtttcccgactggaaagcgggcagtgagcgc
aacgcaattaatgtaagttagctcactcattaggcaccgggatctcgaccgatgcccttgagag
ccttcaacccagtcagctccttccggtgggcgcggggcatgactatcgtcgccgcacttatgac
tgtcttctttatcatgcaactcgtaggacaggtgccggcagcgctctgggtcattttcggcgag
gaccgctttcgctggagcgcgacgatgatcggcctgtcgcttgcggtattcggaatcttgcacg
ccctcgctcaagcttcgtcactggtcccgccaccaaacgtttcggcgagaagcaggccattat
cgccggcatggcggccgacgcgctgggctacgtcttgctggcgttcgcgacgcgaggctggatg
gccttcccattatgattcttctcgcttccggcggcatcgggatgcccgcgttgcaggccatgc
tgtccaggcaggtagatgacgaccatcagggacagcttcaaggatcgctcgcggctcttaccag
cctaacttcgatcactggaccgctgatcgtcacggcgatttatgccgcctcggcgagcacatgg
aacgggttggcatggattgtaggcgccgcctataccttgtctgcctccccgcgttgcgtcgcg
gtgcatggagccgggccacctcgacctgaatggaagccggcggcacctcgctaacggattcacc
actccaagaattggagccaatcaattcttgcggagaactgtgaatgcgcaaaccaacccttggc
agaacatatccatcgcgtccgccatctccagcagccgcacgcggcgcatctcgggcagcgttgg
gtcctggccacgggtgcgcatgatcgtgctcctgtcgttgaggacccggctaggctggcggggt
tgccttactggttagcagaatgaatcaccgatacgcgagcgaacgtgaagcgactgctgctgca
aaacgtctgcgacctgagcaacaacatgaatggtcttcggtttccgtgtttcgtaaagtctgga
aacgcggaagtcagcgccctgcaccattatgttccggatctgcatcgcaggatgctgctggcta
ccctgtggaacacctacatctgtattaacgaagcgctggcattgaccctgagtgattttctct
ggtcccgccgcatccataccgccagttgtttaccctcacaacgttccagtaaccgggcatgttc
atcatcagtaaccgtatcgtgagcatcctctctcgtttcatcggtatcattaccccatgaac
agaaatccccttacacggaggcatcagtgaccaaacaggaaaaaaccgcccttaacatggccc
gctttatcagaagccagacattaacgcttctggagaaactcaacgagctggacgcggatgaaca
ggcagacatctgtgaatcgcttcacgaccacgctgatgagctttaccgcagctgcctcgcgcgt
ttcggtgatgacggtgaaaacctctgacacatgcagctcccggagacggtcacagcttgtctgt
aagcggatgccgggagcagacaagcccgtcagggcgcgtcagcgggtgttggcgggtgtcgggg
cgcagccatgacccagtcacgtagcgatagcggagtgtatactggcttaactatgcggcatcag
agcagattgtactgagagtgcaccatatatgcggtgtgaaataccgcacagatgcgtaaggaga
aaataccgcatcaggcgctcttccgcttcctcgctcactgactcgctgcgctcggtcgttcggc
tgcggcgagcggtatcagctcactcaaaggcggtaatacggttatccacagaatcaggggataa
cgcaggaaagaacatgtgagcaaaaggccagcaaaaggccaggaaccgtaaaaaggccgcgttg
ctggcgttttccataggctccgcccccctgacgagcatcacaaaaatcgacgctcaagtcaga
```

FIG. 5C ggtggcgaaacccgacaggactataaagataccaggcgtttccccctggaagctccctcgtgcg
ctctcctgttccgaccctgccgcttaccggatacctgtccgccttttctcccttcgggaagcgtg
gcgctttctcatagctcacgctgtaggtatctcagttcggtgtaggtcgttcgctccaagctgg
gctgtgtgcacgaaccccccgttcagcccgaccgctgcgccttatccggtaactatcgtcttga
gtccaacccggtaagacacgacttatcgccactggcagcagccactggtaacaggattagcaga
gcgaggtatgtaggcggtgctacagagttcttgaagtggtggcctaactacggctacactagaa
ggacagtatttggtatctgcgctctgctgaagccagttaccttcggaaaaagagttggtagctc
ttgatccggcaaacaaaccaccgctggtagcggtggttttttgtttgcaagcagcagattacg
cgcagaaaaaaggatctcaagaagatcctttgatcttttctacggggtctgacgctcagtgga
acgaaaactcacgttaagggattttggtcatgagattatcaaaaaggatcttcacctagatcct
tttaaattaaaaatgaagttttaaatcaatctaaagtatatatgagtaaacttggtctgacagt
taccaatgcttaatcagtgaggcacctatctcagcgatctgtctatttcgttcatccatagttg
cctgactccccgtcgtgtagataactacgatacgggagggcttaccatctggccccagtgctgc
aatgataccgcgagacccacgctcaccggctccagatttatcagcaataaaccagccagccgga
agggccgagcgcagaagtggtcctgcaactttatccgcctccatccagtctattaattgttgcc
gggaagctagagtaagtagttcgccagttaatagtttgcgcaacgttgttgccattgctgcagg
catcgtggtgtcacgctcgtcgtttggtatggcttcattcagctccggttcccaacgatcaagg
cgagttacatgatccccatgttgtgcaaaaagcggttagctccttcggtcctccgatcgttg
tcagaagtaagttggccgcagtgttatcactcatggttatgcagcactgcataattctcttac
tgtcatgccatccgtaagatgcttttctgtgactggtgagtactcaaccaagtcattctgagaa
tagtgtatgcggcgaccgagttgctcttgcccggcgtcaacacgggataataccgcgccacata
gcagaactttaaaagtgctcatcattggaaaacgttcttcggggcgaaaactctcaaggatctt
accgctgttgagatccagttcgatgtaacccactcgtgcacccaactgatcttcagcatcttt
actttcaccagcgtttctgggtgagcaaaaacaggaaggcaaaatgccgcaaaaaagggaataa
gggcgacacggaaatgttgaatactcatactcttcctttttcaatattattgaagcatttatca
gggttattgtctcatgagcggatacatatttgaatgtatttagaaaaataaacaaatagggtt
ccgcgcacatttccccgaaaagtgccacctgacgtctaagaaaccattattatcatgacattaa
cctataaaaataggcgtatcacgaggccctttcgtcttcaagaa
(SEQ ID NO:5)

FIG. 7A

1-
cccgtcttactgtcgggaattcgcgttggccgattcattaatgcagctggcacgacaggtttcc
cgactggaaagcgggcagtgagcgcaacgcaattaatgtgagttagctcactcattaggcaccc
caggctttacactttatgcttccggctcgtatgttgtgtggaattgtgagcggataacaatttc
acacaggaaacagctatgaccatgattacgccaagcttgtatcgattaaataaggaggaataaa
ccatgtgtgcgacctcttctcaatttactcagattaccgagcataattcccgtcgttccgcaaa
ctatcagccaaacctgtggaatttcgaattcctgcaatccctggagaacgacctgaaagtggaa
aagctggaggagaaagcgaccaaactggaggaagaagttcgctgcatgatcaaccgtgtagaca
cccagccgctgtccctgctggagctgatcgacgatgtgcagcgcctgggtctgacctacaaatt
tgaaaaagacatcattaaagccctggaaaacatcgtactgctggacgaaaacaaaagaacaaa
tctgacctgcacgcaaccgctctgtctttccgtctgctgcgtcagcacggtttcgaggtttctc
aggatgttttgagcgtttcaaggataaagaaggtggtttcagcggtgaactgaaaggtgacgt
ccaaggcctgctgagcctgtatgaagcgtcttacctgggtttcgagggtgagaacctgctggag
gaggcgcgtaccttttccatcacccacctgaagaacaacctgaaagaaggcattaataccaagg
ttgcagaacaagtgagccacgccctggaactgccatatcaccagcgtctgcaccgtctggaggc
acgttggttcctggataaatacgaaccgaaagaaccgcatcaccagctgctgctggagctggcg
aagctggattttaacatggtacagaccctgcaccagaaagagctgcaagatctgtcccgctggt
ggaccgagatgggcctggctagcaaactggattttgtacgcgaccgcctgatggaagtttattt
ctgggcactgggtatggcgccagacccgcagtttggtgaatgtcgcaaagctgttactaaaatg
tttggtctggtgacgatcatcgatgacgtgtatgacgtttatggcactctggacgaactgcaac
tgttcaccgatgctgtagagcgctgggacgttaacgctattaacaccctgccggactatatgaa
actgtgtttcctggcactgtacaacaccgttaacgacacgtcctattctattctgaaagagaaa
ggtcataacaacctgtcctatctgacgaaaagctggcgtgaactgtgcaaagcctttctgcaag
aggcgaaatggtccaacaacaaaattatcccggctttctccaagtacctggaaaacgccagcgt
ttcctcctccggtgtagcgctgctggcgccgtcttactttccgtatgccagcagcaggaagac
atctccgaccacgcgctgcgttccctgaccgacttccatggtctggtgcgttctagctgcgtta
tcttccgcctgtgcaacgatctggccacctctgcggcggagctggaacgtggcgagactaccaa
ttctatcattagctacatgcacgaaaacgatggtaccagcgaggaacaggcccgcgaagaactg
cgtaaactgatcgacgccgaatggaaaaagatgaatcgtgaacgcgttagcgactccaccctgc
tgcctaaagcgttcatggaaatcgcagttaacatggcacgtgtttcccactgcacctaccagta
tggcgatggtctgggtcgcccagactacgcgactgaaaaccgcatcaaactgctgctgattgac
cctttcccgattaaccagctgatgtatgtctaactgcaggtcgactctagaggatccccgggta
ccgagctcgaattcactggccgtcgttttacaacgtcgtgactgggaaaaccctggcgttaccc
aacttaatcgccttgcagcacatcccctttcgccagctggcgtaatagcgaagaggcccgcac
cgatcgcccttcccaacagttgcgcagcctgaatggcgaatggcgcctgatgcggtattttctc
cttacgcatctgtgcggtatttcacaccgcatatggtgcactctcagtacaatctgctctgatg
ccgcatagttaagccagccccgacacccgccaacacccgctgacgagcttagtaaagccctcgc
tagattttaatgcggatgttgcgattacttcgccaactattgcgataacaagaaaaagccagcc
tttcatgatatatctcccatttgtgtagggcttattatgcacgcttaaaaataataaaagcag
acttgacctgatagtttggctgtgagcaattatgtgcttagtgcatctaacgcttgagttaagc
cgcgccgcgaagcggcgtcggcttgaacgaattgttagacattatttgccgactaccttggtga
tctcgcctttcacgtagtggacaaattcttccaactgatctgcgcgcgaggccaagcgatcttc
ttcttgtccaagataagcctgtctagcttcaagtatgacgggctgatactgggccggcaggcgc
tccattgcccagtcggcagcgacatccttcggcgcgattttgccggttactgcgctgtaccaaa
tgcgggacaacgtaagcactacatttcgctcatcgccagcccagtcgggcggcgagttccatag

FIG. 7B cgttaaggtttcatttagcgcctcaaatagatcctgttcaggaaccggatcaaagagttcctcc
gccgctggacctaccaaggcaacgctatgttctcttgcttttgtcagcaagatagccagatcaa
tgtcgatcgtggctggctcgaagatacctgcaagaatgtcattgcgctgccattctccaaattg
cagttcgcgcttagctggataacgccacggaatgatgtcgtcgtgcacaacaatggtgacttct
acagcgcggagaatctcgctctctccaggggaagccgaagtttccaaaaggtcgttgatcaaag
ctcgccgcgttgtttcatcaagccttacggtcaccgtaaccagcaaatcaatatcactgtgtgg
cttcaggccgccatccactgcggagccgtacaaatgtacggccagcaacgtcggttcgagatgg
cgctcgatgacgccaactacctctgatagttgagtcgatacttcggcgatcaccgcttccctca
tgatgtttaactttgttttagggcgactgccctgctgcgtaacatcgttgctgctccataacat
caaacatcgacccacggcgtaacgcgcttgctgcttggatgcccgaggcatagactgtacccca
aaaaaacagtcataacaagccatgaaaaccgccactgcgccgttaccaccgctgcgttcggtca
aggttctggaccagttgcgtgagcgcatacgctacttgcattacagcttacgaaccgaacaggc
ttatgtccactgggttcgtgccttcatccgtttccacggtgtgcgtcaccggcaaccttgggc
agcagcgaagtcgaggcatttctgtcctggctggcgaacgagcgcaaggtttcggtctccacgc
atcgtcaggcattggcggccttgctgttcttctacggcaaggtgctgtgcacggatctgccctg
gcttcaggagatcggaagacctcggccgtcgcggcgcttccggtggtgctgacccggatgaa
gtggttcgcatcctcggttttctggaaggcgagcatcgtttgttcgcccagcttctgtatggaa
cgggcatgcggatcagtgagggtttgcaactgcgggtcaaggatctggatttcgatcacggcac
gatcatcgtgcgggagggcaagggctccaaggatcgggccttgatgttacccgagagcttggca
cccagcctgcgcgagcaggggaattaattcccacgggttttgctgcccgcaaacgggctgttct
ggtgttgctagtttgttatcagaatcgcagatccggcttcagccggtttgccggctgaaagcgc
tatttcttccagaattgccatgattttttcccacgggaggcgtcactggctcccgtgttgtcg
gcagctttgattcgataagcagcatcgcctgtttcaggctgtctatgtgtgactgttgagctgt
aacaagttgtctcaggtgttcaatttcatgttctagttgctttgttttactggtttcacctgtt
ctattaggtgttacatgctgttcatctgttacattgtcgatctgttcatggtgaacagctttga
atgcaccaaaaactcgtaaaagctctgatgtatctatcttttttacaccgttttcatctgtgca
tatggacagttttcccttttgatatgtaacggtgaacagttgttctacttttgtttgttagtctt
gatgcttcactgatagatacaagagccataagaacctcagatccttccgtatttagccagtatg
ttctctagtgtggttcgttgttttgcgtgagccatgagaacgaaccattgagatcatacttac
tttgcatgtcactcaaaaattttgcctcaaaactggtgagctgaatttttgcagttaaagcatc
gtgtagtgttttcttagtccgttatgtaggtaggaatctgatgtaatggttgttggtattttg
tcaccattcattttatctggttgttctcaagttcggttacgagatccatttgtctatctagtt
caacttggaaaatcaacgtatcagtcgggcggcctcgcttatcaaccaccaatttcatattgct
gtaagtgtttaaatctttacttattggtttcaaaacccattggttaagccttttaaactcatgg
tagttattttcaagcattaacatgaacttaaattcatcaaggctaatctctatatttgccttgt
gagttttcttttgtgttagttcttttaataaccactcataaatcctcatagagtatttgttttc
aaaagacttaacatgttccagattatattttatgaatttttttaactggaaaagataaggcaat
atctcttcactaaaaactaattctaattttcgcttgagaacttggcatagtttgtccactgga
aaatctcaaagcctttaaccaaggattcctgatttccacagttctcgtcatcagctctctggt
tgctttagctaatacaccataagcattttccctactgatgttcatcatctgagcgtattggtta
taagtgaacgataccgtccgttctttccttgtagggttttcaatcgtggggttgagtagtgcca
cacagcataaaattagcttggtttcatgctccgttaagtcatagcgactaatcgctagttcatt
tgctttgaaaacaactaattcagacatacatctcaattggtctaggtgatttaatcactatac
caattgagatgggctagtcaatgataattactagtcctttcctttgagttgtgggtatctgta

FIG. 7C

Aattctgctagacctttgctggaaaacttgtaaattctgctagaccctctgtaaattccgctag
acctttgtgtgttttttttgtttatattcaagtggttataatttatagaataaagaaagaataa
aaaaagataaaaagaatagatcccagccctgtgtataactcactactttagtcagttccgcagt
attacaaaaggatgtcgcaaacgctgtttgctcctctacaaaacagaccttaaaaccctaaagg
cttaagtagcaccctcgcaagctcgggcaaatcgctgaatattccttttgtctccgaccatcag
gcacctgagtcgctgtcttttcgtgacattcagttcgctgcgctcacggctctggcagtgaat
gggggtaaatggcactacaggcgccttttatggattcatgcaaggaaactacccataatacaag
aaaagcccgtcacgggcttctcagggcgttttatggcgggtctgctatgtggtgctatctgact
ttttgctgttcagcagttcctgccctctgatttccagtctgaccacttcggattatcccgtga
caggtcattcagactggctaatgcacccagtaaggcagcggtatcatcaacaggctta
(SEQ ID NO:7)

FIG. 12A

1-
gaattgctccatttcttctgctatcaaaataacagactcgtgatttcccaaacgagctttcaa
aaaagcctctgccccttgcaaatcggatgcctgtctataaaattcccgatattggttaaacagc
ggcgcaatggcggccgcatctgatgtctttgcttggcgaatgttcatcttatttcttcctccct
ctcaataattttttcattctatccttttctgtaaagtttattttcagaatactttatcatc
atgctttgaaaaatatcacgataatatccattgttctcacggaagcacacgcaggtcatttga
acgaattttttcgacaggaatttgccgggactcaggagcatttaacctaaaaagcatgacatt
tcagcataatgaacatttactcatgtctattttcgttcttttctgtatgaaaatagttatttcg
agtctctacggaaatagcgagagatgatatacctaaatagagataaaatcatctcaaaaaatg
ggtctactaaaatattattccatctattacaataaattcacagaatagtcttttaagtaagtct
actctgaatttttttaaaaggagagggtaaagagtgtgtgcgacctcttctcaatttactcaga
ttaccgagcataattcccgtcgttccgcaaactatcagccaaacctgtggaatttcgaattcct
gcaatccctggagaacgacctgaaagtggaaaagctggaggagaaagcgaccaaactggaggaa
gaagttcgctgcatgatcaaccgtgtagacacccagccgctgtccctgctggagctgatcgacg
atgtgcagcgcctgggtctgacctacaaatttgaaaaagacatcattaaagccctggaaaacat
cgtactgctggacgaaaacaaaaagaacaaatctgacctgcacgcaaccgctctgtctttccgt
ctgctgcgtcagcacggtttcgaggtttctcaggatgttttttgagcgtttcaaggataaagaag
gtggtttcagcggtgaactgaaaggtgacgtccaaggcctgctgagcctgtatgaagcgtctta
cctgggtttcgagggtgagaacctgctggaggaggcgcgtaccttttccatcacccacctgaag
aacaacctgaaagaaggcattaataccaaggttgcagaacaagtgagccacgcctggaactgc
catatcaccagcgtctgcaccgtctggaggcacgttggttcctggataaatacgaaccgaaaga
accgcatcaccagctgctgctggagctggcgaagctggatttaacatggtacagaccctgcac
cagaaagagctgcaagatctgtcccgctggtggaccgagatgggcctggctagcaaactggatt
ttgtacgcgaccgcctgatggaagtttatttctgggcactgggtatggcgccagacccgcagtt
tggtgaatgtcgcaaagctgttactaaaatgtttggtctggtgacgatcatcgatgacgtgtat
gacgtttatggcactctggacgaactgcaactgttcaccgatgctgtagagcgctgggacgtta
acgctattaacaccctgccggactatatgaaactgtgtttcctggcactgtacaacaccgttaa
cgacacgtcctattctattctgaaagagaaaggtcataacaacctgtcctatctgacgaaaagc
tggcgtgaactgtgcaaagcctttctgcaagaggcgaaatggtccaacaacaaaattatcccgg
ctttctccaagtacctggaaaacgccagcgtttcctcctccggtgtagcgctgctggcgccgtc
ttacttttccgtatgccagcagcaggaagacatctccgaccacgcgctgcgttccctgaccgac
ttccatggtctggtgcgttctagctgcgttatcttccgcctgtgcaacgatctggccacctctg
cggcggagctggaacgtggcgagactaccaattctatcattagctacatgcacgaaaacgatgg
taccagcgaggaacaggcccgcgaagaactgcgtaaactgatcgacgccgaatggaaaagatg
aatcgtgaacgcgttagcgactccaccctgctgcctaaagcgttcatggaaatcgcagttaaca
tggcacgtgtttcccactgcacctaccagtatggcgatggtctgggtcgcccagactacgcgac
tgaaaaccgcatcaaactgctgctgattgaccctttcccgattaaccagctgatgtatgtctaa
aaaaaaccggccttggccccgccggttttttattattttcttcctccgcatgttcaatccgct
ccataatcgacggatggctccctctgaaaattttaacgagaaacggcgggttgacccggctcag
tcccgtaacggccaagtcctgaaacgtctcaatcgccgcttcccggtttccggtcagctcaatg
ccgtaacggtcggcggcgttttcctgataccgggagacggcattcgtaatcggatcctctagag
tcgacctgcaggcatgcaagctttgcctcgcgcgtttcggtgatgacggtgaaaacctctgaca
catgcagctcccggagacggtcacagcttgtctgtaagcggatgccgggagcagacaagcccgt
cagggcgcgtcagcgggtgttggcgggtgtcgggcgcagccatgacccagtcacgtagcgata

FIG. 12B

```
gcggagtgtatactggcttaactatgcggcatcagagcagattgtactgagagtgcaccatatg
cggtgtgaaataccgcacagatgcgtaaggagaaaataccgcatcaggcgctcttccgcttcct
cgctcactgactcgctgcgctcggtcgttcggctgcggcgagcggtatcagctcactcaaaggc
ggtaatacggttatccacagaatcaggggataacgcaggaaagaacatgtgagcaaaaggccag
caaaaggccaggaaccgtaaaaaggccgcgttgctggcgttttttccataggctccgcccccctg
acgagcatcacaaaaatcgacgctcaagtcagaggtggcgaaacccgacaggactataaagata
ccaggcgtttccccctggaagctccctcgtgcgctctcctgttccgaccctgccgcttaccgga
tacctgtccgcctttctcccttcgggaagcgtggcgctttctcaatgctcacgctgtaggtatc
tcagttcggtgtaggtcgttcgctccaagctgggctgtgtgcacgaaccccccgttcagcccga
ccgctgcgccttatccggtaactatcgtcttgagtccaacccggtaagacacgacttatcgcca
ctggcagcagccactggtaacaggattagcagagcgaggtatgtaggcggtgctacagagttct
tgaagtggtggcctaactacggctacactagaaggacagtatttggtatctgcgctctgctgaa
gccagttaccttcggaaaaagagttggtagctcttgatccggcaaacaaaccaccgctggtagc
ggtggtttttttgtttgcaagcagcagattacgcgcagaaaaaaaggatctcaagaagatcctt
tgatcttttctacggggtctgacgctcagtggaacgaaaactcacgttaagggattttggtcat
gagattatcaaaaggatcgaagtcggttcagaaaagaaggatatggatctggagctgtaata
taaaaccttcttcaactaacggggcaggttagtgacattagaaaaccgactgtaaaaagtaca
gtcggcattatctcatattataaaagccagtcattaggcctatctgacaattcctgaatagagt
tcataaacaatcctgcatgataaccatcacaaacagaatgatgtacctgtaaagatagcggtaa
atatattgaattaccttttattaatgaattttcctgctgtaataatgggtagaaggtaattacta
ttattgatatttaagttaaacccagtaaatgaagtccatggaataatagaaagagaaaaag
cattttcaggtataggtgttttgggaaacaatttaaaagaaccattatatttctctacatcaga
aaggtataaatcataaaactctttgaagtcattctttacaggagtccaaataccagagaatgtt
ttagatacaccatcaaaaattgtataaagtggctctaacttatcccaataacctaactctccgt
cgctattgtaaccagttctaaaagctgtatttgagtttatcacccttgtcactaagaaaataaa
tgcagggtaaaatttatatccttcttgttttatgtttcggtataaaacactaatatcaatttct
gtggttatactaaaagtcgtttgttggttcaaataatgattaaatatctcttttctcttccaat
tgtctaaatcaatttattaaagttcatttgatatgcctcctaaattttatctaaagtgaatt
taggaggcttacttgtctgctttcttcattagaatcaatccttttttaaagtcaatattactgt
aacataaatatatattttaaaaatatcccactttatccaattttcgtttgttgaactaatgggt
gctttagttgaagaataaagaccacattaaaaaatgtggtcttttgtgttttttaaaggattt
gagcgtacgcgaaaaatccttttctttctttcttatcttgataataagggtaactattgccggt
tgtccattcatggctgaactctgcttcctctgttgacatgacacacatcatctcaatatccgaa
tagggcccatcagtctgacgaccaagagagccataaacaccaatagccttaacatcatcccat
atttatccaatattcgttccttaatttcatgaacaatcttcattcttttcttctcagtcattat
tattggtccattcactattctcattcccttttcagataattttagatttgcttttctaaataag
aatatttggagagcaccgttcttattcagctattaataactcgtcttcctaagcatccttcaat
ccttttaataacaattatagcatctaatcttcaacaaactggcccgtttgttgaactactcttt
aataaaataattttccgttcccaattccacattgcaataatagaaaatccatcttcatcggct
ttttcgtcatcatctgtatgaatcaaatcgccttcttctgtgtcatcaaggtttaattttttat
gtatttcttttaacaaaccaccataggagattaacctttacggtgtaaaccttcctccaaatc
agacaaacgtttcaaattcttttcttcatcatcggtcataaaatccgtatcctttacaggatat
tttgcagtttcgtcaattgccgattgtatatccgatttatatttattttcggtcgaatcattt
gaacttttacatttggatcatagtctaatttcattgccttttccaaaattgaatccattgttt
```

FIG. 12C

```
ttgattcacgtagttttctgttattctaaaataagttggttccacacataccattacatgcatg
tgctgattataagaattatctttattatttattgtcacatccgttgcacgcataaaaccaacaa
gattttattaattttttatattgcatcattcggcgaaatccttgagccatatctgtcaaact
cttatttaattcttcgccatcataaacattttaactgttaatgtgagaaacaaccaacgaact
gttggcttttgtttaataacttcagcaacaaccttttgtgactgaatgccatgtttcattgctc
tcctccagttgcacattggacaaagcctggatttgcaaaaccacactcgataccactttctttc
gcctgtttcacgattttgtttatactctaatatttcagcacaatcttttactctttcagccttt
ttaaattcaagaatatgcagaagttcaaagtaatcaacattagcgatttcttttctctccatg
gtctcacttttccacttttgtcttgtccactaaaaccttgattttcatctgaataaatgct
actattaggacacataatattaaaagaaacccccatctatttagttatttgtttagtcacttat
aactttaacagatggggttttctgtgcaaccaattttaagggttttcaatactttaaaacaca
tacataccaacacttcaacgcacctttcagcaactaaaataaaaatgacgttatttctatatgt
atcaagataagaaagaacaagttcaaaaccatcaaaaaaagacacctttcaggtgcttttttt
attttataaactcattccctgatctcgacttcgttcttttttacctctcggttatgagttagt
tcaaattcgttcttttaggttctaaatcgtgtttttcttggaattgtgctgttttatcctta
ccttgtctacaaaccccttaaaaacgttttaaaggcttttaagccgtctgtacgttccttaag
```

(SEQ ID NO:57)

FIG. 13

```
ATGTGTGCAACCTCCTCCCAGTTTACTCAGATTACCGAGCATAATTCTCGACGATCTGCTAACT
ACCAGCCGAACCTTTGGAACTTTGAGTTTCTCCAGTCTCTCGAAAATGACCTGAAGGTGGAAAA
GCTCGAGGAGAAGGCGACCAAACTCGAGGAGGAGGTGCGATGTATGATCAACAGAGTTGACACC
CAACCCCTGTCTTTGCTGGAGCTGATCGACGATGTGCAGCGGTTGGGTTTGACTTATAAATTCG
AGAAGGACATTATCAAGGCACTGGAGAACATTGTGCTCCTCGACGAGAACAAGAAGAACAAGTC
TGATCTTCACGCTACCGCTCTCTCTTTCCGACTTCTTCGACAACACGGCTTCGAGGTGTCGCAG
GACGTCTTCGAGAGATTTAAGGACAAGGAGGGAGGATTTAGCGGCGAGCTGAAGGGAGACGTTC
AGGGTCTTCTCTCCTTGTACGAGGCGTCCTACCTGGGATTCGAGGGAGAGAACCTCCTGGAGGA
AGCTCGTACATTTTCCATCACTCACCTTAAGAATAACCTTAAGGAGGGAATTAACACCAAGGTG
GCCGAGCAGGTTCTCACGCCCTGGAGCTCCCCTACCACCAACGGCTCCATAGACTGGAGGCTC
GTTGGTTCCTGGACAAATATGAGCCAAAGGAGCCTCATCATCAGTTGCTGTTGGAGTTGGCCAA
GCTGGACTTCAATATGGTTCAGACGCTGCACCAAAAGGAGTTGCAGGACCTGTCTCGATGGTGG
ACCGAGATGGGATTGGCCTCGAAGCTGGATTTTGTCCGTGACCGACTTATGGAGGTCTATTTTT
GGGCCCTTGGAATGGCGCCTGACCCCAGTTCGGAGAGTGCCGGAAGGCGGTGACGAAGATGTT
CGGTCTTGTGACTATCATCGACGACGTCTACGATGTCTACGGCACACTCGACGAGTTGCAGCTG
TTCACTGACGCCGTCGAGCGATGGGATGTGAACGCCATTAATACTCTCCCTGACTATATGAAGC
TGTGCTTCCTGGCTCTGTACAACACTGTCAACGATACCTCGTACTCTATCCTCAAGGAGAAGGG
ACACAACAATCTCTCCTACTTGACCAAATCCTGGCGAGAACTGTGCAAGGCTTTTCTGCAGGAG
GCTAAATGGTCCAATAACAAGATCATTCCTGCTTTTTCTAAATACCTGGAAAATGCCTCGGTGT
CGAGCTCTGGCGTCGCCCTTCTGGCCCCTTCCTACTTCTCCGTCTGCCAGCAGCAGGAGGATAT
TTCCGATCATGCTCTTAGATCGCTGACCGATTTTCACGGCCTCGTGCGATCTTCCTGCGTGATT
TTTCGGTTGTGTAATGACCTTGCGACCTCTGCTGCTGAGCTGGAACGAGGCGAGACTACAAATT
CCATTATTTCTTACATGCACGAAAACGATGGAACATCTGAAGAACAGGCTAGAGAGGAACTGCG
AAAGTTGATCGACGCCGAGTGGAAGAAGATGAACAGAGAGCGGGTGTCCGACTCTACCCTGCTT
CCCAAGGCCTTCATGGAGATCGCCGTGAACATGGCTCGAGTTTCCCATTGTACTTACCAGTACG
GTGACGGCCTGGGTCGTCCGGACTACGCTACAGAGAACCGAATCAAGCTGCTGCTCATCGACCC
CTTCCCTATCAACCAATTGATGTACGTGTAA
```
(SEQ ID NO:8)

FIG. 15A

```
   1 TCGACCGGTG AGAAGAACAG CATCGGGACA AGGGAAGGAA GAACAAAGAC AAAGAAAACA
  61 AAAGAAAGCA ATTGAAAACA AAACAAAACA ATTTTCATTC CTTCTCTTAT CATTCCTTTT
 121 CTTTTCTTTT CTCTCATTCA ACGCACTCCA TCGTATCCGT ATTCCTCTTA TTTTTTCTCT
 181 TTCTCTATAT CCATTTCTTT CTCTCTAGGT GTGTCCTCTC TCTCTCTTCA ATTTCTCTAC
 241 TCCGCATTCC AACGCATCCT TCCCCCAACC TCCCATTTCC TCCTTACGGC CCGATAGCGA
 301 TCGTCTTTCC CTCGCTATCA CTCGCTACCG GCCCCTCCTC TGCACCGTAA CCTCCTACGT
 361 ATTTACCATA TCATAAAGTT TTTTCCGACG CTTATCGCTG ACCCCCTGTC GCCCTCCTAT
 421 TGGCTTCCGG ATTATCTTCT TGTCCATAAG GTGATCCATG CTTCCTGAAG ATTCCCGAAA
 481 TGTGTCCACT TTGGCGGGGA ATCATTCCAT CCACTTCTTT CTCTCTCGCT TTCCTCATTC
 541 GGCGCTCCCC TTCCGCGTCT CATTGGTCTT CCGCTCCGTT TTTGCTTTGC CGATGTTACT
 601 TGGGGAGAGG TGCGATAATC CTTTCGCAAA AACTCGGTTT GACGCCTCCC ATGGTATAAA
 661 TAGTGGGTGG TGGACAGGTG CCTTCGCTTT TCTTTAAGCA AGAGAATCCC ATTGTCTTGA
 721 CTATCACGAA TTCACATACA TTATGAAGAT CACCGCTGTC ATTGCCCTTT TATTCTCACT
 781 TGCTGCTGCC TCACCTATTC CAGTTGCCGA TCCTGGTGTG GTTTCAGTTA GCAAGTCATA
 841 TGCTGATTTC CTTCGTGTTT ACCAAAGTTG AACACTTTT GCTAATCCTG ATAGACCCAA
 901 CCTTAAGAAG AGAAATGATA CACCTGCAAG TGGATATCAA GTTGAAAAAG TCGTAATTTT
 961 GTCACGTCAC GGTGTTAGGG CCCCTACAAA AATGACTCAA ACCATGCGTG ATGTCACTCC
1021 TAATACATGG CCAGAATGGC CCGTTAAATT AGGATATATT ACACCAAGAG GTGAACACTT
1081 GATATCACTT ATGGGCGGTT TTTACCGTCA AAAATTCCAG CAACAAGGAA TCCTTTCTCA
1141 GGGCTCCTGT CCTACTCCTA ACTCCATATA TGTCTGGGCT GACGTCGATC AGCGTACTTT
1201 AAAAACTGGT GAAGCATTCC TTGCTGGTTT GGCACCACAA TGTGGCTTGA CAATTCATCA
1261 CCAACAAAAT CTTGAGAAAG CTGATCCTCT TTTTCATCCC GTTAAAGCTG GAACCTGCTC
1321 TATGGATAAA ACTCAAGTTC AACAAGCTGT TGAGAAGGAG GCACAAACTC CTATAGATAA
1381 TTTGAATCAA CATTACATCC CCTTTTTAGC TTTAATGAAT ACAACATTAA ATTTTAGTAC
1441 TTCTGCCTGG TGCCAAAAAC ACTCTGCTGA TAAATCCTGT GACCTAGGTT TATCCATGCC
1501 TTCTAAATTG TCCATAAAAG ATAATGGTAA CAAGGTCGCA TTGGATGGAG CTATTGGTCT
1561 ATCCTCTACT TTGGCCGAGA TTTTCTTCT TGAATATGCT CAAGGCATGC CTCAAGCTGC
1621 TTGGGGTAAC ATCCACTCAG AGCAAGAGTG GGCTTCCTTG CTAAAGTTGC ATAATGTTCA
1681 ATTCGATTTG ATGGCCCGAA CACCTTATAT TGCTCGACAT AACGGTACTC CTTTATTGCA
1741 AGCTATATCA AATGCCCTTA ATCCCAACGC CACTGAATCA AAACTTCCAG ATATTTCACC
1801 TGATAACAAA ATATTGTTCA TTGCAGGTCA TGACACAAAT ATTGCTAATA TAGCCGGCAT
1861 GTTAAATATG CGTTGGACAT TACCAGGTCA ACCAGATAAT ACTCCTCCAG GTGGTGCCCT
1921 AGTATTTGAA CGTCTTGCTG ATAAAAGTGG AAAACAATAT GTTTCTGTAT CTATGGTTTA
1981 TCAAACACTA GAACAACTTC GATCACAGAC TCCCCTTTCT CTAAATCAGC CTGCCGGATC
2041 TGTTCAACTT AAAAATTCCAG GTTGCAATGA TCAAACAGCC GAGGGTACT GTCCTCTTTC
2101 CACTTTTACA AGAGTTGTTT CCCAATCTGT TGAACCTGGA TGCCAACTTC AATAATGAGG
2161 ATCCAAGTAA GGGAATGAGA ATGTGATCCA CTTTTAATTC CTAATGAATA CATGCCTATA
2221 GTTCTTTTCT TTTGTTCTTT ATGTCGTTTT TCGATGGTAC GGCCGTTGTC AATCTCAGTT
2281 TGTGTGCTTG GTTGCAGCTT GGTTTCAAAT CTGTTCATCT CATGAATCTT TTACCATTTC
2341 ACCACACGTT TATACCATTC TCTCATAGAA TCTTCATCAA ACCATCTCGG GGTTAGAGTG
2401 GAAAGAAAGT CTTGTTCTTT TATTTCCTTT TTTCCATCTT CAAGGCTTTT CTTTTCTTCC
2461 TCCTCCTCGT TCATCTTGAG GTTTGACGTG TCTGTTTAGA ATTTTGAGCT GTTGCAGCAT
2521 CTTATTTTTT GTTTTGCGAA AACGAAGCGC TTTACTCTCT TCATCAGTTG GACGATTGTA
2581 CCTTTGAAAA CCAACTACTT TTGCATGTTT TGTATAGAAA TCAATGATAT TAGAATCCCA
2641 TCCTTTAATT TCTTTCAAAG TAGTTGAGCT ATAGTTAAGT GTAAGGGCCC TACTGCGAAA
2701 GCATTTGCCA AGGATGTTTT CATTAATCAA GAACGAAAGT TAGGGGATCG AAGACGATCA
2761 GATACCGTCG TAGTCTTAAC CATAAACTAT GCCGACTAGG GATCGGGCAA TGTTTCATTT
2821 ATCGACTTGC TCGGCACCTT ACGAGAAATC AAAGTCTTTG GGTTCCGGGG GGAGTATGGT
2881 CGCAAGGCTG AAACTTAAAG GAATTGACGG AAGGGCACCA CAATGGAGTG GAGCCTGCGG
2941 CTTAATTTGA CTCAACACGG GGAAACTCAC CAGGTCCAGA CATAGTAAGG ATTGACAGAT
3001 TGAGAGCTCT TTCTTGATTC TATGGGTGGT GGTGCATGGC CGTTCTTAGT TGGTGGAGTG
3061 ATTTGTCTGC TTAATTGCGA TAACGAACGA GACCTTAACC TGCTAAATAG CTGGATCAGC
3121 CATTTTGGCT GATCATTAGC TTCTTAGAGG ACTATTGGC ATAAAGCCAA TGGAAGTTTG
3181 AGGCAATAAC AGGTCTGTGA TGCCCTTAGA TGTTCTGGGC CGCACGCGCG CTACACTGAC
3241 GGAGCCAACG AGTTGAAAAA AATCTTTTGA TTTTTTATCC TTGGCCGGAA GGTCTGGGTA
3301 ATCTTGTTAA ACTCCGTCGT GCTGGGGATA GAGCATTGCA ATTATTGCGG CCGCTCCTCA
3361 ATTCGATGTT GCAGATTTTA CAAGTTTTTA AAATGTATTT CATTATTACT TTTTATATGC
3421 CTAATAAAAA AGCCATAGTT TAATCTATAG ATAACTTTTT TTCCAGTGCA CTAACGGACG
```

FIG. 15B

```
3481 TTACATTCCC ATACAAAACT GCGTAGTTAA AGCTAAGGAA AAGTTAATAT CATGTTAATT
3541 AAATACGCTA TTTACAATAA GACATTGAAC TCATTTATAT CGTTGAATAT GAATAACCAA
3601 TTTCAGCGAA TTTTTAACAA ACATCGTTCA CCTCGTTTAA GGATATCTTG TGTATGGGGT
3661 GTTGACTTGC TTTATCGAAT AATTACCGTA CCTGTAATTG GCTTGCTGGA TATAGCGGTA
3721 GTCTAATATC TAGCAAAAAT CTTTTGGGTG AAAAGGCTTG CAATTCACG ACACCGAACT
3781 ATTTGTCATT TTTTAATAAG GAAGTTTTCC ATAAATTCCT GTAATTCTCG GTTGATCTAA
3841 TTGAAAAGAG TAGTTTTGCA TCACGATGAG GAGGGCTTTT GTAGAAAGAA ATACGAACGA
3901 AACGAAAATC AGCGTTGCCA TCGCTTTGGA CAAAGCTCCC TTACCTGAAG AGTCGAATTT
3961 TATTGATGAA CTTATAACTT CCAAGCATGC AAACCAAAAG GGAGAACAAG TAATCCAAGT
4021 AGACACGGGA ATTGGATTCT TGGATCACAT GTATCATGCA CTGGCTAAAC ATGCAGGCTG
4081 GAGCTTACGA CTTTACTCAA GAGGTGATTT AATCATCGAT GATCATCACA CTGCAGAAGA
4141 TACTGCTATT GCACTTGGTA TTGCATTCAA GCAGGCTATG GGTAACTTTG CCGGCGTTAA
4201 AAGATTTGGA CATGCTTATT GTCCACTTGA CGAAGCTCTT TCTAGAAGCG TAGTTGACTT
4261 GTCGGGACGG CCCTATGCTG TTATCGATTT GGGATTAAAG CGTGAAAAGG TTGGGGAATT
4321 GTCCTGTGAA ATGATCCCTC ACTTACTATA TTCCTTTTCG GTAGCAGCTG GAATTACTTT
4381 GCATGTTACC TGCTTATATG GTAGTAATGA CCATCATCGT GCTGAAAGCG CTTTTAAATC
4441 TCTGGCTGTT GCCATGCGCG CGGCTACTAG TCTTACTGGA AGTTCTGAAG TCCCAAGCAC
4501 GAAGGGAGTG TTGTAAAGAT GAATTGGATT ATGTCAGGAA AAGAACGACA ATTTTGCATC
4561 CAAATTGTCT AAATTTTAGA GTTGCTTGAA AACAATAGAA CCTTACTTGC TTTATAATTA
4621 CGTTAATTAG AAGCGTTATC TCGTGAAGGA ATATAGTACG TAGCCGTATA AATTGAATTG
4681 AATGTTCAGC TTATAGAATA GAGACACTTT GCTGTTCAAT GCGTCGTCAC TTACCATACT
4741 CACTTTATTA TACGACTTTA AGTATAAACT CCGCGGTTAT GGTAAAATTA ATGATGCACA
4801 AACGTCCGAT TCCATATGGG TACACTACAA TTAAATACTT TTAAGCTGAT CCCCCACACA
4861 CCATAGCTTC AAAATGTTTC TACTCCTTTT TTACTCTTCC AGATTTTCTC GGACTCCGCG
4921 CATCGCCGTA CCACTTCAAA ACACCCAAGC ACAGCATACT AAATTTTCCC TCTTTCTTCC
4981 TCTAGGGTGT CGTTAATTAC CCGTACTAAA GGTTTGGAAA AGAAAAAAGA GACCGCCTCG
5041 TTTCTTTTTC TTCGTCGAAA AAGGCAATAA AAATTTTTAT CACGTTTCTT TTTCTTGAAA
5101 TTTTTTTTTT TAGTTTTTTT CTCTTTCAGT GACCTCCATT GATATTTAAG TTAATAAACG
5161 GTCTTCAATT TCTCAAGTTT CAGTTTCATT TTTCTTGTTC TATTACAACT TTTTTTACTT
5221 CTTGTTCATT AGAAAGAAAG CATAGCAATC TAATCTAAGG GCGGTGTTGA CAATTAATCA
5281 TCGGCATAGT ATATCGGCAT AGTATAATAC GACAAGGTGA GGAACTAAAC CATGGCCAAG
5341 TTGACCAGTG CCGTTCCGGT GCTCACCGCG CGCGACGTCG CCGGAGCGGT CGAGTTCTGG
5401 ACCGACCGGC TCGGGTTCTC CCGGGACTTC GTGGAGGACG ACTTCGCCGG TGTGGTCCGG
5461 GACGACGTGA CCCTGTTCAT CAGCGCGGTC CAGGACCAGG TGGTGCCGGA CAACACCCTG
5521 GCCTGGGTGT GGGTGCGCGG CCTGGACGAG CTGTACGCCG AGTGGTCGGA GGTCGTGTCC
5581 ACGAACTTCC GGGACGCCTC CGGGCCGGCC ATGACCGAGA TCGGCGAGCA GCCGTGGGGG
5641 CGGGAGTTCG CCCTGCGCGA CCCGGCCGGC AACTGCGTGC ACTTCGTGGC CGAGGAGCAG
5701 GACTGACACG TCCGACGGCG GCCCACGGGT CCCAGGCCTC GGAGATCCGT CCCCCTTTTC
5761 CTTTGTCGAT ATCATGTAAT TAGTTATGTC ACGCTTACAT TCACGCCCTC CCCCCACATC
5821 CGCTCTAACC GAAAAGGAAG GAGTTAGACA ACCTGAAGTC TAGGTCCCTA TTTATTTTTT
5881 TATAGTTATG TTAGTATTAA GAACGTTATT TATATTTCAA ATTTTTCTTT TTTTTCTGTA
5941 CAGACGCGAG CTTCCCAGTA AATGTGCCAT CTCGTAGGCA GAAAACGGTT CCCCCGTAGG
6001 GTCTCTCTCT TGGCCTCCTT TCTAGGTCGG GCTGATTGCT CTTGAAGCTC TCTAGGGGGG
6061 CTCACACCAT AGGCAGATAA CGTTCCCCAC CGGCTCGCCT CGTAAGCCGA CAAGGACTGC
6121 TCCCAAAGAT CCTAGGCGGG ATTTCGGCCTA TTTCGGCCTA AAGGAACCGG AACACGTAGA
6181 AAGCCAGTCC GCAGAAACGG TGCTGACCCC GGATGAATGT CAGCTACTGG GCTATCTGGA
6241 CAAGGGAAAA CGCAAGCGCA AAGAGAAAGC AGGTAGCTTG CAGTGGGCTT ACATGGCGAT
6301 AGCTAGACTG GGCGGTTTTA TGGACAGCAA GCGAACCGGA ATTGCCAGCT GGGGCGCCCT
6361 CTGGTAAGGT TGGGAAGCCC TGCAAAGTAA ACTGGATGGC TTTCTTGCCG CCAAGGATCT
6421 GATGGCGCAG GGGATCAAGA TCTGATCAAG AGACAGGATG AGGATCGTTT CGCATGATTG
6481 AACAAGATGG ATTGCACGCA GGTTCTCCGG CCGCTTGGGT GGAGAGGCTA TTCGGCTATG
6541 ACTGGGCACA ACAGACAATC GGCTGCTCTG ATGCCGCCGT GTTCCGGCTG TCAGCGCAGG
6601 GGCGCCCGGT TCTTTTTGTC AAGACCGACC TGTCCGGTGC CCTGAATGAA CTGCAGGACG
6661 AGGCAGCGCG GCTATCGTGG CTGGCCACGA CGGGCGTTCC TTGCGCAGCT GTGCTCGACG
6721 TTGTCACTGA AGCGGGAAGG GACTGGCTGC TATTGGGCGA AGTGCCGGGG CAGGATCTCC
6781 TGTCATCTCG CCTTGCTCCT GCCGAGAAAG TATCCATCAT GGCTGATGCA ATGCGGCGGC
6841 TGCATACGCT TGATCCGGCT ACCTGCCCAT TCGACCACCA AGCGAAACAT CGCATCGAGC
6901 GAGCACGTAC TCGGATGGAA GCCGGTCTTG TCGATCAGGA TGATCTGGAC GAAGAGCATC
6961 AGGGGCTCGC GCCAGCCGAA CTGTTCGCCA GGCTCAAGGC GCGCATGCCC GACGGCGAGG
```

FIG. 15C

```
7021 ATCTCGTCGT GATCCATGGC GATGCCTGCT TGCCGAATAT CATGGTGGAA AATGGCCGCT
7081 TTTCTGGATT CAACGACTGT GGCCGGCTGG GTGTGGCGGA CCGCTATCAG GACATAGCGT
7141 TGGATACCCG TGATATTGCT GAAGAGCTTG GCGGCGAATG GGCTGACCGC TTCCTCGTGC
7201 TTTACGGTAT CGCCGCTCCC GATTCGCAGC GCATCGCCTT CTATCGCCTT CTTGACGAGT
7261 TCTTCTGAAT TGAAAAAGGT ACCAAGTTTA CTCATATATA CTTTAGATTG ATTTAAAACT
7321 TCATTTTTAA TTTAAAAGGA TCTAGGTGAA GATCCTTTTT GATAATCTCA TGACCAAAAT
7381 CCCTTAACGT GAGTTTTCGT TCCACTGAGC GTCAGACCCC GTAGAAAAGA TCAAAGGATC
7441 TTCTTGAGAT CCTTTTTTTC TGCGCGTAAT CTGCTGCTTG CAAACAAAAA AACCACCGCT
7501 ACCAGCGGTG GTTTGTTTGC CGGATCAAGA GCTACCAACT CTTTTTCCGA AGGTAACTGG
7561 CTTCAGCAGA GCGCAGATAC CAAATACTGT CCTTCTAGTG TAGCCGTAGT TAGGCCACCA
7621 CTTCAAGAAC TCTGTAGCAC CGCCTACATA CCTCGCTCTG CTAATCCTGT TACCAGTGGC
7681 TGCTGCCAGT GGCGATAAGT CGTGTCTTAC CGGGTTGGAC TCAAGACGAT AGTTACCGGA
7741 TAAGGCGCAG CGGTCGGGCT GAACGGGGGG TTCGTGCACA CAGCCCAGCT TGGAGCGAAC
7801 GACCTACACC GAACTGAGAT ACCTACAGCG TGAGCATTGA GAAAGCGCCA CGCTTCCCGA
7861 AGGGAGAAAG GCGGACAGGT ATCCGGTAAG CGGCAGGGTC GGAACAGGAG AGCGCACGAG
7921 GGAGCTTCCA GGGGGAAACG CCTGGTATCT TTATAGTCCT GTCGGGTTTC GCCACCTCTG
7981 ACTTGAGCGT CGATTTTTGT GATGCTCGTC AGGGGGGCGG AGCCTATGGA AAAACGCCAG
8041 CAACGCGGCC TTTTTACGGT TCCTGGCCTT TTGCTGGCCT TTTGCTCACA TGTTCTTTCC
8101 TGCGTTATCC CCTGATTCTG TGGATAACCG TATTACCGCC TTTGAGTGAG CTGATACCGC
8161 TCGCCGCAGC CGAACGACCG AGCGCAGCGA G
```

(SEQ ID NO:11)

FIG. 16

```
   1 GAATTCAAAA CAAAATGTGT GCAACCTCCT CCCAGTTTAC TCAGATTACC GAGCATAATT
  61 CTCGACGATC TGCTAACTAC CAGCCGAACC TTTGGAACTT TGAGTTTCTC CAGTCTCTCG
 121 AAAATGACCT GAAGGTGGAA AAGCTCGAGG AGAAGGCGAC CAAACTCGAG GAGGAGGTGC
 181 GATGTATGAT CAACAGAGTT GACACCCAAC CCCTGTCTTT GCTGGAGCTG ATCGACGATG
 241 TGCAGCGGTT GGGTTTGACT TATAAATTCG AGAAGGACAT TATCAAGGCA CTGGAGAACA
 301 TTGTGCTCCT CGACGAGAAC AAGAAGAACA AGTCTGATCT TCACGCTACC GCTCTCTCTT
 361 TCCGACTTCT TCGACAACAC GGCTTCGAGG TGTCGCAGGA CGTCTTCGAG AGATTTAAGG
 421 ACAAGGAGGG AGGATTTAGC GGCGAGCTGA AGGGAGACGT TCAGGGTCTT CTCTCCTTGT
 481 ACGAGGCGTC CTACCTGGGA TTCGAGGGAG AGAACCTCCT GGAGGAAGCT CGTACATTTT
 541 CCATCACTCA CCTTAAGAAT AACCTTAAGG AGGGAATTAA CACCAAGGTG GCCGAGCAGG
 601 TTTCTCACGC CCTGGAGCTC CCCTACCACC AACGGCTCCA TAGACTGGAG GCTCGTTGGT
 661 TCCTGGACAA ATATGAGCCA AAGGAGCCTC ATCATCAGTT GCTGTTGGAG TTGGCCAAGC
 721 TGGACTTCAA TATGGTTCAG ACGCTGCACC AAAAGGAGTT GCAGGACCTG TCTCGATGGT
 781 GGACCGAGAT GGGATTGGCC TCGAAGCTGG ATTTTGTCCG TGACCGACTT ATGGAGGTCT
 841 ATTTTTGGGC CCTTGGAATG GCGCCTGACC CCCAGTTCGG AGAGTGCCGG AAGGCGGTGA
 901 CGAAGATGTT CGGTCTTGTG ACTATCATCG ACGACGTCTA CGATGTCTAC GGCACACTCG
 961 ACGAGTTGCA GCTGTTCACT GACGCCGTCG AGCGATGGCA TGTGAACGCC ATTAATACTC
1021 TCCCTGACTA TATGAAGCTG TGCTTCCTGG CTCTGTACAA CACTGTCAAC GATACCTCGT
1081 ACTCTATCCT CAAGGAGAAG GGACACAACA ATCTCTCCTA CTTGACCAAA TCCTGGCGAG
1141 AACTGTGCAA GGCTTTTCTG CAGGAGGCTA ATGGTCCAA TAACAAGATC ATTCCTGCTT
1201 TTTCTAAATA CCTGGAAAAT GCCTCGGTGT CGAGCTCTGG CGTCGCCCTT CTGGCCCCTT
1261 CCTACTTCTC CGTCTGCCAG CAGCAGGAGG ATATTTCCGA TCATGCTCTT AGATCGCTGA
1321 CCGATTTTCA CGGCCTCGTG CGATCTTCCT GCGTGATTTT TCGGTTGTGT AATGACCTTG
1381 CGACCTCTGC TGCTGAGCTG GAACGAGGCG AGACTACAAA TTCCATTATT TCTTACATGC
1441 ACGAAAACGA TGGAACATCT GAAGAACAGG CTAGAGAGGA ACTGCGAAAG TTGATCGACG
1501 CCGAGTGGAA GAAGATGAAC AGAGAGCGGG TGTCCGACTC TACCCTGCTT CCCAAGGCCT
1561 TCATGGAGAT CGCCGTGAAC ATGGCTCGAG TTTCCATTG TACTTACCAG TACGGTGACG
1621 GCCTGGGTCG TCCGGACTAC GCTACAGAGA ACCGAATCAA GCTGCTGCTC ATCGACCCCT
1681 TCCCTATCAA CCAATTGATG TACGTGTAAT AGTCTAGAGG ATCC
```
(SEQ ID NO:12)

FIG. 17

```
   1 GAATTCAACA AAAATGTGCT CTGTTTCCAC TGAGAACGTG TCCTTTACTG AGACTGAGAC
  61 TGAAGCACGT AGAAGCGCCA ACTACGAACC CAACTCCTGG GATTATGACT TTCTGCTGTC
 121 TTCTGACACC GACGAGTCGA TCGAGGTTTA TAAGGATAAG GCCAAGAAAC TTGAGGCCGA
 181 GGTCAGACGA GAGATTAACA ACGAGAAGGC CGAGTTCCTG ACCCTTCTTG AGCTGATCGA
 241 CAACGTTCAA CGACTTGGTC TTGGTTACCG TTTCGAATCC GATATCCGAC GTGCATTGGA
 301 TCGATTTGTC TCGTCCGGAG GTTTCGATGG TGTGACTAAG ACGTCGCTGC ACGCCACAGC
 361 TCTTTCCTTC AGACTGTTGC GGCAGCATGG ATTTGAGGTT TCCCAGGAAG CCTTTTCTGG
 421 TTTCAAGGAT CAGAACGGAA ACTTTTTGGA GAATCTCAAG GAGGACACCA AGGCCATCCT
 481 GTCGTTGTAT GAGGCCTCGT TCCTGGCTCT TGAGGGCGAG AATATTCTGG ATGAGGCTCG
 541 GGTTTTCGCT ATTCGCACC TGAAGGAGTT GTCGGAGGAA AAGATCGGAA AGGAACTGGC
 601 CGAGCAGGTC AACCATGCAC TTGAACTTCC CCTGCATCGA CGTACCCAGC GACTGGAGGC
 661 CGTGTGGAGC ATCGAGGCGT ACAGAAAAAA GGAGGATGCT AATCAGGTTC TGCTCGAACT
 721 CGCTATCCTC GACTATAACA TGATTCAGAG CGTGTACCAG CGTGACTTGC GAGAGACAAG
 781 CCGGTGGTGG CGACGGGTGG GACTGGCCAC GAAGCTCCAC TTTGCTAAAG ATCGATTGAT
 841 TGAGTCGTTC TACTGGGCAG TGGGTGTGGC CTTTGAGCCT CAGTACTCCG ACTGCCGAAA
 901 CTCCGTTGCA AAGATGTTTT CTTTTGTCAC TATCATCGAC GACATCTACG ATGTTTACGG
 961 CACTCTCGAT GAACTCGAAC TCTTCACGGA CGCTGTCGAG CGATGGGATG TGAATGCCAT
1021 TAATGATCTG CCAGATTATA TGAAGTTGTG TTTCTTGGCG CTCTACAACA CAATTAATGA
1081 AATTGCCTAC GACAACCTCA AGGACAAGGG AGAGAACATT CTGCCCTACC TTACTAAAGC
1141 CTGGGCCGAC CTGTGTAACG CCTTTTTGCA GGAAGCCAAG TGGCTCTATA ACAAATCTAC
1201 TCCTACATTT GATGACTACT TCGGCAACGC TTGGAAGTCT TCCAGCGGCC CTCTCCAGTT
1261 GATCTTCGCT TACTTTGCAG TGGTCCAGAA CATCAAGAAA GAGGAGATTG AGAACCTCCA
1321 GAAGTATCAC GACATCATCT CCCGACCTTC GCACATCTTT CGACTGTGCA ATGACCTTGC
1381 CTCCGCATCC GCTGAGATTG CCCGAGGAGA AACAGCCAAT TCTGTGTCGT GTTACATGCG
1441 TACAAAGGGC ATCTCCGAGG AGCTGGCTAC CGAGTCTGTG ATGAACCTGA TCGATGAAAC
1501 CTGTAAGAAG ATGAACAAAG AGAAACTGGG CGGTTCTCTG TTCGCCAAAC CATTTGTTGA
1561 AACCGCGATC AATCTGGCTC GTCAGTCTCA TTGTACTTAC CATAACGGTG ACGCGCACAC
1621 TTCGCCGGAC GAATTGACCC GTAAGCGTGT GCTTTCGGTG ATTACCGAGC CGATCCTGCC
1681 GTTCGAAAGA TAATAGGATC C
```

(SEQ ID NO:13)

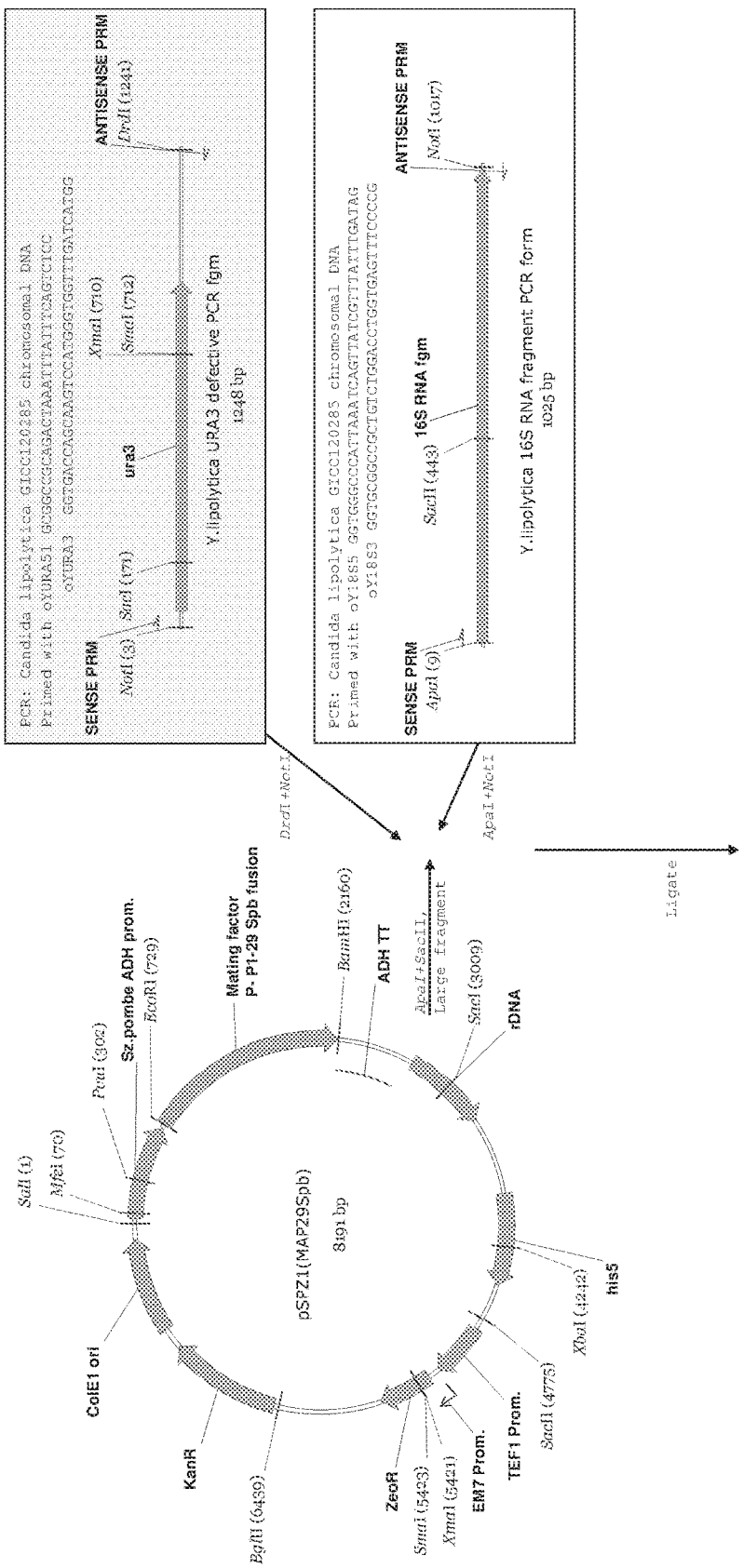
FIG. 18A(1)

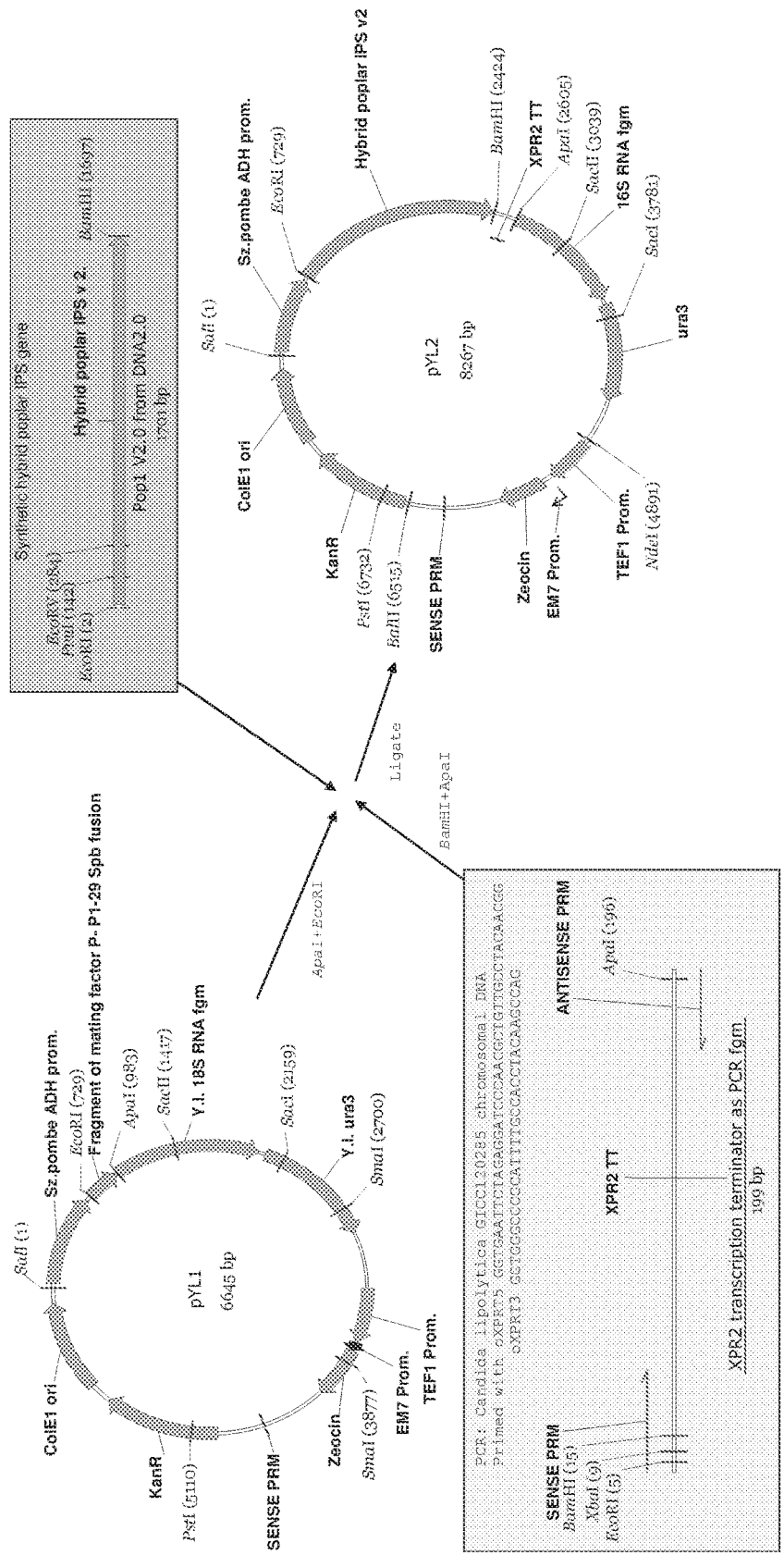
FIG. 18A(2)

FIG. 20
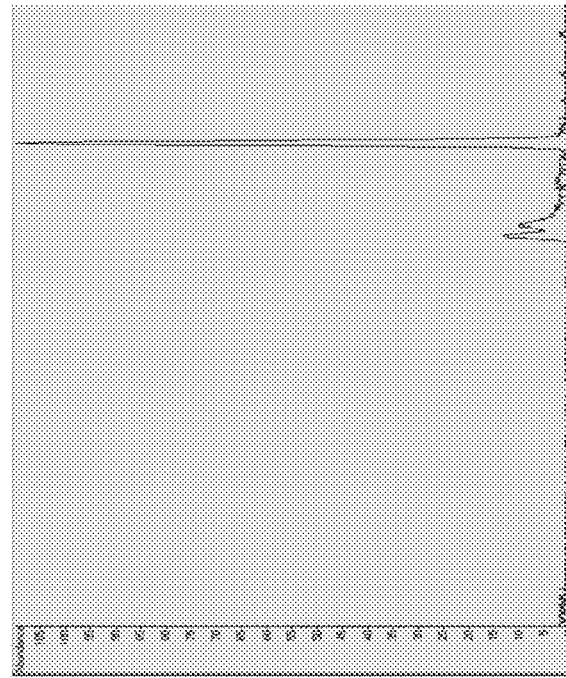
*Y. lipolytica* CLIB122:: pYLA(KZ1)
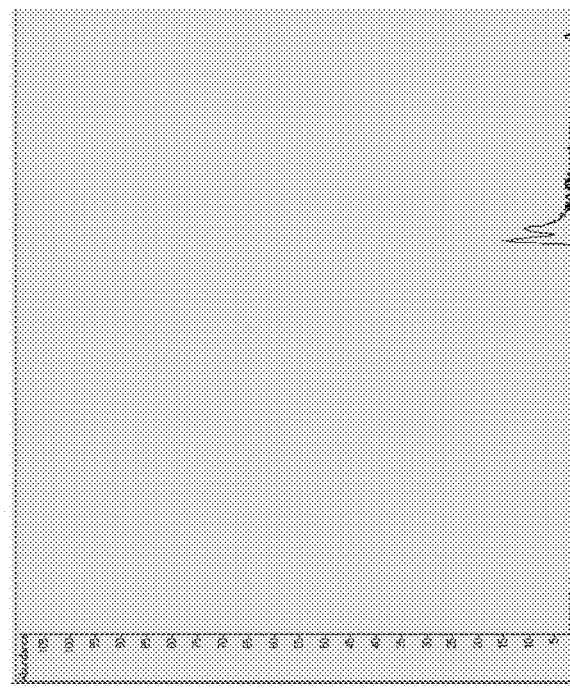
*Y. lipolytica* CLIB122:: pYLA(MAP29)

FIG. 22A 1-
gctggtaccatatgggaattcgaagctttctagaacaaaaactcatctcagaagaggatctgaa
tagcgccgtcgaccatcatcatcatcatcattgagtttaaacggtctccagcttggctgttttg
gcggatgagagaagattttcagcctgatacagattaaatcagaacgcagaagcggtctgataaa
acagaatttgcctggcggcagtagcgcggtggtcccacctgacccatgccgaactcagaagtg
aaacgccgtagcgccgatggtagtgtgggtctcccatgcgagagtagggaactgccaggcat
caaataaaacgaaaggctcagtcgaaagactgggcctttcgttttatctgttgtttgtcggtga
acgctctcctgagtaggacaaatccgccgggagcggatttgaacgttgcgaagcaacggcccgg
agggtggcgggcaggacgcccgccataaactgccaggcatcaaattaagcagaaggccatcctg
acggatggcctttttgcgtttctacaaactcttttgtttattttctaaatacattcaaatat
gtatccgcttaaccggaattgccagctggggcgccctctggtaaggttgggaagccctgcaaag
taaactggatggctttctcgccgccaaggatctgatggcgcaggggatcaagctctgatcaaga
gacaggatgaggatcgtttcgcatgattgaacaagatggattgcacgcaggttctccggccgct
tgggtggagaggctattcggctatgactgggcacaacagacaatcggctgctctgatgccgccg
tgttccggctgtcagcgcaggggcgcccggttcttttgtcaagaccgacctgtccggtgccct
gaatgaactgcaagacgaggcagcgcggctatcgtggctggccacgacgggcgttccttgcgca
gctgtgctcgacgttgtcactgaagcgggaagggactggctgctattgggcgaagtgccggggc
aggatctcctgtcatctcaccttgctcctgccgagaaagtatccatcatggctgatgcaatgcg
gcggctgcatacgcttgatccggctacctgcccattcgaccaccaagcgaaacatcgcatcgag
cgagcacgtactcggatggaagccggtcttgtcgatcaggatgatctggacgaagagcatcagg
ggctcgcgccagccgaactgttcgccaggctcaaggcgagcatgcccgacggcgaggatctcgt
cgtgacccatggcgatgcctgcttgccgaatatcatggtggaaaatggccgcttttctggattc
atcgactgtggccggctgggtgtggcggaccgctatcaggacatagcgttggctacccgtgata
ttgctgaagagcttggcggcgaatgggctgaccgcttcctcgtgctttacggtatcgccgctcc
cgattcgcagcgcatcgccttctatcgccttcttgacgagttcttctgacatgaccaaaatccc
ttaacgtgagttttcgttccactgagcgtcagaccccgtagaaaagatcaaaggatcttcttga
gatcctttttttctgcgcgtaatctgctgcttgcaaacaaaaaaaccaccgctaccagcggtgg
tttgtttgccggatcaagagctaccaactctttttccgaaggtaactggcttcagcagagcgca
gataccaaatactgtccttctagtgtagccgtagttaggccaccacttcaagaactctgtagca
ccgcctacatacctcgctctgctaatcctgttaccagtggctgctgccagtggcgataagtcgt
gtcttaccgggttggactcaagacgatagttaccggataaggcgcagcggtcgggctgaacggg
gggttcgtgcacacagcccagcttggagcgaacgacctacaccgaactgagatacctacagcgt
gagctatgagaaagcgccacgcttcccgaagggagaaaggcggacaggtatccggtaagcggca
gggtcggaacaggagagcgcacgagggagcttccaggggaaacgcctggtatctttatagtcc
tgtcgggtttcgccacctctgacttgagcgtcgattttgtgatgctcgtcaggggcggagc
ctatggaaaaacgccagcaacgcggccttttacgttcctggccttttgctggccttttgctc
acatgttctttcctgcgttatccctgattctgtggataaccgtattaccgcctttgagtgagc
tgataccgctcgccgcagccgaacgaccgagcgcagcgagtcagtgagcgaggaagcggaagag
cgcctgatgcggtattttctccttacgcatctgtgcggtatttcacaccgcatatggtgcactc
tcagtacaatctgctctgatgccgcatagttaagccagtatacactccgctatcgctacgtgac
tgggtcatggctgcgccccgacacccgccaacacccgctgacgcgccctgacgggcttgtctgc
tcccggcatccgcttacagacaagctgtgaccgtctccgggagctgcatgtgtcagaggttttc
accgtcatcaccgaaacgcgcgaggcagcagatcaattcgcgcgcgaaggcgaagcggcatgca
tttacgttgacaccatcgaatggtgcaaaacctttcgcggtatggcatgatagcgcccggaaga

FIG. 22B

```
gagtcaattcagggtggtgaatgtgaaaccagtaacgttatacgatgtcgcagagtatgccggt
gtctcttatcagaccgtttcccgcgtggtgaaccaggccagccacgtttctgcgaaaacgcggg
aaaaagtggaagcggcgatggcggagctgaattacattcccaaccgcgtggcacaacaactggc
gggcaaacagtcgttgctgattggcgttgccacctccagtctggccctgcacgcgccgtcgcaa
attgtcgcggcgattaaatctcgcgccgatcaactgggtgccagcgtggtggtgtcgatggtag
aacgaagcggcgtcgaagcctgtaaagcggcggtgcacaatcttctcgcgcaacgcgtcagtgg
gctgatcattaactatccgctggatgaccaggatgccattgctgtggaagctgcctgcactaat
gttccggcgttatttcttgatgtctctgaccagacacccatcaacagtattattttctcccatg
aagacggtacgcgactgggcgtggagcatctggtcgcattgggtcaccagcaaatcgcgctgtt
agcgggcccattaagttctgtctcggcgcgtctgcgtctggctggctggcataaatatctcact
cgcaatcaaattcagccgatagcggaacgggaaggcgactggagtgccatgtccggttttcaac
aaaccatgcaaatgctgaatgagggcatcgttcccactgcgatgctggttgccaacgatcagat
ggcgctgggcgcaatgcgcgccattaccgagtccgggctgcgcgttggtgcggatatctcggta
gtgggatacgacgataccgaagacagctcatgttatatcccgccgtcaaccaccatcaaacagg
attttcgcctgctggggcaaaccagcgtggaccgcttgctgcaactctctcagggccaggcggt
gaagggcaatcagctgttgcccgtctcactggtgaaaagaaaaaccaccctggcgcccaatacg
caaaccgcctctccccgcgcgttggccgattcattaatgcagctggcacgacaggtttcccgac
tggaaagcgggcagtgagcgcaacgcaattaatgtgagttagcgcgaattgatctggtttgaca
gcttatcatcgactgcacggtgcaccaatgcttctggcgtcaggcagccatcggaagctgtggt
atggctgtgcaggtcgtaaatcactgcataattcgtgtcgctcaaggcgcactcccgttctgga
taatgttttttgcgccgacatcataacggttctggcaaatattctgaaatgagctgttgacaat
taatcatccggctcgtataatgtgtggaattgtgagcggataacaatttcacacaggaaacagc
gccgctgagaaaagcgaagcggcactgctctttaacaatttatcagacaatctgtgtgggcac
tcgaccggaattatcgattaactttattattaaaaattaagaggtatatattaatgtatcgat
taaataaggaggaataaaccatgtgtgcgacctcttctcaatttactcagattaccgagcataa
ttcccgtcgttccgcaaactatcagccaaacctgtggaatttcgaattcctgcaatccctggag
aacgacctgaaagtggaaaagctggaggagaaagcgaccaaactggaggaagaagttcgctgca
tgatcaaccgtgtagacacccagccgctgtccctgctggagctgatcgacgatgtgcagcgcct
gggtctgacctacaaatttgaaaagacatcattaaagccctggaaaacatcgtactgctggac
gaaaacaaaagaacaaatctgacctgcacgcaaccgctctgtctttccgtctgctgcgtcagc
acggtttcgaggtttctcaggatgtttttgagcgtttcaaggataaagaaggtggtttcagcgg
tgaactgaaaggtgacgtccaaggcctgctgagcctgtatgaagcgtcttacctgggtttcgag
ggtgagaacctgctggaggaggcgcgtaccttttccatcacccacctgaagaacaacctgaaag
aaggcattaataccaaggttgcagaacaagtgagccacgccctggaactgccatatcaccagcg
tctgcaccgtctggaggcacgttggttcctggataaatacgaaccgaaagaaccgcatcaccag
ctgctgctggagctggcgaagctggattttaacatggtacagaccctgcaccagaaagagctgc
aagatctgtcccgctggtggaccgagatgggcctggctagcaaactggattttgtacgcgaccg
cctgatggaagtttatttctgggcactgggtatggcgccagacccgcagtttggtgaatgtcgc
aaagctgttactaaaatgtttggtctggtgacgatcatcgatgacgtgtatgacgtttatggca
ctctggacgaactgcaactgttcaccgatgctgtagagcgctgggacgttaacgctattaacac
cctgccggactatatgaaactgtgtttcctggcactgtacaacaccgttaacgacacgtcctat
tctattctgaaagagaaaggtcataacaacctgtcctatctgacgaaaagctggcgtgaactgt
gcaaagcctttctgcaagaggcgaaatggtccaacaacaaaattatcccggctttctccaagta
cctggaaaacgccagcgtttcctcctccggtgtagcgctgctggcgccgtcttacttttccgta
```

FIG. 22C

```
tgccagcagcaggaagacatctccgaccacgcgctgcgttccctgaccgacttccatggtctgg
tgcgttctagctgcgttatcttccgcctgtgcaacgatctggccacctctgcggcggagctgga
acgtggcgagactaccaattctatcattagctacatgcacgaaaacgatggtaccagcgaggaa
caggcccgcgaagaactgcgtaaactgatcgacgccgaatggaaaagatgaatcgtgaacgcg
ttagcgactccaccctgctgcctaaagcgttcatggaaatcgcagttaacatggcacgtgtttc
ccactgcacctaccagtatggcgatggtctgggtcgcccagactacgcgactgaaaaccgcatc
aaactgctgctgattgaccctttccgattaaccagctgatgtatgtctaactgcatcgccctt
aggaggtaaaaaaaatgactgccgacaacaatagtatgccccatggtgcagtatctagttacg
ccaaattagtgcaaaaccaaacacctgaagacattttggaagagtttcctgaaattattccatt
acaacaaagacctaatacccgatctagtgagacgtcaaatgacgaaagcggagaaacatgtttt
tctggtcatgatgaggagcaaattaagttaatgaatgaaaattgtattgttttggattgggacg
ataatgctattggtgccggtaccaagaaagtttgtcatttaatggaaaatattgaaaagggttt
actacatcgtgcattctccgtctttattttcaatgaacaaggtgaattacttttacaacaaaga
gccactgaaaaaataactttccctgatctttggactaacacatgctgctctcatccactatgta
ttgatgacgaattaggtttgaagggtaagctagacgataagattaagggcgctattactgcggc
ggtgagaaaactagatcatgaattaggtattccagaagatgaaactaagacaaggggtaagttt
cacttttttaaacagaatccattacatggcaccaagcaatgaaccatgggtgaacatgaaattg
attacatcctatttataagatcaacgctaaagaaaacttgactgtcaacccaaacgtcaatga
agttagagacttcaaatgggtttcaccaaatgatttgaaaactatgtttgctgacccaagttac
aagtttacgccttggtttaagattatttgcgagaattacttattcaactggtgggagcaattag
atgacctttctgaagtggaaaatgacaggcaaattcatagaatgctataacaacgcgtcctgca
ttcgcccttaggaggtaaaaaaacatgagttttgatattgccaaatacccgaccctggcactgg
tcgactccacccaggagttacgactgttgccgaaagagagtttaccgaaactctgcgacgaact
gcgccgctatttactcgacagcgtgagccgttccagcgggcacttcgcctccgggctgggcacg
gtcgaactgaccgtggcgctgcactatgtctacaacaccccgtttgaccaattgatttgggatg
tggggcatcaggcttatccgcataaaattttgaccggacgccgcgacaaaatcggcaccatccg
tcagaaaggcggtctgcacccgttcccgtggcgcggcgaaagcgaatatgacgtattaagcgtc
gggcattcatcaacctccatcagtgccggaattggtattgcggttgctgccgaaaaagaaggca
aaaatcgccgcaccgtctgtgtcattggcgatggcgcgattaccgcaggcatggcgtttgaagc
gatgaatcacgcgggcgatatccgtcctgatatgctggtgattctcaacgacaatgaaatgtcg
atttccgaaaatgtcggcgcgctcaacaaccatctggcacagctgctttccggtaagctttact
cttcactgcgcgaaggcgggaaaaagttttctctggcgtgccgccaattaaagagctgctcaa
acgcaccgaagaacatattaaaggcatggtagtgcctggcacgttgtttgaagagctgggcttt
aactacatcggcccggtggacggtcacgatgtgctggggcttatcaccacgctaaagaacatgc
gcgacctgaaaggcccgcagttcctgcatatcatgaccaaaaaaggtcgtggttatgaaccggc
agaaaaagacccgatcactttccacgccgtgcctaaatttgatcctccagcggttgtttgccg
aaaagtagcggcggtttgccgagctattcaaaaatctttggcgactggttgtgcgaaacggcag
cgaaagacaacaagctgatggcgattactccggcgatgcgtgaaggttccggcatggtcgagtt
ttcacgtaaattcccggatcgctacttcgacgtggcaattgccgagcaacacgcggtgaccttt
gctgcgggtctggcgattggtgggtacaaacccattgtcgcgatttactccactttcctgcaac
gcgcctatgatcaggtgctgcatgacgtggcgattcaaaagcttccggtcctgttcgccatcga
ccgcgcgggcattgttggtgctgacggtcaaacccatcagggtgcttttgatctctcttacctg
cgctgcataccggaaatggtcattatgaccccgagcgatgaaaacgaatgtcgccagatgctct
ataccggctatcactataacgatggcccgtcagcggtgcgctacccgcgtggcaacgcggtcgg
```

FIG. 22D

```
cgtggaactgacgccgctggaaaaactaccaattggcaaaggcattgtgaagcgtcgtggcgag
aaactggcgatccttaactttggtacgctgatgccagaagcggcgaaagtcgccgaatcgctga
acgccacgctggtcgatatgcgttttgtgaaaccgcttgatgaagcgttaattctggaaatggc
cgccagccatgaagcgctggtcaccgtagaagaaaacgccattatgggcggcgcaggcagcggc
gtgaacgaagtgctgatggcccatcgtaaaccagtacccgtgctgaacattggcctgccggact
tctttattccgcaaggaactcaggaagaaatgcgcgccgaactcggcctcgatgccgctggtat
ggaagccaaaatcaaggcctggctggcataactgca
```
(SEQ ID NO:20)

FIG. 25A

5'-
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaagcgaagcggcactgctctttaacaatttatcagacaatctgt
gtgggcactcgaccggaattatcgattaactttattattaaaaattaaagaggtatatattaat
gtatcgattaaataaggaggaataaaccatggatccgagctcggatccactagtaacggccgcc
agtgtgctggaattcgcccttaggagtaaaaaaacatgtcattaccgttcttaacttctgcac
cgggaaaggttattattttggtgaacactctgctgtgtacaacaagcctgccgtcgctgctag
tgtgtctgcgttgagaacctacctgctaataagcgagtcatctgcaccagatactattgaattg
gacttcccggacattagctttaatcataagtggtccatcaatgatttcaatgccatcaccgagg
atcaagtaaactcccaaaaattggccaaggctcaacaagccaccgatggcttgtctcaggaact
cgttagtcttttggatccgttgttagctcaactatccgaatccttccactaccatgcagcgttt
tgtttcctgtatatgtttgtttgcctatgccccatgccaagaatattaagttttctttaaagt
ctactttacccatcggtgctggttgggctcaagcgcctctatttctgtatcactggccttagc
tatggcctacttgggggggttaataggatctaatgacttggaaaagctgtcagaaaacgataag
catatagtgaatcaatgggccttcataggtgaaaagtgtattcacggtacccttcaggaatag
ataacgctgtggccacttatggtaatgccctgctatttgaaaagactcacataatggaacaat
aaacacaaacaattttaagttcttagatgatttcccagccattccaatgatcctaacctatact
agaattccaaggtctacaaaagatcttgttgctcgcgttcgtgtgttggtcaccgagaaatttc
ctgaagttatgaagccaattctagatgccatggtgaatgtgccctacaaggcttagagatcat
gactaagttaagtaaatgtaaaggcaccgatgacgaggctgtagaaactaataatgaactgtat
gaacaactattggaattgataagaataaatcatggactgcttgtctcaatcggtgtttctcatc
ctggattagaacttattaaaaatctgagcgatgatttgagaattggctccacaaaacttaccgg
tgctggtggcggcggttgctctttgactttgttacgaagagacattactcaagagcaaattgac
agcttcaaaaagaaattgcaagatgatttagttacgagacatttgaaacagacttgggtggga
ctggctgctgtttgttaagcgcaaaaaatttgaataaagatcttaaaatcaaatccctagtatt
ccaattatttgaaaataaaactaccacaaagcaacaaattgacgatctattattgccaggaaac
acgaatttaccatggacttcataagctaatttgcgataggcctgcacccttaaggaggaaaaaa
acatgtcagagttgagagccttcagtgccccagggaaagcgttactagctggtggatatttagt
tttagatacaaaatatgaagcatttgtagtcggattatcggcaagaatgcatgctgtagcccat
ccttacggttcattgcaagggtctgataagtttgaagtgcgtgtgaaaagtaaacaatttaaag
atggggagtggctgtaccatataagtcctaaaagtggcttcattcctgtttcgataggcggatc
taagaacccctttcattgaaaaagttatcgctaacgtatttagctactttaaacctaacatggac
gactactgcaatagaaacttgttcgttattgatattttctctgatgatgcctaccattctcagg
aggatagcgttaccgaacatcgtggcaacagaagattgagttttcattcgcacagaattgaaga
agttcccaaaacagggctgggctcctcggcaggtttagtcacagttttaactacagctttggcc
tccttttttgtatcggacctggaaaataatgtagacaaatatagagaagttattcataatttag
cacaagttgctcattgtcaagctcagggtaaattggaagcgggtttgatgtagcggcggcagc
atatggatctatcagatatagaagattcccacccgcattaatctctaatttgccagatattgga
agtgctacttacggcagtaaactggcgcatttggttgatgaagaagactggaatattacgatta
aaagtaaccatttaccttcgggattaactttatggatgggcgatattaagaatggttcagaaac
agtaaaactggtccagaaggtaaaaaattggtatgattcgcatatgccagaaagcttgaaaata

FIG. 25B

```
tatacagaactcgatcatgcaaattctagatttatggatggactatctaaactagatcgcttac
acgagactcatgacgattacagcgatcagatatttgagtctcttgagaggaatgactgtacctg
tcaaaagtatcctgaaatcacagaagttagagatgcagttgccacaattagacgttcctttaga
aaaataactaaagaatctggtgccgatatcgaacctccgtacaaactagcttattggatgatt
gccagaccttaaaaggagttcttacttgcttaatacctggtgctggtggttatgacgccattgc
agtgattactaagcaagatgttgatcttagggctcaaaccgctaatgacaaaagatttctaag
gttcaatggctggatgtaactcaggctgactggggtgttaggaaagaaaaagatccggaactt
atcttgataaataacttaaggtagctgcatgcagaattcgcccttaaggaggaaaaaaaatga
ccgtttacacagcatccgttaccgcacccgtcaacatcgcaacccttaagtattggggaaaag
ggacacgaagttgaatctgcccaccaattcgtccatatcagtgactttatcgcaagatgacctc
agaacgttgacctctgcggctactgcacctgagtttgaacgcgacactttgtggttaaatggag
aaccacacagcatcgacaatgaaagaactcaaaattgtctgcgcgacctacgccaattaagaaa
ggaaatggaatcgaaggacgcctcattgcccacattatctcaatggaaactccacattgtctcc
gaaaataactttcctacagcagctggtttagcttcctccgctgctggctttgctgcattggtct
ctgcaattgctaagttataccaattaccacagtcaacttcagaaatatctagaatagcaagaaa
ggggtctggttcagcttgtagatcgttgtttggcggatacgtggcctgggaaatgggaaaagct
gaagatggtcatgattccatggcagtacaaatcgcagacagctctgactggcctcagatgaaag
cttgtgtcctagttgtcagcgatattaaaaaggatgtgagttccactcagggtatgcaattgac
cgtggcaacctccgaactatttaaagaagaattgaacatgtcgtaccaaagagatttgaagtc
atgcgtaaagccattgttgaaaagatttcgccacctttgcaaaggaaacaatgatggattcca
actctttccatgccacatgtttggactcttccctccaatattctacatgaatgacacttccaa
gcgtatcatcagttggtgccacaccattaatcagttttacggagaaacaatcgttgcatacacg
tttgatgcaggtccaaatgctgtgttgtactacttagctgaaaatgagtcgaaactctttgcat
ttatctataaattgtttggctctgttcctggatgggacaagaaatttactactgagcagcttga
ggctttcaaccatcaatttgaatcatctaactttactgcacgtgaattggatcttgagttgcaa
aaggatgttgccagagtgattttaactcaagtcggttcaggcccacaagaaacaaacgaatctt
tgattgacgcaaagactggtctaccaaaggaataagatcaattcgctgcatcgcccttaggagg
taaaaaaaatgactgccgacaacaatagtatgccccatggtgcagtatctagttacgccaaat
tagtgcaaaaccaaacacctgaagacattttggaagagtttcctgaaattattccattacaaca
aagacctaatacccgatctagtgagacgtcaaatgacgaaagcggagaaacatgttttttctggt
catgatgaggagcaaattaagttaatgaatgaaaattgtattgttttggattgggacgataatg
ctattggtgccggtaccaagaaagtttgtcatttaatggaaaatattgaaaagggtttactaca
tcgtgcattctccgtctttatttttcaatgaacaaggtgaattacttttacaacaaagagccact
gaaaaaataactttccctgatctttggactaacacatgctgctctcatccactatgtattgatg
acgaattaggtttgaagggtaagctagacgataagattaagggcgctattactgcggcggtgag
aaaactagatcatgaattaggtattccagaagatgaaactaagacaaggggtaagtttcacttt
ttaaacagaatccattacatggcaccaagcaatgaaccatgggtgaacatgaaattgattaca
tcctattttataagatcaacgctaaagaaacttgactgtcaacccaaacgtcaatgaagttag
agacttcaaatgggtttcaccaaatgatttgaaaactatgtttgctgacccaagttacaagttt
acgccttggtttaagattattgcgagaattacttattcaactggtgggagcaattagatgacc
tttctgaagtggaaaatgacaggcaaattcatagaatgctataacaacgcgtcctgcattcgcc
cttaggaggtaaaaaacatgtgtgcgacctcttctcaatttactcagattaccgagcataatt
cccgtcgttccgcaaactatcagccaaacctgtggaatttcgaattcctgcaatccctggagaa
cgacctgaaagtggaaaagctggaggagaaagcgaccaaactggaggaagaagttcgctgcatg
```

FIG. 25C

```
atcaaccgtgtagacacccagccgctgtccctgctggagctgatcgacgatgtgcagcgcctgg
gtctgacctacaaatttgaaaaagacatcattaaagccctggaaaacatcgtactgctggacga
aaacaaaaagaacaaatctgacctgcacgcaaccgctctgtctttccgtctgctgcgtcagcac
ggtttcgaggtttctcaggatgtttttgagcgtttcaaggataaagaaggtggtttcagcggtg
aactgaaaggtgacgtccaaggcctgctgagcctgtatgaagcgtcttacctgggtttcgaggg
tgagaacctgctggaggaggcgcgtaccttttccatcacccacctgaagaacaacctgaaagaa
ggcattaataccaaggttgcagaacaagtgagccacgccctggaactgccatatcaccagcgtc
tgcaccgtctggaggcacgttggttcctggataaatacgaaccgaaagaaccgcatcaccagct
gctgctggagctggcgaagctggattttaacatggtacagaccctgcaccagaaagagctgcaa
gatctgtcccgctggtggaccgagatgggcctggctagcaaactggattttgtacgcgaccgcc
tgatggaagtttatttctgggcactgggtatggcgccagacccgcagtttggtgaatgtcgcaa
agctgttactaaaatgtttggtctggtgacgatcatcgatgacgtgtatgacgtttatggcact
ctggacgaactgcaactgttcaccgatgctgtagagcgctgggacgttaacgctattaacaccc
tgccggactatatgaaactgtgtttcctggcactgtacaacaccgttaacgacacgtcctattc
tattctgaaagagaaaggtcataacaacctgtcctatctgacgaaaagctggcgtgaactgtgc
aaagcctttctgcaagaggcgaaatggtccaacaacaaaattatcccggctttctccaagtacc
tggaaaacgccagcgtttcctcctccggtgtagcgctgctggcgccgtcttacttttccgtatg
ccagcagcaggaagacatctccgaccacgcgctgcgttccctgaccgacttccatggtctggtg
cgttctagctgcgttatcttccgcctgtgcaacgatctggccacctctgcggcggagctggaac
gtggcgagactaccaattctatcattagctacatgcacgaaaacgatggtaccagcgaggaaca
ggcccgcgaagaactgcgtaaactgatcgacgccgaatggaaaaagatgaatcgtgaacgcgtt
agcgactccaccctgctgcctaaagcgttcatggaaatcgcagttaacatggcacgtgtttccc
actgcacctaccagtatggcgatggtctgggtcgcccagactacgcgactgaaaaccgcatcaa
actgctgctgattgacccttcccgattaaccagctgatgtatgtctaactgcagctggtacca
tatgggaattcgaagctttctagaacaaaaactcatctcagaagaggatctgaatagcgccgtc
gaccatcatcatcatcatcattgagtttaaacggtctccagcttggctgttttggcggatgaga
gaagattttcagcctgatacagattaaatcagaacgcagaagcggtctgataaaacagaatttg
cctggcggcagtagcgcggtggtcccacctgaccccatgccgaactcagaagtgaaacgccgta
gcgccgatggtagtgtggggtctccccatgcgagagtagggaactgccaggcatcaaataaaac
gaaaggctcagtcgaaagactgggcctttcgttttatctgttgtttgtcggtgaacgctctcct
gagtaggacaaatccgccgggagcggatttgaacgttgcgaagcaacggcccggagggtggcgg
gcaggacgcccgccataaactgccaggcatcaaattaagcagaaggccatcctgacggatggcc
ttttgcgtttctacaaactcttttgttattttctaaatacattcaaatatgtatccgctt
aaccggaattgccagctggggcgccctctggtaaggttgggaagccctgcaaagtaaactggat
ggctttctcgccgccaaggatctgatggcgcaggggatcaagctctgatcaagagacaggatga
ggatcgtttcgcatgattgaacaagatggattgcacgcaggttctccggccgcttgggtggaga
ggctattcggctatgactgggcacaacagacaatcggctgctctgatgccgccgtgttccggct
gtcagcgcaggggcgcccggttcttttttgtcaagaccgacctgtccggtgccctgaatgaactg
caagacgaggcagcgcggctatcgtggctggccacgacgggcgttccttgcgcagctgtgctcg
acgttgtcactgaagcgggaagggactggctgctattgggcgaagtgccggggcaggatctcct
gtcatctcaccttgctcctgccgagaaagtatccatcatggctgatgcaatgcggcggctgcat
acgcttgatccggctacctgcccattcgaccaccaagcgaaacatcgcatcgagcgagcacgta
ctcggatggaagccggtcttgtcgatcaggatgatctggacgaagagcatcagggctcgcgcc
agccgaactgttcgccaggctcaaggcgagcatgcccgacggcgaggatctcgtcgtgacccat
```

FIG. 25D

```
ggcgatgcctgcttgccgaatatcatggtggaaaatggccgcttttctggattcatcgactgtg
gccggctgggtgtggcggaccgctatcaggacatagcgttggctacccgtgatattgctgaaga
gcttggcggcgaatgggctgaccgcttcctcgtgctttacggtatcgccgctcccgattcgcag
cgcatcgccttctatcgccttcttgacgagttcttctgacgcatgaccaaaatcccttaacgtg
agttttcgttccactgagcgtcagaccccgtagaaaagatcaaaggatcttcttgagatccttt
ttttctgcgcgtaatctgctgcttgcaaacaaaaaaaccaccgctaccagcggtggtttgtttg
ccggatcaagagctaccaactcttttttccgaaggtaactggcttcagcagagcgcagataccaa
atactgtccttctagtgtagccgtagttaggccaccacttcaagaactctgtagcaccgcctac
atacctcgctctgctaatcctgttaccagtggctgctgccagtggcgataagtcgtgtcttacc
gggttggactcaagacgatagttaccggataaggcgcagcggtcgggctgaacgggggttcgt
gcacacagcccagcttggagcgaacgacctacaccgaactgagatacctacagcgtgagctatg
agaaagcgccacgcttcccgaagggagaaaggcggacaggtatccggtaagcggcagggtcgga
acaggagagcgcacgagggagcttccaggggaaacgcctggtatctttatagtcctgtcgggt
ttcgccacctctgacttgagcgtcgattttgtgatgctcgtcaggggggcggagcctatggaa
aaacgccagcaacgcggccttttacggttcctggccttttgctggccttttgctcacatgttc
tttcctgcgttatcccctgattctgtggataaccgtattaccgcctttgagtgagctgataccg
ctcgccgcagccgaacgaccgagcgcagcgagtcagtgagcgaggaagcggaagagcgcctgat
gcggtatttctccttacgcatctgtgcggtatttcacaccgcatatggtgcactctcagtaca
atctgctctgatgccgcatagttaagccagtatacactccgctatcgctacgtgactgggtcat
ggctgcgccccgacacccgccaacacccgctgacgcgccctgacgggcttgtctgctcccggca
tccgcttacagacaagctgtgaccgtctccgggagctgcatgtgtcagaggttttcaccgtcat
caccgaaacgcgcgaggcagcagatcaattcgcgcgcgaaggcgaagcggcatgcatttacgtt
gacaccatcgaatggtgcaaaacctttcgcggtatggcatgatagcgccggaagagagtcaat
tcagggtggtgaatgtgaaaccagtaacgttatacgatgtcgcagagtatgccggtgtctctta
tcagaccgtttccgcgtggtgaaccaggccagccacgtttctgcgaaaacgcgggaaaagtg
gaagcggcgatggcggagctgaattacattcccaaccgcgtggcacaacaactggcgggcaaac
agtcgttgctgattggcgttgccacctccagtctggccctgcacgcgccgtcgcaaattgtcgc
ggcgattaaatctcgcgccgatcaactgggtgccagcgtggtggtgtcgatggtagaacgaagc
ggcgtcgaagcctgtaaagcggcggtgcacaatcttctcgcgcaacgcgtcagtggctgatca
ttaactatccgctggatgaccaggatgccattgctgtggaagctgcctgcactaatgttccggc
gttatttcttgatgtctctgaccagacacccatcaacagtattattttctcccatgaagacggt
acgcgactgggcgtggagcatctggtcgcattgggtcaccagcaaatcgcgctgttagcgggcc
cattaagttctgtctcggcgcgtctgcgtctggctggctggcataaatatctcactcgcaatca
aattcagccgatagcggaacgggaaggcgactggagtgccatgtccggttttcaacaaaccatg
caaatgctgaatgagggcatcgttcccactgcgatgctggttgccaacgatcagatggcgctgg
gcgcaatgcgcgccattaccgagtccgggctgcgcgttggtgcggatatctcggtagtgggata
cgacgataccgaagacagctcatgttatatcccgccgtcaaccaccatcaaacaggattttcgc
ctgctggggcaaaccagcgtggaccgcttgctgcaactctctcagggccaggcggtgaaggca
atcagctgttcccgtctcactggtgaaagaaaaccaccctggcgcccaatacgcaaaccgc
ctctcccgcgcgttggccgattcattaatgcagctggcacgacaggtttcccgactggaaagc
gggcagtgagcgcaacgcaattaatgtgagttagcgcgaattgatctg
```
(SEQ ID NO:33)

FIG. 27A

5'-
cccgtcttactgtcgggaattcgcgttggccgattcattaatgcagattctgaaatgagctgtt
gacaattaatcatccggctcgtataatgtgtggaattgtgagcggataacaatttcacacagga
aacagcgccgctgagaaaagcgaagcggcactgctctttaacaatttatcagacaatctgtgt
gggcactcgaccggaattatcgattaactttattattaaaaattaaagaggtatatattaatgt
atcgattaaataaggaggaataaaccatggatccgagctcaggaggtaaaaaaacatgaaaaca
gtagttattattgatgcattacgaacaccaattggaaaatataaaggcagcttaagtcaagtaa
gtgccgtagacttaggaacacatgttacaacacaacttttaaaaagacattccactatttctga
agaaattgatcaagtaatctttggaaatgttttacaagctggaaatggccaaaatcccgcacga
caaatagcaataaacagcggtttgtctcatgaaattcccgcaatgacggttaatgaggtctgcg
gatcaggaatgaaggccgttattttggcgaaacaattgattcaattaggagaagcggaagtttt
aattgctggcgggattgagaatatgtcccaagcacctaaattacaacgttttaattacgaaaca
gaaagctacgatgcgccttttttctagtatgatgtatgatggattaacggatgcctttagtggtc
aggcaatgggcttaactgctgaaaatgtggccgaaaagtatcatgtaactagagaagagcaaga
tcaattttctgtacattcacaattaaaagcagctcaagcacaagcagaagggatattcgctgac
gaaatagccccattagaagtatcaggaacgcttgtggagaaagatgaagggattcgccctaatt
cgagcgttgagaagctaggaacgcttaaaacagtttttaaagaagacggtactgtaacagcagg
gaatgcatcaaccattaatgatggggcttctgctttgattattgcttcacaagaatatgccgaa
gcacacggtcttccttatttagctattattcgagacagtgtggaagtcggtattgatccagcct
atatgggaatttcgccgattaaagccattcaaaaactgttagcgcgcaatcaacttactacgga
agaaattgatctgtatgaaatcaacgaagcatttgcagcaacttcaatcgtggtccaaagagaa
ctggctttaccagaggaaaaggtcaacatttatggtggcggtatttcattaggtcatgcgattg
gtgccacaggtgctcgtttattaacgagtttaagttatcaattaaatcaaaagaaaagaaata
tggagtggcttctttatgtatcggcggtggcttaggactcgctatgctactagagagacctcag
caaaaaaaaacagccgatttatcaaatgagtcctgaggaacgcctggcttctcttcttaatg
aaggccagatttctgctgatacaaaaaagaatttgaaaatacggctttatcttcgcagattgc
caatcatatgattgaaaatcaaatcagtgaaacagaagtgccgatgggcgttggcttacattta
acagtggacgaaactgattatttggtaccaatggcgacagaagagccctcagttattgcggctt
tgagtaatggtgcaaaaatagcacaaggatttaaaacagtgaatcaacaacgcttaatgcgtgg
acaaatcgttttttacgatgttgcagatcccgagtcattgattgataaactacaagtaagagaa
gcggaagtttttcaacaagcagagttaagttatccatctatcgttaaacggggcggcggcttaa
gagatttgcaatatcgtacttttgatgaatcatttgtatctgtcgacttttagtagatgttaa
ggatgcaatgggggcaaatatcgttaacgctatgttggaaggtgtggccgagttgttccgtgaa
tggtttgcggagcaaaagattttattcagtattttaagtaattatgccacggagtcggttgtta
cgatgaaaacggctattccagtttcacgtttaagtaaggggagcaatggccgggaaattgctga
aaaaattgttttagcttcacgctatgcttcattagatccttatcgggcagtcacgcataacaaa
ggaatcatgaatggcattgaagctgtagttttagctacaggaaatgatacacgcgctgttagcg
cttcttgtcatgcttttgcggtgaaggaaggtcgctaccaaggcttgactagttggacgctgga
tggcgaacaactaattggtgaaatttcagttccgcttgctttagccacggttggcggtgccaca
aaagtcttacctaaatctcaagcagctgctgatttgttagcagtgacggatgcaaaagaactaa
gtcgagtagtagcggctgttggtttggcacaaaatttagcggcgttacgggccttagtctctga
aggaattcaaaaggacacatggctctacaagcacgttctttagcgatgacggtcggagctact
ggtaaagaagttgaggcagtcgctcaacaattaaaacgtcaaaaaacgatgaaccaagaccgag
ccatggctattttaaatgatttaagaaaacaataaaggaggtaaaaaaacatgacaattgggat

FIG. 27B

```
tgataaaattagttttttttgtgcccccttattatattgatatgacggcactggctgaagccaga
aatgtagaccctggaaaatttcatattggtattgggcaagaccaaatggcggtgaacccaatca
gccaagatattgtgacatttgcagccaatgccgcagaagcgatcttgaccaaagaagataaaga
ggccattgatatggtgattgtcgggactgagtccagtatcgatgagtcaaaagcggccgcagtt
gtcttacatcgtttaatggggattcaaccttttcgctcgctctttcgaaatcaaggaagcttgtt
acggagcaacagcaggcttacagttagctaagaatcacgtagccttacatccagataaaaagt
cttggtcgtagcggcagatattgcaaaatatggcttaaattctggcggtgagcctacacaagga
gctggggcggttgcaatgttagttgctagtgaaccgcgcattttggctttaaaagaggataatg
tgatgctgacgcaagatatctatgacttttggcgtccaacaggccaccgtatcctatggtcga
tggtcctttgtcaaacgaaacctacatccaatcttttgcccaagtctgggatgaacataaaaaa
cgaaccggtcttgattttgcagattatgatgctttagcgttccatattccttacacaaaaatgg
gcaaaaagccttattagcaaaaatctccgaccaaactgaagcagaacaggaacgaattttagc
ccgttatgaagaaagtatcgtctatagtcgtcgcgtaggaaacttgtatacgggttcactttat
ctgggactcatttcccttttagaaaatgcaacgactttaaccgcaggcaatcaaattggtttat
tcagttatggttctggtgctgtcgctgaattttttcactggtgaattagtagctggttatcaaaa
tcatttacaaaaagaaactcatttagcactgctggataatcggacagaacttctatcgctgaa
tatgaagccatgtttgcagaaactttagacacagacattgatcaaacgttagaagatgaattaa
aatatagtatttctgctattaataataccgttcgttcttatcgaaactaagagatctgcagctg
gtaccatatgggaattcgaagcttgggcccgaacaaaaactcatctcagaagaggatctgaata
gcgccgtcgaccatcatcatcatcattgagtttaaacggtctccagcttggctgttttggc
ggatgagagaagattttcagcctgatacagattaaatcagaacgcagaagcggtctgataaaac
agaatttgcctggcggcagtagcgcggtggtcccacctgacccatgccgaactcagaagtgaa
acgccgtagcgccgatggtagtgtggggtctcccatgcgagagtagggaactgccaggcatca
aataaaacgaaaggctcagtcgaaagactgggcctttcgttttatctgttgtttgtcggtgaac
gctctcctgagtaggacaaatccgccgggagcggatttgaacgttgcgaagcaacggcccggag
ggtggcgggcaggacgcccgccataaactgccaggcatcaaattaagcagaaggccatcctgac
ggatggccttttttgcgtttctacaaactctttttgttttattttctaaatacattcaaatatgt
atccgctcatgagacaataaccctgataaatgcttcaataatctggcgtaatagcgaagaggcc
cgcaccgatcgcccttcccaacagttgcgcagcctgaatggcgaatggcgcctgatgcggtatt
ttctccttacgcatctgtgcggtatttcacaccgcatatggtgcactctcagtacaatctgctc
tgatgccgcatagttaagccagccccgacacccgccaacacccgctgacgagcttagtaaagcc
ctcgctagattttaatgcggatgttgcgattacttcgccaactattgcgataacaagaaaaagc
cagccttttcatgatatatctcccaatttgtgtagggcttattatgcacgcttaaaaataataaa
agcagacttgacctgatagtttggctgtgagcaattatgtgcttagtgcatctaacgcttgagt
taagccgcgccgcgaagcggcgtcggcttgaacgaattgttagacattatttgccgactaccctt
ggtgatctcgcctttcacgtagtggacaaattcttccaactgatctgcgcgcgaggccaagcga
tcttcttcttgtccaagataagcctgtctagcttcaagtatgacgggctgatactgggccggca
ggcgctccattgcccagtcggcagcgacatccttcggcgcgattttgccggttactgcgctgta
ccaaatgcgggacaacgtaagcactacatttcgctcatcgcagcccagtcgggcggcgagttc
catagcgttaaggtttcatttagcgcctcaaatagatcctgttcaggaaccggatcaaagagtt
cctccgccgctggacctaccaaggcaacgctatgttctcttgcttttgtcagcaagatagccag
atcaatgtcgatcgtggctggctcgaagatacctgcaagaatgtcattgcctgccattctcca
aattgcagttcgcgcttagctggataacgccacggaatgatgtcgtcgtgcacaacaatggtga
cttctacagcgcggagaatctcgctctctccaggggaagccgaagtttccaaaaggtcgttgat
```

FIG. 27C

```
caaagctcgccgcgttgtttcatcaagccttacggtcaccgtaaccagcaaatcaatatcactg
tgtggcttcaggccgccatccactgcggagccgtacaaatgtacggccagcaacgtcggttcga
gatggcgctcgatgacgccaactacctctgatagttgagtcgatacttcggcgatcaccgcttc
cctcatgatgtttaactttgttttagggcgactgccctgctgcgtaacatcgttgctgctccat
aacatcaaacatcgacccacggcgtaacgcgcttgctgcttggatgcccgaggcatagactgta
ccccaaaaaaacagtcataacaagccatgaaaaccgccactgcgccgttaccaccgctgcgttc
ggtcaaggttctggaccagttgcgtgagcgcatacgctacttgcattacagcttacgaaccgaa
caggcttatgtccactgggttcgtgccttcatccgtttccacggtgtgcgtcacccggcaacct
tgggcagcagcgaagtcgaggcatttctgtcctggctggcgaacgagcgcaaggtttcggtctc
cacgcatcgtcaggcattggcggccttgctgttcttctacggcaaggtgctgtgcacggatctg
ccctggcttcaggagatcggaagacctcggccgtcgcggcgcttgccggtggtgctgaccccgg
atgaagtggttcgcatcctcggttttctggaaggcgagcatcgtttgttcgcccagcttctgta
tggaacgggcatgcggatcagtgagggtttgcaactgcgggtcaaggatctggatttcgatcac
ggcacgatcatcgtgcgggagggcaagggctccaaggatcgggccttgatgttacccgagagct
tggcacccagcctgcgcgagcaggggaattaattcccacgggttttgctgcccgcaaacgggct
gttctggtgttgctagtttgttatcagaatcgcagatccggcttcagccggtttgccggctgaa
agcgctatttcttccagaattgccatgattttttcccacgggaggcgtcactggctcccgtgt
tgtcggcagctttgattcgataagcagcatcgcctgtttcaggctgtctatgtgtgactgttga
gctgtaacaagttgtctcaggtgttcaatttcatgttctagttgctttgttttactggtttcac
ctgttctattaggtgttacatgctgttcatctgttacattgtcgatctgttcatggtgaacagc
tttgaatgcaccaaaaactcgtaaaagctctgatgtatctatcttttttacaccgttttcatct
gtgcatatggacagttttccctttgatatgtaacggtgaacagttgttctacttttgtttgtta
gtcttgatgcttcactgatagatacaagagccataagaacctcagatccttccgtatttagcca
gtatgttctctagtgtggttcgttgttttgcgtgagccatgagaacgaaccattgagatcata
cttactttgcatgtcactcaaaaattttgcctcaaaactggtgagctgaattttgcagttaaa
gcatcgtgtagtgttttcttagtccgttatgtaggtaggaatctgatgtaatggttgttggta
ttttgtcaccattcattttatctggttgttctcaagttcggttacgagatccatttgtctatc
tagttcaacttggaaaatcaacgtatcagtcgggcggcctcgcttatcaaccaccaatttcata
ttgctgtaagtgtttaaatctttacttattggtttcaaaacccattggttaagccttttaaact
catggtagttattttcaagcattaacatgaacttaaattcatcaaggctaatctctatatttgc
cttgtgagttttcttttgtgttagttcttttaataaccactcataaatcctcatagagtatttg
ttttcaaaagacttaacatgttccagattatattttatgaattttttaactggaaaagataag
gcaatatctcttcactaaaaactaattctaattttcgcttgagaacttggcatagtttgtcca
ctggaaaatctcaaagcctttaaccaaggattcctgatttccacagttctcgtcatcagctct
ctggttgctttagctaatacaccataagcattttccctactgatgttcatcatctgagcgtatt
ggttataagtgaacgataccgtccgttctttccttgtagggttttcaatcgtggggttgagtag
tgccacacagcataaaattagcttggtttcatgctccgttaagtcatagcgactaatcgctagt
tcatttgctttgaaaacaactaattcagacatacatctcaattggtctaggtgattttaatcac
tataccaattgagatgggctagtcaatgataattactagtccttttcctttgagttgtgggtat
ctgtaaattctgctagacctttgctggaaaacttgtaaattctgctagaccctctgtaaattcc
gctagacctttgtgtgtttttttgtttatattcaagtggttataatttatagaataaagaaag
aataaaaaagataaaagaatagatcccagccctgtgtataactcactactttagtcagttcc
gcagtattacaaaggatgtcgcaaacgctgtttgcctctacaaaacagaccttaaaaccct
aaaggcttaagtagcaccctcgcaagctcgggcaaatcgctgaatattccttttgtctccgacc
```

FIG. 27D

Atcaggcacctgagtcgctgtcttttcgtgacattcagttcgctgcgctcacggctctggcag
tgaatgggggtaaatggcactacaggcgccttttatggattcatgcaaggaaactacccataat
acaagaaaagcccgtcacgggcttctcagggcgttttatggcgggtctgctatgtggtgctatc
tgacttttgctgttcagcagttcctgccctctgattttccagtctgaccacttcggattatcc
cgtgacaggtcattcagactggctaatgcacccagtaaggcagcggtatcatcaacaggctta
(SEQ ID NO:46)

Lower Pathway Bacillus Cassette
9371 bp

FIG. 29A

5'-
tgtaacctttgctttcaaatgagtagaaataatgcacatccatgtttgtatcgtgcaaataaag
tgtttcatccgtaggaaaaaatgactttagtatctgttccgcttttctgatgaaatgtgctcc
ccgacaaaattgaatgaatcatggacatttgctggctttgatacagcgaaagcagccgttcta
tgttatatatcggatttaacagcaggacaaaaaacaccatgacagccatcgtcacccacttatt
cacacgcacataaacctttcctgacttttggaacagatgatagctcatcaaaaatcccgccatt
gccaaataaatcgtatatggcattactgcaccataatcttttgagatttgattgggatatggcg
caagcagcaagacaagcagtccgataatcagcgtataaaataagcctagtaagatcttatccgt
tctccaatacagcttgaaaaacactacattcaacgcaatgggaagagtgatgatgaaaaacaga
aacacgaatgcaatcggctccatccatccgggtattccttccaatacgaaaagaaactaaaaa
tcatttgtacgatcggcaaactgacaacagcaaggtcgaacgtataaaacttacccttccgcc
atgatcacgcggcatcagcatatagtgaaaagccgtcagcagcacatatccgtataacaaaaaa
tgcagcagcggcagcagttcttttccgtcctctcttaagtaagcgctggtgaagtttgttgatt
gcacctggtgaataagttcaacagacactcccgccagcagcacaatccgcaatataacacccgc
caagaacattgtgcgctgccggtttatttgggatgatgcaccaaaagatataagcccgccaga
acaacaattgaccattgaatcagcagggtgctttgtctgttaatataaaataacgttcgaaat
gcaatacataatgactgaataactccaacacgaacaacaactccattttcttctgctatcaaaa
taacagactcgtgattttccaaacgagctttcaaaaaagcctctgccccttgcaaatcggatgc
ctgtctataaaattcccgatattggttaaacagcggcgcaatggcggccgcatctgatgtcttt
gcttggcgaatgttcatcttatttcttcctccctctcaataattttttcattctatccttttc
tgtaaagtttattttcagaatacttttatcatcatgctttgaaaaaatatcacgataatatcc
attgttctcacggaagcacacgcaggtcatttgaacgaattttttcgacaggaatttgccggga
ctcaggagcatttaacctaaaaagcatgacatttcagcataatgaacatttactcatgtctat
tttcgttcttttctgtatgaaaatagttatttcgagtctctacggaaatagcgagagatgatat
acctaaatagagataaaatcatctcaaaaatgggtctactaaatattattccatctattac
aataaattcacagaatagtcttttaagtaagtctactctgaattttttaaaaggagagggtaa
agagtgtcattaccgttcttaacttctgcaccgggaaaggttattattttggtgaacactctg
ctgtgtacaacaagcctgccgtcgctgctagtgtgtctgcgttgagaacctacctgctaataag
cgagtcatctgcaccagatactattgaattggacttcccggacattagctttaatcataagtgg
tccatcaatgatttcaatgccatcaccgaggatcaagtaaactcccaaaaattggccaaggctc
aacaagccaccgatggcttgtctcaggaactcgttagtcttttggatccgttgttagctcaact
atccgaatccttccactaccatgcagcgttttgtttcctgtatatgtttgtttgcctatgcccc
catgccaagaatattaagttttcttttaaagtctactttacccatcggtgctgggttgggctcaa
gcgcctctatttctgtatcactggccttagctatggcctacttggggggttaataggatctaa
tgacttggaaaagctgtcagaaaacgataagcatatagtgaatcaatgggccttcataggtgaa
aagtgtattcacggtacccttcaggaatagataacgctgtggccacttatggtaatgccctgc
tatttgaaaagactcataatggaacaataaacaaacaattttaagttcttagatgattt
cccagccattccaatgatcctaacctatactagaattccaaggtctacaaagatcttgttgct
cgcgttcgtgtgttggtcaccgagaaatttcctgaagttatgagccaattctagatgccatgg
gtgaatgtgccctacaaggcttagagatcatgactaagttaagtaaatgtaaaggcaccgatga
cgaggctgtagaaactaataatgaactgtatgaacaactattggaattgataagaataaatcat
ggactgcttgtctcaatcggtgtttctcatcctggattagaacttattaaaaatctgagcgatg
atttgagaattggctccacaaaacttaccggtgctggtggcggcggttgctcttttgactttgtt
acgaagagacattactcaagagcaaattgacagcttcaaaaagaaattgcaagatgatttagt

FIG. 29B

```
tacgagacatttgaaacagacttgggtgggactggctgctgtttgttaagcgcaaaaatttga
ataaagatcttaaaatcaaatccctagtattccaattatttgaaaataaaactaccacaaagca
acaaattgacgatctattattgccaggaaacacgaatttaccatggacttcataaaaggagagg
gtgtcagagttgagagccttcagtgccccagggaaagcgttactagctggtggatatttagttt
tagatacaaaatatgaagcatttgtagtcggattatcggcaagaatgcatgctgtagcccatcc
ttacggttcattgcaagggtctgataagtttgaagtgcgtgtgaaaagtaaacaatttaaagat
ggggagtggctgtaccatataagtcctaaaagtggcttcattcctgtttcgataggcggatcta
agaacccttcattgaaaaagttatcgctaacgtatttagctactttaaacctaacatggacga
ctactgcaatagaaacttgttcgttattgatattttctctgatgatgcctaccattctcaggag
gatagcgttaccgaacatcgtggcaacagaagattgagttttcattcgcacagaattgaagaag
ttcccaaaacagggctgggctcctcggcaggtttagtcacagttttaactacagctttggcctc
cttttttgtatcggacctggaaaataatgtagacaaatatagagaagttattcataatttagca
caagttgctcattgtcaagctcagggtaaaattggaagcgggtttgatgtagcggcggcagcat
atggatctatcagatatagaagattcccacccgcattaatctctaatttgccagatattggaag
tgctacttacggcagtaaactggcgcatttggttgatgaagaagactggaatattacgattaaa
agtaaccatttaccttcgggattaactttatggatgggcgatattaagaatggttcagaaacag
taaaactggtccagaaggtaaaaaattggtatgattcgcatatgccagaaagcttgaaaatata
tacagaactcgatcatgcaaattctagatttatggatggactatctaaactagatcgcttacac
gagactcatgacgattacagcgatcagatatttgagtctcttgagaggaatgactgtacctgtc
aaaagtatcctgaaatcacagaagttagagatgcagttgccacaattagacgttcctttagaaa
ataactaaagaatctggtgccgatatcgaacctccgtacaaactagcttattggatgattgc
cagaccttaaaaggagttcttacttgcttaatacctggtgctggtggttatgacgccattgcag
tgattactaagcaagatgttgatcttagggctcaaaccgctaatgacaaaagattttctaaggt
tcaatggctggatgtaactcaggctgactggggtgttaggaaagaaaaagatccggaaacttat
cttgataaataaaaggagagggtgaccgtttacacagcatccgttaccgcacccgtcaacatcg
caacccttaagtattggggaaaagggacacgaagttgaatctgcccaccaattcgtccatatc
agtgactttatcgcaagatgacctcagaacgttgacctctgcggctactgcacctgagtttgaa
cgcgacactttgtggttaaatggagaaccacacagcatcgacaatgaaagaactcaaaattgtc
tgcgcgacctacgccaattaagaaaggaaatggaatcgaaggacgcctcattgcccacattatc
tcaatggaaactccacattgtctccgaaaataactttcctacagcagctggtttagcttcctcc
gctgctggctttgctgcattggtctctgcaattgctaagttataccaattaccacagtcaactt
cagaaatatctagaatagcaagaaaggggtctggttcagcttgtagatcgttgtttggcggata
cgtggcctgggaaatgggaaaagctgaagatggtcatgattccatggcagtacaaatcgcagac
agctctgactggcctcagatgaaagcttgtgtcctagttgtcagcgatattaaaaaggatgtga
gttccactcagggtatgcaattgaccgtggcaacctccgaactatttaaagaaagaattgaaca
tgtcgtaccaaagagatttgaagtcatgcgtaaagccattgttgaaaaagatttcgccacctt
gcaaaggaaacaatgatggattccaactctttccatgccacatgtttggactctttccctccaa
tattctacatgaatgacacttccaagcgtatcatcagttggtgccacaccattaatcagtttta
cggagaaacaatcgttgcatacacgtttgatgcaggtccaaatgctgtgttgtactacttagct
gaaaatgagtcgaaactctttgcatttatctataaattgtttggctctgttcctggatgggaca
agaaatttactactgagcagcttgaggctttcaaccatcaatttgaatcatctaactttactgc
acgtgaattggatcttgagttgcaaaggatgttgccagagtgattttaactcaagtcggttca
ggcccacaagaaacaaacgaatctttgattgacgcaaagactggtctaccaaaggaataaaagg
agagggtgactgccgacaacaatagtatgccccatggtgcagtatctagttacgccaaattagt
```

FIG. 29C

```
gcaaaaccaaacacctgaagacatttggaagagtttcctgaaattattccattacaacaaaga
cctaatacccgatctagtgagacgtcaaatgacgaaagcggagaaacatgttttctggtcatg
atgaggagcaaattaagttaatgaatgaaaattgtattgttttggattgggacgataatgctat
tggtgccggtaccaagaaagtttgtcatttaatggaaaatattgaaagggtttactacatcgt
gcattctccgtctttattttcaatgaacaaggtgaattacttttacaacaaagagccactgaaa
aaataactttccctgatctttggactaacacatgctgctctcatccactatgtattgatgacga
attaggtttgaagggtaagctagacgataagattaagggcgctattactgcggcggtgagaaaa
ctagatcatgaattaggtattccagaagatgaaactaagacaaggggtaagtttcacttttaa
acagaatccattacatggcaccaagcaatgaaccatgggtgaacatgaaattgattacatcct
attttataagatcaacgctaaagaaaacttgactgtcaacccaaacgtcaatgaagttagagac
ttcaaatgggtttcaccaaatgatttgaaaactatgtttgctgacccaagttacaagtttacgc
cttggtttaagattatttgcgagaattacttattcaactggtgggagcaattagatgacctttc
tgaagtggaaaatgacaggcaaattcatagaatgctataaaaaaaccggccttggccccgccg
gttttttattattttcttcctccgcatgttcaatccgctccataatcgacggatggctccctc
tgaaaattttaacgagaaacggcgggttgacccggctcagtccgtaacggccaagtcctgaaa
cgtctcaatcgccgcttcccggtttccggtcagctcaatgccgtaacggtcggcggcgttttcc
tgataccgggagacggcattcgtaatttgaatacatacgaacaaattaataaagtgaaaaaaat
acttcggaaacatttaaaaaataaccttattggtacttacatgtttggatcaggagttgagagt
ggactaaaaccaaatagtgatcttgacttttagtcgtcgtatctgaaccattgacagatcaaa
gtaaagaaatacttatacaaaaaattagacctatttcaaaaaaaataggagataaaagcaactt
acgatatattgaattaacaattattattcagcaagaaatggtaccgtggaatcatcctcccaaa
caagaatttatttatggagaatggttacaagagctttatgaacaaggatacattcctcagaagg
aattaaattcagatttaaccataatgctttaccaagcaaaacgaaaaaataaaagaatatacgg
aaattatgacttagaggaattactacctgatattccatttctgatgtgagaagagccattatg
gattcgtcagaggaattaatagataattatcaggatgatgaaaccaactctatattaactttat
gccgtatgattttaactatggacacgggtaaaatcataccaaaagatattgcgggaaatgcagt
ggctgaatcttctccattagaacatagggagagaattttgttagcagttcgtagttatcttgga
gagaatattgaatggactaatgaaaatgtaaatttaactataaactatttaaataacagattaa
aaaaattataatgtaacctttgctttcaaatgagtagaaataatgcacatccatgtttgtatcg
tgcaaataaagtgtttcatccgtaggaaaaaatgactttagtatctgttccgcttttctgatg
aaatgtgctccccgacaaaattgaatgaatcatggacatttgctggctttgatacagcgaaagc
agccgttcctatgttatatatcggatttaacagcaggacaaaaaacaccatgacagccatcgtc
acccacttattcacacgcacataaacctttcctgacttttggaacagatgatagctcatcaaaa
atcccgccattgccaaataaatcgtatatggcattactgcaccataatcttttgagatttgatt
gggatatggcgcaagcagcaagacaagcagtccgataatcagcgtataaaataagcctagtaag
atcttatccgttctccaatacagcttgaaaaacactacattcaacgcaatgggaagagtgatga
tgaaaaacagaaacacgaatgcaatcggctccatcccatccgggtattccttccaatacgaaaa
gaaactaaaaatcatttgtacgatcggcaaactgacaacagcaaggtcgaacgtataaaactta
cccttccgccatgatcacgcggcatcagcatatagtgaaagccgtcagcagcacatatccgt
ataacaaaaatgcagcagcggcagcagttcttttccgtcctctcttaagtaagcgctggtgaa
gtttgttgattgcacctggtgaataagttcaacagacactcccgccagcagcacaatccgcaat
ataacacccgccaagaacattgtgcgctgccggtttattttgggatgatgcaccaaaagatata
agcccgccagaacaacaattgaccattgaatcagcagggtgctttgtctgcttaatataaaata
acgttcgaaatgcaatacataatgactgaataactccaacacgaacaacaaaagtgcgcatttt
```

FIG. 29D

```
Ataaaagctaatgattcagtccacataattgatagacgaattctgctacaggtcacgtggctat
gtgaaggatcgcgcgtccagttaagagcaaaaacattgacaaaaaaatttatttatgctaaaat
ttactattaatatatttgtatgtataataagattctcctggccaggggaatcttattttttgtg
gaggatcatttcatgaggaaaaatgagtccagcttaacgtctctaatttcagcttttgcccgtg
catatcacagccgatatgacacacctcttattttgatgatttatcgcaaaagatctcattaa
cgaaaagagtttatcgacatcagtaaaaatatgattcaagaaatatcgttttcaacaaagag
atcgccgaacgtcttcaaaatgatcctgaaaaaatattaaaatgggttgcacaaatccagctgt
ctccaacgcccctagcacgtgcttcttattgtgaaaaagtcttgcacaacgaattaatcctggg
ggcaaaacagtatgtcattcttggagcgggactggatactttctgctttcggcatccagaatta
gaaaacagcttacaggttttcgaggttgatcatccggccacacagcaattgaaaaaaaataagc
tgaaggatgcaaatctgacaattccgggtcatcttcatttgttcctatggatttcaccaaaac
gttttcgtatgatcctctcttagatgaaggatttaaaaacacaaaaacattcttcagccttctc
ggagtgtcttattatgtaacacgggaagaaaatgcaagcttgatcagcaatttatttctcatg
tcccgcctggaagctctattgttttgattatgcggacgaaacacttttacagcaaaagggac
gtcgaatcgagttgaacatatggtgaagatggctgccgcaagcggggaaccgatgaaatcatgt
ttcacttatcaagagattgaacatctg
```
(SEQ ID NO:47)

FIG. 31A

5'-
tagaaaaactcatcgagcatcaaatgaaactgcaatttattcatatcaggattatcaataccat
attttttgaaaaagccgtttctgtaatgaaggagaaaactcaccgaggcagttccataggatggc
aagatcctggtatcggtctgcgattccgactcgtccaacatcaatacaacctattaatttcccc
tcgtcaaaaataaggttatcaagtgagaaatcaccatgagtgacgactgaatccggtgagaatg
gcaaaagtttatgcatttctttccagacttgttcaacaggccagccattacgctcgtcatcaaa
atcactcgcatcaaccaaaccgttattcattcgtgattgcgcctgagcgaggcgaaatacgcga
tcgctgttaaaggacaattacaaacaggaatcgagtgcaaccggcgcaggaacactgccagcg
catcaacaatattttcacctgaatcaggatattcttctaatacctggaacgctgttttttccggg
gatcgcagtggtgagtaaccatgcatcatcaggagtacggataaaatgcttgatggtcggaagt
ggcataaattccgtcagccagtttagtctgaccatctcatctgtaacatcattggcaacgctac
ctttgccatgtttcagaaacaactctggcgcatcgggcttcccatacaagcgatagattgtcgc
acctgattgcccgacattatcgcgagcccatttatacccatataaatcagcatccatgttggaa
tttaatcgcggcctcgacgtttccgttgaatatggctcatattcttccttttcaatattatt
gaagcatttatcagggttattgtctcatgagcggatacatatttgaatgtatttagaaaaataa
acaaataggggtcagtgttacaaccaattaaccaattctgaacattatcgcgagcccatttata
cctgaatatggctcataacacccttgtttgcctggcggcagtagcgcggtggtcccacctgac
cccatgccgaactcagaagtgaaacgccgtagcgccgatggtagtgtgggactcccatgcga
gagtagggaactgccaggcatcaaataaaacgaaaggctcagtcgaaagactgggcctttcgcc
cgggctaattagggggtgtcgcccttagtcgctgaacatgtgctctgtttctaccgagaacgt
ttccttcactgagacggaaaccgaggcacgtcgtagcgcgaactacgagccgaatagctgggac
tacgatttcctgctgtcttccgatactgacgaatctattgaggtgtacaaagacaaagcaaaga
aactggaggctgaagtgcgccgcgaaattaacaacgagaaagctgaattcctgactctgctgga
gctgatcgataacgtacagcgcctgggtctgggttaccgcttcgaatctgatatccgtcgcgca
ctggatcgtttcgtaagcagcggcggtttcgatggcgtgaccaaaacgagcctgcacgctaccg
cgctgtccttccgtctgctgcgtcagcacggcttcgaagtttctcaggaagcattctccggttt
caaagatcaaaacggtaacttcctggaaaacctgaaagaagacactaaggcgatcctgagcctg
tatgaggcaagctttctggccctggagggtgagaacatcctggatgaggcgcgcgtattcgcca
tctcccatctgaaagagctgtctgaagagaaatcggtaaggaactggcagagcaggttaatca
cgcactggaactgccgctgcatcgtcgtacccagcgtctggaggcggtttggtccatcgaagcg
taccgcaaaaaggaggatgctaaccaggttctgctggaactggccatcctggactacaacatga
tccagtccgtttaccagcgtgatctgcgtgaaacctcccgttggtggcgccgtgtgggcctggc
gaccaaactgcacttcgctaaggaccgcctgattgagtcttttactgggcagtcggcgttgcg
ttcgaacctcagtattctgactgccgtaacagcgttgcgaaaatgttcagcttcgttactatta
tcgacgacatctacgacgtttacggtactctggacgagctggaactgtttaccgacgctgtcga
acgttgggatgttaacgccatcaacgatctgcctgactacatgaaactgtgcttcctggcactg
tataacacgatcaacgaaattgcatacgacaacctgaaagacaaaggtgaaaacatcctgccgt
acctgactaaagcgtgggcggatctgtgtaacgcttttctgcaagaagcgaaatggctgtataa
caaatccactccgaccttgacgattatttcggcaatgcctggaaatccagctctggcccgctg
caactgatcttcgcttattttgcggttgtccaaaacatcaaaaggaggaaattgaaacctgc
aaaaataccacgatatcattagccgtccttctcatatctttcgcctgtgcaacgacctggcaag
cgcgtccgcagagatcgcacgtggcgaaaccgctaactctgtttcctgctacatgcgcaccaag
ggcatttccgaagagctggcaaccgagagcgtaatgaatctgatcgacgaaacctgtaagaaaa
tgaacaaagaaaaactgggtggctccctgttcgctaaaccgttcgtagagactgctattaacct

FIG. 31B

```
ggcacgtcagagccactgcacctaccacaatggtgacgcacatactagcccggatgaactgact
cgtaaacgtgtactgtctgttatcaccgaaccgattctgccgttcgaacgttaactgcagcgtc
aatcgaaagggcgacacaaaatttattctaaatgcataataaatactgataacatcttatagtt
tgtattatattttgtattatcgttgacatgtataattttgatatcaaaaactgattttcccttt
attattttcgagatttattttcttaattctctttaacaaactagaaatattgtatatacaaaaa
atcataaataatagatgaatagtttaattataggtgttcatcaatcgaaaaagcaacgtatctt
atttaaagtgcgttgcttttttctcatttataaggttaaataattctcatatatcaagcaaagt
gacaggcgcccttaaatattctgacaaatgctctttccctaaactcccccataaaaaaacccg
ccgaagcgggttttacgttatttgcggattaacgattactcgttatcagaaccgcccaggggg
cccgagcttaagactggccgtcgttttacaacacagaaagagtttgtagaaacgcaaaaaggcc
atccgtcagggggccttctgcttagtttgatgcctggcagttccctactctcgccttccgcttcc
tcgctcactgactcgctgcgctcggtcgttcggctgcggcgagcggtatcagctcactcaaagg
cggtaatacggttatccacagaatcaggggataacgcaggaaagaacatgtgagcaaaaggcca
gcaaaaggccaggaaccgtaaaaaggccgcgttgctggcgttttttccataggctccgcccccct
gacgagcatcacaaaaatcgacgctcaagtcagaggtggcgaaacccgacaggactataaagat
accaggcgtttccccctggaagctccctcgtgcgctctcctgttccgaccctgccgcttaccgg
atacctgtccgcctttctcccttcgggaagcgtggcgctttctcatagctcacgctgtaggtat
ctcagttcggtgtaggtcgttcgctccaagctgggctgtgtgcacgaaccccccgttcagcccg
accgctgcgccttatccggtaactatcgtcttgagtccaacccggtaagacacgacttatcgcc
actggcagcagccactggtaacaggattagcagagcgaggtatgtaggcggtgctacagagttc
ttgaagtggtgggctaactacggctacactagaagaacagtatttggtatctgcgctctgctga
agccagttaccttcggaaaaagagttggtagctcttgatccggcaaacaaaccaccgctggtag
cggtggtttttttgtttgcaagcagcagattacgcgcagaaaaaaaggatctcaagaagatcct
ttgatcttttctacggggtctgacgctcagtggaacgacgcgcgtaactcacgttaagggat
tttggtcatgagcttgcgccgtcccgtcaagtcagcgtaatgctctgcttt
```
(SEQ ID NO:48)

FIG. 33A

5'-
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaagcgaagcggcactgctctttaacaatttatcagacaatctgt
gtgggcactcgaccggaattatcgattaactttattattaaaaattaagaggtatatattaat
gtatcgattaaataaggaggaataaaccatgtgctctgtttctaccgagaacgtttccttcact
gagacggaaaccgaggcacgtcgtagcgcgaactacgagccgaatagctgggactacgatttcc
tgctgtcttccgatactgacgaatctattgaggtgtacaaagacaaagcaaagaaactggaggc
tgaagtgcgccgcgaaattaacaacgagaaagctgaattcctgactctgctggagctgatcgat
aacgtacagcgcctggtctggttaccgcttcgaatctgatatccgtcgcgcactggatcgtt
tcgtaagcagcggcggtttcgatggcgtgaccaaaacgagcctgcacgctaccgcgctgtcctt
ccgtctgctgcgtcagcacggcttcgaagtttctcaggaagcattctccggtttcaaagatcaa
aacggtaacttcctggaaaacctgaaagaagacactaaggcgatcctgagcctgtatgaggcaa
gctttctggccctggagggtgagaacatcctggatgaggcgcgcgtattcgccatctcccatct
gaaagagctgtctgaagagaaaatcggtaaggaactggcagagcaggttaatcacgcactggaa
ctgccgctgcatcgtcgtacccagcgtctggaggcggtttggtccatcgaagcgtaccgcaaaa
aggaggatgctaaccaggttctgctggaactggccatcctggactacaacatgatccagtccgt
ttaccagcgtgatctgcgtgaaacctcccgttggtggcgccgtgtgggcctggcgaccaaactg
cacttcgctaaggaccgcctgattgagtcttttactgggcagtcggcgttgcgttcgaacctc
agtattctgactgccgtaacagcgttgcgaaaatgttcagcttcgttactattcgacgacat
ctacgacgtttacggtactctggacgagctggaactgtttaccgacgctgtcgaacgttgggat
gttaacgccatcaacgatctgcctgactacatgaaactgtgcttcctggcactgtataacacga
tcaacgaaattgcatacgacaacctgaaagacaaaggtgaaaacatcctgccgtacctgactaa
agcgtgggcggatctgtgtaacgcttttctgcaagaagcgaaatggctgtataacaaatccact
ccgacctttgacgattatttcggcaatgcctggaaatccagctctggcccgctgcaactgatct
tcgcttattttgcggttgtccaaaacatcaaaaaggaggaaattgaaacctgcaaaaatacca
cgatatcattagccgtccttctcatatctttcgcctgtgcaacgacctggcaagcgcgtccgca
gagatcgcacgtggcgaaaccgctaactctgtttcctgctacatgcgcaccaagggcatttccg
aagagctggcaaccgagagcgtaatgaatctgatcgacgaaacctgtaagaaaatgaacaaaga
aaaactgggtggctcctgttcgctaaaccgttcgtagagactgctattaacctggcacgtcag
agccactgcacctaccacaatggtgacgcacatactagcccggatgaactgactcgtaaacgtg
tactgtctgttatcaccgaaccgattctgccgttcgaacgttaactgcagctggtaccatatgg
gaattcgaagctttctagaacaaaaactcatctcagaagaggatctgaatagcgccgtcgacca
tcatcatcatcatcattgagtttaaacggtctccagcttggctgttttggcggatgagagaaga
ttttcagcctgatacagattaaatcagaacgcagaagcggtctgataaaacagaatttgcctgg
cggcagtagcgcggtggtcccacctgaccccatgccgaactcagaagtgaaacgccgtagcgcc
gatggtagtgtggggtctccccatgcgagagtagggaactgccaggcatcaaataaaacgaaag
gctcagtcgaaagactgggcctttcgttttatctgttgtttgtcggtgaacgctctcctgagta
ggacaaatccgccgggagcggatttgaacgttgcgaagcaacggcccggagggtggcgggcagg
acgcccgccataaactgccaggcatcaattaagcagaaggccatcctgacggatggcctttt
gcgtttctacaaactctttttgtttatttttctaaatacattcaaatatgtatccgctcatgag
acaataaccctgataaatgcttcaataatattgaaaaggaagagtatgagtattcaacatttc

FIG. 33B

```
cgtgtcgcccttattccctttttttgcggcattttgccttcctgttttttgctcacccagaaacgc
tggtgaaagtaaaagatgctgaagatcagttgggtgcacgagtgggttacatcgaactggatct
caacagcggtaagatccttgagagttttcgccccgaagaacgttttccaatgatgagcacttttt
aaagttctgctatgtggcgcggtattatcccgtgttgacgccgggcaagagcaactcggtcgcc
gcatacactattctcagaatgacttggttgagtactcaccagtcacagaaaagcatcttacgga
tggcatgacagtaagagaattatgcagtgctgccataaccatgagtgataacactgcggccaac
ttacttctgacaacgatcggaggaccgaaggagctaaccgcttttttgcacaacatggggggatc
atgtaactcgccttgatcgttgggaaccggagctgaatgaagccataccaaacgacgagcgtga
caccacgatgcctgtagcaatggcaacaacgttgcgcaaactattaactggcgaactacttact
ctagcttcccggcaacaattaatagactggatggaggcggataaagttgcaggaccacttctgc
gctcggcccttccggctggctggtttattgctgataaatctggagccggtgagcgtgggtctcg
cggtatcattgcagcactggggccagatggtaagccctcccgtatcgtagttatctacacgacg
gggagtcaggcaactatggatgaacgaaatagacagatcgctgagataggtgcctcactgatta
agcattggtaactgtcagaccaagtttactcatatatactttagattgatttaaaacttcattt
ttaatttaaaaggatctaggtgaagatcctttttgataatctcatgaccaaaatcccttaacgt
gagttttcgttccactgagcgtcagacccgtagaaaagatcaaaggatcttcttgagatcctt
ttttttctgcgcgtaatctgctgcttgcaaacaaaaaaaccaccgctaccagcggtggtttgttt
gccggatcaagagctaccaactcttttttccgaaggtaactggcttcagcagagcgcagatacca
aatactgtccttctagtgtagccgtagttaggccaccacttcaagaactctgtagcaccgccta
catacctcgctctgctaatcctgttaccagtggctgctgccagtggcgataagtcgtgtcttac
cgggttggactcaagacgatagttaccggataaggcgcagcggtcgggctgaacggggggttcg
tgcacacagcccagcttggagcgaacgacctacaccgaactgagatacctacagcgtgagctat
gagaaagcgccacgcttcccgaagggagaaaggcggacaggtatccggtaagcggcagggtcgg
aacaggagagcgcacgagggagcttccagggggaaacgcctggtatctttatagtcctgtcggg
tttcgccacctctgacttgagcgtcgatttttgtgatgctcgtcaggggggcggagcctatgga
aaaacgccagcaacgcggcctttttacggttcctggccttttgctggccttttgctcacatgtt
ctttcctgcgttatcccctgattctgtggataaccgtattaccgcctttgagtgagctgatacc
gctcgccgcagccgaacgaccgagcgcagcgagtcagtgagcgaggaagcggaagagcgcctga
tgcggtattttctccttacgcatctgtgcggtatttcacaccgcatatggtgcactctcagtac
aatctgctctgatgccgcatagttaagccagtatacactccgctatcgctacgtgactgggtca
tggctgcgccccgacacccgccaacacccgctgacgcgccctgacgggcttgtctgctcccggc
atccgcttacagacaagctgtgaccgtctccgggagctgcatgtgtcagaggttttcaccgtca
tcaccgaaacgcgcgaggcagcagatcaattcgcgcgcgaaggcgaagcggcatgcatttacgt
tgacaccatcgaatggtgcaaaacctttcgcggtatggcatgatagcgcccggaagagagtcaa
ttcagggtggtgaatgtgaaaccagtaacgttatacgatgtcgcagagtatgccggtgtctctt
atcagaccgtttccgcgtggtgaaccaggccagccacgtttctgcgaaaacgcgggaaaaagt
ggaagcggcgatggcggagctgaattacattcccaaccgcgtggcacaacaactggcgggcaaa
cagtcgttgctgattggcgttgccacctccagtctggccctgcacgcgccgtcgcaaattgtcg
cggcgattaaatctcgcgccgatcaactgggtgccagcgtggtggtgtcgatggtagaacgaag
cggcgtcgaagcctgtaaagcggcggtgcacaatcttctcgcgcaacgcgtcagtggctgatc
attaactatccgctggatgaccaggatgccattgctgtggaagctgcctgcactaatgttccgg
cgttatttcttgatgtctctgaccagacacccatcaacagtattattttctcccatgaagacgg
tacgcgactgggcgtggagcatctggtcgcattgggtcaccagcaaatcgcgctgttagcgggc
ccattaagttctgtctcggcgcgtctgcgtctggctggctggcataaatatctcactcgcaatc
```

FIG. 33C aaattcagccgatagcggaacgggaaggcgactggagtgccatgtccggttttcaacaaaccat
gcaaatgctgaatgagggcatcgttcccactgcgatgctggttgccaacgatcagatggcgctg
ggcgcaatgcgcgccattaccgagtccgggctgcgcgttggtgcggatatctcggtagtgggat
acgacgataccgaagacagctcatgttatatcccgccgtcaaccaccatcaaacaggattttcg
cctgctggggcaaaccagcgtggaccgcttgctgcaactctctcagggccaggcggtgaagggc
aatcagctgttgcccgtctcactggtgaaaagaaaaaccaccctggcgcccaatacgcaaaccg
cctctccccgcgcgttggccgattcattaatgcagctggcacgacaggtttcccgactggaaag
cgggcagtgagcgcaacgcaattaatgtgagttagcgcgaattgatctg
(SEQ ID NO:49)

FIG. 35A

5'-
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaaccttcgcggtatggcatgatagcgc
ccggaagagagtcaattcagggtggtgaatgtgaaaccagtaacgttatacgatgtcgcagagt
atgccggtgtctcttatcagaccgtttccgcgtggtgaaccaggccagccacgtttctgcgaa
aacgcgggaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct
gcactaatgttccggcgttatttcttgatgtctctgaccagacacccatcaacagtattattt
ctcccatgaagacggtacgcgactgggcgtggagcatctggtcgcattgggtcaccagcaaatc
gcgctgttagcgggcccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatcccgccgtcaaccaccat
caaacaggattttcgcctgctggggcaaaccagcgtggaccgcttgctgcaactctctcagggc
caggcggtgaagggcaatcagctgttgcccgtctcactggtgaaaagaaaaaccaccctggcgc
ccaatacgcaaaccgcctctccccgcgcgttggccgattcattaatgcagctggcacgacaggt
ttcccgactggaaagcgggcagtgagcgcaacgcaattaatgtgagttagcgcgaattgatctg
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacacccagccgctgtccctgctggagctgatcgacgatgtg
cagcgcctgggtctgacctacaaatttgaaaagacatcattaaagccctggaaaacatcgtac
tgctggacgaaaacaaaagaacaaatctgacctgcacgcaaccgctctgtctttccgtctgct
gcgtcagcacggtttcgaggttctcaggatgtttttgagcgtttcaaggataaagaaggtggt
ttcagcggtgaactgaaaggtgacgtccaaggcctgctgagcctgtatgaagcgtcttacctgg
gtttcgagggtgagaacctgctggaggaggcgcgtacctttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggatttgta
cgcgaccgcctgatggaagtttatttctgggcactgggtatggcgccagacccgcagtttggtg
aatgtcgcaaagctgttactaaaatgtttggtctggtgacgatcatcgatgacgtgtatgacgt

FIG. 35B

```
ttatggcactctggacgaactgcaactgttcaccgatgctgtagagcgctgggacgttaacgct
attaaccccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggctttc
tccaagtacctggaaaacgccagcgtttcctcctccggtgtagcgctgctggcgccgtcttact
tttccgtatgccagcagcaggaagacatctccgaccacgcgctgcgttccctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccaatggaaaaagatgaatcg
tgaacgcgttagcgactccaccctgctgcctaaagcgttcatggaaatcgcagttaacatggca
cgtgtttcccactgcacctaccagtatggcgatggtctgggtcgcccagactacgcgactgaaa
accgcatcaaactgctgctgattgacccctttcccgattaaccagctgatgtatgtctaactgca
tcgcccttaggaggtaaaaaaaatgactgccgacaacaatagtatgccccatggtgcagtatc
tagttacgccaaattagtgcaaaaccaaacacctgaagacattttggaagagtttcctgaaatt
attccattacaacaaagacctaatacccgatctagtgagacgtcaaatgacgaaagcggagaaa
catgttttctggtcatgatgaggagcaaattaagttaatgaatgaaaattgtattgttttgga
ttgggacgataatgctattggtgccggtaccaagaaagtttgtcatttaatggaaaatattgaa
aagggtttactacatcgtgcattctccgtctttatttcaatgaacaaggtgaattacttttac
aacaaagagccactgaaaaaataactttccctgatctttggactaacacatgctgctctcatcc
actatgtattgatgacgaattaggtttgaaggggtaagctagacgataagattaagggcgctatt
actgcggcggtgagaaaactagatcatgaattaggtattccagaagatgaaactaagacaaggg
gtaagtttcacttttttaaacagaatccattacatggcaccaagcaatgaaccatggggtgaaca
tgaaattgattacatcctatttataagatcaacgctaaagaaaacttgactgtcaacccaaac
gtcaatgaagttagagacttcaaatgggtttccaaatgatttgaaaactatgtttgctgacc
caagttacaagtttacgccttggtttaagattatttgcgagaattacttattcaactggtggga
gcaattagatgacctttctgaagtggaaaatgacaggcaaattcatagaatgctataacaacgc
gtcctgcagctggtaccatatgggaattcgaagctttctagaacaaaaactcatctcagaagag
gatctgaatagcgccgtcgaccatcatcatcatcattgagtttaaacggtctccagcttgg
ctgttttggcggatgagagaagattttcagcctgatacagattaaatcagaacgcagaagcggt
ctgataaaacagaatttgcctggcggcagtagcgcggtggtcccacctgaccccatgccgaact
cagaagtgaaacgccgtagcgccgatggtagtgtggggtctccccatgcgagagtagggaactg
ccaggcatcaaataaaacgaaaggctcagtcgaaagactgggccttcgttttatctgttgttt
gtcggtgaacgctctcctgagtaggacaaatccgccgggagcggatttgaacgttgcgaagcaa
cggcccggagggtggcgggcaggacgcccgccataaactgccaggcatcaaattaagcagaagg
ccatcctgacggatggccttttgcgtttctacaaactcttttgtttatttttctaaatacat
tcaaatatgtatccgcttaaccggaattgccagctggggcgccctctggtaaggttgggaagcc
ctgcaaagtaaactggatggctttctcgccgccaaggatctgatggcgcaggggatcaagctct
gatcaagagacaggatgaggatcgtttcgcatgattgaacaagatggattgcacgcaggttctc
cggccgcttgggtggagaggctattcggctatgactgggcacaacagacaatcggctgctctga
tgccgccgtgttccggctgtcagcgcaggggcgcccggttcttttgtcaagaccgacctgtcc
ggtgccctgaatgaactgcaagacgaggcagcgcggctatcgtggctggccacgacgggcgttc
cttgcgcagctgtgctcgacgttgtcactgaagcgggaagggactggctgctattgggcgaagt
gccggggcaggatctcctgtcatctcaccttgctcctgccgagaaagtatccatcatggctgat
```

FIG. 35C

```
gcaatgcggcggctgcatacgcttgatccggctacctgcccattcgaccaccaagcgaaacatc
gcatcgagcgagcacgtactcggatggaagccggtcttgtcgatcaggatgatctggacgaaga
gcatcagggctcgcgccagccgaactgttcgccaggctcaaggcgagcatgcccgacggcgag
gatctcgtcgtgacccatggcgatgcctgcttgccgaatatcatggtggaaaatggccgctttt
ctggattcatcgactgtggccggctgggtgtggcggaccgctatcaggacatagcgttggctac
ccgtgatattgctgaagagcttggcggcgaatgggctgaccgcttcctcgtgctttacggtatc
gccgctcccgattcgcagcgcatcgccttctatcgccttcttgacgagttcttctgacatgacc
aaaatcccttaacgtgagttttcgttccactgagcgtcagacccgtagaaaagatcaaaggat
cttcttgagatcctttttttctgcgcgtaatctgctgcttgcaaacaaaaaaaccaccgctacc
agcggtggtttgtttgccggatcaagagctaccaactcttttccgaaggtaactggcttcagc
agagcgcagataccaaatactgtccttctagtgtagccgtagttaggccaccacttcaagaact
ctgtagcaccgcctacatacctcgctctgctaatcctgttaccagtggctgctgccagtggcga
taagtcgtgtcttaccgggttggactcaagacgatagttaccggataaggcgcagcggtcgggc
tgaacggggggttcgtgcacacagcccagcttggagcgaacgacctacaccgaactgagatacc
tacagcgtgagctatgagaaagcgccacgcttcccgaagggagaaaggcggacaggtatccggt
aagcggcagggtcggaacaggagagcgcacgagggagcttcagggggaaacgcctggtatctt
tatagtcctgtcgggtttcgccacctctgacttgagcgtcgatttttgtgatgctcgtcagggg
ggcggagcctatggaaaaacgccagcaacgcggccttttacggttcctggccttttgctggcc
ttttgctcacatgttctttcctgcgttatcccctgattctgtggataaccgtattaccgccttt
gagtgagctgataccgctcgccgcagccgaacgaccgagcgcagcgagtcagtgagcgaggaag
cggaagagcgcctgatgcggtattttctccttacgcatctgtgcggtatttcacaccgcatatg
gtgcactctcagtacaatctgctctgatgccgcatagttaagccagtatacactccgctatcgc
tacgtgactgggtcatggctgcgccccgacacccgccaacacccgctgacgcgccctgacgggc
```
(SEQ ID NO:50)

FIG. 37A

5'-
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaaccttttcgcggtatggcatgatagcgc
ccggaagagagtcaattcagggtggtgaatgtgaaaccagtaacgttatacgatgtcgcagagt
atgccggtgtctcttatcagaccgtttccgcgtggtgaaccaggccagccacgtttctgcgaa
aacgcgggaaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct
gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggcccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatcccgccgtcaaccaccat
caaacaggattttcgcctgctggggcaaaccagcgtggaccgcttgctgcaactctctcagggc
caggcggtgaagggcaatcagctgttgccgtctcactggtgaaaagaaaaaccaccctggcgc
ccaatacgcaaaccgcctctcccgcgcgttggccgattcattaatgcagctggcacgacaggt
tcccgactggaaagcgggcagtgagcgcaacgcaattaatgtgagttagcgcgaattgatctg
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgtgcgacctcttctcaatttactcagattacc
gagcataattcccgtcgttccgcaaactatcagccaaacctgtggaatttcgaattcctgcaat
ccctggagaacgacctgaaagtggaaagctggaggagaaagcgaccaaactggaggaagaagt
tcgctgcatgatcaaccgtgtagacacccagccgctgtccctgctggagctgatcgacgatgtg
cagcgcctgggtctgacctacaaatttgaaaagacatcattaaagccctggaaaacatcgtac
tgctggacgaaaacaaaaagaacaaatctgacctgcacgcaaccgctctgtctttccgtctgct
gcgtcagcacggtttcgaggtttctcaggatgttttgagcgtttcaaggataaagaaggtggt
ttcagcggtgaactgaaaggtgacgtccaaggcctgctgagcctgtatgagcgtcttacctgg
gtttcgagggtgagaacctgctggaggaggcgcgtaccttttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggattttgta
cgcgaccgcctgatggaagtttatttctgggcactgggtatggcgccagacccgcagtttggtg
aatgtcgcaaagctgttactaaaatgtttggtctggtgacgatcatcgatgacgtgtatgacgt
ttatggcactctggacgaactgcaactgttcaccgatgctgtagagcgctgggacgttaacgct

FIG. 37B

```
attaacaccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggctttc
tccaagtacctggaaaacgccagcgtttcctcctccggtgtagcgctgctggcgccgtcttact
tttccgtatgccagcagcaggaagacatctccgaccacgcgctgcgttcctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccgaatggaaaaagatgaatcg
tgaacgcgttagcgactccaccctgctgcctaaagcgttcatggaaatcgcagttaacatggca
cgtgtttcccactgcacctaccagtatggcgatggtctgggtcgcccagactacgcgactgaaa
accgcatcaaactgctgctgattgaccctttcccgattaaccagctgatgtatgtctaactgca
ttcgcccttaggaggtaaaaaaacatgagttttgatattgccaaatacccgaccctggcactgg
tcgactccacccaggagttacgactgttgccgaaagagagtttaccgaaactctgcgacgaact
gcgccgctatttactcgacagcgtgagccgttccagcgggcacttcgcctccgggctgggcacg
gtcgaactgaccgtggcgctgcactatgtctacaacacccgtttgaccaattgatttgggatg
tggggcatcaggcttatccgcataaaattttgaccggacgccgcgacaaaatcggcaccatccg
tcagaaaggcggtctgcacccgttcccgtggcgcggcgaaagcgaatatgacgtattaagcgtc
gggcattcatcaacctccatcagtgccggaattggtattgcggttgctgccgaaaaagaaggca
aaaatcgccgcaccgtctgtgtcattggcgatggcgcgattaccgcaggcatggcgtttgaagc
gatgaatcacgcgggcgatatccgtcctgatatgctggtgattctcaacgacaatgaaatgtcg
atttccgaaaatgtcggcgcgctcaacaaccatctggcacagctgctttccggtaagctttact
cttcactgcgcgaaggcgggaaaaaagttttctctggcgtgccgccaattaaagagctgctcaa
acgcaccgaagaacatattaaaggcatggtagtgcctggcacgttgtttgaagagctgggcttt
aactacatcggcccggtggacggtcacgatgtgctggggcttatcaccacgctaaagaacatgc
gcgacctgaaaggcccgcagttcctgcatatcatgaccaaaaaaggtcgtggttatgaaccggc
agaaaagacccgatcactttccacgccgtgcctaaatttgatccctccagcggttgtttgccg
aaaagtagcggcggtttgccgagctattcaaaaatctttggcgactggttgtgcgaaacggcag
cgaaagacaacaagctgatggcgattactccggcgatgcgtgaaggttccggcatggtcgagtt
ttcacgtaaattcccggatcgctacttcgacgtggcaattgccgagcaacacgcggtgacctt
gctgcgggtctggcgattggtgggtacaaaccccattgtcgcgatttactccactttcctgcaac
gcgcctatgatcaggtgctgcatgacgtggcgattcaaaagcttccggtcctgttcgccatcga
ccgcgcgggcattgttggtgctgacggtcaaacccatcagggtgcttttgatctctcttacctg
cgctgcataccggaaatggtcattatgaccccgagcgatgaaaacgaatgtcgccagatgctct
ataccggctatcactataacgatggcccgtcagcggtgcgctaccgcgtggcaacgcggtcgg
cgtggaactgacgccgctggaaaaactaccaattggcaaaggcattgtgaagcgtcgtggcgag
aaactggcgatccttaactttggtacgctgatgccagaagcggcgaaagtcgccgaatcgctga
acgccacgctggtcgatatgcgttttgtgaaaccgcttgatgaagcgttaattctggaaatggc
cgccagccatgaagcgctggtcaccgtagaagaaaacgccattatgggcggcgcaggcagcggc
gtgaacgaagtgctgatggcccatcgtaaaccagtacccgtgctgaacattggcctgccggact
tctttattccgcaaggaactcaggaagaaatgcgcgccgaactcggcctcgatgccgctggtat
ggaagccaaaatcaaggcctggctggcataactgcagctggtaccatatgggaattcgaagctt
tctagaacaaaaactcatctcagaagaggatctgaatagcgccgtcgaccatcatcatcatcat
cattgagtttaaacggtctccagcttggctgttttggcggatgagagaagattttcagcctgat
acagattaaatcagaacgcagaagcggtctgataaaacagaatttgcctggcggcagtagcgcg
```

FIG. 37C

```
gtggtcccacctgaccccatgccgaactcagaagtgaaacgccgtagcgccgatggtagtgtgg
ggtctccccatgcgagagtagggaactgccaggcatcaaataaaacgaaaggctcagtcgaaag
actgggcctttcgttttatctgttgtttgtcggtaacgctctcctgagtaggacaaatccgcc
gggagcggatttgaacgttgcgaagcaacggcccggagggtggcgggcaggacgcccgccataa
actgccaggcatcaaattaagcagaaggccatcctgacggatggccttttgcgtttctacaaa
ctcttttgtttattttctaaatacattcaaatatgtatccgcttaaccggaattgccagctg
gggcgccctctggtaaggttgggaagccctgcaaagtaaactggatggctttctcgccgccaag
gatctgatggcgcagggatcaagctctgatcaagagacaggatgaggatcgtttcgcatgatt
gaacaagatggattgcacgcaggttctccggccgcttgggtggagaggctattcggctatgact
gggcacaacagacaatcggctgctctgatgccgccgtgttccggctgtcagcgcaggggcgccc
ggttctttttgtcaagaccgacctgtccggtgccctgaatgaactgcaagacgaggcagcgcgg
ctatcgtggctggccacgacgggcgttccttgcgcagctgtgctcgacgttgtcactgaagcgg
gaagggactggctgctattgggcgaagtgccggggcaggatctcctgtcatctcaccttgctcc
tgccgagaaagtatccatcatggctgatgcaatgcggcggctgcatacgcttgatccggctacc
tgcccattcgaccaccaagcgaaacatcgcatcgagcgagcacgtactcggatggaagccggtc
ttgtcgatcaggatgatctggacgaagagcatcaggggctcgcgccagccgaactgttcgccag
gctcaaggcgagcatgcccgacggcgaggatctcgtcgtgacccatggcgatgcctgcttgccg
aatatcatggtggaaaatggccgcttttctggattcatcgactgtggccggctgggtgtggcgg
accgctatcaggacatagcgttggctacccgtgatattgctgaagagcttggcggcgaatgggc
tgaccgcttcctcgtgctttacggtatcgccgctccgattcgcagcgcatcgccttctatcgc
cttcttgacgagttcttctgacgcatgaccaaaatcccttaacgtgagttttcgttccactgag
cgtcagacccgtagaaaagatcaaaggatcttcttgagatcctttttttctgcgcgtaatctg
ctgcttgcaaacaaaaaaaccaccgctaccagcggtggtttgtttgccggatcaagagctacca
actcttttccgaaggtaactggcttcagcagagcgcagataccaaatactgtccttctagtgt
agccgtagttaggccaccacttcaagaactctgtagcaccgcctacatacctcgctctgctaat
cctgttaccagtggctgctgccagtggcgataagtcgtgtcttaccgggttggactcaagacga
tagttaccggataaggcgcagcggtcgggctgaacggggggttcgtgcacacagcccagcttgg
agcgaacgacctacaccgaactgagatacctacagcgtgagctatgagaaagcgccacgcttcc
cgaagggagaaaggcggacaggtatccggtaagcggcagggtcggaacaggagagcgcacgagg
gagcttccaggggggaaacgcctggtatctttatagtcctgtcgggtttcgccacctctgacttg
agcgtcgatttttgtgatgctcgtcaggggggcggagcctatggaaaaacgccagcaacgcggc
cttttacggttcctggccttttgctggccttttgctcacatgttctttcctgcgttatcccct
gattctgtggataaccgtattaccgcctttgagtgagctgataccgctcgccgcagccgaacga
ccgagcgcagcgagtcagtgagcgaggaagcggaagagcgcctgatgcggtattttctccttac
gcatctgtgcggtatttcacaccgcatatggtgcactctcagtacaatctgctctgatgccgca
tagttaagccagtatacactccgctatcgctacgtgactgggtcatggctgcgccccgacaccc
gccaacacccgctgacgcgccctgacgggc
```
(SEQ ID NO:51)

FIG. 39A

5'-
ctggcgtaatagcgaagaggcccgcaccgatcgcccttcccaacagttgcgcagcctgaatggc
gaatggcgcctgatgcggtattttctccttacgcatctgtgcggtatttcacaccgcatatggt
gcactctcagtacaatctgctctgatgccgcatagttaagccagccccgacacccgccaacacc
cgctgacgagcttagtaaagccctcgctagattttaatgcggatgttgcgattacttcgccaac
tattgcgataacaagaaaaagccagcctttcatgatatatctcccaatttgtgtagggcttatt
atgcacgcttaaaaataataaaagcagacttgacctgatagtttggctgtgagcaattatgtgc
ttagtgcatctaacgcttgagttaagccgcgccgcgaagcggcgtcggcttgaacgaattgtta
gacattatttgccgactaccttggtgatctcgcctttcacgtagtggacaaattcttccaactg
atctgcgcgcgaggccaagcgatcttcttcttgtccaagataagcctgtctagcttcaagtatg
acgggctgatactgggccggcaggcgctccattgcccagtcggcagcgacatccttcggcgcga
ttttgccggttactgcgctgtaccaaatgcgggacaacgtaagcactacatttcgctcatcgcc
agcccagtcgggcggcgagttccatagcgttaaggtttcatttagcgcctcaaatagatcctgt
tcaggaaccggatcaaagagttcctccgccgctggacctaccaaggcaacgctatgttctcttg
cttttgtcagcaagatagccagatcaatgtcgatcgtggctggctcgaagatacctgcaagaat
gtcattgcgctgccattctccaaattgcagttcgcgcttagctggataacgccacggaatgatg
tcgtcgtgcacaacaatggtgacttctacagcgcggagaatctcgctctctcaggggaagccg
aagtttccaaaaggtcgttgatcaaagctcgccgcgttgtttcatcaagcttacggtcaccgt
aaccagcaaatcaatatcactgtgtggcttcaggccgccatccactgcggagccgtacaaatgt
acggccagcaacgtcggttcgagatggcgctcgatgacgccaactacctctgatagttgagtcg
atacttcggcgatcaccgcttccctcatgatgtttaactttgttttagggcgactgccctgctg
cgtaacatcgttgctgctccataacatcaaacatcgacccacggcgtaacgcgcttgctgcttg
gatgcccgaggcatagactgtaccccaaaaaaacagtcataacaagccatgaaaaccgccactg
cgccgttaccaccgctgcgttcggtcaaggttctggaccagttgcgtgagcgcatacgctactt
gcattacagcttacgaaccgaacaggcttatgtccactgggttcgtgccttcatccgtttccac
ggtgtgcgtcacccggcaaccttgggcagcagcgaagtcgaggcatttctgtcctggctggcga
acgagcgcaaggtttcggtctccacgcatcgtcaggcattggcggccttgctgttcttctacgg
caaggtgctgtgcacggatctgccctggcttcaggagatcggaagacctcggccgtcgcggcgc
ttgccggtggtgctgaccccggatgaagtggttcgcatcctcggttttctggaaggcgagcatc
gtttgttcgcccagcttctgtatggaacgggcatgcggatcagtgagggtttgcaactgcggt
caaggatctggatttcgatcacggcacgatcatcgtgcgggagggcaagggctccaaggatcgg
gccttgatgttacccgagagcttggcaccagcctgcgcgagcagggaattaattcccacggg
ttttgctgcccgcaaacgggctgttctggtgttgctagtttgttatcagaatcgcagatccggc
ttcagccggtttgccggctgaaagcgctatttcttccagaattgccatgattttttccccacgg
gaggcgtcactggctccgtgttgtcggcagctttgattcgataagcagcatcgcctgtttcag
gctgtctatgtgtgactgttgagctgtaacaagttgtctcaggtgttcaatttcatgttctagt
tgctttgttttactggtttcacctgttctattaggtgttacatgctgttcatctgttacattgt
cgatctgttcatggtgaacagctttgaatgcaccaaaaactcgtaaaagctctgatgtatctat
cttttttacaccgttttcatctgtgcatatggacagttttcccttttgatatgtaacggtgaaca
gttgttctacttttgtttgttagtcttgatgcttcactgatagataagagccataagaacct
cagatccttccgtatttagccagtatgttctctagtgtggttcgttgttttgcgtgagccatg
agaacgaaccattgagatcatacttactttgcatgtcactcaaaaattttgcctcaaaactggt
gagctgaattttgcagttaaagcatcgtgtagtgtttttcttagtccgttatgtaggtaggaa
tctgatgtaatggttgttggtattttgtcaccattcattttatctggttgttctcaagttcgg

FIG. 39B ttacgagatccatttgtctatctagttcaacttggaaaatcaacgtatcagtcgggcggcctcg
cttatcaaccaccaatttcatattgctgtaagtgtttaaatctttacttattggtttcaaaacc
cattggttaagccttttaaactcatggtagttattttcaagcattaacatgaacttaaattcat
caaggctaatctctatatttgccttgtgagttttcttttgtgttagttcttttaataaccactc
ataaatcctcatagagtatttgttttcaaaagacttaacatgttccagattatattttatgaat
tttttttaactggaaaagataaggcaatatctcttcactaaaaactaattctaattttttcgcttg
agaacttggcatagtttgtccactggaaaatctcaaagcctttaaccaaaggattcctgatttc
cacagttctcgtcatcagctctctggttgctttagctaatacaccataagcattttccctactg
atgttcatcatctgagcgtattggttataagtgaacgatacgtccgttctttccttgtagggt
tttcaatcgtggggttgagtagtgccacacagcataaaattagcttggtttcatgctccgttaa
gtcatagcgactaatcgctagttcatttgctttgaaaacaactaattcagacatacatctcaat
tggtctaggtgattttaatcactataccaattgagatgggctagtcaatgataattactagtcc
ttttcctttgagttgtgggtatctgtaaattctgctagacctttgctggaaaacttgtaaattc
tgctagaccctctgtaaattccgctagacctttgtgtgttttttttgtttatattcaagtggtt
ataatttatagaataaagaaagaataaaaaaagataaaaagaatagatcccagccctgtgtata
actcactactttagtcagttccgcagtattacaaaaggatgtcgcaaacgctgtttgctcctct
acaaaacagaccttaaaaccctaaaggcttaagtagcaccctcgcaagctcgggcaaatcgctg
aatattccttttgtctccgaccatcaggcacctgagtcgctgtcttttcgtgacattcagttc
gctgcgctcacggctctggcagtgaatgggggtaaatggcactacaggcgcctttatggattc
atgcaaggaaactacccataatacaagaaaagcccgtcacgggcttctcagggcgttttatggc
gggtctgctatgtggtgctatctgacttttgctgttcagcagttcctgccctctgattttcca
gtctgaccacttcggattatcccgtgacaggtcattcagactggctaatgcacccagtaaggca
gcggtatcatcaacaggcttacccgtcttactgtcgggaattcgcgttggccgattcattaatg
cagattctgaaatgagctgttgacaattaatcatccggctcgtataatgtgtggaattgtgagc
ggataacaatttcacacaggaaacagcgccgctgagaaaaagcgaagcggcactgctctttaac
aatttatcagacaatctgtgtgggcactcgaccggaattatcgattaactttattattaaaaat
taaagaggtatatattaatgtatcgattaaataaggaggaataaaccatgtgtgcgacctcttc
tcaatttactcagattaccgagcataattcccgtcgttccgcaaactatcagccaaacctgtgg
aatttcgaattcctgcaatccctggagaacgacctgaaagtggaaaagctggaggagaaagcga
ccaaactggaggaagaagttcgctgcatgatcaaccgtgtagacacccagccgctgtccctgct
ggagctgatcgacgatgtgcagcgcctgggtctgacctacaaatttgaaaaagacatcattaaa
gccctggaaaacatcgtactgctggacgaaaacaaaaagaacaaatctgacctgcacgcaaccg
ctctgtctttccgtctgctgcgtcagcacggtttcgaggtttctcaggatgttttgagcgttt
caaggataaagaaggtggtttcagcggtgaactgaaaggtgacgtccaaggcctgctgagcctg
tatgaagcgtcttacctgggtttcgagggtgagaacctgctggaggaggcgcgtacctttcca
tcacccacctgaagaacaacctgaaagaaggcattaataccaaggttgcagaacaagtgagcca
cgccctggaactgccatatcaccagcgtctgcaccgtctggaggcacgttggttcctggataaa
tacgaaccgaaagaaccgcatcaccagctgctgctggagctggcgagctggattttaacatgg
tacagaccctgcaccagaaagagctgcaagatctgtcccgctggtggaccgagatgggcctggc
tagcaaactggattttgtacgcgaccgcctgatggaagtttattctgggcactgggtatggcg
ccagacccgcagtttggtgaatgtcgcaaagctgttactaaaatgtttggtctggtgacgatca
tcgatgacgtgtatgacgtttatggcactctggacgaactgcaactgttcaccgatgctgtaga
gcgctgggacgttaacgctattaacaccctgccggactatatgaaactgtgtttcctggcactg
tacaacaccgttaacgacacgtcctattctattctgaaagagaaaggtcataacaacctgtcct

FIG. 39C

```
atctgacgaaaagctggcgtgaactgtgcaaagcctttctgcaagaggcgaaatggtccaacaa
caaaattatcccggctttctccaagtacctggaaaacgccagcgtttcctcctccggtgtagcg
ctgctggcgccgtcttacttttccgtatgccagcagcaggaagacatctccgaccacgcgctgc
gttccctgaccgacttccatggtctggtgcgttctagctgcgttatcttccgcctgtgcaacga
tctggccacctctgcggcggagctggaacgtggcgagactaccaattctatcattagctacatg
cacgaaaacgatggtaccagcgaggaacaggcccgcgaagaactgcgtaaactgatcgacgccg
aatggaaaagatgaatcgtgaacgcgttagcgactccaccctgctgcctaaagcgttcatgga
aatcgcagttaacatggcacgtgtttcccactgcacctaccagtatggcgatggtctgggtcgc
ccagactacgcgactgaaaaccgcatcaaactgctgctgattgacccttttcccgattaaccagc
tgatgtatgtctaactgcagctggtaccatatgggaattcgaagctttctagaacaaaaactca
tctcagaagaggatctgaatagcgccgtcgaccatcatcatcatcatcattgagtttaaacggt
ctccagcttggctgttttggcggatgagagaagattttcagcctgatacagattaaatcagaac
gcagaagcggtctgataaaacagaatttgcctggcggcagtagcgcggtggtcccacctgaccc
catgccgaactcagaagtgaaacgccgtagcgccgatggtagtgtggggtctcccatgcgaga
gtagggaactgccaggcatcaaataaaacgaaaggctcagtcgaaagactgggccttcgtttt
atctgttgtttgtcggtgaacgctctcctgagtaggacaaatccgccgggagcggatttgaacg
ttgcgaagcaacggcccggagggtggcgggcaggacgcccgccataaactgccaggcatcaaat
taagcagaaggccatcctgacggatggcctttttgcgtttctacaaactcttttttgtttatttt
tctaaatacattcaaatatgtatccgctcatgagacaataaccctgataaatgcttcaataat
```
(SEQ ID NO:52)

FIG. 41A

5'-
cccgtcttactgtcgggaattcgcgttggccgattcattaatgcagattattgaagcatttatc
agggttattgtctcatgagcggatacatatttgaatgtatttagaaaaataaacaaaaagagtt
tgtagaaacgcaaaaaggccatccgtcaggatggccttctgcttaatttgatgcctggcagttt
atggcgggcgtcctgcccgccaccctccgggccgttgcttcgcaacgttcaaatccgctcccgg
cggatttgtcctactcaggagagcgttcaccgacaaacaacagataaaacgaaaggcccagtct
ttcgactgagcctttcgttttatttgatgcctggcagttccctactctcgcatggggagacccc
acactaccatcggcgctacggcgtttcacttctgagttcggcatggggtcaggtgggaccaccg
cgctactgccgccaggcaaattctgttttatcagaccgcttctgcgttctgatttaatctgtat
caggctgaaaatcttctctcatccgccaaaacagccaagctggagaccgtttaaactcaatgat
gatgatgatgatggtcgacggcgctattcagatcctcttctgagatgagttttttgttctagaaa
gcttcgaattcccatatggtaccagctgcagttagacatacatcagctggttaatcgggaaagg
gtcaatcagcagcagtttgatgcggttttcagtcgcgtagtctgggcgacccagaccatcgcca
tactggtaggtgcagtgggaaacacgtgccatgttaactgcgatttccatgaacgctttaggca
gcagggtggagtcgctaacgcgttcacgattcatcttttccattcggcgtcgatcagtttacg
cagttcttcgcgggcctgttcctcgctggtaccatcgttttcgtgcatgtagctaatgatagaa
ttggtagtctcgccacgttccagctccgccgcagaggtggccagatcgttgcacaggcggaaga
taacgcagctagaacgcaccagaccatggaagtcggtcagggaacgcagcgcgtggtcggagat
gtcttcctgctgctggcatacggaaaagtaagacggcgccagcagcgctacaccggaggaggaa
acgctggcgttttccaggtacttggagaaagccgggataatttgttgttggaccatttcgcct
cttgcagaaaggctttgcacagttcacgccagcttttcgtcagataggacaggttgttatgacc
tttctctttcagaatagaataggacgtgtcgttaacggtgttgtacagtgccaggaaacacagt
ttcatatagtccggcagggtgttaatagcgttaacgtcccagcgctctacagcatcggtgaaca
gttgcagttcgtccagagtgccataaacgtcatacacgtcatcgatgatcgtcaccagaccaaa
catttttagtaacagctttgcgacattcaccaaactgcgggtctggcgccatacccagtgcccag
aaataaacttccatcaggcggtcgcgtacaaaatccagtttgctagccaggccatctcggtcc
accagcgggacagatcttgcagctcttctggtgcagggtctgtaccatgttaaaatccagctt
cgccagctccagcagcagctggtgatgcggttctttcggttcgtatttatccaggaaccaacgt
gcctccagacggtgcagacgctggtgatatggcagttccagggcgtggctcacttgttctgcaa
ccttggtattaatgccttctttcaggttgttcttcaggtgggtgatggaaaaggtacgcgcctc
ctccagcaggttctcaccctcgaaacccaggtaagacgcttcatacaggctcagcaggccttgg
acgtcacctttcagttcaccgctgaaaccaccttctttatccttgaaacgctcaaaaacatcct
gagaaacctcgaaaccgtgctgacgcagcagacggaaagacagagcggttgcgtgcaggtcaga
tttgttcttttttgttttcgtccagcagtacgatgttttccagggctttaatgatgtctttttca
aatttgtaggtcagacccaggcgctgcacatcgtcgatcagctccagcagggacagcggctggg
tgtctacacggttgatcatgcagcgaacttcttcctccagtttggtcgctttctcctccagctt
ttccactttcaggtcgttctccagggattgcaggaattcgaaattccacaggtttggctgatag
tttgcggaacgacgggaattatgctcggtaatctgagtaaattgagaagaggtcgcacacatgg
tttattcctccttatttaatcgatacattaatatacctctttaattttaataataaagtta
atcgataattccggtcgagtgcccacacagattgtctgataaattgttaaagagcagtgcgct
tcgcttttctcagcggcgctgtttcctgtgtgaaattgttatccgctcacaattccacacatt
atacgagccggatgattaattgtcaacagctcatttcagaatctggcgtaatagcgaagaggcc
cgcaccgatcgcccttcccaacagttgcgcagcctgaatggcgaatggcgcctgatgcggtatt
ttctccttacgcatctgtgcggtatttcacaccgcatatggtgcactctcagtacaatctgctc

FIG. 41B

```
tgatgccgcatagttaagccagccccgacacccgccaacacccgctgacgagcttagtaaagcc
ctcgctagattttaatgcggatgttgcgattacttcgccaactattgcgataacaagaaaaagc
cagccttcatgatatatctcccaatttgtgtagggcttattatgcacgcttaaaaataataaa
agcagacttgacctgatagtttggctgtgagcaattatgtgcttagtgcatctaacgcttgagt
taagccgcgccgcgaagcggcgtcggcttgaacgaattgttagacattatttgccgactactt
ggtgatctcgcctttcacgtagtggacaaattcttccaactgatctgcgcgcgaggccaagcga
tcttcttcttgtccaagataagcctgtctagcttcaagtatgacgggctgatactgggccggca
ggcgctccattgcccagtcggcagcgacatccttcggcgcgattttgccggttactgcgctgta
ccaaatgcgggacaacgtaagcactacatttcgctcatcgccagccagtcgggcggcgagttc
catagcgttaaggtttcatttagcgcctcaaatagatcctgttcaggaaccggatcaaagagtt
cctccgccgctggacctaccaaggcaacgctatgttctcttgcttttgtcagcaagatagccag
atcaatgtcgatcgtggctggctcgaagatacctgcaagaatgtcattgcgctgccattctcca
aattgcagttcgcgcttagctggataacgccacggaatgatgtcgtcgtgcacaacaatggtga
cttctacagcgcggagaatctcgctctctcaggggaagccgaagtttccaaaaggtcgttgat
caaagctcgccgcgttgtttcatcaagccttacggtcaccgtaaccagcaaatcaatatcactg
tgtggcttcaggccgccatccactgcggagccgtacaaatgtacggccagcaacgtcggttcga
gatggcgctcgatgacgccaactacctctgatagttgagtcgatacttcggcgatcaccgcttc
cctcatgatgtttaactttgttttagggcgactgccctgctgcgtaacatcgttgctgctccat
aacatcaaacatcgacccacggcgtaacgcgcttgctgcttggatgcccgaggcatagactgta
ccccaaaaaaacagtcataacaagccatgaaaaccgccactgcgccgttaccaccgctgcgttc
ggtcaaggttctggaccagttgcgtgagcgcatacgctacttgcattacagcttacgaaccgaa
caggcttatgtccactgggttcgtgccttcatccgtttccacggtgtgcgtcacccggcaacct
tgggcagcagcgaagtcgaggcatttctgtcctggctggcgaacgagcgcaaggtttcggtctc
cacgcatcgtcaggcattggcggccttgctgttcttctacggcaaggtgctgtgcacggatctg
ccctggcttcaggagatcggaagacctcggccgtcgcggcgcttgccggtggtgctgaccccgg
atgaagtggttcgcatcctcggttttctggaaggcgagcatcgtttgttcgcccagcttctgta
tggaacgggcatgcggatcagtgagggtttgcaactgcgggtcaaggatctggatttcgatcac
ggcacgatcatcgtgcgggagggcaagggctccaaggatcgggccttgatgttacccgagagct
tggcacccagcctgcgcgagcaggggaattaattcccacgggttttgctgcccgcaaacgggct
gttctggtgttgctagtttgttatcagaatcgcagatccggcttcagccggtttgccggctgaa
agcgctatttcttccagaattgccatgatttttccccacgggaggcgtcactggctcccgtgt
tgtcggcagctttgattcgataagcagcatcgcctgtttcaggctgtctatgtgtgactgttga
gctgtaacaagttgtctcaggtgttcaatttcatgttctagttgctttgttttactggtttcac
ctgttctattaggtgttacatgctgttcatctgttacattgtcgatctgttcatggtgaacagc
tttgaatgcaccaaaaactcgtaaaagctctgatgtatctatcttttttacaccgttttcatct
gtgcatatggacagttttcccttgatatgtaacggtgaacagttgttctactttgtttgtta
gtcttgatgcttcactgatagatacaagagccataagaacctcagatccttcgtatttagcca
gtatgttctctagtgtggttcgttgttttgcgtgagccatgagaacgaaccattgagatcata
cttactttgcatgtcactcaaaaattttgcctcaaaactggtgagctgaattttgcagttaaa
gcatcgtgtagtgttttcttagtccgttatgtaggtaggaatctgatgtaatggttgttggta
ttttgtcaccattcatttatctggttgttctcaagttcggttacgagatccatttgtctatc
tagttcaacttggaaaatcaacgtatcagtcgggcggcctcgcttatcaaccaccaatttcata
ttgctgtaagtgtttaaatcttacttattggtttcaaaacccattggttaagccttttaaact
catggtagttattttcaagcattaacatgaacttaaattcatcaaggctaatctctatatttgc
```

FIG. 41C

```
cttgtgagttttcttttgtgttagttcttttaataaccactcataaatcctcatagagtatttg
ttttcaaaagacttaacatgttccagattatattttatgaattttttaactggaaaagataag
gcaatatctcttcactaaaaactaattctaattttttcgcttgagaacttggcatagtttgtcca
ctggaaaatctcaaagcctttaaccaaaggattcctgatttccacagttctcgtcatcagctct
ctggttgctttagctaatacaccataagcattttccctactgatgttcatcatctgagcgtatt
ggttataagtgaacgataccgtccgttctttccttgtagggttttcaatcgtggggttgagtag
tgccacacagcataaaattagcttggtttcatgctccgttaagtcatagcgactaatcgctagt
tcatttgctttgaaaacaactaattcagacatacatctcaattggtctaggtgattttaatcac
tataccaattgagatgggctagtcaatgataattactagtccttttcctttgagttgtgggtat
ctgtaaattctgctagacctttgctggaaaacttgtaaattctgctagaccctctgtaaattcc
gctagacctttgtgtgttttttttgtttatattcaagtggttataatttatagaataaagaaag
aataaaaaagataaaagaatagatcccagccctgtgtataactcactactttagtcagttcc
gcagtattacaaaaggatgtcgcaaacgctgtttgctcctctacaaaacagaccttaaaaccct
aaaggcttaagtagcaccctcgcaagctcgggcaaatcgctgaatattccttttgtctccgacc
atcaggcacctgagtcgctgtcttttcgtgacattcagttcgctgcgctcacggctctggcag
tgaatgggggtaaatggcactacaggcgccttttatggattcatgcaaggaaactacccataat
acaagaaaagcccgtcacgggcttctcagggcgtttatggcgggtctgctatgtggtgctatc
tgacttttgctgttcagcagttcctgccctctgattttccagtctgaccacttcggattatcc
cgtgacaggtcattcagactggctaatgcacccagtaaggcagcggtatcatcaacaggctta
(SEQ ID NO:53)
```

FIG. 43A

5'-
ctggcgtaatagcgaagaggcccgcaccgatcgcccttcccaacagttgcgcagcctgaatggc
gaatggcgcctgatgcggtattttctccttacgcatctgtgcggtatttcacaccgcatatggt
gcactctcagtacaatctgctctgatgccgcatagttaagccagccccgacacccgccaacacc
cgctgacgagcttagtaaagccctcgctagattttaatgcggatgttgcgattacttcgccaac
tattgcgataacaagaaaagccagccttcatgatatctcccaatttgtgtagggcttatt
atgcacgcttaaaaataataaaagcagacttgacctgatagtttggctgtgagcaattatgtgc
ttagtgcatctaacgcttgagttaagccgcgccgcgaagcggcgtcggcttgaacgaattgtta
gacattatttgccgactaccttggtgatctcgcctttcacgtagtggacaaattcttccaactg
atctgcgcgcgaggccaagcgatcttcttcttgtccaagataagcctgtctagcttcaagtatg
acgggctgatactgggccggcaggcgctccattgcccagtcggcagcgacatccttcggcgcga
ttttgccggttactgcgctgtaccaaatgcgggacaacgtaagcactacatttcgctcatcgcc
agcccagtcgggcggcgagttccatagcgttaaggtttcatttagcgcctcaaatagatcctgt
tcaggaaccggatcaaagagttcctccgccgctggacctaccaaggcaacgctatgttctcttg
cttttgtcagcaagatagccagatcaatgtcgatcgtggctggctcgaagatacctgcaagaat
gtcattgcgctgccattctccaaattgcagttcgcgcttagctggataacgccacggaatgatg
tcgtcgtgcacaacaatggtgacttctacagcgcggagaatctcgctctctccaggggaagccg
aagtttccaaaggtcgttgatcaaagctcgccgcgttgtttcatcaagccttacggtcaccgt
aaccagcaaatcaatatcactgtgtggcttcaggccgccatccactgcggagccgtacaaatgt
acggccagcaacgtcggttcgagatggcgctcgatgacgccaactacctctgatagttgagtcg
atacttcggcgatcaccgcttccctcatgatgtttaactttgttttagggcgactgccctgctg
cgtaacatcgttgctgctccataacatcaaacatcgacccacggcgtaacgcgcttgctgcttg
gatgccgaggcatagactgtaccccaaaaaaacagtcataacaagccatgaaaaccgccactg
cgccgttaccaccgctgcgttcggtcaaggttctggaccagttgcgtgagcgcatacgctactt
gcattacagcttacgaaccgaacaggcttatgtccactgggttcgtgccttcatccgtttccac
ggtgtgcgtcacccggcaaccttgggcagcagcgaagtcgaggcatttctgtcctggctggcga
acgagcgcaaggtttcggtctccacgcatcgtcaggcattggcggccttgctgttcttctacgg
caaggtgctgtgcacggatctgccctggcttcaggagatcggaagacctcggccgtcgcggcgc
ttgccggtggtgctgaccccggatgaagtggttcgcatcctcggttttctggaaggcgagcatc
gtttgttcgcccagcttctgtatggaacgggcatgcggatcagtgagggtttgcaactgcggt
caaggatctggatttcgatcacggcacgatcatcgtgcgggagggcaagggctccaaggatcgg
gccttgatgttacccgagagcttggcacccagcctgcgcgagcaggggaattaattcccacggg
ttttgctgcccgcaaacgggctgttctggtgttgctagtttgttatcagaatcgcagatccggc
ttcagccggtttgccggctgaaagcgctatttcttccagaattgccatgattttttccccacgg
gaggcgtcactggctcccgtgttgtcggcagctttgattcgataagcagcatcgcctgtttcag
gctgtctatgtgtgactgttgagctgtaacaagttgtctcaggtgttcaatttcatgttctagt
tgctttgttttactggtttcacctgttctattaggtgttacatgctgttcatctgttacattgt
cgatctgttcatggtgaacagctttgaatgcaccaaaaactcgtaaaagctctgatgtatctat
cttttttacaccgttttcatctgtgcatatggacagttttcccttttgatatgtaacggtgaaca
gttgttctactttgtttgttagtcttgatgcttcactgatagataagagccataagaacct
cagatccttccgtatttagccagtatgttctctagtgtggttcgttgttttgcgtgagccatg
agaacgaaccattgagatcatacttactttgcatgtcactcaaaaattttgcctcaaaactggt
gagctgaattttgcagttaaagcatcgtgtagtgttttcttagtccgttatgtaggtaggaa
tctgatgtaatggttgttggtattttgtcaccattcatttttatctggttgttctcaagttcgg

FIG. 43B

```
ttacgagatccatttgtctatctagttcaacttggaaaatcaacgtatcagtcgggcggcctcg
cttatcaaccaccaatttcatattgctgtaagtgtttaaatctttacttattggtttcaaaacc
cattggttaagccttttaaactcatggtagttattttcaagcattaacatgaacttaaattcat
caaggctaatctctatatttgccttgtgagttttcttttgtgttagttcttttaataaccactc
ataaatcctcatagagtatttgttttcaaaagacttaacatgttccagattatattttatgaat
tttttaactggaaaagataaggcaatatctcttcactaaaaactaattctaattttcgcttg
agaacttggcatagtttgtccactggaaaatctcaaagcctttaaccaaaggattcctgatttc
cacagttctcgtcatcagctctctggttgctttagctaatacaccataagcattttccctactg
atgttcatcatctgagcgtattggttataagtgaacgataccgtccgttctttccttgtagggt
tttcaatcgtggggttgagtagtgccacacagcataaaattagcttggtttcatgctccgttaa
gtcatagcgactaatcgctagttcatttgctttgaaaacaactaattcagacatacatctcaat
tggtctaggtgattttaatcactataccaattgagatgggctagtcaatgataattactagtcc
ttttcctttgagttgtgggtatctgtaaattctgctagacctttgctggaaaacttgtaaattc
tgctagaccctctgtaaattccgctagacctttgtgtgttttttttgtttatattcaagtggtt
ataatttatagaataaagaaagaataaaaaaagataaaaagaatagatcccagccctgtgtata
actcactactttagtcagttccgcagtattacaaaaggatgtcgcaaacgctgtttgctcctct
acaaaacagaccttaaaaccctaaaggcttaagtagcaccctcgcaagctcgggcaaatcgctg
aatattccttttgtctccgaccatcaggcacctgagtcgctgtcttttcgtgacattcagttc
gctgcgctcacggctctggcagtgaatggggtaaatggcactacaggcgccttttatggattc
atgcaaggaaactacccataatacaagaaaagcccgtcacgggcttctcagggcgttttatggc
gggtctgctatgtggtgctatctgacttttgctgttcagcagttcctgccctctgattttcca
gtctgaccacttcggattatcccgtgacaggtcattcagactggctaatgcacccagtaaggca
gcggtatcatcaacaggcttacccgtcttactgtcgggaattcgcgttggccgattcattaatg
cagattctgaaatgagctgttgacaattaatcatccggctcgtataatgtgtggaattgtgagc
ggataacaatttcacacaggaaacagcgccgctgagaaaaagcgaagcggcactgctcttaac
aatttatcagacaatctgtgtgggcactcgaccggaattatcgattaactttattattaaaaat
taaagaggtatatattaatgtatcgattaaataaggaggaataaaccatgtgtgcgacctcttc
tcaatttactcagattaccgagcataattcccgtcgttccgcaaactatcagccaaacctgtgg
aatttcgaattcctgcaatccctggagaacgacctgaaagtggaaaagctggaggagaaagcga
ccaaactggaggaagaagttcgctgcatgatcaaccgtgtagacacccagccgctgtccctgct
ggagctgatcgacgatgtgcagcgcctgggtctgacctacaaatttgaaaagacatcattaaa
gccctggaaaacatcgtactgctggacgaaaacaaaaagaacaaatctgacctgcacgcaaccg
ctctgtctttccgtctgctgcgtcagcacggtttcgaggtttctcaggatgtttttgagcgttt
caaggataaagaaggtggtttcagcggtgaactgaaaggtgacgtccaaggcctgctgagcctg
tatgaagcgtcttacctgggtttcgagggtgagaacctgctggaggagcgcgtaccttttcca
tcacccacctgaagaacaacctgaaagaaggcattaataccaaggttgcagaacaagtgagcca
cgccctggaactgccatatcaccagcgtctgcaccgtctggaggcacgttggttcctggataaa
tacgaaccgaaagaaccgcatcaccagctgctgctggagctggcgaagctggattttaacatgg
tacagaccctgcaccagaaagagctgcaagatctgtcccgctggtggaccgagatgggcctggc
tagcaaactggattttgtacgcgaccgcctgatggaagtttatttctgggcactgggtatggcg
ccagaccgcagtttggtgaatgtcgcaaagctgttactaaaatgtttggtctggtgacgatca
tcgatgacgtgtatgacgtttatggcactctggacgaactgcaactgttcaccgatgctgtaga
gcgctgggacgttaacgctattaacaccctgccggactatatgaaactgtgttcctggcactg
tacaacaccgttaacgacacgtccattctattctgaaagagaaaggtcataacaacctgtcct
```

FIG. 43C atctgacgaaaagctggcgtgaactgtgcaaagcctttctgcaagaggcgaaatggtccaacaa
caaaattatcccggctttctccaagtacctggaaaacgccagcgtttcctcctccggtgtagcg
ctgctggcgcgtcttacttttccgtatgccagcagcaggaagacatctccgaccacgcgctgc
gttccctgaccgacttccatggtctggtgcgttctagctgcgttatcttccgcctgtgcaacga
tctggccacctctgcggcggagctggaacgtggcgagactaccaattctatcattagctacatg
cacgaaaacgatggtaccagcgaggaacaggcccgcgaagaactgcgtaaactgatcgacgccg
aatggaaaagatgaatcgtgaacgcgttagcgactccaccctgctgcctaaagcgttcatgga
aatcgcagttaacatggcacgtgtttcccactgcacctaccagtatggcgatggtctgggtcgc
ccagactacgcgactgaaaaccgcatcaaactgctgctgattgacccttttcccgattaaccagc
tgatgtatgtctaactgcatcgcccttaggaggtaaaaaaaaatgactgccgacaacaatagta
tgccccatggtgcagtatctagttacgccaaattagtgcaaaaccaaacacctgaagacatttt
ggaagagtttcctgaaattattccattacaacaaagacctaatacccgatctagtgagacgtca
aatgacgaaagcggagaaacatgtttttctggtcatgatgaggagcaaattaagttaatgaatg
aaaattgtattgttttggattgggacgataatgctattggtgccggtaccaagaaagtttgtca
tttaatggaaaatattgaaaagggtttactacatcgtgcattctccgtctttattttcaatgaa
caaggtgaattacttttacaacaaagagccactgaaaaaataactttccctgatctttggacta
acacatgctgctctcatccactatgtattgatgacgaattaggtttgaagggtaagctagacga
taagattaagggcgctattactgcggcggtgagaaaactagatcatgaattaggtattccagaa
gatgaaactaagacaaggggtaagtttcacttttaaacagaatccattacatggcaccaagca
atgaaccatgggtgaacatgaaattgattacatcctattttataagatcaacgctaaagaaaa
cttgactgtcaacccaaacgtcaatgaagttagagacttcaaatgggtttcaccaaatgatttg
aaaactatgtttgctgacccaagttacaagtttacgccttggtttaagattatttgcgagaatt
acttattcaactggtgggagcaattagatgacctttctgaagtggaaaatgacaggcaaattca
tagaatgctataacgacgcgtcctgcagctggtaccatatgggaattcgaagctttctagaacg
aaaactcatctcagaagaggatctgaatagcgccgtcgaccatcatcatcatcatcattgagtt
taaacggtctccagcttggctgttttggcggatgagagaagattttcagcctgatacagattaa
atcagaacgcagaagcggtctgataaaacagaatttgcctggcggcagtagcgcggtggtccca
cctgaccccatgccgaactcagaagtgaaacgccgtagcgccgatggtagtgtggggtctccc
atgcgagagtagggaactgccaggcatcaaataaaacgaaaggctcagtcgaaagactgggcct
ttcgttttatctgttgtttgtcggtgaacgctctcctgagtaggacaaatccgccgggagcgga
tttgaacgttgcgaagcaacggcccggagggtggcgggcaggacgcccgccataaactgccagg
catcaaattaagcagaaggccatcctgacggatggcctttttgcgtttctacaaactcttttg
tttattttctaaatacattcaaatatgtatccgctcatgagacaataaccctgataaatgctt
caataat
(SEQ ID NO:54)

FIG. 45A

5'-
cccgtcttactgtcgggaattcgcgttggccgattcattaatgcagattattgaagcatttatc
agggttattgtctcatgagcggatacatatttgaatgtatttagaaaaataaacaaaaagagtt
tgtagaaacgcaaaaaggccatccgtcaggatggccttctgcttaatttgatgcctggcagttt
atggcgggcgtcctgcccgccaccctccgggccgttgcttcgcaacgttcaaatccgctcccgg
cggatttgtcctactcaggagagcgttcaccgacaaacaacagataaaacgaaaggcccagtct
ttcgactgagcctttcgtttatttgatgcctggcagttccctactctcgcatggggagacccc
acactaccatcggcgctacggcgtttcacttctgagttcggcatggggtcaggtgggaccaccg
cgctactgccgccaggcaaattctgttttatcagaccgcttctgcgttctgatttaatctgtat
caggctgaaaatcttctctcatccgccaaaacagccaagctggagaccgtttaaactcaatgat
gatgatgatgatggtcgacggcgctattcagatcctcttctgagatgagttttttgttctagaaa
gcttcgaattcccatatggtaccagctgcagttatgccagccaggccttgattttggcttccat
accagcggcatcgaggccgagttcggcgcgcatttcttcctgagttccttgcggaataaagaag
tccggcaggccaatgttcagcacgggtactggtttacgatgggccatcagcacttcgttcacgc
cgctgcctgcgccgcccataatggcgttttcttctacggtgaccagcgcttcatggctggcggc
catttccagaattaacgcttcatcaagcggtttcacaaaacgcatatcgaccagcgtggcgttc
agcgattcggcgactttcgccgcttctggcatcagcgtaccaaagttaaggatcgccagtttct
cgccacgacgcttcacaatgcctttgccaattggtagttttccagcggcgtcagttccacgcc
gaccgcgttgccacgcgggtagcgcaccgctgacgggccatcgttatagtgatagccggtatag
agcatctggcgacattcgttttcatcgctcggggtcataatgaccatttccggtatgcagcgca
ggtaagagagatcaaaagcaccctgatgggtttgaccgtcagcaccaacaatgcccgcgcggtc
gatggcgaacaggaccggaagcttttgaatcgccacgtcatgcagcacctgatcataggcgcgt
tgcaggaaagtggagtaaatcgcgacaatgggtttgtacccaccaatcgccagacccgcagcaa
aggtcaccgcgtgttgctcggcaattgccacgtcgaagtagcgatccgggaatttacgtgaaaa
ctcgaccatgccggaaccttcacgcatcgccggagtaatcgccatcagcttgttgtctttcgct
gccgtttcgcacaaccagtcgccaaagattttgaatagctcggcaaaccgccgctacttttcg
gcaaacaaccgctggagggatcaaatttaggcacggcgtggaaagtgatcgggtcttttctgc
cggttcataaccacgaccttttttggtcatgatatgcaggaactgcgggccttcaggtcgcgc
atgttctttagcgtggtgataagccccagcacatcgtgaccgtccaccgggccgatgtagttaa
agcccagctcttcaaacaacgtgccaggcactaccatgcctttaatatgttcttcggtgcgttt
gagcagctcttttaattggcggcacgccagagaaaacttttttcccgccttcgcgcagtgaagag
taaagcttaccggaaagcagctgtgccagatggttgttgagcgcgccgacattttcggaaatcg
acatttcattgtcgttgagaatcaccagcatatcaggacggatatcgcccgcgtgattcatcgc
ttcaaacgccatgcctgcggtaatcgcgccatcgccaatgacacagacggtgcggcgattttttg
ccttcttttcggcagcaaccgcaataccaattccggcactgatggaggttgatgaatgcccga
cgcttaatacgtcatattcgctttcgccgcgccacgggaacgggtgcagaccgcctttctgacg
gatggtgccgattttgtcgcggcgtccggtcaaaattttatgcggataagcctgatgccccaca
tcccaaatcaattggtcaaacggggtgttgtagacatagtgcagcgccacggtcagttcgaccg
tgcccagcccggaggcgaagtgcccgctggaacggctcacgctgtcgagtaaatagcggcgcag
ttcgtcgcagagtttcggtaaactctctttcggcaacagtcgtaactcctgggtggagtcgacc
agtgccagggtcgggtatttggcaatatcaaaactcatgttttttacctcctaagggcgaatg
cagttagacatacatcagctggttaatcgggaaagggtcaatcagcagcagtttgatgcggttt
tcagtcgcgtagtctgggcgacccagaccatcgccatactggtaggtgcagtgggaaacacgtg
ccatgttaactgcgatttccatgaacgctttaggcagcagggtggagtcgctaacgcgttcacg

FIG. 45B attcatctttttccattcggcgtcgatcagtttacgcagttcttcgcgggcctgttcctcgctg
gtaccatcgttttcgtgcatgtagctaatgatagaattggtagtctcgccacgttccagctccg
ccgcagaggtggccagatcgttgcacaggcggaagataacgcagctagaacgcaccagaccatg
gaagtcggtcagggaacgcagcgcgtggtcggagatgtcttcctgctgctggcatacggaaaag
taagacggcgccagcagcgctacaccggaggaggaaacgctggcgttttccaggtacttggaga
aagccgggataattttgttgttggaccatttcgctcttgcagaaaggctttgcacagttcacg
ccagcttttcgtcagataggacaggttgttatgacctttctctttcagaatagaataggacgtg
tcgttaacggtgttgtacagtgccaggaaacacagtttcatatagtccggcagggtgttaatag
cgttaacgtcccagcgctctacagcatcggtgaacagttgcagttcgtccagagtgccataaac
gtcatacacgtcatcgatgatcgtcaccagaccaaacattttagtaacagctttgcgacattca
ccaaactgcgggtctggcgccatacccagtgcccagaaataaacttccatcaggcggtcgcgta
caaaatccagtttgctagccaggcccatctcggtccaccagcgggacagatcttgcagctcttt
ctggtgcagggtctgtaccatgttaaaatccagcttcgccagctccagcagcagctggtgatgc
ggttctttcggttcgtatttatccaggaaccaacgtgcctccagacggtgcagacgctggtgat
atggcagttccagggcgtggctcacttgttctgcaaccttggtattaatgccttctttcaggtt
gttcttcaggtgggtgatggaaaaggtacgcgcctcctccagcaggttctcaccctcgaaaccc
aggtaagacgcttcatacaggctcagcaggccttggacgtcacctttcagttcaccgctgaaac
caccttctttatccttgaaacgctcaaaaacatcctgagaaacctcgaaaccgtgctgacgcag
cagacggaaagacagagcggttgcgtgcaggtcagatttgttcttttgtttcgtccagcagt
acgatgttttccagggctttaatgatgtctttttcaaatttgtaggtcagacccaggcgctgca
catcgtcgatcagctccagcagggacagcggctggtgtctacacggttgatcatgcagcgaac
ttcttcctccagtttggtcgctttctcctccagcttttccactttcaggtcgttctccagggat
tgcaggaattcgaaattccacaggtttggctgatagtttgcggaacgacgggaattatgctcgg
taatctgagtaaattgagaagaggtcgcacacatggtttattcctccttatttaatcgatacat
taatatatacctctttaattttaataataaagttaatcgataattccggtcgagtgcccacac
agattgtctgataaattgttaaagagcagtgccgcttcgcttttctcagcggcgctgttcct
gtgtgaaattgttatccgctcacaattccacacattatacgagccggatgattaattgtcaaca
gctcatttcagaatctggcgtaatagcgaagaggcccgcaccgatcgcccttccaacagttgc
gcagcctgaatggcgaatggcgcctgatgcggtattttctccttacgcatctgtgcggtatttc
acaccgcatatggtgcactctcagtacaatctgctctgatgccgcatagttaagccagccccga
cacccgccaacaccgctgacgagcttagtaaagccctcgctagattttaatgcggatgttgcg
attacttcgccaactattgcgataacaagaaaagccagcctttcatgatatatctcccaattt
gtgtagggcttattatgcacgcttaaaaataataaaagcagacttgacctgatagtttggctgt
gagcaattatgtgcttagtgcatctaacgcttgagttaagccgcgccgcgaagcggcgtcggct
tgaacgaattgttagacattatttgccgactaccttggtgatctcgcctttcacgtagtggaca
aattcttccaactgatctgcgcgcgaggccaagcgatcttcttcttgtccaagataagcctgtc
tagcttcaagtatgacgggctgatactgggccggcaggcgctccattgcccagtcggcagcgac
atccttcggcgcgattttgccggttactgcgctgtaccaaatgcgggacaacgtaagcactaca
tttcgctcatcgccagcccagtcgggcggcgagttccatagcgttaaggtttcatttagcgcct
caaatagatcctgttcaggaaccggatcaaagagttcctccgccgctggacctaccaaggcaac
gctatgttctcttgcttttgtcagcaagatagccagatcaatgtcgatcgtggctggctcgaag
atacctgcaagaatgtcattgcgctgccattctccaaattgcagttcgcgcttagctggataac
gccacggaatgatgtcgtcgtgcacaacaatggtgacttctacagcgcggagaatctcgctctc
tccaggggaagccgaagtttccaaaaggtcgttgatcaaagctcgccgcgttgtttcatcaagc

FIG. 45C

```
cttacggtcaccgtaaccagcaaatcaatatcactgtgtggcttcaggccgccatccactgcgg
agccgtacaaatgtacggccagcaacgtcggttcgagatggcgctcgatgacgccaactacctc
tgatagttgagtcgatacttcggcgatcaccgcttccctcatgatgtttaactttgttttaggg
cgactgccctgctgcgtaacatcgttgctgctccataacatcaaacatcgacccacggcgtaac
gcgcttgctgcttggatgcccgaggcatagactgtaccccaaaaaaacagtcataacaagccat
gaaaaccgccactgcgccgttaccaccgctgcgttcggtcaaggttctggaccagttgcgtgag
cgcatacgctacttgcattacagcttacgaaccgaacaggcttatgtccactgggttcgtgcct
tcatccgtttccacggtgtgcgtcacccggcaaccttgggcagcagcgaagtcgaggcatttct
gtcctggctggcgaacgagcgcaaggtttcggtctccacgcatcgtcaggcattggcggccttg
ctgttcttctacggcaaggtgctgtgcacggatctgccctggcttcaggagatcggaagacctc
ggccgtcgcggcgcttgccggtggtgctgacccggatgaagtggttcgcatcctcggttttct
ggaaggcgagcatcgtttgttcgcccagcttctgtatggaacgggcatgcggatcagtgagggt
ttgcaactgcgggtcaaggatctggatttcgatcacggcacgatcatcgtgcgggagggcaagg
gctccaaggatcgggccttgatgttacccgagagcttggcacccagcctgcgcgagcaggggaa
ttaattcccacgggttttgctgcccgcaaacgggctgttctggtgttgctagtttgttatcaga
atcgcagatccggcttcagccggtttgccggctgaaagcgctatttcttccagaattgccatga
ttttttccccacgggaggcgtcactggctcccgtgttgtcggcagctttgattcgataagcagc
atcgcctgtttcaggctgtctatgtgtgactgttgagctgtaacaagttgtctcaggtgttcaa
tttcatgttctagttgctttgttttactggtttcacctgttctattaggtgttacatgctgttc
atctgttacattgtcgatctgttcatggtgaacagctttgaatgcaccaaaaactcgtaaagc
tctgatgtatctatctttttacaccgttttcatctgtgcatatggacagttttcccttttgata
tgtaacggtgaacagttgttctacttttgtttgttagtcttgatgcttcactgatagatacaag
agccataagaacctcagatccttccgtatttagccagtatgttctctagtgtggttcgttgttt
ttgcgtgagccatgagaacgaaccattgagatcatacttactttgcatgtcactcaaaaatttt
gcctcaaaactggtgagctgaatttttgcagttaaagcatcgtgtagtgtttttcttagtccgt
tatgtaggtaggaatctgatgtaatggttgttggtattttgtcaccattcatttttatctggtt
gttctcaagttcggttacgagatccatttgtctatctagttcaacttggaaaatcaacgtatca
gtcgggcggcctcgcttatcaaccaccaatttcatattgctgtaagtgtttaaatctttactta
ttggtttcaaaacccattggttaagccttttaaactcatggtagttattttcaagcattaacat
gaacttaaattcatcaaggctaatctctatatttgccttgtgagttttcttttgtgttagttct
tttaataaccactcataaatcctcatagagtatttgttttcaaaagacttaacatgttccagat
tatatttatgaattttttaactggaaaagataaggcaatatctcttcactaaaaactaattc
taattttttcgcttgagaacttggcatagtttgtccactggaaaatctcaaagcctttaaccaaa
ggattcctgatttccacagttctcgtcatcagctctctggttgctttagctaatacaccataag
cattttccctactgatgttcatcatctgagcgtattggttataagtgaacgataccgtccgttc
tttccttgtagggttttcaatcgtggggttgagtagtgccacacagcataaaattagcttggtt
tcatgctccgttaagtcatagcgactaatcgctagttcatttgctttgaaaacaactaattcag
acatacatctcaattggtctaggtgattttaatcactataccaattgagatgggctagtcaatg
ataattactagtccttttcctttgagttgtgggtatctgtaaattctgctagaccttttgctgga
aaacttgtaaattctgctagaccctctgtaaattccgctagacctttgtgtgttttttttgttt
atattcaagtggttataatttatagaataaagaagaataaaaaaagataaaagaatagatcc
cagccctgtgtataactcactactttagtcagttccgcagtattacaaaaggatgtcgcaaacg
ctgtttgctcctctacaaaacagaccttaaaaccctaaaggcttaagtagcaccctcgcaagct
cgggcaaatcgctgaatattccttttgtctccgaccatcaggcacctgagtcgctgtcttttc
```

FIG. 45D

Gtgacattcagttcgctgcgctcacggctctggcagtgaatgggggtaaatggcactacaggcg
cctttatggattcatgcaaggaaactacccataatacaagaaaagcccgtcacgggcttctca
gggcgttttatggcgggtctgctatgtggtgctatctgacttttgctgttcagcagttcctgc
cctctgatttccagtctgaccacttcggattatcccgtgacaggtcattcagactggctaatg
cacccagtaaggcagcggtatcatcaacaggctta
(SEQ ID NO:55)

FIG. 51A

5'-
tcgctgcgctcggtcgttcggctgcggcgagcggtatcagctcactcaaaggcggtaatacggt
tatccacagaatcaggggataacgcaggaaagaacatgtgagcaaaaggccagcaaaaggccag
gaaccgtaaaaaggccgcgttgctggcgtttttccataggctccgcccccctgacgagcatcac
aaaaatcgacgctcaagtcagaggtggcgaaacccgacaggactataaagataccaggcgtttc
cccctggaagctccctcgtgcgctctcctgttccgaccctgccgcttaccggatacctgtccgc
ctttctcccttcgggaagcgtggcgctttctcatagctcacgctgtaggtatctcagttcggtg
taggtcgttcgctccaagctgggctgtgtgcacgaaccccgttcagcccgaccgctgcgcct
tatccggtaactatcgtcttgagtccaacccggaagacacgacttatcgccactggcagcagc
cactggtaacaggattagcagagcgaggtatgtaggcggtgctacagagttcttgaagtggtgg
cctaactacggctacactagaagaacagtatttggtatctgcgctctgctgaagccagttacct
tcggaaaaagagttggtagctcttgatccggcaaacaaaccaccgctggtagcggtggttttt
tgtttgcaagcagcagattacgcgcagaaaaaaaggatctcaagaagatcctttgatcttttct
acggggtctgacgctcagtggaacgaaaactcacgttaagggattttggtcatgagattatcaa
aaaggatcttcacctagatccttttaaattaaaaatgaagttttaaatcaatctaaagtatata
tgagtaaacttggtctgacagttaccaatgcttaatcagtgaggcacctatctcagcgatctgt
ctatttcgttcatccatagttgcctgactccccgtcgtgtagataactacgatacgggagggct
taccatctggccccagtgctgcaatgataccgcgagacccacgctcaccggctccagatttatc
agcaataaaccagccagccggaagggccgagcgcagaagtggtcctgcaactttatccgcctcc
atccagtctattaattgttgccgggaagctagagtaagtagttcgccagttaatagtttgcgca
acgttgttgccattgctacaggcatcgtggtgtcacgctcgtcgtttggtatggcttcattcag
ctccggttcccaacgatcaaggcgagttacatgatccccatgttgtgcaaaaaagcggttagc
tccttcggtcctccgatcgttgtcagaagtaagttggccgcagtgttatcactcatggttatgg
cagcactgcataattctcttactgtcatgccatccgtaagatgcttttctgtgactggtgagta
ctcaaccaagtcattctgagaatagtgtatgcggcgaccgagttgctcttgcccggcgtcaata
cgggataataccgcgccacatagcagaactttaaaagtgctcatcattggaaaacgttcttcgg
ggcgaaaactctcaaggatcttaccgctgttgagatccagttcgatgtaacccactcgtgcacc
caactgatcttcagcatcttttactttcaccagcgtttctgggtgagcaaaaacaggaaggcaa
aatgccgcaaaaaagggaataagggcgacacggaaatgttgaatactcatactcttccttttc
aatattattgaagcatttatcagggttattgtctcatgagcggatacatatttgaatgtattta
gaaaaataaacaataggggttccgcgcacatttccccgaaaagtgccacctgacgtctaagaa
accattattcatgacattaacctataaaaataggcgtatcacgaggccctttcgtctcgcgc
gtttcggtgatgacggtgaaaacctctgacacatgcagctcccggagacggtcacagcttgtct
gtaagcggatgccgggagcagacaagcccgtcagggcgcgtcagcgggtgttggcgggtgtcgg
ggctggcttaactatgcggcatcagagcagattgtactgagagtgcaccatagatctggagctg
taatataaaaaccttcttcaactaacggggcaggttagtgacattagaaaaccgactgtaaaaa
gtacagtcggcattatctcatattataaaagccagtcattaggcctatctgacaattcctgaat
agagttcataaacaatcctgcatgataaccatcacaaacagaatgatgtacctgtaaagatagc
ggtaaatatattgaattacctttattaatgaattttcctgctgtaataatgggtagaaggtaat
tactattattattgatatttaagttaaacccagtaaatgaagtccatggaataatagaaagaga
aaagcatttcaggtataggtgttgggaaacaattccccgaaccattatatttctctaca
tcagaaaggtataaatcataaaactctttgaagtcattctttacaggagtccaaataccagaga
atgttttagataccatcaaaaattgtataaagtggctctaacttatcccaataacctaactc
tccgtcgctattgtaaccagttctaaaagctgtatttgagtttatcaccttgtcactaagaaa
ataaatgcagggtaaaatttatatccttcttgttttatgtttc

FIG. 51B ggtataaaacactaatatcaatttctgtggttatactaaaagtcgtttgttggttcaaataatg
attaaatatctcttttctcttccaattgtctaaatcaattttattaaagttcatttgatatgcc
tcctaaattttatctaaagtgaatttaggaggcttacttgtctgctttcttcattagaatcaa
tccttttttaaaagtcaatattactgtaacataaatatatattttaaaaatatcccactttatc
caatttcgtttgttgaactaatgggtgctttagttgaagaataaaagacctatgcggtgtgaa
ataccgcacagatgcgtaaggagaaaataccgcatcaggcgccattcgccattcaggctgcgca
actgttgggaagggcgatcggtgcgggcctcttcgctattacgccagctggcgaaaggggatg
tgctgcaaggcgattaagttgggtaacgccagggttttcccagtcacgacgttgtaaaacgacg
gccagtgccaagcttgcatgcctgcactccatttcttctgctatcaaaataacagactcgtga
ttttccaaacgagctttcaaaaagcctctgccccttgcaaatcggatgcctgtctataaatt
cccgatattggttaaacagcggcgcaatgcggccgcatctgatgtctttgcttggcgaatgtt
catcttatttcttcctccctctcaataattttttcattctatccttttctgtaaagtttattt
ttcagaatacttttatcatcatgctttgaaaaaatatcacgataatatccattgttctcacgga
agcacacgcaggtcatttgaacgaattttttcgacaggaatttgccgggactcaggagcattta
acctaaaaagcatgacatttcagcataatgaacatttactcatgtctattttcgttcttttct
gtatgaaaatagttatttcgagtctctacggaaatagcgagagatgatatacctaaatagagat
aaaatcatctcaaaaaatgggtctactaaaatattattccatctattacaataaattcacaga
atagtcttttaagtaagtctactctgaatttttttaaaaggagagggtaaagagtgaaaacagt
agttattattgatgcattacgaacaccaattggaaaatataaaggcagcttaagtcaagtaagt
gccgtagacttaggaacacatgttacaacacaacttttaaaaagacattccactatttctgaag
aaattgatcaagtaatctttggaaatgttttacaagctggaaatggccaaaatcccgcacgaca
aatagcaataaacagcggtttgtctcatgaaattcccgcaatgacggttaatgaggtctgcgga
tcaggaatgaaggccgttattttggcgaaacaattgattcaattaggagaagcggaagttttaa
ttgctggcgggattgagaatatgtcccaagcacctaaattacaacgttttaattacgaaacaga
aagctacgatgcgccttttttctagtatgatgtatgatggattaacggatgcctttagtggtcag
gcaatgggcttaactgctgaaaatgtggccgaaaagtatcatgtaactagagaagagcaagatc
aattttctgtacattcacaattaaaagcagctcaagcacaagcagaagggatattcgctgacga
aatagcccattagaagtatcaggaacgcttgtggagaaagatgaagggattcgccctaattcg
agcgttgagaagctaggaacgcttaaaacagttttttaaagaagacggtactgtaacagcaggga
atgcatcaaccattaatgatggggcttctgctttgattattgcttcacaagaatatgccgaagc
acacggtcttccttatttagctattattcgagacagtgtggaagtcggtattgatccagcctat
atgggaatttcgccgattaaagccattcaaaaactgttagcgcgcaatcaacttactacggaag
aaattgatctgtatgaaatcaacgaagcatttgcagcaacttcaatcgtggtccaaagagaact
ggctttaccagaggaaaaggtcaacatttatggtggcggtatttcattaggtcatgcgattggt
gccacaggtgctcgtttattaacgagtttaagttatcaattaaatcaaaaagaaaagaaatatg
gagtggcttctttatgtatcggcggtggcttaggactcgctatgctactagagagacctcagca
aaaaaaaacagccgatttatcaaatgagtcctgaggaacgcctggcttctcttcttaatgaa
ggccagatttctgctgatacaaaaaagaatttgaaaatacggctttatcttcgcagattgcca
atcatatgattgaaatcaaatcagtgaaacagaagtgccgatgggcgttggcttacatttaac
agtggacgaaactgattatttggtaccaatggcgacagaagagccctcagttattgcggctttg
agtaatggtgcaaaaatagcacaaggatttaaaacagtgaatcaacaacgcttaatgcgtggac
aaatcgttttttacgatgttgcagatcccgagtcattgattgataaactacaagtaagagaagc
ggaagttttcaacaagcagagttaagttatccatctatcgttaaacggggcggcggcttaaga
gatttgcaatatcgtacttttgatgaatcatttgtatctgtcgacttttagtagatgttaagg
atgcaatgggggcaaatatcgttaacgctatgttggaaggtgtg

FIG. 51C

```
gccgagttgttccgtgaatggtttgcggagcaaaagattttattcagtattttaagtaattatg
ccacggagtcggttgttacgatgaaaacggctattccagtttcacgtttaagtaaggggagcaa
tggccgggaaattgctgaaaaaattgttttagcttcacgctatgcttcattagatccttatcgg
gcagtcacgcataacaaaggaatcatgaatggcattgaagctgtagttttagctacaggaaatg
atacacgcgctgttagcgcttcttgtcatgcttttgcggtgaaggaaggtcgctaccaaggctt
gactagttggacgctggatggcgaacaactaattggtgaaatttcagttccgcttgctttagcc
acggttggcggtgccacaaaagtcttacctaaatctcaagcagctgctgatttgttagcagtga
cggatgcaaaagaactaagtcgagtagtagcggctgttggtttggcacaaaatttagcggcgtt
acgggccttagtctctgaaggaattcaaaaggacacatggctctacaagcacgttctttagcg
atgacggtcggagctactggtaaagaagttgaggcagtcgctcaacaattaaaacgtcaaaaaa
cgatgaaccaagaccgagccatggctatttaaatgatttaagaaaacaataaaaggagagggt
gacaattgggattgataaaattagttttttgtgccccttattatattgatatgacggcactg
gctgaagccagaaatgtagaccctggaaaatttcatattggtattgggcaagaccaaatggcgg
tgaacccaatcagccaagatattgtgacatttgcagccaatgccgcagaagcgatcttgaccaa
agaagataaagaggccattgatatggtgattgtcgggactgagtccagtatcgatgagtcaaaa
gcggccgcagttgtcttacatcgtttaatggggattcaacctttcgctcgctctttcgaaatca
aggaagcttgttacggagcaacagcaggcttacagttagctaagaatcacgtagccttacatcc
agataaaaaagtcttggtcgtagcggcagatattgcaaaatatggcttaaattctggcggtgag
cctacacaaggagctggggcggttgcaatgttagttgctagtgaaccgcgcattttggctttaa
aagaggataatgtgatgctgacgcaagatatctatgacttttggcgtccaacaggccaccgta
tcctatggtcgatggtcctttgtcaaacgaaacctacatccaatcttttgcccaagtctgggat
gaacataaaaaacgaaccggtcttgatttgcagattatgatgctttagcgttccatattcctt
acacaaaaatgggcaaaaaagccttattagcaaaaatctccgaccaaactgaagcagaacagga
acgaattttagcccgttatgaagaaagtatcgtctatagtcgtcgcgtaggaaacttgtatacg
ggttcactttatctgggactcatttcccttttagaaaatgcaacgactttaaccgcaggcaatc
aaattggtttattcagttatggttctggtgctgtcgctgaattttcactggtgaattagtagc
tggttatcaaaatcatttacaaaagaaactcatttagcactgctggataatcggacagaactt
tctatcgctgaatatgaagccatgtttgcagaaactttagacacagacattgatcaaacgttag
aagatgaattaaaatatagtatttctgctattaataataccgttcgttcttatcgaaactaaaa
aaaaccggccttggccccgccggttttttattattttcttcctccgcatgttcaatccgctcc
ataatcgacggatggctccctctgaaaattttaacgagaaacggcgggttgacccggctcagtc
ccgtaacggccaagtcctgaaacgtctcaatcgccgcttccggtttccggtcagctcaatgcc
gtaacggtcggcggcgttttcctgataccgggagacggcattcgtaatcgggatccccgggtac
cgagctcgaattcgtaatcatgtcatagctgtttcctgtgtgaaattgttatccgctcacaatt
ccacacaacatacgagccggaagcataaagtgtaaagcctggggtgcctaatgagtgagctaac
tcacattaattgcgttgcgctcactgcccgctttccagtcgggaaacctgtcgtgccagctgca
ttaatgaatcggccaacgcgcggggagaggcggtttgcgtattgggcgctcttccgcttcctcg
ctcactgac
```
(SEQ ID NO:56)

FIG. 55A 1-
tggcgaatgggacgcgccctgtagcggcgcattaagcgcggcgggtgtggtggttacgcgcagcgtgaccgctacacttgccagcgccc
tagcgcccgctccttttcgctttcttcccttccttctctcgccacgttcgccggctttccccgtcaagctctaaatcggggggctcccttagggttcc
gatttagtgctttacggcacctcgaccccaaaaaacttgattagggtgatggttcacgtagtgggccatcgccctgatagacggttttcgccc
tttgacgttggagtccacgttctttaatagtggactcttgttccaaactggaacaacactcaaccctatctcggtctattctttgatttataagggat
tttgccgatttcggcctattggttaaaaaatgagctgatttaacaaaaatttaacgcgaattttaacaaaatattaacgtttacaatttcaggtggca
cttttcggggaaatgtgcgcggaaccccctatttgtttattttttctaaatacattcaaatatgtatccgctcatgaattaattcttagaaaaactcatcg
agcatcaaatgaaactgcaatttattcatatcaggattatcaataccatattttgaaaaagccgtttctgtaatgaaggagaaaactcaccgag
gcagttccataggatggcaagatcctggtatcggtctgcgattccgactcgtccaacatcaatacaacctattaatttcccctcgtcaaaaataa
ggttatcaagtgagaaatcaccatgagtgacgactgaatccggtgagaatggcaaaagtttatgcatttctttccagacttgttcaacaggcca
gccattacgctcgtcatcaaaatcactcgcatcaaccaaaccgttattcattcgtgattgcgcctgagcgagacgaaatacgcgatcgctgtta
aaaggacaattacaaacaggaatcgaatgcaaccggcgcaggaacactgccagcgcatcaacaatattttcacctgaatcaggatattcttc
taatacctggaatgctgttttcccggggatcgcagtggtgagtaaccatgcatcatcaggagtacggataaaatgcttgatggtcggaagag
gcataaattccgtcagccagtttagtctgaccatctcatctgtaacatcattggcaacgctacctttgccatgtttcagaaacaactctggcgcat
cgggcttcccatacaatcgatagattgtcgcacctgattgcccgacattatcgcgagcccatttataccccatataaatcagcatccatgttggaa
tttaatcgcggcctagagcaagacgtttcccgttgaatatggctcataacacccccttgtattactgtttatgtaagcagacagttttattgttcatga
ccaaaatcccttaacgtgagttttcgttccactgagcgtcagacccccgtagaaaagatcaaaggatcttcttgagatccttttttctgcgcgtaa
tctgctgcttgcaaacaaaaaaaccaccgctaccagcggtggtttgtttgccggatcaagagctaccaactcttttttccgaaggtaactggctt
cagcagagcgcagataccaaatactgtccttctagtgtagccgtagttaggccaccacttcaagaactctgtagcaccgcctacatacctcgc
tctgctaatcctgttaccagtggctgctgccagtggcgataagtcgtgtcttaccgggttggactcaagacgatagttaccggataaggcgca
gcggtcgggctgaacggggggttcgtgcacacagcccagcttggagcgaacgacctacaccgaactgagatacctacagcgtgagctat
gagaaagcgccacgcttcccgaagggagaaaggcggacaggtatccggtaagcggcagggtcggaacaggagagcgcacgaggga
gcttccaggggggaaacgcctggtatctttatagtcctgtcgggtttcgccacctctgacttgagcgtcgatttttgtgatgctcgtcaggggggg
cggagcctatggaaaaacgccagcaacgcggcctttttacggttcctggccttttgctggccttttgctcacatgttctttcctgcgttatcccct
gattctgtggataaccgtattaccgcctttgagtgagctgataccgctcgccgcagccgaacgaccgagcgcagcgagtcagtgagcgag
gaagcggaagagcgcctgatgcggtattttctccttacgcatctgtgcggtatttcacaccgcatatatggtgcactctcagtacaatctgctct
gatgccgcatagttaagccagtatacactccgctatcgctacgtgactgggtcatggctgcgccccgacaccgccaacacccgctgacgc
gccctgacgggcttgtctgctcccggcatccgcttacagacaagctgtgaccgtctccgggagctgcatgtgtcagaggttttcaccgtcatc
accgaaacgcgcgaggcagctgcggtaaagctcatcagcgtggtcgtgaagcgattcacagatgtctgcctgttcatccgcgtccagctcg
ttgagtttctccagaagcgttaatgtctggcttctgataaagcgggccatgttaagggcggttttttcctgtttggtcactgatgcctccgtgtaag
ggggatttctgttcatgggggtaatgataccgatgaaacgagagaggatgctcacgatacggttactgatgatgaacatgcccggttactg
gaacgttgtgagggtaaacaactggcggtatggatgcggcgggaccagagaaaaatcactcagggtcaatgccagcgcttcgttaataca
gatgtaggtgttccacagggtagccagcagcatcctgcgatgcagatccggaacataatggtgcagggcgctgacttccgcgtttccagac
tttacgaaacacggaaaccgaagaccattcatgttgttgctcaggtcgcagacgttttgcagcagcagtcgcttcacgttcgctcgcgtatcg
gtgattcattctgctaaccagtaaggcaaccccgccagcctagccgggtcctcaacgacaggagcacgatcatgcgcacccgtggggcc
gccatgccggcgataatggcctgcttctcgccgaaacgtttggtggcgggaccagtgacgaaggcttgagcgagggcgtgcaagattccg
aataccgcaagcgacaggccgatcatcgtcgcgctccagcgaaagcggtcctcgccgaaaatgacccagagcgctgccggcacctgtc
ctacgagttgcatgataaagaagacagtcataagtgcggcgacgatagtcatgccccgcgcccaccggaaggagctgactgggttgaag
gctctcaagggcatcggtcgagatcccggtgcctaatgagtgagctaacttacattaattgcgttgcgctcactgcccgctttccagtcggga
aacctgtcgtgccagctgcattaatgaatcggccaacgcgcggggagaggcggtttgcgtattgggcgccagggtggtttttcttttcacca
gtgagacgggcaacagctgattgcccttcaccgcctggccctgagagagttgcagcaagcggtccacgctggtttgccccagcaggcga
aaatcctgtttgatggtggttaacggcgggatataacatgagctgtcttcggtatcgtcgtatcccactaccgagatatccgcaccaacgcgc
agcccggactcggtaatggcgcgcattgcgcccagcgccatctgatcgttggcaaccagcatcgcagtgggaacgatgccctcattcagc
atttgcatggtttgttgaaaaccggacatggcactccagtcgccttcccgttccgctatcggctgaatttgattgcgagtgagatatttatgccag

FIG. 55B ccagccagacgcagacgcgccgagacagaacttaatgggcccgctaacagcgcgatttgctggtgacccaatgcgaccagatgctccac
gcccagtcgcgtaccgtcttcatgggagaaaataatactgttgatgggtgtctggtcagagacatcaagaaataacgccggaacattagtgc
aggcagcttccacagcaatggcatcctggtcatccagcggatagttaatgatcagcccactgacgcgttgcgcgagaagattgtgcaccgc
cgctttacaggcttcgacgccgcttcgttctaccatcgacaccaccacgctggcacccagttgatcggcgcgagatttaatcgccgcgacaa
tttgcgacggcgcgtgcagggccagactggaggtggcaacgccaatcagcaacgactgtttgcccgccagttgttgtgccacgcggttgg
gaatgtaattcagctccgccatcgccgcttccacttttcccgcgttttcgcagaaacgtggctggcctggttcaccacgcgggaaacggtct
gataagagacaccggcatactctgcgacatcgtataacgttactggtttcacattcaccaccctgaattgactctcttccgggcgctatcatgc
cataccgcgaaaggttttgcgccattcgatggtgtccgggatctcgacgctctcccttatgcgactcctgcattaggaagcagcccagtagta
ggttgaggccgttgagcaccgccgccgcaaggaatggtgcatgcaaggagatggcgcccaacagtcccccggccacggggcctgcca
ccatacccacgccgaaacaagcgctcatgagcccgaagtggcgagcccgatcttccccatcggtgatgtcggcgatataggcgccagca
accgcacctgtggcgccggtgatgccggccacgatgcgtccggcgtagaggatcgagatctcgatcccgcgaaattaatacgactcacta
taggggaattgtgagcggataacaattcccctctagaaataattttgtttaactttaagaaggagatatacatatgcgttgtagcgtgtccaccg
aaaatgtgtctttcaccgaaactgaaaccgaagctcgtcgttctgcgaactacgaacctaacagctgggactatgattacctgctgtcctccga
cacggacgagtccatcgaagtatacaaagacaaagcgaaaaagctggaagccgaagttcgtcgcgagattaataacgaaaaagcagaat
ttctgaccctgctggaactgattgacaacgtccagcgcctgggcctgggttaccgtttcgagtctgatatccgtggtgcgctggatcgcttcgt
ttcctccggcggcttcgatgcggtaaccaagacttccctgcacggtacggcactgtctttccgtctgctgcgtcaacacggttttgaggtttctc
aggaagcgttcagcggcttcaaagaccaaaacggcaacttcctggagaacctgaaggaagatatcaaagctatcctgagcctgtacgagg
ccagcttcctggctctggaaggcgaaaacatcctggacgaggcgaaggttttcgcaatctctcatctgaaagaactgtctgaagaaaagatc
ggtaaagagctggcagaacaggtgaaccatgcactggaactgccactgcatcgccgtactcagcgtctggaagcagtatggtctatcgag
gcctaccgtaaaaaggaggacgcgaatcaggttctgctggagctggcaattctggattacaacatgatccagtctgtataccagcgtgatct
gcgtgaaacgtcccgttggtggcgtcgtgtgggtctggcgaccaaactgcactttgctcgtgaccgcctgattgagagcttctactgggccg
tgggtgtagcattcgaaccgcaatactccgactgccgtaactccgtcgcaaaaatgttttctttcgtaaccattatcgacgatatctacgatgtat
acggcaccctggacgaactggagctgtttactgatgcagttgagcgttgggacgtaaacgccatcaacgacctgccggattacatgaaact
gtgctttctggctctgtataacactattaacgaaatcgcctacgacaacctgaaagataaaggtgagaacatcctgccgtatctgaccaaagc
ctgggctgacctgtgcaacgctttcctgcaagaagccaagtggctgtacaacaaatctactccgacctttgacgactacttcggcaacgcatg
gaaatcctcttctggcccgctgcaactggtgttcgcttacttcgctgtcgtgcagaacattaaaaaggaagagatcgaaaacctgcaaaaata
ccatgacaccatctctcgtccttcccatatcttccgtctgtgcaatgacctggctagcgcgtctgcggaaattgcgcgtggtgaaaccgcaaat
agcgtttcttgttacatgcgcactaaaggtatctccgaagaactggctaccgaaagcgtgatgaatctgatcgatgaaacctggaaaaagatg
aacaaggaaaaactgggtggtagcctgttcgcgaaaccgttcgtggaaaccgcgatcaacctggcacgtcaatctcactgcacttatcataa
cggcgacgcgcataccctccggatgagctgacccgcaaacgcgttctgtctgtaatcactgaaccgattctgccgtttgaacgctaaggat
ccgaattcgagctccgtcgacaagcttgcggccgcactcgagcaccaccaccaccaccactgagatccggctgctaacaaagcccgaaa
ggaagctgagttggctgctgccaccgctgagcaataactagcataaccccttggggcctctaaacgggtcttgaggggttttttgctgaaag
gaggaactatatccggat (SEQ ID NO:87)

FIG. 58A 1-
gtttgacagcttatcatcgactgcacggtgcaccaatgcttctggcgtcaggcagccatcggaagctgtggtatggctgtgcaggtcgtaaat
cactgcataattcgtgtcgctcaaggcgcactcccgttctggataatgttttttgcgccgacatcataacggttctggcaaatattctgaaatgag
ctgttgacaattaatcatccggctcgtataatgtgtggaattgtgagcggataacaatttcacacaggaaacagcgccgctgagaaaaagcg
aagcggcactgctctttaacaatttatcagacaatctgtgtgggcactcgaccggaattatcgattaactttattattaaaaattaaagaggtatat
attaatgtatcgattaaataaggaggaataaaccatgagatgtagcgtgtccaccgaaaatgtgtctttcaccgaaactgaaaccgaagctcg
tcgttctgcgaactacgaacctaacagctgggactatgattacctgctgtcctccgacacggacgagtccatcgaagtatacaaagacaaag
cgaaaaagctggaagccgaagttcgtcgcgagattaataacgaaaaagcagaattctgaccctgctggaactgattgacaacgtccagcg
cctgggcctgggttaccgtttcgagtctgatatccgtggtgcgctggatcgcttcgtttcctccggcggcttcgatgcggtaaccaagacttcc
ctgcacggtacggcactgtctttccgtctgctgcgtcaacacggttttgaggtttctcaggaagcgttcagcggcttcaaagaccaaaacggc
aacttcctggagaacctgaaggaagatatcaaagctatcctgagcctgtacgaggccagcttcctggctctggaaggcgaaaacatcctgg
acgaggcgaaggtttcgcaatctctcatctgaaagaactgtctgaagaaaagatcggtaaagagctggcagaacaggtgaaccatgcact
ggaactgccactgcatcgccgtactcagcgtctggaagcagtatggtctatcgaggcctaccgtaaaaaggaggacgcgaatcaggttctg
ctggagctggcaattctggattacaacatgatccagtctgtataccagcgtgatctgcgtgaaacgtcccgttggtggcgtcgtgtgggtctg
gcgaccaaactgcactttgctcgtgaccgcctgattgagagcttctactgggccgtgggtgtagcattcgaaccgcaatactccgactgccg
taactccgtcgcaaaaatgttttctttcgtaaccattatcgacgatatctacgatgtatacggcaccctggacgaactggagctgtttactgatgc
agttgagcgttgggacgtaaacgccatcaacgacctgccggattacatgaaactgtgctttctggctctgtataacactattaacgaaatcgcc
tacgacaacctgaaagataaaggtgagaacatcctgccgtatctgaccaaagcctgggctgacctgtgcaacgctttcctgcaagaagcca
agtggctgtacaacaaatctactccgaccttgacgactacttcggcaacgcatggaaatcctcttctggcccgctgcaactggtgttcgctta
cttcgctgtcgtgcagaacattaaaaaggaagagatcgaaaacctgcaaaaataccatgacaccatctctcgtccttcccatatcttccgtctg
tgcaatgacctggctagcgcgtctgcggaaattgcgcgtggtgaaaccgcaaatagcgtttcttgttacatgcgcactaaaggtatctccgaa
gaactggctaccgaaagcgtgatgaatctgatcgatgaaacctggaaaaagatgaacaaggaaaaactgggtggtagcctgttcgcgaaa
ccgttcgtggaaaccgcgatcaacctggcacgtcaatctcactgcacttatcataacggcgacgcgcataccctccggatgagctgaccc
gcaaacgcgttctgtctgtaatcactgaaccgattctgccgtttgaacgctaactgcagctggtaccatatgggaattcgaagctttctagaac
aaaaaactcatctcagaagaggatcgaatagcgccgtcgaccatcatcatcatcatcattgagtttaaacggtctccagcttggctgtttggcg
gatgagagaagattttcagcctgatacagattaaatcagaacgcagaagcggtctgataaaacagaatttgcctggcggcagtagcgcggt
ggtcccacctgaccccatgccgaactcagaagtgaaacgccgtagcgccgatggtagtgtggggtctcccatgcgagagtagggaact
gccaggcatcaaataaaacgaaaggctcagtcgaaagactgggccttcgttttatctgttgtttgtcggtgaacgctctcctgagtaggacaa
atccgccgggagcggatttgaacgttgcgaagcaacggcccggagggtggcgggcaggacgcccgccataaactgccaggcatcaaat
taagcagaaggccatcctgacggatggcctttttgcgtttctacaaactcttttttgtttatttttctaaatacattcaaatatgtatccgctcatgaga
caataaccctgataaatgcttcaataatattgaaaaaggaagagtatgagtattcaacatttccgtgtcgcccttattccctttttgcggcattttg
ccttcctgttttgctcacccagaaacgctggtgaaagtaaaagatgctgaagatcagttgggtgcacgagtgggttacatcgaactggatctc
aacagcggtaagatccttgagagttttcgccccgaagaacgttttccaatgatgagcacttttaaagttctgctatgtggcgcggtattcccg
tgttgacgccgggcaagagcaactcggtcgccgcatacactattctcagaatgacttggttgagtactcaccagtcacagaaaagcatctta
cggatggcatgacagtaagagaattatgcagtgctgccataaccatgagtgataacactgcggccaacttacttctgacaacgatcggagga
ccgaaggagctaaccgcttttttgcacaacatgggggatcatgtaactcgccttgatcgttgggaaccggagctgaatgaagccataccaaa
cgacgagcgtgacaccacgatgcctgtagcaatggcaacaacgttgcgcaaactattaactggcgaactacttactctagcttcccggcaac
aattaatagactggatggaggcggataaagttgcaggaccacttctgcgctcggcccttccggctggctggtttattgctgataaatctggag
ccggtgagcgtgggtctcgcggtatcattgcagcactggggccagatggtaagccctcccgtatcgtagttatctacacgacggggagtca
ggcaactatggatgaacgaaatagacagatcgctgagataggtgcctcactgattaagcattggtaactgtcagaccaagtttactcatatata
ctttagattgatttaaaacttcattttaattaaaaggatctaggtgaagatcctttttgataatctcatgaccaaaatcccttaacgtgagttttcgtt
ccactgagcgtcagacccccgtagaaaagatcaaaggatcttcttgagatcctttttttctgcgcgtaatctgctgcttgcaaacaaaaaaacca
ccgctaccagcggtggtttgtttgccggatcaagagctaccaactctttttccgaaggtaactggcttcagcagagcgcagataccaaatact
gtccttctagtgtagccgtagttaggccaccacttcaagaactctgtagcaccgcctacatacctcgctctgctaatcctgttaccagtggctgc

FIG. 58B tgccagtggcgataagtcgtgtcttaccgggttggactcaagacgatagttaccggataaggcgcagcggtcgggctgaacgggggttc
gtgcacacagcccagcttggagcgaacgacctacaccgaactgagatacctacagcgtgagctatgagaaagcgccacgcttcccgaag
ggagaaaggcggacaggtatccggtaagcggcagggtcggaacaggagagcgcacgagggagcttccaggggaaacgcctggtat
ctttatagtcctgtcgggtttcgccacctctgacttgagcgtcgatttttgtgatgctcgtcaggggggcggagcctatggaaaaacgccagca
acgcggccttttacggttcctggccttttgctggccttttgctcacatgttctttcctgcgttatccctgattctgtggataaccgtattaccgcct
ttgagtgagctgataccgctcgccgcagccgaacgaccgagcgcagcgagtcagtgagcgaggaagcggaagagcgcctgatgcggt
atttctccttacgcatctgtgcggtatttcacaccgcatatggtgcactctcagtacaatctgctctgatgccgcatagttaagccagtatacact
ccgctatcgctacgtgactgggtcatggctgcgccccgacacccgccaacacccgctgacgcgccctgacgggcttgtctgctcccggca
tccgcttacagacaagctgtgaccgtctccgggagctgcatgtgtcagaggttttcaccgtcatcaccgaaacgcgcgaggcagcagatca
attcgcgcgcgaaggcgaagcggcatgcatttacgttgacaccatcgaatggtgcaaaacctttcgcggtatggcatgatagcgcccggaa
gagagtcaattcagggtggtgaatgtgaaaccagtaacgttatacgatgtcgcagagtatgccggtgtctcttatcagaccgtttcccgcgtg
gtgaaccaggccagccacgtttctgcgaaaacgcgggaaaaagtggaagcggcgatggcggagctgaattacattcccaaccgcgtggc
acaacaactggcgggcaaacagtcgttgctgattggcgttgccacctccagtctggccctgcacgcgccgtcgcaaattgtcgcggcgatt
aaatctcgcgccgatcaactgggtgccagcgtggtggtgtcgatggtagaacgaagcggcgtcgaagcctgtaaagcggcggtgcacaa
tcttctcgcgcaacgcgtcagtgggctgatcattaactatccgctggatgaccaggatgccattgctgtggaagctgcctgcactaatgttccg
gcgttattcttgatgtctctgaccagacacccatcaacagtattatttctcccatgaagacggtacgcgactgggcgtggagcatctggtcgc
attgggtcaccagcaaatcgcgctgttagcgggcccattaagttctgtctcggcgcgtctgcgtctggctggctggcataaatatctcactcg
caatcaaattcagccgatagcggaacgggaaggcgactggagtgccatgtccggttttcaacaaaccatgcaaatgctgaatgagggcatc
gttcccactgcgatgctggttgccaacgatcagatggcgctgggcgcaatgcgcgccattaccgagtccgggctgcgcgttggtgcggat
atctcggtagtgggatacgacgataccgaagacagctcatgttatatcccgccgtcaaccaccatcaaacaggattttcgcctgctggggca
aaccagcgtggaccgcttgctgcaactctctcagggccaggcggtgaagggcaatcagctgttgcccgtctcactggtgaaaagaaaaac
caccctggcgcccaatacgcaaaccgcctctccccgcgcgttggccgattcattaatgcagctggcacgacaggtttcccgactggaaagc
gggcagtgagcgcaacgcaattaatgtgagttagcgcgaattgatctg (SEQ ID NO:88)

FIG. 61A 1-
gtttgacagcttatcatcgactgcacggtgcaccaatgcttctggcgtcaggcagccatcggaagctgtggtatggctgtgcaggtcgtaaat
cactgcataattcgtgtcgctcaaggcgcactcccgttctggataatgttttttgcgccgacatcataacggttctggcaaatattctgaaatgag
ctgttgacaattaatcatccggctcgtataatgtgtggaattgtgagcggataacaatttcacacaggaaacagcgccgctgagaaaaagcg
aagcggcactgctctttaacaatttatcagacaatctgtgtgggcactcgaccggaattatcgattaactttattattaaaaattaaagaggtatat
attaatgtatcgattaaataaggaggaataaaccatgagatgtagcgtgtccaccgaaaatgtgtctttcaccgaaactgaaaccgaagctcg
tcgttctgcgaactacgaacctaacagctgggactatgattacctgctgtcctccgacacggacgagtccatcgaagtatacaaagacaaag
cgaaaaagctggaagccgaagttcgtcgcgagattaataacgaaaaagcagaatttctgaccctgctggaactgattgacaacgtccagcg
cctgggcctgggttaccgttcgagtctgatatccgtggtgcgctggatcgcttcgtttcctccggcggcttcgatgcggtaaccaagacttcc
ctgcacggtacggcactgtctttccgtctgctgcgtcaacacggttttgaggtttctcaggaagcgttcagcggcttcaaagaccaaaacggc
aacttcctggagaacctgaaggaagatatcaaagctatcctgagcctgtacgaggccagcttcctggctctggaaggcgaaaacatcctgg
acgaggcgaaggttttcgcaatctctcatctgaaagaactgtctgaagaaaagatcggtaaagagctggcagaacaggtgaaccatgcact
ggaactgccactgcatcgccgtactcagcgtctgaagcagtatggtctatcgaggcctaccgtaaaaaggaggacgcgaatcaggttctg
ctggagctggcaattctggattacaacatgatccagtctgtataccagcgtgatctgcgtgaaacgtcccgttggtggcgtcgtgtgggtctg
gcgaccaaactgcactttgctcgtgaccgcctgattgagagcttctactgggccgtgggtgtagcattcgaaccgcaatactccgactgccg
taactccgtcgcaaaaatgttttctttcgtaaccattatcgacgatatctacgatgtatacggcacctggacgaactggagctgtttactgatgc
agttgagcgttgggacgtaaacgccatcaacgacctgccggattacatgaaactgtgcttctggctctgtataacactattaacgaaatcgcc
tacgacaacctgaaagataaaggtgagaacatcctgccgtatctgaccaaagcctgggctgacctgtgcaacgctttcctgcaagaagcca
agtggctgtacaacaaatctactccgacctttgacgactacttcggcaacgcatggaaatcctcttctggcccgctgcaactggtgttcgctta
cttcgctgtcgtgcagaacattaaaaaggaagagatcgaaaacctgcaaaaataccatgacaccatctctcgtccttcccatatcttccgtctg
tgcaatgacctggctagcgcgtctgcggaaattgcgcgtggtgaaaccgcaaatagcgtttcttgttacatgcgcactaaaggtatctccgaa
gaactggctaccgaaagcgtgatgaatctgatcgatgaaacctggaaaaagatgaacaaggaaaaactgggtggtagcctgttcgcgaaa
ccgttcgtggaaaccgcgatcaacctggcacgtcaatctcactgcacttatcataacggcgacgcgcatacctctccggatgagctgaccc
gcaaacgcgttctgtctgtaatcactgaaccgattctgccgtttgaacgctaactgcataaaggaggtaaaaaaacatggtatcctgttctgcg
ccgggtaagatttacctgttcggtgaacacgccgtagtttatggcgaaactgcaattgcgtgtgcggtggaactgcgtacccgtgttcgcgcg
gaactcaatgactctatcactattcagagccagatcggccgcaccggtctggatttcgaaaagcacccttatgtgtctgcggtaattgagaaa
atgcgcaaatctattcctattaacggtgttttcttgaccgtcgattccgacatcccggtgggctccggtctgggtagcagcgcagccgttactat
cgcgtctattggtgcgctgaacgagctgttcggctttggcctcagcctgcaagaaatcgctaaactgggccacgaaatcgaaattaaagtac
agggtgccgcgtccccaaccgatacgtatgtttctaccttcggcggcgtggttaccatcccggaacgtcgcaaactgaaaactccggactg
cggcattgtgattggcgataccggcgttttctcctccaccaaagagttagtagctaacgtacgtcagctgcgcgaaagctacccggatttgat
cgaaccgctgatgacctctattggcaaaatctctcgtatcggcgaacaactggttctgtctggcgactacgcatccatcggccgcctgatgaa
cgtcaaccagggtctcctggacgccctgggcgttaacatcttagaactgagccagctgatctattccgctcgtgcggcaggtgcgtttggcg
ctaaaatcacgggcgctggcggcggtggctgtatggttgcgctgaccgctccggaaaaatgcaaccaagtggcagaagcggtagcaggc
gctggcggtaaagtgactatcactaaaccgaccgagcaaggtctgaaagtagattaaagtctagttaaagtttaaacggtctccagcttggct
gttttggcggatgagagaagattttcagcctgatacagattaaatcagaacgcagaagcggtctgataaaacagaatttgcctggcggcagt
agcgcggtggtcccacctgaccccatgccgaactcagaagtgaaacgccgtagcgccgatggtagtgtggggtctcccatgcgagagt
agggaactgccaggcatcaaataaaacgaaaggctcagtcgaaagactgggcctttcgttttatctgttgtttgtcggtgaacgctctcctgag
taggacaaatccgccgggagcggatttgaacgttgcgaagcaacgcccggagggtggcgggcaggacgcccgccataaactgccag
gcatcaaattaagcagaaggccatcctgacggatggcctttttgcgtttctacaaactctttttgtttatttttctaaatacattcaaatatgtatccg
ctcatgagacaataaccctgataaatgcttcaataatattgaaaaaggaagagtatgagtattcaacatttccgtgtcgcccttattcctttttttg
cggcattttgccttcctgtttttgctcacccagaaacgctggtgaaagtaaaagatgctgaagatcagttgggtgcacgagtgggttacatcga
actggatctcaacagcggtaagatccttgagagttttcgccccgaagaacgttttccaatgatgagcacttttaaagttctgctatgtggcgcg
gtattatcccgtgttgacgccgggcaagagcaactcggtcgccgcatacactattctcagaatgacttggttgagtactcaccagtcacagaa
aagcatcttacggatggcatgacagtaagagaattatgcagtgctgccataaccatgagtgataacactgcggccaacttacttctgacaacg

FIG. 61B atcggaggaccgaaggagctaaccgcttttttgcacaacatgggggatcatgtaactcgccttgatcgttgggaaccggagctgaatgaag
ccataccaaacgacgagcgtgacaccacgatgcctgtagcaatggcaacaacgttgcgcaaactattaactggcgaactacttactctagct
tcccggcaacaattaatagactggatggaggcggataaagttgcaggaccacttctgcgctcggcccttccggctggctggtttattgctgat
aaatctggagccggtgagcgtgggtctcgcggtatcattgcagcactggggccagatggtaagccctcccgtatcgtagttatctacacgac
ggggagtcaggcaactatggatgaacgaaatagacagatcgctgagataggtgcctcactgattaagcattggtaactgtcagaccaagttt
actcatatatactttagattgatttaaaacttcatttttaatttaaaaggatctaggtgaagatcctttttgataatctcatgaccaaaatcccttaacgt
gagttttcgttccactgagcgtcagaccccgtagaaaagatcaaaggatcttcttgagatcctttttttctgcgcgtaatctgctgcttgcaaaca
aaaaaaccaccgctaccagcggtggtttgtttgccggatcaagagctaccaactctttttccgaaggtaactggcttcagcagagcgcagat
accaaatactgtccttctagtgtagccgtagttaggccaccacttcaagaactctgtagcaccgcctacatacctcgctctgctaatcctgttac
cagtggctgctgccagtggcgataagtcgtgtcttaccgggttggactcaagacgatagttaccggataaggcgcagcggtcgggctgaa
cggggggttcgtgcacacagcccagcttggagcgaacgacctacaccgaactgagatacctacagcgtgagctatgagaaagcgccac
gcttcccgaaggggagaaaggcggacaggtatccggtaagcggcagggtcggaacaggagagcgcacgagggagcttccaggggaa
acgcctggtatctttatagtcctgtcgggtttcgccacctctgacttgagcgtcgatttttgtgatgctcgtcaggggggcggagcctatggaaa
aacgccagcaacgcggcctttttacggttcctggccttttgctggccttttgctcacatgttctttcctgcgttatcccctgattctgtggataacc
gtattaccgcctttgagtgagctgataccgctcgccgcagccgaacgaccgagcgcagcgagtcagtgagcgaggaagcggaagagcg
cctgatgcggtattttctccttacgcatctgtgcggtatttcacaccgcatatggtgcactctcagtacaatctgctctgatgccgcatagttaag
ccagtatacactccgctatcgctacgtgactgggtcatggctgcgccccgacacccgccaacacccgctgacgcgccctgacgggcttgt
ctgctcccggcatccgcttacagacaagctgtgaccgtctccgggagctgcatgtgtcagaggttttcaccgtcatcaccgaaacgcgcga
ggcagcagatcaattcgcgcgcgaaggcgaagcggcatgcatttacgttgacaccatcgaatggtgcaaaacctttcgcggtatggcatga
tagcgcccggaagagagtcaattcagggtggtgaatgtgaaaccagtaacgttatacgatgtcgcagagtatgccggtgtctcttatcagac
cgtttcccgcgtggtgaaccaggccagccacgtttctgcgaaaacgcgggaaaaagtggaagcggcgatggcggagctgaattacattcc
caaccgcgtggcacaacaactggcgggcaaacagtcgttgctgattggcgttgccacctccagtctggccctgcacgcgccgtcgcaaatt
gtcgcggcgattaaatctcgcgccgatcaactgggtgccagcgtggtggtgtcgatggtagaacgaagcggcgtcgaagcctgtaaagcg
gcggtgcacaatcttctcgcgcaacgcgtcagtgggctgatcattaactatccgctggatgaccaggatgccattgctgtggaagctgcctg
cactaatgttccggcgttatttcttgatgtctctgaccagacacccatcaacagtattattttctcccatgaagacggtacgcgactgggcgtgg
agcatctggtcgcattgggtcaccagcaaatcgcgctgttagcgggcccattaagttctgtctcggcgcgtctgcgtctggctggctggcata
aatatctcactcgcaatcaaattcagccgatagcggaacgggaaggcgactggagtgccatgtccggttttcaacaaaccatgcaaatgctg
aatgagggcatcgttcccactgcgatgctggttgccaacgatcagatggcgctgggcgcaatgcgcgccattaccgagtccgggctgcgc
gttggtgcggatatctcggtagtgggatacgacgataccgaagacagctcatgttatatcccgccgtcaaccaccatcaaacaggattttcgc
ctgctggggcaaaccagcgtggaccgcttgctgcaactctctcagggccaggcggtgaagggcaatcagctgttgcccgtctcactggtg
aaaagaaaaaccaccctggcgcccaatacgcaaaccgcctctccccgcgcgttggccgattcattaatgcagctggcacgacaggtttccc
gactggaaagcgggcagtgagcgcaacgcaattaatgtgagttagcgcgaattgatctg (SEQ ID NO:89)

FIG. 63A 1-
aagggcgagctcaacgatccggctgctaacaaagcccgaaaggaagctgagttggctgctgccaccgctgagcaataactagcataacc
ccttggggcctctaaacgggtcttgaggagtttttgctgaaaggaggaactatatccggatatcccgcaagaggcccggcagtaccggcat
aaccaagcctatgcctacagcatccagggtgacggtgccgaggatgacgatgagcgcattgttagatttcatacacggtgcctgactgcgtt
agcaatttaactgtgataaactaccgcattaaagcttatcgatgataagctgtcaaacatgagaattaattcttgaagacgaaagggcctcgtg
atacgcctattttttataggttaatgtcatgataataatggtttcttagacgtcaggtggcacttttcggggaaatgtgcgcggaacccctatttgttt
attttctaaatacattcaaatatgtatccgctcatgagacaataaccctgataaatgcttcaataatattgaaaaaggaagagtatgattgaacaa
gatggattgcacgcaggttctccggccgcttgggtggagaggctattcggctatgactgggcacaactgacaatcggctgtctgatgccg
ccgtgttccggctgtcagcgcaggggcgcccggttctttttgtcaagaccgacctgtccggtgccctgaatgaactgcaggacgaggcagc
gcggctatcgtggctggccacgacgggcgttccttgcgcagctgtgctcgacgttgtcactgaagcgggaagggactggctgctattggg
cgaagtgccggggcaggatctcctgtcatctcaccttgctcctgccgagaaagtatccatcatggctgatgcaatgcggcggctgcatacgc
ttgatccggctacctgcccattcgaccaccaagcgaaacatcgcatcgagcgggcacgtactcggatggaagccggtcttgtcgatcagga
tgatctggacgaagagcatcaggggctcgcgccagccgaactgttcgccaggctcaaggcgcgcatgcccgacggcgaggatctcgtc
gtgacacatggcgatgcctgcttgccgaatatcatggtggaaaatggccgcttttctggattcatcgactgtggccggctgggtgtggcgga
ccgctatcaggacatagcgttggctacccgtgatattgctgaagagcttggcggcgaatgggctgaccgcttcctcgtgctttacggtatcgc
cgctcccgattcgcagcgcatcgccttctatcgccttcttgacgagttcttctgagcgggactctggggttcgaaatgaccgaccaagcgac
gcctaactgtcagaccaagtttactcatatatactttagattgatttaaaacttcattttaatttaaaaggatctaggtgaagatccttttgataatct
catgaccaaaatcccttaacgtgagttttcgttccactgagcgtcagacccgtagaaaagatcaaaggatcttcttgagatcctttttttctgcg
cgtaatctgctgcttgcaaacaaaaaaaccaccgctaccagcggtggtttgtttgccggatcaagagctaccaactctttttccgaaggtaact
ggcttcagcagagcgcagataccaaatactgtccttctagtgtagccgtagttaggccaccacttcaagaactctgtagcaccgcctacatac
ctcgctctgctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatacctacagcgtg
agctatgagaaagcgccacgcttcccgaagggagaaaggcggacaggtatccggtaagcggcagggtcggaacaggagagcgcacg
agggagcttccaggggaaacgcctggtatctttatagtcctgtcgggtttcgccacctctgacttgagcgtcgatttttgtgatgctcgtcagg
ggggcggagcctatggaaaaacgccagcaacgcggcctttttacggttcctggccttttgctggccttttgctcacatgttcttcctgcgttat
cccctgattctgtggataaccgtattaccgcctttgagtgagctgataccgctcgccgcagccgaacgaccgagcgcagcgagtcagtgag
cgaggaagcggaagagcgcctgatgcggtattttctccttacgcatctgtgcggtatttcacaccgcaatggtgcactctcagtacaatctgct
ctgatgccgcatagttaagccagtatacactccgctatcgctacgtgactgggtcatggctgcgccccgacacccgccaacacccgctgac
gcgccctgacgggcttgtctgctcccggcatccgcttacagacaagctgtgaccgtctccgggagctgcatgtgtcagaggttttcaccgtc
atcaccgaaacgcgcgaggcagctgcggtaaagctcatcagcgtggtcgtgaagcgattcacagatgtctgcctgttcatccgcgtccagc
tcgttgagtttctccagaagcgttaatgtctggcttctgataaagcgggccatgttaagggcggttttttcctgtttggtcactgatgcctccgtgt
aagggggatttctgttcatgggggtaatgataccgatgaaacgagagaggatgctcacgatacgggttactgatgatgaacatgcccggtta
ctggaacgttgtgagggtaaacaactggcggtatggatgcggcgggaccagagaaaaatcactcagggtcaatgccagcgcttcgttaat
acagatgtaggtgttcacagggtagccagcagcatcctgcgatgcagatccggaacataatggtgcagggcgctgacttccgcgtttcca
gactttacgaaacacggaaaccgaagaccattcatgttgttgctcaggtcgcagacgttttgcagcagcagtcgcttcacgttcgctcgcgta
tcggtgattcattctgctaaccagtaaggcaaccccgccagcctagccgggtcctcaacgacaggagcacgatcatgcgcacccgtggcc
aggacccaacgctgcccgagatgcgccgcgtgcggctgctggagatggcggacgcgatggatatgttctgccaagggttggtttgcgcat
tcacagttctccgcaagaattgattggctccaattcttggagtggtgaatccgttagcgaggtgccgccggcttccattcaggtcgaggtggc
ccggctccatgcaccgcgacgcaacgcggggaggcagacaaggtatagggcggcgcctacaatccatgccaacccgttccatgtgctc
gccgaggcggcataaatcgccgtgacgatcagcggtcaatgatcgaagttaggctggtaagagccgcgagcgatccttgaagctgtccc
tgatggtcgtcatctacctgcctggacagcatggcctgcaacgcgggcatcccgatgccgccgaagcgagaagaatcataatggggaa
ggccatccagcctcgcgtcgcgaacgccagcaagacgtagcccagcgcgtcggccgccatgccggcgataatggcctgcttctcgccg
aaacgtttggtggcgggaccagtgacgaaggcttgagcgagggcgtgcaagattccgaataccgcaagcgacaggccgatcatcgtcgc
gctccagcgaaagcggtcctcgccgaaaatgacccagagcgctgccggcacctgtcctacgagttgcatgataaagaagacagtcataag

FIG. 63B tgcggcgacgatagtcatgccccgcgcccaccggaaggagctgactgggttgaaggctctcaagggcatcggtcgagatcccggtgcct
aatgagtgagctaacttacattaattgcgttgcgctcactgcccgctttccagtcgggaaacctgtcgtgccagctgcattaatgaatcggcca
acgcgcggggagaggcggtttgcgtattgggcgccagggtggtttttcttttcaccagtgagacgggcaacagctgattgccccttcaccgcc
tggcccctgagagagttgcagcaagcggtccacgctggtttgccccagcaggcgaaaatcctgtttgatggtggttaacggcgggatataac
atgagctgtcttcggtatcgtcgtatcccactaccgagatatccgcaccaacgcgcagcccggactcggtaatggcgcgcattgcgcccag
cgccatctgatcgttggcaaccagcatcgcagtgggaacgatgccctcattcagcatttgcatggtttgttgaaaaccggacatggcactcca
gtcgccttcccgttccgctatcggctgaatttgattgcgagtgagatatttatgccagccagccagacgcagacgcgccgagacagaactta
atgggcccgctaacagcgcgatttgctggtgacccaatgcgaccagatgctccacgcccagtcgcgtaccgtcttcatgggagaaaataat
actgttgatgggtgtctggtcagagacatcaagaaataacgccggaacattagtgcaggcagcttccacagcaatggcatcctggtcatcca
gcggatagttaatgatcagcccactgacgcgttgcgcgagaagattgtgcaccgccgctttacaggcttcgacgccgcttcgttctaccatc
gacaccaccacgctggcacccagttgatcggcgcgagatttaatcgccgcgacaatttgcgacggcgcgtgcagggccagactggaggt
ggcaacgccaatcagcaacgactgtttgcccgccagttgttgtgccacgcggttgggaatgtaattcagctccgccatcgccgcttccacttt
ttcccgcgttttcgcagaaacgtggctggcctggttcaccacgcgggaaacggtctgataagagacaccggcatactctgcgacatcgtata
acgttactggtttcacattcaccaccctgaattgactctcttccgggcgctatcatgccataccgcgaaaggttttgcgccattcgatggtgtcc
gggatctcgacgctctcccttatgcgactcctgcattaggaagcagcccagtagtaggttgaggccgttgagcaccgccgccgcaaggaat
ggtgcatgcaaggagatggcgcccaacagtccccggccacggggcctgccaccatacccacgccgaaacaagcgctcatgagcccg
aagtggcgagcccgatcttccccatcggtgatgtcggcgatataggcgccagcaaccgcacctgtggcgccggtgatgccggccacgat
gcgtccggcgtagaggatcgagatctcgatcccgcgaaattaatacgactcactatagggggaattgtgagcggataacaattcccctctaga
aataattttgtttaactttaagaaggagatatacatatgaattaaccctcactaaagggcggccgcgaagttcctattctctagaaagtataggaa
cttcattctaccgggtaggggaggcgcttttcccaaggcagtctggagcatgcgctttagcagccccgctgggcacttggcgctacacaagt
ggcctctggcctcgcacacattccacatccaccggtaggcgccaaccggctccgttcttggtggcccttcgcgccaccttccactcctcc
cctagtcaggaagttcccccccgccccgcagctcgcgtcgtgcaggacgtgacaaatggaagtagcacgtctcactagtctcgtgcagatg
gacagcaccgctgagcaatggaagcgggtaggcctttggggcagcggccaatagcagctttgctccttcgctttctgggctcagaggctg
ggaagggtgggtccggggcgggctcaggggcgggctcaggggcggggcgggcgcccgaaggtcctccggaggcccggcattct
gcacgcttcaaaagcgcacgtctgccgcgctgttctcctcttcctcatctccgggcctttcgacctgcagcagcacgtgttgacaattaatcat
cggcatagtatatcggcatagtataatacgacaaggtgaggaactaaaccatggagaaaaaatcactggatataccaccgttgatatatcc
caatggcatcgtaaagaacatttgaggcatttcagtcagttgctcaatgtacctataaccagaccgttcagctggatattacggcctttttaaag
accgtaaagaaaaataagcacaagttttatccggcctttattcacattcttgcccgcctgatgaatgctcatccggaattccgtatggcaatgaa
agacggtgagctggtgatatgggatagtgttcacccttgttacaccgttttccatgagcaaactgaaacgtttcatcgctctggagtgaatacc
acgacgatttccggcagtttctacacatatattcgcaagatgtggcgtgttacggtgaaaacctggcctatttccctaaagggtttattgagaat
atgtttttcgtctcagccaatccctgggtgagtttcaccagttttgatttaaacgtggccaatatggacaacttcttcgcccccgttttcaccatgg
gcaaatattatacgcaaggcgacaaggtgctgatgccgctggcgattcaggttcatcatgccgtttgtgatggcttccatgtcggcagaatgc
ttaatgaattacaacagtactgcgatgagtggcagggcggggcgtaagcgggactctggggttcgaataaagaccgaccaagcgacgtct
gagagctccctggcgaattcggtaccaataaaagagctttattttcatgatctgtgtgttggttttgtgtgcggcgcggaagttcctattctctag
aaagtataggaacttcctcgagcccttatgtgagtcgtattagatcgcggccgcgcccttgacaatgccacatcctgagcaaataattcaacc
actaattgtgagcggataacaaggaggtaaaaaaacatggtatcctgttctgcgccgggtaagatttacctgttcggtgaacacgccgtagt
ttatggcgaaactgcaattgcgtgtgcggtggaactgcgtacccgtgttcgcgcggaactcaatgactctatcactattcagagccagatcgg
ccgcaccggtctggatttcgaaaagcacccttatgtgtctgcggtaattgagaaaatgcgcaaatctattcctattaacggtgtttcttgaccgt
cgattccgacatcccggtgggctccggtctgggtagcagcgcagccgttactatcgcgtctattggtgcgctgaacgagctgttcggctttg
gcctcagcctgcaagaaatcgctaaactgggccacgaaatcgaattaaagtacagggtgccgcgtcccaaccgatacgtatgtttctacc
ttcggcggcgtggttaccatcccggaacgtcgcaaactgaaaactccggactgcggcattgtgattggcgataccggcgttttctcctccac
caaagagttagtagctaacgtacgtcagctgcgcgaaagctacccggatttgatcgaaccgctgatgacctctattggcaaaatctctcgtat
cggcgaacaactggtctgtctggcgactacgcatccatcggccgcctgatgaacgtcaaccagggtctcctggacgccctgggcgttaac
atcttagaactgagccagctgatctattccgctcgtgcggcaggtgcgtttggcgctaaaatcacgggcgctggcggcggtggctgtatggt

FIG. 63C tgcgctgaccgctccggaaaaatgcaaccaagtggcagaagcggtagcaggcgctggcggtaaagtgactatcactaaaccgaccgag caaggtctgaaagtagattaa (SEQ ID NO:90)

FIG. 64A

1-
aagggcgagctcaacgatccggctgctaacaaagcccgaaaggaagctgagttggctgctgccaccgctgagcaataactagcataacc
ccttgggggcctctaaacgggtcttgaggagttttttgctgaaaggaggaactatatccggatatcccgcaagaggcccggcagtaccggcat
aaccaagcctatgcctacagcatccagggtgacggtgccgaggatgacgatgagcgcattgttagatttcatacacggtgcctgactgcgtt
agcaatttaactgtgataaactaccgcattaaagcttatcgatgataagctgtcaaacatgagaattaattcttgaagacgaaagggcctcgtg
atacgcctattttataggttaatgtcatgataataatggtttcttagacgtcaggtggcacttttcggggaaatgtgcgcggaaccccctatttgttt
attttctaaatacattcaaatatgtatccgctcatgagacaataaccctgataaatgcttaataatattgaaaaaggaagagtatgattgaacaa
gatggattgcacgcaggttctccggccgcttgggtggagaggctattcggctatgactgggcacaactgacaatcggctgctctgatgccg
ccgtgttccggctgtcagcgcaggggcgcccggttcttttttgtcaagaccgacctgtccggtgccctgaatgaactgcaggacgaggcagc
gcggctatcgtggctggccacgacgggcgttccttgcgcagctgtgctcgacgttgtcactgaagcgggaagggactggctgctattggg
cgaagtgccggggcaggatcctgtcatctcaccttgctcctgccgagaaagtatccatcatggctgatgcaatgcggcggctgcatacgc
ttgatccggctacctgcccattcgaccaccaagcgaaacatcgcatcgagcgggcacgtactcggatggaagccggtcttgtcgatcagga
tgatctggacgaagagcatcaggggctcgcgccagccgaactgttcgccaggctcaaggcgcgcatgcccgacggcgaggatctcgtc
gtgacacatggcgatgcctgcttgccgaatatcatggtggaaaatggccgcttttctggattcatcgactgtggccggctgggtgtggcgga
ccgctatcaggacatagcgttggctacccgtgatattgctgaagagcttggcggcgaatgggctgaccgcttcctcgtgctttacggtatcgc
cgctcccgattcgcagcgcatcgccttctatcgccttcttgacgagttcttctgagcgggactctggggttcgaaatgaccgaccaagcgac
gcctaactgtcagaccaagtttactcatatatactttagattgatttaaaacttcattttaatttaaaaggatctaggtgaagatcctttttgataatct
catgaccaaaatcccttaacgtgagttttcgttccactgagcgtcagaccccgtagaaaagatcaaaggatcttcttgagatccttttttctgcg
cgtaatctgctgcttgcaaacaaaaaaaccaccgctaccagcggtggtttgtttgccggatcaagagctaccaactctttttccgaaggtaact
ggcttcagcagagcgcagataccaaatactgtccttctagtgtagccgtagttaggccaccacttcaagaactctgtagcaccgcctacatac
ctcgctctgctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatacctacagcgtg
agctatgagaaagcgccacgcttcccgaagggagaaaggcggacaggtatccggtaagcggcagggtcggaacaggagagcgcacg
agggagcttccaggggggaaacgcctggtatctttatagtcctgtcgggtttcgccacctctgacttgagcgtcgatttttgtgatgctcgtcagg
ggggcggagcctatggaaaaacgccagcaacgcggccttttacggttcctggccttttgctggccttttgctcacatgttcttcctgcgttat
cccctgattctgtggataaccgtattaccgcctttgagtgagctgataccgctcgccgcagccgaacgaccgagcgcagcgagtcagtgag
cgaggaagcggaagagcgcctgatgcggtattttctccttacgcatctgtgcggtatttcacaccgcaatggtgcactctcagtacaatctgct
ctgatgccgcatagttaagccagtatacactccgctatcgctacgtgactgggtcatggctgcgccccgacacccgccaacacccgctgac
gcgccctgacgggcttgtctgctcccggcatccgcttacagacaagctgtgaccgtctccgggagctgcatgtgtcagaggttttcaccgtc
atcaccgaaacgcgcgaggcagctgcggtaaagctcatcagcgtggtcgtgaagcgattcacagatgtctgcctgttcatccgcgtccagc
tcgttgagtttctccagaagcgttaatgtctggcttctgataaagcgggccatgttaagggcggttttttcctgtttggtcactgatgcctccgtgt
aagggggatttctgttcatgggggtaatgataccgatgaaacgagagaggatgctcacgatacgggttactgatgatgaacatgcccggtta
ctggaacgttgtgagggtaaacaactggcggtatggatgcggcgggaccagagaaaaatcactcagggtcaatgccagcgcttcgttaat
acagatgtaggtgttccacagggtagccagcagcatcctgcgatgcagatccggaacataatggtgcagggcgctgacttccgcgtttcca
gactttacgaaacacggaaaccgaagaccattcatgttgttgctcaggtcgcagacgttttgcagcagcagtcgcttcacgttcgctcgcgta
tcggtgattcattctgctaaccagtaaggcaaccccgccagcctagccgggtcctcaacgacaggagcacgatcatgcgcacccgtggcc
aggacccaacgctgcccgagatgcgccgcgtgcggctgctggagatgcggacgcgatggatatgttctgccaagggttggtttgcgcat
tcacagttctccgcaagaattgattggctccaattcttggagtggtgaatccgttagcgaggtgccgccggcttccattcaggtcgaggtggc
ccggctccatgcaccgcgacgcaacgcggggaggcagacaaggtataggggcggcgcctacaatccatgccaacccgttccatgtgctc
gccgaggcggcataaatcgccgtgacgatcagcggtccaatgatcgaagttaggctggtaagagccgcgagcgatccttgaagctgtccc
tgatggtcgtcatctaccctgcctggacagcatggcctgcaacgcgggcatcccgatgccgccggaagcgagaagaatcataatggggaa
ggccatccagcctcgcgtcgcgaacgccagcaagacgtagcccagcgcgtcggccgccatgccggcgataatgcctgcttctcgccg
aaacgtttggtggcgggaccagtgacgaaggcttgagcgagggcgtgcaagattccgaataccgcaagcgacaggccgatcatcgtcgc
gctccagcgaaagcggtcctcgccgaaaatgacccagagcgctgccggcacctgtcctacgagttgcatgataaagaagacagtcataag

FIG. 64B tgcggcgacgatagtcatgccccgcgcccaccggaaggagctgactgggttgaaggctctcaagggcatcggtcgagatcccggtgcct
aatgagtgagctaacttacattaattgcgttgcgctcactgcccgctttccagtcgggaaacctgtcgtgccagctgcattaatgaatcggcca
acgcgcggggagaggcggtttgcgtattgggcgccagggtggttttctttcaccagtgagacgggcaacagctgattgcccttcaccgcc
tggccctgagagagttgcagcaagcggtccacgctggtttgccccagcaggcgaaaatcctgtttgatggtggttaacggcgggatataac
atgagctgtcttcggtatcgtcgtatcccactaccgagatatccgccaccaacgcgcagcccggactcggtaatggcgcgcattgcgcccag
cgccatctgatcgttggcaaccagcatcgcagtgggaacgatgccctcattcagcattgcatggtttgttgaaaaccggacatggcactcca
gtcgccttcccgttccgctatcggctgaatttgattgcgagtgagatatttatgccagccagccagacgcagacgcgccgagacagaactta
atgggcccgctaacagcgcgatttgctggtgacccaatgcgaccagatgctccacgcccagtcgcgtaccgtcttcatgggagaaaataat
actgttgatgggtgtctggtcagagacatcaagaaataacgccggaacattagtgcaggcagcttccacagcaatggcatcctggtcatcca
gcggatagttaatgatcagcccactgacgcgttgcgcgagaagattgtgcaccgccgctttacaggcttcgacgccgcttcgttctaccatc
gacaccaccacgctggcacccagttgatcggcgcgagatttaatcgccgcgacaatttgcgacggcgcgtgcagggccagactggaggt
ggcaacgccaatcagcaacgactgtttgcccgccagttgttgtgccacgcggttgggaatgtaattcagctccgccatcgccgcttccacttt
ttcccgcgttttcgcagaaacgtggctggcctggttcaccacgcgggaaacggtctgataagagacaccggcatactctgcgacatcgtata
acgttactggtttcacattcaccaccctgaattgactctcttccgggcgctatcatgccataccgcgaaaggttttgcgccattcgatggtgtcc
gggatctcgacgctctcccttatgcgactcctgcattaggaagcagcccagtagtaggttgaggccgttgagcaccgccgccgcaaggaat
ggtgcatgcaaggagatggcgcccaacagtccccggccacggggcctgccaccatacccacgccgaaacaagcgctcatgagcccg
aagtggcgagcccgatcttccccatcggtgatgtcggcgatataggcgccagcaaccgcacctgtggcgccggtgatgccggccacgat
gcgtccggcgtagaggatcgagatctcgatcccgcgaaattaatacgactcactatagggggaattgtgagcggataacaattcccctctaga
aataattttgtttaactttaagaaggagatatacatatgaattaaccctcactaaagggcggccgcgaagttcctatctctagaaagtataggaa
cttcattctaccgggtaggggaggcgcttttcccaaggcagtctggagcatgcgctttagcagccccgctgggcacttggcgctacacaagt
ggcctctggcctcgcacacattccacatccaccggtaggcgccaaccggctccgttctttggtggccccttcgcgccaccttccactcctcc
cctagtcaggaagttccccccgccccgcagctcgcgtcgtgcaggacgtgacaaatggaagtagcacgtctcactagtctcgtgcagatg
gacagcaccgctgagcaatggaagcgggtaggcctttggggcagcggccaatagcagctttgctccttcgctttctgggctcagaggctg
ggaagggtgggtccggggcgggctcaggggcgggctcaggggcggggcgggcgcccgaaggtcctccggaggcccggcattct
gcacgcttcaaaagcgcacgtctgccgcgctgttctcctcttcctcatctccgggcctttcgacctgcagcagcacgtgttgacaattaatcat
cggcatagtatatcggcatagtataatacgacaaggtgaggaactaaaccatggagaaaaaatcactggatataccaccgttgatatatcc
caatggcatcgtaaagaacattttgaggcatttcagtcagttgctcaatgtacctataaccagaccgttcagctggatattacggcctttaaag
accgtaaagaaaaataagcacaagtttatccggcctttattcacattcttgcccgcctgatgaatgctcatccggaattccgtatggcaatgaa
agacggtgagctggtgatatgggatagtgttcacccttgttacaccgttttccatgagcaaactgaaacgttttcatcgctctggagtgaatacc
acgacgatttccggcagtttctacacatatattcgcaagatgtggcgtgttacggtgaaaacctggcctatttccctaaagggtttattgagaat
atgtttttcgtctcagccaatccctgggtgagtttcaccagttttgatttaaacgtggccaatatggacaacttcttcgcccccgttttcaccatgg
gcaaatattatacgcaaggcgacaaggtgctgatgccgctggccgattcaggttcatcatgccgtttgtgatggcttccatgtcggcagaatgc
ttaatgaattacaacagtactgcgatgagtggcagggcggggcgtaagcgggactctggggttcgaataaagaccgaccaagcgacgtct
gagagctccctggccgaattcggtaccaataaaagagcttatttcatgatctgtgtgttggttttgtgtgcggcgcggaagttcctatctctag
aaagtataggaacttcctcgagcccctatagtgagtcgtattagatcgcggccgcgcccttgaccatgccacatcctgagcaaataattcaacc
actaattgtgagcggataacaaaggaggtaaaaaaacatggtatcctgttctgcgccgggtaagatttacctgttcggtgaacacgccgtagt
ttatggcgaaactgcaattgcgtgtgcggtggaactgcgtacccgtgttcgcgcggaactcaatgactctatcactattcagagccagatcgg
ccgcaccggtctggatttcgaaaagcacccttatgtgtctgcggtaattgagaaaatgcgcaaatctattcctattaacggtgtttcttgaccgt
cgattccgacatcccggtgggctccggtctgggtagcagcgcagccgttactatcgcgtcattggtgcgctgaacgagctgttcggctttg
gcctcagcctgcaagaaatcgctaaactgggccacgaaatcgaattaaagtacagggtgccgcgtccccaaccgatacgtatgtttctacc
ttcggcggcgtggttaccatcccggaacgtcgcaaactgaaaactccggactgcggcattgtgattggcgataccggcgttttctcctccac
caaagagttagtagctaacgtacgtcagctgcgcgaaagctacccggatttgatcgaaccgctgatgacctctattggcaaaatctctcgtat
cggcgaacaactggttctgtctggcgactacgcatccatcgccgcctgatgaacgtcaaccagggtctcctggacgccctgggcgttaac
atcttagaactgagccagctgatctattccgctcgtgcggcaggtgcgtttggcgctaaaatcacggggcgctggcggcggtggctgtatggt

FIG. 64C tgcgctgaccgctccggaaaaatgcaaccaagtggcagaagcggtagcaggcgctggcggtaaagtgactatcactaaaccgaccgagcaaggtctgaaagtagattaa (SEQ ID NO:91)

FIG. 65A 1-
aagggcgagctcaacgatccggctgctaacaaagcccgaaaggaagctgagttggctgctgccaccgctgagcaataactagcataacc
ccttgggggcctctaaacgggtcttgaggagttttttgctgaaaggaggaactatatccggatatcccgcaagaggcccggcagtaccggcat
aaccaagcctatgcctacagcatccaggtgtgacggtgccgaggatgacgatgagcgcattgttagattcatacacggtgcctgactgcgtt
agcaatttaactgtgataaactaccgcattaaagcttatcgatgataagctgtcaaacatgagaattaattcttgaagacgaaagggcctcgtg
atacgcctattttataggttaatgtcatgataataatggtttcttagacgtcaggtggcacttttcggggaaatgtgcgcggaaccccctatttgtt
attttctaaatacattcaaatatgtatccgctcatgagacaataaccctgataaatgcttcaataatattgaaaaaggaagagtatgattgaacaa
gatggattgcacgcaggttctccggccgcttgggtggagaggctattcggctatgactgggcacaactgacaatcggctgctctgatgccg
ccgtgttccggctgtcagcgcaggggcgcccggttctttttgtcaagaccgacctgtccggtgccctgaatgaactgcaggacgaggcagc
gcggctatcgtggctggccacgacgggcgttccttgcgcagctgtgctcgacgttgtcactgaagcgggaagggactggctgctattggg
cgaagtgccggggcaggatctcctgtcatctcaccttgctcctgccgagaaagtatccatcatggctgatgcaatgcggcggctgcatacgc
ttgatccggctacctgcccattcgaccaccaagcgaaacatcgcatcgagcgggcacgtactcggatggaagccggtcttgtcgatcagga
tgatctggacgaagagcatcaggggctcgcgccagccgaactgttcgccaggctcaaggcgcgcatgcccgacggcgaggatctcgtc
gtgacacatggcgatgcctgcttgccgaatatcatggtggaaaatggccgcttttctggattcatcgactgtggccggctgggtgtggcgga
ccgctatcaggacatagcgttggctacccgtgatattgctgaagagcttggcggcgaatgggctgaccgcttcctcgtgctttacggtatcgc
cgctcccgattcgcagcgcatcgccttctatcgccttcttgacgagttcttctgagcgggactctggggttcgaaatgaccgaccaagcgac
gcctaactgtcagaccaagtttactcatatatactttagattgatttaaaacttcatttttaatttaaaaggatctaggtgaagatcctttttgataatct
catgaccaaaatcccttaacgtgagttttcgttccactgagcgtcagaccccgtagaaaagatcaaaggatcttcttgagatcctttttttctgcg
cgtaatctgctgcttgcaaacaaaaaaaccaccgctaccagcggtggtttgtttgccggatcaagagctaccaactctttttccgaaggtaact
ggcttcagcagagcgcagataccaaatactgtccttctagtgtagccgtagttaggccaccacttcaagaactctgtagcaccgcctacatac
ctcgctctgctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatacctacagcgtg
agctatgagaaagcgccacgcttcccgaagggagaaaggcggacaggtatccggtaagcggcagggtcggaacaggagagcgcacg
agggagcttccaggggaaacgcctggtatctttatagtcctgtcgggtttcgccacctctgacttgagcgtcgatttttgtgatgctcgtcagg
ggggcggagcctatggaaaaacgccagcaacgcggcctttttacggttcctggccttttgctggccttttgctcacatgttctttcctgcgttat
cccctgattctgtggataaccgtattaccgcctttgagtgagctgataccgctcgccgcagccgaacgaccgagcgcagcgagtcagtgag
cgaggaagcggaagagcgcctgatgcggtattttctccttacgcatctgtgcggtatttcacaccgcaatggtgcactctcagtacaatctgct
ctgatgccgcatagttaagccagtatacactccgctatcgctacgtgactgggtcatggctgcgccccgacacccgccaacacccgctgac
gcgccctgacgggcttgtctgctcccggcatccgcttacagacaagctgtgaccgtctccgggagctgcatgtgtcagaggttttcaccgtc
atcaccgaaacgcgcgaggcagctgcggtaaagctcatcagcgtggtcgtgaagcgattcacagatgtctgcctgttcatccgcgtccagc
tcgttgagtttctccagaagcgttaatgtctggcttctgataaagcgggccatgttaagggcggttttttcctgtttggtcactgatgcctccgtgt
aagggggatttctgttcatgggggtaatgataccgatgaaacgagagaggatgctcacgatacgggttactgatgatgaacatgcccggtta
ctggaacgttgtgagggtaaacaactggcggtatggatgcggcgggaccagagaaaaatcactcaggtcaatgccagcgcttcgttaat
acagatgtaggtgttccacagggtagccagcagcatcctgcgatgcagatccggaacataatggtgcagggcgctgacttccgcgtttcca
gactttacgaaacacggaaaccgaagaccattcatgttgttgctcaggtcgcagacgttttgcagcagcagtcgcttcacgttcgctcgcgta
tcggtgattcattctgctaaccagtaaggcaacccgccagcctagccgggtcctcaacgacaggagcacgatcatgcgcacccgtggcc
aggacccaacgctgcccgagatgcgccgcgtgcggctgctggagatggcggacgcgatggatatgttctgccaagggttggtttgcgcat
tcacagttctccgcaagaattgattggctccaattcttggagtggtgaatccgttagcgaggtgccgccggcttccattcaggtcgaggtggc
ccggctccatgcaccgcgacgcaacgcggggaggcagacaaggtataggcgcgcctacaatccatgccaacccgttccatgtgctc
gccgaggcggcataaatcgccgtgacgatcagcggtccaatgatcgaagttaggctggtaagagccgcgagcgatccttgaagctgtccc
tgatggtcgtcatctacctgcctggacagcatggcctgcaacgcgggcatcccgatgccgccggaagcgagaagaatcataatggggaa
ggccatccagcctcgcgtcgcgaacgccagcaagacgtagcccagcgcgtcggccgccatgccggcgataatggcctgcttctcgccg
aaacgtttggtggcgggaccagtgacgaaggcttgagcgagggcgtgcaagattccgaataccgcaagcgacaggccgatcatcgtcgc
gctccagcgaaagcggtcctcgccgaaaatgacccagagcgctgccggcacctgtcctacgagttgcatgataaagaagacagtcataag

FIG. 65B tgcggcgacgatagtcatgccccgcgcccaccggaaggagctgactgggttgaaggctctcaagggcatcggtcgagatcccggtgcct
aatgagtgagctaacttacattaattgcgttgcgctcactgcccgctttccagtcgggaaacctgtcgtgccagctgcattaatgaatcggcca
acgcgcggggagaggcggtttgcgtattgggcgccagggtggtttttcttttcaccagtgagacgggcaacagctgattgcccttcaccgcc
tggccctgagagagttgcagcaagcggtccacgctggtttgccccagcaggcgaaaatcctgtttgatggtggttaacggcgggatataac
atgagctgtcttcggtatcgtcgtatcccactaccgagatatccgccaacgcgcagcccggactcggtaatggcgcgcattgcgcccag
cgccatctgatcgttggcaaccagcatcgcagtgggaacgatgccctcattcagcatttgcatggtttgttgaaaaccggacatggcactcca
gtcgccttcccgttccgctatcggctgaatttgattgcgagtgagatatttatgccagccagccagacgcagacgcgccgagacagaactta
atgggccgctaacagcgcgatttgctggtgacccaatgcgaccagatgctccacgcccagtcgcgtaccgtcttcatgggagaaaataat
actgttgatgggtgtctggtcagagacatcaagaaataacgccggaacattagtgcaggcagcttccacagcaatggcatcctggtcatcca
gcggatagttaatgatcagcccactgacgcgttgcgcgagaagattgtgcaccgccgctttacaggcttcgacgccgcttcgttctaccatc
gacaccaccacgctggcacccagttgatcggcgcgagatttaatcgccgcgacaatttgcgacggcgcgtgcagggccagactggaggt
ggcaacgccaatcagcaacgactgtttgcccgccagttgttgtgccacgcggtgggaatgtaattcagctccgccatcgccgcttccacttt
ttcccgcgttttcgcagaaacgtggctggcctggttcaccacgcgggaaacggtctgataagagacaccggcatactctgcgacatcgtata
acgttactggtttcacattcaccaccctgaattgactctcttccgggcgctatcatgccataccgcgaaaggttttgcgccattcgatggtgtcc
gggatctcgacgctctcccttatgcgactcctgcattaggaagcagcccagtagtaggttgaggccgttgagcaccgccgccgcaaggaat
ggtgcatgcaaggagatggcgcccaacagtcccccggccacggggcctgccaccatacccacgccgaaacaagcgctcatgagcccg
aagtggcgagcccgatcttccccatcggtgatgtcggcgatataggcgccagcaaccgcacctgtggcgccggtgatgccggccacgat
gcgtccggcgtagaggatcgagatctcgatcccgcgaaattaatacgactcactatagggggaattgtgagcggataacaattcccctctaga
aataattttgtttaactttaagaaggagatatacatatgaattaaccctcactaagggcggccgcgaagttcctatctctagaaagtataggaa
cttcattctaccgggtaggggaggcgcttttcccaaggcagtctggagcatgcgctttagcagccccgctgggcacttggcgctacacaagt
ggcctctggcctcgcacacattccacatccaccggtaggcgccaaccggctccgttctttggtggcccttcgcgccaccttccactcctcc
cctagtcaggaagttccccccccgccccgcagctcgcgtcgtgcaggacgtgacaaatggaagtagcacgtctcactagtctcgtgcagatg
gacagcaccgctgagcaatggaagcgggtaggcctttggggcagcggccaatagcagctttgctccttcgctttctgggctcagaggctg
ggaagggtgggtccgggggcgggctcaggggcgggctcagggcggggcgggcgcccgaaggtcctccggaggcccggcattct
gcacgcttcaaaagcgcacgtctgccgcgctgttctcctcttcctcatctccgggcctttcgacctgcagcagcacgtgttgacaattaatcat
cggcatagtatatcggcatagtataatacgacaaggtgaggaactaaaccatggagaaaaaatcactggatataccaccgttgatatatcc
caatggcatcgtaaagaacattttgaggcatttcagtcagttgctcaatgtacctataaccagaccgttcagctggatattacggccttttaaag
accgtaaagaaaaataagcacaagtttatccggcctttattcacattcttgcccgcctgatgaatgctcatccggaattccgtatggcaatgaa
agacggtgagctggtgatatgggatagtgttcacccttgttacaccgttttccatgagcaaactgaaacgttttcatcgctctggagtgaatacc
acgacgatttccggcagtttctacacatatattcgcaagatgtggcgtgttacggtgaaaacctggcctatttccctaaagggtttattgagaat
atgtttttcgtctcagccaatccctgggtgagtttcaccagttttgatttaaacgtggccaatatggacaacttcttcgccccgttttcaccatgg
gcaaatattatacgcaaggcgacaaggtgctgatgccgctggccgattcaggttcatcatgccgtttgtgatggcttccatgtcggcagaatgc
ttaatgaattacaacagtactgcgatgagtggcagggcggggcgtaagcgggactctggggttcgaataaagaccgaccaagcgacgtct
gagagctccctggccgaattcggtaccaataaaagagctttattttcatgatctgtgtgttggttttgtgtgcggcgcggaagttcctattctctag
aaagtataggaacttcctcgagcccctatagtgagtcgtattagatcgcggccgcgcccttgacgatgccacatcctgagcaaataattcaacc
actaattgtgagcggataacaaggaggtaaaaaaacatgtatcctgttctgcgccggggtaagatttacctgttcggtgaacacgccgtagt
ttatggcgaaactgcaattgcgtgtgcggtggaactgcgtacccgtgttcgcgcggaactcaatgactctatcactattcagagccagatcgg
ccgcaccggtctggatttcgaaaagcaccctatgtgtctgcggtaattgagaaaatgcgcaaatctattcctattaacggtgttttcttgaccgt
cgattccgacatcccggtgggctccggtctgggtagcagcgcagccgttactatcgcgtctattggtgcgctgaacgagctgttcggctttg
gcctcagcctgcaagaaatcgctaaactgggccacgaaatcgaaattaaagtacagggtgccgcgtcccaaccgatacgtatgtttctacc
ttcggcggcgtggttaccatcccggaacgtcgcaaactgaaaactccggactgcggcattgtgattggcgataccggcgttttctcctccac
caaagagttagtagctaacgtacgtcagctgcgcgaaagctacccggatttgatcgaaccgctgatgacctctattggcaaaatctctcgtat
cggcgaacaactggttctgtctggcgactacgcatccatcggccgcctgatgaacgtcaaccagggtctcctggacgccctgggcgttaac
atcttagaactgagccagctgatctattccgctcgtgcggcaggtgcgtttggcgctaaaatcacgggcgctggcggcggtggctgtatggt

FIG. 65C tgcgctgaccgctccggaaaaatgcaaccaagtggcagaagcggtagcaggcgctggcggtaaagtgactatcactaaaccgaccgag
caaggtctgaaagtagattaa (SEQ ID NO:92)

FIG. 66A

1-
aagggcgagctcaacgatccggctgctaacaaagcccgaaaggaagctgagttggctgctgccaccgctgagcaataactagcataacc
ccttggggcctctaaacgggtcttgaggagttttttgctgaaaggaggaactatatccggatatcccgcaagaggcccggcagtaccggcat
aaccaagcctatgcctacagcatccaggtgacggtgccgaggatgacgatgagcgcattgttagatttcatacacggtgcctgactgcgtt
agcaatttaactgtgataaactaccgcattaaagcttatcgatgataagctgtcaaacatgagaattaattcttgaagacgaaagggcctcgtg
atacgcctatttttataggttaatgtcatgataataatggttlcttagacgtcaggtggcacttttcggggaaatgtgcgcggaaccccatttgttt
attttttctaaatacattcaaatatgtatccgctcatgagacaataaccctgataaatgcttcaataatattgaaaaaggaagagtatgattgaacaa
gatggattgcacgcaggttctccggccgcttgggtggagaggctattcggctatgactgggcacaactgacaatcggctgctctgatgccg
ccgtgttccggctgtcagcgcaggggcgcccggttcttttgtcaagaccgacctgtccggtgccctgaatgaactgcaggacgaggcagc
gcggctatcgtggctggccacgacgggcgttccttgcgcagctgtgctcgacgttgtcactgaagcgggaagggactggctgctattggg
cgaagtgccggggcaggatctcctgtcatctcaccttgctcctgccgagaaagtatccatcatggctgatgcaatgcggcggctgcatacgc
ttgatccggctacctgcccattcgaccaccaagcgaaacatcgcatcgagcgggcacgtactcggatggaagccggtcttgtcgatcagga
tgatctggacgaagagcatcaggggctcgcgccagccgaactgttcgccaggctcaaggcgcgcatgcccgacggcgaggatctcgtc
gtgacacatggcgatgcctgcttgccgaatatcatggtggaaaatggccgcttttctggattcatcgactgtggccggctgggtgtggcgga
ccgctatcaggacatagcgttggctacccgtgatattgctgaagagcttggcggcgaatgggctgaccgcttcctcgtgctttacggtatcgc
cgctcccgattcgcagcgcatcgccttctatcgccttcttgacgagttcttctgagcgggactctggggttcgaaatgaccgaccaagcgac
gcctaactgtcagaccaagtttactcatatatactttagattgatttaaaacttcatttttaatttaaaaggatctaggtgaagatcctttttgataatct
catgaccaaaatcccttaacgtgagttttcgttccactgagcgtcagaccccgtagaaaagatcaaaggatcttcttgagatcctttttttctgcg
cgtaatctgctgcttgcaaacaaaaaaaccaccgctaccagcggtggtttgtttgccggatcaagagctaccaactctttttccgaaggtaact
ggcttcagcagagcgcagataccaaatactgtccttctagtgtagccgtagttaggccaccacttcaagaactctgtagcaccgcctacatac
ctcgctctgctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatacctacagcgtg
agctatgagaaagcgccacgcttcccgaagggagaaaggcggacaggtatccggtaagcggcagggtcggaacaggagagcgcacg
agggagcttccaggggggaaacgcctggtatctttatagtcctgtcgggtttcgccacctctgacttgagcgtcgatttttgtgatgctcgtcagg
ggggcggagcctatgaaaaacgccagcaacgcggcctttttacggttcctggccttttgctggccttttgctcacatgttctttcctgcgttat
cccctgattctgtggataaccgtattaccgcctttgagtgagctgataccgctcgccgcagccgaacgaccgagcgcagcgagtcagtgag
cgaggaagcggaagagcgcctgatgcggtattttctccttacgcatctgtgcggtatttcacaccgcaatggtgcactctcagtacaatctgct
ctgatgccgcatagttaagccagtatacactccgctatcgctacgtgactgggtcatggctgcgccccgacacccgccaacacccgctgac
gcgccctgacgggcttgtctgctcccggcatccgcttacagacaagctgtgaccgtctccgggagctgcatgtgtcagaggttttcaccgtc
atcaccgaaacgcgcgaggcagctgcggtaaagctcatcagcgtggtcgtgaagcgattcacagatgtctgcctgttcatccgcgtccagc
tcgttgagtttctccagaagcgttaatgtctggcttctgataaagcgggccatgttaagggcggttttttcctgtttggtcactgatgcctccgtgt
aagggggatttctgttcatgggggtaatgataccgatgaaacgagagaggatgctcacgatacgggttactgatgatgaacatgcccggtta
ctggaacgttgtgagggtaaacaactggcggtatggatgcggcgggaccagagaaaaatcactcagggtcaatgccagcgcttcgttaat
acagatgtaggtgttccacaggggtagccagcagcatcctgcgatgcagatccggaacataatggtgcagggcgctgacttccgcgtttcca
gactttacgaaacacggaaaccgaagaccattcatgttgttgctcaggtcgcagacgttttgcagcagcagtcgcttcacgttcgctcgcgta
tcggtgattcattctgctaaccagtaaggcaaccccgccagcctagccgggtcctcaacgacaggagcacgatcatgcgcacccgtggcc
aggacccaacgctgcccgagatgcgccgcgtgcggctgctggagatggcggacgcgatggatatgttctgccaagggttggtttgcgcat
tcacagttctccgcaagaattgattggctccaattcttggagtggtgaatccgttagcgaggtgccgccggcttccattcaggtcgaggtggc
ccggctccatgcaccgcgacgcaacgcggggaggcagacaaggtatagggcggcgcctacaatccatgccaacccgttccatgtgctc
gccgaggcggcataaatcgccgtgacgatcagcggtccaatgatcgaagttaggctggtaagagccgcgagcgatccttgaagctgtccc
tgatggtcgtcatctacctgcctggacagcatggcctgcaacgcgggcatcccgatgccgccggaagcgagaagaatcataatggggaa
ggccatccagcctcgcgtcgcgaacgccagcaagacgtagcccagcgcgtcggccgccatgccggcgataatggcctgcttctcgccg
aaacgtttggtggcgggaccagtgacgaaggcttgagcgagggcgtgcaagattccgaataccgcaagcgacaggccgatcatcgtcgc
gctccagcgaaagcggtcctcgccgaaaatgacccagagcgctgccggcacctgtcctacgagttgcatgataaagaagacagtcataag

FIG. 66B tgcggcgacgatagtcatgccccgcgcccaccggaaggagctgactgggttgaaggctctcaagggcatcggtcgagatcccggtgcct
aatgagtgagctaacttacattaattgcgttgcgctcactgcccgctttccagtcgggaaacctgtcgtgccagctgcattaatgaatcggcca
acgcgcggggagaggcggtttgcgtattgggcgccagggtggttttctttcaccagtgagacgggcaacagctgattgcccttcaccgcc
tggccctgagagagttgcagcaagcggtccacgctggtttgccccagcaggcgaaaatcctgtttgatggtggttaacggcgggatataac
atgagctgtcttcggtatcgtcgtatcccactaccgagatatccgcaccaacgcgcagcccggactcggtaatggcgcgcattgcgcccag
cgccatctgatcgttggcaaccagcatcgcagtgggaacgatgccctcattcagcatttgcatggtttgttgaaaaccggacatggcactcca
gtcgccttcccgttccgctatcggctgaatttgattgcgagtgagatatttatgccagccagccagacgcagacgcgccgagacagaactta
atgggcccgctaacagcgcgatttgctggtgacccaatgcgaccagatgctccacgcccagtcgcgtaccgtcttcatgggagaaaataat
actgttgatgggtgtctggtcagagacatcaagaaataacgccggaacattagtgcaggcagcttccacagcaatggcatcctggtcatcca
gcggatagttaatgatcagcccactgacgcgttgcgcgagaagattgtgcaccgccgctttacaggcttcgacgccgcttcgttctaccatc
gacaccaccacgctggcacccagttgatcggcgcgagatttaatcgccgcgacaatttgcgacggcgcgtgcagggccagactggaggt
ggcaacgccaatcagcaacgactgtttgcccgccagttgttgtgccacgcggttgggaatgtaattcagctccgccatcgccgcttccacttt
ttcccgcgttttcgcagaaacgtggctggcctggttcaccacgcgggaaacggtctgataagagacaccggcatactctgcgacatcgtata
acgttactggtttcacattcaccaccctgaattgactctcttccgggcgctatcatgccataccgcgaaaggttttgcgccattcgatggtgtcc
gggatctcgacgctctcccttatgcgactcctgcattaggaagcagcccagtagtaggttgaggccgttgagcaccgccgccgcaaggaat
ggtgcatgcaaggagatggcgcccaacagtcccccggccacggggcctgccaccatacccacgccgaaacaagcgctcatgagcccg
aagtggcgagcccgatcttccccatcggtgatgtcggcgatataggcgccagcaaccgcacctgtggcgccggtgatgccggccacgat
gcgtccggcgtagaggatcgagatctcgatcccgcgaaattaatacgactcactatagggaattgtgagcggataacaattcccctctaga
aataattttgtttaactttaagaaggagatacatatgaattaaccctcactaaagggcggccgcgaagttcctattctctagaaagtataggaa
cttcattctaccgggtaggggaggcgcttttcccaaggcagtctggagcatgcgctttagcagccccgctgggcacttggcgctacacaagt
ggcctctggcctcgcacacattccacatccaccggtaggcgccaaccggctccgttcttggtggcccttcgcgccaccttccactcctcc
cctagtcaggaagttcccccccgccccgcagctcgcgtcgtgcaggacgtgacaaatggaagtagcacgtctcactagtctcgtgcagatg
gacagcaccgctgagcaatggaagcgggtaggcctttggggcagcggccaatagcagctttgctccttcgctttctgggctcagaggctg
ggaagggtgggtccgggggcgggctcaggggcgggctcagggggcgggcgggcgcccgaaggtcctccggaggcccggcattct
gcacgcttcaaaagcgcacgtctgccgcgctgttctcctcttcctcatctccgggcctttcgacctgcagcagcacgtgttgacaattaatcat
cggcatagtatatcggcatagtataatacgacaaggtgaggaactaaaccatggagaaaaaaatcactggatataccaccgttgatatatcc
caatggcatcgtaaagaacattttgaggcatttcagtcagttgctcaatgtacctataaccagaccgttcagctggatattacggcctttttaaag
accgtaaagaaaaataagcacaagttttatccggcctttattcacattcttgcccgcctgatgaatgctcatccggaattccgtatggcaatgaa
agacggtgagctggtgatatgggatagtgttcacccttgttacaccgttttccatgagcaaactgaaacgttttcatcgctctggagtgaatacc
acgacgatttccggcagtttctacacatatattcgcaagatgtggcgtgttacggtgaaaacctggcctatttccctaaagggttattgagaat
atgtttttcgtctcagccaatccctgggtgagtttcaccagttttgatttaaacgtggccaatatggacaacttcttcgcccccgttttcaccatgg
gcaaatattatacgcaaggcgacaaggtgctgatgccgctggcgattcaggttcatcatgccgtttgtgatggcttccatgtcggcagaatgc
ttaatgaattacaacagtactgcgatgagtggcagggcggggcgtaagcgggactctggggttcgaataaagaccgaccaagcgacgtct
gagagctccctggcgaattcggtaccaataaaagagctttattttcatgatctgtgtgttggttttgtgtgcggcgcggaagttcctattctctag
aaagtataggaacttcctcgagccctatagtgagtcgtattagatcgcggccgcgcccttgactatgccacatcctgagcaaataattcaacc
actaattgtgagcggataacaaaggaggtaaaaaaacatggtatcctgttctgcgccgggtaagatttacctgttcggtgaacacgccgtagt
ttatggcgaaactgcaattgcgtgtgcggtggaactgcgtaccgtgttcgcgcggaactcaatgactctatcactattcagagccagatcgg
ccgcaccggtctggatttcgaaaagcaccctatgtgtctgcggtaattgagaaaatgcgcaaatctattcctattaacggtgttttcttgaccgt
cgattccgacatcccggtgggctccggtctgggtagcagcgcagccgttactatcgcgtctattggtgcgctgaacgagctgttcggctttg
gcctcagcctgcaagaaatcgctaaactgggccacgaaatcgaattaaagtacaggggtgccgcgtccccaaccgatacgtatgtttctacc
ttcggcggcgtggttaccatcccggaacgtcgcaaactgaaaactccggactgcggcattgtgattggcgataccggcgttttctcctccac
caaagagttagtagctaacgtacgtcagctgcgcgaaagctacccggatttgatcgaaccgctgatgacctctattggcaaaatctctcgtat
cggcgaacaactggttctgtctggcgactacgcatccatcggccgcctgatgaacgtcaaccagggtctcctggacgccctgggcgttaac
atcttagaactgagccagctgatctattccgctcgtgcggcaggtgcgtttggcgctaaaatcacgggcgctggcggcggtggctgtatggt

FIG. 66C tgcgctgaccgctccggaaaaatgcaaccaagtggcagaagcggtagcaggcgctggcggtaaagtgactatcactaaaccgaccgag
caaggtctgaaagtagattaa (SEQ ID NO:93)

FIG. 73B(1)

gcggccgcgcccttgacgatgccacatcctgagcaaataattcaaccactaattgtgagcggataacacaaggaggaaacagc
catggtatcctgttctgcgccgggtaagatttacctgttcggtgaacacgccgtagtttatggcgaaactgcaattgcgtgtgcggt
ggaactgcgtacccgtgttcgcgcggaactcaatgactctatcactattcagagccagatcggccgcaccggtctggatttcgaa
aagcacccttatgtgtctgcggtaattgagaaaatgcgcaaatctattcctattaacggtgttttcttgaccgtcgattccgacatccc
ggtgggctccggtctgggtagcagcgcagccgttactatcgcgtctattggtgcgctgaacgagctgttcggctttggcctcagc
ctgcaagaaatcgctaaactgggccacgaaatcgaattaaagtacagggtgccgcgtccccaaccgatacgtatgtttctacct
tcggcggcgtggttaccatcccggaacgtcgcaaactgaaaactccggactgcggcattgtgattggcgataccggcgttttctc
ctccaccaaagagttagtagctaacgtacgtcagctgcgcgaaagctacccggatttgatcgaaccgctgatgacctctattggc
aaaatctctcgtatcggcgaacaactggttctgtctggcgactacgcatccatcggccgcctgatgaacgtcaaccagggtctcct
ggacgccctgggcgttaacatcttagaactgagccagctgatctattccgctcgtgcggcaggtgcgtttggcgctaaaatcacg
ggcgctggcggcggtggctgtatggttgcgctgaccgctccggaaaaatgcaaccaagtggcagaagcggtagcaggcgct
ggcggtaaagtgactatcactaaaccgaccgagcaaggtctgaaagtagattaagccttgacttaatagctgcttatttcgcccta
tggtacctagtaggaggaaaaaaacatggaaatgcgtcaaccggctgtcgcaggtcaattctacccactgcgttgcgagaacct
ggaaaacgaactgaaacgctgcttcgaaggcctggagatccgcgaacaagaagtgctgggcgcagtctgtccgcacgccggt
tatatgtactctggcaaagttgcggcgcacgtctatgccactctgccggaagctgatacctacgtaatcttcggcccgaaccacac
cggctacggtagccctgtctctgtgagccgtgaaacttggaagaccccgttgggcaatatcgatgttgacctggaactggcgga
cggcttcctgggttccatcgtagatgcggatgaactcggtcacaaatacgaacactctatcgaagttcagctgccgtttctgcaata
ccgttttgaacgcgatttcaaaattctgccaatctgcatgggtatgcaagacgaagaaaccgcggtcgaagtaggtaacctgctg
gcggatctgatcagcgagtccggtaaacgtgctgtgatcatcgcaagctctgatttcacccactatgagacggctgaacgtgcca
aagaaatcgattccgaagttattgattctatcctgaactttgacatctctggcatgtacgatcgcctgtatcgccgtaacgcctctgttt
gcggttacggcccgatcaccgctatgctgacggcaagcaaaaagctgggcggctctcgtgcgactttgctgaaatacgcaaac
agcggtgacgtgtccggtgataaagacgctgtggtgggctacgccgccatcatcgttgagtaagctgattaaaggttgaacagat
aggatttcgtcatggatcctacaaggaggaaaaaaacatgaatgcttctaatgaaccggtgattctgaaactgggtggctctgcta
ttaccgacaaaggtgcctacgaaggcgtagttaaggaagctgatttgctgcgcatcgcacaggaagttagcggtttccgtggca
agatgatcgtggttcatggtgctggtagcttcggccatacgtacgcgaagaaatacggcctggaccgtaccttcgacccagagg
gcgcaattgttactcatgaatctgttaaaaagctcgcctccaaagttgtaggtgctctgaatagcttcggcgtgcgtgctatcgcgg
tgcatcctatggactgcgcagtatgccgtaacggtcgtatcgaaacgatgtatctggactccatcaagttaatgctggaaaaaggt
ctggtgccggttctgcacgcgacgtcgcaatggatattgaactgggcacttgtatcctgtccggtgatcaaatcgttccttacctg
gccaaagaactgggtatctcccgcctcggcctgggcagcgcagaggatggtgtgctggatatggagggcaaacctgtaccgg
aaatcaccccagaaactttcgaagagttccgccactgcatcggtggttctggttctactgatgtaaccggtggcatgctgggcaaa
gtgctggaacttctggaattgagcaaaaattcttccattactagctacattttcaacgctggtaaagcagacaacatctaccgctttct
gaatggtgagtccatcggcactcgcatcagcccggacaagcgtgtttaagctagttattaacctaaatgctctaaaccagttatga
gctctacaaggaggaaaaaaacatgattaacactaccagccgccgcaaaattgaacacctgaaactctgcgcagaatccccgg
ttgaagcgcgtcaggtatctgccggctttgaagacgttactctgatccaccgcgctttaccggagctgaacatggatgaactgga
cctcagcgttgatttcctgggtaaacgcatcaaagcgccgttcctgattgcgtctatcacgggtggtcacccagataccatcccgg
ttaacgctgcgctggcagctgctgctgaggagctgggtgttggcatcggcgttggctctcagcgcgcggccattgatgatccga
gccaggaagacagcttccgtgtagtgcgtgatgaagccccagatgcgtttgtttatggcaacgtcggcgcagcacagatccgtc
agtatggtgttgaaggtgttgaaaaactgatcgaaatgattgacgcagatgccttggcaatccacctgaacttctgcaagaagcg
gtccaaccggaaggtgaccgcgacgcgaccggttgcctggacatgattaccgaaatttgctctcagattaaaactccggtaatcg
tgaaagaaaccggtgcaggcattagccgtgaagatgcgattctgttccagaaagctggcgtgagcgcaatcgacgttggcggc
gcgggcggcacctcctgggctggcgtcgaggtctaccgtgctaaagaaagccgtgactctgttagcgagcgtttaggtgagct
gttttgggatttcggcattccgacggtagcttctctgattgaatcccgcgtttccttgccgctgatcgcaaccggcggtatccgtaac
ggtctggacattgctaaaagcattgctctcggcgcaagcgctgccagcgccgctctgccgttcgttggtccgtccctggagggc
aaagaatccgttgtacgtgtgctgagctgcatgctggaagaatttaaagcagcaatgttttgtgcggttgcggcaacatcaaaga

FIG. 73B(2)

cctgcacaactctccagtagtggtaactggttggacccgcgaatacctggagcagcgcggttttaacgttaaggacctctccctg
ccgggcaacgctctgtaagcttcaacgcgtctacaaataaaaaaggcacgtcagatgacgtgccttttttcttgtctaga
(SEQ ID NO:113)

FIG. 74B(1)

aagggcgagctcaacgatccggctgctaacaaagcccgaaaggaagctgagttggctgctgccaccgctgagcaataactag
cataaccccttggggcctctaaacgggtcttgaggagttttttgctgaaaggaggaactatatccggatatcccgcaagaggccc
ggcagtaccggcataaccaagcctatgcctacagcatccagggtgacggtgccgaggatgacgatgagcgcattgttagatttc
atacacggtgcctgactgcgttagcaatttaactgtgataaactaccgcattaaagcttatcgatgataagctgtcaaacatgagaa
ttaattcttgaagacgaaagggcctcgtgatacgcctattttataggttaatgtcatgataataatggtttcttagacgtcaggtggca
cttttcggggaaatgtgcgcggaaccccctatttgtttatttttctaaatacattcaaatatgtatccgctcatgagacaataaccctgat
aaatgcttcaataatattgaaaaaggaagagtatgattgaacaagatggattgcacgcaggttctccggccgcttgggtggagag
gctattcggctatgactgggcacaactgacaatcggctgctctgatgccgccgtgttccggctgtcagcgcaggggcgcccggt
tcttttgtcaagaccgacctgtccggtgccctgaatgaactgcaggacgaggcagcgcggctatcgtggctggccacgacgg
gcgttccttgcgcagctgtgctcgacgttgtcactgaagcggggaagggactggctgctattgggcgaagtgccggggcaggat
ctcctgtcatctcaccttgctcctgccgagaaagtatccatcatggctgatgcaatgcggcggctgcatacgcttgatccggctac
ctgcccattcgaccaccaagcgaaacatcgcatcgagcgggcacgtactcggatggaagccggtcttgtcgatcaggatgatct
ggacgaagagcatcaggggctcgcgccagccgaactgttcgccaggctcaaggcgcgcatgcccgacggcgaggatctcgt
cgtgacacatggcgatgcctgcttgccgaatatcatggtggaaaatggccgcttttctggattcatcgactgtggccggctgggtg
tggcggaccgctatcaggacatagcgttggctacccgtgatattgctgaagagcttggcggcgaatgggctgaccgcttcctcgt
gctttacggtatcgccgctcccgattcgcagcgcatcgccttctatcgccttcttgacgagttcttctgagcgggactctggggttc
gaaatgaccgaccaagcgacgcctaactgtcagaccaagtttactcatatatactttagattgatttaaaacttcatttttaatttaaaa
ggatctaggtgaagatcctttttgataatctcatgaccaaaatcccttaacgtgagttttcgttccactgagcgtcagaccccgtaga
aaagatcaaaggatcttcttgagatccttttttctgcgcgtaatctgctgcttgcaaacaaaaaaaccaccgctaccagcggtggtt
tgtttgccggatcaagagctaccaactctttttccgaaggtaactggcttcagcagagcgcagataccaaatactgtccttctagtgt
agccgtagttaggccaccacttcaagaactctgtagcaccgcctacatacctcgctctgctaatcctgttaccagtggctgctgcc
agtggcgataagtcgtgtcttaccgggttggactcaagacgatagttaccggataaggcgcagcggtcgggctgaacggggg
gttcgtgcacacagcccagcttggagcgaacgacctacaccgaactgagatacctacagcgtgagctatgagaaagcgccac
gcttcccgaagggagaaaggcggacaggtatccggtaagcggcagggtcggaacaggagagcgcacgagggagcttcca
gggggaaacgcctggtatctttatagtcctgtcgggtttcgccacctctgacttgagcgtcgatttttgtgatgctcgtcaggggggg
cggagcctatggaaaaacgccagcaacgcggccttttacggttcctggccttttgctggccttttgctcacatgttcttcctgcgtt
atcccctgattctgtggataaccgtattaccgcctttgagtgagctgataccgctcgccgcagccgaacgaccgagcgcagcga
gtcagtgagcgaggaagcggaagagcgcctgatgcggtattttctccttacgcatctgtgcggtatttcacaccgcaatggtgca
ctctcagtacaatctgctctgatgccgcatagttaagccagtatacactccgctatcgctacgtgactgggtcatggctgcgcccc
gacacccgccaacacccgctgacgcgccctgacgggcttgtctgctcccggcatccgcttacagacaagctgtgaccgtctcc
gggagctgcatgtgtcagaggttttcaccgtcatcaccgaaacgcgcgaggcagctgcggtaaagctcatcagcgtggtcgtg
aagcgattcacagatgtctgcctgttcatccgcgtccagctcgttgagtttctccagaagcgttaatgtctggcttctgataaagcgg
gccatgttaagggcggttttttcctgtttggtcactgatgcctccgtgtaagggggatttctgttcatgggggtaatgataccgatga
aacgagagaggatgctcacgatacgggttactgatgatgaacatgcccggttactggaacgttgtgagggtaaacaactggcg
gtatggatgcggcgggaccagagaaaaatcactcagggtcaatgccagcgcttcgttaatacagatgtaggtgttccacagggt
agccagcagcatcctgcgatgcagatccggaacataatggtgcagggcgctgacttccgcgtttccagactttacgaaacacgg
aaaccgaagaccattcatgttgttgctcaggtcgcagacgttttgcagcagcagtcgcttcacgttcgctcgcgtatcggtgattca
ttctgctaaccagtaaggcaaccccgccagcctagccgggtcctcaacgacaggagcacgatcatgcgcacccgtggccagg
acccaacgctgcccgagatgcgccgcgtgcggctgctggagatggcggacgcgatggatatgttctgccaagggttggtttgc
gcattcacagttctccgcaagaattgattggctccaattcttggagtggtgaatccgttagcgaggtgccgccggcttccattcagg
tcgaggtggcccggctccatgcaccgcgacgcaacgcggggaggcagacaagtatagggcggcgcctacaatccatgcc
aacccgttccatgtgctcgccgaggcggcataaatcgccgtgacgatcagcggtccaatgatcgaagttaggctggtaagagc
cgcgagcgatccttgaagctgtccctgatggtcgtcatctacctgcctggacagcatggcctgcaacgcgggcatcccgatgcc
gccggaagcgagaagaatcataatggggaaggccatccagcctcgcgtcgcgaacgccagcaagacgtagcccagcgcgt

FIG. 74B(2)

cggccgccatgccggcgataatggcctgcttctcgccgaaacgtttggtggcgggaccagtgacgaaggcttgagcgagggc
gtgcaagattccgaataccgcaagcgacaggccgatcatcgtcgcgctccagcgaaagcggtcctcgccgaaaatgacccag
agcgctgccggcacctgtcctacgagttgcatgataaagaagacagtcataagtgcggcgacgatagtcatgccccgcgccca
ccggaaggagctgactgggttgaaggctctcaagggcatcggtcgagatcccggtgcctaatgagtgagctaacttacattaatt
gcgttgcgctcactgcccgctttccagtcgggaaacctgtcgtgccagctgcattaatgaatcggccaacgcgcggggagagg
cggtttgcgtattgggcgccagggtggttttttctttcaccagtgagacgggcaacagctgattgcccttcaccgcctggccctga
gagagttgcagcaagcggtccacgctggtttgccccagcaggcgaaaatcctgtttgatggtggttaacggcgggatataacat
gagctgtcttcggtatcgtcgtatcccactaccgagatatccgcaccaacgcgcagcccggactcggtaatggcgcgcattgcg
cccagcgccatctgatcgttggcaaccagcatcgcagtgggaacgatgccctcattcagcatttgcatggtttgttgaaaaccgg
acatggcactccagtcgccttcccgttccgctatcggctgaatttgattgcgagtgagatatttatgccagccagccagacgcaga
cgcgccgagacagaacttaatgggcccgctaacagcgcgatttgctggtgacccaatgcgaccagatgctccacgcccagtcg
cgtaccgtcttcatgggagaaaataatactgttgatgggtgtctggtcagagacatcaagaaataacgccggaacattagtgcag
gcagcttccacagcaatggcatcctggtcatccagcggatagttaatgatcagcccactgacgcgttgcgcgagaagattgtgc
accgccgctttacaggcttcgacgccgcttcgttctaccatcgacaccaccacgctggcacccagttgatcggcgcgagatttaa
tcgccgcgacaatttgcgacggcgcgtgcagggccagactggaggtggcaacgccaatcagcaacgactgtttgcccgccag
ttgttgtgccacgcggttgggaatgtaattcagctccgccatgccgcttccacttttttcccgcgtttttcgcagaaacgtggctggc
ctggttcaccacgcgggaaacggtctgataagagacaccggcatactctgcgacatcgtataacgttactggtttcacattcacca
ccctgaattgactctcttccgggcgctatcatgccataccgcgaaaggttttgcgccattcgatggtgtccgggatctcgacgctct
cccttatgcgactcctgcattaggaagcagcccagtagtaggttgaggccgttgagcaccgccgccgcaaggaatggtgcatg
caaggagatggcgcccaacagtcccccggccacgggggcctgccaccatacccacgccgaaacaagcgctcatgagcccga
agtggcgagcccgatcttccccatcggtgatgtcggcgatataggcgccagcaaccgcacctgtggcgccggtgatgccggc
cacgatgcgtccggcgtagaggatcgagatctcgatcccgcgaaattaatacgactcactatagggggaattgtgagcggataac
aattcccctctagaaataattttgtttaactttaagaaggagatatacatatgcgggggttctcatcatcatcatcatcatggtatggcta
gcatgactggtggacagcaaatgggtcgggatctgtacgacgatgacgataaggatcatcccttcaccatggtatcctgttctgc
gccgggtaagatttacctgttcggtgaacacgccgtagtttatggcgaaactgcaattgcgtgtgcggtggaactgcgtacccgt
gttcgcgcggaactcaatgactctatcactattcagagccagatcggccgcaccggtctggatttcgaaaagcacccttatgtgtc
tgcggtaattgagaaaatgcgcaaatctattccattaacggtgttttcttgaccgtcgattccgacatcccggtgggctccggtctg
ggtagcagcgcagccgttactatcgcgtctattggtgcgctgaacgagctgttcggctttggcctcagcctgcaagaaatcgcta
aactgggccacgaaatcgaaattaaagtacagggtgccgcgtcccaaccgatacgtatgtttctaccttcggcggcgtggttac
catcccggaacgtcgcaaactgaaaactccggactgcggcattgtgattggcgataccggcgttttctcctccaccaaagagtta
gtagctaacgtacgtcagctgcgcgaaagctaccggatttgatcgaaccgctgatgacctctattggcaaaatctctcgtatcgg
cgaacaactggttctgtctggcgactacgcatccatcggccgcctgatgaacgtcaaccaggtctcctggacgccctgggcgt
taacatcttagaactgagccagctgatctattccgctcgtgcggcaggtgcgtttggcgctaaaatcacgggcgctggcggcggt
ggctgtatggttgcgctgaccgctccggaaaaatgcaaccaagtggcagaagcggtagcaggcgctggcggtaaagtgactat
cactaaaccgaccgagcaaggtctgaaagtagattaa
(SEQ ID NO:114)

CDS 2: Gentamycin resistance gene; CDS1: E. coli replication protein.

FIG. 77A 1-
ctcgggccgtctcttgggcttgatcggccttcttgcgcatctcacgcgctcctgcggcggcctgtagggcaggctcatacccctgccgaacc
gcttttgtcagccggtcggccacggcttccggcgtctcaacgcgctttgagattcccagcttttcggccaatccctgcggtgcataggcgcgt
ggctcgaccgcttgcgggctgatggtgacgtggcccactggtggccgctccagggcctcgtagaacgcctgaatgcgcgtgtgacgtgc
cttgctgccctcgatgccccgttgcagccctagatcggccacagcggccgcaaacgtggtctggtcgcgggtcatctgcgctttgttgccga
tgaactccttggccgacagcctgccgtcctgcgtcagcggcaccacgaacgcggtcatgtgcgggctggtttcgtcacggtggatgctggc
cgtcacgatgcgatccgccccgtacttgtccgccagccacttgtgcgccttctcgaagaacgccgcctgctgttcttggctggccgacttcca
ccattccgggctggccgtcatgacgtactcgaccgccaacacagcgtccttgcgccgcttctctggcagcaactcgcgcagtcggcccatc
gcttcatcggtgctgctggccgcccagtgctcgttctctggcgtcctgctggcgtcagcgttgggcgtctcgcgctcgcggtaggcgtgctt
gagactggccgccacgttgcccattttcgccagcttcttgcatcgcatgatcgcgtatgccgccatgcctgcccctcccttttggtgtccaacc
ggctcgacgggggcagcgcaaggcggtgcctccggcgggccactcaatgcttgagtatactcactagactttgcttcgcaaagtcgtgac
cgcctacggcggctgcggcgccctacgggcttgctctccgggcttcgccctgcgcggtcgctgcgctcccttgccagcccgtggatatgtg
gacgatggccgcgagcggccaccggctggctcgcttcgctcggcccgtggacaaccctgctggacaagctgatggacaggctgcgcct
gcccacgagcttgaccacagggattgcccaccggctacccagccttcgaccacatacccaccggctccaactgcgcggcctgcggcctt
gccccatcaatttttttaattttctctggggaaaagcctccggcctgcggcctgcgcgcttcgcttgccggttggacaccaagtggaaggcgg
gtcaaggctcgcgcagcgaccgcgcagcggcttggccttgacgcgcctggaacgacccaagcctatgcgagtgggggcagtcgaagg
cgaagcccgcccgcctgccccccgagcctcacggcggcgagtgcgggggttccaagggggcagcgccaccttgggcaaggccgaag
gccgcgcagtcgatcaacaagccccggaggggccactttttgccggaggggagccgcgccgaaggcgtgggggaaccccgcaggg
gtgcccttctttgggcaccaaagaactagatataggggcgaaatgcgaaagacttaaaaatcaacaacttaaaaaaggggggtacgcaacag
ctcattgcggcaccccccgcaatagctcattgcgtaggttaaagaaaatctgtaattgactgccactttacgcaacgcataattgttgtcgcgc
tgccgaaaagttgcagctgattgcgcatggtgccgcaaccgtgcggcaccctaccgcatggagataagcatggccacgcagtccagaga
aatcggcattcaagccaagaacaagcccggtcactgggtgcaaacggaacgcaaagcgcatgaggcgtgggccgggcttattgcgagg
aaacccacggcggcaatgctgctgcatcacctcgtggcgcagatgggccaccagaacgccgtggtggtcagccagaagacactttccaa
gctcatcggacgttctttgcggacggtccaatacgcagtcaaggacttggtggccgagcgctggatctccgtcgtgaagctcaacggcccc
ggcaccgtgtcggcctacgtggtcaatgaccgcgtggcgtggggccagccccgcgaccagttgcgcctgtcggtgttcagtgccgccgt
ggtggttgatcacgacgaccaggacgaatcgctgttggggcatggcgacctgcgccgcatcccgaccctgtatccgggcgagcagcaac
taccgaccggccccggcgaggagccgcccagccagcccggcattccgggcatggaaccagacctgccagccttgaccgaaacggag
gaatgggaacggcgcgggcagcagcgcctgccgatgccgatgagccgtgttttctggacgatggcgagccgttggagccgccgacac
gggtcacgctgccgcgccggtagcacttgggttgcgcagcaaccgtaagtgcgctgttccagactatcggctgtagccgcctcgccgcc
ctatccttgtctgcctccccgcgttgcgtcgcggtgcatggagccgggccacctcgacctgaatggaagccggcggcacctcgctaacg
gattcaccgtttttatcaggctctgggaggcagaataaatgatcatatcgtcaattattacctccacggggagagcctgagcaaactggcctca
ggcatttgagaagcacacggtcacactgcttccggtagtcaataaaccggtaaaccagcaatagacataagcggctatttaacgaccctgcc
ctgaaccgacgaccgggtcgaatttgcttcgaattctgccattcatccgcttattatcacttattcaggcgtagcaccaggcgtttaagggca
ccaataactgccttaaaaaaattacgccccgccctgccactcatcgcagtcggccattggttaaaaaatgagctgatttaacaaaaattaac
gcgaattttaacaaaatattaacgcttacaatttccattcgccattcaggctgcgcaactgttgggaagggcgatcggtgcgggcctcttcgct
attacgccagctggcgaaaggggggatgtgctgcaaggcgattaagttgggtaacgccagggtttttcccagtcacgacgttgtaaaacgacg
gccagtgagcgcgcgtaatacgactcactatagggcgaattggagctccaccgcggtggcggccgctctagaactagtggatccccgg
gctgcatgctcgagcggccgccagtgtgatggatatctgcagaattcgcccttcttgatatcttagtgtgcgttaaccaccaccacattggtc
cctgcccgaccgcatagcggccttttcatgcagtagcccctgctcgccaacaatttcgtataccgagatgtggtgagattttgccggcgg
caatcagatacttgccgctgtgatcaacattgaagccgcgcggctgggtttccgttggctggaagccttctttactcaacacgctgccatcttc
cgaaacgctgaaaacggtaatcaggctggcggtacggtcgcaggcgtataatggcgaccatccgggggtgatatgaatatcagccgccc
aacgggtgtcggagaagttttccggcatcatatccagcgtctggacacattcgatattaccgtgcggatctttcagttcccagacatccactga
gctgtttaactcattgacgcaatacgcatattgtcgtttggatggaataccatatgacgcgggccggcccccttcaacggtggtcacttccgca
gggtcctgcgccacgagatgaccatcatcgctgaccgtaaacaggcaaatgcgatcctgctttaatgccggaacccacagcgtacggtgt

FIG. 77B ccggtgagatattggcggaatggcaaccgtccagcccctcgaccacatcgacgacgcccactggcaggccatcttccagacgcgttacgc
tcacgttacccgcattgtaagaacctacaaagacaaactgcccctggtgatcggtggaaatatgcgtcggactaccggcagcgcagactc
tgcggcaaaggtcagtgcgccatcgtccggggcgatacgatacgccaggacgcgaaactcagggcgaacaccaacatagagataacgt
ttgtccgggctgaccaccatcggctgcacctgccccggcacatcgacaacctgtgtcagcgtcagtgcgccttcatgattcagattccagac
gtgaatttgctggctctcagggctggcgatataaactgtttgcttcatgaatgctcctttgggttacctccgggaaacgcggttgatttgtttagtg
gttgaattatttgctcaggatgtggcatagtcaagggcgtgacggctcgctaatacaactcactatagggctcgaggaagttcctatactttcta
gagaataggaacttccgcgccgcacacaaaaaccaacacacagatcatgaaaataaagctcttttattggtaccgaattcgccagggagct
ctcagacgtcgcttggtcggtctttattcgaaccccagagtcccgcttacgccccgccctgccactcatcgcagtactgttgtaattcattaagc
attctgccgacatggaagccatcacaaacggcatgatgaacctgaatcgccagcggcatcagcaccttgtcgccttgcgtataatatttgccc
atggtgaaaacgggggcgaagaagttgtccatattggccacgtttaaatcaaaactggtgaaactcacccaggattggctgagacgaaaa
acatattctaataaacccttagggaaataggccaggttttcaccgtaacacgccacatcttgcgaatatatgtgtagaaactgccggaaatc
gtcgtggtattcactccagagcgatgaaaacgtttcagtttgctcatggaaaacggtgtaacaagggtgaacactatcccatatcaccagctc
accgtctttcattgccatacggaattccggatgagcattcatcaggcgggcaagaatgtgaataaaggccggataaaacttgtgcttattttct
ttacggtctttaaaaaggccgtaatatccagctgaacggtctggttataggtacattgagcaactgactgaaatgcctcaaaatgttctttacgat
gccattgggatatatcaacggtggtatatccagtgatttttttctccatggttagttcctcaccttgtcgtattatactatgccgatatactatgccg
atgattaattgtcaacacgtgctgctgcaggtcgaaaggcccggagatgaggaagaggagaacagcgcggcagacgtgcgcttttgaag
cgtgcagaatgccgggcctccggaggaccttcgggcgcccgccccgccctgagcccgccctgagcccgccccggacccacccctt
cccagcctctgagcccagaaagcgaaggagcaaagctgctattggccgctgccccaaaggcctaccgcttccattgctcagcggtgctg
tccatctgcacgagactagtgagacgtgctacttccatttgtcacgtcctgcacgacgcgagctgcggggcggggggaacttcctgacta
ggggaggagtggaaggtggcgcgaaggggccaccaagaacggagccggttggcgcctaccggtggatgtggaatgtgtgcgaggc
cagaggccacttgtgtagcgccaagtgcccagcggggctgctaaagcgcatgctccagactgccttgggaaaagcgcctcccctacccg
gtagaatgaagttcctatactttctagagaataggaacttcgcggccgcccctttagtgagggttaattcaactgactgtaacagctaaaattagt
cgcttttggcggtaagggcgaattccagcacactggcggccgttactagtggatccgagctcggtaccaagcttgatgcaggaattcgatat
caagcttatcgataccgtcgacctcgaggggggggcccggtacccagcttttgttccctttagtgagggttaattgcgcgcttggcgtaatcatg
gtcatagctgtttcctgtgtgaaattgttatccgctcacaattccacacaacatacgagccggaagcataaagtgtaaagcctggggtgcctaa
tgagtgagctaactcacattaattgcgttgcgctcactgcccgctttccagtcgggaaacctgtcgtgccagctgcattaatgaatcggccaac
gcgcggggagaggcggtttgcgtattgggcgcatgcataaaaactgttgtaattcattaagcattctgccgacatggaagccatcacaaacg
gcatgatgaacctgaatcgccagcggcatcagcaccttgtcgccttgcgtataatatttgcccatggacgcacaccgtggaaacggatgaa
ggcacgaacccagttgacataagcctgttcggttcgtaaactgtaatgcaagtagcgtatgcgctcacgcaactggtccagaaccttgaccg
aacgcagcggtggtaacggcgcagtggcggttttcatggcttgttatgactgtttttttgtacagtctatgcctcgggcatccaagcagcaagc
gcgttacgccgtgggtcgatgtttgatgttatggagcagcaacgatgttacgcagcagcaacgatgttacgcagcagggcagtcgccctaa
aacaaagttaggtggctcaagtatgggcatcattcgcacatgtaggctcggccctgaccaagtcaaatccatgcgggctgctcttgatctttc
ggtcgtgagttcggagacgtagccacctactcccaacatcagccggactccgattacctcgggaacttgctccgtagtaagacattcatcgc
gcttgctgccttcgaccaagaagcggttgttggcgctctcgcggcttacgttctgcccaggtttgagcagccgcgtagtgagatctatatctat
gatctcgcagtctccggcgagcaccggaggcagggcattgccaccgcgctcatcaatctcctcaagcatgaggccaacgcgcttggtgct
tatgtgatctacgtgcaagcagattacggtgacgatcccgcagtggctctctatacaaagttgggcatacgggaagaagtgatgcacttgat
atcgacccaagtaccgccacctaacaattcgttcaagccgagatcggcttcccggccgcgcgagttgttcggtaaattgtcacaacgccgcc
aggtggcacttttcggggaaatgtgcgcgcccgcgttcctgctggcgctggcctgtttctggcgctggacttcccgctgttccgtcagcag
ctttcgcccacggccttgatgatcgcggcggccttggcctgcatatcccgattcaacggccccaggcgtccagaacgggcttcaggcgc
tcccgaaggt (SEQ ID NO:122).

FIG. 79B(1)

5'-
tagaaaaactcatcgagcatcaaatgaaactgcaatttattcatatcaggattatcaataccatattttgaaaaagccgtttctgtaatgaagga
gaaaactcaccgaggcagttccataggatggcaagatcctggtatcggtctgcgattccgactcgtccaacatcaatacaacctattaatttcc
cctcgtcaaaaataaggttatcaagtgagaaatcaccatgagtgacgactgaatccggtgagaatggcaaaagtttatgcatttctttccagac
ttgttcaacaggccagccattacgctcgtcatcaaaatcactcgcatcaaccaaaccgttattcattcgtgattgcgcctgagcgaggcgaaat
acgcgatcgctgttaaaaggacaattacaaacaggaatcgagtgcaaccggcgcaggaacactgccagcgcatcaacaatattttcacctg
aatcaggatattcttctaatacctggaacgctgtttttccggggatcgcagtggtgagtaaccatgcatcatcaggagtacggataaaatgctt
gatggtcggaagtggcataaattccgtcagccagtttagtctgaccatctcatctgtaacatcattggcaacgctacctttgccatgtttcagaa
acaactctggcgcatcgggcttcccatacaagcgatagattgtcgcacctgattgcccgacattatcgcgagcccatttatacccatataaatc
agcatccatgttggaatttaatcgcggcctcgacgtttcccgttgaatatggctcatattcttccttttcaatattattgaagcatttatcagggttat
tgtctcatgagcggatacatatttgaatgtatttagaaaaataaacaaataggggtcagtgttacaaccaattaaccaattctgaacattatcgcg
agcccatttatacctgaatatggctcataacaccccttgtttgcctggcggcagtagcgcggtggtcccacctgacccatgccgaactcaga
agtgaaacgccgtagcgccgatggtagtgtggggactcccccatgcgagagtagggaactgccaggcatcaaataaaacgaaaggctcag
tcgaaagactgggcctttcgcccgggctaattaggggggtgtcgcccttcgattgacggttacgggatcctcacacgtacatcagctggttgat
ggggaacgggtcgatgagcagcagcttgatgcggttctcggtggcgtaatccgggcggcccagcccgtcccatattggtaggtgcagtg
gctcacgcgggccatgttcacggcgatctccatgaacgccttcggcagcagggtgctgtccgacacgcgctcgcggttcattttcttccact
cggcgtcgatcagcttgcgcagctcttcgcgggcctgttcctcgctcgtgccgtcgttctcgtgcatgtagctgatgatgctgttggtggtttcg
ccgcgttcgagttccgccgccgaggtcgccagatcgttgcacagccgaaagatcacgcaggacgagcgcaccaggccgtggaagtcgg
tcagggagcggagggcgtggtccgagatatcttcctgctgctggcagaccgagaagtagctcggcgccagcagcgcgacccccgctgga
ggacacgctggcgttctccaggtacttgctgaaggcggggatgatcttgttattgctccacttggcttcttgcaggaaggccttgcacagttcg
cgccagcttttggtcagatagctcaggttattgtggcccttctccttcaggatggagtaggacgtgtcgttcacggtgttgtacagggccagga
agcacagcttcatatagtcgggcagcgtgttgatggcgttcacgtcccagcgttccaccgcgtcggtgaagagctgcagttcgtccagggta
ccgtacacgtcatagacgtcatcgataatggtgaccagaccgaacatcttggtgacggccttgcggcattcgccgaactgcgggtccggcg
ccatgcccagcgcccagaagtacacttccatcaggcggtcccgcacgaaatccagcttgctggcgaggcccatctcggtccaccaccgg
ctcaggtcctgcagctctttttggtgcagggtctggaccatgttgaaatcgagtttggccagttccagcagcagctggtgatgcggctccttgg
gttcgtacttgtccagaaaccaccgcgcctccaggcggtgcaggcgttgatgatacggcagctccagcgcgtgggacacctgctcggcca
ccttcgtgttgatcccctccttgaggttgttcttcagatgggtgatgctgaaggtacgggcctcctccagcagattttcgccttcgaaaccgaga
tagctggcctcgtacaggctcagcaggccctgcacgtcacccttcagttccccggagaagcccccttctttgtccttgaagcgctcgaacac
gtcctggctcacctcaaagccatgctgccgcagcaggcggaagctcagggcggtcgcgtgcagatcgcttttgttcttcttattctcgtccag
caggacgatgttctccagcgccttgatgatatctttctcaaacttgtaggtcaggcccaggcgctgcacgtcgtcgatgagctccagcaggct
caggggctgggtgtccacccggttgatcatgcaacgcacctcctcctccagcttggtggccttctcttcgagcttctccaccttcaggtcgtttt
ccaggctctgcaggaactcgaagttccacaggttgggctggtagttcgcggaccgacggctattatgctcggtgatctgggtgaactggctg
ctggtggcgcacatatgtatatctccttcttaaagttaaacaagcttaagatgttcagcgacaagggcgacacaaaatttattctaaatgcataat
aaatactgataacatcttatagtttgtattatattttgtattatcgttgacatgtataatttgatatcaaaaactgattttcccttattatttcgagattta
ttttcttaattctctttaacaaactagaaatattgtatatacaaaaaatcataaataatagatgaatagtttaattataggtgttcatcaatcgaaaag
caacgtatcttatttaaagtgcgttgcttttttctcatttataaggttaaataattctcatatatcaagcaaagtgacaggcgcccttaaatattctga
caaatgctctttccctaaactcccccataaaaaaaccgccgaagcgggttttacgttatttgcggattaacgattactcgttatcagaaccg
cccaggggcccgagcttaagactggccgtcgttttacaacacagaaagagtttgtagaaacgcaaaaaggccatccgtcaggggccttct
gcttagtttgatgcctggcagttccctactctcgccttccgcttcctcgctcactgactcgctgcgctcggtcgttcggctgcggcgagcggtat
cagctcactcaaaggcggtaatacggttatccacagaatcaggggataacgcaggaaagaacatgtgagcaaaaggccagcaaaaggc
caggaaccgtaaaaaggccgcgttgctggcgtttttccataggctccgcccccctgacgagcatcacaaaaatcgacgctcaagtcagag
gtggcgaaacccgacaggactataaagataccaggcgtttccccctggaagctccctcgtgcgctctcctgttccgaccctgccgcttaccg
gatacctgtccgcctttctcccttcgggaagcgtggcgctttctcatagctcacgctgtaggtatctcagttcggtgtaggtcgttcgctccaag
ctgggctgtgtgcacgaaccccccgttcagcccgaccgctgcgccttatccggtaactatcgtcttgagtccaacccggtaagacacgactt

FIG. 79B(2)

atcgccactggcagcagccactggtaacaggattagcagagcgaggtatgtaggcggtgctacagagttcttgaagtggtgggctaactac
ggctacactagaagaacagtatttggtatctgcgctctgctgaagccagttaccttcggaaaaagagttggtagctcttgatccggcaaacaa
accaccgctggtagcggtggttttttttgtttgcaagcagcagattacgcgcagaaaaaaaggatctcaagaagatcctttgatcttttctacgg
ggtctgacgctcagtggaacgacgcgcgcgtaactcacgttaagggattttggtcatgagcttgcgccgtcccgtcaagtcagcgtaatgct
ctgcttt (SEQ ID NO:123)

Figure 79C atcgccactggcagcagccactggtaacaggattagcagagcgaggtatgtaggcggtgctacagagttcttgaagtggtgggctaactac
ggctacactagaagaacagtatttggtatctgcgctctgctgaagccagttaccttcggaaaaagagttggtagctcttgatccggcaaacaa
accaccgctggtagcggtggttttttgtttgcaagcagcagattacgcgcagaaaaaaaggatctcaagaagatcctttgatcttttctacgg
ggtctgacgctcagtggaacgacgcgcgcgtaactcacgttaagggattttggtcatgagcttgcgccgtcccgtcaagtcagcgtaatgct
ctgcttt (SEQ ID NO:123)

SEQUENCE LISTING

<160> NUMBER OF SEQ ID NOS: 123

<210> SEQ ID NO 1
<211> LENGTH: 1701
<212> TYPE: DNA
<213> ORGANISM: Artificial Sequence
<220> FEATURE:
<223> OTHER INFORMATION: Synthetic Construct

<400> SEQUENCE: 1
atgtgtgcga cctcttctca atttactcag attaccgagc ataattcccg tcgttccgca    60
aactatcagc aaaacctgtg gaatttcgaa ttcctgcaat ccctggagaa cgacctgaaa   120

```
gtggaaaagc tggaggagaa agcgaccaaa ctggaggaag aagttcgctg catgatcaac      180
cgtgtagaca cccagccgct gtccctgctg gagctgatcg acgatgtgca gcgcctgggt      240
ctgacctaca aatttgaaaa agacatcatt aaagccctgg aaaacatcgt actgctggac      300
gaaaacaaaa gaacaaatc tgacctgcac gcaaccgctc tgtctttccg tctgctgcgt       360
cagcacggtt tcgaggtttc tcaggatgtt tttgagcgtt tcaaggataa agaaggtggt      420
ttcagcggtg aactgaaagg tgacgtccaa ggcctgctga gcctgtatga agcgtcttac      480 ctgggttcg agggtgagaa cctgctggag gaggcgcgta ccttttccat cacccacctg       540
aagaacaacc tgaaagaagg cattaatacc aaggttgcag aacaagtgag ccacgccctg      600
gaactgccat atcaccagcg tctgcaccgt ctggaggcac gttggttcct ggataaatac      660
gaaccgaaag aaccgcatca ccagctgctg ctggagctgg cgaagctgga ttttaacatg      720
gtacagaccc tgcaccagaa agagctgcaa gatctgtccc gctggtggac cgagatgggc      780
ctggctagca aactggattt tgtacgcgac cgcctgatgg aagtttatt ctgggcactg       840 ggtatggcgc cagacccgca gtttggtgaa tgtcgcaaag ctgttactaa aatgtttggt      900
ctggtgacga tcatcgatga cgtgtatgac gtttatggca ctctggacga actgcaactg      960
ttcaccgatg ctgtagagcg ctgggacgtt aacgctatta cacccctgcc ggactatatg     1020
aaactgtgtt tcctggcact gtacaacacc gttaacgaca cgtcctattc tattctgaaa     1080
gagaaaggtc ataacaacct gtcctatctg acgaaaagct ggcgtgaact gtgcaaagcc     1140
tttctgcaag aggcgaaatg gtccaacaac aaaattatcc cggctttctc caagtacctg     1200
gaaaacgcca gcgtttcctc ctccggtgta gcgctgctgg cgccgtctta cttttccgta     1260
tgccagcagc aggaagacat ctccgaccac gcgctgcgtt ccctgaccga cttccatggt     1320
ctggtgcgtt ctagctgcgt tatcttccgc ctgtgcaacg atctggccac ctctgcggcg     1380
gagctggaac gtggcgagac taccaattct atcattagct acatgcacga aaacgatggt     1440
accagcgagg aacaggcccg cgaagaactg cgtaaactga tcgacgccga atggaaaaag     1500
atgaatcgtg aacgcgttag cgactccacc ctgctgccta aagcgttcat ggaaatcgca     1560
gttaacatgg cacgtgtttc ccactgcacc taccagtatg cgatggtct gggtcgccca      1620 gactacgcga ctgaaaaccg catcaaactg ctgctgattg acccttcc gattaaccag        1680 ctgatgtatg tctaactgca g                                                1701

<210> SEQ ID NO 2
<211> LENGTH: 6080
<212> TYPE: DNA
<213> ORGANISM: Artificial Sequence
<220> FEATURE:
<223> OTHER INFORMATION: Synthetic Construct

<400> SEQUENCE: 2
gtttgacagc ttatcatcga ctgcacggtg caccaatgct ctggcgtca ggcagccatc        60 ggaagctgtg gtatggctgt gcaggtcgta aatcactgca taattcgtgt cgctcaaggc      120
gcactcccgt tctggataat gttttttgcg ccgacatcat aacggttctg gcaaatattc      180
tgaaatgagc tgttgacaat taatcatccg gctcgtataa tgtgtggaat tgtgagcgga      240
taacaatttc acacaggaaa cagcgccgct gagaaaaagc gaagcggcac tgctctttaa      300
caatttatca gacaatctgt gtgggcactc gaccggaatt atcgattaac tttattatta     360
aaaattaaag aggtatata taatgtatcg attaaataag gaggaataaa ccatgtgtgc        420
```

-continued

```
gacctcttct caatttactc agattaccga gcataattcc cgtcgttccg caaactatca    480
gccaaacctg tggaatttcg aattcctgca atccctggag aacgacctga agtggaaaa    540
gctggaggag aaagcgacca aactggagga agaagttcgc tgcatgatca accgtgtaga   600
cacccagccg ctgtccctgc tggagctgat cgacgatgtg cagcgcctgg gtctgaccta   660
caaatttgaa aaagacatca ttaaagccct ggaaaacatc gtactgctgg acgaaaacaa   720
aaagaacaaa tctgacctgc acgcaaccgc tctgtctttc cgtctgctgc gtcagcacgg   780
tttcgaggtt tctcaggatg tttttgagcg tttcaaggat aaagaaggtg gtttcagcgg   840
tgaactgaaa ggtgacgtcc aaggcctgct gagcctgtat gaagcgtctt acctgggttt   900
cgagggtgag aacctgctgg aggaggcgcg tacctttccc atcacccacc tgaagaacaa   960
cctgaaagaa ggcattaata ccaaggttgc agaacaagtg agccacgccc tggaactgcc  1020
atatcaccag cgtctgcacc gtctggaggc acgttggttc ctggataaat acgaaccgaa  1080
agaaccgcat caccagctgc tgctggagct ggcgaagctg gattttaaca tggtacagac  1140
cctgcaccag aaagagctgc aagatctgtc ccgctggtgg accgagatgg gcctggctag  1200
caaactggat tttgtacgcg accgcctgat ggaagtttat ttctgggcac tgggtatggc  1260
gccagacccg cagtttggtg aatgtcgcaa agctgttact aaaatgtttg gtctggtgac  1320
gatcatcgat gacgtgtatg acgtttatgg cactctggac gaactgcaac tgttcaccga  1380
tgctgtagag cgctgggacg ttaacgctat taacaccctg ccggactata tgaaactgtg  1440
tttcctggca ctgtacaaca ccgttaacga cacgtcctat tctattctga aagagaaagg  1500
tcataacaac ctgtccctatc tgacgaaaag ctggcgtgaa ctgtgcaaag cctttctgca  1560
agaggcgaaa tggtccaaca acaaaattat cccggctttc tccaagtacc tggaaaacgc  1620
cagcgttttcc tcctccggtg tagcgctgct ggcgccgtct tacttttccg tatgccagca  1680
gcaggaagac atctccgacc acgcgctgcg ttccctgacc gacttccatg gtctggtgcg  1740
ttctagctgc gttatcttcc gcctgtgcaa cgatctggcc acctctgcgg cggagctgga  1800
acgtggcgag actaccaatt ctatcattag ctacatgcac gaaaacgatg gtaccagcga  1860
ggaacaggcc cgcgaagaac tgcgtaaact gatcgacgcc gaatggaaaa agatgaatcg  1920
tgaacgcgtt agcgactcca ccctgctgcc taaagcgttc atggaaatcg cagttaacat  1980
ggcacgtgtt tcccactgca cctaccagta tggcgatggt ctgggtcgcc cagactacgc  2040
gactgaaaac cgcatcaaac tgctgctgat tgacccttttc ccgattaacc agctgatgta  2100
tgtctaactg cagctggtac catatgggaa ttcgaagctt tctagaacaa aaactcatct  2160
cagaagagga tctgaatagc gccgtcgacc atcatcatca tcatcattga gtttaaacgg  2220
tctccagctt ggctgttttg gcggatgaga agattttc agcctgatac agattaaatc  2280
agaacgcaga agcggtctga taaaacagaa tttgcctggc ggcagtagcg cggtggtccc  2340
acctgacccc atgccgaact cagaagtgaa acgccgtagc gccgatggta gtgtgggtc  2400
tccccatgcg agagtaggga actgccaggc atcaaataaa acgaaaggct cagtcgaaag  2460
actgggcctt tcgttttatc tgttgtttgt cggtgaacgc tctcctgagt aggacaaatc  2520
cgccgggagc ggatttgaac gttgcgaagc aacggcccgg agggtggcgg caggacgcc  2580
cgccataaac tgccaggcat caaattaagc agaaggccat cctgacggat ggcctttttg  2640
cgtttctaca aactcttttt gtttattttt ctaaatacat tcaaatatgt atccgctcat  2700
gagacaataa ccctgataaa tgcttcaata atattgaaaa aggaagagta tgagtattca  2760
acatttccgt gtcgccctta ttcccttttt tgcggcattt tgccttcctg tttttgctca  2820
```

```
cccagaaacg ctggtgaaag taaaagatgc tgaagatcag ttgggtgcac gagtgggtta    2880
catcgaactg gatctcaaca gcggtaagat ccttgagagt tttcgccccg aagaacgttt    2940
tccaatgatg agcacttta aagttctgct atgtggcgcg gtattatccc gtgttgacgc    3000
cgggcaagag caactcggtc gccgcataca ctattctcag aatgacttgg ttgagtactc    3060
accagtcaca gaaaagcatc ttacggatgg catgacagta agagaattat gcagtgctgc    3120
cataaccatg agtgataaca ctgcggccaa cttacttctg acaacgatcg gaggaccgaa    3180
ggagctaacc gcttttttgc acaacatggg ggatcatgta actcgccttg atcgttggga    3240
accggagctg aatgaagcca taccaaacga cgagcgtgac accacgatgc ctgtagcaat    3300
ggcaacaacg ttgcgcaaac tattaactgg cgaactactt actctagctt cccggcaaca    3360
attaatagac tggatggagg cggataaagt tgcaggacca cttctgcgct cggcccttcc    3420
ggctggctgg tttattgctg ataaatctgg agccggtgag cgtgggtctc gcggtatcat    3480
tgcagcactg gggccagatg gtaagccctc ccgtatcgta gttatctaca cgacggggag    3540
tcaggcaact atggatgaac gaaatagaca gatcgctgag ataggtgcct cactgattaa    3600
gcattggtaa ctgtcagacc aagtttactc atatatactt tagattgatt taaaacttca    3660
tttttaattt aaaaggatct aggtgaagat cctttttgat aatctcatga ccaaaatccc    3720
ttaacgtgag ttttcgttcc actgagcgtc agaccccgta gaaagatcaa aggatcttc    3780 ttgagatcct ttttttctgc gcgtaatctg ctgcttgcaa acaaaaaaac caccgctacc    3840
agcggtggtt tgtttgccgg atcaagagct accaactctt tttccgaagg taactggctt    3900
cagcagagcg cagataccaa atactgtcct tctagtgtag ccgtagttag gccaccactt    3960
caagaactct gtagcaccgc ctacatacct cgctctgcta atcctgttac cagtggctgc    4020
tgccagtggc gataagtcgt gtcttaccgg gttggactca agacgatagt taccggataa    4080
ggcgcagcgg tcgggctgaa cggggggttc gtgcacacag cccagcttgg agcgaacgac    4140
ctacaccgaa ctgagatacc tacagcgtga gctatgagaa agcgccacgc ttcccgaagg    4200
gagaaaggcg gacaggtatc cggtaagcgg cagggtcgga acaggagagc gcacgaggga    4260
gcttccaggg ggaaacgcct ggtatcttta tagtcctgtc gggtttcgcc acctctgact    4320
tgagcgtcga ttttgtgat gctcgtcagg gggcggagc ctatgaaaa acgccagcaa    4380 cgcggccttt ttacggttcc tggccttttg ctggcctttt gctcacatgt tctttcctgc    4440
gttatcccct gattctgtgg ataaccgtat taccgccttt gagtgagctg ataccgctcg    4500
ccgcagccga acgaccgagc gcagcgagtc agtgagcgag gaagcggaag agcgcctgat    4560
gcggtatttt ctccttacgc atctgtgcgg tatttcacac cgcatatggt gcactctcag    4620
tacaatctgc tctgatgccg catagttaag ccagtataca ctccgctatc gctacgtgac    4680
tgggtcatgg ctgcgccccg acacccgcca cacccgctg acgcgccctg acgggcttgt    4740
ctgctcccgg catccgctta cagacaagct gtgaccgtct ccgggagctg catgtgtcag    4800
aggttttcac cgtcatcacc gaaacgcgcg aggcagcaga tcaattcgcg cgcgaaggcg    4860
aagcggcatg catttacgtt gacaccatcg aatggtgcaa aacctttcgc ggtatggcat    4920
gatagcgccc ggaagagagt caattcaggg tggtgaatgt gaaaccagta acgttatacg    4980
atgtcgcaga gtatgccggt gtctcttatc agaccgtttc ccgcgtggtg aaccaggcca    5040
gccacgtttc tgcgaaaacg cgggaaaaag tggaagcggc gatggcggag ctgaattaca    5100
ttcccaaccg cgtggcacaa caactggcgg gcaaacagtc gttgctgatt ggcgttgcca    5160
```

```
cctccagtct ggccctgcac gcgccgtcgc aaattgtcgc ggcgattaaa tctcgcgccg    5220
atcaactggg tgccagcgtg gtggtgtcga tggtagaacg aagcggcgtc gaagcctgta    5280
aagcggcggt gcacaatctt ctcgcgcaac gcgtcagtgg gctgatcatt aactatccgc    5340
tggatgacca ggatgccatt gctgtggaag ctgcctgcac taatgttccg gcgttatttc    5400
ttgatgtctc tgaccagaca cccatcaaca gtattatttt ctcccatgaa gacggtacgc    5460
gactgggcgt ggagcatctg gtcgcattgg gtcaccagca atcgcgctg ttagcgggcc     5520 cattaagttc tgtctcggcg cgtctgcgtc tggctggctg cataaatat ctcactcgca     5580 atcaaattca gccgatagcg gaacgggaag gcgactggag tgccatgtcc ggttttcaac    5640
aaaccatgca aatgctgaat gagggcatcg ttcccactgc gatgctggtt gccaacgatc    5700
agatggcgct gggcgcaatg cgcgccatta ccgagtccgg gctgcgcgtt ggtgcggata    5760
tctcggtagt gggatacgac gataccgaag acagctcatg ttatatcccg ccgtcaacca    5820
ccatcaaaca ggattttcgc ctgctggggc aaaccagcgt ggaccgcttg ctgcaactct    5880
ctcagggcca ggcggtgaag ggcaatcagc tgttgcccgt ctcactggtg aaagaaaaa     5940 ccaccctggc gcccaatacg caaaccgcct ctccccgcgc gttggccgat tcattaatgc    6000
agctggcaca acaggtttcc cgactggaaa gcgggcagtg agcgcaacgc aattaatgtg    6060
agttagcgcg aattgatctg                                                6080
```

`<210> SEQ ID NO 3`
`<211> LENGTH: 37`
`<212> TYPE: DNA`
`<213> ORGANISM: Artificial Sequence`
`<220> FEATURE:`
`<223> OTHER INFORMATION: Synthetic Construct`

`<400> SEQUENCE: 3`

```
cgtgagatca tatgtgtgcg acctcttctc aatttac                               37
```

`<210> SEQ ID NO 4`
`<211> LENGTH: 38`
`<212> TYPE: DNA`
`<213> ORGANISM: Artificial Sequence`
`<220> FEATURE:`
`<223> OTHER INFORMATION: Synthetic Construct`

`<400> SEQUENCE: 4`

```
cggtcgacgg atccctgcag ttagacatac atcagctg                              38
```

`<210> SEQ ID NO 5`
`<211> LENGTH: 7404`
`<212> TYPE: DNA`
`<213> ORGANISM: Artificial Sequence`
`<220> FEATURE:`
`<223> OTHER INFORMATION: Synthetic Construct`

`<400> SEQUENCE: 5`

```
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccgqtactgc cgggcctctt    180 gcgggatatc cggatatagt tcctcctttc agcaaaaaac ccctcaagac ccgtttagag    240
gccccaaggg gttatgctag ttattgctca gcggtggcag cagccaactc agcttccttt    300
cgggctttgt tagcagccgg atccctgcag ttagacatac atcagctggt taatcgggaa    360
agggtcaatc agcagcagtt tgatgcggtt ttcagtcgcg tagtctgggc gacccagacc    420
```

```
atcgccatac tggtaggtgc agtgggaaac acgtgccatg ttaactgcga tttccatgaa    480
cgctttaggc agcagggtgg agtcgctaac gcgttcacga ttcatctttt tccattcggc    540
gtcgatcagt ttacgcagtt cttcgcgggc ctgttcctcg ctggtaccat cgttttcgtg    600
catgtagcta atgatagaat tggtagtctc gccacgttcc agctccgccg cagaggtggc    660
cagatcgttg cacaggcgga agataacgca gctagaacgc accagaccat ggaagtcggt    720
cagggaacgc agcgcgtggt cggagatgtc ttcctgctgc tggcatacgg aaaagtaaga    780
cggcgccagc agcgctacac cggaggagga aacgctggcg ttttccaggt acttggagaa    840
agccgggata attttgttgt tggaccattt cgcctcttgc agaaaggctt tgcacagttc    900
acgccagctt ttcgtcagat aggacaggtt gttatgacct ttctctttca gaatagaata    960
ggacgtgtcg ttaacggtgt tgtacagtgc caggaaacac agtttcatat agtccggcag   1020
ggtgttaata gcgttaacgt cccagcgctc tacagcatcg gtgaacagtt gcagttcgtc   1080
cagagtgcca taaacgtcat acacgtcatc gatgatcgtc accagaccaa acattttagt   1140
aacagctttg cgacattcac caaactgcgg gtctggcgcc atacccagtg cccagaaata   1200
aacttccatc aggcggtcgc gtacaaaatc cagtttgcta gccaggccca tctcggtcca   1260
ccagcgggac agatcttgca gctctttctg gtgcagggtc tgtaccatgt taaaatccag   1320
cttcgccagc tccagcagca gctggtgatg cggttctttc ggttcgtatt tatccaggaa   1380
ccaacgtgcc tccagacggt gcagacgctg gtgatatggc agttccaggg cgtggctcac   1440
ttgttctgca accttggtat taatgccttc tttcaggttg ttcttcaggt gggtgatgga   1500
aaaggtacgc gcctcctcca gcaggttctc accctcgaaa cccaggtaag acgcttcata   1560
caggctcagc aggccttgga cgtcaccttt cagttcaccg ctgaaaccac cttctttatc   1620
cttgaaacgc tcaaaaacat cctgagaaac ctcgaaaccg tgctgacgca gcagacggaa   1680
agacagagcg gttgcgtgca ggtcagattt gttcttttg ttttcgtcca gcagtacgat   1740
gttttccagg gctttaatga tgtctttttc aaatttgtag gtcagaccca ggcgctgcac   1800
atcgtcgatc agctccagca gggacagcgc ctgggtgtct acacggttga tcatgcagcg   1860
aacttcttcc tccagtttgg tcgctttctc ctccagcttt tccactttca ggtcgttctc   1920
cagggattgc aggaattcga aattccacag gtttggctga tagtttgcgg aacgacggga   1980
attatgctcg gtaatctgag taaattgaga agaggtcgca cacatatgac gaccttcgat   2040
atggccgctg ctgtgatgat gatgatgatg atgatgatga tggcccatgg tatatctcct   2100
tcttaaagtt aaacaaaatt atttctagag gggaattgtt atccgctcac aattccccta   2160
tagtgagtcg tattaatttc gcgggatcga gatctcgatc ctctacgccg gacgcatcgt   2220
ggccggcatc accggcgcca caggtgcggt tgctggcgcc tatatcgccg acatcaccga   2280
tggggaagat cgggctcgcc acttcgggct catgagcgct tgtttcggcg tgggtatggt   2340
ggcaggcccc gtggccgggg gactgttggg cgccatctcc ttgcatgcac cattccttgc   2400
ggcggcggtg ctcaacggcc tcaacctact actgggctgc ttcctaatgc aggagtcgca   2460
taagggagag cgtcgagatc ccggacacca tcgaatggcg caaaaccttt cgcggtatgg   2520
catgatagcg cccggaagag agtcaattca gggtggtgaa tgtgaaacca gtaacgttat   2580
acgatgtcgc agagtatgcc ggtgtctctt atcagaccgt ttcccgcgtg gtgaaccagg   2640
ccagccacgt ttctgcgaaa acgcgggaaa aagtggaagc ggcgatggcg gagctgaatt   2700
acattcccaa ccgcgtggca caacaactgg cgggcaaaca gtcgttgctg attggcgttg   2760
```

```
ccacctccag tctggccctg cacgcgccgt cgcaaattgt cgcggcgatt aaatctcgcg    2820
ccgatcaact gggtgccagc gtggtggtgt cgatggtaga acgaagcggc gtcgaagcct    2880
gtaaagcggc ggtgcacaat cttctcgcgc aacgcgtcag tgggctgatc attaactatc    2940
cgctggatga ccaggatgcc attgctgtgg aagctgcctg cactaatgtt ccggcgttat    3000
ttcttgatgt ctctgaccag acacccatca acagtattat tttctcccat gaagacggta    3060
cgcgactggg cgtggagcat ctggtcgcat gggtcacca gcaaatcgcg ctgttagcgg     3120
gcccattaag ttctgtctcg gcgcgtctgc gtctggctgg ctggcataaa tatctcactc    3180
gcaatcaaat tcagccgata gcggaacggg aaggcgactg gagtgccatg tccggttttc    3240
aacaaaccat gcaaatgctg aatgagggca tcgttcccac tgcgatgctg gttgccaacg    3300
atcagatggc gctgggcgca atgcgcgcca ttaccgagtc cgggctgcgc gttggtgcgg    3360
atatctcggt agtgggatac gacgataccg aagacagctc atgttatatc ccgccgttaa    3420
ccaccatcaa acaggatttt cgcctgctgg ggcaaaccag cgtggaccgc ttgctgcaac    3480
tctctcaggg ccaggcggtg aagggcaatc agctgttgcc cgtctcactg gtgaaaagaa    3540
aaaccaccct ggcgcccaat acgcaaaccg cctctccccg cgcgttggcc gattcattaa    3600
tgcagctggc acgacaggtt tcccgactgg aaagcgggca gtgagcgcaa cgcaattaat    3660
gtaagttagc tcactcatta ggcaccggga tctcgaccga tgcccttgag agccttcaac    3720
ccagtcagct ccttccggtg ggcgcggggc atgactatcg tcgccgcact tatgactgtc    3780
ttctttatca tgcaactcgt aggacaggtg ccggcagcgc tctgggtcat tttcggcgag    3840
gaccgctttc gctggagcgc gacgatgatc ggcctgtcgc ttgcggtatt cggaatcttg    3900
cacgccctcg ctcaagcctt cgtcactggt cccgccacca aacgtttcgg cgagaagcag    3960
gccattatcg ccggcatggc ggccgacgcg ctgggctacg tcttgctggc gttcgcgacg    4020
cgaggctgga tggccttccc cattatgatt cttctcgctt ccggcggcat cgggatgccc    4080
gcgttgcagg ccatgctgtc caggcaggta atgacgacc atcagggaca gcttcaagga    4140
tcgctcgcgg ctcttaccag cctaacttcg atcactggac cgctgatcgt cacggcgatt    4200
tatgccgcct cggcgagcac atggaacggg ttggcatgga ttgtaggcgc cgccctatac    4260
cttgtctgcc tccccgcgtt gcgtcgcggt gcatggagcc gggccacctc gacctgaatg    4320
gaagccggcg gcacctcgct aacggattca ccactccaag aattggagcc aatcaattct    4380
tgcggagaac tgtgaatgcg caaaccaacc cttggcagaa catatccatc gcgtccgcca    4440
tctccagcag ccgcacgcgg cgcatctcgg gcagcgttgg gtcctggcca cgggtgcgca    4500
tgatcgtgct cctgtcgttg aggacccggc taggctggcg gggttgcctt actggttagc    4560
agaatgaatc accgatacgc gagcgaacgt gaagcgactg ctgctgcaaa acgtctgcga    4620
cctgagcaac aacatgaatg gtcttcggtt tccgtgtttc gtaaagtctg gaaacgcgga    4680
agtcagcgcc ctgcaccatt atgttccgga tctgcatcgc aggatgctgc tggctaccct    4740
gtggaacacc tacatctgta ttaacgaagc gctggcattg accctgagtg atttttctct    4800
ggtcccgccg catccatacc gccagttgtt taccctcaca acgttccagt aaccgggcat    4860
gttcatcatc agtaacccgt atcgtgagca tcctctctcg tttcatcggt atcattaccc    4920
ccatgaacag aaatccccct tacacggagg catcagtgac caaacaggaa aaaccgccc    4980
ttaacatggc ccgctttatc agaagccaga cattaacgct tctggagaaa ctcaacgagc    5040
tggacgcgga tgaacaggca gacatctgtg aatcgcttca cgaccacgct gatgagcttt    5100
accgcagctg cctcgcgcgt ttcggtgatg acggtgaaaa cctctgacac atgcagctcc    5160
```

```
cggagacggt cacagcttgt ctgtaagcgg atgccgggag cagacaagcc cgtcagggcg      5220
cgtcagcggg tgttggcggg tgtcggggcg cagccatgac ccagtcacgt agcgatagcg      5280
gagtgtatac tggcttaact atgcggcatc agagcagatt gtactgagag tgcaccatat      5340
atgcggtgtg aaataccgca cagatgcgta aggagaaaat accgcatcag gcgctcttcc      5400
gcttcctcgc tcactgactc gctgcgctcg tcgttcggc tgcggcgagc ggtatcagct       5460
cactcaaagg cggtaatacg gttatccaca gaatcagggg ataacgcagg aaagaacatg      5520
tgagcaaaag gccagcaaaa ggccaggaac cgtaaaaagg ccgcgttgct ggcgttttc      5580 cataggctcc gcccccctga cgagcatcac aaaaatcgac gctcaagtca gaggtggcga     5640
aacccgacag gactataaag ataccaggcg tttccccctg gaagctccct cgtgcgctct     5700
cctgttccga ccctgccgct taccggatac ctgtccgcct ttctcccttc gggaagcgtg     5760
gcgctttctc atagctcacg ctgtaggtat ctcagttcgg tgtaggtcgt tcgctccaag     5820
ctgggctgtg tgcacgaacc ccccgttcag cccgaccgct cgccttatc cggtaactat      5880 cgtcttgagt ccaacccggt aagacacgac ttatcgccac tggcagcagc cactggtaac     5940
aggattagca gagcgaggta tgtaggcggt gctacagagt tcttgaagtg gtggcctaac     6000
tacggctaca ctagaaggac agtatttggt atctgcgctc tgctgaagcc agttaccttc     6060
ggaaaaagag ttggtagctc ttgatccggc aaacaaacca ccgctggtag cggtggtttt     6120
tttgtttgca agcagcagat tacgcgcaga aaaaaggat ctcaagaaga tcctttgatc      6180
ttttctacgg ggtctgacgc tcagtggaac gaaaactcac gttaagggat tttggtcatg     6240
agattatcaa aaaggatctt cacctagatc cttttaaatt aaaaatgaag ttttaaatca     6300
atctaaagta tatatgagta aacttggtct gacagttacc aatgcttaat cagtgaggca     6360
cctatctcag cgatctgtct atttcgttca tccatagttg cctgactccc cgtcgtgtag     6420
ataactacga tacgggaggg cttaccatct ggccccagtg ctgcaatgat accgcgagac     6480
ccacgctcac cggctccaga tttatcagca ataaccagc cagccggaag ggccgagcgc      6540
agaagtggtc ctgcaacttt atccgcctcc atccagtcta ttaattgttg ccgggaagct     6600
agagtaagta gttcgccagt taatagtttg cgcaacgttg ttgccattgc tgcaggcatc     6660
gtggtgtcac gctcgtcgtt tggtatggct tcattcagct ccggttccca acgatcaagg     6720
cgagttacat gatcccccat gttgtgcaaa aaagcggtta gctccttcgg tcctccgatc     6780
gttgtcagaa gtaagttggc cgcagtgtta tcactcatgg ttatggcagc actgcataat     6840
tctcttactg tcatgccatc cgtaagatgc ttttctgtga ctggtgagta ctcaaccaag     6900
tcattctgag aatagtgtat gcggcgaccg agttgctctt gcccggcgtc aacacgggat     6960
aataccgcgc cacatagcag aactttaaaa gtgctcatca ttggaaaacg ttcttcgggg     7020
cgaaaactct caaggatctt accgctgttg agatccagtt cgatgtaacc cactcgtgca     7080
cccaactgat cttcagcatc ttttactttc accagcgttt ctgggtgagc aaaaacagga     7140
aggcaaaatg ccgcaaaaaa gggaataagg gcgacacgga aatgttgaat actcatactc     7200 ttccttttc aatattattg aagcatttat cagggttatt gtctcatgag cggatacata     7260
tttgaatgta tttagaaaaa taaacaaata ggggttccgc gcacatttcc ccgaaaagtg     7320
ccacctgacg tctaagaaac cattattatc atgacattaa cctataaaaa taggcgtatc     7380
acgaggccct ttcgtcttca agaa                                            7404
```

<210> SEQ ID NO 6

```
<211> LENGTH: 41
<212> TYPE: DNA
<213> ORGANISM: Artificial Sequence
<220> FEATURE:
<223> OTHER INFORMATION: Synthetic Construct

<400> SEQUENCE: 6
catatgaaag cttgtatcga ttaaataagg aggaataaac c                          41

<210> SEQ ID NO 7
<211> LENGTH: 6266
<212> TYPE: DNA
<213> ORGANISM: Artificial Sequence
<220> FEATURE:
<223> OTHER INFORMATION: Synthetic Construct

<400> SEQUENCE: 7
cccgtcttac tgtcgggaat tcgcgttggc cgattcatta atgcagctgg cacgacaggt      60
ttcccgactg gaaagcgggc agtgagcgca acgcaattaa tgtgagttag ctcactcatt     120
aggcacccca ggctttacac tttatgcttc cggctcgtat gttgtgtgga attgtgagcg     180
gataacaatt tcacacagga aacagctatg accatgatta cgccaagctt gtatcgatta     240
aataaggagg aataaaccat gtgtgcgacc tcttctcaat ttactcagat taccgagcat     300
aattcccgtc gttccgcaaa ctatcagcca aacctgtgga atttcgaatt cctgcaatcc     360
ctggagaacg acctgaaagt ggaaaagctg gaggagaaag cgaccaaact ggaggaagaa     420
gttcgctgca tgatcaaccg tgtagacacc cagccgctgt ccctgctgga gctgatcgac     480
gatgtgcagc gcctgggtct gacctacaaa tttgaaaaag acatcattaa agccctggaa     540
aacatcgtac tgctggacga aaacaaaaag aacaaatctg acctgcacgc aaccgctctg     600
tctttccgtc tgctgcgtca gcacggtttc gaggtttctc aggatgtttt tgagcgtttc     660
aaggataaag aaggtggttt cagcggtgaa ctgaaaggtg acgtccaagg cctgctgagc     720
ctgtatgaag cgtcttacct gggtttcgag ggtgagaacc tgctgaggga ggcgcgtacc     780
ttttccatca cccacctgaa gaacaacctg aaagaaggca ttaataccaa ggttgcagaa     840
caagtgagcc acgccctgga actgccatat caccagcgtc tgcaccgtct ggaggcacgt     900
tggttcctgg ataaatacga accgaaagaa ccgcatcacc agctgctgct ggagctggcg     960
aagctggatt ttaacatggt acagaccctg caccagaaag agctgcaaga tctgtcccgc    1020
tggtggaccg agatgggcct ggctagcaaa ctggattttg tacgcgaccg cctgatggaa    1080
gtttatttct gggcactggg tatggcgcca gacccgcagt ttggtgaatg tcgcaaagct    1140
gttactaaaa tgtttggtct ggtgacgatc atcgatgacg tgtatgacgt ttatggcact    1200
ctggacgaac tgcaactgtt caccgatgct gtagagcgct gggacgttaa cgctattaac    1260
accctgccgg actatatgaa actgtgtttc ctggcactgt acaacaccgt taacgacacg    1320
tcctattcta ttctgaaaga aaaggtcat aacaacctgt cctatctgac gaaaagctgg    1380
cgtgaactgt gcaaagcctt tctgcaagag gcgaatggt ccaacaacaa aattatcccg    1440
gctttctcca gtacctggaa aacgccagc gttttcctcct ccggtgtagc gctgctggcg    1500
ccgtcttact tttccgtatg ccagcagcag gaagacatct ccgaccacgc gctgcgttcc    1560
ctgaccgact ccatggtct ggtgcgttct agctgcgtta tcttccgcct gtgcaacgat    1620
ctggccacct ctgcggcgga gctggaacgt ggcgagacta ccaattctat cattagctac    1680
atgcacgaaa acgatggtac cagcgaggaa caggcccgcg aagaactgcg taaactgatc    1740
gacgccgaat ggaaaagat gaatcgtgaa cgcgttagcg actccaccct gctgcctaaa    1800
```

```
gcgttcatgg aaatcgcagt taacatggca cgtgtttccc actgcaccta ccagtatggc    1860
gatggtctgg gtcgcccaga ctacgcgact gaaaaccgca tcaaactgct gctgattgac    1920
ccttcccga ttaaccagct gatgtatgtc taactgcagg tcgactctag aggatccccg     1980
ggtaccgagc tcgaattcac tggccgtcgt tttacaacgt cgtgactggg aaaaccctgg    2040
cgttacccaa cttaatcgcc ttgcagcaca tccccctttc gccagctggc gtaatagcga    2100
agaggcccgc accgatcgcc cttcccaaca gttgcgcagc ctgaatggcg aatgcgcct     2160
gatgcggtat tttctcctta cgcatctgtg cggtatttca caccgcatat ggtgcactct    2220
cagtacaatc tgctctgatg ccgcatagtt aagccagccc cgacacccgc caacacccgc    2280
tgacgagctt agtaaagccc tcgctagatt ttaatgcgga tgttgcgatt acttcgccaa    2340
ctattgcgat aacaagaaaa agccagcctt catgatata tctcccaatt tgtgtagggc     2400
ttattatgca cgcttaaaaa taataaaagc agacttgacc tgatagtttg gctgtgagca    2460
attatgtgct tagtgcatct aacgcttgag ttaagccgcg ccgcgaagcg cgtcggctt     2520
gaacgaattg ttagacatta tttgccgact accttggtga tctcgccttt cacgtagtgg    2580
acaaattctt ccaactgatc tgcgcgcgag gccaagcgat cttcttcttg tccaagataa    2640
gcctgtctag cttcaagtat gacgggctga tactgggccg gcaggcgctc cattgcccag    2700
tcggcagcga catccttcgg cgcgattttg ccggttactg cgctgtacca aatgcgggac    2760
aacgtaagca ctacatttcg ctcatcgcca gcccagtcgg gcggcgagtt ccatagcgtt    2820
aaggtttcat ttagcgcctc aaatagatcc tgttcaggaa ccggatcaaa gagttcctcc    2880
gccgctggac ctaccaaggc aacgctatgt tctcttgctt ttgtcagcaa gatagccaga    2940
tcaatgtcga tcgtggctgg ctcgaagata cctgcaagaa tgtcattgcg ctgccattct    3000
ccaaattgca gttcgcgctt agctggataa cgccacggaa tgatgtcgtc gtgcacaaca    3060
atggtgactt ctacgcgcg gagaatctcg ctctctccag gggaagccga agtttccaaa     3120
aggtcgttga tcaaagctcg ccgcgttgtt tcatcaagcc ttacggtcac cgtaaccagc    3180
aaatcaatat cactgtgtgg cttcaggccg ccatccactg cggagccgta caaatgtacg    3240
gccagcaacg tcggttcgag atggcgctcg atgacgccaa ctacctctga tagttgagtc    3300
gatacttcgg cgatcaccgc ttccctcatg atgtttaact ttgttttagg gcgactgccc    3360
tgctgcgtaa catcgttgct gctccataac atcaaacatc gacccacggc gtaacgcgct    3420
tgctgcttgg atgcccgagg catagactgt accccaaaaa aacagtcata acaagccatg    3480
aaaaccgcca ctgcgccgtt accaccgctg cgttcggtca aggttctgga ccagttgcgt    3540
gagcgcatac gctacttgca ttacagctta cgaaccgaac aggcttatgt ccactgggtt    3600
cgtgccttca tccgtttcca cggtgtgcgt cacccgcaa ccttgggcag cagcgaagtc     3660
gaggcatttc tgtcctggct ggcgaacgag cgcaaggttt cggtctccac gcatcgtcag    3720
gcattggcgg ccttgctgtt cttctacggc aaggtgctgt gcacggatct gccctggctt    3780
caggagatcg aagacctcg gccgtcgcgg cgcttgccgg tggtgctgac cccggatgaa     3840
gtggttcgca tcctcggttt tctggaaggc gagcatcgtt tgttcgccca gcttctgtat    3900
ggaacgggca tgcggatcag tgagggtttg caactgcggg tcaaggatct ggatttcgat    3960
cacggcacga tcatcgtgcg ggagggcaag ggctccaagg atcgggcctt gatgttaccc    4020
gagagcttgg cacccagcct gcgcgagcag gggaattaat ccccacgggt tttgctgccc    4080
gcaaacgggc tgttctggtg ttgctagttt gttatcagaa tcgcagatcc ggcttcagcc    4140
```

```
ggtttgccgg ctgaaagcgc tatttcttcc agaattgcca tgattttttc cccacgggag    4200
gcgtcactgg ctcccgtgtt gtcggcagct ttgattcgat aagcagcatc gcctgtttca    4260
ggctgtctat gtgtgactgt tgagctgtaa caagttgtct caggtgttca atttcatgtt    4320
ctagttgctt tgttttactg gtttcacctg ttctattagg tgttacatgc tgttcatctg    4380
ttacattgtc gatctgttca tggtgaacag ctttgaatgc accaaaaact cgtaaaagct    4440
ctgatgtatc tatcttttt acaccgtttt catctgtgca tatggacagt tttccctttg     4500
atatgtaacg gtgaacagtt gttctacttt tgtttgttag tcttgatgct tcactgatag    4560
atacaagagc cataagaacc tcagatcctt ccgtatttag ccagtatgtt ctctagtgtg    4620
gttcgttgtt tttgcgtgag ccatgagaac gaaccattga gatcatactt actttgcatg    4680
tcactcaaaa attttgcctc aaaactggtg agctgaattt ttgcagttaa agcatcgtgt    4740 agtgttttc ttagtccgtt atgtaggtag gaatctgatg taatggttgt tggtattttg     4800
tcaccattca tttttatctg gttgttctca agttcggtta cgagatccat ttgtctatct    4860
agttcaactt ggaaaatcaa cgtatcagtc gggcggcctc gcttatcaac caccaatttc    4920
atattgctgt aagtgtttaa atctttactt attggtttca aaaccattg gttaagcctt      4980 ttaaactcat ggtagttatt ttcaagcatt aacatgaact taaattcatc aaggctaatc    5040
tctatatttg ccttgtgagt tttcttttgt gttagttctt ttaataacca ctcataaatc    5100
ctcatagagt atttgttttc aaaagactta acatgttcca gattatattt tatgaatttt    5160
tttaactgga aaagataagg caatatctct tcactaaaaa ctaattctaa tttttcgctt    5220
gagaacttgg catagtttgt ccactggaaa atctcaaagc ctttaaccaa aggattcctg    5280
atttccacag ttctcgtcat cagctctctg gttgctttag ctaatacacc ataagcattt    5340
tccctactga tgttcatcat ctgagcgtat tggttataag tgaacgatac cgtccgttct    5400
ttccttgtag ggttttcaat cgtgggggttg agtagtgcca cacagcataa aattagcttg    5460
gtttcatgct ccgttaagtc atagcgacta atcgctagtt catttgcttt gaaaacaact    5520
aattcagaca tacatctcaa ttggtctagg tgattttaat cactatacca attgagatgg    5580
gctagtcaat gataattact agtccttttc ctttgagttg tgggtatctg taaattctgc    5640
tagacctttg ctggaaaact tgtaaattct gctagaccct ctgtaaattc cgctagacct    5700
ttgtgtgttt tttttgttta tattcaagtg gttataattt atagaataaa gaaagaataa    5760
aaaaagataa aaagaataga tcccagccct gtgtataact cactacttta gtcagttccg    5820
cagtattaca aaaggatgtc gcaaacgctg tttgctcctc tacaaaacag accttaaaac    5880
cctaaaggct taagtagcac cctcgcaagc tcgggcaaat cgctgaatat tccttttgtc    5940
tccgaccatc aggcacctga gtcgctgtct ttttcgtgac attcagttcg ctgcgctcac    6000
ggctctggca gtgaatgggg gtaaatggca ctacaggcgc cttttatgga ttcatgcaag    6060
gaaactaccc ataatacaag aaaagcccgt cacgggcttc tcagggcgtt ttatggcggg    6120
tctgctatgt ggtgctatct gacttttgc tgttcagcag ttcctgccct ctgatttcc     6180 agtctgacca cttcggatta tcccgtgaca ggtcattcag actggctaat gcacccagta    6240
aggcagcggt atcatcaaca ggctta                                         6266
```

<210> SEQ ID NO 8
<211> LENGTH: 1695
<212> TYPE: DNA
<213> ORGANISM: Artificial Sequence
<220> FEATURE:
<223> OTHER INFORMATION: Synthetic Construct

<400> SEQUENCE: 8

```
atgtgtgcaa cctcctccca gtttactcag attaccgagc ataattctcg acgatctgct      60
aactaccagc cgaacctttg gaactttgag tttctccagt ctctcgaaaa tgacctgaag     120
gtggaaaagc tcgaggagaa ggcgaccaaa ctcgaggagg aggtgcgatg tatgatcaac     180
agagttgaca cccaacccct gtctttgctg gagctgatcg acgatgtgca gcggttgggt     240
ttgacttata aattcgagaa ggacattatc aaggcactgg agaacattgt gctcctcgac     300
gagaacaaga gaacaagtc tgatcttcac gctaccgctc tctctttccg acttcttcga      360
caacacggct tcgaggtgtc gcaggacgtc ttcgagagat ttaaggacaa ggagggagga     420
tttagcggcg agctgaaggg agacgttcag ggtcttctct ccttgtacga ggcgtcctac     480
ctgggattcg agggagagaa cctcctggag gaagctcgta cattttccat cactcacctt     540
aagaataacc ttaaggaggg aattaacacc aaggtggccg agcaggtttc tcacgccctg     600
gagctcccct accaccaacg gctccataga ctggaggctc gttggttcct ggacaaatat     660
gagccaaagg agcctcatca tcagttgctg ttggagttgg ccaagctgga cttcaatatg     720
gttcagacgc tgcaccaaaa ggagttgcag gacctgtctc gatggtggac cgagatggga     780
ttggcctcga agctggattt tgtccgtgac cgacttatgg aggtctattt ttgggccctt     840
ggaatggcgc ctgaccccca gttcggagag tgccggaagg cggtgacgaa gatgttcggt     900
cttgtgacta tcatcgacga cgtctacgat gtctacggca cactcgacga gttgcagctg     960
ttcactgacg ccgtcgagcg atgggatgtg aacgccatta atactctccc tgactatatg    1020
aagctgtgct tcctggctct gtacaacact gtcaacgata cctcgtactc tatcctcaag    1080
gagaagggac acaacaatct ctcctacttg accaaatcct ggcgagaact gtgcaaggct    1140
tttctgcagg aggctaaatg gtccaataac aagatcattc ctgcttttc taaatacctg     1200
gaaaatgcct cggtgtcgag ctctggcgtc gcccttctgg ccccttccta cttctccgtc    1260
tgccagcagc aggaggatat ttccgatcat gctcttagat cgctgaccga ttttcacggc    1320
ctcgtgcgat cttcctgcgt gatttttcgg ttgtgtaatg accttgcgac ctctgctgct    1380
gagctggaac gaggcgagac tacaaattcc attatttctt acatgcacga aaacgatgga    1440
acatctgaag aacaggctag agaggaactg cgaaagttga tcgacgccga gtggaagaag    1500
atgaacagag agcgggtgtc cgactctacc ctgcttccca aggccttcat ggagatcgcc    1560
gtgaacatgg ctcgagtttc ccattgtact taccagtacg gtgacggcct gggtcgtccg    1620
gactacgcta cagagaaccg aatcaagctg ctgctcatcg accccttccc tatcaaccaa    1680
ttgatgtacg tgtaa                                                      1695
```

<210> SEQ ID NO 9
<211> LENGTH: 40
<212> TYPE: DNA
<213> ORGANISM: Artificial Sequence
<220> FEATURE:
<223> OTHER INFORMATION: Synthetic Construct

<400> SEQUENCE: 9

```
gcttatggat cctctagact attacacgta catcaattgg                            40
```

<210> SEQ ID NO 10
<211> LENGTH: 30
<212> TYPE: DNA
<213> ORGANISM: Artificial Sequence
<220> FEATURE:

<223> OTHER INFORMATION: Synthetic Construct

<400> SEQUENCE: 10
caccatgtgt gcaacctcct cccagtttac                                        30

<210> SEQ ID NO 11
<211> LENGTH: 8191
<212> TYPE: DNA
<213> ORGANISM: Artificial Sequence
<220> FEATURE:
<223> OTHER INFORMATION: Synthetic Construct

<400> SEQUENCE: 11

| | | | | | |
|---|---|---|---|---|---|
| tcgaccggtg | agaagaacag | catcgggaca | agggaaggaa | gaacaaagac | aaagaaaaca | 60 |
| aaagaaagca | attgaaaaca | aaacaaaaca | attttcattc | cttctcttat | cattcctttt | 120 |
| cttttctttt | ctctcattca | acgcactcca | tcgtatccgt | attcctctta | ttttttctct | 180 |
| ttctctatat | ccatttcttt | ctctctaggt | gtgtcctctc | tctctcttca | atttctctac | 240 |
| tccgcattcc | aacgcatcct | tcccccaacc | tcccatttcc | tccttacggc | ccgatagcga | 300 |
| tcgtctttcc | ctcgctatca | ctcgctaccg | gcccctcctc | tgcaccgtaa | cctcctacgt | 360 |
| atttaccata | tcataaagtt | ttttccgacg | cttatcgctg | acccctgtc | gccctcctat | 420 |
| tggcttccgg | attatcttct | tgtccataag | gtgatccatg | cttcctgaag | attcccgaaa | 480 |
| tgtgtccact | ttggcgggga | atcattccat | ccacttcttt | ctctctcgct | ttcctcattc | 540 |
| ggcgctcccc | ttccgcgtct | cattggtctt | ccgctccgtt | tttgctttgc | cgatgttact | 600 |
| tggggagagg | tgcgataatc | ctttcgcaaa | aactcggttt | gacgcctccc | atggtataaa | 660 |
| tagtgggtgg | tggacaggtg | ccttcgcttt | tctttaagca | agagaatccc | attgtcttga | 720 |
| ctatcacgaa | ttcacataca | ttatgaagat | caccgctgtc | attgcccttt | tattctcact | 780 |
| tgctgctgcc | tcacctattc | cagttgccga | tcctggtgtg | gtttcagtta | gcaagtcata | 840 |
| tgctgatttc | cttcgtgttt | accaaagttg | gaacactttt | gctaatcctg | atagacccaa | 900 |
| ccttaagaag | agaaatgata | cacctgcaag | tggatatcaa | gttgaaaaag | tcgtaatttt | 960 |
| gtcacgtcac | ggtgttaggg | cccctacaaa | aatgactcaa | accatgcgtg | atgtcactcc | 1020 |
| taatacatgg | ccagaatggc | ccgttaaatt | aggatatatt | acaccaagag | gtgaacactt | 1080 |
| gatatcactt | atgggcggtt | tttaccgtca | aaaattccag | caacaaggaa | tcctttctca | 1140 |
| gggctcctgt | cctactccta | actccatata | tgtctgggct | gacgtcgatc | agcgtacttt | 1200 |
| aaaaactggt | gaagcattcc | ttgctggttt | ggcaccacaa | tgtggcttga | caattcatca | 1260 |
| ccaacaaaat | cttgagaaag | ctgatcctct | ttttcatccc | gttaaagctg | gaacctgctc | 1320 |
| tatggataaa | actcaagttc | aacaagctgt | tgagaaggag | gcacaaactc | ctatagataa | 1380 |
| tttgaatcaa | cattacatcc | ccttttttagc | tttaatgaat | acaacattaa | attttagtac | 1440 |
| ttctgcctgg | tgccaaaaac | actctgctga | taaatcctgt | gacctaggtt | tatccatgcc | 1500 |
| ttctaaattg | tccataaaag | ataatggtaa | caaggtcgca | ttggatggag | ctattggtct | 1560 |
| atcctctact | ttggccgaga | ttttttcttct | tgaatatgct | caaggcatgc | ctcaagctgc | 1620 |
| ttggggtaac | atccactcag | agcaagagtg | ggcttccttg | ctaaagttgc | ataatgttca | 1680 |
| attcgatttg | atgcccgaa | caccttatat | tgctcgacat | aacggtactc | ctttattgca | 1740 |
| agctatatca | aatgcccctta | atcccaacgc | cactgaatca | aaacttccag | atatttcacc | 1800 |
| tgataacaaa | atattgttca | ttgcaggtca | tgacacaaat | attgctaata | tagccggcat | 1860 |
| gttaaatatg | cgttggacat | taccaggtca | accagataat | actcctccag | gtggtgccct | 1920 |

```
agtatttgaa cgtcttgctg ataaaagtgg aaaacaatat gtttctgtat ctatggttta   1980
tcaaacacta gaacaacttc gatcacagac tccccttttct ctaaatcagc ctgccggatc   2040
tgttcaactt aaaattccag gttgcaatga tcaaacagcc gagggttact gtcctctttc   2100
cacttttaca agagttgttt cccaatctgt tgaacctgga tgccaacttc aataatgagg   2160
atccaagtaa gggaatgaga atgtgatcca cttttaattc ctaatgaata catgcctata   2220
gttcttttct tttgttcttt atgtcgtttt tcgatggtac ggccgttgtc aatctcagtt   2280
tgtgtgcttg gttgcagctt ggtttcaaat ctgttcatct catgaatctt ttaccatttc   2340
accacacgtt tataccattc tctcatagaa tcttcatcaa accatctcgg ggttagagtg   2400
gaaagaaagt cttgttcttt tatttccttt tttccatctt caaggctttt cttttcttcc   2460
tcctcctcgt tcatcttgag gtttgacgtg tctgtttaga attttgagct gttgcagcat   2520
cttatttttt gttttgcgaa aacgaagcgc tttactctct tcatcagttg gacgattgta   2580
cctttgaaaa ccaactactt ttgcatgttt tgtatagaaa tcaatgatat tagaatccca   2640
tcctttaatt tctttcaaag tagttgagct atagttaagt gtaagggccc tactgcgaaa   2700
gcatttgcca aggatgtttt cattaatcaa gaacgaaagt tagggatcg aagacgatca   2760
gataccgtcg tagtcttaac cataaactat gccgactagg gatcgggcaa tgtttcattt   2820
atcgacttgc tcggcacctt acgagaaatc aaagtctttg ggttccgggg ggagtatggt   2880
cgcaaggctg aaacttaaag gaattgacgg aagggcacca caatggagtg gagcctgcgg   2940
cttaatttga ctcaacacgg ggaaactcac caggtccaga catagtaagg attgacagat   3000
tgagagctct ttcttgattc tatgggtggt ggtgcatggc cgttcttagt tggtggagtg   3060
atttgtctgc ttaattgcga taacgaacga gaccttaacc tgctaaatag ctggatcagc   3120
cattttggct gatcattagc ttcttagagg gactattggc ataaagccaa tggaagtttg   3180
aggcaataac aggtctgtga tgcccttaga tgttctgggc cgcacgcgcg ctacactgac   3240
ggagccaacg agttgaaaaa atcttttga tttttttatcc ttggccggaa ggtctgggta   3300
atcttgttaa actccgtcgt gctggggata gagcattgca attattgcgg ccgctcctca   3360
attcgatgtt gcagatttta caagttttta aaatgtattt cattattact ttttatatgc   3420
ctaataaaaa agccatagtt taatctatag ataacttttt ttccagtgca ctaacggacg   3480
ttacattccc atacaaaact gcgtagttaa agctaaggaa aagttaatat catgttaatt   3540
aaatacgcta tttacaataa gacattgaac tcatttatat cgttgaatat gaataaccaa   3600
tttcagcgaa ttttttaacaa acatcgttca cctcgtttaa ggatatcttg tgtatggggt   3660
gttgacttgc tttatcgaat aattaccgta cctgtaattg gcttgctgga tatagcggta   3720
gtctaatatc tagcaaaaat cttttgggtg aaaaggcttg caatttcacg acaccgaact   3780
atttgtcatt ttttaataag gaagttttcc ataaattcct gtaattctcg gttgatctaa   3840
ttgaaaagag tagttttgca tcacgatgag gagggctttt gtagaaagaa atacgaacga   3900
aacgaaaatc agcgttgcca tcgctttgga caaagctccc ttacctgaag agtcgaattt   3960
tattgatgaa cttataactt ccaagcatgc aaaccaaaag ggagaacaag taatccaagt   4020
agacacggga attggattct tggatcacat gtatcatgca ctggctaaac atgcaggctg   4080
gagcttacga ctttactcaa gaggtgattt aatcatcgat gatcatcaca ctgcagaaga   4140
tactgctatt gcacttggta ttgcattcaa gcaggctatg ggtaactttg ccggcgttaa   4200
aagatttgga catgcttatt gtccacttga cgaagctctt tctagaagcg tagttgactt   4260
```

```
gtcgggacgg ccctatgctg ttatcgattt gggattaaag cgtgaaaagg ttggggaatt    4320
gtcctgtgaa atgatccctc acttactata ttccttttcg gtagcagctg gaattacttt    4380
gcatgttacc tgcttatatg gtagtaatga ccatcatcgt gctgaaagcg cttttaaatc    4440
tctggctgtt gccatgcgcg cggctactag tcttactgga agttctgaag tcccaagcac    4500
gaagggagtg ttgtaaagat gaattggatt atgtcaggaa aagaacgaca attttgcatc    4560
caaattgtct aaattttaga gttgcttgaa acaatagaa ccttacttgc tttataatta    4620
cgttaattag aagcgttatc tcgtgaagga atatagtacg tagccgtata aattgaattg    4680
aatgttcagc ttatagaata gagacacttt gctgttcaat gcgtcgtcac ttaccatact    4740
cactttatta tacgacttta agtataaact ccgcggttat ggtaaaatta atgatgcaca    4800
aacgtccgat tccatatggg tacactacaa ttaaatactt ttaagctgat cccccacaca    4860
ccatagcttc aaaatgtttc tactcctttt ttactcttcc agattttctc ggactccgcg    4920
catcgccgta ccacttcaaa acacccaagc acagcatact aaattttccc tctttcttcc    4980
tctagggtgt cgttaattac ccgtactaaa ggtttggaaa agaaaaaga gaccgcctcg    5040 tttcttttc ttcgtcgaaa aaggcaataa aaatttttat cacgtttctt tttcttgaaa    5100
tttttttttt tagttttttt ctctttcagt gacctccatt gatatttaag ttaataaacg    5160
gtcttcaatt tctcaagttt cagtttcatt tttcttgttc tattacaact ttttttactt    5220
cttgttcatt agaaagaaag catagcaatc taatctaagg gcggtgttga caattaatca    5280
tcggcatagt atatcggcat agtataatac gacaaggtga ggaactaaac catggccaag    5340
ttgaccagtg ccgttccggt gctcaccgcg cgcgacgtcg ccgagcggt cgagttctgg    5400 accgaccggc tcgggttctc ccgggacttc gtggaggacg acttcgccgg tgtggtccgg    5460
gacgacgtga ccctgttcat cagcgcggtc caggaccagg tggtgccgga caacaccctg    5520
gcctgggtgt gggtgcgcgg cctggacgag ctgtacgccg agtggtcgga ggtcgtgtcc    5580
acgaacttcc gggacgcctc cgggccggcc atgaccgaga tcggcgagca gccgtggggg    5640
cgggagttcg ccctgcgcga cccggccggc aactgcgtgc acttcgtggc cgaggagcag    5700
gactgacacg tccgacggcg gcccacgggt cccaggcctc ggagatccgt ccccctttc    5760 ctttgtcgat atcatgtaat tagttatgtc acgcttacat tcacgccctc cccccacatc    5820
cgctctaacc gaaaaggaag gagttagaca acctgaagtc taggtcccta tttattttt    5880 tatagttatg ttagtattaa gaacgttatt tatatttcaa attttttcttt tttttctgta    5940 cagacgcgag cttcccagta aatgtgccat ctcgtaggca gaaacggtt cccccgtagg    6000 gtctctctct tggcctcctt tctaggtcgg gctgattgct cttgaagctc tctagggggg    6060
ctcacaccat aggcagataa cgttccccac cggctcgcct cgtaagcgca caaggactgc    6120
tcccaaagat cctaggcggg attttgccga tttcggccta aggaaccgg aacacgtaga    6180 aagccagtcc gcagaaacgg tgctgacccc ggatgaatgt cagctactgg gctatctgga    6240
caagggaaaa cgcaagcgca aagagaaagc aggtagcttg cagtgggctt acatggcgat    6300
agctagactg ggcggtttta tggacagcaa gcgaaccgga attgccagct ggggcgccct    6360
ctggtaaggt tgggaagccc tgcaaagtaa actggatggc tttcttgccg ccaaggatct    6420
gatggcgcag gggatcaaga tctgatcaag agacaggatg aggatcgttt cgcatgattg    6480
aacaagatgg attgcacgca ggttctccgg ccgcttgggt ggagaggcta ttcggctatg    6540
actgggcaca acagacaatc ggctgctctg atgccgccgt gttccggctg tcagcgcagg    6600
ggcgcccggt tctttttgtc aagaccgacc tgtccggtgc cctgaatgaa ctgcaggacg    6660
```

```
aggcagcgcg gctatcgtgg ctggccacga cgggcgttcc ttgcgcagct gtgctcgacg   6720
ttgtcactga agcgggaagg gactggctgc tattgggcga agtgccgggg caggatctcc   6780
tgtcatctcg ccttgctcct gccgagaaag tatccatcat ggctgatgca atgcggcggc   6840
tgcatacgct tgatccggct acctgccccat tcgaccacca agcgaaacat cgcatcgagc   6900
gagcacgtac tcggatggaa gccggtcttg tcgatcagga tgatctggac gaagagcatc   6960
aggggctcgc gccagccgaa ctgttcgcca ggctcaaggc gcgcatgccc gacggcgagg   7020
atctcgtcgt gatccatggc gatgcctgct tgccgaatat catggtggaa aatggccgct   7080
tttctggatt caacgactgt ggccggctgg gtgtggcgga ccgctatcag gacatagcgt   7140
tggatacccg tgatattgct gaagagcttg gcggcgaatg ggctgaccgc ttcctcgtgc   7200
tttacggtat cgccgctccc gattcgcagc gcatcgcctt ctatcgcctt cttgacgagt   7260
tcttctgaat tgaaaaaggt accaagttta ctcatatata ctttagattg atttaaaact   7320 tcattttttaa tttaaaagga tctaggtgaa gatccttttt gataatctca tgaccaaaat   7380
cccttaacgt gagttttcgt tccactgagc gtcagacccc gtagaaaaga tcaaaggatc   7440
ttcttgagat cctttttttc tgcgcgtaat ctgctgcttg caaacaaaaa aaccaccgct   7500
accagcggtg gtttgtttgc cggatcaaga gctaccaact ctttttccga aggtaactgg   7560
cttcagcaga gcgcagatac caaatactgt ccttctagtg tagccgtagt taggccacca   7620
cttcaagaac tctgtagcac cgcctacata cctcgctctg ctaatcctgt taccagtggc   7680
tgctgccagt ggcgataagt cgtgtcttac cgggttggac tcaagacgat agttaccgga   7740
taaggcgcag cggtcgggct gaacggggggg ttcgtgcaca cagcccagct tggagcgaac   7800
gacctacacc gaactgagat acctacagcg tgagcattga aaagcgcca cgcttcccga   7860 agggagaaag gcggacaggt atccggtaag cggcagggtc ggaacaggag agcgcacgag   7920
ggagcttcca gggggaaacg cctggtatct ttatagtcct gtcgggtttc gccacctctg   7980
acttgagcgt cgatttttgt gatgctcgtc aggggggcgg agcctatgga aaaacgccag   8040
caacgcggcc ttttttacggt tcctggcctt ttgctggcct tttgctcaca tgttctttcc   8100
tgcgttatcc cctgattctg tggataaccg tattaccgcc tttgagtgag ctgataccgc   8160
tcgccgcagc cgaacgaccg agcgcagcga g                                  8191
```

<210> SEQ ID NO 12
<211> LENGTH: 1724
<212> TYPE: DNA
<213> ORGANISM: Artificial Sequence
<220> FEATURE:
<223> OTHER INFORMATION: Synthetic Construct

<400> SEQUENCE: 12

```
gaattcaaaa caaaatgtgt gcaacctcct cccagtttac tcagattacc gagcataatt    60
ctcgacgatc tgctaactac cagccgaacc tttggaactt tgagtttctc cagtctctcg   120
aaaatgacct gaaggtggaa aagctcgagg agaaggcgac caaactcgag gaggaggtgc   180
gatgtatgat caacagagtt gacacccaac ccctgtcttt gctggagctg atcgacgatg   240
tgcagcggtt gggtttgact tataaattcg agaaggacat tatcaaggca ctggagaaca   300
ttgtgctcct cgacgagaac aagaagaaca agtctgatct tcacgctacc gctctctctt   360
tccgacttct tcgacaacac ggcttcgagg tgtcgcagga cgtcttcgag agatttaagg   420
acaaggaggg aggatttagc ggcgagctga agggagacgt tcagggtctt ctctccttgt   480
```

```
acgaggcgtc ctacctggga ttcgagggag agaacctcct ggaggaagct cgtacatttt      540
ccatcactca ccttaagaat aaccttaagg agggaattaa caccaaggtg gccgagcagg      600
tttctcacgc cctggagctc ccctaccacc aacggctcca tagactggag gctcgttggt      660
tcctggacaa atatgagcca aaggagcctc atcatcagtt gctgttggag ttggccaagc      720
tggacttcaa tatggttcag acgctgcacc aaaaggagtt gcaggacctg tctcgatggt      780
ggaccgagat gggattggcc tcgaagctgg attttgtccg tgaccgactt atggaggtct      840
attttggggc ccttggaatg cgcctgacc cccagttcgg agagtgccgg aaggcggtga      900
cgaagatgtt cggtcttgtg actatcatcg acgacgtcta cgatgtctac ggcacactcg      960
acgagttgca gctgttcact gacgccgtcg agcgatggga tgtgaacgcc attaatactc     1020
tccctgacta tatgaagctg tgcttcctgg ctctgtacaa cactgtcaac gatacctcgt     1080
actctatcct caaggagaag ggacacaaca atctctccta cttgaccaaa tcctggcgag     1140
aactgtgcaa ggcttttctg caggaggcta aatggtccaa taacaagatc attcctgctt     1200 tttctaaaata cctggaaaat gcctcggtgt cgagctctgg cgtcgccctt ctggcccctt     1260
cctacttctc cgtctgccag cagcaggagg atatttccga tcatgctctt agatcgctga     1320
ccgattttca cggcctcgtg cgatcttcct gcgtgatttt tcggttgtgt aatgaccttg     1380
cgacctctgc tgctgagctg aacgaggcg agactacaaa ttccattatt tcttacatgc     1440
acgaaaacga tggaacatct gaagaacagg ctagagagga actgcgaaag ttgatcgacg     1500
ccgagtggaa gaagatgaac agagagcggg tgtccgactc taccctgctt cccaaggcct     1560
tcatggagat cgccgtgaac atggctcgag tttcccattg tacttaccag tacggtgacg     1620
gcctgggtcg tccggactac gctacagaga accgaatcaa gctgctgctc atcgaccct     1680 tccctatcaa ccaattgatg tacgtgtaat agtctagagg atcc                     1724
```

<210> SEQ ID NO 13
<211> LENGTH: 1701
<212> TYPE: DNA
<213> ORGANISM: Artificial Sequence
<220> FEATURE:
<223> OTHER INFORMATION: Synthetic Construct

<400> SEQUENCE: 13

```
gaattcaaca aaaatgtgct ctgttttccac tgagaacgtg tcctttactg agactgagac       60
tgaagcacgt agaagcgcca actacgaacc caactcctgg gattatgact ttctgctgtc      120
ttctgacacc gacgagtcga tcgaggttta aaggataag gccaagaaac ttgaggccga      180
ggtcagacga gagattaaca acgagaaggc cgagttcctg acccttcttg agctgatcga      240
caacgttcaa cgacttggtc ttggttaccg tttcgaatcc gatatccgac gtgcattgga      300
tcgatttgtc tcgtccggag gtttcgatgg tgtgactaag acgtcgctgc acgccacagc      360
tctttccttc agactgttgc ggcagcatgg atttgaggtt tcccaggaag ccttttctgg      420
tttcaaggat cagaacggaa acttttttgga gaatctcaag gaggacacca aggccatcct      480
gtcgttgtat gaggcctcgt tcctggctct tgagggcgag aatattctgg atgaggctcg      540
ggttttcgct atttcgcacc tgaaggagtt gtcggaggaa aagatcggaa aggaactggc      600
cgagcaggtc aaccatgcac ttgaacttcc cctgcatcga cgtacccagc gactggaggc      660
cgtgtggagc atcgaggcgt acagaaaaaa ggaggatgct aatcaggttc tgctcgaact      720
cgctatcctc gactataaca tgattcagag cgtgtaccag cgtgacttgc gagagacaag      780
ccggtggtgg cgacgggtgg gactggccac gaagctccac tttgctaaag atcgattgat      840
```

```
tgagtcgttc tactgggcag tgggtgtggc ctttgagcct cagtactccg actgccgaaa    900
ctccgttgca aagatgtttt cttttgtcac tatcatcgac gacatctacg atgtttacgg    960
cactctcgat gaactcgaac tcttcacgga cgctgtcgag cgatgggatg tgaatgccat   1020
taatgatctg ccagattata tgaagttgtg tttcttggcg ctctacaaca caattaatga   1080
aattgcctac gacaacctca aggacaaggg agagaacatt ctgccctacc ttactaaagc   1140
ctgggccgac ctgtgtaacg ccttttttgca ggaagccaag tggctctata acaaatctac   1200
tcctacattt gatgactact cggcaacgc ttggaagtct ccagcggcc ctctccagtt   1260 gatcttcgct tactttgcag tggtccagaa catcaagaaa gaggagattg agaacctcca   1320
gaagtatcac gacatcatct cccgaccttc gcacatcttt cgactgtgca atgaccttgc   1380
ctccgcatcc gctgagattg cccgaggaga aacagccaat tctgtgtcgt gttacatgcg   1440
tacaaagggc atctccgagg agctggctac cgagtctgtg atgaacctga tcgatgaaac   1500
ctgtaagaag atgaacaaag agaaactggg cggttctctg ttcgccaaac catttgttga   1560
aaccgcgatc aatctggctc gtcagtctca ttgtacttac cataacggtg acgcgcacac   1620
ttcgccggac gaattgaccc gtaagcgtgt gctttcggtg attaccgagc cgatcctgcc   1680
gttcgaaaga taataggatc c                                              1701

<210> SEQ ID NO 14
<211> LENGTH: 28
<212> TYPE: DNA
<213> ORGANISM: Artificial Sequence
<220> FEATURE:
<223> OTHER INFORMATION: Synthetic Construct

<400> SEQUENCE: 14
gatcaagctt aaccggaatt gccagctg                                         28

<210> SEQ ID NO 15
<211> LENGTH: 33
<212> TYPE: DNA
<213> ORGANISM: Artificial Sequence
<220> FEATURE:
<223> OTHER INFORMATION: Synthetic Construct

<400> SEQUENCE: 15
gatccgatcg tcagaagaac tcgtcaagaa ggc                                   33

<210> SEQ ID NO 16
<211> LENGTH: 38
<212> TYPE: DNA
<213> ORGANISM: Artificial Sequence
<220> FEATURE:
<223> OTHER INFORMATION: Synthetic Construct

<400> SEQUENCE: 16
catcaatgca tcgcccttag gaggtaaaaa aaaatgac                              38

<210> SEQ ID NO 17
<211> LENGTH: 26
<212> TYPE: DNA
<213> ORGANISM: Artificial Sequence
<220> FEATURE:
<223> OTHER INFORMATION: Synthetic Construct

<400> SEQUENCE: 17
ccttctgcag gacgcgttgt tatagc                                           26
```

<210> SEQ ID NO 18
<211> LENGTH: 60
<212> TYPE: DNA
<213> ORGANISM: Artificial Sequence
<220> FEATURE:
<223> OTHER INFORMATION: Synthetic Construct

<400> SEQUENCE: 18
gatcatgcat tcgcccttag gaggtaaaaa aacatgagtt ttgatattgc caaatacccg    60

<210> SEQ ID NO 19
<211> LENGTH: 30
<212> TYPE: DNA
<213> ORGANISM: Artificial Sequence
<220> FEATURE:
<223> OTHER INFORMATION: Synthetic Construct

<400> SEQUENCE: 19
catgctgcag ttatgccagc caggccttga                                     30

<210> SEQ ID NO 20
<211> LENGTH: 8804
<212> TYPE: DNA
<213> ORGANISM: Artificial Sequence
<220> FEATURE:
<223> OTHER INFORMATION: Synthetic Construct

<400> SEQUENCE: 20
gctggtacca tatgggaatt cgaagctttc tagaacaaaa actcatctca gaagaggatc    60
tgaatagcgc cgtcgaccat catcatcatc atcattgagt ttaaacggtc tccagcttgg   120
ctgttttggc ggatgagaga agattttcag cctgatacag attaaatcag aacgcagaag   180
cggtctgata aaacagaatt tgcctggcgg cagtagcgcg gtggtccac ctgaccccat    240 gccgaactca gaagtgaaac gccgtagcgc cgatggtagt gtggggtctc cccatgcgag   300
agtagggaac tgccaggcat caaataaaac gaaaggctca gtcgaaagac tgggcctttc   360
gttttatctg ttgtttgtcg gtgaacgctc tcctgagtag acaaatccg ccgggagcgg    420 atttgaacgt tgcgaagcaa cggcccggag ggtggcgggc aggacgcccg ccataaactg   480
ccaggcatca aattaagcag aaggccatcc tgacggatgg cctttttgcg tttctacaaa   540 ctcttttgt ttattttct aaatacattc aaatatgtat ccgcttaacc ggaattgcca    600 gctgggcgc cctctggtaa ggttgggaag ccctgcaaag taaactggat ggctttctcg    660
ccgccaagga tctgatggcg caggggatca agctctgatc aagagacagg atgaggatcg   720
tttcgcatga ttgaacaaga tggattgcac gcaggttctc cggccgcttg ggtggagagg   780
ctattcggct atgactgggc acaacagaca atcggctgct ctgatgccgc cgtgttccgg   840
ctgtcagcgc aggggcgccc ggttcttttt gtcaagaccg acctgtccgg tgccctgaat   900
gaactgcaag acgaggcagc gcggctatcg tggctggcca cgacgggcgt tccttgcgca   960
gctgtgctcg acgttgtcac tgaagcggga agggactggc tgctattggg cgaagtgccg  1020
gggcaggatc tcctgtcatc tcaccttgct cctgccgaga agtatccat catggctgat   1080 gcaatgcggc ggctgcatac gcttgatccg gctacctgcc cattcgacca ccaagcgaaa  1140
catcgcatcg agcgagcacg tactcggatg aagccggtc ttgtcgatca ggatgatctg   1200
gacgaagagc atcaggggct cgcgccagcc gaactgttcg ccaggctcaa ggcgagcatg  1260
cccgacggcg aggatctcgt cgtgacccat ggcgatgcct gcttgccgaa tatcatggtg  1320
gaaaatggcc gcttttctgg attcatcgac tgtggccggc tgggtgtggc ggaccgctat  1380

```
caggacatag cgttggctac ccgtgatatt gctgaagagc ttggcggcga atgggctgac    1440
cgcttcctcg tgctttacgg tatcgccgct cccgattcgc agcgcatcgc cttctatcgc    1500
cttcttgacg agttcttctg acatgaccaa aatcccttaa cgtgagtttt cgttccactg    1560
agcgtcagac cccgtagaaa agatcaaagg atcttcttga gatccttttt ttctgcgcgt    1620
aatctgctgc ttgcaaacaa aaaaaccacc gctaccagcg gtggtttgtt tgccggatca    1680
agagctacca actcttttc cgaaggtaac tggcttcagc agagcgcaga taccaaatac    1740
tgtccttcta gtgtagccgt agttaggcca ccacttcaag aactctgtag caccgcctac    1800
atacctcgct ctgctaatcc tgttaccagt ggctgctgcc agtggcgata agtcgtgtct    1860
taccgggttg gactcaagac gatagttacc ggataaggcg cagcggtcgg gctgaacggg    1920
gggttcgtgc acacagccca gcttggagcg aacgacctac accgaactga gatacctaca    1980
gcgtgagcta tgagaaagcg ccacgcttcc cgaagggaga aaggcggaca ggtatccggt    2040
aagcggcagg gtcggaacag gagagcgcac gagggagctt ccagggggaa acgcctggta    2100
tctttatagt cctgtcgggt ttcgccacct ctgacttgag cgtcgatttt tgtgatgctc    2160
gtcagggggg cggagcctat ggaaaaacgc cagcaacgcg gccttttac ggttcctggc    2220 cttttgctgg ccttttgctc acatgttctt cctgcgtta tcccctgatt ctgtggataa    2280
ccgtattacc gcctttgagt gagctgatac cgctcgccgc agccaacga ccgagcgcag    2340 cgagtcagtg agcgaggaag cggaagagcg cctgatgcgg tattttctcc ttacgcatct    2400
gtgcggtatt tcacaccgca tatggtgcac tctcagtaca atctgctctg atgccgcata    2460
gttaagccag tatacactcc gctatcgcta cgtgactggg tcatggctgc gccccgacac    2520
ccgccaacac ccgctgacgc gccctgacgg gcttgtctgc tcccggcatc cgcttacaga    2580
caagctgtga ccgtctccgg gagctgcatg tgtcagaggt tttcaccgtc atcaccgaaa    2640
cgcgcgaggc agcagatcaa ttcgcgcgcg aaggcgaagc ggcatgcatt tacgttgaca    2700
ccatcgaatg gtgcaaaacc tttcgcggta tggcatgata gcgcccggaa gagagtcaat    2760
tcagggtggt gaatgtgaaa ccagtaacgt tatacgatgt cgcagagtat gccggtgtct    2820
cttatcagac cgtttcccgc gtggtgaacc aggccagcca cgtttctgcg aaaacgcggg    2880
aaaaagtgga agcggcgatg gcggagctga attacattcc caaccgcgtg gcacaacaac    2940
tggcgggcaa acagtcgttg ctgattggcg ttgccacctc cagtctggcc ctgcacgcgc    3000
cgtcgcaaat tgtcgcggcg attaaatctc gcgccgatca actgggtgcc agcgtggtgg    3060
tgtcgatggt agaacgaagc ggcgtcgaag cctgtaaagc ggcggtgcac aatcttctcg    3120
cgcaacgcgt cagtgggctg atcattaact atccgctgga tgaccaggat gccattgctg    3180
tggaagctgc ctgcactaat gttccggcgt tatttcttga tgtctctgac cagacaccca    3240
tcaacagtat tattttctcc catgaagacg gtacgcgact gggcgtggag catctggtcg    3300
cattgggtca ccagcaaatc gcgctgttag cgggcccatt aagttctgtc tcggcgcgtc    3360
tgcgtctggc tggctggcat aaatatctca ctcgcaatca aattcagccg atagcggaac    3420
gggaaggcga ctggagtgcc atgtccggtt ttcaacaaac catgcaaatg ctgaatgagg    3480
gcatcgttcc cactgcgatg ctggttgcca acgatcagat ggcgctgggc gcaatgcgcg    3540
ccattaccga gtccgggctg cgcgttggtg cggatatctc ggtagtggga tacgacgata    3600
ccgaagacag ctcatgttat atcccgccgt caaccaccat caaacaggat ttcgcctgc    3660 tggggcaaac cagcgtggac cgcttgctgc aactctctca gggccaggcg gtgaagggca    3720
```

```
atcagctgtt gcccgtctca ctggtgaaaa gaaaaaccac cctggcgccc aatacgcaaa    3780
ccgcctctcc ccgcgcgttg gccgattcat taatgcagct ggcacgacag gtttcccgac    3840
tggaaagcgg gcagtgagcg caacgcaatt aatgtgagtt agcgcgaatt gatctggttt    3900
gacagcttat catcgactgc acggtgcacc aatgcttctg cgtcaggca gccatcggaa     3960 gctgtggtat ggctgtgcag gtcgtaaatc actgcataat tcgtgtcgct caaggcgcac    4020
tcccgttctg gataatgttt tttgcgccga catcataacg gttctggcaa atattctgaa    4080
atgagctgtt gacaattaat catccggctc gtataatgtg tggaattgtg agcggataac    4140
aatttcacac aggaaacagc gccgctgaga aaaagcgaag cggcactgct ctttaacaat    4200
ttatcagaca atctgtgtgg gcactcgacc ggaattatcg attaacttta ttattaaaaa    4260
ttaaagaggt atatattaat gtatcgatta aataaggagg aataaaccat gtgtgcgacc    4320
tcttctcaat ttactcagat taccgagcat aattcccgtc gttccgcaaa ctatcagcca    4380
aacctgtgga atttcgaatt cctgcaatcc ctggagaacg acctgaaagt ggaaaagctg    4440
gaggagaaag cgaccaaact ggaggaagaa gttcgctgca tgatcaaccg tgtagacacc    4500
cagccgctgt ccctgctgga gctgatcgac gatgtgcagc gcctgggtct gacctacaaa    4560
tttgaaaaag acatcattaa agccctggaa acatcgtac tgctggacga aaacaaaaag     4620
aacaaatctg acctgcacgc aaccgctctg tctttccgtc tgctgcgtca gcacggtttc    4680
gaggtttctc aggatgtttt tgagcgtttc aaggataaag aaggtggttt cagcggtgaa    4740
ctgaaaggtg acgtccaagg cctgctgagc ctgtatgaag cgtcttacct gggtttcgag    4800
ggtgagaacc tgctggagga ggcgcgtacc ttttccatca cccacctgaa gaacaacctg    4860
aaagaaggca ttaataccaa ggttgcagaa caagtgagcc acgccctgga actgccatat    4920
caccagcgtc tgcaccgtct ggaggcacgt tggttcctgg ataaatacga accgaaagaa    4980
ccgcatcacc agctgctgct ggagctggcg aagctggatt ttaacatggt acagaccctg    5040
caccagaaag agctgcaaga tctgtcccgc tggtggaccg agatgggcct ggctagcaaa    5100
ctggattttg tacgcgaccg cctgatggaa gtttatttct gggcactggg tatggcgcca    5160
gacccgcagt ttggtgaatg tcgcaaagct gttactaaaa tgtttggtct ggtgacgatc    5220
atcgatgacg tgtatgacgt ttatggcact ctggacgaac tgcaactgtt caccgatgct    5280
gtagagcgct gggacgttaa cgctattaac accctgccgg actatatgaa actgtgtttc    5340
ctggcactgt acaacaccgt taacgacacg tcctattcta ttctgaaaga gaaaggtcat    5400
aacaacctgt cctatctgac gaaaagctgg cgtgaactgt gcaaagcctt tctgcaagag    5460
gcgaaatggt ccaacaacaa aattatcccg gctttctcca gtacctgga aaacgccagc     5520 gtttcctcct ccggtgtagc gctgctggcg ccgtcttact tttccgtatg ccagcagcag    5580
gaagacatct ccgaccacgc gctgcgttcc ctgaccgact ccatggtct ggtgcgttct     5640 agctgcgtta tcttccgcct gtgcaacgat ctggccacct ctgcggcgga gctgaacgt     5700 ggcgagacta ccaattctat cattagctac atgcacgaaa acgatggtac cagcgaggaa    5760
caggcccgcg aagaactgcg taaactgatc gacgccgaat ggaaaagat gaatcgtgaa     5820 cgcgttagcg actccaccct gctgcctaaa gcgttcatgg aaatcgcagt taacatggca    5880
cgtgtttccc actgcaccta ccagtatggc gatggtctgg gtcgcccaga ctacgcgact    5940
gaaaaccgca tcaaactgct gctgattgac ccttccccga ttaaccagct gatgtatgtc    6000
taactgcatc gcccttagga ggtaaaaaaa aatgactgcc gacaacaata gtatgcccca    6060
tggtgcagta tctagttacg ccaaattagt gcaaaaccaa acacctgaag acattttgga    6120
```

```
agagtttcct gaaattattc cattacaaca aagacctaat acccgatcta gtgagacgtc    6180
aaatgacgaa agcggagaaa catgttttc tggtcatgat gaggagcaaa ttaagttaat    6240
gaatgaaaat tgtattgttt tggattggga cgataatgct attggtgccg gtaccaagaa    6300
agtttgtcat ttaatggaaa atattgaaaa gggtttacta catcgtgcat tctccgtctt    6360
tattttcaat gaacaaggtg aattacttt acaacaaaga gccactgaaa aaataacttt    6420
ccctgatctt tggactaaca catgctgctc tcatccacta tgtattgatg acgaattagg    6480
tttgaagggt aagctagacg ataagattaa gggcgctatt actgcggcgg tgagaaaact    6540
agatcatgaa ttaggtattc cagaagatga aactaagaca aggggtaagt ttcactttt    6600 aaacagaatc cattacatgg caccaagcaa tgaaccatgg ggtgaacatg aaattgatta    6660
catcctattt tataagatca acgctaaaga aaacttgact gtcaacccaa acgtcaatga    6720
agttagagac ttcaaatggg tttcaccaaa tgatttgaaa actatgtttg ctgacccaag    6780
ttacaagttt acgccttggt ttaagattat ttgcgagaat tacttattca actggtggga    6840
gcaattagat gacctttctg aagtggaaaa tgacaggcaa attcatagaa tgctataaca    6900
acgcgtcctg cattcgccct taggaggtaa aaaacatga gttttgatat tgccaaatac    6960
ccgaccctgg cactggtcga ctccacccag gagttacgac tgttgccgaa agagagttta    7020
ccgaaactct gcgacgaact gcgccgctat ttactgacca gcgtgagccg ttccagcggg    7080
cacttcgcct ccgggctggg cacggtcgaa ctgaccgtgg cgctgcacta tgtctacaac    7140
accccgtttg accaattgat ttgggatgtg gggcatcagg cttatccgca taaaattttg    7200
accggacgcc gcgacaaaat cggcaccatc cgtcagaaag gcggtctgca cccgttcccg    7260
tggcgcggcg aaagcgaata tgacgtatta agcgtcgggc attcatcaac ctccatcagt    7320
gccggaattg gtattgcggt tgctgccgaa aaagaaggca aaaatcgccg caccgtctgt    7380
gtcattggcg atggcgcgat taccgcaggc atggcgtttg aagcgatgaa tcacgcgggc    7440
gatatccgtc ctgatatgct ggtgattctc aacgacaatg aaatgtcgat ttccgaaaat    7500
gtcggcgcgc tcaacaacca tctggcacag ctgctttccg gtaagcttta ctcttcactg    7560
cgcgaaggcg ggaaaaaagt tttctctggc gtgccgccaa ttaaagagct gctcaaacgc    7620
accgaagaac atattaaagg catggtagtg cctggcacgt tgtttgaaga gctgggcttt    7680
aactacatcg gccggtgga cggtcacgat gtgctggggc ttatcaccac gctaaagaac    7740
atgcgcgacc tgaaaggccc gcagttcctg catatcatga ccaaaaaagg tcgtggttat    7800
gaaccggcag aaaaagaccc gatcactttc cacgccgtgc ctaaatttga tccctccagc    7860
ggttgtttgc cgaaaagtag cggcggtttg ccgagctatt caaaaatctt tggcgactgg    7920
ttgtgcgaaa cggcagcgaa agacaacaag ctgatgcgca ttactccggc gatgcgtgaa    7980
ggttccggca tggtcgagtt ttcacgtaaa ttcccggatc gctacttcga cgtggcaatt    8040
gccgagcaac acgcggtgac cttgctgcg ggtctggcga ttggtgggta caaacccatt    8100
gtcgcgattt actccacttt cctgcaacgc gcctatgatc aggtgctgca tgacgtggcg    8160
attcaaaagc ttccggtcct gttcgccatc gaccgcgcgg gcattgttgg tgctgacggt    8220
caaacccatc agggtgcttt tgatctctct tacctgcgct gcataccgga atggtcatt    8280 atgaccccga gcgatgaaaa cgaatgtcgc cagatgctct ataccggcta tcactataac    8340
gatgccccgt cagcggtgcg ctaccccgcgt ggcaacgcgg tcggcgtgga actgacgccg    8400
ctggaaaaac taccaattgg caaaggcatt gtgaagcgtc gtggcgagaa actggcgatc    8460
```

```
cttaactttg gtacgctgat gccagaagcg gcgaaagtcg ccgaatcgct gaacgccacg    8520
ctggtcgata tgcgttttgt gaaaccgctt gatgaagcgt taattctgga aatggccgcc    8580
agccatgaag cgctggtcac cgtagaagaa aacgccatta tgggcggcgc aggcagcggc    8640
gtgaacgaag tgctgatggc ccatcgtaaa ccagtacccg tgctgaacat ggcctgccg     8700 gacttcttta ttccgcaagg aactcaggaa gaaatgcgcg ccgaactcgg cctcgatgcc    8760
gctggtatgg aagccaaaat caaggcctgg ctggcataac tgca                     8804
```

<210> SEQ ID NO 21
<211> LENGTH: 41
<212> TYPE: DNA
<213> ORGANISM: Artificial Sequence
<220> FEATURE:
<223> OTHER INFORMATION: Synthetic Construct

<400> SEQUENCE: 21

```
aggaggtaaa aaaacatgtc attaccgttc ttaacttctg c                        41
```

<210> SEQ ID NO 22
<211> LENGTH: 52
<212> TYPE: DNA
<213> ORGANISM: Artificial Sequence
<220> FEATURE:
<223> OTHER INFORMATION: Synthetic Construct

<400> SEQUENCE: 22

```
atggctgcag gcctatcgca aattagctta tgaagtccat ggtaaattcg tg            52
```

<210> SEQ ID NO 23
<211> LENGTH: 23
<212> TYPE: DNA
<213> ORGANISM: Artificial Sequence
<220> FEATURE:
<223> OTHER INFORMATION: Synthetic Construct

<400> SEQUENCE: 23

```
gaattcgccc ttctgcagct acc                                            23
```

<210> SEQ ID NO 24
<211> LENGTH: 38
<212> TYPE: DNA
<213> ORGANISM: Artificial Sequence
<220> FEATURE:
<223> OTHER INFORMATION: Synthetic Construct

<400> SEQUENCE: 24

```
cgactggtgc acccttaagg aggaaaaaaa catgtcag                            38
```

<210> SEQ ID NO 25
<211> LENGTH: 25
<212> TYPE: DNA
<213> ORGANISM: Artificial Sequence
<220> FEATURE:
<223> OTHER INFORMATION: Synthetic Construct

<400> SEQUENCE: 25

```
gtgctggaat tcgcccttct gcagc                                          25
```

<210> SEQ ID NO 26
<211> LENGTH: 32
<212> TYPE: DNA
<213> ORGANISM: Artificial Sequence
<220> FEATURE:
<223> OTHER INFORMATION: Synthetic Construct

```
<400> SEQUENCE: 26
gtagatgcat gcagaattcg cccttaagga gg                                32

<210> SEQ ID NO 27
<211> LENGTH: 26
<212> TYPE: DNA
<213> ORGANISM: Artificial Sequence
<220> FEATURE:
<223> OTHER INFORMATION: Synthetic Construct

<400> SEQUENCE: 27
ccttctgcag gacgcgttgt tatagc                                       26

<210> SEQ ID NO 28
<211> LENGTH: 38
<212> TYPE: DNA
<213> ORGANISM: Artificial Sequence
<220> FEATURE:
<223> OTHER INFORMATION: Synthetic Construct

<400> SEQUENCE: 28
catcaatgca tcgcccttag gaggtaaaaa aaaatgac                          38

<210> SEQ ID NO 29
<211> LENGTH: 25
<212> TYPE: DNA
<213> ORGANISM: Artificial Sequence
<220> FEATURE:
<223> OTHER INFORMATION: Synthetic Construct

<400> SEQUENCE: 29
gtgtgatgga tatctgcaga attcg                                        25

<210> SEQ ID NO 30
<211> LENGTH: 36
<212> TYPE: DNA
<213> ORGANISM: Artificial Sequence
<220> FEATURE:
<223> OTHER INFORMATION: Synthetic Construct

<400> SEQUENCE: 30
catcaatgca tcgcccttag gaggtaaaaa aacatg                            36

<210> SEQ ID NO 31
<211> LENGTH: 60
<212> TYPE: DNA
<213> ORGANISM: Artificial Sequence
<220> FEATURE:
<223> OTHER INFORMATION: Synthetic Construct

<400> SEQUENCE: 31
gatcatgcat tcgcccttag gaggtaaaaa aacatgtgtg cgacctcttc tcaatttact  60

<210> SEQ ID NO 32
<211> LENGTH: 38
<212> TYPE: DNA
<213> ORGANISM: Artificial Sequence
<220> FEATURE:
<223> OTHER INFORMATION: Synthetic Construct

<400> SEQUENCE: 32
cggtcgacgg atccctgcag ttagacatac atcagctg                          38

<210> SEQ ID NO 33
```

<211> LENGTH: 10992
<212> TYPE: DNA
<213> ORGANISM: Artificial Sequence
<220> FEATURE:
<223> OTHER INFORMATION: Synthetic Construct

<400> SEQUENCE: 33

| | |
|---|---|
| gtttgacagc ttatcatcga ctgcacggtg caccaatgct tctggcgtca ggcagccatc | 60 |
| ggaagctgtg gtatggctgt gcaggtcgta aatcactgca taattcgtgt cgctcaaggc | 120 |
| gcactcccgt tctggataat gttttttgcg ccgacatcat aacggttctg gcaaatattc | 180 |
| tgaaatgagc tgttgacaat taatcatccg gctcgtataa tgtgtggaat tgtgagcgga | 240 |
| taacaatttc acacaggaaa cagcgccgct gagaaaaagc gaagcggcac tgctctttaa | 300 |
| caatttatca gacaatctgt gtgggcactc gaccggaatt atcgattaac tttattatta | 360 |
| aaaattaaag aggtatatat taatgtatcg attaaataag gaggaataaa ccatggatcc | 420 |
| gagctcggat ccactagtaa cggccgccag tgtgctggaa ttcgcccta ggaggtaaaa | 480 |
| aaacatgtca ttaccgttct taacttctgc accgggaaag gttattattt ttggtgaaca | 540 |
| ctctgctgtg tacaacaagc ctgccgtcgc tgctagtgtg tctgcgttga aacctacct | 600 |
| gctaataagc gagtcatctg caccagatac tattgaattg acttcccgg acattagctt | 660 |
| taatcataag tggtccatca atgatttcaa tgccatcacc gaggatcaag taaactccca | 720 |
| aaaattggcc aaggctcaac aagccaccga tggcttgtct caggaactcg ttagtctttt | 780 |
| ggatccgttg ttagctcaac tatccgaatc cttccactac catgcagcgt tttgtttcct | 840 |
| gtatatgttt gtttgcctat gcccccatgc caagaatatt aagttttctt taaagtctac | 900 |
| tttacccatc ggtgctgggt tgggctcaag cgcctctatt tctgtatcac tggccttagc | 960 |
| tatggcctac ttgggggggt taataggatc taatgacttg gaaaagctgt cagaaaacga | 1020 |
| taagcatata gtgaatcaat gggccttcat aggtgaaaag tgtattcacg gtaccccttc | 1080 |
| aggaatagat aacgctgtgg ccacttatgg taatgccctg ctatttgaaa aagactcaca | 1140 |
| taatggaaca ataaacacaa acaattttaa gttcttagat gatttcccag ccattccaat | 1200 |
| gatcctaacc tatactagaa ttccaaggtc tacaaaagat cttgttgctc gcgttcgtgt | 1260 |
| gttggtcacc gagaaatttc ctgaagttat gaagccaatt ctagatgcca tgggtgaatg | 1320 |
| tgccctacaa ggcttagaga tcatgactaa gttaagtaaa tgtaaaggca ccgatgacga | 1380 |
| ggctgtagaa actaataatg aactgtatga caactattg gaattgataa gaataaatca | 1440 |
| tggactgctt gtctcaatcg gtgtttctca tcctggatta gaacttatta aaaatctgag | 1500 |
| cgatgatttg agaattggct ccacaaaact taccggtgct ggtggcggcg ttgctctttt | 1560 |
| gactttgtta cgaagagaca ttactcaaga gcaaattgac agcttcaaaa agaaattgca | 1620 |
| agatgatttt agttacgaga catttgaaac agacttgggt gggactggct gctgtttgtt | 1680 |
| aagcgcaaaa aatttgaata agatcttaa aatcaaatcc ctagtattcc aattatttga | 1740 |
| aaataaaact accacaaagc aacaaattga cgatctatta ttgccaggaa acacgaattt | 1800 |
| accatggact tcataagcta atttgcgata ggcctgcacc cttaaggagg aaaaaaacat | 1860 |
| gtcagagttg agagccttca gtgccccagg gaaagcgtta ctagctggtg atatttagt | 1920 |
| tttagataca aaatatgaag catttgtagt cggattatcg gcaagaatgc atgctgtagc | 1980 |
| ccatccttac ggttcattgc aagggtctga taagtttgaa gtgcgtgtga aaagtaaaca | 2040 |
| atttaaagat ggggagtggc tgtaccatat aagtcctaaa agtggcttca ttcctgtttc | 2100 |
| gataggcgga tctaagaacc ctttcattga aaaagttatc gctaacgtat ttagctactt | 2160 |

```
taaacctaac atggacgact actgcaatag aaacttgttc gttattgata ttttctctga     2220
tgatgcctac cattctcagg aggatagcgt taccgaacat cgtggcaaca gaagattgag     2280
ttttcattcg cacagaattg aagaagttcc caaaacaggg ctgggctcct cggcaggttt     2340
agtcacagtt ttaactacag ctttggcctc cttttttgta tcggacctgg aaaataatgt     2400
agacaaatat agagaagtta ttcataattt agcacaagtt gctcattgtc aagctcaggg     2460
taaaattgga agcgggtttg atgtagcggc ggcagcatat ggatctatca gatatagaag     2520
attcccaccc gcattaatct ctaatttgcc agatattgga agtgctactt acggcagtaa     2580
actggcgcat ttggttgatg aagaagactg gaatattacg attaaaagta accatttacc     2640
ttcgggatta actttatgga tgggcgatat taagaatggt tcagaaacag taaaactggt     2700
ccagaaggta aaaaattggt atgattcgca tatgccagaa agcttgaaaa tatatacaga     2760
actcgatcat gcaaattcta gatttatgga tggactatct aaactagatc gcttacacga     2820
gactcatgac gattacagcg atcagatatt tgagtctctt gagaggaatg actgtacctg     2880
tcaaaagtat cctgaaatca cagaagttag agatgcagtt gccacaatta gacgttcctt     2940
tagaaaaata actaaagaat ctggtgccga tatcgaacct cccgtacaaa ctagcttatt     3000
ggatgattgc cagaccttaa aaggagttct tacttgctta atacctggtg ctggtggtta     3060
tgacgccatt gcagtgatta ctaagcaaga tgttgatctt agggctcaaa ccgctaatga     3120
caaaagattt tctaaggttc aatggctgga tgtaactcag gctgactggg gtgttaggaa     3180
agaaaaagat ccggaaactt atcttgataa ataacttaag gtagctgcat gcagaattcg     3240
cccttaagga ggaaaaaaaa atgaccgttt acacagcatc cgttaccgca cccgtcaaca     3300
tcgcaaccct taagtattgg gggaaaaggg acacgaagtt gaatctgccc accaattcgt     3360
ccatatcagt gactttatcg caagatgacc tcagaacgtt gacctctgcg gctactgcac     3420
ctgagtttga acgcgacact tgtgggttaa atggagaacc acacagcatc gacaatgaaa     3480
gaactcaaaa ttgtctgcgc gacctacgcc aattaagaaa ggaaatggaa tcgaaggacg     3540
cctcattgcc cacattatct caatggaaac tccacattgt ctccgaaaat aactttccta     3600
cagcagctgg tttagcttcc tccgctgctg gctttgctgc attggtctct gcaattgcta     3660
agttataccc attaccacag tcaacttcag aaatatctag aatagcaaga aaggggtctg     3720
gttcagcttg tagatcgttg tttggcggat acgtggcctg ggaaatggga aaagctgaag     3780
atggtcatga ttccatggca gtacaaatcg cagacagctc tgactggcct cagatgaaag     3840
cttgtgtcct agttgtcagc gatattaaaa aggatgtgag ttccactcag ggtatgcaat     3900
tgaccgtggc aacctccgaa ctatttaaag aaagaattga acatgtcgta ccaaagagat     3960
ttgaagtcat gcgtaaagcc attgttgaaa agatttcgc cacctttgca aaggaaacaa     4020
tgatggattc caactctttc catgccacat gtttggactc tttccctcca atattctaca     4080
tgaatgacac ttccaagcgt atcatcagtt ggtgccacac cattaatcag tttttacggag    4140
aaacaatcgt tgcatacacg tttgatgcag gtccaaatgc tgtgttgtac tacttagctg     4200
aaaatgagtc gaaactcttt gcatttatct ataaattgtt tggctctgtt cctggatggg     4260
acaagaaatt tactactgag cagcttgagg ctttcaacca tcaatttgaa tcatctaact     4320
ttactgcacg tgaattggat cttgagtttc aaaaggatgt tgccagagtg attttaactc     4380
aagtcggttc aggcccacaa gaaacaaacg aatctttgat tgacgcaaag actggtctac     4440
caaaggaata agatcaattc gctgcatcgc ccttaggagg taaaaaaaaa tgactgccga     4500
```

```
caacaatagt atgccccatg gtgcagtatc tagttacgcc aaattagtgc aaaaccaaac    4560
acctgaagac attttggaag agtttcctga aattattcca ttacaacaaa gacctaatac    4620
ccgatctagt gagacgtcaa atgacgaaag cggagaaaca tgttttctg gtcatgatga     4680 ggagcaaatt aagttaatga atgaaaattg tattgttttg gattgggacg ataatgctat    4740
tggtgccggt accaagaaag tttgtcattt aatggaaaat attgaaaagg gtttactaca    4800
tcgtgcattc tccgtcttta ttttcaatga acaaggtgaa ttacttttac aacaaagagc    4860
cactgaaaaa ataactttcc ctgatctttg gactaacaca tgctgctctc atccactatg    4920
tattgatgac gaattaggtt tgaagggtaa gctagacgat aagattaagg gcgctattac    4980
tgcggcggtg agaaaactag atcatgaatt aggtattcca gaagatgaaa ctaagacaag    5040
gggtaagttt cacttttaa acagaatcca ttacatggca ccaagcaatg aaccatgggg     5100
tgaacatgaa attgattaca tcctatttta taagatcaac gctaaagaaa acttgactgt    5160
caacccaaac gtcaatgaag ttagagactt caaatgggtt tcaccaaatg atttgaaaac    5220
tatgtttgct gacccaagtt acaagtttac gccttggttt aagattattt gcgagaatta    5280
cttattcaac tggtgggagc aattagatga ccttttctgaa gtggaaaatg acaggcaaat   5340
tcatagaatg ctataacaac gcgtcctgca ttcgccctta ggaggtaaaa aaacatgtgt    5400
gcgacctctt ctcaatttac tcagattacc gagcataatt cccgtcgttc cgcaaactat    5460
cagccaaacc tgtggaattt cgaattcctg caatccctgg agaacgacct gaaagtggaa    5520
aagctggagg agaaagcgac caaactggag gaagaagttc gctgcatgat caaccgtgta    5580
gacacccagc cgctgtccct gctggagctg atcgacgatg tgcagcgcct gggtctgacc    5640
tacaaatttg aaaaagacat cattaaagcc ctggaaaaca tcgtactgct ggacgaaaac    5700
aaaaagaaca atctgacct gcacgcaacc gctctgtctt ccgtctgct gcgtcagcac      5760 ggtttcgagg tttctcagga tgttttgag cgtttcaagg ataagaagg tggtttcagc      5820 ggtgaactga aggtgacgt ccaaggcctg ctgagcctgt atgaagcgtc ttacctgggt     5880
ttcgagggtg agaacctgct ggaggaggcg cgtaccttt ccatcaccca cctgaagaac     5940
aacctgaaag aaggcattaa taccaaggtt gcagaacaag tgagccacgc cctggaactg    6000
ccatatcacc agcgtctgca ccgtctggag gcacgttggt tcctggataa atacgaaccg    6060
aaagaaccgc atcaccagct gctgctggag ctggcgaagc tggattttaa catggtacag    6120
accctgcacc agaaagagct gcaagatctg tcccgctggt ggaccgagat gggcctggct    6180
agcaaactgg attttgtacg cgaccgcctg atggaagttt attctgggc actgggtatg     6240 gcgccagacc cgcagtttgg tgaatgtcgc aaagctgtta ctaaaatgtt tggtctggtg    6300
acgatcatcg atgacgtgta tgacgtttat ggcactctgg acgaactgca actgttcacc    6360
gatgctgtag agcgctggga cgttaacgct attaacaccc tgccggacta tatgaaactg    6420
tgtttcctgg cactgtacaa caccgttaac gacacgtcct attctattct gaaagagaaa    6480
ggtcataaca acctgtccta tctgacgaaa agctggcgtg aactgtgcaa agcctttctg    6540
caagaggcga atggtccaa caacaaaatt atcccggctt ctccaagta cctggaaaac      6600 gccagcgttt cctcctccgg tgtagcgctg ctggcgccgt cttactttc cgtatgccag     6660 cagcaggaag acatctccga ccacgcgctg cgttccctga ccgacttcca tggtctggtg    6720
cgttctagct gcgttatctt ccgcctgtgc aacgatctgg ccacctctgc ggcggagctg    6780
gaacgtggcg agactaccaa ttctatcatt agctacatgc acgaaaacga tggtaccagc    6840
gaggaacagg cccgcgaaga actgcgtaaa ctgatcgacg ccgaatggaa aaagatgaat    6900
```

| | | | | |
|---|---|---|---|---|
| cgtgaacgcg | ttagcgactc | caccctgctg | cctaaagcgt | tcatggaaat cgcagttaac | 6960 |
| atggcacgtg | tttcccactg | cacctaccag | tatggcgatg | gtctgggtcg cccagactac | 7020 |
| gcgactgaaa | accgcatcaa | actgctgctg | attgaccctt | tcccgattaa ccagctgatg | 7080 |
| tatgtctaac | tgcagctggt | accatatggg | aattcgaagc | tttctagaac aaaaactcat | 7140 |
| ctcagaagag | gatctgaata | gcgccgtcga | ccatcatcat | catcatcatt gagtttaaac | 7200 |
| ggtctccagc | ttggctgttt | tggcggatga | gagaagattt | tcagcctgat acagattaaa | 7260 |
| tcagaacgca | gaagcggtct | gataaaacag | aatttgcctg | gcggcagtag cgcggtggtc | 7320 |
| ccacctgacc | ccatgccgaa | ctcagaagtg | aaacgccgta | gcgccgatgg tagtgtgggg | 7380 |
| tctcccatg | cgagagtagg | gaactgccag | gcatcaaata | aaacgaaagg ctcagtcgaa | 7440 |
| agactgggcc | tttcgtttta | tctgttgttt | gtcggtgaac | gctctcctga gtaggacaaa | 7500 |
| tccgccggga | gcggatttga | acgttgcgaa | gcaacggccc | ggagggtggc gggcaggacg | 7560 |
| cccgccataa | actgccaggc | atcaaattaa | gcagaaggcc | atcctgacgg atggcctttt | 7620 |
| tgcgtttcta | caaactcttt | ttgtttattt | ttctaaatac | attcaaatat gtatccgctt | 7680 |
| aaccggaatt | gccagctggg | gcgcccctctg | gtaaggttgg | gaagccctgc aaagtaaact | 7740 |
| ggatggcttt | ctcgccgcca | aggatctgat | ggcgcagggg | atcaagctct gatcaagaga | 7800 |
| caggatgagg | atcgtttcgc | atgattgaac | aagatggatt | gcacgcaggt tctccgccg | 7860 |
| cttgggtgga | gaggctattc | ggctatgact | gggcacaaca | gacaatcggc tgctctgatg | 7920 |
| ccgccgtgtt | ccggctgtca | gcgcaggggc | gcccggttct | ttttgtcaag accgacctgt | 7980 |
| ccggtgccct | gaatgaactg | caagacgagg | cagcgcggct | atcgtggctg gccacgacgg | 8040 |
| gcgttccttg | cgcagctgtg | ctcgacgttg | tcactgaagc | gggaagggac tggctgctat | 8100 |
| tgggcgaagt | gccggggcag | gatctcctgt | catctcacct | tgctcctgcc gagaaagtat | 8160 |
| ccatcatggc | tgatgcaatg | cggcggctg | atacgcttga | tccggctacc tgcccattcg | 8220 |
| accaccaagc | gaaacatcgc | atcgagcgag | cacgtactcg | gatggaagcc ggtcttgtcg | 8280 |
| atcaggatga | tctggacgaa | gagcatcagg | ggctcgcgcc | agccgaactg ttcgccaggc | 8340 |
| tcaaggcgag | catgcccgac | ggcgaggatc | tcgtcgtgac | ccatggcgat gcctgcttgc | 8400 |
| cgaatatcat | ggtggaaaat | ggccgctttt | ctggattcat | cgactgtggc cggctgggtg | 8460 |
| tggcggaccg | ctatcaggac | atagcgttgg | ctacccgtga | tattgctgaa gagcttggcg | 8520 |
| gcgaatgggc | tgaccgcttc | ctcgtgcttt | acggtatcgc | cgctcccgat tcgcagcgca | 8580 |
| tcgccttcta | tcgccttctt | gacgagttct | tctgacgcat | gaccaaaatc ccttaacgtg | 8640 |
| agttttcgtt | ccactgagcg | tcagaccccg | tagaaaagat | caaaggatct tcttgagatc | 8700 |
| cttttttct | gcgcgtaatc | tgctgcttgc | aaacaaaaaa | accaccgcta ccagcggtgg | 8760 |
| tttgtttgcc | ggatcaagag | ctaccaactc | tttttccgaa | ggtaactggc ttcagcagag | 8820 |
| cgcagatacc | aaatactgtc | cttctagtgt | agccgtagtt | aggccaccac ttcaagaact | 8880 |
| ctgtagcacc | gcctacatac | ctcgctctgc | taatcctgtt | accagtggct gctgccagtg | 8940 |
| gcgataagtc | gtgtcttacc | gggttggact | caagacgata | gttaccggat aaggcgcagc | 9000 |
| ggtcgggctg | aacggggggt | tcgtgcacac | agcccagctt | ggagcgaacg acctacaccg | 9060 |
| aactgagata | cctacagcgt | gagctatgag | aaagcgccac | gcttcccgaa gggagaaagg | 9120 |
| cggacaggta | tccggtaagc | ggcagggtcg | gaacaggaga | gcgcacgagg gagcttccag | 9180 |
| ggggaaacgc | ctggtatctt | tatagtcctg | tcgggtttcg | ccacctctga cttgagcgtc | 9240 |

```
gatttttgtg atgctcgtca gggggggcgga gcctatggaa aaacgccagc aacgcggcct    9300
ttttacggtt cctggccttt tgctggcctt ttgctcacat gttctttcct gcgttatccc    9360
ctgattctgt ggataaccgt attaccgcct ttgagtgagc tgataccgct cgccgcagcc    9420
gaacgaccga gcgcagcgag tcagtgagcg aggaagcgga agagcgcctg atgcggtatt    9480
ttctccttac gcatctgtgc ggtatttcac accgcatatg gtgcactctc agtacaatct    9540
gctctgatgc cgcatagtta agccagtata cactccgcta tcgctacgtg actgggtcat    9600
ggctgcgccc cgacacccgc caacacccgc tgacgcgccc tgacgggctt gtctgctccc    9660
ggcatccgct tacagacaag ctgtgaccgt ctccgggagc tgcatgtgtc agaggttttc    9720
accgtcatca ccgaaacgcg cgaggcagca gatcaattcg cgcgcgaagg cgaagcggca    9780
tgcatttacg ttgacaccat cgaatggtgc aaaacctttc gcggtatggc atgatagcgc    9840
ccggaagaga gtcaattcag ggtggtgaat gtgaaaccag taacgttata cgatgtcgca    9900
gagtatgccg gtgtctctta tcagaccgtt tcccgcgtgg tgaaccaggc cagccacgtt    9960
tctgcgaaaa cgcgggaaaa agtggaagcg gcgatggcgg agctgaatta cattcccaac   10020
cgcgtggcac aacaactggc gggcaaacag tcgttgctga ttggcgttgc cacctccagt   10080
ctggccctgc acgcgccgtc gcaaattgtc gcggcgatta atctcgcgc cgatcaactg    10140 ggtgccagcg tggtggtgtc gatggtagaa cgaagcggcg tcgaagcctg taaagcggcg   10200
gtgcacaatc ttctcgcgca acgcgtcagt gggctgatca ttaactatcc gctggatgac   10260
caggatgcca ttgctgtgga agctgcctgc actaatgttc cggcgttatt tcttgatgtc   10320
tctgaccaga cacccatcaa cagtattatt ttctcccatg aagacggtac gcgactgggc   10380
gtggagcatc tggtcgcatt gggtcaccag caaatcgcgc tgttagcggg cccattaagt   10440
tctgtctcgg cgcgtctgcg tctggctggc tggcataaat atctcactcg caatcaaatt   10500
cagccgatag cggaacggga aggcgactgg agtgccatgt ccggttttca acaaaccatg   10560
caaatgctga atgagggcat cgttcccact gcgatgctgg ttgccaacga tcagatggcg   10620
ctgggcgcaa tgcgcgccat taccgagtcc gggctgcgcg ttggtgcgga tatctcggta   10680
gtgggatacg acgataccga agacagctca tgttatatcc cgccgtcaac caccatcaaa   10740
caggattttc gcctgctggg gcaaaccagc gtggaccgct tgctgcaact ctctcagggc   10800
caggcggtga agggcaatca gctgttgccc gtctcactgg tgaaaagaaa aaccaccctg   10860
gcgcccaata cgcaaaccgc ctctccccgc gcgttggccg attcattaat gcagctggca   10920
cgacaggttt cccgactgga aagcgggcag tgagcgcaac gcaattaatg tgagttagcg   10980
cgaattgatc tg                                                      10992
```

<210> SEQ ID NO 34
<211> LENGTH: 49
<212> TYPE: DNA
<213> ORGANISM: Artificial Sequence
<220> FEATURE:
<223> OTHER INFORMATION: Synthetic Construct

<400> SEQUENCE: 34

```
gagacatgag ctcaggaggt aaaaaaacat gaaaacagta gttattatt              49
```

<210> SEQ ID NO 35
<211> LENGTH: 54
<212> TYPE: DNA
<213> ORGANISM: Artificial Sequence
<220> FEATURE:
<223> OTHER INFORMATION: Synthetic Construct

```
<400> SEQUENCE: 35
tttatcaatc ccaattgtca tgttttttta cctcctttat tgttttctta aatc        54

<210> SEQ ID NO 36
<211> LENGTH: 54
<212> TYPE: DNA
<213> ORGANISM: Artificial Sequence
<220> FEATURE:
<223> OTHER INFORMATION: Synthetic Construct

<400> SEQUENCE: 36
gatttaagaa aacaataaag gaggtaaaaa aacatgacaa ttgggattga taaa        54

<210> SEQ ID NO 37
<211> LENGTH: 40
<212> TYPE: DNA
<213> ORGANISM: Artificial Sequence
<220> FEATURE:
<223> OTHER INFORMATION: Synthetic Construct

<400> SEQUENCE: 37
gacatgacat agatctttag tttcgataag aacgaacggt                        40

<210> SEQ ID NO 38
<211> LENGTH: 26
<212> TYPE: DNA
<213> ORGANISM: Artificial Sequence
<220> FEATURE:
<223> OTHER INFORMATION: Synthetic Construct

<400> SEQUENCE: 38
atgaaaacag tagttattat tgatgc                                       26

<210> SEQ ID NO 39
<211> LENGTH: 33
<212> TYPE: DNA
<213> ORGANISM: Artificial Sequence
<220> FEATURE:
<223> OTHER INFORMATION: Synthetic Construct

<400> SEQUENCE: 39
atgttattgt tttcttaaat catttaaaat agc                               33

<210> SEQ ID NO 40
<211> LENGTH: 26
<212> TYPE: DNA
<213> ORGANISM: Artificial Sequence
<220> FEATURE:
<223> OTHER INFORMATION: Synthetic Construct

<400> SEQUENCE: 40
atgacaattg ggattgataa aattag                                       26

<210> SEQ ID NO 41
<211> LENGTH: 24
<212> TYPE: DNA
<213> ORGANISM: Artificial Sequence
<220> FEATURE:
<223> OTHER INFORMATION: Synthetic Construct

<400> SEQUENCE: 41
ttagtttcga taagaacgaa cggt                                         24

<210> SEQ ID NO 42
```

```
<211> LENGTH: 23
<212> TYPE: DNA
<213> ORGANISM: Artificial Sequence
<220> FEATURE:
<223> OTHER INFORMATION: Synthetic Construct

<400> SEQUENCE: 42
gaaatagccc cattagaagt atc                                             23

<210> SEQ ID NO 43
<211> LENGTH: 24
<212> TYPE: DNA
<213> ORGANISM: Artificial Sequence
<220> FEATURE:
<223> OTHER INFORMATION: Synthetic Construct

<400> SEQUENCE: 43
ttgccaatca tatgattgaa aatc                                            24

<210> SEQ ID NO 44
<211> LENGTH: 25
<212> TYPE: DNA
<213> ORGANISM: Artificial Sequence
<220> FEATURE:
<223> OTHER INFORMATION: Synthetic Construct

<400> SEQUENCE: 44
gctatgcttc attagatcct tatcg                                           25

<210> SEQ ID NO 45
<211> LENGTH: 25
<212> TYPE: DNA
<213> ORGANISM: Artificial Sequence
<220> FEATURE:
<223> OTHER INFORMATION: Synthetic Construct

<400> SEQUENCE: 45
gaaacctaca tccaatcttt tgccc                                           25

<210> SEQ ID NO 46
<211> LENGTH: 8703
<212> TYPE: DNA
<213> ORGANISM: Artificial Sequence
<220> FEATURE:
<223> OTHER INFORMATION: Synthetic Construct

<400> SEQUENCE: 46
cccgtcttac tgtcgggaat tcgcgttggc cgattcatta atgcagattc tgaaatgagc      60
tgttgacaat taatcatccg gctcgtataa tgtgtggaat tgtgagcgga taacaatttc     120
acacaggaaa cagcgccgct gagaaaaagc gaagcggcac tgctctttaa caatttatca     180
gacaatctgt gtgggcactc gaccggaatt atcgattaac tttattatta aaaattaaag     240
aggtatatat taatgtatcg attaaataag gaggaataaa ccatggatcc gagctcagga     300
ggtaaaaaaa catgaaaaca gtagttatta ttgatgcatt acgaacacca attggaaaat     360
ataaaggcag cttaagtcaa gtaagtgccg tagacttagg aacacatgtt acaacacaac     420
ttttaaaaag acattccact atttctgaag aaattgatca agtaatcttt ggaaatgttt     480
tacaagctgg aaatggccaa aatcccgcac gacaaatagc aataaacagc ggtttgtctc     540
atgaaattcc cgcaatgacg gttaatgagg tctgcggatc aggaatgaag gccgttatttt    600 tggcgaaaca attgattcaa ttaggagaag cggaagtttt aattgctggc gggattgaga     660
atatgtccca agcacctaaa ttacaacgtt ttaattacga aacagaaagc tacgatgcgc     720
```

-continued

```
cttttttctag tatgatgtat gatggattaa cggatgcctt tagtggtcag gcaatgggct      780
taactgctga aaatgtggcc gaaaagtatc atgtaactag agaagagcaa gatcaatttt      840
ctgtacattc acaattaaaa gcagctcaag cacaagcaga agggatattc gctgacgaaa      900
tagccccatt agaagtatca ggaacgcttg tggagaaaga tgaagggatt cgccctaatt      960
cgagcgttga gaagctagga acgcttaaaa cagtttttaa agaagacggt actgtaacag     1020
cagggaatgc atcaaccatt aatgatgggg cttctgcttt gattattgct tcacaagaat     1080
atgccgaagc acacggtctt ccttatttag ctattattcg agacagtgtg gaagtcggta     1140
ttgatccagc ctatatggga atttcgccga ttaaagccat tcaaaaactg ttagcgcgca     1200
atcaacttac tacggaagaa attgatctgt atgaaatcaa cgaagcattt gcagcaactt     1260
caatcgtggt ccaaagagaa ctggctttac cagaggaaaa ggtcaacatt tatggtggcg     1320
gtatttcatt aggtcatgcg attggtgcca caggtgctcg tttattaacg agtttaagtt     1380
atcaattaaa tcaaaaagaa aagaaatatg gagtggcttc tttatgtatc ggcggtggct     1440
taggactcgc tatgctacta gagagacctc agcaaaaaaa aaacagccga ttttatcaaa     1500
tgagtcctga ggaacgcctg gcttctcttc ttaatgaagg ccagatttct gctgatacaa     1560
aaaaagaatt tgaaaatacg gctttatctt cgcagattgc caatcatatg attgaaaatc     1620
aaatcagtga aacagaagtg ccgatgggcg ttggcttaca tttaacagtg gacgaaactg     1680
attatttggt accaatggcg acagaagagc cctcagttat tgcggctttg agtaatggtg     1740
caaaaatagc acaaggattt aaaacagtga atcaacaacg cttaatgcgt ggacaaatcg     1800 tttttttacga tgttgcagat cccgagtcat tgattgataa actacaagta agagaagcgg     1860 aagttttttca acaagcagag ttaagttatc catctatcgt taaacggggc ggcggcttaa     1920
gagatttgca atatcgtact tttgatgaat catttgtatc tgtcgacttt ttagtagatg     1980
ttaaggatgc aatgggggca aatatcgtta acgctatgtt ggaaggtgtg gccgagttgt     2040
tccgtgaatg gtttgcggag caaaagattt tattcagtat tttaagtaat tatgccacgg     2100
agtcggttgt tacgatgaaa acggctattc cagtttcacg tttaagtaag gggagcaatg     2160
gccgggaaat tgctgaaaaa attgttttag cttcacgcta tgcttcatta gatccttatc     2220
gggcagtcac gcataacaaa ggaatcatga atggcattga agctgtagtt ttagctacag     2280
gaaatgatac acgcgctgtt agcgcttctt gtcatgcttt tgcggtgaag gaaggtcgct     2340
accaaggctt gactagttgg acgctggatg gcgaacaact aattggtgaa atttcagttc     2400
cgcttgcttt agccacggtt ggcggtgcca caaaagtctt acctaaatct caagcagctg     2460
ctgatttgtt agcagtgacg gatgcaaaag aactaagtcg agtagtagcg gctgttggtt     2520
tggcacaaaa tttagcggcg ttacgggcct tagtctctga aggaattcaa aaaggacaca     2580
tggctctaca agcacgttct ttagcgatga cggtcggagc tactggtaaa gaagttgagg     2640
cagtcgctca acaattaaaa cgtcaaaaaa cgatgaacca agaccgagcc atggctattt     2700
taaatgattt aagaaaacaa taaggaggt aaaaaaacat gacaattggg attgataaaa     2760
ttagtttttt tgtgccccct tattatattg atatgacggc actggctgaa gccagaaatg     2820
tagaccctgg aaaatttcat attggtattg ggcaagacca aatggcggtg aacccaatca     2880
gccaagatat tgtgacattt gcagccaatg ccgcagaagc gatcttgacc aaagaagata     2940
aagaggccat tgatatggtg attgtcggga ctgagtccag tatcgatgag tcaaaagcgg     3000
ccgcagttgt cttacatcgt ttaatgggga ttcaacccttt cgctcgctct ttcgaaatca     3060
```

```
aggaagcttg ttacggagca acagcaggct tacagttagc taagaatcac gtagccttac   3120
atccagataa aaaagtcttg gtcgtagcgg cagatattgc aaaatatggc ttaaattctg   3180
gcggtgagcc tacacaagga gctggggcgg ttgcaatgtt agttgctagt gaaccgcgca   3240
ttttggcttt aaaagaggat aatgtgatgc tgacgcaaga tatctatgac ttttggcgtc   3300
caacaggcca cccgtatcct atggtcgatg gtcctttgtc aaacgaaacc tacatccaat   3360
cttttgccca gtctgggat gaacataaaa acgaaccgg tcttgatttt gcagattatg   3420
atgctttagc gttccatatt ccttacacaa aaatgggcaa aaaagcctta ttagcaaaaa   3480
tctccgacca aactgaagca gaacaggaac gaattttagc ccgttatgaa gaaagtatcg   3540
tctatagtcg tcgcgtagga aacttgtata cgggttcact ttatctggga ctcatttccc   3600
ttttagaaaa tgcaacgact ttaaccgcag gcaatcaaat tggtttattc agttatggtt   3660
ctggtgctgt cgctgaattt ttcactggtg aattagtagc tggttatcaa aatcatttac   3720
aaaaagaaac tcatttagca ctgctggata atcggacaga actttctatc gctgaatatg   3780
aagccatgtt tgcagaaact ttagacacag acattgatca aacgttagaa gatgaattaa   3840
aatatagtat ttctgctatt aataataccg ttcgttctta tcgaaactaa gagatctgca   3900
gctggtacca tatgggaatt cgaagcttgg gcccgaacaa aaactcatct cagaagagga   3960
tctgaatagc gccgtcgacc atcatcatca tcatcattga gtttaaacgg tctccagctt   4020
ggctgttttg gcggatgaga gaagattttc agcctgatac agattaaatc agaacgcaga   4080
agcggtctga taaaacagaa tttgcctggc ggcagtagcg cggtggtccc acctgacccc   4140
atgccgaact cagaagtgaa acgccgtagc gccgatggta gtgtggggtc tccccatgcg   4200
agagtaggga actgccaggc atcaaataaa acgaaaggct cagtcgaaag actgggcctt   4260
tcgttttatc tgttgtttgt cggtgaacgc tctcctgagt aggacaaatc cgccgggagc   4320
ggatttgaac gttgcgaagc aacggcccgg agggtggcgg gcaggacgcc cgccataaac   4380
tgccaggcat caaattaagc agaaggccat cctgacggat ggccttttg cgtttctaca   4440
aactcttttt gtttattttt ctaaatacat tcaaatatgt atccgctcat gagacaataa   4500
ccctgataaa tgcttcaata atctggcgta atagcgaaga ggcccgcacc gatcgccctt   4560
cccaacagtt gcgcagcctg aatggcgaat ggcgcctgat gcggtatttt ctccttacgc   4620
atctgtgcgg tatttcacac cgcatatggt gcactctcag tacaatctgc tctgatgccg   4680
catagttaag ccagccccga cacccgccaa cacccgctga cgagcttagt aaagccctcg   4740
ctagattta atgcggatgt tgcgattact tcgccaacta ttgcgataac aagaaaaagc   4800
cagcctttca tgatatatct cccaatttgt gtagggctta ttatgcacgc ttaaaaataa   4860
taaaagcaga cttgacctga tagtttggct gtgagcaatt atgtgcttag tgcatctaac   4920
gcttgagtta agccgcgccg cgaagcggcg tcggcttgaa cgaattgtta gacattattt   4980
gccgactacc ttggtgatct cgcctttcac gtagtggaca aattcttcca actgatctgc   5040
gcgcgaggcc aagcgatctt cttcttgtcc aagataagcc tgtctagctt caagtatgac   5100
gggctgatac tgggccggca ggcgctccat gcccagtcg gcagcgacat ccttcggcgc   5160
gattttgccg gttactgcgc tgtaccaaat gcgggacaac gtaagcacta catttcgctc   5220
atcgccagcc cagtcgggcg gcgagttcca tagcgttaag gtttcattta gcgcctcaaa   5280
tagatcctgt tcaggaaccg gatcaaagag ttcctccgcc gctggaccta ccaaggcaac   5340
gctatgttct cttgctttg tcagcaagat agccagatca atgtcgatcg tggctggctc   5400
gaagatacct gcaagaatgt cattgcgctg ccattctcca aattgcagtt cgcgcttagc   5460
```

```
tggataacgc cacggaatga tgtcgtcgtg cacaacaatg gtgacttcta cagcgcggag    5520
aatctcgctc tctccagggg aagccgaagt ttccaaaagg tcgttgatca aagctcgccg    5580
cgttgtttca tcaagcctta cggtcaccgt aaccagcaaa tcaatatcac tgtgtggctt    5640
caggccgcca tccactgcgg agccgtacaa atgtacggcc agcaacgtcg gttcgagatg    5700
gcgctcgatg acgccaacta cctctgatag ttgagtcgat acttcggcga tcaccgcttc    5760
cctcatgatg tttaactttg ttttagggcg actgccctgc tgcgtaacat cgttgctgct    5820
ccataacatc aaacatcgac ccacggcgta acgcgcttgc tgcttggatg cccgaggcat    5880
agactgtacc ccaaaaaaac agtcataaca agccatgaaa accgccactg cgccgttacc    5940
accgctgcgt tcggtcaagg ttctggacca gttgcgtgag cgcatacgct acttgcatta    6000
cagcttacga accgaacagg cttatgtcca ctgggttcgt gccttcatcc gtttccacgg    6060
tgtgcgtcac ccggcaacct tgggcagcag cgaagtcgag gcatttctgt cctggctggc    6120
gaacgagcgc aaggtttcgg tctccacgca tcgtcaggca ttggcggcct tgctgttctt    6180
ctacggcaag gtgctgtgca cggatctgcc ctggcttcag gagatcggaa gacctcggcc    6240
gtcgcggcgc ttgccggtgg tgctgacccc ggatgaagtg gttcgcatcc tcggttttct    6300
ggaaggcgag catcgtttgt tcgcccagct tctgtatgga acgggcatgc ggatcagtga    6360
gggtttgcaa ctgcgggtca aggatctgga tttcgatcac ggcacgatca tcgtgcggga    6420
gggcaagggc tccaaggatc gggccttgat gttacccgag agcttggcac ccagcctgcg    6480
cgagcagggg aattaattcc cacgggtttt gctgcccgca aacgggctgt tctggtgttg    6540
ctagtttgtt atcagaatcg cagatccggc ttcagccggt ttgccggctg aaagcgctat    6600
ttcttccaga attgccatga ttttttcccc acgggaggcg tcactggctc ccgtgttgtc    6660
ggcagctttg attcgataag cagcatcgcc tgtttcaggc tgtctatgtg tgactgttga    6720
gctgtaacaa gttgtctcag gtgttcaatt tcatgttcta gttgctttgt tttactggtt    6780
tcacctgttc tattaggtgt tacatgctgt tcatctgtta cattgtcgat ctgttcatgg    6840
tgaacagctt tgaatgcacc aaaaactcgt aaaagctctg atgtatctat cttttttaca    6900
ccgttttcat ctgtgcatat ggacagtttt cccttttgata tgtaacggtg aacagttgtt    6960
ctacttttgt ttgttagtct tgatgcttca ctgatagata caagagccat aagaacctca    7020
gatccttccg tatttagcca gtatgttctc tagtgtggtt cgttgttttt gcgtgagcca    7080
tgagaacgaa ccattgagat catacttact ttgcatgtca ctcaaaaatt ttgcctcaaa    7140
actggtgagc tgaattttg cagttaaagc atcgtgtagt gtttttctta gtccgttatg    7200
taggtaggaa tctgatgtaa tggttgttgg tattttgtca ccattcattt ttatctggtt    7260
gttctcaagt tcggttacga gatccatttg tctatctagt tcaacttgga aaatcaacgt    7320
atcagtcggg cggcctcgct tatcaaccac caatttcata ttgctgtaag tgtttaaatc    7380
tttacttatt ggtttcaaaa cccattggtt aagccttta aactcatggt agttattttc    7440
aagcattaac atgaacttaa attcatcaag gctaatctct atatttgcct tgtgagtttt    7500
cttttgtgtt agttctttta ataaccactc ataaatcctc atagagtatt tgttttcaaa    7560
agacttaaca tgttccagat tatattttat gaattttttt aactggaaaa gataaggcaa    7620
tatctcttca ctaaaaacta attctaattt ttcgcttgag aacttggcat agtttgtcca    7680
ctggaaaatc tcaaagcctt taaccaaagg attcctgatt tccacagttc tcgtcatcag    7740
ctctctggtt gctttagcta atacaccata agcatttcc ctactgatgt tcatcatctg    7800
```

| | |
|---|---|
| agcgtattgg ttataagtga acgataccgt ccgttctttc cttgtagggt tttcaatcgt | 7860 |
| ggggttgagt agtgccacac agcataaaat tagcttggtt tcatgctccg ttaagtcata | 7920 |
| gcgactaatc gctagttcat ttgctttgaa aacaactaat tcagacatac atctcaattg | 7980 |
| gtctaggtga ttttaatcac tataccaatt gagatgggct agtcaatgat aattactagt | 8040 |
| cctttccctt tgagttgtgg gtatctgtaa attctgctag acctttgctg gaaaacttgt | 8100 |
| aaattctgct agaccctctg taaattccgc tagacctttg tgtgtttttt ttgtttatat | 8160 |
| tcaagtggtt ataatttata gaataaagaa agaataaaaa aagataaaaa gaatagatcc | 8220 |
| cagccctgtg tataactcac tactttagtc agttccgcag tattacaaaa ggatgtcgca | 8280 |
| aacgctgttt gctcctctac aaaacagacc ttaaaaccct aaaggcttaa gtagcaccct | 8340 |
| cgcaagctcg ggcaaatcgc tgaatattcc ttttgtctcc gaccatcagg cacctgagtc | 8400 |
| gctgtctttt tcgtgacatt cagttcgctg cgctcacggc tctggcagtg aatgggggta | 8460 |
| aatggcacta caggcgcctt ttatggattc atgcaaggaa actacccata atacaagaaa | 8520 |
| agcccgtcac gggcttctca gggcgtttta tggcgggtct gctatgtggt gctatctgac | 8580 |
| tttttgctgt tcagcagttc ctgccctctg attttccagt ctgaccactt cggattatcc | 8640 |
| cgtgacaggt cattcagact ggctaatgca cccagtaagg cagcggtatc atcaacaggc | 8700 |
| tta | 8703 |

<210> SEQ ID NO 47
<211> LENGTH: 9371
<212> TYPE: DNA
<213> ORGANISM: Artificial Sequence
<220> FEATURE:
<223> OTHER INFORMATION: Synthetic Construct

<400> SEQUENCE: 47

| | |
|---|---|
| tgtaaccttt gctttcaaat gagtagaaat aatgcacatc catgtttgta tcgtgcaaat | 60 |
| aaagtgtttc atccgtagga aaaatgact ttagtatctg ttccgctttt tctgatgaaa | 120 |
| tgtgctcccc gacaaaattg aatgaatcat ggacatttgc tggctttgat acagcgaaag | 180 |
| cagccgttcc tatgttatat atcggattta acagcaggac aaaaaacacc atgacagcca | 240 |
| tcgtcaccca cttattcaca cgcacataaa cctttcctga cttttggaac agatgatagc | 300 |
| tcatcaaaaa tcccgccatt gccaaataaa tcgtatatgg cattactgca ccataatctt | 360 |
| ttgagatttg attgggatat ggcgcaagca gcaagacaag cagtccgata atcagcgtat | 420 |
| aaaataagcc tagtaagatc ttatccgttc tccaatacag cttgaaaaac actacattca | 480 |
| acgcaatggg aagagtgatg atgaaaaaca gaaacacgaa tgcaatcggc tccatcccat | 540 |
| ccgggtattc cttccaatac gaaagaaac taaaaatcat ttgtacgatc ggcaaactga | 600 |
| caacagcaag gtcgaacgta taaaacttac cctttccgcc atgatcacgc ggcatcagca | 660 |
| tatagtgaaa agccgtcagc agcacatatc cgtataacaa aaatgcagc agcggcagca | 720 |
| gttcttttcc gtcctctctt aagtaagcgc tggtgaagtt tgttgattgc acctggtgaa | 780 |
| taagttcaac agacactccc gccagcagca caatccgcaa tataacaccc gccaagaaca | 840 |
| ttgtgcgctg ccggtttatt ttgggatgat gcaccaaaag atataagccc gccagaacaa | 900 |
| caattgacca ttgaatcagc agggtgcttt gtctgcttaa tataaaataa cgttcgaaat | 960 |
| gcaatacata atgactgaat aactccaaca cgaacaacaa ctccattttc ttctgctatc | 1020 |
| aaaataacag actcgtgatt ttccaaacga gctttcaaaa aagcctctgc cccttgcaaa | 1080 |
| tcggatgcct gtctataaaa ttcccgatat tggttaaaca gcggcgcaat ggcggccgca | 1140 |

```
tctgatgtct tgcttggcg aatgttcatc ttatttcttc ctccctctca ataatttttt   1200
cattctatcc cttttctgta aagtttattt ttcagaatac ttttatcatc atgctttgaa   1260
aaaatatcac gataatatcc attgttctca cggaagcaca cgcaggtcat ttgaacgaat   1320
tttttcgaca ggaatttgcc gggactcagg agcatttaac ctaaaaaagc atgacatttc   1380
agcataatga acatttactc atgtctattt tcgttctttt ctgtatgaaa atagttattt   1440
cgagtctcta cggaaatagc gagagatgat atacctaaat agagataaaa tcatctcaaa   1500
aaaatgggtc tactaaaata ttattccatc tattacaata aattcacaga atagtctttt   1560
aagtaagtct actctgaatt tttttaaaag gagagggtaa agagtgtcat taccgttctt   1620
aacttctgca ccgggaaagg ttattatttt tggtgaacac tctgctgtgt acaacaagcc   1680
tgccgtcgct gctagtgtgt ctgcgttgag aacctacctg ctaataagcg agtcatctgc   1740
accagatact attgaattgg acttcccgga cattagcttt aatcataagt ggtccatcaa   1800
tgatttcaat gccatcaccg aggatcaagt aaactcccaa aaattggcca aggctcaaca   1860
agccaccgat ggcttgtctc aggaactcgt tagtcttttg gatccgttgt tagctcaact   1920
atccgaatcc ttccactacc atgcagcgtt ttgtttcctg tatatgtttg tttgcctatg   1980 ccccatgcc aagaatatta agttttcttt aaagtctact ttacccatcg gtgctgggtt   2040
gggctcaagc gcctctattt ctgtatcact ggccttagct atggcctact tggggggtt   2100 aataggatct aatgacttgg aaaagctgtc agaaaacgat aagcatatag tgaatcaatg   2160
ggccttcata ggtgaaaagt gtattcacgg tacccttca ggaatagata cgctgtggc   2220 cacttatggt aatgccctgc tatttgaaaa agactcacat aatggaacaa taaacacaaa   2280 caatttaag ttcttagatg atttcccagc cattccaatg atcctaacct atactagaat   2340
tccaaggtct acaaaagatc ttgttgctcg cgttcgtgtg ttggtcaccg agaaatttcc   2400
tgaagttatg aagccaattc tagatgccat gggtgaatgt gccctacaag cttagagat   2460 catgactaag ttaagtaaat gtaaaggcac cgatgacgag gctgtagaaa ctaataatga   2520
actgtatgaa caactattgg aattgataag aataaatcat ggactgcttg tctcaatcgg   2580
tgtttctcat cctggattag aacttattaa aaatctgagc gatgatttga gaattggctc   2640
cacaaaactt accggtgctg gtggcggcgg ttgctctttg actttgttac gaagagacat   2700
tactcaagag caaattgaca gcttcaaaaa gaaattgcaa gatgatttta gttacgagac   2760
atttgaaaca gacttgggtg ggactggctg ctgtttgtta agcgcaaaaa atttgaataa   2820
agatcttaaa atcaaatccc tagtattcca attatttgaa aataaaacta ccacaaagca   2880
acaaattgac gatctattat tgccaggaaa cacgaattta ccatggactt cataaaagga   2940
gagggtgtca gagttgagag ccttcagtgc cccaggaaa gcgttactag ctggtggata   3000
tttagtttta gatacaaaat atgaagcatt tgtagtcgga ttatcggcaa gaatgcatgc   3060
tgtagcccat ccttacggtt cattgcaagg gtctgataag tttgaagtgc gtgtgaaaag   3120
taaacaattt aaagatgggg agtggctgta ccatataagt cctaaaagtg gcttcattcc   3180
tgtttcgata ggcggatcta agaaccctt cattgaaaaa gttatcgcta acgtatttag   3240
ctactttaaa cctaacatgg acgactactg caatagaaac ttgttcgtta ttgatatttt   3300
ctctgatgat gcctaccatt ctcaggagga tagcgttacc gaacatcgtg caacagaag   3360 attgagtttt cattcgcaca gaattgaaga agttcccaaa acagggctgg gctcctcggc   3420
aggtttagtc acagttttaa ctacagcttt ggcctccttt tttgtatcgg acctggaaaa   3480
```

```
taatgtagac aaatatagag aagttattca taatttagca caagttgctc attgtcaagc   3540
tcagggtaaa attggaagcg ggtttgatgt agcggcggca gcatatggat ctatcagata   3600
tagaagattc ccacccgcat taatctctaa tttgccagat attggaagtg ctacttacgg   3660
cagtaaactg gcgcatttgg ttgatgaaga agactggaat attacgatta aaagtaacca   3720
tttaccttcg ggattaactt tatggatggg cgatattaag aatggttcag aaacagtaaa   3780
actggtccag aagtaaaaaa attggtatga ttcgcatatg ccagaaagct tgaaaatata   3840
tacagaactc gatcatgcaa attctagatt tatggatgga ctatctaaac tagatcgctt   3900
acacagagact catgacgatt acagcgatca gatatttgag tctcttgaga ggaatgactg   3960
tacctgtcaa aagtatcctg aaatcacaga agttagagat gcagttgcca caattagacg   4020
ttcctttaga aaaataacta aagaatctgg tgccgatatc gaacctcccg tacaaactag   4080
cttattggat gattgccaga ccttaaaagg agttcttact tgcttaatac ctggtgctgg   4140
tggttatgac gccattgcag tgattactaa gcaagatgtt gatcttaggg ctcaaaccgc   4200
taatgacaaa agatttcta aggttcaatg gctggatgta actcaggctg actggggtgt   4260
taggaaagaa aaagatccgg aaacttatct tgataaataa aaggagaggg tgaccgttta   4320
cacagcatcc gttaccgcac ccgtcaacat cgcaaccctt aagtattggg ggaaaaggga   4380
cacgaagttg aatctgccca ccaattcgtc catatcagtg actttatcgc aagatgacct   4440
cagaacgttg acctctgcgg ctactgcacc tgagtttgaa cgcgacactt tgtggttaaa   4500
tggagaacca cacagcatcg acaatgaaag aactcaaaat tgtctgcgcg acctacgcca   4560
attaagaaag gaaatggaat cgaaggacgc ctcattgccc acattatctc aatgaaaact   4620
ccacattgtc tccgaaaata actttcctac agcagctggt ttagcttcct ccgctgctgg   4680
ctttgctgca ttggtctctg caattgctaa gttataccaa ttaccacagt caacttcaga   4740
aatatctaga atagcaagaa aggggtctgg ttcagcttgt agatcgttgt ttggcggata   4800
cgtggcctgg gaaatgggaa aagctgaaga tggtcatgat tccatggcag tacaaatcgc   4860
agacagctct gactggcctc agatgaaagc ttgtgtccta gttgtcagcg atattaaaaa   4920
ggatgtgagt tccactcagg gtatgcaatt gaccgtggca acctccgaac tatttaaaga   4980
aagaattgaa catgtcgtac caaagagatt tgaagtcatg cgtaaagcca ttgttgaaaa   5040
agatttcgcc acctttgcaa aggaaacaat gatggattcc aactctttcc atgccacatg   5100
tttggactct ttccctccaa tattctacat gaatgacact tccaagcgta tcatcagttg   5160
gtgccacacc attaatcagt tttacggaga acaatcgtt gcatacacgt ttgatgcagg   5220
tccaaatgct gtgttgtact acttagctga aaatgagtcg aaactctttg catttatcta   5280
taaattgttt ggctctgttc ctggatggga caagaaattt actactgagc agcttgaggc   5340
tttcaaccat caatttgaat catctaactt tactgcacgt gaattggatc ttgagttgca   5400
aaaggatgtt gccagagtga ttttaactca agtcggttca ggcccacaag aaacaaacga   5460
atctttgatt gacgcaaaga ctggtctacc aaaggaataa aaggagaggg tgactgccga   5520
caacaatagt atgccccatg gtgcagtatc tagttacgcc aaattagtgc aaaaccaaac   5580
acctgaagac attttggaag agtttcctga aattattcca ttacaacaaa gacctaatac   5640
ccgatctagt gagacgtcaa atgacgaaag cggagaaaca tgttttctg gtcatgatga   5700
ggagcaaatt aagttaatga atgaaaattg tattgttttg gattgggacg ataatgctat   5760
tggtgccggt accaagaaag tttgtcattt aatgaaaaat attgaaaagg gtttactaca   5820
tcgtgcattc tccgtcttta ttttcaatga acaaggtgaa ttacttttac aacaaagagc   5880
```

```
cactgaaaaa ataactttcc ctgatctttg gactaacaca tgctgctctc atccactatg   5940
tattgatgac gaattaggtt tgaagggtaa gctagacgat aagattaagg gcgctattac   6000
tgcggcggtg agaaaactag atcatgaatt aggtattcca gaagatgaaa ctaagacaag   6060
gggtaagttt cacttttaa acagaatcca ttacatggca ccaagcaatg aaccatgggg   6120
tgaacatgaa attgattaca tcctatttta aagatcaac gctaaagaaa acttgactgt   6180
caacccaaac gtcaatgaag ttagagactt caaatgggtt tcaccaaatg atttgaaaac   6240
tatgtttgct gacccaagtt acaagtttac gccttggttt aagattattt gcgagaatta   6300
cttattcaac tggtgggagc aattagatga cctttctgaa gtggaaaatg acaggcaaat   6360
tcatagaatg ctataaaaaa aaccggcctt ggccccgccg gttttttatt attttttcttc   6420 ctccgcatgt tcaatccgct ccataatcga cggatggctc cctctgaaaa ttttaacgag   6480
aaacggcggg ttgacccggc tcagtcccgt aacggccaag tcctgaaacg tctcaatcgc   6540
cgcttcccgg tttccggtca gctcaatgcc gtaacggtcg gcggcgtttt cctgataccg   6600
ggagacggca ttcgtaattt gaatacatac gaacaaatta ataaagtgaa aaaaatactt   6660
cggaaacatt taaaaaataa ccttattggt acttacatgt ttggatcagg agttgagagt   6720
ggactaaaac caaatagtga tcttgacttt ttagtcgtcg tatctgaacc attgacagat   6780
caaagtaaag aaatacttat acaaaaaatt agacctattt caaaaaaaat aggagataaa   6840
agcaacttac gatatattga attaacaatt attattcagc aagaaatggt accgtggaat   6900
catcctccca aacaagaatt tatttatgga gaatggttac aagagcttta tgaacaagga   6960
tacattcctc agaaggaatt aaattcagat ttaaccataa tgctttacca agcaaaacga   7020
aaaaataaaa gaatatacgg aaattatgac ttagaggaat tactacctga tattccattt   7080
tctgatgtga gaagagccat tatggattcg tcagaggaat taatagataa ttatcaggat   7140
gatgaaacca actctatatt aactttatgc cgtatgattt taactatgga cacgggtaaa   7200
atcataccaa aagatattgc gggaaatgca gtggctgaat cttctccatt agaacatagg   7260
gagagaattt tgttagcagt tcgtagttat cttggagaga atattgaatg gactaatgaa   7320
aatgtaaatt taactataaa ctatttaaat aacagattaa aaaaattata atgtaacctt   7380
tgctttcaaa tgagtagaaa taatgcacat ccatgtttgt atcgtgcaaa taaagtgttt   7440
catccgtagg aaaaaatgac tttagtatct gttccgcttt ttctgatgaa atgtgctccc   7500
cgacaaaatt gaatgaatca tggacatttg ctggctttga tacagcgaaa gcagccgttc   7560
ctatgttata tatcggattt aacagcagga caaaaaacac catgacagcc atcgtcaccc   7620
acttattcac acgcacataa acctttcctg acttttggaa cagatgatag ctcatcaaaa   7680
atcccgccat tgccaaataa atcgtatatg gcattactgc accataatct tttgagattt   7740
gattgggata tggcgcaagc agcaagacaa gcagtccgat aatcagcgta taaaataagc   7800
ctagtaagat cttatccgtt ctccaataca gcttgaaaaa cactacattc aacgcaatgg   7860
gaagagtgat gatgaaaaac agaaacacga atgcaatcgg ctccatccca tccgggtatt   7920
ccttccaata cgaaagaaa ctaaaaatca tttgtacgat cggcaaactg acaacagcaa   7980
ggtcgaacgt ataaaactta ccctttccgc catgatcacg cggcatcagc atatagtgaa   8040
aagccgtcag cagcacatat ccgtataaca aaaaatgcag cagcggcagc agttctttc    8100 cgtcctctct taagtaagcg ctggtgaagt ttgttgattg cacctggtga ataagttcaa   8160
cagacactcc cgccagcagc acaatccgca atataacacc cgccaagaac attgtgcgct   8220
```

```
gccggtttat tttgggatga tgcaccaaaa gatataagcc cgccagaaca acaattgacc    8280
attgaatcag cagggtgctt tgtctgctta atataaaata acgttcgaaa tgcaatacat    8340
aatgactgaa taactccaac acgaacaaca aaagtgcgca ttttataaaa gctaatgatt    8400
cagtccacat aattgataga cgaattctgc tacaggtcac gtggctatgt gaaggatcgc    8460
gcgtccagtt aagagcaaaa acattgacaa aaaaatttat ttatgctaaa atttactatt    8520
aatatatttg tatgtataat aagattctcc tggccagggg aatcttattt tttgtggagg    8580
atcatttcat gaggaaaaat gagtccagct taacgtctct aatttcagct tttgcccgtg    8640
catatcacag ccgatatgac acacctctta tttttgatga ttttatcgca aaagatctca    8700
ttaacgaaaa agagtttatc gacatcagta aaaatatgat tcaagaaata tcgtttttca    8760
acaaagagat cgccgaacgt cttcaaaatg atcctgaaaa aatattaaaa tgggttgcac    8820
aaatccagct gtctccaacg cccctagcac gtgcttctta ttgtgaaaaa gtcttgcaca    8880
acgaattaat cctgggggca aaacagtatg tcattcttgg agcgggactg gatactttct    8940
gcttccggca tccagaatta gaaaacagct tacaggtttt cgaggttgat catccggcca    9000
cacagcaatt gaaaaaaaat aagctgaagg atgcaaatct gacaattccg ggtcatcttc    9060
attttgttcc tatggatttc accaaaacgt tttcgtatga tcctctctta gatgaaggat    9120
ttaaaaacac aaaaacattc ttcagccttc tcggagtgtc ttattatgta acacgggaag    9180
aaaatgcaag cttgatcagc aatttatttt ctcatgtccc gcctggaagc tctattgttt    9240
ttgattatgc ggacgaaaca cttttttacag caaaagggac gtcgaatcga gttgaacata    9300
tggtgaagat ggctgccgca agcggggaac cgatgaaatc atgtttcact tatcaagaga    9360
ttgaacatct g                                                         9371

<210> SEQ ID NO 48
<211> LENGTH: 4339
<212> TYPE: DNA
<213> ORGANISM: Artificial Sequence
<220> FEATURE:
<223> OTHER INFORMATION: Synthetic Construct

<400> SEQUENCE: 48
tagaaaaact catcgagcat caaatgaaac tgcaatttat tcatatcagg attatcaata      60
ccatattttt gaaaaagccg tttctgtaat gaaggagaaa actcaccgag gcagttccat     120
aggatggcaa gatcctggta tcggtctgcg attccgactc gtccaacatc aatacaacct     180
attaatttcc cctcgtcaaa ataaggttca caagtgagaa atcaccatga agtgacgact     240
gaatccggtg agaatggcaa aagtttatgc atttcttttcc agacttgttc aacaggccag     300
ccattacgct cgtcatcaaa atcactcgca tcaaccaaac cgttattcat tcgtgattgc     360
gcctgagcga ggcgaaatac gcgatcgctg ttaaaaggac aattacaaac aggaatcgag     420
tgcaaccggc gcaggaacac tgccagcgca tcaacaatat tttcacctga atcaggatat     480
tcttctaata cctggaacgc tgttttttccg gggatcgcag tggtgagtaa ccatgcatca     540
tcaggagtac ggataaaatg cttgatggtc ggaagtggca taaattccgt cagccagttt     600
agtctgacca tctcatctgt aacatcattg caacgctac cttgccatg tttcagaaac     660 aactctggcg catcgggctt cccatacaag cgatagattg tcgcacctga ttgcccgaca     720
ttatcgcgag cccatttata cccatataaa tcagcatcca tgttggaatt taatcgcggc     780
ctcgacgttt cccgttgaat atggctcata ttcttccttt ttcaatatta ttgaagcatt     840
tatcagggtt attgtctcat gagcggatac atatttgaat gtatttagaa aaataaacaa     900
```

```
ataggggtca gtgttacaac caattaacca attctgaaca ttatcgcgag cccatttata    960
cctgaatatg gctcataaca cccettgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggcctttcg cccgggctaa ttaggggggtg tcgcccttta gtcgctgaac atgtgctctg   1200
tttctaccga gaacgtttcc ttcactgaga cggaaaccga ggcacgtcgt agcgcgaact   1260
acgagccgaa tagctgggac tacgatttcc tgctgtcttc cgatactgac gaatctattg   1320
aggtgtacaa agacaaagca aagaaactgg aggctgaagt gcgccgcgaa attaacaacg   1380
agaaagctga attcctgact ctgctggagc tgatcgataa cgtacagcgc ctgggtctgg   1440
gttaccgctt cgaatctgat atccgtcgcg cactggatcg tttcgtaagc agcggcggtt   1500
tcgatggcgt gaccaaaacg agcctgcacg ctaccgcgct gtccttccgt ctgctgcgtc   1560
agcacgcgtt cgaagtttct caggaagcat tctccggttt caaagatcaa aacggtaact   1620
tcctggaaaa cctgaaagaa gacactaagg cgatcctgag cctgtatgag gcaagctttc   1680
tggccctgga gggtgagaac atcctggatg aggcgcgcgt attcgccatc tcccatctga   1740
aagagctgtc tgaagagaaa atcggtaagg aactggcaga gcaggttaat cacgcactgg   1800
aactgccgct gcatcgtcgt acccagcgtc tggaggcggt ttggtccatc gaagcgtacc   1860
gcaaaaagga ggatgctaac caggttctgc tggaactggc catcctggac tacaacatga   1920
tccagtccgt ttaccagcgt gatctgcgtg aaacctcccg ttggtggcgc cgtgtgggcc   1980
tggcgaccaa actgcacttc gctaaggacc gcctgattga gtcttttttac tgggcagtcg   2040
gcgttgcgtt cgaacctcag tattctgact gccgtaacag cgttgcgaaa atgttcagct   2100
tcgttactat tatcgacgac atctacgacg tttacggtac tctggacgag ctggaactgt   2160
ttaccgacgc tgtcgaacgt tgggatgtta acgccatcaa cgatctgcct gactacatga   2220
aactgtgctt cctggcactg tataacacga tcaacgaaat tgcatacgac aacctgaaag   2280
acaaaggtga aaacatcctg ccgtacctga ctaaagcgtg gcggatctg tgtaacgctt   2340
ttctgcaaga agcgaaatgg ctgtataaca aatccactcc gaccttttgac gattatttcg   2400
gcaatgcctg gaaatccagc tctggcccgc tgcaactgat cttcgcttat tttgcggttg   2460
tccaaaacat caaaaaggag gaaattgaaa acctgcaaaa ataccacgat atcattagcc   2520
gtccttctca tatctttcgc ctgtgcaacg acctggcaag cgcgtccgca gagatcgcac   2580
gtggcgaaac cgctaactct gtttcctgct acatgcgcac caagggcatt tccgaagagc   2640
tggcaaccga gagcgtaatg aatctgatcg acgaaacctg taagaaaatg aacaaagaaa   2700
aactgggtgg ctccctgttc gctaaaccgt tcgtagagac tgctattaac ctggcacgtc   2760
agagccactg cacctaccac aatggtgacg cacatactag cccggatgaa ctgactcgta   2820
aacgtgtact gtctgttatc accgaaccga ttctgccgtt cgaacgttaa ctgcagcgtc   2880
aatcgaaagg gcgacacaaa atttattcta aatgcataat aaatactgat aacatcttat   2940
agtttgtatt atattttgta ttatcgttga catgtataat tttgatatca aaaactgatt   3000
ttcccttat tattttcgag attttatttttc ttaattctct ttaacaaact agaaatattg   3060
tatatacaaa aaatcataaa taatagatga atagtttaat tataggtgtt catcaatcga   3120
aaaagcaacg tatcttattt aaagtgcgtt gcttttttttct catttataag gttaaataat   3180
tctcatatat caagcaaagt gacaggcgcc cttaaatatt ctgacaaatg ctctttccct   3240
```

```
aaactccccc cataaaaaaa cccgccgaag cgggttttta cgttatttgc ggattaacga    3300
ttactcgtta tcagaaccgc caggggggcc cgagcttaag actggccgtc gttttacaac    3360
acagaaagag tttgtagaaa cgcaaaaagg ccatccgtca ggggccttct gcttagtttg    3420
atgcctggca gttccctact ctcgccttcc gcttcctcgc tcactgactc gctgcgctcg    3480
gtcgttcggc tgcggcgagc ggtatcagct cactcaaagg cggtaatacg gttatccaca    3540
gaatcagggg ataacgcagg aaagaacatg tgagcaaaag gccagcaaaa ggccaggaac    3600
cgtaaaaagg ccgcgttgct ggcgtttttc cataggctcc gcccccctga cgagcatcac    3660
aaaaatcgac gctcaagtca gaggtggcga acccgacag gactataaag ataccaggcg     3720
tttccccctg gaagctccct cgtgcgctct cctgttccga ccctgccgct taccggatac    3780
ctgtccgcct ttctcccttc gggaagcgtg gcgctttctc atagctcacg ctgtaggtat    3840
ctcagttcgg tgtaggtcgt tcgctccaag ctgggctgtg tgcacgaacc ccccgttcag    3900
cccgaccgct gcgccttatc cggtaactat cgtcttgagt ccaacccggt aagacacgac    3960
ttatcgccac tggcagcagc cactggtaac aggattagca gagcgaggta tgtaggcggt    4020
gctacagagt tcttgaagtg gtgggctaac tacggctaca ctagaagaac agtatttggt    4080
atctgcgctc tgctgaagcc agttaccttc ggaaaaagag ttggtagctc ttgatccggc    4140
aaacaaacca ccgctggtag cggtggtttt tttgtttgca agcagcagat tacgcgcaga    4200
aaaaaaggat ctcaagaaga tcctttgatc ttttctacgg ggtctgacgc tcagtggaac    4260
gacgcgcgcg taactcacgt taagggattt tggtcatgag cttgcgccgt cccgtcaagt    4320
cagcgtaatg ctctgctttt                                                4339

<210> SEQ ID NO 49
<211> LENGTH: 6065
<212> TYPE: DNA
<213> ORGANISM: Artificial Sequence
<220> FEATURE:
<223> OTHER INFORMATION: Synthetic Construct

<400> SEQUENCE: 49
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatgtgctc     420
tgtttctacc gagaacgttt ccttcactga gacggaaacc gaggcacgtc gtagcgcgaa     480
ctacgagccg aatagctggg actacgattt cctgctgtct tccgatactg acgaatctat     540
tgaggtgtac aaagacaaag caaagaaact ggaggctgaa gtgcgccgcg aaattaacaa     600
cgagaaagct gaattcctga ctctgctgga gctgatcgat aacgtacagc gcctgggtct     660
gggttaccgt tcgaatctg atatccgtcg cgcactggat cgtttcgtaa gcagcggcgg     720
tttcgatggc gtgaccaaaa cgagcctgca cgctaccgcg ctgtccttcc gtctgctgcg     780
tcagcacggc ttcgaagttt ctcaggaagc attctccggt ttcaaagatc aaaacggtaa     840
cttcctggaa aacctgaaag aagacactaa ggcgatcctg agcctgtatg aggcaagctt     900 tctggcccctg gagggtgaga acatcctgga tgaggcgcgc gtattcgcca tctcccatct     960
```

```
gaaagagctg tctgaagaga aaatcggtaa ggaactggca gagcaggtta atcacgcact    1020
ggaactgccg ctgcatcgtc gtacccagcg tctggaggcg gtttggtcca tcgaagcgta    1080
ccgcaaaaag gaggatgcta accaggttct gctggaactg ccatcctgg actacaacat     1140 gatccagtcc gtttaccagc gtgatctgcg tgaaacctcc cgttggtggc gccgtgtggg    1200
cctggcgacc aaactgcact tcgctaagga ccgcctgatt gagtcttttt actgggcagt    1260
cggcgttgcg ttcgaacctc agtattctga ctgccgtaac agcgttgcga aaatgttcag    1320
cttcgttact attatcgacg acatctacga cgtttacggt actctggacg agctggaact    1380
gtttaccgac gctgtcgaac gttgggatgt taacgccatc aacgatctgc ctgactacat    1440
gaaactgtgc ttcctggcac tgtataacac gatcaacgaa attgcatacg acaacctgaa    1500
agacaaaggt gaaaacatcc tgccgtacct gactaaagcg tgggcggatc tgtgtaacgc    1560
ttttctgcaa gaagcgaaat ggctgtataa caaatccact ccgacctttg acgattattt    1620
cggcaatgcc tggaaatcca gctctggccc gctgcaactg atcttcgctt attttgcggt    1680
tgtccaaaac atcaaaaagg aggaaattga aaacctgcaa aaataccacg atatcattag    1740
ccgtccttct catatctttc gcctgtgcaa cgacctggca agcgcgtccg cagagatcgc    1800
acgtggcgaa accgctaact ctgtttcctg ctacatgcgc accaagggca tttccgaaga    1860
gctggcaacc gagagcgtaa tgaatctgat cgacgaaacc tgtaagaaaa tgaacaaaga    1920
aaaactgggt ggctccctgt cgctaaacc gttcgtagag actgctatta acctggcacg    1980
tcagagccac tgcacctacc acaatggtga cgcacatact agcccggatg aactgactcg    2040
taaacgtgta ctgtctgtta tcaccgaacc gattctgccg ttcgaacgtt aactgcagct    2100
ggtaccatat gggaattcga agcttttctag aacaaaaact catctcagaa gaggatctga    2160
atagcgccgt cgaccatcat catcatcatc attgagttta acggtctcc agcttggctg    2220 ttttggcgga tgagaagaa ttttcagcct gatacagatt aaatcagaac gcagaagcgg    2280
tctgataaaa cagaatttgc ctggcggcag tagcgcggtg gtcccacctg accccatgcc    2340
gaactcagaa gtgaaacgcc gtagcgccga tggtagtgtg gggtctcccc atgcgagagt    2400
agggaactgc caggcatcaa ataaaacgaa aggctcagtc gaaagactgg gcctttcgtt    2460
ttatctgttg tttgtcggtg aacgctctcc tgagtaggac aaatccgccg ggagcggatt    2520
tgaacgttgc gaagcaacgg cccggagggt ggcgggcagg acgcccgcca taaactgcca    2580
ggcatcaaat taagcagaag gccatcctga cggatggcct ttttgcgttt ctacaaactc    2640
tttttgttta tttttctaaa tacattcaaa tatgtatccg ctcatgagac aataaccctg    2700
ataaatgctt caataatatt gaaaaggaa gagtatgagt attcaacatt tccgtgtcgc    2760
ccttattccc tttttgcgg cattttgcct tcctgttttt gctcacccag aaacgctggt    2820
gaaagtaaaa gatgctgaag atcagttggg tgcacgagtg ggttacatcg aactggatct    2880
caacagcggt aagatcctg agagttttcg ccccgaagaa cgttttccaa tgatgagcac    2940
ttttaaagtt ctgctatgtg gcgcggtatt atcccgtgtt gacgccgggc aagagcaact    3000
cggtcgccgc atacactatt ctcagaatga cttggttgag tactcaccag tcacagaaaa    3060
gcatcttacg gatggcatga cagtaagaga attatgcagt gctgccataa ccatgagtga    3120
taacactgcg gccaacttac ttctgacaac gatcggagga ccgaaggagc taaccgcttt    3180
tttgcacaac atgggggatc atgtaactcg ccttgatcgt tgggaaccgg agctgaatga    3240
agccatacca aacgacgagc gtgacaccac gatgcctgta gcaatggcaa caacgttgcg    3300
```

```
caaactatta actggcgaac tacttactct agcttcccgg caacaattaa tagactggat    3360
ggaggcggat aaagttgcag gaccacttct gcgctcggcc cttccggctg ctggtttat     3420
tgctgataaa tctggagccg gtgagcgtgg gtctcgcggt atcattgcag cactggggcc    3480
agatggtaag ccctcccgta tcgtagttat ctacacgacg gggagtcagg caactatgga    3540
tgaacgaaat agacagatcg ctgagatagg tgcctcactg attaagcatt ggtaactgtc    3600
agaccaagtt tactcatata tactttagat tgatttaaaa cttcattttt aatttaaaag    3660
gatctaggtg aagatccttt ttgataatct catgaccaaa atcccttaac gtgagttttc    3720
gttccactga gcgtcagacc ccgtagaaaa gatcaaagga tcttcttgag atccttttt     3780
tctgcgcgta atctgctgct tgcaaacaaa aaaaccaccg ctaccagcgg tggtttgttt    3840
gccggatcaa gagctaccaa ctcttttttcc gaaggtaact ggcttcagca gagcgcagat   3900
accaaatact gtccttctag tgtagccgta gttaggccac cacttcaaga actctgtagc    3960
accgcctaca tacctcgctc tgctaatcct gttaccagtg ctgctgcca gtggcgataa     4020
gtcgtgtctt accgggttgg actcaagacg atagttaccg gataaggcgc agcggtcggg    4080
ctgaacgggg ggttcgtgca cacagcccag cttggagcga acgacctaca ccgaactgag    4140
atacctacag cgtgagctat gagaaagcgc cacgcttccc gaagggagaa aggcggacag    4200
gtatccggta agcggcaggg tcggaacagg agagcgcacg agggagcttc caggggggaaa   4260
cgcctggtat ctttatagtc ctgtcgggtt tcgccacctc tgacttgagc gtcgattttt    4320
gtgatgctcg tcagggggc ggagcctatg gaaaaacgcc agcaacgcgg cctttttacg     4380
gttcctggcc ttttgctggc cttttgctca catgttcttt cctgcgttat cccctgattc    4440
tgtggataac cgtattaccg cctttgagtg agctgatacc gctcgccgca gccgaacgac    4500
cgagcgcagc gagtcagtga gcgaggaagc ggaagagcgc ctgatgcggt attttctcct    4560
tacgcatctg tgcggtattt cacaccgcat atggtgcact ctcagtacaa tctgctctga    4620
tgccgcatag ttaagccagt atacactccg ctatcgctac gtgactgggt catggctgcg    4680
ccccgacacc cgccaacacc cgctgacgcg ccctgacggg cttgtctgct cccggcatcc    4740
gcttacagac aagctgtgac cgtctccggg agctgcatgt gtcagaggtt ttcaccgtca    4800
tcaccgaaac gcgcgaggca gcagatcaat tcgcgcgcga aggcgaagcg gcatgcattt    4860
acgttgacac catcgaatgg tgcaaaacct ttcgcggtat ggcatgatag cgcccggaag    4920
agagtcaatt cagggtggtg aatgtgaaac cagtaacgtt atacgatgtc gcagagtatg    4980
ccggtgtctc ttatcagacc gtttcccgcg tggtgaacca ggccagccac gtttctgcga    5040
aaacgcggga aaaagtggaa gcggcgatgg cggagctgaa ttacattccc aaccgcgtgg    5100
cacaacaact ggcgggcaaa cagtcgttgc tgattggcgt tgccacctcc agtctggccc    5160
tgcacgcgcc gtcgcaaatt gtcgcggcga ttaaatctcg cgccgatcaa ctgggtgcca    5220
gcgtggtggt gtcgatggta gaacgaagcg gcgtcgaagc ctgtaaagcg gcggtgcaca    5280
atcttctcgc gcaacgcgtc agtgggctga tcattaacta tccgctggat gaccaggatg    5340
ccattgctgt ggaagctgcc tgcactaatg ttccggcgtt atttcttgat gtctctgacc    5400
agacacccat caacagtatt attttctccc atgaagacgg tacgcgactg ggcgtggagc    5460
atctggtcgc attgggtcac cagcaaatcg cgctgttagc gggcccatta agttctgtct    5520
cggcgcgtct gcgtctggct ggctggcata aatatctcac tcgcaatcaa attcagccga    5580
tagcggaacg ggaaggcgac tggagtgcca tgtccggttt tcaacaaacc atgcaaatgc    5640
tgaatgaggg catcgttccc actgcgatgc tggttgccaa cgatcagatg gcgctgggcg    5700
```

```
caatgcgcgc cattaccgag tccgggctgc gcgttggtgc ggatatctcg gtagtgggat    5760
acgacgatac cgaagacagc tcatgttata tcccgccgtc aaccaccatc aaacaggatt    5820
ttcgcctgct ggggcaaacc agcgtggacc gcttgctgca actctctcag gccaggcgg     5880 tgaagggcaa tcagctgttg cccgtctcac tggtgaaaag aaaaaccacc ctggcgccca    5940
atacgcaaac cgcctctccc cgcgcgttgg ccgattcatt aatgcagctg gcacgacagg    6000
tttcccgact ggaaagcggg cagtgagcgc aacgcaatta atgtgagtta gcgcgaattg    6060
atctg                                                               6065
```

<210> SEQ ID NO 50
<211> LENGTH: 6912
<212> TYPE: DNA
<213> ORGANISM: Artificial Sequence
<220> FEATURE:
<223> OTHER INFORMATION: Synthetic Construct

<400> SEQUENCE: 50

```
ttgtctgctc ccggcatccg cttacagaca agctgtgacc gtctccggga gctgcatgtg      60
tcagaggttt tcaccgtcat caccgaaacg cgcgaggcag cagatcaatt cgcgcgcgaa     120
ggcgaagcgg catgcattta cgttgacacc atcgaatggt gcaaaacctt cgcggtatg      180 gcatgatagc gcccggaaga gagtcaattc agggtggtga atgtgaaacc agtaacgtta    240
tacgatgtcg cagagtatgc cggtgtctct tatcagaccg tttcccgcgt ggtgaaccag    300
gccagccacg tttctgcgaa aacgcgggaa aaagtggaag cggcgatggc ggagctgaat    360
tacattccca accgcgtggc acaacaactg gcgggcaaac agtcgttgct gattggcgtt    420
gccacctcca gtctggccct gcacgcgccg tcgcaaattg tcgcggcgat taaatctcgc    480
gccgatcaac tgggtgccag cgtggtggtg tcgatggtag aacgaagcgg cgtcgaagcc    540
tgtaaagcgg cggtgcacaa tcttctcgcg caacgcgtca gtgggctgat cattaactat    600
ccgctggatg accaggatgc cattgctgtg gaagctgcct gcactaatgt tccggcgtta    660
tttcttgatg tctctgacca gacacccatc aacagtatta ttttctccca tgaagacggt    720
acgcgactgg gcgtggagca tctggtcgca ttgggtcacc agcaaatcgc gctgttagcg    780
ggcccattaa gttctgtctc ggcgcgtctg cgtctggctg gctggcataa atatctcact    840
cgcaatcaaa ttcagccgat agcggaacgg gaaggcgact ggagtgccat gtccggtttt    900
caacaaacca tgcaaatgct gaatgagggc atcgttccca ctgcgatgct ggttgccaac    960
gatcagatgg cgctgggcgc aatgcgcgcc attaccgagt ccgggctgcg cgttggtgcg   1020
gatatctcgg tagtgggata cgacgatacc gaagacagct catgttatat cccgccgtca   1080
accaccatca acaggatttt cgcctgctg ggcaaaacca gcgtggaccg cttgctgcaa    1140
ctctctcagg ccaggcggt gaagggcaat cagctgttgc ccgtctcact ggtgaaaga     1200 aaaaccaccc tggcgcccaa tacgcaaacc gcctctcccc gcgcgttggc cgattcatta   1260
atgcagctgg cacgacaggt ttcccgactg gaaagcgggc agtgagcgca acgcaattaa   1320
tgtgagttag cgcgaattga tctggttga cagcttatca tcgactgcac ggtgcaccaa    1380
tgcttctggc gtcaggcagc catcggaagc tgtggtatgg ctgtgcaggt cgtaaatcac   1440
tgcataattc gtgtcgctca aggcgcactc ccgttctgga taatgttttt tgcgccgaca   1500
tcataacggt tctggcaaat attctgaaat gagctgttga caattaatca tccggctcgt   1560
ataatgtgtg gaattgtgag cggataacaa tttcacacag gaaacagcgc cgctgagaaa   1620
```

```
aagcgaagcg gcactgctct ttaacaattt atcagacaat ctgtgtgggc actcgaccgg   1680
aattatcgat taactttatt attaaaaatt aaagaggtat atattaatgt atcgattaaa   1740
taaggaggaa taaaccatgt gtgcgacctc ttctcaattt actcagatta ccgagcataa   1800
ttcccgtcgt tccgcaaact atcagccaaa cctgtggaat ttcgaattcc tgcaatccct   1860
ggagaacgac ctgaaagtgg aaaagctgga ggagaaagcg accaaactgg aggaagaagt   1920
tcgctgcatg atcaaccgtg tagacaccca gccgctgtcc ctgctggagc tgatcgacga   1980
tgtgcagcgc ctgggtctga cctacaaatt tgaaaaagac atcattaaag ccctggaaaa   2040
catcgtactg ctggacgaaa acaaaaagaa caaatctgac ctgcacgcaa ccgctctgtc   2100
tttccgtctg ctgcgtcagc acggtttcga ggtttctcag gatgttttg agcgtttcaa    2160 ggataaagaa ggtggtttca gcggtgaact gaaaggtgac gtccaaggcc tgctgagcct   2220
gtatgaagcg tcttacctgg gtttcgaggg tgagaacctg ctggaggagg cgcgtacctt   2280
ttccatcacc cacctgaaga caacctgaa agaaggcatt aataccaagg ttgcagaaca    2340
agtgagccac gccctggaac tgccatatca ccagcgtctg caccgtctgg aggcacgttg   2400
gttcctggat aaatacgaac cgaaagaacc gcatcaccag ctgctgctgg agctggcgaa   2460
gctggatttt aacatggtac agaccctgca ccagaaagag ctgcaagatc tgtcccgctg   2520
gtggaccgag atgggcctgg ctagcaaact ggattttgta cgcgaccgcc tgatggaagt   2580
ttatttctgg gcactgggta tggcgccaga cccgcagttt ggtgaatgtc gcaaagctgt   2640
tactaaaatg tttggtctgg tgacgatcat cgatgacgtg tatgacgttt atggcactct   2700
ggacgaactg caactgttca ccgatgctgt agagcgctgg gacgttaacg ctattaacac   2760
cctgccggac tatatgaaac tgtgtttcct ggcactgtac aacaccgtta cgacacgtc    2820 ctattctatt ctgaaagaga aaggtcataa caacctgtcc tatctgacga aaagctggcg   2880
tgaactgtgc aaagcctttc tgcaagaggc gaaatggtcc aacaacaaaa ttatcccggc   2940
tttctccaag tacctggaaa acgccagcgt ttcctcctcc ggtgtagcgc tgctggcgcc   3000
gtcttacttt tccgtatgcc agcagcagga agacatctcc gaccacgcgc tgcgttccct   3060
gaccgacttc catggtctgg tgcgttctag ctgcgttatc ttccgcctgt gcaacgatct   3120
ggccacctct gcggcggagc tggaacgtgg cgagactacc aattctatca ttagctacat   3180
gcacgaaaac gatggtacca gcgaggaaca ggcccgcgaa gaactgcgta aactgatcga   3240
cgccgaatgg aaaagatga atcgtgaacg cgttagcgac tccaccctgc tgcctaaagc    3300
gttcatggaa atcgcagtta acatggcacg tgtttcccac tgcacctacc agtatgcga    3360 tggtctgggt cgcccagact acgcgactga aaccgcatc aaactgctgc tgattgaccc    3420
tttcccgatt aaccagctga tgtatgtcta actgcatcgc ccttaggagg taaaaaaaaa   3480
tgactgccga caacaatagt atgccccatg gtgcagtatc tagttacgcc aaattagtgc   3540
aaaaccaaac acctgaagac attttggaag agtttcctga attattcca ttacaacaaa    3600 gacctaatac ccgatctagt gagacgtcaa atgacgaaag cggagaaaca tgttttctg    3660 gtcatgatga ggagcaaatt aagttaatga atgaaaattg tattgttttg gattgggacg   3720
ataatgctat tggtgccggt accaagaaag tttgtcattt aatggaaaat attgaaaagg   3780
gtttactaca tcgtgcattc tccgtcttta ttttcaatga acaaggtgaa ttacttttac   3840
aacaaagagc cactgaaaaa ataacttttc ctgatctttg gactaacaca tgctgctctc   3900
atccactatg tattgatgac gaattaggtt tgaagggtaa gctagcgat aagattaagg    3960 gcgctattac tgcggcggtg agaaaactag atcatgaatt aggtattcca gaagatgaaa   4020
```

```
ctaagacaag gggtaagttt cacttttaa acagaatcca ttacatggca ccaagcaatg    4080
aaccatgggg tgaacatgaa attgattaca tcctatttta taagatcaac gctaaagaaa    4140
acttgactgt caacccaaac gtcaatgaag ttagagactt caaatgggtt tcaccaaatg    4200
atttgaaaac tatgtttgct gacccaagtt acaagtttac gccttggttt aagattattt    4260
gcgagaatta cttattcaac tggtgggagc aattagatga cctttctgaa gtggaaaatg    4320
acaggcaaat tcatagaatg ctataacaac gcgtcctgca gctggtacca tatgggaatt    4380
cgaagctttc tagaacaaaa actcatctca gaagaggatc tgaatagcgc cgtcgaccat    4440
catcatcatc atcattgagt ttaaacggtc tccagcttgg ctgttttggc ggatgagaga    4500
agattttcag cctgatacag attaaatcag aacgcagaag cggtctgata aaacagaatt    4560
tgcctggcgg cagtagcgcg gtggtcccac ctgaccccat gccgaactca gaagtgaaac    4620
gccgtagcgc cgatggtagt gtggggtctc cccatgcgag agtagggaac tgccaggcat    4680
caaataaaac gaaaggctca gtcgaaagac tgggcctttc gttttatctg ttgtttgtcg    4740
gtgaacgctc tcctgagtag acaaatccg  ccgggagcgg atttgaacgt tgcgaagcaa    4800
cggcccggag ggtggcgggc aggacgcccg ccataaactg ccaggcatca aattaagcag    4860
aaggccatcc tgacggatgg cctttttgcg tttctacaaa ctcttttgt  ttatttttct    4920
aaatacattc aaatatgtat ccgcttaacc ggaattgcca gctggggcgc cctctggtaa    4980
ggttgggaag ccctgcaaag taaactggat ggctttctcg ccgccaagga tctgatggcg    5040
caggggatca gctctgatc  aagagacagg atgaggatcg tttcgcatga ttgaacaaga    5100
tggattgcac gcaggttctc cggccgcttg ggtggagagg ctattcggct atgactgggc    5160
acaacagaca atcggctgct ctgatgccgc cgtgttccgg ctgtcagcgc aggggcgccc    5220
ggttctttt  gtcaagaccg acctgtccgg tgccctgaat gaactgcaag acgaggcagc    5280
gcggctatcg tggctggcca cgacgggcgt tccttgcgca gctgtgctcg acgttgtcac    5340
tgaagcggga agggactggc tgctattggg cgaagtgccg gggcaggatc tcctgtcatc    5400
tcaccttgct cctgccgaga aagtatccat catggctgat gcaatgcggc ggctgcatac    5460
gcttgatccg gctacctgcc cattcgacca ccaagcgaaa catcgcatcg agcgagcacg    5520
tactcggatg gaagccggtc ttgtcgatca ggatgatctg gacgaagagc atcaggggct    5580
cgcgccagcc gaactgttcg ccaggctcaa ggcgagcatg cccgacggcg aggatctcgt    5640
cgtgacccat ggcgatgcct gcttgccgaa tatcatggtg gaaaatggcc gcttttctgg    5700
attcatcgac tgtggccggc tgggtgtggc ggaccgctat caggacatag cgttggctac    5760
ccgtgatatt gctgaagagc ttggcggcga atgggctgac cgcttcctcg tgctttacgg    5820
tatcgccgct cccgattcgc agcgcatcgc cttctatcgc cttcttgacg agttcttctg    5880
acatgaccaa aatcccttaa cgtgagtttt cgttccactg agcgtcagac cccgtagaaa    5940
agatcaaagg atcttcttga gatcctttt  ttctgcgcgt aatctgctgc ttgcaaacaa    6000
aaaaaccacc gctaccagcg gtggtttgtt tgccggatca gagctacca  actctttttc    6060
cgaaggtaac tggcttcagc agagcgcaga taccaaatac tgtccttcta gtgtagccgt    6120
agttaggcca ccacttcaag aactctgtag caccgcctac atacctcgct ctgctaatcc    6180
tgttaccagt ggctgctgcc agtggcgata gtcgtgtct  taccggggttg gactcaagac    6240
gatagttacc ggataaggcg cagcggtcgg gctgaacggg gggttcgtgc acacagccca    6300
gcttggagcg aacgacctac accgaactga gatacctaca gcgtgagcta tgagaaagcg    6360
```

| | |
|---|---|
| ccacgcttcc cgaagggaga aaggcggaca ggtatccggt aagcggcagg gtcggaacag | 6420 |
| gagagcgcac gagggagctt ccaggggaa acgcctggta tctttatagt cctgtcgggt | 6480 |
| ttcgccacct ctgacttgag cgtcgatttt tgtgatgctc gtcaggggg cggagcctat | 6540 |
| ggaaaaacgc cagcaacgcg gccttttac ggttcctggc cttttgctgg cttttgctc | 6600 |
| acatgttctt tcctgcgtta tccctgatt ctgtggataa ccgtattacc gcctttgagt | 6660 |
| gagctgatac cgctcgccgc agccgaacga ccgagcgcag cgagtcagtg agcgaggaag | 6720 |
| cggaagagcg cctgatgcgg tattttctcc ttacgcatct gtgcggtatt tcacaccgca | 6780 |
| tatggtgcac tctcagtaca atctgctctg atgccgcata gttaagccag tatacactcc | 6840 |
| gctatcgcta cgtgactggg tcatggctgc ccccgacac ccgccaacac ccgctgacgc | 6900 |
| gccctgacgg gc | 6912 |

<210> SEQ ID NO 51
<211> LENGTH: 7902
<212> TYPE: DNA
<213> ORGANISM: Artificial Sequence
<220> FEATURE:
<223> OTHER INFORMATION: Synthetic Construct

<400> SEQUENCE: 51

| | |
|---|---|
| ttgtctgctc ccggcatccg cttacagaca agctgtgacc gtctccggga gctgcatgtg | 60 |
| tcagaggttt tcaccgtcat caccgaaacg cgcgaggcag cagatcaatt cgcgcgcgaa | 120 |
| ggcgaagcgg catgcattta cgttgacacc atcgaatggt gcaaaacctt tcgcggtatg | 180 |
| gcatgatagc gcccggaaga gagtcaattc agggtggtga atgtgaaacc agtaacgtta | 240 |
| tacgatgtcg cagagtatgc cggtgtctct tatcagaccg tttcccgcgt ggtgaaccag | 300 |
| gccagccacg tttctgcgaa aacgcgggaa aagtggaag cggcgatggc ggagctgaat | 360 |
| tacattccca accgcgtggc acaacaactg gcgggcaaac agtcgttgct gattggcgtt | 420 |
| gccacctcca gtctggccct gcacgcgccg tcgcaaattg tcgcggcgat taaatctcgc | 480 |
| gccgatcaac tgggtgccag cgtggtggtg tcgatggtag aacgaagcgg cgtcgaagcc | 540 |
| tgtaaagcgg cggtgcacaa tcttctcgcg caacgcgtca gtgggctgat cattaactat | 600 |
| ccgctggatg accaggatgc cattgctgtg gaagctgcct gcactaatgt tccggcgtta | 660 |
| tttcttgatg tctctgacca gacacccatc aacagtatta ttttctccca tgaagacggt | 720 |
| acgcgactgg gcgtggagca tctggtcgca ttgggtcacc agcaaatcgc gctgttagcg | 780 |
| ggcccattaa gttctgtctc ggcgcgtctg cgtctggctg ctggcataa atatctcact | 840 |
| cgcaatcaaa ttcagccgat agcggaacgg gaaggcgact ggagtgccat gtccggtttt | 900 |
| caacaaacca tgcaaatgct gaatgagggc atcgttccca ctgcgatgct ggttgccaac | 960 |
| gatcagatgg cgctgggcgc aatgcgcgcc attaccgagt ccgggctgcg cgttggtgcg | 1020 |
| gatatctcgg tagtgggata cgacgatacc gaagacagct catgttatat cccgccgtca | 1080 |
| accaccatca acaggattt cgcctgctg gggcaaacca cgtggaccg cttgctgcaa | 1140 |
| ctctctcagg gccaggcggt gaagggcaat cagctgttgc ccgtctcact ggtgaaaaga | 1200 |
| aaaaccaccc tggcgcccaa tacgcaaacc gcctctcccc gcgcgttggc cgattcatta | 1260 |
| atgcagctgg cacgacaggt ttcccgactg gaaagcgggc agtgagcgca acgcaattaa | 1320 |
| tgtgagttag cgcgaattga tctggtttga cagcttatca tcgactgcac ggtgcaccaa | 1380 |
| tgcttctggc gtcaggcagc catcggaagc tgtggtatgg ctgtgcaggt cgtaaatcac | 1440 |
| tgcataattc gtgtcgctca aggcgcactc ccgttctgga taatgttttt tgcgccgaca | 1500 |

```
tcataacggt tctggcaaat attctgaaat gagctgttga caattaatca tccggctcgt    1560
ataatgtgtg gaattgtgag cggataacaa tttcacacag gaaacagcgc cgctgagaaa    1620
aagcgaagcg gcactgctct ttaacaattt atcagacaat ctgtgtgggc actcgaccgg    1680
aattatcgat taactttatt attaaaaatt aaagaggtat atattaatgt atcgattaaa    1740
taaggaggaa taaccatgt gtgcgacctc ttctcaattt actcagatta ccgagcataa    1800
ttcccgtcgt tccgcaaact atcagccaaa cctgtgaat ttcgaattcc tgcaatccct    1860
ggagaacgac ctgaaagtgg aaaagctgga ggagaaagcg accaaactgg aggaagaagt    1920
tcgctgcatg atcaaccgtg tagacaccca gccgctgtcc ctgctggagc tgatcgacga    1980
tgtgcagcgc ctgggtctga cctacaaatt tgaaaagac atcattaaag ccctggaaaa    2040
catcgtactg ctggacgaaa acaaaaagaa caaatctgac ctgcacgcaa ccgctctgtc    2100
tttccgtctg ctgcgtcagc acggtttcga ggtttctcag gatgtttttg agcgtttcaa    2160
ggataaagaa ggtggtttca gcggtgaact gaaaggtgac gtccaaggcc tgctgagcct    2220
gtatgaagcg tcttacctgg gtttcgaggg tgagaacctg ctggaggagg cgcgtacctt    2280
ttccatcacc cacctgaaga acaacctgaa agaaggcatt aataccaagg ttgcagaaca    2340
agtgagccac gccctggaac tgccatatca ccagcgtctg caccgtctgg aggcacgttg    2400
gttcctggat aaatacgaac cgaaagaacc gcatcaccag ctgctgctgg agctggcgaa    2460
gctggatttt aacatggtac agaccctgca ccagaaagag ctgcaagatc tgtcccgctg    2520
gtggaccgag atgggcctgg ctagcaaact ggattttgta cgcgaccgcc tgatggaagt    2580
ttatttctgg gcactgggta tggcgccaga cccgcagttt ggtgaatgtc gcaaagctgt    2640
tactaaaatg tttggtctgg tgacgatcat cgatgacgtg tatgcgtttt atggcactct    2700
ggacgaactg caactgttca ccgatgctgt agagcgctgg gacgttaacg ctattaacac    2760
cctgccggac tatatgaaac tgtgtttcct ggcactgtac aacaccgtta acgacacgtc    2820
ctattctatt ctgaaagaga aggtcataa caacctgtcc tatctgacga aaagctggcg    2880
tgaactgtgc aaagccttc tgcaagaggc gaaatggtcc aacaacaaaa ttatcccggc    2940
tttctccaag tacctggaaa acgccagcgt ttcctcctcc ggtgtagcgc tgctggcgcc    3000
gtcttacttt tccgtatgcc agcagcagga agacatctcc gaccacgcgc tgcgttccct    3060
gaccgacttc catggtctgg tgcgttctag ctgcgttatc ttccgcctgt gcaacgatct    3120
ggccacctct gcggcggagc tggaacgtgg cgagactacc aattctatca ttagctacat    3180
gcacgaaaac gatggtacca gcgaggaaca ggcccgcgaa gaactgcgta aactgatcga    3240
cgccgaatgg aaaagatga atcgtgaacg cgttagcgac tccaccctgc tgcctaaagc    3300
gttcatggaa atcgcagtta acatggcacg tgtttcccac tgcacctacc agtatggcga    3360
tggtctgggt cgcccagact acgcgactga aaaccgcatc aaactgctgc tgattgaccc    3420
tttcccgatt aaccagctga tgtatgtcta actgcattcg cccttaggag gtaaaaaaac    3480
atgagttttg atattgccaa ataccgacc ctggcactgg tcgactccac ccaggagtta    3540
cgactgttgc cgaaagagag tttaccgaaa ctctgcgacg aactgcgccg ctatttactc    3600
gacagcgtga gccgttccag cgggcacttc gcctccgggc tgggcacggt cgaactgacc    3660
gtggcgctgc actatgtcta caacaccccg tttgaccaat tgatttggga tgtggggcat    3720
caggcttatc cgcataaat tttgaccgga cgccgcgaca aaatcggcac catccgtcag    3780
aaaggcggtc tgcacccgtt cccgtggcgc ggcgaaagcg aatatgacgt attaagcgtc    3840
```

```
gggcattcat caacctccat cagtgccgga attggtattg cggttgctgc cgaaaaagaa    3900
ggcaaaaatc gccgcaccgt ctgtgtcatt ggcgatggcg cgattaccgc aggcatggcg    3960
tttgaagcga tgaatcacgc gggcgatatc cgtcctgata tgctggtgat tctcaacgac    4020
aatgaaatgt cgatttccga aaatgtcggc gcgctcaaca accatctggc acagctgctt    4080
tccggtaagc tttactcttc actgcgcgaa ggcgggaaaa agttttctc tggcgtgccg     4140
ccaattaaag agctgctcaa acgcaccgaa gaacatatta aggcatggt agtgcctggc     4200
acgttgtttg aagagctggg ctttaactac atcggcccgg tggacggtca cgatgtgctg    4260
gggcttatca ccacgctaaa gaacatgcgc gacctgaaag gcccgcagtt cctgcatatc    4320
atgaccaaaa aaggtcgtgg ttatgaaccg gcagaaaaag acccgatcac tttccacgcc    4380
gtgcctaaat ttgatccctc cagcggttgt ttgccgaaaa gtagcggcgg tttgccgagc    4440
tattcaaaaa tctttggcga ctggttgtgc gaaacggcag cgaaagacaa caagctgatg    4500
gcgattactc cggcgatgcg tgaaggttcc ggcatggtcg agttttcacg taaattcccg    4560
gatcgctact tcgacgtggc aattgccgag caacacgcgg tgacctttgc tgcgggtctg    4620
gcgattggtg ggtacaaacc cattgtcgcg atttactcca ctttcctgca acgcgcctat    4680
gatcaggtgc tgcatgacgt ggcgattcaa aagcttccgg tcctgttcgc catcgaccgc    4740
gcgggcattg ttggtgctga cggtcaaacc catcagggtg cttttgatct ctcttacctg    4800
cgctgcatac cggaaatggt cattatgacc ccgagcgatg aaaacgaatg tcgccagatg    4860
ctctataccg gctatcacta taacgatggc ccgtcagcgg tgcgctaccc gcgtggcaac    4920
gcggtcggcg tggaactgac gccgctggaa aaactaccaa ttggcaaagg cattgtgaag    4980
cgtcgtggcg agaaactggc gatccttaac tttggtacgc tgatgccaga agcggcgaaa    5040
gtcgccgaat cgctgaacgc cacgctggtc gatatgcgtt ttgtgaaacc gcttgatgaa    5100
gcgttaattc tggaaatggc cgccagccat gaagcgctgg tcaccgtaga agaaaacgcc    5160
attatgggcg gcgcaggcag cggcgtgaac gaagtgctga tggcccatcg taaaccagta    5220
cccgtgctga acattggcct gccggacttc tttattccgc aaggaactca ggaagaaatg    5280
cgcgccgaac tcggcctcga tgccgctggt atggaagcca aaatcaaggc ctggctggca    5340
taactgcagc tggtaccata tgggaattcg aagctttcta gaacaaaaac tcatctcaga    5400
agaggatctg aatagcgccg tcgaccatca tcatcatcat cattgagttt aaacggtctc    5460
cagcttggct gttttggcgg atgagagaag attttcagcc tgatacagat taaatcagaa    5520
cgcagaagcg gtctgataaa acagaatttg cctggcggca gtagcgcggt ggtcccacct    5580
gaccccatgc cgaactcaga agtgaaacgc cgtagcgccg atggtagtgt ggggtctccc    5640
catgcgagag tagggaactg ccaggcatca aataaaacga aaggctcagt cgaaagactg    5700
ggcctttcgt tttatctgtt gtttgtcggt gaacgctctc ctgagtagga caaatccgcc    5760
gggagcggat ttgaacgttg cgaagcaacg gcccggaggg tggcgggcag gacgcccgcc    5820
ataaactgcc aggcatcaaa ttaagcagaa ggccatcctg acggatggcc tttttgcgtt    5880
tctacaaact cttttgtttt atttttctaa atacattcaa atatgtatcc gcttaaccgg    5940
aattgccagc tggggcgccc tctggtaagg ttgggaagcc ctgcaaagta aactggatgg    6000
ctttctcgcc gccaaggatc tgatggcgca ggggatcaag ctctgatcaa gagacaggat    6060
gaggatcgtt tcgcatgatt gaacaagatg gattgcacgc aggttctccg gccgcttggg    6120
tggagaggct attcggctat gactgggcac aacagacaat cggctgctct gatgccgccg    6180
tgttccggct gtcagcgcag gggcgcccgg ttcttttgt caagaccgac ctgtccggtg    6240
```

-continued

```
ccctgaatga actgcaagac gaggcagcgc ggctatcgtg gctggccacg acgggcgttc    6300
cttgcgcagc tgtgctcgac gttgtcactg aagcgggaag ggactggctg ctattgggcg    6360
aagtgccggg gcaggatctc ctgtcatctc accttgctcc tgccgagaaa gtatccatca    6420
tggctgatgc aatgcggcgg ctgcatacgc ttgatccggc tacctgccca ttcgaccacc    6480
aagcgaaaca tcgcatcgag cgagcacgta ctcggatgga agccggtctt gtcgatcagg    6540
atgatctgga cgaagagcat caggggctcg cgccagccga actgttcgcc aggctcaagg    6600
cgagcatgcc cgacggcgag gatctcgtcg tgacccatgg cgatgcctgc ttgccgaata    6660
tcatggtgga aaatggccgc ttttctggat tcatcgactg tggccggctg ggtgtggcgg    6720
accgctatca ggacatagcg ttggctaccc gtgatattgc tgaagagctt ggcggcgaat    6780
gggctgaccg cttcctcgtg ctttacggta tcgccgctcc cgattcgcag cgcatcgcct    6840
tctatcgcct tcttgacgag ttcttctgac gcatgaccaa aatcccttaa cgtgagtttt    6900
cgttccactg agcgtcagac cccgtagaaa agatcaaagg atcttcttga tccttttt     6960 ttctgcgcgt aatctgctgc ttgcaaacaa aaaaaccacc gctaccagcg gtggtttgtt    7020
tgccggatca agagctacca actcttttc cgaaggtaac tggcttcagc agagcgcaga    7080
taccaaatac tgtccttcta gtgtagccgt agttaggcca ccacttcaag aactctgtag    7140
caccgcctac atacctcgct ctgctaatcc tgttaccagt ggctgctgcc agtggcgata    7200
agtcgtgtct taccgggttg gactcaagac gatagttacc ggataaggcg cagcggtcgg    7260
gctgaacggg gggttcgtgc acacagccca gcttggagcg aacgacctac accgaactga    7320
gatacctaca gcgtgagcta tgagaaagcg ccacgcttcc cgaagggaga aaggcggaca    7380
ggtatccggt aagcggcagg gtcggaacag gagagcgcac gagggagctt ccaggggaa    7440 acgcctggta tctttatagt cctgtcgggt ttcgccacct ctgacttgag cgtcgatttt    7500
tgtgatgctc gtcagggggg cggagcctat ggaaaaacgc cagcaacgcg gcctttttac    7560
ggttcctggc cttttgctgg ccttttgctc acatgttctt tcctgcgtta tccctgatt     7620 ctgtggataa ccgtattacc gcctttgagt gagctgatac cgctcgccgc agccgaacga    7680
ccgagcgcag cgagtcagtg agcgaggaag cggaagagcg cctgatgcgg tattttctcc    7740
ttacgcatct gtgcggtatt tcacaccgca tatggtgcac tctcagtaca atctgctctg    7800
atgccgcata gttaagccag tatacactcc gctatcgcta cgtgactggg tcatggctgc    7860
gccccgacac ccgccaacac ccgctgacgc gccctgacgg gc                       7902
```

<210> SEQ ID NO 52
<211> LENGTH: 6783
<212> TYPE: DNA
<213> ORGANISM: Artificial Sequence
<220> FEATURE:
<223> OTHER INFORMATION: Synthetic Construct

<400> SEQUENCE: 52

```
ctggcgtaat agcgaagagg cccgcaccga tcgcccttcc caacagttgc gcagcctgaa      60
tggcgaatgg cgcctgatgc ggtatttttct ccttacgcat ctgtgcggta tttcacaccg    120
catatggtgc actctcagta caatctgctc tgatgccgca tagttaagcc agccccgaca    180
cccgccaaca cccgctgacg agcttagtaa agccctcgct agattttaat gcggatgttg    240
cgattacttc gccaactatt gcgataacaa gaaaaagcca gcctttcatg atatatctcc    300
caatttgtgt agggcttatt atgcacgctt aaaaataata aaagcagact tgacctgata    360
```

-continued

```
gtttggctgt gagcaattat gtgcttagtg catctaacgc ttgagttaag ccgcgccgcg    420
aagcggcgtc ggcttgaacg aattgttaga cattatttgc cgactacctt ggtgatctcg    480
cctttcacgt agtggacaaa ttcttccaac tgatctgcgc gcgaggccaa gcgatcttct    540
tcttgtccaa gataagcctg tctagcttca agtatgacgg gctgatactg ggccggcagg    600
cgctccattg cccagtcggc agcgacatcc ttcggcgcga ttttgccggt tactgcgctg    660
taccaaatgc gggacaacgt aagcactaca tttcgctcat cgccagccca gtcgggcggc    720
gagttccata gcgttaaggt ttcatttagc gcctcaaata gatcctgttc aggaaccgga    780
tcaaagagtt cctccgccgc tggacctacc aaggcaacgc tatgttctct tgcttttgtc    840
agcaagatag ccagatcaat gtcgatcgtg gctggctcga agataccgtgc aagaatgtca    900
ttgcgctgcc attctccaaa ttgcagttcg cgcttagctg ataacgcca cggaatgatg    960
tcgtcgtgca caacaatggt gacttctaca gcgcggagaa tctcgctctc tccaggggaa   1020
gccgaagttt ccaaaaggtc gttgatcaaa gctcgccgcg ttgtttcatc aagccttacg   1080
gtcaccgtaa ccagcaaatc aatatcactg tgtggcttca ggccgccatc cactgcggag   1140
ccgtacaaat gtacggccag caacgtcggt tcgagatggc gctcgatgac gccaactacc   1200
tctgatagtt gagtcgatac ttcggcgatc accgcttccc tcatgatgtt taactttgtt   1260
ttagggcgac tgccctgctg cgtaacatcg ttgctgctcc ataacatcaa acatcgaccc   1320
acggcgtaac gcgcttgctg cttggatgcc cgaggcatag actgtacccc aaaaaaacag   1380
tcataacaag ccatgaaaac cgccactgcg ccgttaccac cgctgcgttc ggtcaaggtt   1440
ctggaccagt tgcgtgagcg catacgctac ttgcattaca gcttacgaac cgaacaggct   1500
tatgtccact gggttcgtgc cttcatccgt ttccacggtg tgcgtcaccc ggcaaccttg   1560
ggcagcagcg aagtcgaggc atttctgtcc tggctggcga acgagcgcaa ggtttcggtc   1620
tccacgcatc gtcaggcatt ggcggccttg ctgttcttct acggcaaggt gctgtgcacg   1680
gatctgccct ggcttcagga gatcggaaga cctcggccgt cgcggcgctt gccggtggtg   1740
ctgaccccgg atgaagtggt tcgcatcctc ggttttctgg aaggcgagca tcgtttgttc   1800
gcccagcttc tgtatggaac gggcatgcgc atcagtgagg gtttgcaact gcgggtcaag   1860
gatctggatt tcgatcacgg cacgatcatc gtgcgggagg gcaagggctc caaggatcgg   1920
gccttgatgt tacccgagag cttggcaccc agcctgcgcg agcaggggaa ttaattccca   1980
cgggttttgc tgcccgcaaa cgggctgttc tggtgttgct agtttgttat cagaatcgca   2040
gatccggctt cagccggttt gccggctgaa agcgctattt cttccagaat tgccatgatt   2100
tttcccac gggaggcgtc actggctccc gtgttgtcgg cagctttgat tcgataagca   2160
gcatcgcctg tttcaggctg tctatgtgtg actgttgagc tgtaacaagt tgtctcaggt   2220
gttcaatttc atgttctagt tgctttgttt tactggtttc acctgttcta ttaggtgtta   2280
catgctgttc atctgttaca ttgtcgatct gttcatggtg aacagctttg aatgcaccaa   2340
aaactcgtaa aagctctgat gtatctatct tttttacacc gttttcatct gtgcatatgg   2400
acagttttcc ctttgatatg taacggtgaa cagttgttct acttttgttt gttagtcttg   2460
atgcttcact gatagataca agagccataa gaacctcaga tccttccgta tttagccagt   2520
atgttctcta gtgtggttcg ttgttttgc gtgagccatg agaacgaacc attgagatca   2580
tacttacttt gcatgtcact caaaaatttt gcctcaaaac tggtgagctg aattttttgca   2640
gttaaagcat cgtgtagtgt ttttcttagt ccgttatgta ggtaggaatc tgatgtaatg   2700
gttgttggta ttttgtcacc attcattttt atctggttgt tctcaagttc ggttacgaga   2760
```

```
tccatttgtc tatctagttc aacttggaaa atcaacgtat cagtcgggcg gcctcgctta   2820
tcaaccacca atttcatatt gctgtaagtg tttaaatctt tacttattgg tttcaaaacc   2880
cattggttaa gccttttaaa ctcatggtag ttattttcaa gcattaacat gaacttaaat   2940
tcatcaaggc taatctctat atttgccttg tgagttttct tttgtgttag ttcttttaat   3000
aaccactcat aaatcctcat agagtatttg ttttcaaaag acttaacatg ttccagatta   3060
tattttatga attttttttaa ctggaaaaga taaggcaata tctcttcact aaaaactaat   3120
tctaattttt cgcttgagaa cttggcatag tttgtccact ggaaaatctc aaagccttta   3180
accaaaggat tcctgatttc cacagttctc gtcatcagct ctctggttgc tttagctaat   3240
acaccataag catttcccct actgatgttc atcatctgag cgtattggtt ataagtgaac   3300
gataccgtcc gttctttcct tgtagggttt tcaatcgtgg ggttgagtag tgccacacag   3360
cataaaatta gcttggtttc atgctccgtt aagtcatagc gactaatcgc tagttcattt   3420
gctttgaaaa caactaattc agacatacat ctcaattggt ctaggtgatt ttaatcacta   3480
taccaattga gatgggctag tcaatgataa ttactagtcc ttttcctttg agttgtgggt   3540
atctgtaaat tctgctagac cttkgctgga aaacttgtaa attctgctag accctctgta   3600
aattccgcta gacctttgtg tgtttttttt gtttatattc aagtggttat aatttataga   3660
ataaagaaag aataaaaaaa gataaaaaga atagatccca gccctgtgta taactcacta   3720
ctttagtcag ttccgcagta ttacaaaagg atgtcgcaaa cgctgtttgc tcctctacaa   3780
aacagacctt aaaaccctaa aggcttaagt agcaccctcg caagctcggg caaatcgctg   3840
aatattcctt ttgtctccga ccatcaggca cctgagtcgc tgtcttttc gtgacattca    3900 gttcgctgcg ctcacggctc tggcagtgaa tgggggtaaa tggcactaca ggcgcctttt   3960
atggattcat gcaaggaaac tacccataat acaagaaaag cccgtcacgg gcttctcagg   4020
gcgttttatg gcgggtctgc tatgtggtgc tatctgactt tttgctgttc agcagttcct   4080
gccctctgat tttccagtct gaccacttcg gattatcccg tgacaggtca ttcagactgg   4140
ctaatgcacc cagtaaggca gcggtatcat caacaggctt acccgtctta ctgtcgggaa   4200
ttcgcgttgg ccgattcatt aatgcagatt ctgaaatgag ctgttgacaa ttaatcatcc   4260
ggctcgtata atgtgtggaa ttgtgagcgg ataacaattt cacacaggaa acagcgccgc   4320
tgagaaaaag cgaagcggca ctgctcttta caaatttatc agacaatctg tgtgggcact   4380
cgaccggaat tatcgattaa ctttattatt aaaaattaaa gaggtatata ttaatgtatc   4440
gattaaataa ggaggaataa accatgtgtg cgacctcttc tcaatttact cagattaccg   4500
agcataattc ccgtcgttcc gcaaactatc agccaaacct gtggaatttc gaattcctgc   4560
aatccctgga gaacgacctg aaagtggaaa agctggagga gaaagcgacc aaactggagg   4620
aagaagttcg ctgcatgatc aaccgtgtag acacccagcc gctgtccctg ctggagctga   4680
tcgacgatgt gcagcgcctg ggtctgacct acaaatttga aaagacatc attaagccc     4740 tggaaaacat cgtactgctg gacgaaaaca aaaagaacaa atctgacctg cacgcaaccg   4800
ctctgtcttt ccgtctgctg cgtcagcacg gtttcgaggt ttctcaggat gttttttgagc  4860 gtttcaagga taaagaaggt ggtttcagcg gtgaactgaa aggtgacgtc caaggcctgc   4920
tgagcctgta tgaagcgtct tacctggttt tcgagggtga gaacctgctg gaggaggcgc   4980
gtaccttttc catcacccac ctgaagaaca acctgaaaga aggcattaat accaaggttc   5040
cagaacaagt gagccacgcc ctggaactgc catatcacca gcgtctgcac cgtctggagg   5100
```

```
cacgttggtt cctggataaa tacgaaccga agaaccgca tcaccagctg ctgctggagc    5160
tggcgaagct ggattttaac atggtacaga ccctgcacca gaaagagctg caagatctgt    5220
cccgctggtg gaccgagatg ggcctggcta gcaaactgga ttttgtacgc gaccgcctga    5280
tggaagttta tttctgggca ctgggtatgg cgccagaccc gcagtttggt gaatgtcgca    5340
aagctgttac taaaatgttt ggtctggtga cgatcatcga tgacgtgtat gacgtttatg    5400
gcactctgga cgaactgcaa ctgttcaccg atgctgtaga gcgctgggac gttaacgcta    5460
ttaacaccct gccggactat atgaaactgt gtttcctggc actgtacaac accgttaacg    5520
acacgtccta ttctattctg aaagagaaag gtcataacaa cctgtcctat ctgacgaaaa    5580
gctggcgtga actgtgcaaa gcctttctgc aagaggcgaa atggtccaac aacaaaatta    5640
tcccggcttt ctccaagtac ctggaaaacg ccagcgtttc ctcctccggt gtagcgctgc    5700
tggcgccgtc ttacttttcc gtatgccagc agcaggaaga catctccgac cacgcgctgc    5760
gttccctgac cgacttccat ggtctggtgc gttctagctg cgttatcttc cgcctgtgca    5820
acgatctggc cacctctgcg gcggagctgg aacgtggcga gactaccaat tctatcatta    5880
gctacatgca cgaaaacgat ggtaccagcg aggaacaggc ccgcgaagaa ctgcgtaaac    5940
tgatcgacgc cgaatggaaa aagatgaatc gtgaacgcgt tagcgactcc accctgctgc    6000
ctaaagcgtt catggaaatc gcagttaaca tggcacgtgt tcccactgc acctaccagt    6060 atggcgatgg tctgggtcgc ccagactacg cgactgaaaa ccgcatcaaa ctgctgctga    6120
ttgacccttt cccgattaac cagctgatgt atgtctaact gcagctggta ccatatggga    6180
attcgaagct ttctagaaca aaaactcatc tcagaagagg atctgaatag cgccgtcgac    6240
catcatcatc atcatcattg agtttaaacg gtctccagct tggctgtttt ggcggatgag    6300
agaagatttt cagcctgata cagattaaat cagaacgcag aagcggtctg ataaaacaga    6360
atttgcctgg cggcagtagc gcggtggtcc cacctgaccc catgccgaac tcagaagtga    6420
aacgccgtag cgccgatggt agtgtggggt ctccccatgc gagagtaggg aactgccagg    6480
catcaaataa aacgaaaggc tcagtcgaaa gactgggcct ttcgttttat ctgttgtttg    6540
tcggtgaacg ctctcctgag taggacaaat ccgccgggag cggatttgaa cgttgcgaag    6600
caacggcccg gagggtggcg ggcaggacgc ccgccataaa ctgccaggca tcaaattaag    6660
cagaaggcca tcctgacgga tggcctttt gcgtttctac aaactctttt tgtttatttt    6720
tctaaataca ttcaaatatg tatccgctca tgagacaata accctgataa atgcttcaat    6780
aat                                                                   6783
```

<210> SEQ ID NO 53
<211> LENGTH: 6783
<212> TYPE: DNA
<213> ORGANISM: Artificial Sequence
<220> FEATURE:
<223> OTHER INFORMATION: Synthetic Construct

<400> SEQUENCE: 53

```
cccgtcttac tgtcgggaat tcgcgttggc cgattcatta atgcagatta ttgaagcatt      60
tatcagggtt attgtctcat gagcggatac atatttgaat gtatttagaa aaataaacaa     120
aagagtttgt agaaacgcaa aaaggccat ccgtcaggat ggccttctgc ttaatttgat     180
gcctggcagt ttatgcgggc gtcctgcccc gcaccctcc gggccgttgc ttcgcaacgt     240
tcaaatccgc tcccggcgga tttgtcctac tcaggagagc gttcaccgac aaacaacaga     300
taaaacgaaa ggcccagtct ttcgactgag cctttcgttt tatttgatgc ctggcagttc     360
```

```
cctactctcg catgggaga ccccacacta ccatcggcgc tacggcgttt cacttctgag      420
ttcggcatgg ggtcaggtgg gaccaccgcg ctactgccgc caggcaaatt ctgttttatc      480
agaccgcttc tgcgttctga tttaatctgt atcaggctga aaatcttctc tcatccgcca      540
aaacagccaa gctggagacc gtttaaactc aatgatgatg atgatgatgg tcgacggcgc      600
tattcagatc ctcttctgag atgagttttt gttctagaaa gcttcgaatt cccatatggt      660
accagctgca gttagacata catcagctgg ttaatcggga aagggtcaat cagcagcagt      720
ttgatgcggt tttcagtcgc gtagtctggg cgacccagac catcgccata ctggtaggtg      780
cagtgggaaa cacgtgccat gttaactgcg atttccatga acgctttagg cagcagggtg      840
gagtcgctaa cgcgttcacg attcatcttt tccattcgg cgtcgatcag tttacgcagt      900
tcttcgcggg cctgttcctc gctggtacca tcgttttcgt gcatgtagct aatgatagaa      960
ttggtagtct cgccacgttc cagctccgcc gcagaggtgg ccagatcgtt gcacaggcgg     1020
aagataacgc agctagaacg caccagacca tggaagtcgg tcaggaacg cagcgcgtgg     1080 tcggagatgt cttcctgctg ctggcatacg gaaaagtaag acggcgccag cagcgctaca     1140
ccggaggagg aaacgctggc gttttccagg tacttggaga aagccgggat aattttgttg     1200
ttggaccatt tcgcctcttg cagaaaggct ttgcacagtt cacgccagct tttcgtcaga     1260
taggacaggt tgttatgacc tttctctttc agaatagaat aggacgtgtc gttaacggtg     1320
ttgtacagtg ccaggaaaca cagtttcata tagtccggca gggtgttaat agcgttaacg     1380
tcccagcgct ctacagcatc ggtgaacagt tgcagttcgt ccagagtgcc ataaacgtca     1440
tacacgtcat cgatgatcgt caccagacca aacatttag taacagcttt gcgacattca     1500
ccaaactgcg ggtctggcgc catacccagt gcccagaaat aaacttccat caggcggtcg     1560
cgtacaaaat ccagtttgct agccaggccc atctcggtcc accagcggga cagatcttgc     1620 agctcttct ggtgcagggt ctgtaccatg ttaaaatcca gcttcgccag ctccagcagc     1680
agctggtgat gcggttcttt cggttcgtat ttatccagga ccaacgtgc ctccagacgg     1740 tgcagacgct ggtgatatgg cagttccagg gcgtggctca cttgttctgc aaccttggta     1800
ttaatgcctt ctttcaggtt gttcttcagg tgggtgatgg aaaaggtacg cgcctcctcc     1860
agcaggttct caccctcgaa acccaggtaa gacgcttcat acaggctcag caggccttgg     1920
acgtcacctt tcagttcacc gctgaaacca ccttctttat ccttgaaacg ctcaaaaaca     1980
tcctgagaaa cctcgaaacc gtgctgacgc agcagacgga aagacagagc ggttgcgtgc     2040
aggtcagatt tgttcttttt gttttcgtcc agcagtacga tgttttccag ggctttaatg     2100
atgtcttttt caaatttgta ggtcagaccc aggcgctgca catcgtcgat cagctccagc     2160
agggacagcg gctgggtgtc tacacggttg atcatgcagc gaacttcttc ctccagtttg     2220
gtcgctttct cctccagctt ttccactttc aggtcgttct ccagggattg caggaattcg     2280
aaattccaca ggtttggctg atagtttgcg gaacgacggg aattatgctc ggtaatctga     2340
gtaaattgag aagaggtcgc acacatggtt tattcctcct tatttaatcg atacattaat     2400
atatacctct ttaattttta ataataaagt taatcgataa ttccggtcga gtgcccacac     2460
agattgtctg ataaattgtt aaagagcagt gccgcttcgc ttttttctcag cggcgctgtt     2520 tcctgtgtga aattgttatc cgctcacaat tccacacatt atacgagccg atgattaat     2580 tgtcaacagc tcatttcaga atctggcgta atagcgaaga ggcccgcacc gatcgccctt     2640
cccaacagtt gcgcagcctg aatggcgaat ggcgcctgat gcggtatttt ctccttacgc     2700
```

```
atctgtgcgg tatttcacac cgcatatggt gcactctcag tacaatctgc tctgatgccg    2760
catagttaag ccagcccga cacccgccaa caccgctga cgagcttagt aaagccctcg      2820
ctagatttta atgcggatgt tgcgattact tcgccaacta ttgcgataac aagaaaaagc    2880
cagcctttca tgatatatct cccaatttgt gtagggctta ttatgcacgc ttaaaaataa    2940
taaaagcaga cttgacctga tagtttggct gtgagcaatt atgtgcttag tgcatctaac    3000
gcttgagtta agccgcgccg cgaagcggcg tcggcttgaa cgaattgtta gacattattt    3060
gccgactacc ttggtgatct cgcctttcac gtagtggaca aattcttcca actgatctgc    3120
gcgcgaggcc aagcgatctt cttcttgtcc aagataagcc tgtctagctt caagtatgac    3180
gggctgatac tgggccggca ggcgctccat tgcccagtcg gcagcgacat ccttcggcgc    3240
gattttgccg gttactgcgc tgtaccaaat gcgggacaac gtaagcacta catttcgctc    3300
atcgccagcc cagtcgggcg cgagttcca tagcgttaag gtttcattta gcgcctcaaa     3360
tagatcctgt tcaggaaccg gatcaaagag ttcctccgcc gctggaccta ccaaggcaac    3420
gctatgttct cttgcttttg tcagcaagat agccagatca atgtcgatcg tggctggctc    3480
gaagatacct gcaagaatgt cattgcgctg ccattctcca aattgcagtt cgcgcttagc    3540
tggataacgc cacggaatga tgtcgtcgtg cacaacaatg gtgacttcta cagcgcggag    3600
aatctcgctc tctccagggg aagccgaagt ttccaaaagg tcgttgatca agctcgccg     3660
cgttgtttca tcaagcctta cggtcaccgt aaccagcaaa tcaatatcac tgtgtggctt    3720
caggccgcca tccactgcgg agccgtacaa atgtacggcc agcaacgtcg gttcgagatg    3780
gcgctcgatg acgccaacta cctctgatag ttgagtcgat acttcggcga tcaccgcttc    3840
cctcatgatg tttaactttg ttttagggcg actgccctgc tgcgtaacat cgttgctgct    3900
ccataacatc aaacatcgac ccacggcgta acgcgcttgc tgcttggatg cccgaggcat    3960
agactgtacc ccaaaaaaac agtcataaca agccatgaaa accgccactg cgccgttacc    4020
accgctgcgt tcgtcaagg ttctggacca gttgcgtgag cgcatacgct acttgcatta     4080
cagcttacga accgaacagg cttatgtcca ctgggttcgt gccttcatcc gtttccacgg    4140
tgtgcgtcac ccggcaacct tgggcagcag cgaagtcgag gcatttctgt cctggctggc    4200
gaacgagcgc aaggtttcgg tctccacgca tcgtcaggca ttggcggcct tgctgttctt    4260
ctacggcaag gtgctgtgca cggatctgcc ctggcttcag gagatcggaa gacctcggcc    4320
gtcgcggcgc ttgccggtgg tgctgacccc ggatgaagtg gttcgcatcc tcggttttct    4380
ggaaggcgag catcgtttgt tcgcccagct tctgtatgga acgggcatgc ggatcagtga    4440
gggtttgcaa ctgcgggtca aggatctgga tttcgatcac ggcacgatca tcgtgcggga    4500
gggcaagggc tccaaggatc gggccttgat gttacccgag agcttggcac ccagcctgcg    4560
cgagcagggg aattaattcc cacgggtttt gctgcccgca acgggctgt tctggtgttg     4620
ctagtttgtt atcagaatcg cagatccggc ttcagccggt ttgccggctg aaagcgctat    4680
ttcttccaga attgccatga ttttttcccc acgggaggcg tcactggctc ccgtgttgtc    4740
ggcagctttg attcgataag cagcatcgcc tgtttcaggc tgtctatgtg tgactgttga    4800
gctgtaacaa gttgtctcag gtgttcaatt tcatgttcta gttgctttgt tttactggtt    4860
tcacctgttc tattaggtgt tacatgctgt tcatctgtta cattgtcgat ctgttcatgg    4920
tgaacagctt tgaatgcacc aaaaactcgt aaaagctctg atgtatctat ctttttttaca   4980
ccgttttcat ctgtgcatat ggacagtttt cccttttgata tgtaacggtg aacagttgtt    5040
ctacttttgt ttgttagtct tgatgcttca ctgatagata caagagccat aagaacctca    5100
```

| | | |
|---|---|---|
| gatccttccg tatttagcca gtatgttctc tagtgtggtt cgttgttttt gcgtgagcca | 5160 | |
| tgagaacgaa ccattgagat catacttact ttgcatgtca ctcaaaaatt ttgcctcaaa | 5220 | |
| actggtgagc tgaattttg cagttaaagc atcgtgtagt gtttttctta gtccgttatg | 5280 | |
| taggtaggaa tctgatgtaa tggttgttgg tattttgtca ccattcattt ttatctggtt | 5340 | |
| gttctcaagt tcggttacga gatccatttg tctatctagt tcaacttgga aaatcaacgt | 5400 | |
| atcagtcggg cggcctcgct tatcaaccac caatttcata ttgctgtaag tgtttaaatc | 5460 | |
| tttacttatt ggtttcaaaa cccattggtt aagccttta aactcatggt agttattttc | 5520 | |
| aagcattaac atgaacttaa attcatcaag gctaatctct atatttgcct tgtgagtttt | 5580 | |
| cttttgtgtt agttctttta ataaccactc ataaatcctc atagagtatt tgttttcaaa | 5640 | |
| agacttaaca tgttccagat tatattttat gaatttttt aactggaaaa gataaggcaa | 5700 | |
| tatctcttca ctaaaaacta attctaattt ttcgcttgag aacttggcat agtttgtcca | 5760 | |
| ctggaaaatc tcaaagcctt taaccaaagg attcctgatt tccacagttc tcgtcatcag | 5820 | |
| ctctctggtt gctttagcta atacaccata agcattttcc ctactgatgt tcatcatctg | 5880 | |
| agcgtattgg ttataagtga acgataccgt ccgttcttc cttgtagggt tttcaatcgt | 5940 | |
| ggggttgagt agtgccacac agcataaaat tagcttggtt tcatgctccg ttaagtcata | 6000 | |
| gcgactaatc gctagttcat ttgctttgaa acaactaat tcagacatac atctcaattg | 6060 | |
| gtctaggtga ttttaatcac tataccaatt gagatgggct agtcaatgat aattactagt | 6120 | |
| cctttccctt tgagttgtgg gtatctgtaa attctgctag acctttgctg gaaaacttgt | 6180 | |
| aaattctgct agaccctctg taaattccgc tagacctttg tgtgttttt ttgtttatat | 6240 | |
| tcaagtggtt ataatttata gaataaagaa agaataaaaa aagataaaaa gaatagatcc | 6300 | |
| cagccctgtg tataactcac tactttagtc agttccgcag tattacaaaa ggatgtcgca | 6360 | |
| aacgctgttt gctcctctac aaaacagacc ttaaaaccct aaaggcttaa gtagcaccct | 6420 | |
| cgcaagctcg ggcaaatcgc tgaatattcc ttttgtctcc gaccatcagg cacctgagtc | 6480 | |
| gctgtctttt tcgtgacatt cagttcgctg cgctcacggc tctggcagtg aatgggggta | 6540 | |
| aatggcacta caggcgcctt ttatggattc atgcaaggaa actacccata atacaagaaa | 6600 | |
| agcccgtcac gggcttctca gggcgtttta tggcgggtct gctatgtggt gctatctgac | 6660 | |
| ttttgctgt tcagcagttc ctgccctctg attttccagt ctgaccactt cggattatcc | 6720 | |
| cgtgacaggt cattcagact ggctaatgca cccagtaagg cagcggtatc atcaacaggc | 6780 | |
| tta | 6783 | |

<210> SEQ ID NO 54
<211> LENGTH: 7687
<212> TYPE: DNA
<213> ORGANISM: Artificial Sequence
<220> FEATURE:
<223> OTHER INFORMATION: Synthetic Construct

<400> SEQUENCE: 54

| | | |
|---|---|---|
| ctggcgtaat agcgaagagg cccgcaccga tcgcccttcc caacagttgc gcagcctgaa | 60 | |
| tggcgaatgg cgcctgatgc ggtatttct ccttacgcat ctgtgcggta tttcacaccg | 120 | |
| catatggtgc actctcagta caatctgctc tgatgccgca tagttaagcc agccccgaca | 180 | |
| cccgccaaca cccgctgacg agcttagtaa agccctcgct agattttaat gcggatgttg | 240 | |
| cgattacttc gccaactatt gcgataacaa gaaaaagcca gcctttcatg atatatctcc | 300 | |

```
caatttgtgt agggcttatt atgcacgctt aaaaataata aaagcagact tgacctgata    360
gtttggctgt gagcaattat gtgcttagtg catctaacgc ttgagttaag ccgcgccgcg    420
aagcggcgtc ggcttgaacg aattgttaga cattatttgc cgactacctt ggtgatctcg    480
cctttcacgt agtggacaaa ttcttccaac tgatctgcgc gcgaggccaa gcgatcttct    540
tcttgtccaa gataagcctg tctagcttca agtatgacgg gctgatactg ggccggcagg    600
cgctccattg cccagtcggc agcgacatcc ttcggcgcga ttttgccggt tactgcgctg    660
taccaaatgc gggacaacgt aagcactaca tttcgctcat cgccagccca gtcgggcggc    720
gagttccata cgttaaggt ttcatttagc gcctcaaata gatcctgttc aggaaccgga    780
tcaaagagtt cctccgccgc tggacctacc aaggcaacgc tatgttctct tgcttttgtc    840
agcaagatag ccagatcaat gtcgatcgtg gctggctcga agatacctgc aagaatgtca    900
ttgcgctgcc attctccaaa ttgcagttcg cgcttagctg gataacgcca cggaatgatg    960
tcgtcgtgca caacaatggt gacttctaca gcgcggagaa tctcgctctc tccaggggaa   1020
gccgaagttt ccaaaaggtc gttgatcaaa gctcgccgcg ttgtttcatc aagccttacg   1080
gtcaccgtaa ccagcaaatc aatatcactg tgtggcttca ggccgccatc cactgcggag   1140
ccgtacaaat gtacggccag caacgtcggt tcgagatggc gctcgatgac gccaactacc   1200
tctgatagtt gagtcgatac ttcggcgatc accgcttccc tcatgatgtt aactttgtt   1260
ttagggcgac tgccctgctg cgtaacatcg ttgctgctcc ataacatcaa acatcgaccc   1320
acggcgtaac gcgcttgctg cttggatgcc cgaggcatag actgtacccc aaaaaaacag   1380
tcataacaag ccatgaaaac cgccactgcg ccgttaccac cgctgcgttc ggtcaaggtt   1440
ctggaccagt tgcgtgagcg catacgctac ttgcattaca gcttacgaac cgaacaggct   1500
tatgtccact gggttcgtgc cttcatccgt ttccacggtg tgcgtcaccc ggcaaccttg   1560
ggcagcagcg aagtcgaggc atttctgtcc tggctggcga acgagcgcaa ggtttcggtc   1620
tccacgcatc gtcaggcatt ggcggccttg ctgttcttct acggcaaggt gctgtgcacg   1680
gatctgccct ggcttcagga gatcggaaga cctcggccgt cgcggcgctt gccggtggtg   1740
ctgaccccgg atgaagtggt tcgcatcctc ggttttctgg aaggcgagca tcgtttgttc   1800
gcccagcttc tgtatggaac gggcatgcgg atcagtgagg gtttgcaact gcgggtcaag   1860
gatctggatt tcgatcacgg cacgatcatc gtgcgggagg gcaagggctc caaggatcgg   1920
gccttgatgt taccccgagag cttggcaccc agcctgcgcg agcagggaa ttaattccca   1980
cggggttttgc tgcccgcaaa cgggctgttc tggtgttgct agtttgttat cagaatcgca   2040
gatccggctt cagccggttt gccggctgaa agcgctattt cttccagaat tgccatgatt   2100
ttttccccac gggaggcgtc actggctccc gtgttgtcgg cagctttgat tcgataagca   2160
gcatcgcctg tttcaggctg tctatgtgtg actgttgagc tgtaacaagt tgtctcaggt   2220
gttcaatttc atgttctagt tgctttgttt tactggtttc acctgttcta ttaggtgtta   2280
catgctgttc atctgttaca ttgtcgatct gttcatggtg aacagctttg aatgcaccaa   2340
aaactcgtaa aagctctgat gtatctatct ttttttacacc gttttcatct gtgcatatgg   2400
acagttttcc ctttgatatg taacggtgaa cagttgttct actttttgttt gttagtcttg   2460
atgcttcact gatagataca agagccataa gaaccctcaga tccttccgta tttagccagt   2520
atgttctcta gtgtggttcg ttgttttttgc gtgagccatg agaacgaacc attgagatca   2580
tacttacttt gcatgtcact caaaaatttt gcctcaaaac tggtgagctg aattttttgca   2640
gttaaagcat cgtgtagtgt ttttcttagt ccgttatgta ggtaggaatc tgatgtaatg   2700
```

```
gttgttggta ttttgtcacc attcattttt atctggttgt tctcaagttc ggttacgaga    2760
tccatttgtc tatctagttc aacttggaaa atcaacgtat cagtcgggcg gcctcgctta    2820
tcaaccacca atttcatatt gctgtaagtg tttaaatctt tacttattgg tttcaaaacc    2880
cattggttaa gccttttaaa ctcatggtag ttattttcaa gcattaacat gaacttaaat    2940
tcatcaaggc taatctctat atttgccttg tgagttttct tttgtgttag ttcttttaat    3000
aaccactcat aaatcctcat agagtatttg ttttcaaaag acttaacatg ttccagatta    3060
tattttatga atttttttaa ctggaaaaga taaggcaata tctcttcact aaaaactaat    3120
tctaattttt cgcttgagaa cttggcatag tttgtccact ggaaaatctc aaagcccttta   3180 accaaaggat tcctgatttc acagttctc gtcatcagct ctctggttgc tttagctaat     3240
acaccataag catttccct actgatgttc atcatctgag cgtattggtt ataagtgaac     3300
gataccgtcc gttctttcct tgtagggttt tcaatcgtgg ggttgagtag tgccacacag    3360
cataaaatta gctggttttc atgctccgtt aagtcatagc gactaatcgc tagttcattt    3420
gctttgaaaa caactaattc agacatacat ctcaattggt ctaggtgatt ttaatcacta    3480
taccaattga gatgggctag tcaatgataa ttactagtcc ttttcctttg agttgtgggt    3540
atctgtaaat tctgctagac ctttgctgga aaacttgtaa attctgctag accctctgta    3600
aattccgcta gacctttgtg tgttttttt gtttatattc aagtggttat aatttatga     3660 ataagaaag aataaaaaa gataaaaga atagatccca gccctgtgta taactcacta      3720
ctttagtcag ttccgcagta ttacaaaagg atgtcgcaaa cgctgtttgc tcctctacaa    3780
aacagacctt aaaaccctaa aggcttaagt agcaccctcg caagctcggg caaatcgctg    3840
aatattcctt ttgtctccga ccatcaggca cctgagtcgc tgtcttttc gtgacattca    3900 gttcgctgcg ctcacggctc tggcagtgaa tgggggtaaa tggcactaca ggcgcctttt    3960
atggattcat gcaaggaaac tacccataat acaagaaaag cccgtcacgg gcttctcagg    4020
gcgttttatg gcgggtctgc tatgtggtgc tatctgactt tttgctgttc agcagttcct    4080
gccctctgat tttccagtct gaccacttcg gattatcccg tgacaggtca ttcagactgg    4140
ctaatgcacc cagtaaggca gcggtatcat caacaggctt acccgtctta ctgtcgggaa    4200
ttcgcgttgg ccgattcatt aatgcagatt ctgaaatgag ctgttgacaa ttaatcatcc    4260
ggctcgtata atgtgtggaa ttgtgagcgg ataacaattt cacacaggaa acagcgccgc    4320
tgagaaaaag cgaagcggca ctgctcttta caatttatc agacaatctg tgtgggcact    4380
cgaccggaat tatcgattaa ctttattatt aaaaattaaa gaggtatata ttaatgtatc    4440
gattaaataa ggaggaataa accatgtgtg cgacctcttc tcaatttact cagattaccg    4500
agcataattc ccgtcgttcc gcaaactatc agccaaacct gtggaatttc gaattcctgc    4560
aatccctgga gaacgacctg aaagtggaaa agctggagga gaaagcgacc aaactggagg    4620
aagaagttcg ctgcatgatc aaccgtgtag cacccagcc gctgtccctg ctggagctga    4680
tcgacgatgt gcagcgcctg ggtctgacct acaaatttga aaagacatc attaaagccc    4740 tggaaaacat cgtactgctg gacgaaaaca aaagaacaa atctgacctg cacgcaaccg    4800
ctctgtcttt ccgtctgctg cgtcagcacg gtttcgaggt ttctcaggat gtttttgagc    4860
gtttcaagga taagaaggt ggtttcagcg gtgaactgaa aggtgacgtc caaggcctgc    4920
tgagcctgta tgaagcgtct tacctgggtt tcgagggtga gaacctgctg gaggaggcgc    4980 gtacctttc catcacccac ctgaagaaca acctgaaaga aggcattaat accaaggttg    5040
```

```
cagaacaagt gagccacgcc ctggaactgc catatcacca gcgtctgcac cgtctggagg    5100
cacgttggtt cctggataaa tacgaaccga agaaccgca tcaccagctg ctgctggagc     5160
tggcgaagct ggattttaac atggtacaga ccctgcacca gaaagagctg caagatctgt    5220
cccgctggtg gaccgagatg ggcctggcta gcaaactgga ttttgtacgc gaccgcctga    5280
tggaagttta tttctgggca ctgggtatgg cgccagaccc gcagtttggt gaatgtcgca    5340
aagctgttac taaaatgttt ggtctggtga cgatcatcga tgacgtgtat gacgtttatg    5400
gcactctgga cgaactgcaa ctgttcaccg atgctgtaga gcgctgggac gttaacgcta    5460
ttaacaccct gccggactat atgaaactgt gtttcctggc actgtacaac accgttaacg    5520
acacgtccta ttctattctg aaagagaaag gtcataacaa cctgtcctat ctgacgaaaa    5580
gctggcgtga actgtgcaaa gcctttctgc aagaggcgaa atggtccaac aacaaaatta    5640
tcccggcttt ctccaagtac ctggaaaacg ccagcgtttc ctcctccggt gtagcgctgc    5700
tggcgccgtc ttacttttcc gtatgccagc agcaggaaga catctccgac cacgcgctgc    5760
gttccctgac cgacttccat ggtctggtgc gttctagctg cgttatcttc cgcctgtgca    5820
acgatctggc cacctctgcg gcggagctgg aacgtggcga gactaccaat tctatcatta    5880
gctacatgca cgaaaacgat ggtaccagcg aggaacaggc ccgcgaagaa ctgcgtaaac    5940
tgatcgacgc cgaatggaaa aagatgaatc gtgaacgcgt tagcgactcc accctgctgc    6000
ctaaagcgtt catggaaatc gcagttaaca tggcacgtgt tccccactgc acctaccagt    6060
atggcgatgg tctgggtcgc ccagactacg cgactgaaaa ccgcatcaaa ctgctgctga    6120
ttgacccttt cccgattaac cagctgatgt atgtctaact gcatcgccct taggaggtaa    6180
aaaaaaatga ctgccgacaa caatagtatg ccccatggtg cagtatctag ttacgccaaa    6240
ttagtgcaaa accaaacacc tgaagacatt ttggaagagt tcctgaaat tattccatta     6300
caacaaagac ctaatacccg atcagtgag acgtcaaatg acgaaagcgg agaaacatgt     6360
ttttctggtc atgatgagga gcaaattaag ttaatgaatg aaaattgtat tgttttggat    6420
tgggacgata atgctattgg tgccggtacc aagaaagttt gtcatttaat ggaaaatatt    6480
gaaaagggtt tactacatcg tgcattctcc gtctttattt tcaatgaaca aggtgaatta    6540
cttttacaac aaagagccac tgaaaaata acttttccctg atctttggac taacacatgc    6600
tgctctcatc cactatgtat tgatgacgaa ttaggtttga agggtaagct agacgataag    6660
attaagggcg ctattactgc ggcggtgaga aaactagatc atgaattagg tattccagaa    6720
gatgaaacta agacaagggg taagtttcac ttttttaaaca gaatccatta catggcacca    6780
agcaatgaac catggggtga acatgaaatt gattacatcc tattttataa gatcaacgct    6840
aaagaaaact tgactgtcaa cccaaacgtc aatgaagtta gagacttcaa atgggtttca    6900
ccaaatgatt tgaaaactat gtttgctgac ccaagttaca agtttacgcc ttggtttaag    6960
attatttgcg agaattactt attcaactgg tgggagcaat tagatgacct ttctgaagtg    7020
gaaaatgaca ggcaaattca tagaatgcta taacgacgcg tcctgcagct ggtaccatat    7080
gggaattcga agcttctag aacgaaaact catctcagaa gaggatctga atagcgccgt    7140
cgaccatcat catcatcatc attgagttta acggtctcc agcttggctg ttttggcgga    7200
tgagagaaga ttttcagcct gatacagatt aaatcagaac gcagaagcgg tctgataaaa    7260
cagaatttgc ctggcggcag tagcgcggtg gtcccacctg accccatgcc gaactcagaa    7320
gtgaaacgcc gtagcgccga tggtagtgtg ggtctccccc atgcgagagt agggaactgc    7380
caggcatcaa ataaaacgaa aggctcagtc gaaagactgg gcctttcgtt ttatctgttg    7440
```

-continued

| | |
|---|---|
| tttgtcggtg aacgctctcc tgagtaggac aaatccgccg ggagcggatt tgaacgttgc | 7500 |
| gaagcaacgg cccggagggt ggcgggcagg acgcccgcca taaactgcca ggcatcaaat | 7560 |
| taagcagaag gccatcctga cggatggcct ttttgcgttt ctacaaactc tttttgttta | 7620 |
| tttttctaaa tacattcaaa tatgtatccg ctcatgagac aataaccctg ataaatgctt | 7680 |
| caataat | 7687 |

<210> SEQ ID NO 55
<211> LENGTH: 8675
<212> TYPE: DNA
<213> ORGANISM: Artificial Sequence
<220> FEATURE:
<223> OTHER INFORMATION: Synthetic Construct

<400> SEQUENCE: 55

| | |
|---|---|
| cccgtcttac tgtcgggaat tcgcgttggc cgattcatta atgcagatta ttgaagcatt | 60 |
| tatcagggtt attgtctcat gagcggatac atatttgaat gtatttagaa aaataaacaa | 120 |
| aaagagtttg tagaaacgca aaaaggccat ccgtcaggat ggccttctgc ttaatttgat | 180 |
| gcctggcagt ttatggcggg cgtcctgccc gccacccctcc gggccgttgc ttcgcaacgt | 240 |
| tcaaatccgc tcccggcgga tttgtcctac tcaggagagc gttcaccgac aaacaacaga | 300 |
| taaaacgaaa ggcccagtct ttcgactgag ccttcgttt tatttgatgc ctggcagttc | 360 |
| cctactctcg catggggaga ccccacacta ccatcggcgc tacggcgttt cacttctgag | 420 |
| ttcggcatgg ggtcaggtgg gaccaccgcg ctactgccgc caggcaaatt ctgttttatc | 480 |
| agaccgcttc tgcgttctga tttaatctgt atcaggctga aaatcttctc tcatccgcca | 540 |
| aaacagccaa gctggagacc gtttaaactc aatgatgatg atgatgatgg tcgacggcgc | 600 |
| tattcagatc ctcttctgag atgagttttt gttctagaaa gcttcgaatt cccatatggt | 660 |
| accagctgca gttatgccag ccaggccttg attttggctt ccataccagc ggcatcgagg | 720 |
| ccgagttcgg cgcgcatttc ttcctgagtt ccttgcggaa taaagaagtc cggcaggcca | 780 |
| atgttcagca cgggtactgg tttacgatgg gccatcagca cttcgttcac gccgctgcct | 840 |
| gcgccgccca taatggcgtt ttcttctacg gtgaccagcg cttcatggct ggcggccatt | 900 |
| tccagaatta cgcttcatc aagcggtttc acaaaacgca tatcgaccag cgtggcgttc | 960 |
| agcgattcgg cgactttcgc cgcttctggc atcagcgtac caaagttaag gatcgccagt | 1020 |
| ttctcgccac gacgcttcac aatgcctttg ccaattggta gttttttccag cggcgtcagt | 1080 |
| tccacgccga ccgcgttgcc acgcgggtag cgcaccgctg acgggccatc gttatagtga | 1140 |
| tagccggtat agagcatctg gcgacattcg tttttcatcgc tcggggtcat aatgaccatt | 1200 |
| tccggtatgc agcgcaggta agagagatca aaagcaccct gatgggtttg accgtcagca | 1260 |
| ccaacaatgc ccgcgcggtc gatggcgaac aggaccggaa gcttttgaat cgccacgtca | 1320 |
| tgcagcacct gatcataggc gcgttgcagg aaagtgagt aaatcgcgac aatgggtttg | 1380 |
| tacccaccaa tcgccagacc cgcagcaaag gtcaccgcgt gttgctcggc aattgccacg | 1440 |
| tcgaagtagc gatccgggaa tttacgtgaa aactcgacca tgccggaacc ttcacgcatc | 1500 |
| gccggagtaa tcgccatcag cttgttgtct ttcgctgccg tttcgcacaa ccagtcgcca | 1560 |
| aagattttg aatagctcgg caaaccgccg ctactttcg gcaaacaacc gctggaggga | 1620 |
| tcaaatttag gcacgcgtg gaaagtgatc gggtcttttt ctgccggttc ataaccacga | 1680 |
| cctttttggg tcatgatatg caggaactgc gggcctttca ggtcgcgcat gttctttagc | 1740 |

```
gtggtgataa gccccagcac atcgtgaccg tccaccgggc cgatgtagtt aaagcccagc    1800
tcttcaaaca acgtgccagg cactaccatg cctttaatat gttcttcggt gcgtttgagc    1860
agctctttaa ttggcggcac gccagagaaa acttttttcc cgccttcgcg cagtgaagag    1920
taaagcttac cggaaagcag ctgtgccaga tggttgttga gcgcgccgac attttcggaa    1980
atcgacattt cattgtcgtt gagaatcacc agcatatcag gacggatatc gcccgcgtga    2040
ttcatcgctt caaacgccat gcctgcggta atcgcgccat cgccaatgac acagacggtg    2100
cggcgatttt tgccttcttt ttcggcagca accgcaatac caattccggc actgatggag    2160
gttgatgaat gcccgacgct taatacgtca tattcgcttt cgccgcgcca cgggaacggg    2220
tgcagaccgc ctttctgacg gatggtgccg attttgtcgc ggcgtccggt caaaatttta    2280
tgcggataag cctgatgccc cacatcccaa atcaattggt caaacggggt gttgtagaca    2340
tagtgcagcg ccacggtcag ttcgaccgtg cccagcccgg aggcgaagtg cccgctggaa    2400
cggctcacgc tgtcgagtaa atagcggcgc agttcgtcgc agagtttcgg taaactctct    2460
ttcggcaaca gtcgtaactc ctgggtggag tcgaccagtg ccagggtcgg gtatttggca    2520
atatcaaaac tcatgttttt ttacctccta agggcgaatg cagttagaca tacatcagct    2580
ggttaatcgg gaaagggtca atcagcagca gtttgatgcg gttttcagtc gcgtagtctg    2640
ggcgacccag accatcgcca tactggtagg tgcagtggga aacacgtgcc atgttaactg    2700
cgatttccat gaacgcttta ggcagcaggg tggagtcgct aacgcgttca cgattcatct    2760
ttttccattc ggcgtcgatc agtttacgca gttcttcgcg ggcctgttcc tcgctggtac    2820
catcgttttc gtgcatgtag ctaatgatag aattggtagt ctcgccacgt tccagctccg    2880
ccgcagaggt ggccagatcg ttgcacaggc ggaagataac gcagctagaa cgcaccagac    2940
catggaagtc ggtcagggaa cgcagcgcgt ggtcggagat gtcttcctgc tgctggcata    3000
cggaaaagta agacggcgcc agcagcgcta caccggagga ggaaacgctg gcgttttcca    3060
ggtacttgga gaaagccggg ataattttgt tgttggacca tttcgcctct gcagaaaagg    3120 cttttgcacag ttcacgccag cttttcgtca dataggacag gttgttatga cctttctctt    3180
```

```
tcaggtcgtt ctccagggat tgcaggaatt cgaaattcca caggtttggc tgatagtttg    4200
cggaacgacg ggaattatgc tcggtaatct gagtaaattg agaagaggtc gcacacatgg    4260
tttattcctc cttatttaat cgatacatta atatatacct ctttaattt taataataaa    4320 gttaatcgat aattccggtc gagtgcccac acagattgtc tgataaattg ttaaagagca    4380
gtgccgcttc gcttttctc agcggcgctg tttcctgtgt gaaattgtta ccgctcaca     4440 attccacaca ttatacgagc cggatgatta attgtcaaca gctcatttca gaatctggcg    4500
taatagcgaa gaggcccgca ccgatcgccc ttcccaacag ttgcgcagcc tgaatggcga    4560
atggcgcctg atgcggtatt ttctccttac gcatctgtgc ggtatttcac accgcatatg    4620
gtgcactctc agtacaatct gctctgatgc cgcatagtta agccagcccc gacacccgcc    4680 aacaccgct gacgagctta gtaaagccct cgctagattt taatgcggat gttgcgatta    4740
cttcgccaac tattgcgata acaagaaaaa gccagccttt catgatatat ctcccaattt    4800
gtgtagggct tattatgcac gcttaaaaat aataaaagca gacttgacct gatagtttgg    4860
ctgtgagcaa ttatgtgctt agtgcatcta acgcttgagt taagccgcgc cgcgaagcgg    4920
cgtcggcttg aacgaattgt tagacattat ttgccgacta ccttggtgat ctcgcctttc    4980
acgtagtgga caaattcttc caactgatct gcgcgcgagg ccaagcgatc ttcttcttgt    5040
ccaagataag cctgtctagc ttcaagtatg acgggctgat actgggccgg caggcgctcc    5100
attgcccagt cggcagcgac atccttcggc gcgattttgc cggttactgc gctgtaccaa    5160
atgcgggaca acgtaagcac tacatttcgc tcatcgccag cccagtcggg cggcgagttc    5220
catagcgtta aggtttcatt tagcgcctca aatagatcct gttcaggaac cggatcaaag    5280
agttcctccg ccgctggacc taccaaggca acgctatgtt ctcttgcttt tgtcagcaag    5340
atagccagat caatgtcgat cgtggctggc tcgaagatac ctgcaagaat gtcattgcgc    5400
tgccattctc caaattgcag ttcgcgctta gctggataac gccacggaat gatgtcgtcg    5460
tgcacaacaa tggtgacttc tacagcgcgg agaatctcgc tctctccagg ggaagccgaa    5520
gtttccaaaa ggtcgttgat caaagctcgc cgcgttgttt catcaagcct tacggtcacc    5580
gtaaccagca aatcaatatc actgtgtggc ttcaggccgc catccactgc ggagccgtac    5640
aaatgtacgg ccagcaacgt cggttcgaga tggcgctcga tgacgccaac tacctctgat    5700
agttgagtcg atacttcggc gatcaccgct tccctcatga tgtttaactt tgttttaggg    5760
cgactgccct gctgcgtaac atcgttgctg ctccataaca tcaaacatcg acccacggcg    5820
taacgcgctt gctgcttgga tgcccgaggc atagactgta ccccaaaaaa acagtcataa    5880
caagccatga aaaccgccac tgcgccgtta ccaccgctgc gttcggtcaa ggttctggac    5940
cagttgcgtg agcgcatacg ctacttgcat tacagcttac gaaccgaaca ggcttatgtc    6000
cactgggttc gtgccttcat ccgtttccac ggtgtgcgtc acccggcaac cttgggcagc    6060
agcgaagtcg aggcatttct gtcctggctg gcgaacgagc gcaaggtttc ggtctccacg    6120
catcgtcagg cattggcggc cttgctgttc ttctacggca aggtgctgtg cacggatctg    6180
ccctggcttc aggagatcgg aagacctcgg ccgtcgcggc gcttgccggt ggtgctgacc    6240
ccggatgaag tggttcgcat cctcggtttt ctggaaggcg agcatcgttt gttcgcccag    6300
cttctgtatg gaacgggcat gcggatcagt gagggtttgc aactgcgggt caaggatctg    6360
gatttcgatc acggcacgat catcgtgcgg gagggcaagg gctccaagga tcgggccttg    6420
atgttacccg agagcttggc acccagcctg cgcgagcagg ggaattaatt cccacgggtt    6480
```

```
ttgctgcccg caaacgggct gttctggtgt tgctagtttg ttatcagaat cgcagatccg    6540
gcttcagccg gtttgccggc tgaaagcgct atttcttcca gaattgccat gattttttcc    6600
ccacgggagg cgtcactggc tcccgtgttg tcggcagctt tgattcgata agcagcatcg    6660 cctgttttcag gctgtctatg tgtgactgtt gagctgtaac aagttgtctc aggtgttcaa    6720
tttcatgttc tagttgcttt gttttactgg tttcacctgt tctattaggt gttacatgct    6780
gttcatctgt tacattgtcg atctgttcat ggtgaacagc tttgaatgca ccaaaaactc    6840
gtaaaagctc tgatgtatct atcttttta caccgttttc atctgtgcat atggacagtt    6900
ttccctttga tatgtaacgg tgaacagttg ttctactttt gtttgttagt cttgatgctt    6960
cactgataga tacaagagcc ataagaacct cagatccttc cgtatttagc cagtatgttc    7020
tctagtgtgg ttcgttgttt ttgcgtgagc catgagaacg aaccattgag atcatactta    7080 cttttgcatgt cactcaaaaa ttttgcctca aaactggtga gctgaatttt tgcagttaaa    7140
gcatcgtgta gtgttttct tagtccgtta tgtaggtagg aatctgatgt aatggttgtt    7200
ggtattttgt caccattcat ttttatctgg ttgttctcaa gttcggttac gagatccatt    7260
tgtctatcta gttcaacttg gaaaatcaac gtatcagtcg ggcggcctcg cttatcaacc    7320
accaatttca tattgctgta agtgtttaaa tcttttactta ttggtttcaa acccattgg    7380 ttaagccttt taaactcatg gtagttattt tcaagcatta acatgaactt aaattcatca    7440
aggctaatct ctatatttgc cttgtgagtt ttcttttgtg ttagttcttt taataaccac    7500
tcataaatcc tcatagagta tttgttttca aaagacttaa catgttccag attatatttt    7560
atgaattttt ttaactggaa aagataaggc aatatctctt cactaaaaac taattctaat    7620
ttttcgcttg agaacttggc atagtttgtc cactggaaaa tctcaaagcc tttaaccaaa    7680
ggattcctga tttccacagt tctcgtcatc agctctctgg ttgctttagc taatacacca    7740
taagcatttt ccctactgat gttcatcatc tgagcgtatt ggttataagt gaacgatacc    7800
gtccgttctt tccttgtagg gttttcaatc gtggggttga gtagtgccac acagcataaa    7860
attagcttgg tttcatgctc cgttaagtca tagcgactaa tcgctagttc atttgctttg    7920
aaaacaacta attcagacat acatctcaat tggtctaggt gattttaatc actataccaa    7980
ttgagatggg ctagtcaatg ataattacta gtccttttcc tttgagttgt gggtatctgt    8040
aaattctgct agacctttgc tggaaaactt gtaaattctg ctagaccctc tgtaaattcc    8100
gctagacctt tgtgtgtttt ttttgtttat attcaagtgg ttataattta tagaataaag    8160
aaagaataaa aaaagataaa aagaatagat cccagccctg tgtataactc actactttag    8220
tcagttccgc agtattacaa aaggatgtcg caaacgctgt ttgctcctct acaaaacaga    8280
ccttaaaacc ctaaaggctt aagtagcacc ctcgcaagct cgggcaaatc gctgaatatt    8340 cctttttgtct ccgaccatca ggcacctgag tcgctgtctt tttcgtgaca ttcagttcgc    8400
tgcgctcacg gctctggcag tgaatggggg taaatggcac tacaggcgcc ttttatggat    8460
tcatgcaagg aaactaccca taatacaaga aaagcccgtc acgggcttct cagggcgttt    8520
tatggcgggt ctgctatgtg gtgctatctg acttttttgct gttcagcagt tcctgccctc    8580 tgatttttcca gtctgaccac ttcggattat cccgtgacag gtcattcaga ctggctaatg    8640
cacccagtaa ggcagcggta tcatcaacag gctta                               8675
```

<210> SEQ ID NO 56
<211> LENGTH: 8032
<212> TYPE: DNA
<213> ORGANISM: Artificial Sequence
<220> FEATURE:
<223> OTHER INFORMATION: Synthetic Construct

<400> SEQUENCE: 56

```
tcgctgcgct cggtcgttcg gctgcggcga gcggtatcag ctcactcaaa ggcggtaata      60
cggttatcca cagaatcagg ggataacgca ggaaagaaca tgtgagcaaa aggccagcaa     120
aaggccagga accgtaaaaa ggccgcgttg ctggcgtttt tccataggct ccgcccccct     180
gacgagcatc acaaaaatcg acgctcaagt cagaggtggc gaaacccgac aggactataa     240
agataccagg cgtttccccc tggaagctcc ctcgtgcgct ctcctgttcc gaccctgccg     300
cttaccggat acctgtccgc ctttctccct tcgggaagcg tggcgctttc tcatagctca     360
cgctgtaggt atctcagttc ggtgtaggtc gttcgctcca agctgggctg tgtgcacgaa     420
ccccccgttc agcccgaccg ctgcgcctta tccgtaact atcgtcttga gtccaacccg     480
gtaagacacg acttatcgcc actggcagca gccactggta acaggattag cagagcgagg     540
tatgtaggcg gtgctacaga gttcttgaag tggtggccta actacggcta cactagaaga     600
acagtatttg gtatctgcgc tctgctgaag ccagttacct tcggaaaaag agttggtagc     660
tcttgatccg gcaaacaaac caccgctggt agcggtggtt tttttgtttg caagcagcag     720
attacgcgca gaaaaaaagg atctcaagaa gatcctttga tcttttctac ggggtctgac     780
gctcagtgga acgaaaactc acgttaaggg attttggtca tgagattatc aaaaaggatc     840
ttcacctaga tccttttaaa ttaaaaatga agttttaaat caatctaaag tatatatgag     900
taaacttggt ctgacagtta ccaatgctta atcagtgagg cacctatctc agcgatctgt     960
ctatttcgtt catccatagt tgcctgactc cccgtcgtgt agataactac gatacgggag    1020
ggcttaccat ctggccccag tgctgcaatg ataccgcgag acccacgctc accggctcca    1080
gatttatcag caataaacca gccagccgga agggccgagc gcagaagtgg tcctgcaact    1140
ttatccgcct ccatccagtc tattaattgt tgccgggaag ctagagtaag tagttcgcca    1200
gttaatagtt tgcgcaacgt tgttgccatt gctacaggca tcgtggtgtc acgctcgtcg    1260
tttggtatgg cttcattcag ctccggttcc caacgatcaa ggcgagttac atgatccccc    1320
atgttgtgca aaaaagcggt tagctccttc ggtcctccga tcgttgtcag aagtaagttg    1380
gccgcagtgt tatcactcat ggttatggca gcactgcata attctcttac tgtcatgcca    1440
tccgtaagat gcttttctgt gactggtgag tactcaacca agtcattctg agaatagtgt    1500
atgcggcgac cgagttgctc ttgcccggcg tcaatacggg ataataccgc gccacatagc    1560
agaactttaa aagtgctcat cattggaaaa cgttcttcgg ggcgaaaact ctcaaggatc    1620
ttaccgctgt tgagatccag ttcgatgtaa cccactcgtg cacccaactg atcttcagca    1680
tcttttactt tcaccagcgt ttctgggtga gcaaaaacag gaaggcaaaa tgccgcaaaa    1740
aagggaataa gggcgacacg gaaatgttga atactcatac tcttcctttt tcaatattat    1800
tgaagcattt atcagggtta ttgtctcatg agcggataca tatttgaatg tatttagaaa    1860
aataaacaaa taggggttcc gcgcacattt ccccgaaaag tgccacctga cgtctaagaa    1920
accattatta tcatgacatt aacctataaa aataggcgta tcacgaggcc ctttcgtctc    1980
gcgcgtttcg gtgatgacgg tgaaaacctc tgacacatgc agctcccgga gacggtcaca    2040
gcttgtctgt aagcggatgc cgggagcaga caagcccgtc agggcgcgtc agcgggtgtt    2100
ggcgggtgtc ggggctggct taactatgcg gcatcagagc agattgtact gagagtgcac    2160
catagatctg gagctgtaat ataaaaacct tcttcaacta acggggcagg ttagtgacat    2220
```

-continued

```
tagaaaaccg actgtaaaaa gtacagtcgg cattatctca tattataaaa gccagtcatt    2280
aggcctatct gacaattcct gaatagagtt cataaacaat cctgcatgat aaccatcaca    2340
aacagaatga tgtacctgta aagatagcgg taaatatatt gaattacctt tattaatgaa    2400
ttttcctgct gtaataatgg gtagaaggta attactatta ttattgatat ttaagttaaa    2460
cccagtaaat gaagtccatg gaataataga aagagaaaaa gcattttcag gtataggtgt    2520
tttgggaaac aatttccccg aaccattata tttctctaca tcagaaaggt ataaatcata    2580
aaactctttg aagtcattct ttacaggagt ccaaatacca gagaatgttt tagatacacc    2640
atcaaaaatt gtataaagtg gctctaactt atcccaataa cctaactctc cgtcgctatt    2700
gtaaccagtt ctaaaagctg tatttgagtt tatcacccct gtcactaaga aaataaatgc    2760
agggtaaaat ttatatcctt cttgttttat gtttcggtat aaaacactaa tatcaatttc    2820
tgtggttata ctaaaagtcg tttgttggtt caaataatga ttaaatatct cttttctctt    2880
ccaattgtct aaatcaattt tattaaagtt catttgatat gcctcctaaa tttttatcta    2940
aagtgaattt aggaggctta cttgtctgct ttcttcatta gaatcaatcc tttttttaaaa   3000
gtcaatatta ctgtaacata aatatatatt ttaaaaatat cccactttat ccaattttcg    3060
tttgttgaac taatgggtgc tttagttgaa gaataaaaga cctatgcggt gtgaaatacc    3120
gcacagatgc gtaaggagaa ataccgcat caggcgccat cgccattca ggctgcgcaa      3180
ctgttgggaa gggcgatcgg tgcgggcctc ttcgctatta cgccagctgg cgaaaggggg    3240
atgtgctgca aggcgattaa gttgggtaac gccagggttt tcccagtcac gacgttgtaa    3300
aacgacggcc agtgccaagc ttgcatgcct gcactccatt tcttctgct atcaaaataa     3360
cagactcgtg attttccaaa cgagctttca aaaagcctc tgccccttgc aaatcggatg     3420
cctgtctata aaattcccga tattggttaa acagcggcgc aatggcggcc gcatctgatg    3480
tctttgcttg gcgaatgttc atcttatttc ttcctccctc tcaataattt tttcattcta    3540
tccctttct gtaaagttta tttttcagaa tacttttatc atcatgcttt gaaaaaatat     3600
cacgataata tccattgttc tcacggaagc acacgcaggt catttgaacg aatttttttcg   3660
acaggaattt gccgggactc aggagcattt aacctaaaaa agcatgacat ttcagcataa    3720
tgaacattta ctcatgtcta ttttcgttct tttctgtatg aaaatagtta tttcgagtct    3780
ctacggaaat agcgagagat gatataccta aatagagata aaatcatctc aaaaaaatgg   3840
gtctactaaa atattattcc atctattaca ataaattcac agaatagtct tttaagtaag    3900
tctactctga atttttttaa aaggagaggg taaagagtga aaacagtagt tattattgat    3960
gcattacgaa caccaattgg aaaatataaa ggcagcttaa gtcaagtaag tgccgtagac    4020
ttaggaacac atgttacaac acaacttta aaaagacatt ccactatttc tgaagaaatt    4080
gatcaagtaa tctttggaaa tgttttacaa gctggaaatg gccaaaatcc cgcacgacaa    4140
atagcaataa acagcggttt gtctcatgaa attcccgcaa tgacggttaa tgaggtctgc    4200
ggatcaggaa tgaaggccgt tattttggcg aaacaattga ttcaattagg agaagcggaa    4260
gttttaattg ctggcgggat tgagaatatg tcccaagcac ctaaattaca acgttttaat    4320
tacgaaacag aaagctacga tgcgcctttt tctagtatga tgtatgatgg attaacggat    4380
gcctttagtg gtcaggcaat gggcttaact gctgaaaatg tggccgaaaa gtatcatgta    4440
actagagaag agcaagatca attttctgta cattcacaat taaaagcagc tcaagcacaa    4500
gcagaaggga tattcgctga cgaaatagcc ccattagaag tatcaggaac gcttgtggag    4560
aaagatgaag ggattcgccc taattcgagc gttgagaagc taggaacgct taaaacagtt    4620
```

```
tttaaagaag acggtactgt aacagcaggg aatgcatcaa ccattaatga tggggcttct    4680
gctttgatta ttgcttcaca agaatatgcc gaagcacacg gtcttcctta tttagctatt    4740
attcgagaca gtgtggaagt cggtattgat ccagcctata tgggaatttc gccgattaaa    4800
gccattcaaa aactgttagc gcgcaatcaa cttactacgg aagaaattga tctgtatgaa    4860
atcaacgaag catttgcagc aacttcaatc gtggtccaaa gagaactggc tttaccagag    4920
gaaaaggtca acatttatgg tggcggtatt tcattaggtc atgcgattgg tgccacaggt    4980
gctcgtttat taacgagttt aagttatcaa ttaaatcaaa agaaaagaa atatggagtg    5040 gcttctttat gtatcggcgg tggcttagga ctcgctatgc tactagagag acctcagcaa    5100
aaaaaaaaca gccgatttta tcaaatgagt cctgaggaac gcctggcttc tcttcttaat    5160
gaaggccaga tttctgctga tacaaaaaaa gaatttgaaa atacggcttt atcttcgcag    5220
attgccaatc atatgattga aaatcaaatc agtgaaacag aagtgccgat gggcgttggc    5280
ttacatttaa cagtggacga aactgattat ttggtaccaa tggcgacaga agagccctca    5340
gttattgcgg ctttgagtaa tggtgcaaaa atagcacaag gatttaaaac agtgaatcaa    5400
caacgcttaa tgcgtggaca aatcgttttt tacgatgttg cagatcccga gtcattgatt    5460
gataaactac aagtaagaga agcggaagtt tttcaacaag cagagttaag ttatccatct    5520
atcgttaaac ggggcggcgg cttaagagat ttgcaatatc gtactttga tgaatcattt    5580 gtatctgtcg acttttagt agatgttaag gatgcaatgg gggcaaatat cgttaacgct    5640
atgttggaag gtgtggccga gttgttccgt gaatggtttg cggagcaaaa gattttattc    5700
agtattttaa gtaattatgc cacggagtcg gttgttacga tgaaaacggc tattccagtt    5760
tcacgtttaa gtaaggggag caatggccgg gaaattgctg aaaaaattgt tttagcttca    5820
cgctatgctt cattagatcc ttatcgggca gtcacgcata caaaggaat catgaatggc    5880 attgaagctg tagttttagc tacaggaaat gatacgcg ctgttagcgc ttcttgtcat    5940
gcttttgcgg tgaaggaagg tcgctaccaa ggcttgacta gttggacgct ggatggcgaa    6000
caactaattg gtgaaatttc agttccgctt gctttagcca cggttggcgg tgccacaaaa    6060
gtcttaccta aatctcaagc agctgctgat ttgttagcag tgacggatgc aaaagaacta    6120
agtcgagtag tagcggctgt tggttttggc aaaatttag cggcgttacg ggccttagtc    6180
tctgaaggaa ttcaaaaagg acacatggct ctacaagcac gttctttagc gatgacggtc    6240
ggagctactg gtaaagaagt tgaggcagtc gctcaacaat taaaacgtca aaaaacgatg    6300
aaccaagacc gagccatggc tattttaaat gatttaagaa acaataaaa ggagagggtg    6360 acaattggga ttgataaaat tagttttttt gtgcccccctt attatattga tatgacggca    6420
ctggctgaag ccagaaatgt agaccctgga aaatttcata ttggtattgg gcaagaccaa    6480
atggcggtga acccaatcag ccaagatatt gtgacatttg cagccaatgc cgcagaagcg    6540
atcttgacca agaagataa agaggccatt gatatggtga ttgtcgggac tgagtccagt    6600
atcgatgagt caaaagcggc cgcagttgtc ttacatcgtt taatggggat caacctttc    6660 gctcgctctt tcgaaatcaa ggaagcttgt tacggagcaa cagcaggctt acagttagct    6720
aagaatcacg tagccttaca tccagataaa aaagtcttgg tcgtagcggc agatattgca    6780
aaatatggct taaattctgg cggtgagcct acacaaggag ctgggcggt tgcaatgtta    6840 gttgctagtg aaccgcgcat tttgcttta aagaggata atgtgatgct gacgcaagat    6900
atctatgact tttggcgtcc aacaggccac ccgtatccta tggtcgatgg tccttttgtca    6960
```

-continued

```
aacgaaacct acatccaatc tttttgcccaa gtctgggatg aacataaaaa acgaaccggt      7020
cttgattttg cagattatga tgctttagcg ttccatattc cttacacaaa aatgggcaaa      7080
aaagccttat tagcaaaaat ctccgaccaa actgaagcag aacaggaacg aattttagcc      7140
cgttatgaag aaagtatcgt ctatagtcgt cgcgtaggaa acttgtatac gggttcactt      7200
tatctgggac tcatttccct tttagaaaat gcaacgactt taaccgcagg caatcaaatt      7260
ggtttattca gttatggttc tggtgctgtc gctgaatttt tcactggtga attagtagct      7320
ggttatcaaa atcatttaca aaaagaaact catttagcac tgctggataa tcggacagaa      7380
ctttctatcg ctgaatatga agccatgttt gcagaaactt tagacacaga cattgatcaa      7440
acgttagaag atgaattaaa atatagtatt tctgctatta ataataccgt tcgttcttat      7500
cgaaactaaa aaaaccggc cttggccccg ccggttttttt attattttc ttcctccgca      7560 tgttcaatcc gctccataat cgacggatgg ctccctctga aaattttaac gagaaacggc      7620
gggttgaccc ggctcagtcc cgtaacggcc aagtcctgaa acgtctcaat cgccgcttcc      7680
cggtttccgg tcagctcaat gccgtaacgg tcggcggcgt tttcctgata ccgggagacg      7740
gcattcgtaa tcgggatccc cgggtaccga gctcgaattc gtaatcatgt catagctgtt      7800
tcctgtgtga aattgttatc cgctcacaat tccacacaac atacgagccg gaagcataaa      7860
gtgtaaagcc tggggtgcct aatgagtgag ctaactcaca ttaattgcgt tgcgctcact      7920
gcccgctttc cagtcgggaa acctgtcgtg ccagctgcat taatgaatcg gccaacgcgc      7980
ggggagaggc ggtttgcgta ttgggcgctc ttccgcttcc tcgctcactg ac             8032
```

<210> SEQ ID NO 57
<211> LENGTH: 6592
<212> TYPE: DNA
<213> ORGANISM: Artificial Sequence
<220> FEATURE:
<223> OTHER INFORMATION: Synthetic Construct

<400> SEQUENCE: 57

```
gaattgctcc attttcttct gctatcaaaa taacagactc gtgattttcc aaacgagctt        60
tcaaaaaagc ctctgcccct tgcaaatcgg atgcctgtct ataaaattcc cgatattggt       120
taaacagcgg cgcaatggcg gccgcatctg atgtctttgc ttggcgaatg ttcatcttat       180
ttcttcctcc ctctcaataa ttttttcatt ctatcccttt tctgtaaagt ttatttttca       240
gaatactttt atcatcatgc tttgaaaaaa tatcacgata atatccattg ttctcacgga       300
agcacacgca ggtcatttga acgaattttt tcgacaggaa tttgccggga ctcaggagca       360
tttaacctaa aaaagcatga catttcagca taatgaacat ttactcatgt ctattttcgt       420
tcttttctgt atgaaaatag ttatttcgag tctctacgga aatagcgaga gatgatatac       480
ctaaatagag ataaaatcat ctcaaaaaaa tgggtctact aaaatattat tccatctatt       540
acaataaatt cacagaatag tcttttaagt aagtctactc tgaatttttt taaaaggaga       600
gggtaaagag tgtgtgcgac ctcttctcaa tttactcaga ttaccgagca taattcccgt       660
cgttccgcaa actatcagcc aaacctgtgg aatttcgaat tcctgcaatc cctggagaac       720
gacctgaaag tggaaaagct ggaggagaaa gcgaccaaac tggaggaaga agttcgctgc       780
atgatcaacc gtgtagacac ccagccgctg tccctgctgg agctgatcga cgatgtgcag       840
cgcctgggtc tgacctacaa atttgaaaaa gacatcatta agccctggaa aacatcgta       900 ctgctggacg aaaacaaaaa gaacaaatct gacctgcacg caaccgctct gtctttccgt       960
ctgctgcgtc agcacggttt cgaggtttct caggatgttt ttgagcgttt caaggataaa      1020
```

```
gaaggtggtt tcagcggtga actgaaaggt gacgtccaag gcctgctgag cctgtatgaa      1080
gcgtcttacc tgggtttcga gggtgagaac ctgctggagg aggcgcgtac cttttccatc      1140
acccacctga agaacaacct gaaagaaggc attaatacca aggttgcaga acaagtgagc      1200
cacgccctgg aactgccata tcaccagcgt ctgcaccgtc tggaggcacg ttggttcctg      1260
gataaatacg aaccgaaaga accgcatcac cagctgctgc tggagctggc gaagctggat      1320
tttaacatgg tacagaccct gcaccagaaa gagctgcaag atctgtcccg ctggtggacc      1380
gagatgggcc tggctagcaa actggatttt gtacgcgacc gcctgatgga agtttatttc      1440
tgggcactgg gtatggcgcc agacccgcag tttggtgaat gtcgcaaagc tgttactaaa      1500
atgtttggtc tggtgacgat catcgatgac gtgtatgacg tttatggcac tctggacgaa      1560
ctgcaactgt tcaccgatgc tgtagagcgc tgggacgtta acgctattaa cacctgccg       1620 gactatatga aactgtgttt cctggcactg tacaacaccg ttaacgacac gtcctattct      1680
attctgaaag agaaaggtca taacaacctg tcctatctga cgaaaagctg gcgtgaactg      1740
tgcaaagcct ttctgcaaga ggcgaaatgg tccaacaaca aaattatccc ggctttctcc      1800
aagtacctgg aaaacgccag cgtttcctcc tccggtgtag cgctgctggc gccgtcttac      1860 tttccgtat gccagcagca ggaagacatc tccgaccacg cgctgcgttc cctgaccgac       1920
ttccatggtc tggtgcgttc tagctgcgtt atcttccgcc tgtgcaacga tctgccacc       1980 tctgcggcgg agctggaacg tggcgagact accaattcta tcattagcta catgcacgaa      2040
aacgatggta ccagcgagga acaggcccgc gaagaactgc gtaaactgat cgacgccgaa      2100 tggaaaaga tgaatcgtga acgcgttagc gactccaccc tgctgcctaa agcgttcatg       2160
gaaatcgcag ttaacatggc acgtgtttcc cactgcacct accagtatgg cgatggtctg      2220
ggtcgcccag actacgcgac tgaaaaccgc atcaaactgc tgctgattga cccttttccg      2280
attaaccagc tgatgtatgt ctaaaaaaaa ccggccttgg ccccgccggt ttttttattat      2340 ttttcttcct ccgcatgttc aatccgctcc ataatcgacg gatggctccc tctgaaaatt      2400
ttaacgagaa acggcgggtt gacccggctc agtcccgtaa cggccaagtc ctgaaacgtc      2460
tcaatcgccg cttcccggtt tccggtcagc tcaatgccgt aacggtcggc ggcgttttcc      2520
tgataccggg agacggcatt cgtaatcgga tcctctagag tcgacctgca ggcatgcaag      2580
ctttgcctcg cgcgtttcgg tgatgacggt gaaaacctct gacacatgca gctcccggag      2640
acggtcacag cttgtctgta agcggatgcc gggagcagac aagcccgtca gggcgcgtca      2700
gcgggtgttg gcgggtgtcg gggcgcagcc atgacccagt cacgtagcga tagcggagtg      2760
tatactggct taactatgcg gcatcagagc agattgtact gagagtgcac catatgcggt      2820
gtgaaatacc gcacagatgc gtaaggagaa ataccgcat caggcgctct ccgcttcct        2880 cgctcactga ctcgctgcgc tcggtcgttc ggctgcggcg agcggtatca gctcactcaa      2940
aggcggtaat acggttatcc acagaatcag gggataacgc aggaaagaac atgtgagcaa      3000
aaggccagca aaaggccagg aaccgtaaaa aggccgcgtt gctggcgttt ttccataggc      3060 tccgccccc tgacgagcat cacaaaaatc gacgctcaag tcagaggtgg cgaaacccga      3120
caggactata aagataccag gcgtttcccc ctggaagctc cctcgtgcgc tctcctgttc      3180
cgaccctgcc gcttaccgga tacctgtccg cctttctccc ttcgggaagc gtggcgcttt      3240
ctcaatgctc acgctgtagg tatctcagtt cggtgtaggt cgttcgctcc aagctgggct      3300
gtgtgcacga accccccgtt cagcccgacc gctgcgcctt atccggtaac tatcgtcttg      3360
```

```
agtccaaccc ggtaagacac gacttatcgc cactggcagc agccactggt aacaggatta      3420
gcagagcgag gtatgtaggc ggtgctacag agttcttgaa gtggtggcct aactacggct      3480
acactagaag gacagtattt ggtatctgcg ctctgctgaa gccagttacc ttcggaaaaa      3540
gagttggtag ctcttgatcc ggcaaacaaa ccaccgctgg tagcggtggt ttttttgttt      3600
gcaagcagca gattacgcgc agaaaaaaag gatctcaaga agatcctttg atcttttcta      3660
cggggtctga cgctcagtgg aacgaaaact cacgttaagg gattttggtc atgagattat      3720
caaaaaggat cgaagtcggt tcagaaaaag aaggatatgg atctggagct gtaatataaa      3780
aaccttcttc aactaacggg gcaggttagt gacattagaa aaccgactgt aaaaagtaca      3840
gtcggcatta tctcatatta taaaagccag tcattaggcc tatctgacaa ttcctgaata      3900
gagttcataa acaatcctgc atgataacca tcacaaacag aatgatgtac ctgtaaagat      3960
agcggtaaat atattgaatt acctttatta atgaattttc ctgctgtaat aatgggtaga      4020
aggtaattac tattattatt gatatttaag ttaaacccag taaatgaagt ccatggaata      4080
atagaaagag aaaaagcatt ttcaggtata ggtgttttgg gaaacaattt aaaagaacca      4140
ttatatttct ctacatcaga aaggtataaa tcataaaact ctttgaagtc attctttaca      4200
ggagtccaaa taccagagaa tgttttagat acaccatcaa aaattgtata aagtggctct      4260
aacttatccc aataacctaa ctctccgtcg ctattgtaac cagttctaaa agctgtattt      4320
gagtttatca cccttgtcac taagaaaata aatgcagggt aaaatttata tccttcttgt      4380
tttatgtttc ggtataaaac actaatatca atttctgtgg ttatactaaa agtcgtttgt      4440
tggttcaaat aatgattaaa tatctctttt ctcttccaat tgtctaaatc aattttatta      4500
aagttcattt gatatgcctc ctaaattttt atctaaagtg aatttaggag cttacttgt       4560 ctgctttctt cattagaatc aatccttttt taaagtcaat attactgtaa cataaatata      4620
tattttaaaa atatcccact ttatccaatt ttcgtttgtt gaactaatgg gtgctttagt      4680
tgaagaataa agaccacatt aaaaaatgtg gtctttttgtg ttttttttaaa ggatttgagc     4740 gtacgcgaaa aatccttttc tttctttctt atcttgataa taagggtaac tattgccggt      4800
tgtccattca tggctgaact ctgcttcctc tgttgacatg acacacatca tctcaatatc      4860
cgaatagggc ccatcagtct gacgaccaag agagccataa acaccaatag ccttaacatc      4920
atccccatat ttatccaata ttcgttcctt aatttcatga acaatcttca ttctttcttc      4980
tctagtcatt attattggtc cattcactat tctcattccc ttttcagata attttagatt      5040
tgcttttcta aataagaata tttggagagc accgttctta ttcagctatt ataactcgt       5100 cttcctaagc atccttcaat cctttaata acaattatag catctaatct tcaacaaact       5160
ggcccgtttg ttgaactact ctttaataaa ataattttc cgttcccaat tccacattgc       5220
aataatagaa aatccatctt catcggcttt ttcgtcatca tctgtatgaa tcaaatcgcc      5280
ttcttctgtg tcatcaaggt ttaattttt atgtatttct tttaacaaac caccatagga       5340
gattaacctt ttacggtgta aaccttcctc caaatcagac aaacgtttca aattctttc       5400 ttcatcatcg gtcataaaat ccgtatcctt tacaggatat tttgcagttt cgtcaattgc      5460
cgattgtata tccgatttat atttattttt cggtcgaatc atttgaactt ttacatttgg     5520
atcatagtct aatttcattg cctttttcca aaattgaatc cattgttttt gattcacgta      5580
gttttctgtt attctaaaat aagttggttc cacacatacc attacatgca tgtgctgatt      5640
ataagaatta tctttattat ttattgtcac atccgttgca cgcataaaac caacaagatt      5700
tttattaatt tttttatatt gcatcattcg gcgaaatcct tgagccatat ctgtcaaact      5760
```

-continued

```
cttatttaat tcttcgccat cataaacatt tttaactgtt aatgtgagaa acaaccaacg    5820
aactgttggc ttttgtttaa taacttcagc aacaacctttt tgtgactgaa tgccatgttt    5880
cattgctctc ctccagttgc acattggaca aagcctggat ttgcaaaacc acactcgata    5940
ccactttctt tcgccgtttt cacgattttg tttatactct aatatttcag cacaatcttt    6000
tactctttca gccttttttaa attcaagaat atgcagaagt tcaaagtaat caacattagc    6060 gatttttcttt tctctccatg gtctcacttt tccactttttt gtcttgtcca ctaaaaccct    6120
tgatttttca tctgaataaa tgctactatt aggacacata atattaaaag aaaccccat    6180 ctatttagtt atttgtttag tcacttataa ctttaacaga tggggttttt ctgtgcaacc    6240
aattttaagg ttttcaata ctttaaaaca catacatacc aacacttcaa cgcacctttc    6300
agcaactaaa ataaaaatga cgttatttct atatgtatca agataagaaa gaacaagttc    6360
aaaaccatca aaaaagaca ccttttcagg tgcttttttt attttataaa ctcattccct    6420
gatctcgact tcgttctttt tttacctctc ggttatgagt tagttcaaat tcgttctttt    6480
taggttctaa atcgtgttttt tcttggaatt gtgctgttttt atcctttacc ttgtctacaa    6540
accccttaaa aacgttttta aaggctttta agccgtctgt acgttcctta ag            6592
```

```
<210> SEQ ID NO 58
<211> LENGTH: 31
<212> TYPE: DNA
<213> ORGANISM: Artificial Sequence
<220> FEATURE:
<223> OTHER INFORMATION: Synthetic Construct

<400> SEQUENCE: 58
gacatcaatt gctccatttt cttctgctat c                                    31

<210> SEQ ID NO 59
<211> LENGTH: 39
<212> TYPE: DNA
<213> ORGANISM: Artificial Sequence
<220> FEATURE:
<223> OTHER INFORMATION: Synthetic Construct

<400> SEQUENCE: 59
attgagaaga ggtcgcacac actctttacc ctctcctttt                           39

<210> SEQ ID NO 60
<211> LENGTH: 41
<212> TYPE: DNA
<213> ORGANISM: Artificial Sequence
<220> FEATURE:
<223> OTHER INFORMATION: Synthetic Construct

<400> SEQUENCE: 60
taaaaggaga gggtaaagag tgtgtgcgac ctcttctcaa t                         41

<210> SEQ ID NO 61
<211> LENGTH: 41
<212> TYPE: DNA
<213> ORGANISM: Artificial Sequence
<220> FEATURE:
<223> OTHER INFORMATION: Synthetic Construct

<400> SEQUENCE: 61
ccaaggccgg tttttttttag acatacatca gctggttaat c                        41

<210> SEQ ID NO 62
```

```
<211> LENGTH: 41
<212> TYPE: DNA
<213> ORGANISM: Artificial Sequence
<220> FEATURE:
<223> OTHER INFORMATION: Synthetic Construct

<400> SEQUENCE: 62
gattaaccag ctgatgtatg tctaaaaaaa accggccttg g                         41

<210> SEQ ID NO 63
<211> LENGTH: 32
<212> TYPE: DNA
<213> ORGANISM: Artificial Sequence
<220> FEATURE:
<223> OTHER INFORMATION: Synthetic Construct

<400> SEQUENCE: 63
gacatgacgg atccgattac gaatgccgtc tc                                   32

<210> SEQ ID NO 64
<211> LENGTH: 31
<212> TYPE: DNA
<213> ORGANISM: Artificial Sequence
<220> FEATURE:
<223> OTHER INFORMATION: Synthetic Construct

<400> SEQUENCE: 64
gacatcaatt gctccatttt cttctgctat c                                    31

<210> SEQ ID NO 65
<211> LENGTH: 27
<212> TYPE: DNA
<213> ORGANISM: Artificial Sequence
<220> FEATURE:
<223> OTHER INFORMATION: Synthetic Construct

<400> SEQUENCE: 65
gacatgaatt cctccatttt cttctgc                                         27

<210> SEQ ID NO 66
<211> LENGTH: 20
<212> TYPE: DNA
<213> ORGANISM: Artificial Sequence
<220> FEATURE:
<223> OTHER INFORMATION: Synthetic Construct

<400> SEQUENCE: 66
aggagagggt aaagagtgag                                                 20

<210> SEQ ID NO 67
<211> LENGTH: 22
<212> TYPE: DNA
<213> ORGANISM: Artificial Sequence
<220> FEATURE:
<223> OTHER INFORMATION: Synthetic Construct

<400> SEQUENCE: 67
cttttccatc acccacctga ag                                              22

<210> SEQ ID NO 68
<211> LENGTH: 28
<212> TYPE: DNA
<213> ORGANISM: Artificial Sequence
<220> FEATURE:
<223> OTHER INFORMATION: Synthetic Construct

<400> SEQUENCE: 68
```
ggcgaaatgg tccaacaaca aaattatc                                         28

<210> SEQ ID NO 69
<211> LENGTH: 51
<212> TYPE: DNA
<213> ORGANISM: Artificial Sequence
<220> FEATURE:
<223> OTHER INFORMATION: Synthetic Construct

<400> SEQUENCE: 69
ggtgaattca gtctactggg gattcccaaa tctatatata ctgcaggtga c              51

<210> SEQ ID NO 70
<211> LENGTH: 23
<212> TYPE: DNA
<213> ORGANISM: Artificial Sequence
<220> FEATURE:
<223> OTHER INFORMATION: Synthetic Construct

<400> SEQUENCE: 70
gcaggtggga aactatgcac tcc                                              23

<210> SEQ ID NO 71
<211> LENGTH: 36
<212> TYPE: DNA
<213> ORGANISM: Artificial Sequence
<220> FEATURE:
<223> OTHER INFORMATION: Synthetic Construct

<400> SEQUENCE: 71
cctgaattct gttggattgg aggattggat agtggg                                36

<210> SEQ ID NO 72
<211> LENGTH: 30
<212> TYPE: DNA
<213> ORGANISM: Artificial Sequence
<220> FEATURE:
<223> OTHER INFORMATION: Synthetic Construct

<400> SEQUENCE: 72
ggtgtcgacg tacggtcgag cttattgacc                                       30

<210> SEQ ID NO 73
<211> LENGTH: 32
<212> TYPE: DNA
<213> ORGANISM: Artificial Sequence
<220> FEATURE:
<223> OTHER INFORMATION: Synthetic Construct

<400> SEQUENCE: 73
ggtgggcccg cattttgcca cctacaagcc ag                                    32

<210> SEQ ID NO 74
<211> LENGTH: 40
<212> TYPE: DNA
<213> ORGANISM: Artificial Sequence
<220> FEATURE:
<223> OTHER INFORMATION: Synthetic Construct

<400> SEQUENCE: 74
ggtgaattct agaggatccc aacgctgttg cctacaacgg                            40

<210> SEQ ID NO 75
<211> LENGTH: 36
<212> TYPE: DNA

<213> ORGANISM: Artificial Sequence
<220> FEATURE:
<223> OTHER INFORMATION: Synthetic Construct

<400> SEQUENCE: 75
ggtgcggccg ctgtctggac ctggtgagtt tccccg                                36

<210> SEQ ID NO 76
<211> LENGTH: 37
<212> TYPE: DNA
<213> ORGANISM: Artificial Sequence
<220> FEATURE:
<223> OTHER INFORMATION: Synthetic Construct

<400> SEQUENCE: 76
ggtgggccca ttaaatcagt tatcgtttat ttgatag                               37

<210> SEQ ID NO 77
<211> LENGTH: 35
<212> TYPE: DNA
<213> ORGANISM: Artificial Sequence
<220> FEATURE:
<223> OTHER INFORMATION: Synthetic Construct

<400> SEQUENCE: 77
ggtgaccagc aagtccatgg gtggtttgat catgg                                 35

<210> SEQ ID NO 78
<211> LENGTH: 35
<212> TYPE: DNA
<213> ORGANISM: Artificial Sequence
<220> FEATURE:
<223> OTHER INFORMATION: Synthetic Construct

<400> SEQUENCE: 78
ggtgcggccg cctttggagt acgactccaa ctatg                                 35

<210> SEQ ID NO 79
<211> LENGTH: 31
<212> TYPE: DNA
<213> ORGANISM: Artificial Sequence
<220> FEATURE:
<223> OTHER INFORMATION: Synthetic Construct

<400> SEQUENCE: 79
gcggccgcag actaaattta tttcagtctc c                                     31

<210> SEQ ID NO 80
<211> LENGTH: 7
<212> TYPE: DNA
<213> ORGANISM: Artificial Sequence
<220> FEATURE:
<223> OTHER INFORMATION: Synthetic Construct

<400> SEQUENCE: 80 aggaggt                                                                7

<210> SEQ ID NO 81
<211> LENGTH: 7
<212> TYPE: DNA
<213> ORGANISM: Artificial Sequence
<220> FEATURE:
<223> OTHER INFORMATION: Synthetic Construct

<400> SEQUENCE: 81 aaggagg                                                                7

<210> SEQ ID NO 82
<211> LENGTH: 27
<212> TYPE: DNA
<213> ORGANISM: Artificial Sequence
<220> FEATURE:
<223> OTHER INFORMATION: Synthetic Construct

<400> SEQUENCE: 82
gacatctgca gctccatttt cttctgc                                          27

<210> SEQ ID NO 83
<211> LENGTH: 42
<212> TYPE: DNA
<213> ORGANISM: Artificial Sequence
<220> FEATURE:
<223> OTHER INFORMATION: Synthetic Construct

<400> SEQUENCE: 83
caataataac tactgttttc actctttacc ctctcctttt aa                         42

<210> SEQ ID NO 84
<211> LENGTH: 42
<212> TYPE: DNA
<213> ORGANISM: Artificial Sequence
<220> FEATURE:
<223> OTHER INFORMATION: Synthetic Construct

<400> SEQUENCE: 84
ttaaaaggag agggtaaaga gtgaaaacag tagttattat tg                         42

<210> SEQ ID NO 85
<211> LENGTH: 45
<212> TYPE: DNA
<213> ORGANISM: Artificial Sequence
<220> FEATURE:
<223> OTHER INFORMATION: Synthetic Construct

<400> SEQUENCE: 85
cggggccaag gccggttttt tttagtttcg ataagaacga acggt                      45

<210> SEQ ID NO 86
<211> LENGTH: 45
<212> TYPE: DNA
<213> ORGANISM: Artificial Sequence
<220> FEATURE:
<223> OTHER INFORMATION: Synthetic Construct

<400> SEQUENCE: 86
accgttcgtt cttatcgaaa ctaaaaaaaa ccggccttgg ccccg                      45

<210> SEQ ID NO 87
<211> LENGTH: 6957
<212> TYPE: DNA
<213> ORGANISM: Artificial Sequence
<220> FEATURE:
<223> OTHER INFORMATION: Synthetic Construct

<400> SEQUENCE: 87
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcgggggc tccctttagg     180
gttccgattt agtgctttac ggcacctcga ccccaaaaaa cttgattagg gtgatggttc     240

```
acgtagtggg ccatcgccct gatagacggt ttttcgccct tgacgttgg agtccacgtt      300 ctttaatagt ggactcttgt tccaaactgg aacaacactc aaccctatct cggtctattc      360
ttttgattta taagggattt tgccgatttc ggcctattgg ttaaaaaatg agctgattta      420
acaaaaattt aacgcgaatt ttaacaaaat attaacgttt acaatttcag gtggcacttt      480
tcggggaaat gtgcgcggaa cccctatttg tttatttttc taaatacatt caaatatgta      540
tccgctcatg aattaattct tagaaaaact catcgagcat caaatgaaac tgcaatttat      600
tcatatcagg attatcaata ccatattttt gaaaaagccg tttctgtaat gaaggagaaa      660
actcaccgag gcagttccat aggatggcaa gatcctggta tcggtctgcg attccgactc      720
gtccaacatc aatacaacct attaatttcc cctcgtcaaa aataaggtta tcaagtgaga      780
aatcaccatg agtgacgact gaatccggtg agaatggcaa aagtttatgc atttctttcc      840
agacttgttc aacaggccag ccattacgct cgtcatcaaa atcactcgca tcaaccaaac      900
cgttattcat tcgtgattgc gcctgagcga gacgaaatac gcgatcgctg ttaaaaggac      960
aattacaaac aggaatcgaa tgcaaccggc gcaggaacac tgccagcgca tcaacaatat     1020
tttcacctga atcaggatat tcttctaata cctggaatgc tgttttcccg gggatcgcag     1080
tggtgagtaa ccatgcatca tcaggagtac ggataaaatg cttgatggtc ggaagaggca     1140
taaattccgt cagccagttt agtctgacca tctcatctgt aacatcattg gcaacgctac     1200 cttttgccatg tttcagaaac aactctggcg catcgggctt cccatacaat cgatagattg     1260
tcgcacctga ttgcccgaca ttatcgcgag cccatttata cccatataaa tcagcatcca     1320
tgttggaatt taatcgcggc ctagagcaag acgtttcccg ttgaatatgg ctcataacac     1380
cccttgtatt actgtttatg taagcagaca gttttattgt tcatgaccaa aatcccttaa     1440
cgtgagtttt cgttccactg agcgtcagac cccgtagaaa agatcaaagg atcttcttga     1500
gatccttttt ttctgcgcgt aatctgctgc ttgcaaacaa aaaaaccacc gctaccagcg     1560
gtggtttgtt tgccggatca agagctacca actctttttc cgaaggtaac tggcttcagc     1620
agagcgcaga taccaaatac tgtccttcta gtgtagccgt agttaggcca ccacttcaag     1680
aactctgtag caccgcctac atacctcgct ctgctaatcc tgttaccagt ggctgctgcc     1740
agtggcgata agtcgtgtct taccgggttg gactcaagac gatagttacc ggataaggcg     1800
cagcggtcgg gctgaacggg gggttcgtgc acacagccca gcttggagcg aacgacctac     1860
accgaactga gatacctaca gcgtgagcta tgagaaagcg ccacgcttcc cgaagggaga     1920
aaggcggaca ggtatccggt aagcggcagg gtcggaacag gagagcgcac gagggagctt     1980
ccagggggaa acgcctggta tctttatagt cctgtcgggt ttcgccacct ctgacttgag     2040
cgtcgatttt tgtgatgctc gtcagggggg cggagcctat ggaaaaacgc cagcaacgcg     2100
gcctttttac ggttcctggc cttttgctgg cctttttgctc acatgttctt tcctgcgtta     2160
tcccctgatt ctgtggataa ccgtattacc gcctttgagt gagctgatac cgctcgccgc     2220
agccgaacga ccgagcgcag cgagtcagtg agcgaggaag cggaagagcg cctgatgcgg     2280 tatttctcc ttacgcatct gtgcggtatt tcacaccgca tatatggtgc actctcagta     2340
caatctgctc tgatgccgca tagttaagcc agtatacact ccgctatcgc tacgtgactg     2400
ggtcatggct gcgccccgac acccgccaac acccgctgac gcgccctgac gggcttgtct     2460
gctcccggca tccgcttaca gacaagctgt gaccgtctcc gggagctgca tgtgtcagag     2520
gttttcaccg tcatcaccga aacgcgcgag gcagctgcgg taaagctcat cagcgtggtc     2580
gtgaagcgat tcacagatgt ctgcctgttc atccgcgtcc agctcgttga gtttctccag     2640
```

```
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttcccatc ggtgatgtcg gcgatatagg cgccagcaac cgcacctgtg    4920
gcgccggtga tgccggccac gatgcgtccg gcgtagagga tcgagatctc gatcccgcga    4980
```

```
aattaatacg actcactata ggggaattgt gagcggataa caattcccct ctagaaataa      5040
ttttgtttaa ctttaagaag gagatataca tatgcgttgt agcgtgtcca ccgaaaatgt      5100
gtctttcacc gaaactgaaa ccgaagctcg tcgttctgcg aactacgaac ctaacagctg      5160
ggactatgat tacctgctgt cctccgacac ggacgagtcc atcgaagtat acaaagacaa      5220
agcgaaaaag ctggaagccg aagttcgtcg cgagattaat aacgaaaaag cagaatttct      5280
gaccctgctg gaactgattg acaacgtcca gcgcctgggc ctgggttacc gtttcgagtc      5340
tgatatccgt ggtgcgctgg atcgcttcgt ttcctccggc ggcttcgatg cggtaaccaa      5400
gacttccctg cacggtacgg cactgtcttt ccgtctgctg cgtcaacacg ttttgaggt      5460
ttctcaggaa gcgttcagcg gcttcaaaga ccaaaacggc aacttcctgg agaacctgaa      5520
ggaagatatc aaagctatcc tgagcctgta cgaggccagc ttcctggctc tggaaggcga      5580
aaacatcctg gacgaggcga aggttttcgc aatctctcat ctgaaagaac tgtctgaaga      5640
aaagatcggt aaagagctgg cagaacaggt gaaccatgca ctggaactgc cactgcatcg      5700
ccgtactcag cgtctggaag cagtatggtc tatcgaggcc taccgtaaaa aggaggacgc      5760
gaatcaggtt ctgctggagc tggcaattct ggattacaac atgatccagt ctgtatacca      5820
gcgtgatctg cgtgaaacgt cccgttggtg gcgtcgtgtg ggtctggcga ccaaactgca      5880
ctttgctcgt gaccgcctga ttgagagctt ctactgggcc gtgggtgtag cattcgaacc      5940
gcaatactcc gactgccgta actccgtcgc aaaaatgttt ctttcgtaa ccattatcga       6000
cgatatctac gatgtatacg gcaccctgga cgaactggag ctgtttactg atgcagttga      6060
gcgttgggac gtaaacgcca tcaacgacct gccggattac atgaaactgt gctttctggc      6120
tctgtataac actattaacg aaatcgccta cgacaacctg aaagataaag gtgagaacat      6180
cctgccgtat ctgaccaaag cctgggctga cctgtgcaac gctttcctgc aagaagccaa      6240
gtggctgtac aacaaatcta ctccgacctt tgacgactac ttcggcaacg catggaaatc      6300
ctcttctggc ccgctgcaac tggtgttcgc ttacttcgct gtcgtgcaga acattaaaaa      6360
ggaagagatc gaaaacctgc aaaaatacca tgacaccatc tctcgtcctt cccatatctt      6420
ccgtctgtgc aatgacctgg ctagcgcgtc tgcggaaatt gcgcgtggtg aaaccgcaaa      6480
tagcgttct tgttacatgc gcactaaagg tatctccgaa gaactggcta ccgaaagcgt      6540
gatgaatctg atcgatgaaa cctggaaaaa gatgaacaag gaaaaactgg gtggtagcct      6600
gttcgcgaaa ccgttcgtgg aaaccgcgat caacctggca cgtcaatctc actgcactta      6660
tcataacggc gacgcgcata cctctccgga tgagctgacc cgcaaacgcg ttctgtctgt      6720
aatcactgaa ccgattctgc cgtttgaacg ctaaggatcc gaattcgagc tccgtcgaca      6780
agcttgcggc cgcactcgag caccaccacc accaccactg agatccggct gctaacaaag      6840
cccgaaagga agctgagttg ctgctgccaa ccgctgagca ataactagca taacccttg       6900
gggcctctaa acgggtcttg aggggttttt tgctgaaagg aggaactata tccggat        6957
```

<210> SEQ ID NO 88
<211> LENGTH: 6068
<212> TYPE: DNA
<213> ORGANISM: Artificial Sequence
<220> FEATURE:
<223> OTHER INFORMATION: Synthetic Construct

<400> SEQUENCE: 88

```
gtttgacagc ttatcatcga ctgcacggtg caccaatgct tctggcgtca ggcagccatc        60
ggaagctgtg gtatggctgt gcaggtcgta aatcactgca taattcgtgt cgctcaaggc       120
```

```
gcactcccgt tctggataat gttttttgcg ccgacatcat aacggttctg gcaaatattc      180
tgaaatgagc tgttgacaat taatcatccg gctcgtataa tgtgtggaat tgtgagcgga      240
taacaatttc acacaggaaa cagcgccgct gagaaaaagc gaagcggcac tgctctttaa      300
caatttatca gacaatctgt gtgggcactc gaccggaatt atcgattaac tttattatta      360
aaaattaaag aggtatatat taatgtatcg attaaataag gaggaataaa ccatgagatg      420
tagcgtgtcc accgaaaatg tgtctttcac cgaaactgaa accgaagctc gtcgttctgc      480
gaactacgaa cctaacagct gggactatga ttacctgctg tcctccgaca cggacgagtc      540
catcgaagta tacaaagaca aagcgaaaaa gctggaagcc gaagttcgtc gcagagatta a      600 taacgaaaaa gcagaatttc tgaccctgct ggaactgatt gacaacgtcc agcgcctggg      660
cctgggttac cgtttcgagt ctgatatccg tggtgcgctg gatcgcttcg tttcctccgg      720
cggcttcgat gcggtaacca agacttccct gcacggtacg gcactgtctt ccgtctgct      780 gcgtcaacac ggttttgagg tttctcagga agcgttcagc ggcttcaaag accaaaacgg      840
caacttcctg gagaacctga aggaagatat caaagctatc ctgagcctgt acgaggccag      900
cttcctggct ctggaaggcg aaaacatcct ggacgaggcg aaggttttcg caatctctca      960
tctgaaagaa ctgtctgaag aaaagatcgg taaagagctg gcagaacagg tgaaccatgc      1020
actggaactg ccactgcatc gccgtactca gcgtctggaa gcagtatggt ctatcgaggc      1080
ctaccgtaaa aaggaggacg cgaatcaggt tctgctggag ctggcaattc tggattacaa      1140
catgatccag tctgtatacc agcgtgatct gcgtgaaacg tcccgttggt ggcgtcgtgt      1200
gggtctggcg accaaactgc actttgctcg tgaccgcctg attgagagct ctactgggc      1260 cgtgggtgta gcattcgaac cgcaatactc cgactgccgt aactccgtcg caaaaatgtt      1320
ttctttcgta accattatcg acgatatcta cgatgtatac ggcaccctgg acgaactgga      1380
gctgtttact gatgcagttg agcgttggga cgtaaacgcc atcaacgacc tgccggatta      1440
catgaaactg tgctttctgg ctctgtataa cactattaac gaaatcgcct acgacaacct      1500
gaaagataaa ggtgagaaca tcctgccgta tctgaccaaa gcctgggctg acctgtgcaa      1560
cgctttcctg caagaagcca gtggctgta caacaaatct actccgacct tgacgacta      1620 cttcggcaac gcatggaaat cctcttctgg cccgctgcaa ctggtgttcg cttacttcgc      1680
tgtcgtgcag aacattaaaa aggaagagat cgaaaacctg caaaaatacc atgacaccat      1740
ctctcgtcct tcccatatct tccgtctgtg caatgacctg gctagcgcgt ctgcggaaat      1800
tgcgcgtggt gaaaccgcaa atagcgtttc ttgttacatg cgcactaaag gtatctccga      1860
agaactggct accgaaagcg tgatgaatct gatcgatgaa acctggaaaa agatgaacaa      1920
ggaaaaactg gtggtagcc tgttcgcgaa accgttcgtg gaaaccgcga tcaacctggc      1980
acgtcaatct cactgcactt atcataacgg cgacgcgcat acctctccgg atgagctgac      2040
ccgcaaacgc gttctgtctg taatcactga accgattctg ccgtttgaac gctaactgca      2100
gctggtacca tatgggaatt cgaagctttc tagaacaaaa actcatctca gaagaggatc      2160
tgaatagcgc cgtcgaccat catcatcatc atcattgagt ttaaacggtc tccagcttgg      2220
ctgttttggc ggatgagaga agattttcag cctgatacag attaaatcag aacgcagaag      2280
cggtctgata aaacagaatt tgcctggcgg cagtagcgcg gtggtcccac ctgaccccat      2340
gccgaactca gaagtgaaac gccgtagcgc cgatggtagt gtgggtctc cccatgcgag      2400 agtagggaac tgccaggcat caaataaaac gaaaggctca gtcgaaagac tgggcctttc      2460
```

```
gttttatctg ttgtttgtcg gtgaacgctc tcctgagtag gacaaatccg ccgggagcgg    2520
atttgaacgt tgcgaagcaa cggcccggag ggtggcgggc aggacgcccg ccataaactg    2580
ccaggcatca aattaagcag aaggccatcc tgacggatgg cctttttgcg tttctacaaa    2640
ctctttttgt ttattttcct aaatacattc aaatatgtat ccgctcatga gacaataacc    2700
ctgataaatg cttcaataat attgaaaaag gaagagtatg agtattcaac atttccgtgt    2760
cgcccttatt cccttttttg cggcattttg ccttcctgtt tttgctcacc cagaaacgct    2820
ggtgaaagta aaagatgctg aagatcagtt gggtgcacga gtgggttaca tcgaactgga    2880
tctcaacagc ggtaagatcc ttgagagttt tcgccccgaa gaacgttttc caatgatgag    2940
cacttttaaa gttctgctat gtggcgcggt attatcccgt gttgacgccg ggcaagagca    3000
actcggtcgc cgcatacact attctcagaa tgacttggtt gagtactcac cagtcacaga    3060
aaagcatctt acggatggca tgacagtaag agaattatgc agtgctgcca taaccatgag    3120
tgataacact gcggccaact tacttctgac aacgatcgga ggaccgaagg agctaaccgc    3180
ttttttgcac aacatggggg atcatgtaac tcgccttgat cgttgggaac cggagctgaa    3240
tgaagccata ccaaacgacg agcgtgacac cacgatgcct gtagcaatgg caacaacgtt    3300
gcgcaaacta ttaactggcg aactacttac tctagcttcc cggcaacaat taatagactg    3360
gatggaggcg gataaagttg caggaccact tctgcgctcg gcccttccgg ctggctggtt    3420
tattgctgat aaatctggag ccggtgagcg tgggtctcgc ggtatcattg cagcactggg    3480
gccagatggt aagccctccc gtatcgtagt tatctacacg acggggagtc aggcaactat    3540
ggatgaacga aatagacaga tcgctgagat aggtgcctca ctgattaagc attggtaact    3600
gtcagaccaa gtttactcat atatacttta gattgattta aaacttcatt tttaatttaa    3660
aaggatctag gtgaagatcc ttttttgataa tctcatgacc aaaatccctt aacgtgagtt    3720
ttcgttccac tgagcgtcag accccgtaga aaagatcaaa ggatcttctt gagatccttt    3780
ttttctgcgc gtaatctgct gcttgcaaac aaaaaaacca ccgctaccag cggtggtttg    3840
tttgccggat caagagctac caactctttt tccgaaggta actggcttca gcagagcgca    3900
gataccaaat actgtccttc tagtgtagcc gtagttaggc caccacttca agaactctgt    3960
agcaccgcct acatacctcg ctctgctaat cctgttacca gtggctgctg ccagtggcga    4020
taagtcgtgt cttaccgggt tggactcaag acgatagtta ccggataagg cgcagcggtc    4080
gggctgaacg gggggttcgt gcacacagcc cagcttggag cgaacgacct acaccgaact    4140
gagataccta cagcgtgagc tatgagaaag cgccacgctt cccgaaggga gaaaggcgga    4200
caggtatccg gtaagcggca gggtcggaac aggagagcgc acgagggagc ttccaggggg    4260
aaacgcctgg tatctttata gtcctgtcgg gtttcgccac ctctgacttg agcgtcgatt    4320
tttgtgatgc tcgtcagggg ggcggagcct atggaaaaac gccagcaacg cggccttttt    4380
acggttcctg gccttttgct ggccttttgc tcacatgttc tttcctgcgt tatcccctga    4440
ttctgtggat aaccgtatta ccgcctttga gtgagctgat accgctcgcc gcagccgaac    4500
gaccgagcgc agcgagtcag tgagcgagga agcggaagag cgcctgatgc ggtattttct    4560
ccttacgcat ctgtgcggta tttcacaccg catatggtgc actctcagta caatctgctc    4620
tgatgccgca tagttaagcc agtatacact ccgctatcgc tacgtgactg ggtcatggct    4680
gcgccccgac acccgccaac acccgctgac gcgccctgac gggcttgtct gctcccggca    4740
tccgcttaca gacaagctgt gaccgtctcc gggagctgca tgtgtcagag gttttcaccg    4800
tcatcaccga aacgcgcgag gcagcagatc aattcgcgcg cgaaggcgaa gcggcatgca    4860
```

| | |
|---|---|
| tttacgttga caccatcgaa tggtgcaaaa cctttcgcgg tatggcatga tagcgcccgg | 4920 |
| aagagagtca attcagggtg gtgaatgtga aaccagtaac gttatacgat gtcgcagagt | 4980 |
| atgccggtgt ctcttatcag accgtttccc gcgtggtgaa ccaggccagc cacgtttctg | 5040 |
| cgaaaacgcg ggaaaaagtg gaagcggcga tggcggagct gaattacatt cccaaccgcg | 5100 |
| tggcacaaca actggcgggc aaacagtcgt tgctgattgg cgttgccacc tccagtctgg | 5160 |
| ccctgcacgc gccgtcgcaa attgtcgcgg cgattaaatc tcgcgccgat caactgggtg | 5220 |
| ccagcgtggt ggtgtcgatg gtagaacgaa gcggcgtcga agcctgtaaa gcggcggtgc | 5280 |
| acaatcttct cgcgcaacgc gtcagtgggc tgatcattaa ctatccgctg gatgaccagg | 5340 |
| atgccattgc tgtggaagct gcctgcacta atgttccggc gttatttctt gatgtctctg | 5400 |
| accagacacc catcaacagt attattttct cccatgaaga cggtacgcga ctgggcgtgg | 5460 |
| agcatctggt cgcattgggt caccagcaaa tcgcgctgtt agcgggccca ttaagttctg | 5520 |
| tctcggcgcg tctgcgtctg gctggctggc ataaatatct cactcgcaat caaattcagc | 5580 |
| cgatagcgga acgggaaggc gactggagtg ccatgtccgg ttttcaacaa accatgcaaa | 5640 |
| tgctgaatga gggcatcgtt cccactgcga tgctggttgc caacgatcag atggcgctgg | 5700 |
| gcgcaatgcg cgccattacc gagtccgggc tgcgcgttgg tgcggatatc tcggtagtgg | 5760 |
| gatacgacga taccgaagac agctcatgtt atatcccgcc gtcaaccacc atcaaacagg | 5820 |
| attttcgcct gctggggcaa accagcgtgg accgcttgct gcaactctct cagggccagg | 5880 |
| cggtgaaggg caatcagctg ttgcccgtct cactggtgaa aagaaaaacc accctggcgc | 5940 |
| ccaatacgca aaccgcctct ccccgcgcgt tggccgattc attaatgcag ctggcacgac | 6000 |
| aggtttcccg actggaaagc gggcagtgag cgcaacgcaa ttaatgtgag ttagcgcgaa | 6060 |
| ttgatctg | 6068 |

<210> SEQ ID NO 89
<211> LENGTH: 6906
<212> TYPE: DNA
<213> ORGANISM: Artificial Sequence
<220> FEATURE:
<223> OTHER INFORMATION: Synthetic Construct

<400> SEQUENCE: 89

| | |
|---|---|
| gtttgacagc ttatcatcga ctgcacggtg caccaatgct tctggcgtca ggcagccatc | 60 |
| ggaagctgtg gtatggctgt gcaggtcgta aatcactgca taattcgtgt cgctcaaggc | 120 |
| gcactcccgt tctggataat gttttttgcg ccgacatcat aacggttctg gcaaatattc | 180 |
| tgaaatgagc tgttgacaat taatcatccg gctcgtataa tgtgtggaat tgtgagcgga | 240 |
| taacaatttc acacaggaaa cagcgccgct gagaaaaagc gaagcggcac tgctctttaa | 300 |
| caatttatca gacaatctgt gtgggcactc gaccggaatt atcgattaac tttattatta | 360 |
| aaaattaaag aggtatatat taatgtatcg attaaataag gaggaataaa ccatgagatg | 420 |
| tagcgtgtcc accgaaaatg tgtctttcac cgaaactgaa accgaagctc gtcgttctgc | 480 |
| gaactacgaa cctaacagct gggactatga ttacctgctg tcctccgaca cggacgagtc | 540 |
| catcgaagta tacaaagaca aagcgaaaaa gctggaagcc gaagttcgtc gcgagattaa | 600 |
| taacgaaaaa gcagaatttc tgaccctgct ggaactgatt gacaacgtcc agcgcctggg | 660 |
| cctgggttac cgtttcgagt ctgatatccg tggtgcgctg gatcgcttcg tttcctccgg | 720 |
| cggcttcgat gcggtaacca agacttccct gcacggtacg gcactgtctt tccgtctgct | 780 |

```
gcgtcaacac ggttttgagg tttctcagga agcgttcagc ggcttcaaag accaaaacgg      840
caacttcctg gagaacctga aggaagatat caaagctatc ctgagcctgt acgaggccag      900
cttcctggct ctggaaggcg aaaacatcct ggacgaggcg aaggttttcg caatctctca      960
tctgaaagaa ctgtctgaag aaaagatcgg taaagagctg gcagaacagg tgaaccatgc     1020
actggaactg ccactgcatc gccgtactca gcgtctggaa gcagtatggt ctatcgaggc     1080
ctaccgtaaa aaggaggacg cgaatcaggt tctgctggag ctggcaattc tggattacaa     1140
catgatccag tctgtatacc agcgtgatct gcgtgaaacg tcccgttggt ggcgtcgtgt     1200
gggtctggcg accaaactgc actttgctcg tgaccgcctg attgagagct ctactgggc     1260 cgtgggtgta gcattcgaac cgcaatactc cgactgccgt aactccgtcg caaaaatgtt     1320
ttctttcgta accattatcg acgatatcta cgatgtatac ggcaccctgg acgaactgga     1380
gctgtttact gatgcagttg agcgttggga cgtaaacgcc atcaacgacc tgccggatta     1440
catgaaactg tgcttttctgg ctctgtataa cactattaac gaaatcgcct acgacaacct     1500
gaaagataaa ggtgagaaca tcctgccgta tctgaccaaa gcctgggctg acctgtgcaa     1560
cgctttcctg caagaagcca agtggctgta caacaaatct actccgacct ttgacgacta     1620
cttcggcaac gcatggaaat cctcttctgg cccgctgcaa ctggtgttcg cttacttcgc     1680
tgtcgtgcag aacattaaaa aggaagagat cgaaaacctg caaaaatacc atgacaccat     1740
ctctcgtcct tcccatatct tccgtctgtg caatgacctg gctagcgcgt ctgcggaaat     1800
tgcgcgtggt gaaaccgcaa atagcgtttc ttgttacatg cgcactaaag gtatctccga     1860
agaactggac accgaaagcg tgatgaatct gatcgatgaa acctggaaaa agatgaacaa     1920
ggaaaaactg ggtggtagcc tgttcgcgaa accgttcgtg gaaaccgcga tcaacctggc     1980
acgtcaatct cactgcactt atcataacgg cgacgcgcat acctctccgg atgagctgac     2040
ccgcaaacgc gttctgtctg taatcactga accgattctg ccgtttgaac gctaactgca     2100
taaaggaggt aaaaaaacat ggtatcctgt tctgcgccgg gtaagattta cctgttcggt     2160
gaacacgccg tagtttatgg cgaaactgca attgcgtgtg cggtggaact gcgtacccgt     2220
gttcgcgcgc aactcaatga ctctatcact attcagagcc agatcggccg caccggtctg     2280
gatttcgaaa agcacccta tgtgtctgcg gtaattgaga aaatgcgcaa atctattcct     2340
attaacggta ttttcttgac cgtcgattcc gacatcccgg tgggctccgg tctgggtagc     2400
agcgcagccg ttactatcgc gtctattggt gcgctgaacg agctgttcgg ctttggcctc     2460
agcctgcaag aaatcgctaa actgggccac gaaatcgaaa ttaaagtaca gggtgccgcg     2520
tccccaaccg atacgtatgt ttctaccttc ggcggcgtgg ttaccatccc ggaacgtcgc     2580
aaactgaaaa ctccggactg cggcattgtg attggcgata ccggcgtttt ctcctccacc     2640
aaagagttag tagctaacgt acgtcagctg cgcgaaagct acccggattt gatcgaaccg     2700
ctgatgacct ctattggcaa aatctctcgt atcggcgaac aactggttct gtctggcgac     2760
tacgcatcca tcggccgcct gatgaacgtc aaccagggtc tcctggacgc cctgggcgtt     2820
aacatcttag aactgagcca gctgatctat tccgctcgtg cggcaggtgc gtttggcgct     2880
aaaatcacgg gcgctggcgg cggtggctgt atggttgcgc tgaccgctcc ggaaaaatgc     2940
aaccaagtgg cagaagcggt agcaggcgct ggcggtaaag tgactatcac taaaccgacc     3000
gagcaaggtc tgaaagtaga ttaaagtcta gttaaagttt aaacggtctc cagcttggct     3060
gttttggcgc atgagagaag attttcagcc tgatacagat taaatcagaa cgcagaagcg     3120
gtctgataaa acagaatttg cctggcggca gtagcgcggt ggtcccacct gacccccatgc     3180
```

```
cgaactcaga agtgaaacgc cgtagcgccg atggtagtgt ggggtctccc catgcgagag    3240
tagggaactg ccaggcatca aataaaacga aaggctcagt cgaaagactg ggcctttcgt    3300
tttatctgtt gtttgtcggt gaacgctctc ctgagtagga caaatccgcc gggagcggat    3360
ttgaacgttg cgaagcaacg gcccggaggg tggcgggcag gacgcccgcc ataaactgcc    3420
aggcatcaaa ttaagcagaa ggccatcctg acggatggcc ttttgcgtt tctacaaact    3480 cttttgttt atttttctaa atacattcaa atatgtatcc gctcatgaga caataaccct    3540
gataaatgct tcaataatat tgaaaaagga agagtatgag tattcaacat ttccgtgtcg    3600
cccttattcc cttttttgcg gcattttgcc ttcctgtttt tgctcaccca gaaacgctgg    3660
tgaaagtaaa agatgctgaa gatcagttgg gtgcacgagt gggttacatc gaactggatc    3720
tcaacagcgg taagatcctt gagagttttc gccccgaaga acgttttcca atgatgagca    3780
cttttaaagt tctgctatgt ggcgcggtat tatcccgtgt tgacgccggg caagagcaac    3840
tcggtcgccg catacactat tctcagaatg acttggttga gtactcacca gtcacagaaa    3900
agcatcttac ggatggcatg acagtaagag aattatgcag tgctgccata accatgagtg    3960
ataacactgc ggccaactta cttctgacaa cgatcgagg accgaaggag ctaaccgctt    4020
ttttgcacaa catgggggat catgtaactc gccttgatcg ttgggaaccg gagctgaatg    4080
aagccatacc aaacgacgag cgtgacacca cgatgcctgt agcaatggca acaacgttgc    4140
gcaaactatt aactggcgaa ctacttactc tagcttcccg gcaacaatta atagactgga    4200
tggaggcgga taaagttgca ggaccacttc tgcgctcggc ccttccggct ggctggttta    4260
ttgctgataa atctggagcc ggtgagcgtg ggtctcgcgg tatcattgca gcactggggc    4320
cagatggtaa gccctcccgt atcgtagtta tctacacgac ggggagtcag gcaactatgg    4380
atgaacgaaa tagacagatc gctgagatag gtgcctcact gattaagcat tggtaactgt    4440
cagaccaagt ttactcatat atactttaga ttgatttaaa acttcatttt taatttaaaa    4500
ggatctaggt gaagatcctt tttgataatc tcatgaccaa aatcccttaa cgtgagtttt    4560
cgttccactg agcgtcagac cccgtagaaa agatcaaagg atcttcttga gatcctttt    4620 ttctgcgcgt aatctgctgc ttgcaaacaa aaaaaccacc gctaccagcg gtggtttgtt    4680
tgccggatca agagctacca actcttttc cgaaggtaac tggcttcagc agagcgcaga    4740
taccaaatac tgtccttcta gtgtagccgt agttaggcca ccacttcaag aactctgtag    4800
caccgcctac atacctcgct ctgctaatcc tgttaccagt ggctgctgcc agtggcgata    4860
agtcgtgtct taccgggttg gactcaagac gatagttacc ggataaggcg cagcggtcgg    4920
gctgaacggg gggttcgtgc acacagccca gcttggagcg aacgacctac accgaactga    4980
gatacctaca gcgtgagcta tgagaaagcg ccacgcttcc cgaagggaga aaggcggaca    5040
ggtatccggt aagcggcagg gtcggaacag gagagcgcac gagggagctt ccaggggaa    5100 acgcctggta tctttatagt cctgtcgggt ttcgccacct ctgacttgag cgtcgatttt    5160
tgtgatgctc gtcaggggg cggagcctat ggaaaaacgc cagcaacgcg gcctttttac    5220
ggttcctggc cttttgctgg ccttttgctc acatgttctt tcctgcgtta tcccctgatt    5280
ctgtggataa ccgtattacc gcctttgagt gagctgatac cgctcgccgc agccgaacga    5340
ccgagcgcag cgagtcagtg agcgaggaag cggaagagcg cctgatgcgg tattttctcc    5400
ttacgcatct gtgcggtatt tcacaccgca tatggtgcac tctcagtaca atctgctctg    5460
atgccgcata gttaagccag tatacactcc gctatcgcta cgtgactggg tcatggctgc    5520
```

| | |
|---|---|
| gccccgacac ccgccaacac ccgctgacgc gccctgacgg gcttgtctgc tcccggcatc | 5580 |
| cgcttacaga caagctgtga ccgtctccgg gagctgcatg tgtcagaggt tttcaccgtc | 5640 |
| atcaccgaaa cgcgcgaggc agcagatcaa ttcgcgcgcg aaggcgaagc ggcatgcatt | 5700 |
| tacgttgaca ccatcgaatg gtgcaaaacc tttcgcggta tggcatgata gcgcccggaa | 5760 |
| gagagtcaat tcagggtggt gaatgtgaaa ccagtaacgt tatacgatgt cgcagagtat | 5820 |
| gccggtgtct cttatcagac cgtttcccgc gtggtgaacc aggccagcca cgtttctgcg | 5880 |
| aaaacgcggg aaaagtggaa agcggcgatg gcggagctga attacattcc caaccgcgtg | 5940 |
| gcacaacaac tggcgggcaa acagtcgttg ctgattggcg ttgccacctc cagtctggcc | 6000 |
| ctgcacgcgc cgtcgcaaat tgtcgcggcg attaaatctc gcgccgatca actgggtgcc | 6060 |
| agcgtggtgg tgtcgatggt agaacgaagc ggcgtcgaag cctgtaaagc ggcggtgcac | 6120 |
| aatcttctcg cgcaacgcgt cagtgggctg atcattaact atccgctgga tgaccaggat | 6180 |
| gccattgctg tggaagctgc ctgcactaat gttccggcgt tatttcttga tgtctctgac | 6240 |
| cagacaccca tcaacagtat tattttctcc catgaagacg gtacgcgact gggcgtggag | 6300 |
| catctggtcg cattgggtca ccagcaaatc gcgctgttag cgggcccatt aagttctgtc | 6360 |
| tcggcgcgtc tgcgtctggc tggctggcat aaatatctca ctcgcaatca aattcagccg | 6420 |
| atagcggaac gggaaggcga ctggagtgcc atgtccggtt ttcaacaaac catgcaaatg | 6480 |
| ctgaatgagg gcatcgttcc cactgcgatg ctggttgcca acgatcagat ggcgctgggc | 6540 |
| gcaatgcgcg ccattaccga gtccgggctg cgcgttggtg cggatatctc ggtagtggga | 6600 |
| tacgacgata ccgaagacag ctcatgttat atcccgccgt caaccaccat caaacaggat | 6660 |
| tttcgcctgc tggggcaaac cagcgtggac cgcttgctgc aactctctca gggccaggcg | 6720 |
| gtgaagggca atcagctgtt gcccgtctca ctggtgaaaa gaaaaaccac cctggcgccc | 6780 |
| aatacgcaaa ccgcctctcc ccgcgcgttg gccgattcat taatgcagct ggcacgacag | 6840 |
| gtttcccgac tggaaagcgg gcagtgagcg caacgcaatt aatgtgagtt agcgcgaatt | 6900 |
| gatctg | 6906 |

<210> SEQ ID NO 90
<211> LENGTH: 8123
<212> TYPE: DNA
<213> ORGANISM: Artificial Sequence
<220> FEATURE:
<223> OTHER INFORMATION: Synthetic Construct

<400> SEQUENCE: 90

| | |
|---|---|
| aagggcgagc tcaacgatcc ggctgctaac aaagcccgaa aggaagctga gttggctgct | 60 |
| gccaccgctg agcaataact agcataaccc cttggggcct ctaaacgggt cttgaggagt | 120 |
| tttttgctga aaggaggaac tatatccgga tatcccgcaa gaggcccggc agtaccggca | 180 |
| taaccaagcc tatgcctaca gcatccaggg tgacggtgcc gaggatgacg atgagcgcat | 240 |
| tgttagattt catacacggt gcctgactgc gttagcaatt taactgtgat aaactaccgc | 300 |
| attaaagctt atcgatgata agctgtcaaa catgagaatt aattcttgaa gacgaaaggg | 360 |
| cctcgtgata cgcctatttt tataggttaa tgtcatgata ataatggttt cttagacgtc | 420 |
| aggtggcact tttcggggaa atgtgcgcgg aacccctatt tgtttatttt tctaaataca | 480 |
| ttcaaatatg tatccgctca tgagacaata accctgataa atgcttcaat aatattgaaa | 540 |
| aaggaagagt atgattgaac aagatggatt gcacgcaggt tctccggccg cttgggtgga | 600 |
| gaggctattc ggctatgact gggcacaact gacaatcggc tgctctgatg ccgccgtgtt | 660 |

```
ccggctgtca gcgcaggggc gcccggttct ttttgtcaag accgacctgt ccggtgccct    720
gaatgaactg caggacgagg cagcgcggct atcgtggctg ccacgacgg gcgttccttg     780
cgcagctgtg ctcgacgttg tcactgaagc gggaagggac tggctgctat tgggcgaagt    840
gccggggcag gatctcctgt catctcacct tgctcctgcc gagaaagtat ccatcatggc    900
tgatgcaatg cggcggctgc atacgcttga tccggctacc tgcccattcg accaccaagc    960
gaaacatcgc atcgagcggg cacgtactcg gatggaagcc ggtcttgtcg atcaggatga   1020
tctggacgaa gagcatcagg ggctcgcgcc agccgaactg ttcgccaggc tcaaggcgcg   1080
catgcccgac ggcgaggatc tcgtcgtgac acatggcgat gcctgcttgc cgaatatcat   1140
ggtggaaaat ggccgctttt ctggattcat cgactgtggc cggctgggtg tggcggaccg   1200
ctatcaggac atagcgttgg ctacccgtga tattgctgaa gagcttggcg gcgaatgggc   1260
tgaccgcttc ctcgtgcttt acggtatcgc cgctcccgat tcgcagcgca tcgccttcta   1320
tcgccttctt gacgagttct tctgagcggg actctggggt tcgaaatgac cgaccaagcg   1380
acgcctaact gtcagaccaa gtttactcat atatacttta gattgattta aaacttcatt   1440
tttaatttaa aaggatctag gtgaagatcc ttttttgataa tctcatgacc aaaatcccctt   1500
aacgtgagtt ttcgttccac tgagcgtcag accccgtaga aaagatcaaa ggatcttctt   1560
gagatccttt ttttctgcgc gtaatctgct gcttgcaaac aaaaaaacca ccgctaccag   1620
cggtggtttg tttgccggat caagagctac caactctttt tccgaaggta actggcttca   1680
gcagagcgca gataccaaat actgtccttc tagtgtagcc gtagttaggc caccacttca   1740
agaactctgt agcaccgcct acatacctcg ctctgctaat cctgttacca gtggctgctg   1800
ccagtggcga taagtcgtgt cttaccgggt tggactcaag acgatagtta ccggataagg   1860
cgcagcggtc gggctgaacg gggggttcgt gcacacagcc cagcttggag cgaacgacct   1920
acaccgaact gagataccta cagcgtgagc tatgagaaag cgccacgctt cccgaaggga   1980
gaaaggcgga caggtatccg gtaagcggca gggtcggaac aggagagcgc acgagggagc   2040
ttccaggggg aaacgcctgg tatctttata gtcctgtcgg gtttcgccac ctctgacttg   2100
agcgtcgatt tttgtgatgc tcgtcagggg ggcggagcct atggaaaaac gccagcaacg   2160
cggccttttt acggttcctg gccttttgct ggccttttgc tcacatgttc tttcctgcgt   2220
tatcccctga ttctgtggat aaccgtatta ccgcctttga gtgagctgat accgctcgcc   2280
gcagccgaac gaccgagcgc agcgagtcag tgagcgagga agcggaagag cgcctgatgc   2340
ggtattttct ccttacgcat ctgtgcggta tttcacaccg caatggtgca ctctcagtac   2400
aatctgctct gatgccgcat agttaagcca gtatacactc cgctatcgct acgtgactgg   2460
gtcatggctg cgccccgaca cccgccaaca cccgctgacg cgccctgacg gcttgtctg    2520
ctcccggcat ccgcttacag acaagctgtg accgtctccg ggagctgcat gtgtcagagg   2580
ttttcaccgt catcaccgaa acgcgcgagg cagctgcggt aaagctcatc agcgtggtcg   2640
tgaagcgatt cacagatgtc tgcctgttca tccgcgtcca gctcgttgag tttctccaga   2700
agcgttaatg tctggcttct gataaagcgg ccatgttaa gggcggtttt ttcctgtttg    2760
gtcactgatg cctccgtgta aggggggattt ctgttcatgg gggtaatgat accgatgaaa   2820
cgagagagga tgctcacgat acgggttact gatgatgaac atgcccggtt actggaacgt   2880
tgtgagggta acaactggc ggtatggatg cggcgggacc agagaaaaat cactcagggt    2940
caatgccagc gcttcgttaa tacagatgta ggtgttccac agggtagcca gcagcatcct   3000
```

```
gcgatgcaga tccggaacat aatggtgcag ggcgctgact tccgcgtttc cagactttac    3060
gaaacacgga aaccgaagac cattcatgtt gttgctcagg tcgcagacgt tttgcagcag    3120
cagtcgcttc acgttcgctc gcgtatcggt gattcattct gctaaccagt aaggcaaccc    3180
cgccagccta gccgggtcct caacgacagg agcacgatca tgcgcacccg tggccaggac    3240
ccaacgctgc ccgagatgcg ccgcgtgcgg ctgctggaga tggcggacgc gatggatatg    3300
ttctgccaag ggttggtttg cgcattcaca gttctccgca agaattgatt ggctccaatt    3360
cttggagtgg tgaatccgtt agcgaggtgc cgccggcttc cattcaggtc gaggtggccc    3420
ggctccatgc accgcgacgc aacgcgggga ggcagacaag gtataggcg cgcctacaa     3480
tccatgccaa cccgttccat gtgctcgccg aggcggcata aatcgccgtg acgatcagcg    3540
gtccaatgat cgaagttagg ctggtaagag ccgcgagcga tccttgaagc tgtccctgat    3600
ggtcgtcatc tacctgcctg acagcatgg cctgcaacgc gggcatcccg atgccgccgg     3660
aagcgagaag aatcataatg gggaaggcca tccagcctcg cgtcgcgaac gccagcaaga    3720
cgtagcccag cgcgtcggcc gccatgccgg cgataatggc ctgcttctcg ccgaaacgtt    3780
tggtggcggg accagtgacg aaggcttgag cgagggcgtg caagattccg aataccgcaa    3840
gcgacaggcc gatcatcgtc gcgctccagc gaaagcggtc ctcgccgaaa atgacccaga    3900
gcgctgccgg cacctgtcct acgagttgca tgataaagaa gacagtcata agtgcggcga    3960
cgatagtcat gccccgcgcc caccggaagg agctgactgg gttgaaggct ctcaagggca    4020
tcggtcgaga tcccggtgcc taatgagtga gctaacttac attaattgcg ttgcgctcac    4080
tgcccgcttt ccagtcggga aacctgtcgt gccagctgca ttaatgaatc ggccaacgcg    4140
cggggagagg cggtttgcgt attgggcgcc agggtggttt ttcttttcac cagtgagacg    4200
ggcaacagct gattgccctt caccgcctgg ccctgagaga gttgcagcaa gcggtccacg    4260
ctggtttgcc ccagcaggcg aaaatcctgt ttgatggtgg ttaacggcgg gatataacat    4320
gagctgtctt cggtatcgtc gtatcccact accgagatat ccgcaccaac gcgcagcccg    4380
gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc ccgctaacag cgcgatttgc    4620
tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctt ccacagcaat ggcatcctgg tcatccagcg atagttaat gatcagccca     4800
ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acggcgcgtg cagggccaga ctggaggtgg caacgccaat cagcaacgac    4980
tgtttgcccg ccagttgttg tgccacgcgg ttgggaatgt aattcagctc cgccatcgcc    5040
gcttccactt tttcccgcgt tttcgcagaa acgtggctgg cctggttcac cacgcgggaa    5100
acggtctgat aagagacacc ggcatactct gcgacatcgt ataacgttac tggtttcaca    5160
ttcaccaccc tgaattgact ctcttccggg cgctatcatg ccataccgcg aaaggttttg    5220
cgccattcga tggtgtccgg gatctcgacg ctctcccctta tgcgactcct gcattaggaa    5280
gcagcccagt agtaggttga ggccgttgag caccgccgcc gcaaggaatg gtgcatgcaa    5340
ggagatggcg cccaacagtc ccccggccac ggggcctgcc accataccca cgccgaaaca    5400
```

-continued

```
agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaattaata cgactcacta tagggaatt gtgagcggat     5580 aacaattccc ctctagaaat aattttgttt aactttaaga aggagatata catatgaatt    5640
aaccctcact aaagggcggc cgcgaagttc ctattctcta gaaagtatag gaacttcatt    5700
ctaccgggta ggggaggcgc ttttcccaag gcagtctgga gcatgcgctt tagcagcccc    5760
gctgggcact tggcgctaca caagtggcct ctggcctcgc acacattcca catccaccgg    5820
taggcgccaa ccggctccgt tctttggtgg cccttcgcg ccaccttcca ctcctcccct     5880
agtcaggaag ttcccccccg ccccgcagct cgcgtcgtgc aggacgtgac aaatggaagt    5940
agcacgtctc actagtctcg tgcagatgga cagcaccgct gagcaatgga agcgggtagg    6000
cctttggggc agcggccaat agcagctttg ctccttcgct ttctgggctc agaggctggg    6060
aaggggtggg tccgggggcg ggctcagggg cgggctcagg ggcggggcgg gcgcccgaag    6120
gtcctccgga ggcccggcat tctgcacgct tcaaaagcgc acgtctgccg cgctgttctc    6180
ctcttcctca tctccgggcc tttcgacctg cagcagcacg tgttgacaat taatcatcgg    6240
catagtatat cggcatagta ataatacgaca aggtgaggaa ctaaaccatg gagaaaaaaa    6300
tcactggata taccaccgtt gatatatccc aatggcatcg taaagaacat tttgaggcat    6360
ttcagtcagt tgctcaatgt acctataacc agaccgttca gctggatatt acggcctttt    6420
taaagaccgt aaagaaaaat aagcacaagt tttatccggc ctttattcac attcttgccc    6480
gcctgatgaa tgctcatccg gaattccgta tggcaatgaa agacggtgag ctggtgatat    6540
gggatagtgt tcacccttgt tacaccgttt tccatgagca aactgaaacg ttttcatcgc    6600
tctggagtga ataccacgac gatttccggc agtttctaca catatattcg caagatgtgg    6660
cgtgttacgg tgaaaacctg gcctatttcc ctaaagggtt tattgagaat atgttttcg     6720 tctcagccaa tccctgggtg agtttcacca gttttgattt aaacgtggcc aatatggaca    6780
acttcttcgc ccccgttttc accatgggca aatattatac gcaaggcgac aaggtgctga    6840
tgccgctggc gattcaggtt catcatgccg tttgtgatgg cttccatgtc ggcagaatgc    6900
ttaatgaatt acaacagtac tgcgatgagt ggcagggcgg ggcgtaagcg ggactctggg    6960
gttcgaataa agaccgacca agcgacgtct gagagctccc tggcgaattc ggtaccaata    7020
aaagagcttt attttcatga tctgtgtgtt ggttttttgtg tgcggcgcgg aagttcctat    7080
tctctagaaa gtataggaac ttcctcgagc cctatagtga gtcgtattag atcgcggccg    7140
cgcccttgac aatgccacat cctgagcaaa taattcaacc actaattgtg agcggataac    7200
aaaggaggta aaaaaacatg gtatcctgtt ctgcgccggg taagatttac ctgttcggtg    7260
aacacgccgt agtttatggc gaaactgcaa ttgcgtgtgc ggtggaactg cgtacccgtg    7320
ttcgcgcgga actcaatgac tctatcacta ttcagagcca gatcggccgc accggtctgg    7380
atttcgaaaa gcacccttat gtgtctgcgg taattgagaa aatgcgcaaa tctattccta    7440
ttaacggtgt tttcttgacc gtcgattccg acatcccggt gggctccggt ctgggtagca    7500
gcgcagccgt tactatcgcg tctattggtg cgctgaacga gctgttcggc tttggcctca    7560
gcctgcaaga aatcgctaaa ctgggccacg aaatcgaaat taagtacag ggtgccgcgt     7620 ccccaaccga tacgtatgtt tctaccttcg gcggcgtggt taccatcccg gaacgtcgca    7680
aactgaaaac tccggactgc ggcattgtga ttggcgatac cggcgttttc tcctccacca    7740
```

```
aagagttagt agctaacgta cgtcagctgc gcgaaagcta cccggatttg atcgaaccgc    7800
tgatgacctc tattggcaaa atctctcgta tcggcgaaca actggttctg tctggcgact    7860
acgcatccat cggccgcctg atgaacgtca accagggtct cctggacgcc ctgggcgtta    7920
acatcttaga actgagccag ctgatctatt ccgctcgtgc ggcaggtgcg tttggcgcta    7980
aaatcacggg cgctggcggc ggtggctgta tggttgcgct gaccgctccg gaaaaatgca    8040
accaagtggc agaagcggta gcaggcgctg gcggtaaagt gactatcact aaaccgaccg    8100
agcaaggtct gaaagtagat taa                                            8123

<210> SEQ ID NO 91
<211> LENGTH: 8123
<212> TYPE: DNA
<213> ORGANISM: Artificial Sequence
<220> FEATURE:
<223> OTHER INFORMATION: Synthetic Construct

<400> SEQUENCE: 91
aagggcgagc tcaacgatcc ggctgctaac aaagcccgaa aggaagctga gttggctgct      60
gccaccgctg agcaataact agcataaccc cttggggcct ctaaacgggt cttgaggagt     120 ttttgctga aggaggaac tatatccgga tatcccgcaa gaggcccggc agtaccggca       180
taaccaagcc tatgcctaca gcatccaggg tgacggtgcc gaggatgacg atgagcgcat     240
tgttagattt catacacggt gcctgactgc gttagcaatt taactgtgat aaactaccgc     300
attaaagctt atcgatgata agctgtcaaa catgagaatt aattcttgaa gacgaaaggg     360
cctcgtgata cgcctatttt tataggttaa tgtcatgata taatggtttc ttagacgtc     420 aggtggcact tttcggggaa atgtgcgcgg aaccctatt tgtttatttt tctaaataca     480
ttcaaatatg tatccgctca tgagacaata accctgataa atgcttcaat aatattgaaa    540
aaggaagagt atgattgaac aagatggatt gcacgcaggt tctccggccg cttgggtgga    600
gaggctattc ggctatgact gggcacaact gacaatcggc tgctctgatg ccgccgtgtt    660
ccggctgtca gcgcaggggc gcccggttct ttttgtcaag accgacctgt ccggtgccct    720
gaatgaactg caggacgagg cagcgcggct atcgtggctg gccacgacgg gcgttccttg    780
cgcagctgtg ctcgacgttg tcactgaagc gggaagggac tggctgctat tgggcgaagt    840
gccggggcag gatctcctgt catctcacct tgctcctgcc gagaaagtat ccatcatggc    900
tgatgcaatg cggcggctgc atacgcttga tccggctacc tgcccattcg accaccaagc    960
gaaacatcgc atcgagcggg cacgtactcg gatggaagcc ggtcttgtcg atcaggatga   1020
tctggacgaa gagcatcagg ggctcgcgcc agccgaactg ttcgccaggc tcaaggcgcg   1080
catgcccgac ggcgaggatc tcgtcgtgac acatggcgat gcctgcttgc cgaatatcat   1140
ggtggaaaat ggccgctttt ctggattcat cgactgtggc cggctgggtg tggcggaccg   1200
ctatcaggac atagcgttgg ctacccgtga tattgctgaa gagcttggcg gcgaatgggc   1260
tgaccgcttc ctcgtgcttt acggtatcgc cgctcccgat tcgcagcgca tcgccttcta   1320
tcgccttctt gacgagttct tctgagcggg actctggggt tcgaaatgac cgaccaagcg   1380
acgcctaact gtcagaccaa gtttactcat atatacttta gattgattta aaacttcatt   1440
tttaatttaa aaggatctag gtgaagatcc ttttttgataa tctcatgacc aaaatccctt   1500
aacgtgagtt ttcgttccac tgagcgtcag accccgtaga aagatcaaa ggatcttctt    1560 gagatccttt ttttctgcgc gtaatctgct gcttgcaaac aaaaaaacca ccgctaccag   1620
cggtggtttg tttgccggat caagagctac caactctttt tccgaaggta actggcttca   1680
```

```
gcagagcgca gataccaaat actgtccttc tagtgtagcc gtagttaggc caccacttca    1740
agaactctgt agcaccgcct acatacctcg ctctgctaat cctgttacca gtggctgctg    1800
ccagtggcga taagtcgtgt cttacegggt tggactcaag acgatagtta ccggataagg    1860
cgcagcggtc gggctgaacg gggggttcgt gcacacagcc cagcttggag cgaacgacct    1920
acaccgaact gagataccta cagcgtgagc tatgagaaag cgccacgctt cccgaaggga    1980
gaaaggcgga caggtatccg gtaagcggca gggtcggaac aggagagcgc acgagggagc    2040
ttccaggggg aaacgcctgg tatctttata gtcctgtcgg gtttcgccac ctctgacttg    2100
agcgtcgatt tttgtgatgc tcgtcagggg ggcggagcct atggaaaaac gccagcaacg    2160 cggcctttt acgttcctg gccttttgct ggccttttgc tcacatgttc tttcctgcgt    2220
tatcccctga ttctgtggat aaccgtatta ccgcctttga gtgagctgat accgctcgcc    2280
gcagccgaac gaccgagcgc agcgagtcag tgagcgagga agcggaagag cgcctgatgc    2340
ggtattttct ccttacgcat ctgtgcggta tttcacaccg caatggtgca ctctcagtac    2400
aatctgctct gatgccgcat agttaagcca gtatacactc cgctatcgct acgtgactgg    2460
gtcatggctg cgccccgaca cccgccaaca cccgctgacg cgccctgacg ggcttgtctg    2520
ctcccggcat ccgcttacag acaagctgtg accgtctccg ggagctgcat gtgtcagagg    2580
ttttcaccgt catcaccgaa acgcgcgagg cagctgcggt aaagctcatc agcgtggtcg    2640
tgaagcgatt cacagatgtc tgcctgttca tccgcgtcca gctcgttgag tttctccaga    2700
agcgttaatg tctggcttct gataaagcgg ccatgttaa gggcggtttt ttcctgtttg    2760
gtcactgatg cctccgtgta aggggattt ctgttcatgg gggtaatgat accgatgaaa    2820
cgagagagga tgctcacgat acgggttact gatgatgaac atgcccggtt actggaacgt    2880
tgtgagggta aacaactggc ggtatggatg cggcgggacc agagaaaaat cactcagggt    2940
caatgccagc gcttcgttaa tacagatgta ggtgttccac agggtagcca gcagcatcct    3000
gcgatgcaga tccggaacat aatggtgcag ggcgctgact tccgcgtttc cagactttac    3060
gaaacacgga aaccgaagac cattcatgtt gttgctcagg tcgcagacgt tttgcagcag    3120
cagtcgcttc acgttcgctc gcgtatcggt gattcattct gctaaccagt aaggcaaccc    3180
cgccagccta gccgggtcct caacgacagg agcacgatca tgcgcacccg tggccaggac    3240
ccaacgctgc ccgagatgcg ccgcgtgcgg ctgctggaga tggcggacgc gatggatatg    3300
ttctgccaag ggttggtttg cgcattcaca gttctccgca agaattgatt ggctccaatt    3360
cttggagtgg tgaatccgtt agcgaggtgc cgccggcttc cattcaggtc gaggtggccc    3420
ggctccatgc accgcgacgc aacgcgggga ggcagacaag gtatagggcg cgcctacaa    3480 tccatgccaa cccgttccat gtgctcgccg aggcggcata atcgccgtg acgatcagcg    3540 gtccaatgat cgaagttagg ctggtaagag ccgcgagcga tccttgaagc tgtccctgat    3600
ggtcgtcatc tacctgcctg gacagcatgg cctgcaacgc gggcatcccg atgccgccgg    3660
aagcgagaag aatcataatg gggaaggcca tccagcctcg cgtcgcgaac gccagcaaga    3720
cgtagcccag cgcgtcggcc gccatgccgg cgataatggc ctgcttctcg ccgaaacgtt    3780
tggtggcggg accagtgacg aaggcttgag cgagggcgtg caagattccg aataccgcaa    3840
gcgacaggcc gatcatcgtc gcgctccagc gaaagcggtc ctcgccgaaa atgacccaga    3900
gcgctgccgg cacctgtcct acgagttgca tgataaagaa gacagtcata agtgcggcga    3960
cgatagtcat gccccgcgcc caccggaagg agctgactgg gttgaaggct ctcaagggca    4020
```

```
tcggtcgaga tcccggtgcc taatgagtga gctaacttac attaattgcg ttgcgctcac    4080
tgcccgcttt ccagtcggga aacctgtcgt gccagctgca ttaatgaatc ggccaacgcg    4140
cggggagagg cggtttgcgt attgggcgcc agggtggttt ttcttttcac cagtgagacg    4200
ggcaacagct gattgccctt caccgcctgg ccctgagaga gttgcagcaa gcggtccacg    4260
ctggtttgcc ccagcaggcg aaaatcctgt ttgatggtgg ttaacggcgg gatataacat    4320
gagctgtctt cggtatcgtc gtatcccact accgagatat ccgcaccaac gcgcagcccg    4380
gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc ccgctaacag cgcgatttgc    4620
tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctt ccacagcaat ggcatcctgg tcatccagcg gatagttaat gatcagccca    4800
ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acggcgcgtg cagggccaga ctggaggtgg caacgccaat cagcaacgac    4980
tgtttgcccg ccagttgttg tgccacgcgg ttgggaatgt aattcagctc cgccatcgcc    5040
gcttccactt tttcccgcgt tttcgcagaa acgtggctgg cctggttcac cacgcgggaa    5100
acggtctgat aagagacacc ggcatactct gcgacatcgt ataacgttac tggtttcaca    5160
ttcaccaccc tgaattgact ctcttccggg cgctatcatg ccataccgcg aaaggttttg    5220
cgccattcga tggtgtccgg gatctcgacg ctctccctta tgcgactcct gcattaggaa    5280
gcagcccagt agtaggttga ggccgttgag caccgccgcc gcaaggaatg gtgcatgcaa    5340
ggagatggcg cccaacagtc ccccggccac ggggcctgcc accatacccc agccgaaaca    5400
agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaaattaata cgactcacta tagggggaatt gtgagcggat    5580
aacaattccc ctctagaaat aattttgttt aactttaaga aggagatata catatgaatt    5640
aaccctcact aaagggcggc cgcgaagttc ctattctcta gaaagtatag gaacttcatt    5700
ctaccgggta ggggaggcgc ttttcccaag gcagtctgga gcatgcgctt tagcagcccc    5760
gctgggcact ggcgctaca caagtggcct ctggcctcgc acacattcca catccaccgg    5820
taggcgccaa ccggctccgt tctttggtgg ccccttcgcg ccaccttcca ctcctcccct    5880
agtcaggaag ttccccccg ccccgcagct cgcgtcgtgc aggacgtgac aaatggaagt    5940
agcacgtctc actagtctcg tgcagatgga cagcaccgct gagcaatgga agcgggtagg    6000
cctttgggc agcggccaat agcagctttg ctccttcgct ttctgggctc agaggctggg    6060
aaggggtggg tccggggggcg ggctcagggg cgggctcagg ggcggggcgg gcgcccgaag    6120
gtcctccgga ggcccggcat tctgcacgct tcaaaagcgc acgtctgccg cgctgttctc    6180
ctcttcctca tctccgggcc tttcgacctg cagcagcacg tgttgacaat taatcatcgg    6240
catagtatat cggcatagta taatacgaca aggtgaggaa ctaaaccatg gagaaaaaaa    6300
tcactggata taccaccgtt gatatatccc aatggcatcg taaagaacat tttgaggcat    6360
ttcagtcagt tgctcaatgt acctataacc agaccgttca gctggatatt acggcctttt    6420
```

| | |
|---|---|
| taaagaccgt aaagaaaaat aagcacaagt tttatccggc ctttattcac attcttgccc | 6480 |
| gcctgatgaa tgctcatccg gaattccgta tggcaatgaa agacggtgag ctggtgatat | 6540 |
| gggatagtgt tcacccttgt tacaccgttt ccatgagca aactgaaacg ttttcatcgc | 6600 |
| tctggagtga ataccacgac gatttccggc agtttctaca catatattcg caagatgtgg | 6660 |
| cgtgttacgg tgaaaacctg gcctatttcc ctaagggtt tattgagaat atgtttttcg | 6720 |
| tctcagccaa tccctgggtg agtttcacca gttttgattt aaacgtggcc aatatggaca | 6780 |
| acttcttcgc ccccgttttc accatgggca aatattatac gcaaggcgac aaggtgctga | 6840 |
| tgccgctggc gattcaggtt catcatgccg tttgtgatgg cttccatgtc ggcagaatgc | 6900 |
| ttaatgaatt acaacagtac tgcgatgagt ggcagggcgg ggcgtaagcg ggactctggg | 6960 |
| gttcgaataa agaccgacca agcgacgtct gagagctccc tggcgaattc ggtaccaata | 7020 |
| aaagagcttt atttcatga tctgtgtgtt ggttttgtg tgcggcgcgg aagttcctat | 7080 |
| tctctagaaa gtataggaac ttcctcgagc cctatagtga gtcgtattag atcgcggccg | 7140 |
| cgccccttgac catgccacat cctgagcaaa taattcaacc actaattgtg agcggataac | 7200 |
| aaaggaggta aaaaaacatg gtatcctgtt ctgcgccggg taagatttac ctgttcggtg | 7260 |
| aacacgccgt agtttatggc gaaactgcaa ttgcgtgtgc ggtggaactg cgtacccgtg | 7320 |
| ttcgcgcgga actcaatgac tctatcacta ttcagagcca gatcggccgc accggtctgg | 7380 |
| atttcgaaaa gcacccttat gtgtctgcgg taattgagaa aatgcgcaaa tctattccta | 7440 |
| ttaacggtgt tttcttgacc gtcgattccg acatcccggt gggctccggt ctgggtagca | 7500 |
| gcgcagccgt tactatcgcg tctattggtg cgctgaacga gctgttcggc tttggcctca | 7560 |
| gcctgcaaga aatcgctaaa ctgggccacg aaatcgaaat taagtacag ggtgccgcgt | 7620 |
| ccccaaccga tacgtatgtt tctaccttcg gcggcgtggt taccatcccg gaacgtcgca | 7680 |
| aactgaaaac tccggactgc ggcattgtga ttggcgatac cggcgttttc tcctccacca | 7740 |
| aagagttagt agctaacgta cgtcagctgc gcgaaagcta cccggatttg atcgaaccgc | 7800 |
| tgatgaccte tattggcaaa atctctcgta tcggcgaaca actggttctg tctggcgact | 7860 |
| acgcatccat cggccgcctg atgaacgtca accagggtct cctggacgcc ctgggcgtta | 7920 |
| acatcttaga actgagccag ctgatctatt ccgctcgtgc ggcaggtgcg tttggcgcta | 7980 |
| aaatcacggg cgctggcggc ggtggctgta tggttgcgct gaccgctccg gaaaaatgca | 8040 |
| accaagtggc agaagcggta gcaggcgctg gcggtaaagt gactatcact aaaccgaccg | 8100 |
| agcaaggtct gaaagtagat taa | 8123 |

<210> SEQ ID NO 92
<211> LENGTH: 8123
<212> TYPE: DNA
<213> ORGANISM: Artificial Sequence
<220> FEATURE:
<223> OTHER INFORMATION: Synthetic Construct

<400> SEQUENCE: 92

| | |
|---|---|
| aagggcgagc tcaacgatcc ggctgctaac aaagcccgaa aggaagctga gttggctgct | 60 |
| gccaccgctg agcaataact agcataaccc cttggggcct ctaaacgggt cttgaggagt | 120 |
| tttttgctga aaggaggaac tatatccgga tatcccgcaa gaggcccggc agtaccggca | 180 |
| taaccaagcc tatgcctaca gcatccaggg tgacggtgcc gaggatgacg atgagcgcat | 240 |
| tgttagattt catcacggt gcctgactgc gttagcaatt taactgtgat aaactaccgc | 300 |

```
attaaagctt atcgatgata agctgtcaaa catgagaatt aattcttgaa gacgaaaggg    360
cctcgtgata cgcctatttt tataggttaa tgtcatgata ataatggttt cttagacgtc    420
aggtggcact tttcggggaa atgtgcgcgg aacccctatt tgtttatttt tctaaataca    480
ttcaaatatg tatccgctca tgagacaata accctgataa atgcttcaat aatattgaaa    540
aaggaagagt atgattgaac aagatggatt gcacgcaggt tctccggccg cttgggtgga    600
gaggctattc ggctatgact gggcacaact gacaatcggc tgctctgatg ccgccgtgtt    660
ccggctgtca gcgcaggggc gcccggttct ttttgtcaag accgacctgt ccggtgccct    720
gaatgaactg caggacgagg cagcgcggct atcgtggctg gccacgacgg gcgttccttg    780
cgcagctgtg ctcgacgttg tcactgaagc gggaagggac tggctgctat tgggcgaagt    840
gccggggcag gatctcctgt catctcacct tgctcctgcc gagaaagtat ccatcatggc    900
tgatgcaatg cggcggctgc atacgcttga tccggctacc tgcccattcg accaccaagc    960
gaaacatcgc atcgagcggg cacgtactcg gatggaagcc ggtcttgtcg atcaggatga   1020
tctggacgaa gagcatcagg ggctcgcgcc agccgaactg ttcgccaggc tcaaggcgcg   1080
catgcccgac ggcgaggatc tcgtcgtgac acatggcgat gcctgcttgc cgaatatcat   1140
ggtggaaaat ggccgctttt ctggattcat cgactgtggc cggctgggtg tggcggaccg   1200
ctatcaggac atagcgttgg ctacccgtga tattgctgaa gagcttggcg gcgaatgggc   1260
tgaccgcttc ctcgtgcttt acggtatcgc cgctcccgat tcgcagcgca tcgccttcta   1320
tcgccttctt gacgagttct tctgagcggg actctggggt tcgaaatgac cgaccaagcg   1380
acgcctaact gtcagaccaa gtttactcat atatacttta gattgattta aaacttcatt   1440
tttaatttaa aaggatctag gtgaagatcc tttttgataa tctcatgacc aaaatccctt   1500
aacgtgagtt ttcgttccac tgagcgtcag accccgtaga aaagatcaaa ggatcttctt   1560
gagatccttt ttttctgcgc gtaatctgct gcttgcaaac aaaaaaacca ccgctaccag   1620
cggtggtttg tttgccggat caagagctac caactctttt tccgaaggta actggcttca   1680
gcagagcgca gataccaaat actgtccttc tagtgtagcc gtagttaggc caccacttca   1740
agaactctgt agcaccgcct acatacctcg ctctgctaat cctgttacca gtggctgctg   1800
ccagtggcga taagtcgtgt cttaccgggt tggactcaag acgatagtta ccggataagg   1860
cgcagcggtc gggctgaacg gggggttcgt gcacacagcc cagcttggag cgaacgacct   1920
acaccgaact gagatacccta cagcgtgagc tatgagaaag cgccacgctt cccgaaggga   1980
gaaaggcgga caggtatccg gtaagcggca gggtcggaac aggagagcgc acagggagc    2040
ttccaggggg aaacgcctgg tatctttata gtcctgtcgg gtttcgccac ctctgacttg   2100
agcgtcgatt tttgtgatgc tcgtcagggg gcggagcct atggaaaaac gccagcaacg    2160
cggccttttt acggttcctg ccttttgct ggccttttgc tcacatgttc tttcctgcgt    2220
tatcccctga ttctgtggat aaccgtatta ccgcctttga gtgagctgat accgctcgcc   2280
gcagccgaac gaccgagcgc agcgagtcag tgagcgagga agcggaagag cgcctgatgc   2340
ggtattttct ccttacgcat ctgtgcggta tttcacaccg caatggtgca ctctcagtac   2400
aatctgctct gatgccgcat agttaagcca gtatacactc cgctatcgct acgtgactgg   2460
gtcatggctg cgccccgaca cccgccaaca cccgctgacg cgccctgacg ggcttgtctg   2520
ctcccggcat ccgcttacag acaagctgtg accgtctccg ggagctgcat gtgtcagagg   2580
ttttcaccgt catcaccgaa acgcgcgagg cagctgcggt aaagctcatc agcgtggtcg   2640
tgaagcgatt cacagatgtc tgcctgttca tccgcgtcca gctcgttgag tttctccaga   2700
```

```
agcgttaatg tctggcttct gataaagcgg gccatgttaa gggcggtttt ttcctgtttg   2760
gtcactgatg cctccgtgta aggggggattt ctgttcatgg gggtaatgat accgatgaaa   2820
cgagagagga tgctcacgat acgggttact gatgatgaac atgcccggtt actggaacgt   2880
tgtgagggta aacaactggc ggtatggatg cggcgggacc agagaaaaat cactcagggt   2940
caatgccagc gcttcgttaa tacagatgta ggtgttccac agggtagcca gcagcatcct   3000
gcgatgcaga tccggaacat aatggtgcag ggcgctgact ccgcgtttc cagactttac    3060 gaaacacgga aaccgaagac cattcatgtt gttgctcagg tcgcagacgt tttgcagcag   3120
cagtcgcttc acgttcgctc gcgtatcggt gattcattct gctaaccagt aaggcaaccc   3180
cgccagccta gccgggtcct caacgacagg agcacgatca tgcgcacccg tggccaggac   3240
ccaacgctgc ccgagatgcg ccgcgtgcgg ctgctggaga tggcggacgc gatggatatg   3300
ttctgccaag ggttggtttg cgcattcaca gttctccgca agaattgatt ggctccaatt   3360
cttggagtgg tgaatccgtt agcgaggtgc cgccggcttc cattcaggtc gaggtggccc   3420
ggctccatgc accgcgacgc aacgcgggga ggcagacaag gtatagggcg cgcctacaa    3480 tccatgccaa cccgttccat gtgctcgccg aggcggcata atcgccgtg acgatcagcg    3540 gtccaatgat cgaagttagg ctggtaagag ccgcgagcga tccttgaagc tgtccctgat   3600
ggtcgtcatc tacctgcctg acagcatgg cctgcaacgc gggcatcccg atgccgccgg    3660
aagcgagaag aatcataatg gggaaggcca tccagcctcg cgtcgcgaac gccagcaaga   3720
cgtagcccag cgcgtcggcc gccatgccgg cgataatggc ctgcttctcg ccgaaacgtt   3780
tggtggcggg accagtgacg aaggcttgag cgagggcgtg caagattccg aataccgcaa   3840
gcgacaggcc gatcatcgtc gcgctccagc gaaagcggtc ctcgccgaaa atgacccaga   3900
gcgctgccgg cacctgtcct acgagttgca tgataaagaa gacagtcata agtgcggcga   3960
cgatagtcat gccccgcgcc caccggaagg agctgactgg gttgaaggct ctcaagggca   4020
tcggtcgaga tcccggtgcc taatgagtga gctaacttac attaattgcg ttgcgctcac   4080
tgcccgcttt ccagtcggga aacctgtcgt gccagctgca ttaatgaatc ggccaacgcg   4140
cggggagagg cggtttgcgt attgggcgcc agggtggttt ttcttttcac cagtgagacg   4200
ggcaacagct gattgccctt caccgcctgg ccctgagaga gttgcagcaa gcggtccacg   4260
ctggtttgcc ccagcaggcg aaaatcctgt ttgatggtgg ttaacggcgg gatataacat   4320
gagctgtctt cggtatcgtc gtatcccact accgagatat ccgcaccaac gcgcagcccg   4380
gactcggtaa tggcgcgcat tgcgcccagc gccatctgat cgttggcaac cagcatcgca   4440
gtgggaacga tgccctcatt cagcatttgc atggtttgtt gaaaaccgga catggcactc   4500
cagtcgcctt cccgttccgc tatcggctga atttgattgc gagtgagata tttatgccag   4560
ccagccagac gcagacgcgc cgagacagaa cttaatgggc ccgctaacag cgcgatttgc   4620
tggtgaccca atgcgaccag atgctccacg cccagtcgcg taccgtcttc atgggagaaa   4680
ataatactgt tgatgggtgt ctggtcagag acatcaagaa ataacgccgg aacattagtg   4740
caggcagctt ccacagcaat ggcatcctgg tcatccagcg gatagttaat gatcagccca   4800
ctgacgcgtt gcgcgagaag attgtgcacc gccgctttac aggcttcgac gccgcttcgt   4860
tctaccatcg acaccaccac gctggcaccc agttgatcgg cgcgagattt aatcgccgcg   4920
acaatttgcg acgcgcgtg cagggccaga ctggaggtgg caacgccaat cagcaacgac    4980
tgtttgcccg ccagttgttg tgccacgcgg ttgggaatgt aattcagctc cgccatcgcc   5040
```

```
gcttccactt tttcccgcgt tttcgcagaa acgtggctgg cctggttcac cacgcgggaa       5100
acggtctgat aagagacacc ggcatactct gcgacatcgt ataacgttac tggtttcaca       5160
ttcaccaccc tgaattgact ctcttccggg cgctatcatg ccataccgcg aaaggttttg       5220
cgccattcga tggtgtccgg gatctcgacg ctctccctta tgcgactcct gcattaggaa       5280
gcagcccagt agtaggttga ggccgttgag caccgccgcc gcaaggaatg gtgcatgcaa       5340
ggagatggcg cccaacagtc ccccggccac ggggcctgcc accatacccc cgccgaaaca       5400
agcgctcatg agcccgaagt ggcgagcccg atcttcccca tcggtgatgt cggcgatata       5460
ggcgccagca accgcacctg tggcgccggt gatgccggcc acgatgcgtc cggcgtagag       5520
gatcgagatc tcgatcccgc gaaattaata cgactcacta taggggaatt gtgagcggat       5580
aacaattccc ctctagaaat aattttgttt aactttaaga aggagatata catatgaatt       5640
aaccctcact aaagggcggc cgcgaagttc ctattctcta gaaagtatag gaacttcatt       5700
ctaccgggta ggggaggcgc ttttcccaag gcagtctgga gcatgcgctt tagcagcccc       5760
gctgggcact tggcgctaca caagtggcct ctggcctcgc acacattcca catccaccgg       5820
taggcgccaa ccggctccgt tctttggtgg ccccttcgcg ccaccttcca ctcctcccct       5880
agtcaggaag ttccccccgg ccccgcagct cgcgtcgtgc aggacgtgac aaatggaagt       5940
agcacgtctc actagtctcg tgcagatgga cagcaccgct gagcaatgga agcgggtagg       6000
cctttggggc agcggccaat agcagctttg ctccttcgct ttctgggctc agaggctggg       6060
aaggggtggg tccgggggcg ggctcagggg cgggctcagg ggcggggcgg gcgcccgaag       6120
gtcctccgga ggcccggcat tctgcacgct tcaaaagcgc acgtctgccg cgctgttctc       6180
ctcttcctca tctccgggcc tttcgacctg cagcagcacg tgttgacaat taatcatcgg       6240
catagtatat cggcatagta taatacgaca aggtgaggaa ctaaaccatg gagaaaaaaa       6300
tcactggata taccaccgtt gatatatccc aatggcatcg taaagaacat tttgaggcat       6360
ttcagtcagt tgctcaatgt acctataacc agaccgttca gctggatatt acggcctttt       6420
taaagaccgt aaagaaaaat aagcacaagt tttatccggc ctttattcac attcttgccc       6480
gcctgatgaa tgctcatccg gaattccgta tggcaatgaa agacggtgag ctggtgatat       6540
gggatagtgt tcacccttgt tacaccgttt tccatgagca aactgaaacg ttttcatcgc       6600
tctggagtga ataccacgac gatttccggc agtttctaca catatattcg caagatgtgg       6660
cgtgttacgg tgaaaacctg gcctatttcc ctaaagggtt tattgagaat atgttttcg        6720 tctcagccaa tccctgggtg agtttcacca gttttgattt aaacgtggcc aatatggaca       6780
acttcttcgc cccgttttc accatgggca atatattac gcaaggcgac aaggtgctga        6840
tgccgctggc gattcaggtt catcatgccg tttgtgatgg cttccatgtc ggcagaatgc       6900
ttaatgaatt acaacagtac tgcgatgagt ggcagggcgg ggcgtaagcg gactctggg        6960 gttcgaataa agaccgacca agcgacgtct gagagctccc tggcgaattc ggtaccaata       7020
aaagagcttt attttcatga tctgtgtgtt ggttttgtg tgcggcgcgg aagttcctat        7080
tctctagaaa gtataggaac ttcctcgagc cctatagtga gtcgtattag atcgcggccg       7140
cgcccttgac gatgccacat cctgagcaaa taattcaacc actaattgtg agcggataac       7200
aaaggaggta aaaaacatg gtatcctgtt ctgcgccggg taagatttac ctgttcggtg        7260
aacacgccgt agtttatggc gaaactgcaa ttgcgtgtgc ggtggaactg cgtacccgtg       7320
ttcgcgcgga actcaatgac tctatcacta ttcagccca gatcggccgc accggtctgg       7380
atttcgaaaa gcacccttat gtgtctgcgg taattgagaa aatgcgcaaa tctattccta       7440
```

```
ttaacggtgt tttcttgacc gtcgattccg acatcccggt gggctccggt ctgggtagca    7500
gcgcagccgt tactatcgcg tctattggtg cgctgaacga gctgttcggc tttggcctca    7560
gcctgcaaga aatcgctaaa ctgggccacg aaatcgaaat taaagtacag ggtgccgcgt    7620
ccccaaccga tacgtatgtt tctaccttcg gcggcgtggt taccatcccg gaacgtcgca    7680
aactgaaaac tccggactgc ggcattgtga ttggcgatac cggcgttttc tcctccacca    7740
aagagttagt agctaacgta cgtcagctgc gcgaaagcta cccggatttg atcgaaccgc    7800
tgatgacctc tattggcaaa atctctcgta tcggcgaaca actggttctg tctggcgact    7860
acgcatccat cggccgcctg atgaacgtca accagggtct cctggacgcc ctgggcgtta    7920
acatcttaga actgagccag ctgatctatt ccgctcgtgc ggcaggtgcg tttggcgcta    7980
aaatcacggg cgctggcggc ggtggctgta tggttgcgct gaccgctccg gaaaaatgca    8040
accaagtggc agaagcggta gcaggcgctg gcggtaaagt gactatcact aaaccgaccg    8100
agcaaggtct gaaagtagat taa                                             8123

<210> SEQ ID NO 93
<211> LENGTH: 8123
<212> TYPE: DNA
<213> ORGANISM: Artificial Sequence
<220> FEATURE:
<223> OTHER INFORMATION: Synthetic Construct

<400> SEQUENCE: 93
aagggcgagc tcaacgatcc ggctgctaac aaagcccgaa aggaagctga gttggctgct      60
gccaccgctg agcaataact agcataaccc cttggggcct ctaaacgggt cttgaggagt     120 ttttgctga aggaggaac tatatccgga tatcccgcaa gaggcccggc agtaccggca      180
taaccaagcc tatgcctaca gcatccaggg tgacggtgcc gaggatgacg atgagcgcat     240
tgttagattt catacacggt gcctgactgc gttagcaatt taactgtgat aaactaccgc     300
attaaagctt atcgatgata agctgtcaaa catgagaatt aattcttgaa gacgaaaggg     360
cctcgtgata cgcctatttt tataggttaa tgtcatgata ataatggttt cttagacgtc     420
aggtggcact tttcggggaa atgtgcgcgg aaccccatt tgtttatttt tctaaataca     480
ttcaaatatg tatccgctca tgagacaata accctgataa atgcttcaat aatattgaaa     540
aaggaagagt atgattgaac aagatggatt gcacgcaggt tctccggccg cttgggtgga     600
gaggctattc ggctatgact gggcacaact gacaatcggc tgctctgatg ccgccgtgtt     660
ccggctgtca gcgcaggggc gcccggttct ttttgtcaag accgacctgt ccggtgccct     720
gaatgaactg caggacgagg cagcgcggct atcgtggctg gccacgacgg gcgttccttg     780
cgcagctgtg ctcgacgttg tcactgaagc gggaagggac tggctgctat gggcgaagt     840 gccggggcag gatctcctgt catctcacct tgctcctgcc gagaaagtat ccatcatggc     900
tgatgcaatg cggcggctgc atacgcttga tccggctacc tgcccattcg accaccaagc     960
gaaacatcgc atcgagcggg cacgtactcg gatggaagcc ggtcttgtcg atcaggatga    1020
tctggacgaa gagcatcagg ggctcgcgcc agccgaactg ttcgccaggc tcaaggcgcg    1080
catgcccgac ggcgaggatc tcgtcgtgac acatggcgat gcctgcttgc cgaatatcat    1140
ggtggaaaat ggccgctttt ctggattcat cgactgtggc cggctgggtg tggcggaccg    1200
ctatcaggac atagcgttgg ctacccgtga tattgctgaa gagcttggcg gcgaatgggc    1260
tgaccgcttc ctcgtgcttt acggtatcgc cgctcccgat tcgcagcgca tcgccttcta    1320
```

```
tcgccttctt gacgagttct tctgagcggg actctggggt tcgaaatgac cgaccaagcg   1380
acgcctaact gtcagaccaa gtttactcat atatactta  gattgattta aaacttcatt   1440
tttaatttaa aaggatctag gtgaagatcc ttttttgataa tctcatgacc aaaatccctt  1500
aacgtgagtt tcgttccac  tgagcgtcag accccgtaga aaagatcaaa ggatcttctt   1560
gagatccttt ttttctgcgc gtaatctgct gcttgcaaac aaaaaaacca ccgctaccag   1620
cggtggtttg tttgccggat caagagctac caactctttt tccgaaggta actggcttca   1680
gcagagcgca gataccaaat actgtccttc tagtgtagcc gtagttaggc caccacttca   1740
agaactctgt agcaccgcct acatacctcg ctctgctaat cctgttacca gtggctgctg   1800
ccagtggcga taagtcgtgt cttaccgggt tggactcaag acgatagtta ccggataagg   1860
cgcagcggtc gggctgaacg gggggttcgt gcacacagcc cagcttggag cgaacgacct   1920
acaccgaact gagataccta cagcgtgagc tatgagaaag cgccacgctt cccgaaggga   1980
gaaaggcgga caggtatccg gtaagcggca gggtcggaac aggagagcgc acagggagc   2040 ttccaggggg aaacgcctgg tatctttata gtcctgtcgg gtttcgccac ctctgacttg   2100
agcgtcgatt tttgtgatgc tcgtcagggg ggcggagcct atggaaaaac gccagcaacg   2160
cggccttttt acgttcctg  gccttttgct ggccttttgc tcacatgttc tttcctgcgt   2220
tatcccctga ttctgtggat aaccgtatta ccgcctttga gtgagctgat accgctcgcc   2280
gcagccgaac gaccgagcgc agcgagtcag tgagcgagga gcggaagag  cgcctgatgc   2340 ggtattttct ccttacgcat ctgtgcggta tttcacaccg caatggtgca ctctcagtac   2400
aatctgctct gatgccgcat agttaagcca gtatacactc cgctatcgct acgtgactgg   2460
gtcatggctg cgccccgaca cccgccaaca cccgctgacg cgccctgacg gcttgtctg   2520 ctcccggcat ccgcttacag acaagctgtg accgtctccg ggagctgcat gtgtcagagg   2580
ttttcaccgt catcaccgaa acgcgcgagg cagctgcggt aaagctcatc agcgtggtcg   2640
tgaagcgatt cacagatgtc tgcctgttca tccgcgtcca gctcgttgag tttctccaga   2700
agcgttaatg tctggcttct gataaagcgg gccatgttaa gggcggtttt ttcctgtttg   2760
gtcactgatg cctccgtgta aggggattt  ctgttcatgg gggtaatgat accgatgaaa   2820
cgagagagga tgctcacgat acgggttact gatgatgaac atgcccggtt actggaacgt   2880
tgtgagggta aacaactggc ggtatggatg cggcgggacc agagaaaaat cactcagggt   2940
caatgccagc gcttcgttaa tacagatgta ggtgttccac agggtagcca gcagcatcct   3000
gcgatgcaga tccggaacat aatggtgcag ggcgctgact ccgcgtttc  cagactttac   3060 gaaacacgga aaccgaagac cattcatgtt gttgctcagg tcgcagacgt tttgcagcag   3120
cagtcgcttc acgttcgctc gcgtatcggt gattcattct gctaaccagt aaggcaaccc   3180
cgccagccta gccgggtcct caacgacagg agcacgatca tgcgcacccg tggccaggac   3240
ccaacgctgc ccgagatgcg ccgcgtgcgg ctgctggaga tggcggacgc gatggatatg   3300
ttctgccaag ggttggtttg cgcattcaca gttctccgca agaattgatt ggctccaatt   3360
cttggagtgg tgaatccgtt agcgaggtgc cgccggcttc cattcaggtc gaggtggccc   3420
ggctccatgc accgcgacgc aacgcgggga ggcagacaag gtatagggcg cgcctacaa   3480 tccatgccaa cccgttccat gtgctcgccg aggcggcata atcgccgtg  acgatcagcg   3540 gtccaatgat cgaagttagg ctggtaagag ccgcgagcga tccttgaagc tgtccctgat   3600
ggtcgtcatc tacctgcctg gacagcatgg cctgcaacgc gggcatcccg atgccgccgg   3660
aagcgagaag aatcataatg gggaaggcca tccagcctcg cgtcgcgaac gccagcaaga   3720
```

```
cgtagcccag cgcgtcggcc gccatgccgg cgataatggc ctgcttctcg ccgaaacgtt    3780
tggtggcggg accagtgacg aaggcttgag cgagggcgtg caagattccg aataccgcaa    3840
gcgacaggcc gatcatcgtc gcgctccagc gaaagcggtc ctcgccgaaa atgacccaga    3900
gcgctgccgg cacctgtcct acgagttgca tgataaagaa gacagtcata agtgcggcga    3960
cgatagtcat gccccgcgcc caccggaagg agctgactgg gttgaaggct ctcaagggca    4020
tcggtcgaga tcccggtgcc taatgagtga gctaacttac attaattgcg ttgcgctcac    4080
tgcccgcttt ccagtcggga aacctgtcgt gccagctgca ttaatgaatc ggccaacgcg    4140
cggggagagg cggtttgcgt attgggcgcc agggtggttt ttcttttcac cagtgagacg    4200
ggcaacagct gattgccctt caccgcctgg ccctgagaga gttgcagcaa gcggtccacg    4260
ctggtttgcc ccagcaggcg aaaatcctgt ttgatggtgg ttaacggcgg gatataacat    4320
gagctgtctt cggtatcgtc gtatcccact accgagatat ccgcaccaac gcgcagcccg    4380
gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc ccgctaacag cgcgatttgc    4620
tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctt ccacagcaat ggcatcctgg tcatccagcg atagttaat gatcagccca     4800
ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acggcgcgtg cagggccaga ctggaggtgg caacgccaat cagcaacgac    4980
tgtttgcccg ccagttgttg tgccacgcgg ttgggaatgt aattcagctc cgccatcgcc    5040
gcttccactt tttcccgcgt tttcgcagaa acgtggctgg cctggttcac cacgcgggaa    5100
acggtctgat aagagacacc ggcatactct gcgacatcgt ataacgttac tggtttcaca    5160
ttcaccaccc tgaattgact ctcttccggg cgctatcatg ccataccgcg aaaggttttg    5220
cgccattcga tggtgtccgg gatctcgacg ctctccctta tgcgactcct gcattaggaa    5280
gcagcccagt agtaggttga ggccgttgag caccgccgcc gcaaggaatg gtgcatgcaa    5340
ggagatggcg cccaacagtc ccccggccac ggggcctgcc accatacccca cgccgaaaca    5400
agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaaattaata cgactcacta gggaatt gtgagcggat    5580
aacaattccc ctctagaaat aattttgttt aactttaaga aggagatata catatgaatt    5640
aaccctcact aaagggcggc cgcgaagttc ctattctcta gaaagtatag gaacttcatt    5700
ctaccgggta ggggaggcgc ttttcccaag gcagtctgga gcatgcgctt tagcagcccc    5760
gctgggcact tggcgctaca caagtggcct ctggcctcgc acacattcca catccaccgg    5820
taggcgccaa ccggctccgt tctttggtgg ccccttcgcg ccaccttcca ctcctcccct    5880
agtcaggaag ttccccccg ccccgcagct cgcgtcgtgc aggacgtgac aaatggaagt     5940
agcacgtctc actagtctcg tgcagatgga cagcaccgct gagcaatgga agcgggtagg    6000
cctttggggc agcggccaat agcagctttg ctccttcgct ttctgggctc agaggctggg    6060
```

| | | |
|---|---|---|
| aaggggtggg tccggggcg ggctcagggg cgggctcagg ggcggggcgg gcgcccgaag | 6120 | |
| gtcctccgga ggcccggcat tctgcacgct tcaaaagcgc acgtctgccg cgctgttctc | 6180 | |
| ctcttcctca tctccgggcc tttcgacctg cagcagcacg tgttgacaat taatcatcgg | 6240 | |
| catagtatat cggcatagta taatacgaca aggtgaggaa ctaaaccatg gagaaaaaaa | 6300 | |
| tcactggata taccaccgtt gatatatccc aatggcatcg taaagaacat tttgaggcat | 6360 | |
| ttcagtcagt tgctcaatgt acctataacc agaccgttca gctggatatt acggccttt | 6420 | |
| taaagaccgt aaagaaaaat aagcacaagt tttatccggc ctttattcac attcttgccc | 6480 | |
| gcctgatgaa tgctcatccg gaattccgta tggcaatgaa agacggtgag ctggtgatat | 6540 | |
| gggatagtgt tcacccttgt tacaccgttt tccatgagca aactgaaacg ttttcatcgc | 6600 | |
| tctggagtga ataccacgac gatttccggc agtttctaca catatattcg caagatgtgg | 6660 | |
| cgtgttacgg tgaaaacctg gcctatttcc ctaaagggtt tattgagaat atgttttcg | 6720 | |
| tctcagccaa tccctgggtg agtttcacca gttttgattt aaacgtggcc aatatggaca | 6780 | |
| acttcttcgc ccccgttttc accatgggca atattatac gcaaggcgac aaggtgctga | 6840 | |
| tgccgctggc gattcaggtt catcatgccg tttgtgatgg cttccatgtc ggcagaatgc | 6900 | |
| ttaatgaatt acaacagtac tgcgatgagt ggcagggcgg ggcgtaagcg ggactctggg | 6960 | |
| gttcgaataa agaccgacca agcgacgtct gagagctccc tggcgaattc ggtaccaata | 7020 | |
| aaagagcttt attttcatga tctgtgtgtt ggttttgtg tgcggcgcgg aagttcctat | 7080 | |
| tctctagaaa gtataggaac ttcctcgagc cctatagtga gtcgtattag atcgcggccg | 7140 | |
| cgcccttgac tatgccacat cctgagcaaa taattcaacc actaattgtg agcggataac | 7200 | |
| aaaggaggta aaaaaacatg gtatcctgtt ctgcgccggg taagatttac ctgttcggtg | 7260 | |
| aacacgccgt agtttatggc gaaactgcaa ttgcgtgtgc ggtggaactg cgtacccgtg | 7320 | |
| ttcgcgcgga actcaatgac tctatcacta ttcagagcca gatcggccgc accggtctgg | 7380 | |
| atttcgaaaa gcacccttat gtgtctgcgg taattgagaa aatgcgcaaa tctattccta | 7440 | |
| ttaacggtgt tttcttgacc gtcgattccg acatcccggt gggctccggt ctgggtagca | 7500 | |
| gcgcagccgt tactatcgcg tctattggtg cgctgaacga gctgttcggc tttggcctca | 7560 | |
| gcctgcaaga atcgctaaa ctgggccacg aaatcgaaat taaagtacag ggtgccgcgt | 7620 | |
| ccccaaccga tacgtatgtt tctaccttcg gcggcgtggt taccatcccg gaacgtcgca | 7680 | |
| aactgaaaac tccggactgc ggcattgtga ttggcgatac cggcgttttc tcctccacca | 7740 | |
| aagagttagt agctaacgta cgtcagctgc gcgaaagcta cccggatttg atcgaaccgc | 7800 | |
| tgatgaccte tattggcaaa atctctcgta tcggcgaaca actggttctg tctggcgact | 7860 | |
| acgcatccat cggccgcctg atgaacgtca accaggtct cctggacgcc ctgggcgtta | 7920 | |
| acatcttaga actgagccag ctgatctatt ccgctcgtgc ggcaggtgcg tttggcgcta | 7980 | |
| aaatcacggg cgctggcggc ggtggctgta tggttgcgct gaccgctccg gaaaatgca | 8040 | |
| accaagtggc agaagcggta gcaggcgctg gcggtaaagt gactatcact aaaccgaccg | 8100 | |
| agcaaggtct gaaagtagat taa | 8123 | |

<210> SEQ ID NO 94
<211> LENGTH: 19
<212> TYPE: DNA
<213> ORGANISM: Artificial Sequence
<220> FEATURE:
<223> OTHER INFORMATION: Synthetic Construct

<400> SEQUENCE: 94

```
accaattgca cccggcaga                                              19

<210> SEQ ID NO 95
<211> LENGTH: 21
<212> TYPE: DNA
<213> ORGANISM: Artificial Sequence
<220> FEATURE:
<223> OTHER INFORMATION: Synthetic Construct

<400> SEQUENCE: 95
gctaaagcgc atgctccaga c                                           21

<210> SEQ ID NO 96
<211> LENGTH: 20
<212> TYPE: DNA
<213> ORGANISM: Artificial Sequence
<220> FEATURE:
<223> OTHER INFORMATION: Synthetic Construct

<400> SEQUENCE: 96
gactggcctc agatgaaagc                                             20

<210> SEQ ID NO 97
<211> LENGTH: 20
<212> TYPE: DNA
<213> ORGANISM: Artificial Sequence
<220> FEATURE:
<223> OTHER INFORMATION: Synthetic Construct

<400> SEQUENCE: 97
caaacatgtg gcatggaaag                                             20

<210> SEQ ID NO 98
<211> LENGTH: 52
<212> TYPE: DNA
<213> ORGANISM: Artificial Sequence
<220> FEATURE:
<223> OTHER INFORMATION: Synthetic Construct

<400> SEQUENCE: 98
gggcccgttt aaactttaac tagactctgc agttagcgtt caaacggcag aa         52

<210> SEQ ID NO 99
<211> LENGTH: 38
<212> TYPE: DNA
<213> ORGANISM: Artificial Sequence
<220> FEATURE:
<223> OTHER INFORMATION: Synthetic Construct

<400> SEQUENCE: 99
cgcatgcatg tcatgagatg tagcgtgtcc accgaaaa                         38

<210> SEQ ID NO 100
<211> LENGTH: 22
<212> TYPE: DNA
<213> ORGANISM: Artificial Sequence
<220> FEATURE:
<223> OTHER INFORMATION: Synthetic Construct

<400> SEQUENCE: 100
acaatttcac acaggaaaca gc                                          22

<210> SEQ ID NO 101
<211> LENGTH: 23
<212> TYPE: DNA
```

```
<213> ORGANISM: Artificial Sequence
<220> FEATURE:
<223> OTHER INFORMATION: Synthetic Construct

<400> SEQUENCE: 101
ccaggcaaat tctgttttat cag                                             23

<210> SEQ ID NO 102
<211> LENGTH: 22
<212> TYPE: DNA
<213> ORGANISM: Artificial Sequence
<220> FEATURE:
<223> OTHER INFORMATION: Synthetic Construct

<400> SEQUENCE: 102
gcactgtctt tccgtctgct gc                                              22

<210> SEQ ID NO 103
<211> LENGTH: 66
<212> TYPE: DNA
<213> ORGANISM: Artificial Sequence
<220> FEATURE:
<223> OTHER INFORMATION: Synthetic Construct

<400> SEQUENCE: 103
gcgaacgatg cataaaggag gtaaaaaaac atggtatcct gttctgcgcc gggtaagatt     60
tacctg                                                                66

<210> SEQ ID NO 104
<211> LENGTH: 48
<212> TYPE: DNA
<213> ORGANISM: Artificial Sequence
<220> FEATURE:
<223> OTHER INFORMATION: Synthetic Construct

<400> SEQUENCE: 104
gggcccgttt aaactttaac tagactttaa tctactttca gaccttgc                  48

<210> SEQ ID NO 105
<211> LENGTH: 24
<212> TYPE: DNA
<213> ORGANISM: Artificial Sequence
<220> FEATURE:
<223> OTHER INFORMATION: Synthetic Construct

<400> SEQUENCE: 105
gatagtaacg gctgcgctgc tacc                                            24

<210> SEQ ID NO 106
<211> LENGTH: 23
<212> TYPE: DNA
<213> ORGANISM: Artificial Sequence
<220> FEATURE:
<223> OTHER INFORMATION: Synthetic Construct

<400> SEQUENCE: 106
gacagcttat catcgactgc acg                                             23

<210> SEQ ID NO 107
<211> LENGTH: 22
<212> TYPE: DNA
<213> ORGANISM: Artificial Sequence
<220> FEATURE:
<223> OTHER INFORMATION: Synthetic Construct

<400> SEQUENCE: 107
```

```
caccatggta tcctgttctg cg                                            22

<210> SEQ ID NO 108
<211> LENGTH: 22
<212> TYPE: DNA
<213> ORGANISM: Artificial Sequence
<220> FEATURE:
<223> OTHER INFORMATION: Synthetic Construct

<400> SEQUENCE: 108
ttaatctact ttcagacctt gc                                            22

<210> SEQ ID NO 109
<211> LENGTH: 81
<212> TYPE: DNA
<213> ORGANISM: Artificial Sequence
<220> FEATURE:
<223> OTHER INFORMATION: Synthetic Construct

<400> SEQUENCE: 109
aaagtagccg aagatgacgg tttgtcacat ggagttggca ggatgtttga ttaaaagcaa   60
ttaaccctca ctaaagggcg g                                             81

<210> SEQ ID NO 110
<211> LENGTH: 31
<212> TYPE: DNA
<213> ORGANISM: Artificial Sequence
<220> FEATURE:
<223> OTHER INFORMATION: Synthetic Construct

<400> SEQUENCE: 110
gatatacata tgaattaacc ctcactaaag g                                  31

<210> SEQ ID NO 111
<211> LENGTH: 125
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 80
<223> OTHER INFORMATION: n = A,T,C or G

<400> SEQUENCE: 111
gcatgcatga catgtttttt tacctccttt gttatccgct cacaattagt ggttgaatta   60
tttgctcagg atgtggcatn gtcaagggcg cggccgcgat ctaatacgac tcactatagg  120
gctcg                                                              125

<210> SEQ ID NO 112
<211> LENGTH: 87
<212> TYPE: DNA
<213> ORGANISM: Artificial Sequence
<220> FEATURE:
<223> OTHER INFORMATION: Synthetic Construct

<400> SEQUENCE: 112
aggctctcaa ctctgacatg ttttttttcct ccttaagggt gcaggcctat cgcaaattag  60
cttaatctac tttcagacct tgctcgg                                       87

<210> SEQ ID NO 113
<211> LENGTH: 3913
<212> TYPE: DNA
```

<213> ORGANISM: Artificial Sequence
<220> FEATURE:
<223> OTHER INFORMATION: Synthetic Construct

<400> SEQUENCE: 113

```
gcggccgcgc ccttgacgat gccacatcct gagcaaataa ttcaaccact aattgtgagc      60
ggataacaca aggaggaaac agccatggta tcctgttctg cgccgggtaa gatttacctg     120
ttcggtgaac acgccgtagt ttatggcgaa actgcaattg cgtgtgcggt ggaactgcgt     180
acccgtgttc gcgcggaact caatgactct atcactattc agagccagat cggccgcacc     240
ggtctggatt tcgaaaagca cccttatgtg tctgcggtaa ttgagaaaat gcgcaaatct     300
attcctatta acggtgtttt cttgaccgtc gattccgaca tcccggtggg ctccggtctg     360
ggtagcagcg cagccgttac tatcgcgtct attggtgcgc tgaacgagct gttcggcttt     420
ggcctcagcc tgcaagaaat cgctaaactg ggccacgaaa tcgaaattaa agtacagggt     480
gccgcgtccc caaccgatac gtatgtttct accttcggcg cgtggttac catcccggaa     540
cgtcgcaaac tgaaaactcc ggactgcggc attgtgattg cgataccgg cgttttctcc      600
tccaccaaag agttagtagc taacgtacgt cagctgcgcg aaagctaccc ggatttgatc     660
gaaccgctga tgacctctat tggcaaaatc tctcgtatcg cgaacaact ggttctgtct      720
ggcgactacg catccatcgg ccgcctgatg aacgtcaacc agggtctcct ggacgccctg     780
ggcgttaaca tcttagaact gagccagctg atctattccg ctcgtgcggc aggtgcgttt     840
ggcgctaaaa tcacgggcgc tggcggcggt ggctgtatgg ttgcgctgac cgctccggaa     900
aaatgcaacc aagtggcaga agcggtagca ggcgctggcg gtaaagtgac tatcactaaa     960
ccgaccgagc aaggtctgaa agtagattaa gccttgactt aatagctgct tatttcgccc    1020
ttatggtacc tagtaggagg aaaaaaacat ggaaatgcgt caaccggctg tcgcaggtca    1080
attctaccca ctgcgttgcg agaacctgga aaacgaactg aaacgctgct tcgaaggcct    1140
ggagatccgc gaacaagaag tgctgggcgc agtctgtccg cacgccggtt atatgtactc    1200
tggcaaagtt gcggcgcacg tctatgccac tctgccggaa gctgatacct acgtaatctt    1260
cggcccgaac cacaccggct acggtagccc tgtctctgtg agccgtgaaa cttggaagac    1320
cccgttgggc aatatcgatg ttgacctgga actggcggac ggcttcctgg ttccatcgt     1380
agatgcggat gaactcggtc acaaatacga acactctatc gaagttcagc tgccgttct    1440
gcaataccgt tttgaacgcg atttcaaaat tctgccaatc tgcatgggta tgcaagacga    1500
agaaaccgcg gtcgaagtag gtaacctgct ggcggatctg atcagcgagt ccggtaaacg    1560
tgctgtgatc atcgcaagct ctgatttcac ccactatgag acggctgaac gtgccaaaga    1620
aatcgattcc gaagttattg attctatcct gaactttgac atctctggca tgtacgatcg    1680
cctgtatcgc cgtaacgcct ctgtttgcgg ttacggcccg atcaccgcta tgctgacggc    1740
aagcaaaaag ctgggcggct ctcgtgcgac tttgctgaaa tacgcaaaca gcggtgacgt    1800
gtccggtgat aaagacgctg tggtgggcta cgccgccatc atcgttgagt aagctgatta    1860
aaggttgaac agataggatt tcgtcatgga tcctacaagg aggaaaaaaa catgaatgct    1920
tctaatgaac cggtgattct gaaactgggt ggctctgcta ttaccgacaa aggtgcctac    1980
gaaggcgtag ttaaggaagc tgatttgctg cgcatcgcac aggaagttag cggtttccgt    2040
ggcaagatga tcgtggttca tggtgctggt agcttcggcc atacgtacgc gaagaaatac    2100
ggcctggacc gtaccttcga cccagagggc gcaattgtta ctcatgaatc tgttaaaaag    2160
ctcgcctcca agttgtagg tgctctgaat agcttcggcg tgcgtgctat cgcggtgcat    2220
```

```
cctatggact gcgcagtatg ccgtaacggt cgtatcgaaa cgatgtatct ggactccatc   2280
aagttaatgc tggaaaaagg tctggtgccg gttctgcacg gcgacgtcgc aatggatatt   2340
gaactgggca cttgtatcct gtccggtgat caaatcgttc cttacctggc caaagaactg   2400
ggtatctccc gcctcggcct gggcagcgca gaggatggtg tgctggatat ggagggcaaa   2460
cctgtaccgg aaatcacccc agaaactttc gaagagttcc gccactgcat cggtggttct   2520
ggttctactg atgtaaccgg tggcatgctg gcaaagtgc tggaacttct ggaattgagc    2580
aaaaattctt ccattactag ctacattttc aacgctggta agcagacaa catctaccgc    2640 tttctgaatg tgagtccat cggcactcgc atcagcccgg acaagcgtgt ttaagctagt    2700
tattaaccta aatgctctaa accagttatg agctctacaa ggaggaaaaa aacatgatta   2760
acactaccag ccgccgcaaa attgaacacc tgaaactctg cgcagaatcc ccggttgaag   2820
cgcgtcaggt atctgccggc tttgaagacg ttactctgat ccaccgcgct ttaccggagc   2880
tgaacatgga tgaactggac ctcagcgttg atttcctggg taaacgcatc aaagcgccgt   2940
tcctgattgc gtctatcacg ggtggtcacc cagataccat cccggttaac gctgcgctgg   3000
cagctgctgc tgaggagctg ggtgttggca tcggcgttgg ctctcagcgc gcggccattg   3060
atgatccgag ccaggaagac agcttccgtg tagtgcgtga tgaagcccca gatgcgtttg   3120
tttatggcaa cgtcggcgca gcacagatcc gtcagtatgg tgttgaaggt gttgaaaaac   3180
tgatcgaaat gattgacgca gatgccttgg caatccacct gaactttctg caagaagcgg   3240
tccaaccgga aggtgaccgc gacgcgaccg gttgcctgga catgattacc gaaatttgct   3300
ctcagattaa aactccggta atcgtgaaag aaaccggtgc aggcattagc cgtgaagatg   3360
cgattctgtt ccagaaagct ggcgtgagcg caatcgacgt tggcggcgcg gcggcaccgt   3420
cctgggctgg cgtcgaggtc taccgtgcta agaaagccg tgactctgtt agcgagcgtt    3480
taggtgagct gttttgggat tcggcattc gacggtagc ttctctgatt gaatcccgcg     3540
tttccttgcc gctgatcgca accggcggta tccgtaacgg tctggacatt gctaaaagca   3600
ttgctctcgg cgcaagcgct gccagcgccg ctctgccgtt cgttggtccg tccctggagg   3660
gcaaagaatc cgttgtacgt gtgctgagct gcatgctgga agaatttaaa gcagcaatgt   3720
ttttgtgcgg ttgcggcaac atcaaagacc tgcacaactc tccagtagtg gtaactggtt   3780
ggacccgcga atacctggag cagcgcggtt ttaacgttaa ggacctctcc ctgccgggca   3840
acgctctgta agcttcaacg cgtctacaaa taaaaaaggc acgtcagatg acgtgccttt   3900
tttcttgtct aga                                                      3913
```

<210> SEQ ID NO 114
<211> LENGTH: 6648
<212> TYPE: DNA
<213> ORGANISM: Artificial Sequence
<220> FEATURE:
<223> OTHER INFORMATION: Synthetic Construct

<400> SEQUENCE: 114

```
aagggcgagc tcaacgatcc ggctgctaac aaagcccgaa aggaagctga gttggctgct     60
gccaccgctg agcaataact agcataaccc cttggggcct ctaaacgggt cttgaggagt    120
tttttgctga aaggaggaac tatatccgga tatcccgcaa gaggcccggc agtaccggca    180
taaccaagcc tatgcctaca gcatccaggt gacggtgcc gaggatgacg atgagcgcat     240
tgttagattt catacacggt gcctgactgc gttagcaatt taactgtgat aaactaccgc    300
```

-continued

| | |
|---|---|
| attaaagctt atcgatgata agctgtcaaa catgagaatt aattcttgaa gacgaaaggg | 360 |
| cctcgtgata cgcctatttt tataggttaa tgtcatgata taatggttt cttagacgtc | 420 |
| aggtggcact tttcggggaa atgtgcgcgg aaccccatt tgtttatttt tctaaataca | 480 |
| ttcaaatatg tatccgctca tgagacaata accctgataa atgcttcaat aatattgaaa | 540 |
| aaggaagagt atgattgaac aagatggatt gcacgcaggt tctccggccg cttgggtgga | 600 |
| gaggctattc ggctatgact gggcacaact gacaatcggc tgctctgatg ccgccgtgtt | 660 |
| ccggctgtca gcgcagggc gcccggttct ttttgtcaag accgacctgt ccggtgccct | 720 |
| gaatgaactg caggacgagg cagcgcggct atcgtggctg gccacgacgg gcgttccttg | 780 |
| cgcagctgtg ctcgacgttg tcactgaagc gggaagggac tggctgctat gggcgaagt | 840 |
| gccgggcag gatctcctgt catctcacct tgctcctgcc gagaaagtat ccatcatggc | 900 |
| tgatgcaatg cggcggctgc atacgcttga tccggctacc tgcccattcg accaccaagc | 960 |
| gaaacatcgc atcgagcggg cacgtactcg gatggaagcc ggtcttgtcg atcaggatga | 1020 |
| tctggacgaa gagcatcagg ggctcgcgcc agccgaactg ttcgccaggc tcaaggcgcg | 1080 |
| catgcccgac ggcgaggatc tcgtcgtgac acatggcgat gcctgcttgc cgaatatcat | 1140 |
| ggtggaaaat ggccgctttt ctggattcat cgactgtggc cggctgggtg tggcggaccg | 1200 |
| ctatcaggac atagcgttgg ctacccgtga tattgctgaa gagcttggcg gcgaatgggc | 1260 |
| tgaccgcttc ctcgtgcttt acggtatcgc cgctcccgat tcgcagcgca tcgccttcta | 1320 |
| tcgccttctt gacgagttct tctgagcggg actctggggt tcgaaatgac cgaccaagcg | 1380 |
| acgcctaact gtcagaccaa gtttactcat atatacttta gattgattta aaacttcatt | 1440 |
| tttaatttaa aaggatctag gtgaagatcc tttttgataa tctcatgacc aaaatccctt | 1500 |
| aacgtgagtt ttcgttccac tgagcgtcag accccgtaga aaagatcaaa ggatcttctt | 1560 |
| gagatccttt ttttctgcgc gtaatctgct gcttgcaaac aaaaaaacca ccgctaccag | 1620 |
| cggtggtttg tttgccggat caagagctac caactctttt tccgaaggta actggcttca | 1680 |
| gcagagcgca gataccaaat actgtccttc tagtgtagcc gtagttaggc caccacttca | 1740 |
| agaactctgt agcaccgcct acatacctcg ctctgctaat cctgttacca gtggctgctg | 1800 |
| ccagtggcga taagtcgtgt cttaccgggt tggactcaag acgatagtta ccggataagg | 1860 |
| cgcagcggtc gggctgaacg gggggttcgt gcacacagcc cagcttggag cgaacgacct | 1920 |
| acaccgaact gagataccta cagcgtgagc tatgagaaag cgccacgctt cccgaaggga | 1980 |
| gaaaggcgga caggtatccg gtaagcggca gggtcggaac aggagagcgc acgagggagc | 2040 |
| ttccaggggg aaacgcctgg tatctttata gtcctgtcgg gtttcgccac ctctgacttg | 2100 |
| agcgtcgatt tttgtgatgc tcgtcagggg ggcggagcct atggaaaaac gccagcaacg | 2160 |
| cggccttttt acggttcctg ccttttgct ggccttttgc tcacatgttc tttcctgcgt | 2220 |
| tatcccctga ttctgtggat aaccgtatta ccgcctttga gtgagctgat accgctcgcc | 2280 |
| gcagccgaac gaccgagcgc agcgagtcag tgagcgagga agcggaagag cgcctgatgc | 2340 |
| ggtattttct ccttacgcat ctgtgcggta tttcacaccg caatggtgca ctctcagtac | 2400 |
| aatctgctct gatgccgcat agttaagcca gtatacactc cgctatcgct acgtgactgg | 2460 |
| gtcatggctg cgccccgaca cccgccaaca cccgctgacg cgccctgacg ggcttgtctg | 2520 |
| ctcccggcat ccgcttacag acaagctgtg accgtctccg ggagctgcat gtgtcagagg | 2580 |
| ttttcaccgt catcaccgaa acgcgcgagg cagctgcgt aaagctcatc agcgtggtcg | 2640 |
| tgaagcgatt cacagatgtc tgcctgttca tccgcgtcca gctcgttgag tttctccaga | 2700 |

```
agcgttaatg tctggcttct gataaagcgg gccatgttaa gggcggtttt ttcctgtttg    2760
gtcactgatg cctccgtgta aggggattt  ctgttcatgg gggtaatgat accgatgaaa    2820
cgagagagga tgctcacgat acgggttact gatgatgaac atgcccggtt actggaacgt    2880
tgtgagggta aacaactggc ggtatggatg cggcgggacc agagaaaaat cactcagggt    2940
caatgccagc gcttcgttaa tacagatgta ggtgttccac agggtagcca gcagcatcct    3000
gcgatgcaga tccggaacat aatggtgcag gcgctgact  tccgcgtttc cagactttac    3060
gaaacacgga aaccgaagac cattcatgtt gttgctcagg tcgcagacgt tttgcagcag    3120
cagtcgcttc acgttcgctc gcgtatcggt gattcattct gctaaccagt aaggcaaccc    3180
cgccagccta gccgggtcct caacgacagg agcacgatca tgcgcacccg tggccaggac    3240
ccaacgctgc ccgagatgcg ccgcgtgcgg ctgctggaga tggcggacgc gatggatatg    3300
ttctgccaag ggttggtttg cgcattcaca gttctccgca agaattgatt ggctccaatt    3360
cttggagtgg tgaatccgtt agcgaggtgc cgccggcttc cattcaggtc gaggtggccc    3420
ggctccatgc accgcgacgc aacgcgggga ggcagacaag gtatagggcg cgcctacaa     3480 tccatgccaa cccgttccat gtgctcgccg aggcggcata atcgccgtg  acgatcagcg    3540 gtccaatgat cgaagttagg ctggtaagag ccgcgagcga tccttgaagc tgtccctgat    3600
ggtcgtcatc tacctgcctg gacagcatgg cctgcaacgc gggcatcccg atgccgccgg    3660
aagcgagaag aatcataatg gggaaggcca tccagcctcg cgtcgcgaac gccagcaaga    3720
cgtagcccag cgcgtcggcc gccatgccgg cgataatggc ctgcttctcg ccgaaacgtt    3780
tggtggcggg accagtgacg aaggcttgag cgagggcgtg caagattccg aataccgcaa    3840
gcgacaggcc gatcatcgtc gcgctccagc gaaagcggtc ctcgccgaaa atgacccaga    3900
gcgctgccgg cacctgtcct acgagttgca tgataaagaa gacagtcata agtgcggcga    3960
cgatagtcat gccccgcgcc caccggaagg agctgactgg gttgaaggct ctcaagggca    4020
tcggtcgaga tcccggtgcc taatgagtga gctaacttac attaattgcg ttgcgctcac    4080
tgcccgcttt ccagtcggga aacctgtcgt gccagctgca ttaatgaatc ggccaacgcg    4140
cggggagagg cggtttgcgt attgggcgcc agggtggttt ttcttttcac cagtgagacg    4200
ggcaacagct gattgccctt caccgcctgg ccctgagaga gttgcagcaa gcggtccacg    4260
ctggtttgcc ccagcaggcg aaaatcctgt ttgatggtgg ttaacggcgg gatataacat    4320
gagctgtctt cggtatcgtc gtatcccact accgagatat ccgcaccaac gcgcagcccg    4380
gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc ccgctaacag cgcgatttgc    4620
tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctt ccacagcaat ggcatcctgg tcatccagcg gatagttaat gatcagccca    4800
ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acgcgcgtg  cagggccaga ctggaggtgg caacgccaat cagcaacgac    4980
tgtttgcccg ccagttgttg tgccacgcgg ttgggaatgt aattcagctc cgccatcgcc    5040
```

```
gcttccacttt tttcccgcgt tttcgcagaa acgtggctgg cctggttcac cacgcgggaa    5100
acggtctgat aagagacacc ggcatactct gcgacatcgt ataacgttac tggttttcaca    5160 ttcaccaccc tgaattgact ctcttccggg cgctatcatg ccataccgcg aaaggttttg    5220
cgccattcga tggtgtccgg gatctcgacg ctctccctta tgcgactcct gcattaggaa    5280
gcagcccagt agtaggttga ggccgttgag caccgccgcc gcaaggaatg gtgcatgcaa    5340
ggagatggcg cccaacagtc ccccggccac ggggcctgcc accatacccca cgccgaaaca    5400 agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaaattaata cgactcacta gggggaattg tgagcggat    5580 aacaattccc ctctagaaat aattttgttt aactttaaga aggagatata catatgcggg    5640
gttctcatca tcatcatcat catggtatgg ctagcatgac tggtggacag caaatgggtc    5700
gggatctgta cgacgatgac gataaggatc atcccttcac catggtatcc tgttctgcgc    5760
cgggtaagat ttacctgttc ggtgaacacg ccgtagttta tggcgaaact gcaattgcgt    5820
gtgcggtgga actgcgtacc cgtgttcgcg cggaactcaa tgactctatc actattcaga    5880
gccagatcgg ccgcaccggt ctggatttcg aaaagcaccc ttatgtgtct gcggtaattg    5940
agaaaatgcg caaatctatt cctattaacg gtgttttctt gaccgtcgat tccgacatcc    6000
cggtgggctc cggtctgggt agcagcgcag ccgttactat cgcgtctatt ggtgcgctga    6060
acgagctgtt cggctttggc ctcagcctgc aagaaatcgc taaactgggc cacgaaatcg    6120
aaattaaagt acagggtgcc gcgtccccaa ccgatacgta tgtttctacc ttcggcggcg    6180
tggttaccat cccggaacgt cgcaaactga aaactccgga ctgcggcatt gtgattggcg    6240
ataccggcgt tttctcctcc accaaagagt tagtagctaa cgtacgtcag ctgcgcgaaa    6300
gctacccgga tttgatcgaa ccgctgatga cctctattgg caaaatctct cgtatcggcg    6360
aacaactggt tctgttctgg cgactacgca tccatcggcc gcctgatgaa cgtcaaccag    6420
ggtctcctgg acgccctggg cgttaacatc ttagaactga gccagctgat ctattccgct    6480
cgtgcggcag gtgcgtttgg cgctaaaatc acgggcgctg gcggcggtgg ctgtatggtt    6540
gcgctgaccg ctccggaaaa atgcaaccaa gtggcagaag cggtagcagg cgctggcggt    6600
aaagtgacta tcactaaacc gaccgagcaa ggtctgaaag tagattaa              6648
```

```
<210> SEQ ID NO 115
<211> LENGTH: 67
<212> TYPE: DNA
<213> ORGANISM: Artificial Sequence
<220> FEATURE:
<223> OTHER INFORMATION: Synthetic Construct

<400> SEQUENCE: 115
accgccaaaa gcgactaatt ttagctgtta cagtcagttg aattaaccct cactaaaggg    60
cggccgc                                                              67

<210> SEQ ID NO 116
<211> LENGTH: 152
<212> TYPE: DNA
<213> ORGANISM: Artificial Sequence
<220> FEATURE:
<223> OTHER INFORMATION: Synthetic Construct

<400> SEQUENCE: 116
gctggcgata taaactgttt gcttcatgaa tgctcctttg ggttacctcc gggaaacgcg    60
```

```
gttgatttgt ttagtggttg aattatttgc tcaggatgtg gcatagtcaa gggcgtgacg    120
gctcgctaat acgactcact atagggctcg ag                                  152

<210> SEQ ID NO 117
<211> LENGTH: 30
<212> TYPE: DNA
<213> ORGANISM: Artificial Sequence
<220> FEATURE:
<223> OTHER INFORMATION: Synthetic Construct

<400> SEQUENCE: 117
cttgatatct tagtgtgcgt taaccaccac                                     30

<210> SEQ ID NO 118
<211> LENGTH: 21
<212> TYPE: DNA
<213> ORGANISM: Artificial Sequence
<220> FEATURE:
<223> OTHER INFORMATION: Synthetic Construct

<400> SEQUENCE: 118
cgtgaatttg ctggctctca g                                              21

<210> SEQ ID NO 119
<211> LENGTH: 21
<212> TYPE: DNA
<213> ORGANISM: Artificial Sequence
<220> FEATURE:
<223> OTHER INFORMATION: Synthetic Construct

<400> SEQUENCE: 119
ggtttagttc ctcaccttgt c                                              21

<210> SEQ ID NO 120
<211> LENGTH: 21
<212> TYPE: DNA
<213> ORGANISM: Artificial Sequence
<220> FEATURE:
<223> OTHER INFORMATION: Synthetic Construct

<400> SEQUENCE: 120
actgaaacgt tttcatcgct c                                              21

<210> SEQ ID NO 121
<211> LENGTH: 26
<212> TYPE: DNA
<213> ORGANISM: Artificial Sequence
<220> FEATURE:
<223> OTHER INFORMATION: Synthetic Construct

<400> SEQUENCE: 121
accgccaaaa gcgactaatt ttagct                                         26

<210> SEQ ID NO 122
<211> LENGTH: 7519
<212> TYPE: DNA
<213> ORGANISM: Artificial Sequence
<220> FEATURE:
<223> OTHER INFORMATION: Synthetic Construct

<400> SEQUENCE: 122
ctcgggccgt ctcttgggct tgatcggcct tcttgcgcat ctcacgcgct cctgcggcgg    60
cctgtagggc aggctcatac ccctgccgaa ccgcttttgt cagccggtcg gccacggctt    120
```

-continued

| | |
|---|---|
| ccggcgtctc aacgcgcttt gagattccca gcttttcggc caatccctgc ggtgcatagg | 180 |
| cgcgtggctc gaccgcttgc gggctgatgg tgacgtggcc cactggtggc cgctccaggg | 240 |
| cctcgtagaa cgcctgaatg cgcgtgtgac gtgccttgct gccctcgatg ccccgttgca | 300 |
| gccctagatc ggccacagcg gccgcaaacg tggtctggtc gcgggtcatc tgcgctttgt | 360 |
| tgccgatgaa ctccttggcc gacagcctgc cgtcctgcgt cagcggcacc acgaacgcgg | 420 |
| tcatgtgcgg gctggtttcg tcacggtgga tgctggccgt cacgatgcga tccgccccgt | 480 |
| acttgtccgc cagccacttg tgcgccttct cgaagaacgc cgcctgctgt tcttggctgg | 540 |
| ccgacttcca ccattccggg ctggccgtca tgacgtactc gaccgccaac acagcgtcct | 600 |
| tgcgccgctt ctctggcagc aactcgcgca gtcggcccat cgcttcatcg gtgctgctgg | 660 |
| ccgcccagtg ctcgttctct ggcgtcctgc tggcgtcagc gttgggcgtc tcgcgctcgc | 720 |
| ggtaggcgtg cttgagactg gccgccacgt tgcccatttt cgccagcttc ttgcatcgca | 780 |
| tgatcgcgta tgccgccatg cctgcccctc ccttttggtg tccaaccggc tcgacggggg | 840 |
| cagcgcaagg cggtgcctcc ggcgggccac tcaatgcttg agtatactca ctagactttg | 900 |
| cttcgcaaag tcgtgaccgc ctacggcggc tgccggcgcc tacgggcttg ctctccgggc | 960 |
| ttcgccctgc gcggtcgctg cgctcccttg ccagcccgtg gatatgtgga cgatggccgc | 1020 |
| gagcggccac cggctggctc gcttcgctcg gcccgtggac aaccctgctg acaagctga | 1080 |
| tggacaggct gcgcctgccc acgagcttga ccacagggat gcccaccgg ctacccagcc | 1140 |
| ttcgaccaca tacccaccgg ctccaactgc gcggcctgcg gccttgcccc atcaattttt | 1200 |
| ttaattttct ctggggaaaa gcctccggcc tgcggcctgc gcgcttcgct tgccggttgg | 1260 |
| acaccaagtg gaaggcgggt caaggctcgc gcagcgaccg cgcagcggct tggccttgac | 1320 |
| gcgcctggaa cgacccaagc ctatgcgagt ggggcagtc gaaggcgaag cccgcccgcc | 1380 |
| tgccccccga gcctcacggc ggcgagtgcg ggggttccaa gggggcagcg ccaccttggg | 1440 |
| caaggccgaa ggccgcgcag tcgatcaaca agccccggag gggccacttt ttgccggagg | 1500 |
| gggagccgcg ccgaaggcgt gggggaaccc cgcaggggtg cccttctttg gcaccaaag | 1560 |
| aactagatat agggcgaaat gcgaaagact taaaaatcaa caacttaaaa aaggggggta | 1620 |
| cgcaacagct cattgcggca ccccccgcaa tagctcattg cgtaggttaa agaaaatctg | 1680 |
| taattgactg ccacttttac gcaacgcata attgttgtcg cgctgccgaa aagttgcagc | 1740 |
| tgattgcgca tggtgccgca accgtgcggc accctaccgc atggagataa gcatggccac | 1800 |
| gcagtccaga gaaatcggca ttcaagccaa gaacaagccc ggtcactggg tgcaaacgga | 1860 |
| acgcaaagcg catgaggcgt gggccgggct tattgcgagg aaacccacgg cggcaatgct | 1920 |
| gctgcatcac ctcgtggcgc agatgggcca ccagaacgcc gtggtggtca gccagaagac | 1980 |
| actttccaag ctcatcggac gttctttgcg gacggtccaa tacgcagtca aggacttggt | 2040 |
| ggccgagcgc tggatctccg tcgtgaagct caacggcccc ggcaccgtgt cggcctacgt | 2100 |
| ggtcaatgac cgcgtggcgt ggggccagcc ccgcgaccag ttgcgcctgt cggtgttcag | 2160 |
| tgccgccgtg gtggttgatc acgacgacca ggacgaatcg ctgttgggc atggcgacct | 2220 |
| gcgccgcatc ccgaccctgt atccgggcga gcagcaacta ccgaccggcc ccggcgagga | 2280 |
| gccgccagc cagcccggca ttccgggcat ggaaccagac ctgccagcct tgaccgaaac | 2340 |
| ggaggaatgg gaacgcgcg ggcagcagcg cctgccgatg cccgatgagc cgtgttttct | 2400 |
| ggacgatggc gagccgttgg agccgccgac acgggtcacg ctgccgcgcc ggtagcactt | 2460 |
| gggttgcgca gcaacccgta agtgcgctgt tccagactat cggctgtagc cgcctcgccg | 2520 |

```
ccctatacct tgtctgcctc cccgcgttgc gtcgcggtgc atggagccgg gccacctcga    2580
cctgaatgga agccggcggc acctcgctaa cggattcacc gttttatca ggctctggga    2640 ggcagaataa atgatcatat cgtcaattat tacctccacg gggagagcct gagcaaactg   2700
gcctcaggca tttgagaagc acacggtcac actgcttccg gtagtcaata aaccggtaaa   2760
ccagcaatag acataagcgg ctatttaacg accctgccct gaaccgacga ccgggtcgaa   2820
tttgctttcg aatttctgcc attcatccgc ttattatcac ttattcaggc gtagcaccag   2880
gcgtttaagg gcaccaataa ctgccttaaa aaaattacgc cccgccctgc cactcatcgc   2940
agtcggccta ttggttaaaa aatgagctga tttaacaaaa atttaacgcg aattttaaca   3000
aaatattaac gcttacaatt tccattcgcc attcaggctg cgcaactgtt gggaagggcg   3060
atcggtgcgg gcctcttcgc tattacgcca gctggcgaaa gggggatgtg ctgcaaggcg   3120
attaagttgg gtaacgccag ggttttccca gtcacgacgt tgtaaaacga cggccagtga   3180
gcgcgcgtaa tacgactcac tatagggcga attggagctc caccgcggtg gcggccgctc   3240
tagaactagt ggatccccccg gctgcatgc tcgagcggcc gccagtgtga tggatatctg   3300
cagaattcgc ccttcttgat atcttagtgt gcgttaacca cccaccacat tggtccctgc   3360
ccgaccgcat agcggccttt ttcatgcagt agcccctgct cgccaacaat ttcgtatacc   3420
gagatgtggt gagattttg cccggcggca atcagatact tgccgctgtg atcaacattg    3480
aagccgcgcg gctgggtttc cgttggctgg aagccttctt tactcaacac gctgccatct   3540
tccgaaacgc tgaaaacggt aatcaggctg gcggtacggt cgcaggcgta taaatggcga   3600
ccatccgggg tgatatgaat atcagccgcc caacgggtgt cggagaagtt ttccggcatc   3660
atatccagcg tctggacaca ttcgatatta ccgtgcggat ctttcagttc ccagacatcc   3720
actgagctgt ttaactcatt gacgcaatac gcatattgtt cgtttggatg gaataccata   3780
tgacgcgggc cggccccttc aacggtggtc acttccgcag ggtcctgcgc acgagatga    3840 ccatcatcgc tgaccgtaaa caggcaaatg cgatcctgct taatgccgg aacccacagc    3900 gtacggttgt ccggtgagat attggcggaa tggcaaccgt ccagcccctc gaccacatcg   3960
acgacgccca ctggcaggcc atcttccaga cgcgttacgc tcacgttacc cgcattgtaa   4020
gaacctacaa agacaaactg cccctggtga tcggtggaaa tatgcgtcgg actaccggc    4080 agcgcagact ctgcggcaaa ggtcagtgcg ccatcgtccg gggcgatacg atacgccagg   4140
acgcgaaact cagggcgaac accaacatag agataacgtt tgtccgggct gaccaccatc   4200
ggctgcacct gccccggcac atcgacaacc tgtgtcagcg tcagtgcgcc ttcatgattc   4260
agattccaga cgtgaattttg ctggctctca gggctggcga tataaactgt ttgcttcatg  4320
aatgctcctt tgggttacct ccgggaaacg cggttgattt gtttagtggt tgaattattt   4380
gctcaggatg tggcatagtc aagggcgtga cggctcgcta atacaactca ctatagggct   4440
cgaggaagtt cctatacttt ctagagaata ggaacttccg cgccgcacac aaaaaccaac   4500
acacagatca tgaaaataaa gctctttat tggtaccgaa ttcgccaggg agctctcaga    4560
cgtcgcttgg tcggtctta ttcgaacccc agagtcccgc ttacgccccg ccctgccact    4620
catcgcagta ctgttgtaat tcattaagca ttctgccgac atggaagcca tcacaaacgg   4680
catgatgaac ctgaatcgcc agcggcatca gcaccttgtc gccttgcgta taatatttgc   4740
ccatggtgaa acgggggcg aagaagttgt ccatattggc cacgtttaaa tcaaaactgg    4800
tgaaactcac ccagggattg gctgagacga aaaacatatt ctcaataaac cctttaggga   4860
```

-continued

```
aataggccag gttttcaccg taacacgcca catcttgcga atatatgtgt agaaactgcc    4920
ggaaatcgtc gtggtattca ctccagagcg atgaaaacgt ttcagtttgc tcatggaaaa    4980
cggtgtaaca agggtgaaca ctatcccata tcaccagctc accgtctttc attgccatac    5040
ggaattccgg atgagcattc atcaggcggg caagaatgtg aataaaggcc ggataaaact    5100
tgtgcttatt tttctttacg gtctttaaaa aggccgtaat atccagctga acggtctggt    5160
tataggtaca ttgagcaact gactgaaatg cctcaaaatg ttctttacga tgccattggg    5220
atatatcaac ggtggtatat ccagtgattt ttttctccat ggtttagttc ctcaccttgt    5280
cgtattatac tatgccgata tactatgccg atgattaatt gtcaacacgt gctgctgcag    5340
gtcgaaaggc ccggagatga ggaagaggag aacagcgcgg cagacgtgcg cttttgaagc    5400
gtgcagaatg ccgggcctcc ggaggacctt cgggcgcccg ccccgcccct gagcccgccc    5460
ctgagcccgc ccccggaccc accccttccc agcctctgag cccagaaagc gaaggagcaa    5520
agctgctatt ggccgctgcc ccaaaggcct cccgcttcc attgctcagc ggtgctgtcc    5580
atctgcacga gactagtgag acgtgctact tccatttgtc acgtcctgca cgacgcgagc    5640
tgcggggcgg gggggaactt cctgactagg ggaggagtgg aaggtggcgc aaggggcca    5700
ccaaagaacg gagccggttg cgcctaccg gtggatgtgg aatgtgtgcg aggccagagg    5760
ccacttgtgt agcgccaagt gcccagcggg gctgctaaag cgcatgctcc agactgcctt    5820
gggaaaagcg cctcccctac ccggtagaat gaagttccta tactttctag aataggaa    5880
cttcgcggcc gcccttagt gagggttaat tcaactgact gtaacagcta aaattagtcg    5940
cttttggcgg taagggcgaa ttccagcaca ctggcggccg ttactagtgg atccgagctc    6000
ggtaccaagc ttgatgcagg aattcgatat caagcttatc gataccgtcg acctcgaggg    6060
ggggcccggt acccagcttt tgttcccttt agtgagggtt aattgcgcgc ttggcgtaat    6120
catggtcata gctgtttcct gtgtgaaatt gttatccgct cacaattcca cacaacatac    6180
gagccggaag cataaagtgt aaagcctggg gtgcctaatg agtgagctaa ctcacattaa    6240
ttgcgttgcg ctcactgccc gctttccagt cgggaaacct gtcgtgccag ctgcattaat    6300
gaatcggcca acgcgcgggg agaggcggtt tgcgtattgg gcgcatgcat aaaaactgtt    6360
gtaattcatt aagcattctg ccgacatgga agccatcaca aacggcatga tgaacctgaa    6420
tcgccagcgg catcagcacc ttgtcgcctt gcgtataata tttgcccatg gacgcacacc    6480
gtggaaacgg atgaaggcac gaacccagtt gacataagcc tgttcggttc gtaaactgta    6540
atgcaagtag cgtatgcgct cacgcaactg gtccagaacc ttgaccgaac gcagcggtgg    6600
taacggcgca gtggcggttt tcatggcttg ttatgactgt ttttttgtac agtctatgcc    6660
tcgggcatcc aagcagcaag cgcgttacgc cgtgggtcga tgtttgatgt tatggagcag    6720
caacgatgtt acgcagcagc aacgatgtta cgcagcaggg cagtcgccct aaaacaaagt    6780
taggtggctc aagtatgggc atcattcgca catgtaggct cggccctgac caagtcaaat    6840
ccatgcgggc tgctcttgat cttttcggtc gtgagttcgg agacgtagcc acctactccc    6900
aacatcagcc ggactccgat tacctcggga acttgctccg tagtaagaca ttcatcgcgc    6960
ttgctgccct cgaccaagaa gcggttgttg gcgctctcgc ggcttacgtt ctgcccaggt    7020
ttgagcagcc gcgtagtgag atctatatct atgatctcgc agtctccggc gagcaccgga    7080
ggcagggcat tgccaccgcg ctcatcaatc tcctcaagca tgaggccaac gcgcttggtg    7140
cttatgtgat ctacgtgcaa gcagattacg gtgacgatcc gcagtggct ctctatacaa    7200
agttgggcat acgggaagaa gtgatgcact ttgatatcga cccaagtacc gccacctaac    7260
```

```
aattcgttca agccgagatc ggcttcccgg ccgcggagtt gttcggtaaa ttgtcacaac    7320
gccgccaggt ggcacttttc ggggaaatgt gcgcgcccgc gttcctgctg gcgctgggcc    7380
tgtttctggc gctggacttc ccgctgttcc gtcagcagct tttcgcccac ggccttgatg    7440 atcgcgcgg ccttggcctg catatcccga ttcaacggcc ccagggcgtc cagaacgggc     7500
ttcaggcgct cccgaaggt                                                 7519
```

<210> SEQ ID NO 123
<211> LENGTH: 4395
<212> TYPE: DNA
<213> ORGANISM: Artificial Sequence
<220> FEATURE:
<223> OTHER INFORMATION: Synthetic Construct

<400> SEQUENCE: 123

```
tagaaaaact catcgagcat caaatgaaac tgcaatttat tcatatcagg attatcaata     60
ccatattttt gaaaaagccg tttctgtaat gaaggagaaa actcaccgag gcagttccat    120
aggatggcaa gatcctggta tcggtctgcg attccgactc gtccaacatc aatacaacct    180
attaatttcc cctcgtcaaa aataaggtta tcaagtgaga aatcaccatg agtgacgact    240
gaatccggtg agaatggcaa aagtttatgc atttcttttcc agacttgttc aacaggccag    300
ccattacgct cgtcatcaaa atcactcgca tcaaccaaac cgttattcat tcgtgattgc    360
gcctgagcga ggcgaaatac gcgatcgctg ttaaaaggac aattacaaac aggaatcgag    420
tgcaaccggc gcaggaacac tgccagcgca tcaacaatat tttcacctga atcaggatat    480
tcttctaata cctggaacgc tgtttttccg gggatcgcag tggtgagtaa ccatgcatca    540
tcaggagtac ggataaaatg cttgatggtc ggaagtggca taaattccgt cagccagttt    600
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggcctttcg cccgggctaa ttaggggtg tcgcccttcg attgacggtt acgggatcct    1200
cacacgtaca tcagctggtt gatgggaac gggtcgatga gcagcagctt gatgcggttc    1260
tcggtggcgt aatccgggcg gcccagcccg tccccatatt ggtaggtgca gtggctcacg   1320
cgggccatgt tcacgcgat ctccatgaac gccttcggca gcagggtgct gtccgacacg    1380
cgctcgcggt tcattttctt ccactcggcg tcgatcagct tgcgcagctc ttcgcgggcc   1440
tgttcctcgc tcgtgccgtc gttctcgtgc atgtagctga tgatgctgtt ggtggtttcg   1500
ccgcgttcga gttccgccgc cgaggtcgcc agatcgttgc acagccgaaa gatcacgcag   1560
gacgagcgca ccaggccgtg gaagtcggtc agggagcgga gggcgtggtc cgagatatct   1620
tcctgctgct ggcagaccga gaagtagctc ggcgccagca gcgcgacccc gctgaggac    1680 acgctggcgt tctccaggta cttgctgaag gcggggatga tcttgttatt gctccacttg   1740
```

-continued

```
gcttcttgca ggaaggcctt gcacagttcg cgccagcttt tggtcagata gctcaggtta    1800
ttgtggccct tctccttcag gatggagtag gacgtgtcgt tcacggtgtt gtacagggcc    1860
aggaagcaca gcttcatata gtcgggcagc gtgttgatgg cgttcacgtc ccagcgttcc    1920
accgcgtcgg tgaagagctg cagttcgtcc agggtaccgt acacgtcata gacgtcatcg    1980
ataatggtga ccagaccgaa catcttggtg acggccttgc ggcattcgcc gaactgcggg    2040
tccggcgcca tgcccagcgc ccagaagtac acttccatca ggcggtcccg cacgaaatcc    2100
agcttgctgg cgaggcccat ctcggtccac caccggctca ggtcctgcag ctcttttttgg   2160
tgcagggtct ggaccatgtt gaaatcgagt ttggccagtt ccagcagcag ctggtgatgc    2220
ggctccttgg gttcgtactt gtccagaaac caccgcgcct ccaggcggtg caggcgttga    2280
tgatacggca gctccagcgc gtgggacacc tgctcggcca ccttcgtgtt gatcccctcc    2340
ttgaggttgt tcttcagatg ggtgatgctg aaggtacggg cctcctccag cagattttcg    2400
ccttcgaaac cgagatagct ggcctcgtac aggctcagca ggcctgcac gtcacccttc     2460
agttccccgg agaagccccc ttctttgtcc ttgaagcgct cgaacacgtc ctggctcacc    2520
tcaaagccat gctgccgcag caggcggaag ctcagggcgg tcgcgtgcag atcgcttttg    2580
ttcttcttat tctcgtccag caggacgatg ttctccagcg ccttgatgat atcttctctca   2640
aacttgtagg tcaggcccag gcgctgcacg tcgtcgatga gctccagcag gctcaggggc    2700
tgggtgtcca cccggttgat catgcaacgc acctcctcct ccagcttggt ggccttctct    2760
tcgagcttct ccaccttcag gtcgttttcc aggctctgca ggaactcgaa gttccacagg    2820
ttgggctggt agttcgcgga ccgacggcta ttatgctcgg tgatctgggt gaactggctg    2880
ctggtggcgc acatatgtat atctccttct taaagttaaa caagcttaag atgttcagcg    2940
acaagggcga cacaaaattt attctaaatg cataataaat actgataaca tcttatagtt    3000
tgtattatat tttgtattat cgttgacatg tataattttg atatcaaaaa ctgattttcc    3060
ctttattatt ttcgagattt atttttcttaa ttctctttaa caaactagaa atattgtata   3120
tacaaaaaat cataaataat agatgaatag tttaattata ggtgttcatc aatcgaaaaa    3180
gcaacgtatc ttatttaaag tgcgttgctt ttttctcatt tataaggtta aataattctc    3240
atatatcaag caaagtgaca ggcgccctta atattctga caaatgctct ttccctaaac     3300
tccccccata aaaaaacccg ccgaagcggg tttttacgtt atttgcggat taacgattac    3360
tcgttatcag aaccgcccag ggggcccgag cttaagactg gccgtcgttt tacaacacag    3420
aaagagtttg tagaaacgca aaaaggccat ccgtcagggg ccttctgctt agtttgatgc    3480
ctggcagttc cctactctcg ccttccgctt cctcgctcac tgactcgctg cgctcggtcg    3540
ttcggctgcg gcgagcggta tcagctcact caaaggcggt aatacggtta ccacagaat    3600
caggggataa cgcaggaaag aacatgtgag caaaaggcca gcaaaggcc aggaaccgta     3660
aaaaggccgc gttgctggcg ttttccata ggctccgccc ccctgacgag catcacaaa     3720
atcgacgctc aagtcagagg tggcgaaacc cgacaggact ataaagatac caggcgtttc    3780
cccctggaag ctccctcgtg cgctctcctg ttccgaccct gccgcttacc ggatacctgt    3840
ccgcctttct cccttcggga agcgtggcgc tttctcatag ctcacgctgt aggtatctca    3900
gttcggtgta ggtcgttcgc tccaagctgg gctgtgtgca cgaaccccc gttcagcccg     3960
accgctgcgc cttatccggt aactatcgtc ttgagtccaa cccggtaaga cacgacttat    4020
cgccactggc agcagccact ggtaacagga ttagcagagc gaggtatgta ggcggtgcta    4080
cagagttctt gaagtggtgg gctaactacg gctacactag aagaacagta tttggtatct    4140
```

```
gcgctctgct gaagccagtt accttcggaa aaagagttgg tagctcttga tccggcaaac    4200
aaaccaccgc tggtagcggt ggttttttg tttgcaagca gcagattacg cgcagaaaaa    4260
aaggatctca agaagatcct ttgatctttt ctacggggtc tgacgctcag tggaacgacg    4320
cgcgcgtaac tcacgttaag ggatttggt catgagcttg cgccgtcccg tcaagtcagc    4380
gtaatgctct gcttt                                                   4395
```

COMPOSITIONS AND METHODS FOR PRODUCING ISOPRENE

CROSS-REFERENCE TO RELATED APPLICATIONS

This application is a continuation application of U.S. patent application Ser. No. 13/600,132, filed Aug. 30, 2012, now U.S. Pat. No. 9,260,727, which is a divisional application of U.S. patent application Ser. No. 12/335,071, filed Dec. 15, 2008, now U.S. Pat. No. 8,288,148, which claims priority benefit of U.S. Provisional Patent Application No. 61/013,574, filed Dec. 13, 2007, the disclosures of which are herein incorporated by reference in their entireties.

INCORPORATION BY REFERENCE

The content of the following submission on ASCII text file is incorporated herein by reference in its entirety: a computer readable form (CFR) of the Sequence Listing (file name: 48768_501 D02US_Sub_Seq_Listing_032016.txt, dated created Mar. 23, 2016, size 282,884 bytes.

FIELD OF THE INVENTION

The present invention relates generally to methods for producing isoprene from cultured cells and compositions that include these cultured cells.

BACKGROUND OF THE INVENTION

Isoprene (2-methyl-1,3-butadiene) is the critical starting material for a variety of synthetic polymers, most notably synthetic rubbers. Isoprene is naturally produced by a variety of microbial, plant, and animal species. In particular, two pathways have been identified for the biosynthesis of isoprene: the mevalonate (MVA) pathway and the non-mevalonate (DXP) pathway (FIG. 19A and FIG. 19B). However, the yield of isoprene from naturally-occurring organisms is commercially unattractive. About 800,000 tons per year of cis-polyisoprene are produced from the polymerization of isoprene; most of this polyisoprene is used in the tire and rubber industry. Isoprene is also copolymerized for use as a synthetic elastomer in other products such as footwear, mechanical products, medical products, sporting goods, and latex.

Currently, the tire and rubber industry is based on the use of natural and synthetic rubber. Natural rubber is obtained from the milky juice of rubber trees or plants found in the rainforests of Africa. Synthetic rubber is based primarily on butadiene polymers. For these polymers, butadiene is obtained as a co-product from ethylene and propylene manufacture.

While isoprene can be obtained by fractionating petroleum, the purification of this material is expensive and time-consuming. Petroleum cracking of the C5 stream of hydrocarbons produces only about 15% isoprene. Thus, more economical methods for producing isoprene are needed. In particular, methods that produce isoprene at rates, titers, and purity that are sufficient to meet the demands of a robust commercial process are desirable. Also desired are systems for producing isoprene from inexpensive starting materials.

BRIEF SUMMARY OF THE INVENTION

In one aspect, the invention features cells in culture that produce isoprene. In some embodiments, the invention provides cells in culture that produce greater than about 400 nmole of isoprene/gram of cells for the wet weight of the cells/hour (nmole/$g_{wcm}$/hr) of isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, component from a yeast extract, or any combination of two or more of the foregoing.

In some embodiments, the invention provides cells in culture that have an average volumetric productivity of isoprene greater than about 0.1 mg/$L_{broth}$/hr. In some embodiments, the invention provides cells in culture that have a peak volumetric productivity of isoprene greater than about 0.5 mg/$L_{broth}$/hr. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, component from a yeast extract, or any combination of two or more of the foregoing.

In some embodiments, the invention provides cells in culture that convert more than about 0.002% of the carbon in a cell culture medium into isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, component from a yeast extract, or any combination of two or more of the foregoing.

In some embodiments, the invention provides cells in culture that comprise a heterologous nucleic acid encoding an isoprene synthase polypeptide. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, component from a yeast extract, or any combination of two or more of the foregoing.

In one aspect, the invention features methods of producing isoprene, such as methods of using any of the cells described herein to produce isoprene. In some embodiments, the method involves culturing cells under conditions sufficient to produce greater than about 400 nmole/$g_{wcm}$/hr of isoprene. In some embodiments, the method also includes recovering isoprene produced by the cells. In some embodiments, the method includes purifying isoprene produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, component from a yeast extract, or any combination of two or more of the foregoing.

In one aspect, the invention features methods of producing isoprene, such as methods of using any of the cells described herein to produce isoprene. In some embodiments, the method involves culturing cells under conditions resulting in an average volumetric productivity of isoprene greater than about 0.1 mg/$L_{broth}$/hr. In some embodiments, the method involves culturing cells under conditions resulting in a peak volumetric productivity of isoprene greater than about 0.5 mg/$L_{broth}$/hr. In some embodiments, the method also includes recovering isoprene produced by the cells. In some embodiments, the method includes purifying isoprene produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, component from a yeast extract, or any combination of two or more of the foregoing.

In some embodiments, the method includes culturing cells under conditions sufficient to convert more than about 0.002% of the carbon in a cell culture medium into isoprene. In some embodiments, the method also includes recovering isoprene produced by the cells. In some embodiments, the method includes purifying isoprene produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, component from a yeast extract, or any combination of two or more of the foregoing.

In some embodiments of any of the aspects of the invention, the cells in culture produce isoprene at greater than or about 400, 500, 600, 700, 800, 900, 1,000, 1,250, 1,500, 1,750, 2,000, 2,500, 3,000, 4,000, 5,000, 10,000, 12,500, 20,000, 30,000, 40,000, 50,000, 75,000, 100,000, 125,000, 150,000, 188,000, or more nmole/$g_{wcm}$/hr isoprene. In some embodiments, the cells in culture have an average volumetric productivity of isoprene at greater than or about 0.1, 1.0, 10, 25, 50, 100, 150, 200, 250, 300, 400, 500, 600, 700, 800, 900, 1,000, 1100, 1200, 1300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, or more mg of isoprene/L of broth/hr (mg/$L_{broth}$/hr, wherein the volume of broth includes the volume of the cells and the cell medium). In some embodiments, the cells in culture have a peak volumetric productivity of isoprene at greater than or about 0.5, 1.0, 10, 25, 50, 100, 150, 200, 250, 300, 400, 500, 600, 700, 800, 900, 1,000, 1100, 1200, 1300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,750, 4,000, 4,250, 4,500, 4,750, 5,000, 5,250, 5,500, 5,750, 6,000, 6,250, 6,500, 6,750, 7,000, 7,250, 7,500, 7,750, 8,000, 8,250, 8,500, 8,750, 9,000, 9,250, 9,500, 9,750, 10,000, 12,500, 15,000, or more mg of isoprene/L of broth/hr (mg/$L_{broth}$/hr, wherein the volume of broth includes the volume of the cells and the cell medium). In some embodiments of any of the aspects of the invention, the cells in culture convert greater than or about 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 2.0, 2.2, 2.4, 2.6, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 23.2, 23.4, 23.6, 23.8, 24.0, 25.0, 30.0, 31.0, 32.0, 33.0, 35.0, 37.5, 40.0, 45.0, 47.5, 50.0, 55.0, 60.0, 65.0, 70.0, 75.0, 80.0, 85.0, 90.0 molar %, or more of the carbon in the cell culture medium into isoprene. In some embodiments of any of the aspects of the invention, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments of any of the aspects of the invention, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). Other exemplary rates of isoprene production and total amounts of isoprene production are disclosed herein.

In some embodiments of any of the aspects of the invention, the cells further comprise a heterologous nucleic acid encoding an IDI polypeptide. In some embodiments of any of the aspects of the invention, the cells further comprise an insertion of a copy of an endogenous nucleic acid encoding an IDI polypeptide. In some embodiments of any of the aspects of the invention, the cells further comprise a heterologous nucleic acid encoding a DXS polypeptide. In some embodiments of any of the aspects of the invention, the cells further comprise an insertion of a copy of an endogenous nucleic acid encoding a DXS polypeptide. In some embodiments of any of the aspects of the invention, the cells further comprise one or more nucleic acids encoding an IDI polypeptide and a DXS polypeptide. In some embodiments of any of the aspects of the invention, one nucleic acid encodes the isoprene synthase polypeptide, IDI polypeptide, and DXS polypeptide. In some embodiments of any of the aspects of the invention, one vector encodes the isoprene synthase polypeptide, IDI polypeptide, and DXS polypeptide. In some embodiments, the vector comprises a selective marker, such as an antibiotic resistance nucleic acid.

In some embodiments of any of the aspects of the invention, the heterologous isoprene synthase nucleic acid is operably linked to a T7 promoter, such as a T7 promoter contained in a medium or high copy plasmid. In some embodiments of any of the aspects of the invention, the heterologous isoprene synthase nucleic acid is operably linked to a Trc promoter, such as a Trc promoter contained in a medium or high copy plasmid. In some embodiments of any of the aspects of the invention, the heterologous isoprene synthase nucleic acid is operably linked to a Lac promoter, such as a Lac promoter contained in a low copy plasmid. In some embodiments of any of the aspects of the invention, the heterologous isoprene synthase nucleic acid is operably linked to an endogenous promoter, such as an endogenous alkaline serine protease promoter. In some embodiments, the heterologous isoprene synthase nucleic acid integrates into a chromosome of the cells without a selective marker.

In some embodiments of any of the aspects of the invention, at least a portion of the cells maintain the heterologous isoprene synthase nucleic acid for at least or about 5, 10, 20, 40, 50, 60, 65, or more cell divisions in a continuous culture (such as a continuous culture without dilution). In some embodiments of any of the aspects of the invention, the nucleic acid comprising the isoprene synthase, IDI, or DXS nucleic acid also comprises a selective marker, such as an antibiotic resistance nucleic acid.

In some embodiments of any of the aspects of the invention, the cells further comprise a heterologous nucleic acid encoding an MVA pathway polypeptide (such as an MVA pathway polypeptide from *Saccharomyces cerevisi*, *Methanosarcina mazei*, or *Enterococcus faecalis*). In some embodiments of any of the aspects of the invention, the cells further comprise an insertion of a copy of an endogenous nucleic acid encoding an MVA pathway polypeptide (such as an MVA pathway polypeptide from *Saccharomyces cerevisia*, *Methanosarcina mazei*, or *Enterococcus faecalis*). In some embodiments of any of the aspects of the invention, the cells comprise an isoprene synthase, DXS, and MVA pathway nucleic acid. In some embodiments of any of the aspects of the invention, the cells comprise an isoprene synthase nucleic acid, a DXS nucleic acid, an IDI nucleic acid, and a MVA pathway nucleic (in addition to the IDI nucleic acid).

In some embodiments of any of the aspects of the invention, the isoprene synthase polypeptide is a naturally-occurring polypeptide from a plant such as *Pueraria* (e.g., *Pueraria montana*) or *Populus* (e.g., *Populus tremuloides*, *Populus alba* (*P. alba*), *Populus nigra*, *Populus trichocarpa*, or the hybrid, *Populus alba*×*Populus tremula*).

In some embodiments of any of the aspects of the invention, the cells are bacterial cells, such as gram-positive bacterial cells (e.g., *Bacillus* cells such as *Bacillus subtilis* cells or *Streptomyces* cells such as *Streptomyces lividans*, *Streptomyces coelicolor*, *Streptomyces coelicolor*, *Streptomyces albus*, or *Streptomyces griseus* cells). In some embodiments of any of the aspects of the invention, the cells are gram-negative bacterial cells (e.g., *Escherichia* cells such as *Escherichia coli* cells or *Pantoea* cells such as *Pantoea citrea* cells). In some embodiments, the *E. coli* cells are *E. coli* FadR atoC mutant cells. In some embodiments, the *E. coli* cells express (such as constitutively express) ybhE (also known as pgl). In some embodiments of any of the aspects of the invention, the cells are fungal, cells such as filamentous funal cells (e.g., *Trichoderma* cells such as *Trichoderma reesei* cells or *Aspergillus* cells such as *Aspergillus oryzae* and *Aspergillus niger*) or yeast cells (e.g., *Yarrowia* cells such as *Yarrowia lipolytica* cells).

In some embodiments of any of the aspects of the invention, the microbial polypeptide carbon source includes one or more polypeptides from yeast or bacteria. In some embodiments of any of the aspects of the invention, the plant polypeptide carbon source includes one or more polypeptides from soy, corn, canola, jatropha, palm, peanut, sunflower, coconut, mustard, rapeseed, cottonseed, palm kernel, olive, safflower, sesame, or linseed.

In one aspect, the invention provides a tire comprising polyisoprene. In some embodiments, the polyisoprene is produced by (i) polymerizing isoprene from any of the compositions or methods described herein or (ii) polymerizing isoprene recovered from any of the compositions or methods described herein. In some embodiments, the polyisoprene comprises cis-1,4-polyisoprene.

In one aspect, the invention features a product (such as a tire) produced by any of the compositions or methods of the invention.

It is to be understood that one, some, or all of the properties of the various embodiments described herein may be combined to form other embodiments of the present invention. These and other aspects of the invention will become apparent to one of skill in the art.

BRIEF DESCRIPTION OF THE DRAWINGS

FIG. 1 is the nucleotide sequence of a kudzu isoprene synthase gene codon-optimized for expression in *E. coli* (SEQ ID NO: 1). The atg start codon is in italics, the stop codon is in bold and the added PstI site is underlined.

FIG. 3A, FIG. 3B, and FIG. 3C are the nucleotide sequence of pTrcKudzu (SEQ ID NO:2). The RBS is underlined, the kudzu isoprene synthase start codon is in bold capitol letters and the stop codon is in bold, capitol, italics letters. The vector backbone is pTrcHis2B.

FIG. 5A, FIG. 5B and FIG. 5C are the nucleotide sequence of pETNHisKudzu (SEQ ID NO:5).

FIG. 7A, FIG. 7B and FIG. 7C are the nucleotide sequence of pCL-lac-Kudzu (SEQ ID NO:7).

FIG. 12A, FIG. 12B and FIG. 12C are the nucleotide sequence of pBS Kudzu #2 (SEQ ID NO:57).

FIG. 13 is the nucleotide sequence of kudzu isoprene synthase codon-optimized for expression in *Yarrowia* (SEQ ID NO:8).

FIG. 15A, FIG. 15B and FIG. 15C are the nucleotide sequence of vector pSPZ1(MAP29Spb) (SEQ ID NO: 11).

FIG. 16 is the nucleotide sequence of the synthetic kudzu (*Pueraria montana*) isoprene gene codon-optimized for expression in *Yarrowia* (SEQ ID NO: 12).

FIG. 17 is the nucleotide sequence of the synthetic hybrid poplar (*Populus alba*×*Populus tremula*) isoprene synthase gene (SEQ ID NO: 13). The ATG start codon is in bold and the stop codon is underlined.

FIG. 18A(2) shows a schematic outlining construction of the vector pYLA(POP1).

FIG. 20 shows graphs representing results of the GC-MS analysis of isoprene production by recombinant *Y. lipolytica* strains without (left) or with (right) a kudzu isoprene synthase gene. The arrows indicate the elution time of the authentic isoprene standard.

FIG. 22A, FIG. 22B, FIG. 22C and FIG. 22D are the nucleotide sequence of pTrcKudzu yIDI DXS Kan (SEQ ID NO:20).

FIG. 25A, FIG. 25B, FIG, 25C and FIG. 25D are a nucleotide sequence of pTrcKKDyIkIS kan (SEQ ID NO:33).

FIG. 27A, FIG. 27B, FIG. 27C and FIG. 27D are a nucleotide sequence of pCL PtrcUpperPathway (SEQ ID NO:46).

FIG. 29A, FIG. 29B, FIG. 29C and FIG. 29D are a nucleotide sequence of cassette containing the lower MVA pathway and yeast idi for integration into the *B. subtilis* chromosome at the nprE locus (SEQ ID NO:47).

FIG. 31A and FIG. 31B are a nucleotide sequence of p9796-poplar (SEQ ID NO:48).

FIG. 33A, FIG. 33B and FIG. 33C are a nucleotide sequence of pTrcPoplar (SEQ ID NO:49).

FIG. 35A, FIG. 35B and FIG. 35C are a nucleotide sequence of pTrcKudzu yIDI Kan (SEQ ID NO:50).

FIG. 37A, FIG. 37B and FIG. 37C are a nucleotide sequence of pTrcKudzuDXS Kan (SEQ ID NO:51).

FIG. 39A, FIG. 39B and FIG. 39C are a nucleotide sequence of pCL PtrcKudzu (SEQ ID NO:52).

FIG. 41A, FIG. 41B and FIG. 41C are a nucleotide sequence of pCL PtrcKudzu A3 (SEQ ID NO:53).

FIG. 43A, FIG. 43B and FIG. 43C are a nucleotide sequence of pCL PtrcKudzu yIDI (SEQ ID NO:54).

FIG. 45A, FIG. 45B, FIG. 45C and FIG. 45D are a nucleotide sequence of pCL PtrcKudzu DXS (SEQ ID NO:55).

FIG. 46A shows isoprene production from corn stover. 46B shows isoprene production from bagasse, FIG. 46C shows isoprene production from softwood pulp, FIG. 46D shows isoprene production from glucose, and FIG. 46E shows isoprene production from cells with no additional feedstock. Grey squares represent OD$_{600}$ measurements of the cultures at the indicated times post-inoculation and black triangles represent isoprene production at the indicated times post-inoculation.

FIG. 48A shows the time course of optical density within fermentors fed with varying amounts of yeast extract. FIG. 48B shows the time course of isoprene titer within fermentors fed with varying amounts of yeast extract. The titer is defined as the amount of isoprene produced per liter of fermentation broth. FIG. 48C shows the effect of yeast extract on isoprene production in *E. coli* grown in fed-batch culture.

FIG. 49A shows the time course of optical density within the 500-L bioreactor fed with glucose and yeast extract. FIG. 49B shows the time course of isoprene titer within the 500-L bioreactor fed with glucose and yeast extract. The titer is defined as the amount of isoprene produced per liter of fermentation broth. FIG. 49C shows the time course of total isoprene produced from the 500-L bioreactor fed with glucose and yeast extract.

FIG. 51A, FIG. 51B and FIG. 51C are the nucleotide sequence of pJMupperpathway2 (SEQ ID NO:56).

FIG. 55A and FIG. 55B are the nucleotide sequence of plasmid pET24 *P. alba* HGS (SEQ ID NO:87).

FIG. 58A and FIG. 58B are the nucleotide sequence of plasmid EWL230 (SEQ ID NO:88).

FIG. 61A and FIG. 61B are the nucleotide sequence of plasmid EWL244 (SEQ ID NO:89).

FIG. 63A, FIG. 63B and FIG. 63C are the nucleotide sequence of plasmid MCM484 (SEQ ID NO:90).

FIG. 64A, FIG. 64B and FIG. 64C are the nucleotide sequence of plasmid MCM485 (SEQ ID NO:91).

FIG. 65A, FIG. 65B and FIG. 65C are the nucleotide sequence of plasmid MCM486 (SEQ ID NO:92).

FIG. 66A, FIG. 66B and FIG. 66C are the nucleotide sequence of plasmid MCM487 (SEQ ID NO:93).

FIG. 67A shows the time course of optical density within the 15-L bioreactor fed with glucose. FIG. 67B shows the time course of isoprene titer within the 15-L bioreactor fed with glucose. The titer is defined as the amount of isoprene produced per liter of fermentation broth. FIG. 67C shows the time course of total isoprene produced from the 15-L bioreactor fed with glucose. FIG. 67D shows the total carbon dioxide evolution rate (TCER), or metabolic activity profile, within the 15-L bioreactor fed with glucose.

FIG. 68A shows the time course of optical density within the 15-L bioreactor fed with glucose. FIG. 68B shows the time course of isoprene titer within the 15-L bioreactor fed with glucose. The titer is defined as the amount of isoprene produced per liter of fermentation broth. FIG. 68C shows the time course of total isoprene produced from the 15-L bioreactor fed with glucose. FIG. 68D shows the volumetric productivity within the 15-L bioreactor fed with glucose. An average value of 1.1 g/L/hr was maintained for a 40-hour period (23-63 hours) with yeast extract feeding. FIG. 68E shows the carbon dioxide evolution rate (CER), or metabolic activity profile, within the 15-L bioreactor fed with glucose.

FIG. 69A shows growth of *E. coli* EWL256, which contains both the MVA pathway and isoprene synthase, on either glucose, biomass hydrolysate, glycerol, or acetate as the only carbon source. The different carbon sources were added to a concentration of 1% in the media. A negative control with no added carbon source was included. Growth was measured as optical density at 600 nM. FIG. 69B shows specific productivity of isoprene from *E. coli* EWL256 containing both the MVA pathway and isoprene synthase when grown on either glucose, biomass hydrolysate, glycerol, or acetate as only carbon source. The different carbon sources were added to a concentration of 1% in the media. A negative control with no added carbon source was included. Samples were taken 190 minutes, 255 minutes and 317 minutes after inoculation and isoprene produced by the bacteria was measured using GC-MS. FIG. 69C shows growth of *E. coli* EWL256 on either glucose or xylose as the only carbon source. The different carbon sources were added to a concentration of 1% in the media. A negative control with no added carbon source was included. Growth was measured as optical density at 600 nM. FIG. 69D shows specific productivity of isoprene from *E. coli* EWL256 when grown on either glucose or xylose as only carbon source. The carbon sources were added to a concentration of 1% in the media. A negative control with no added carbon source was included. Samples were taken 260 minutes, 322 minutes and 383 minutes after inoculation and isoprene produced by the bacteria was measured using GC-MS.

The culture was grown for several hours and induced with 50 uM IPTG. The left bar shows isoprene assay results four hours after induction followed by a one hour isoprene accumulation assay. The middle bar shows the one hour normalized value for the same culture with the same induction period but analyzed by a 12 hour isoprene accumulation assay. The right bar shows the value for a one hour isoprene accumulation assay of the culture that was induced for 13 hours.

Figure 71:
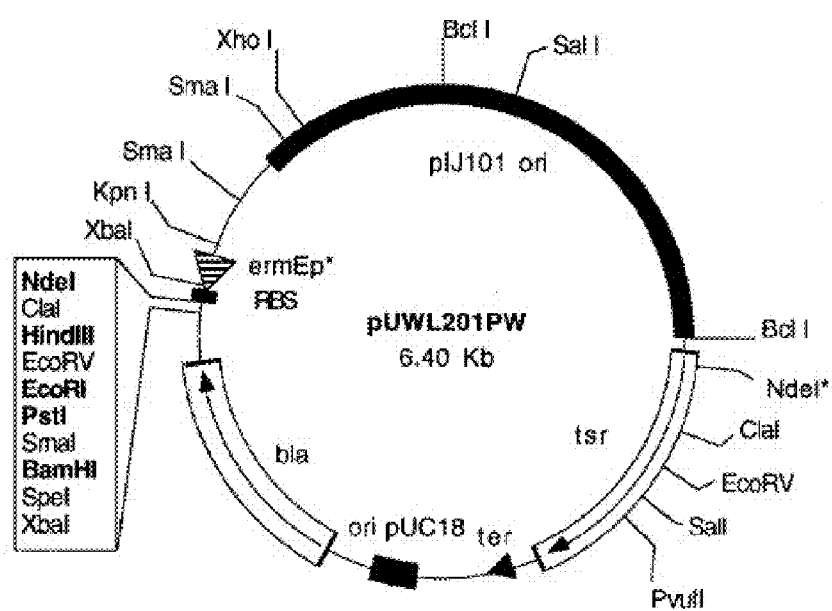

FIG. 71 is a map of the *E. coli-Streptomyces* shuttle vector pUWL201PW (6400 bp) used for cloning isoprene synthase from Kudzu. Tsr, thiostrepton resistance gene. Picture is taken from Doumith et al., *Mol. Gen. Genet.* 264: 477-485, 2000.

Figure 72:
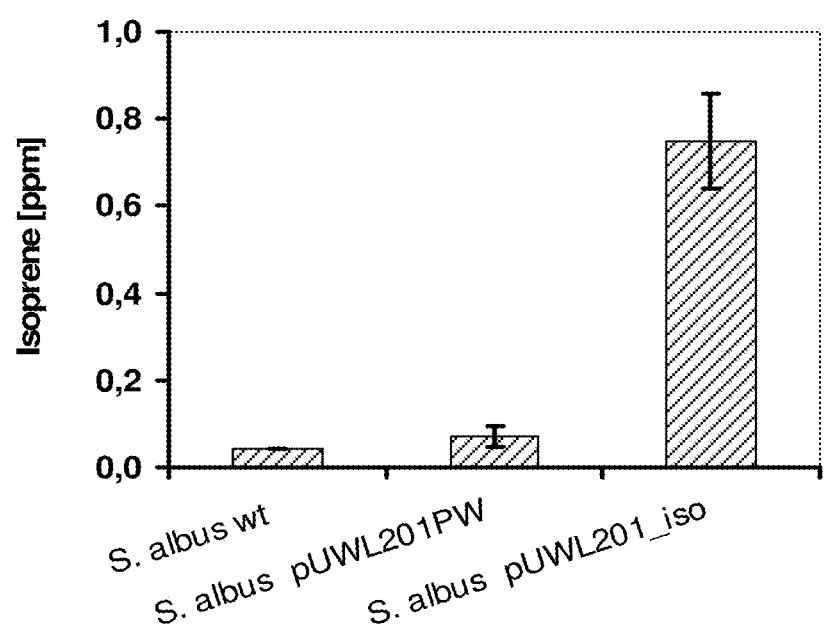

FIG. 72 shows isoprene formation by *Streptomyces albus* wild type strain ("wt") and strains harboring plasmid pUWL201PW (negative control) or pUWL201_iso (encoding isoprene synthase from Kudzu).

Figure 73A:
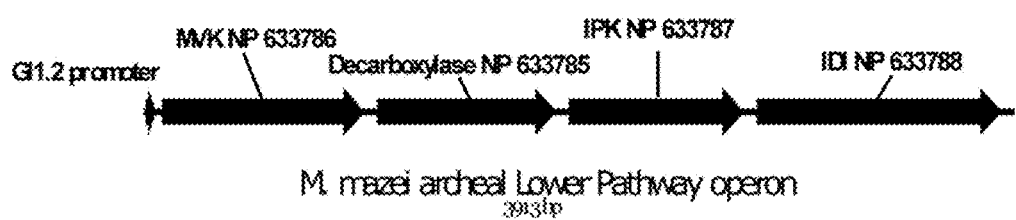

FIG. 73A is a map of the *M. mazei* archaeal Lower Pathway operon.

FIG. 73B(1) and FIG. 73B(2) are the nucleotide sequence of the *M. mazei* archaeal lower Pathway operon (SEQ ID NO: 113).

Figure 74A:
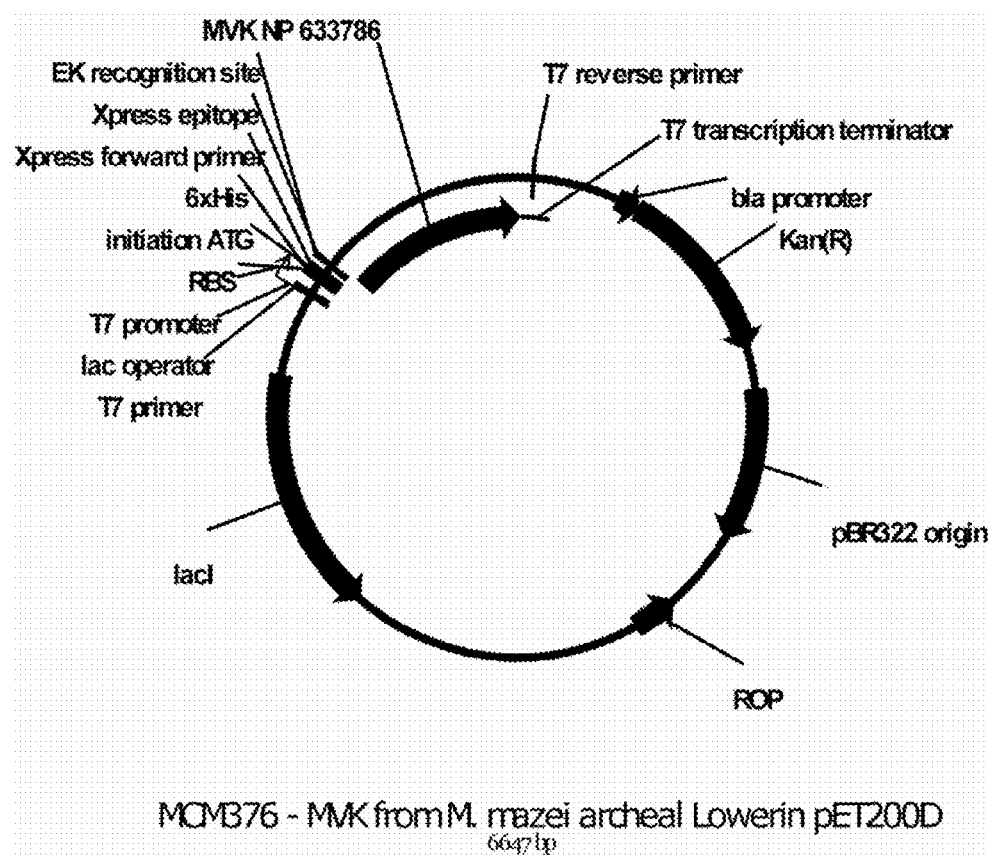
Figure 75A:
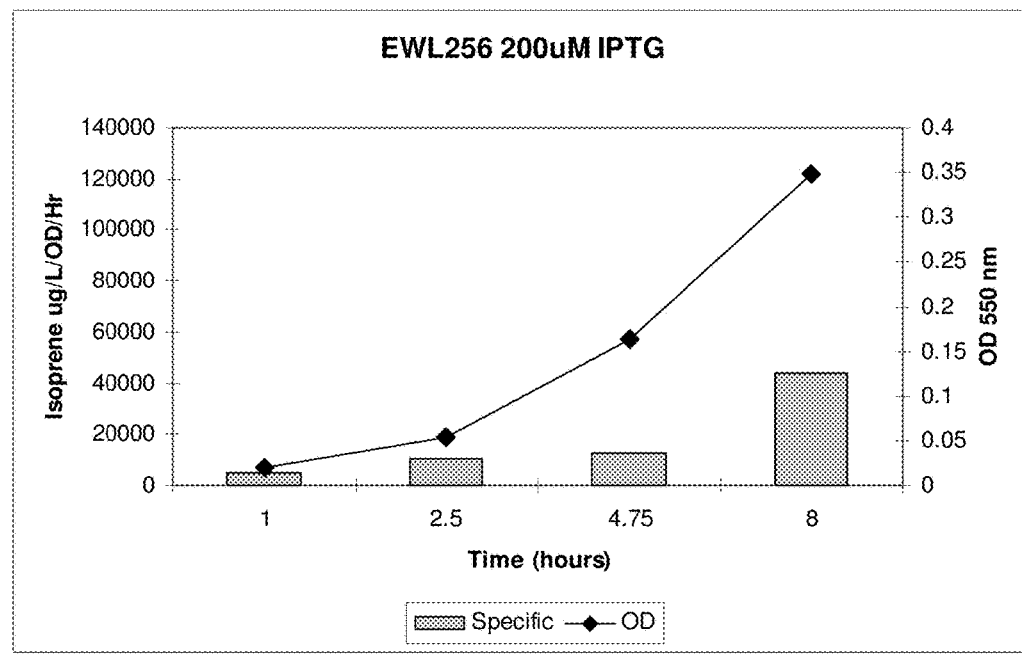
Figure 75B:
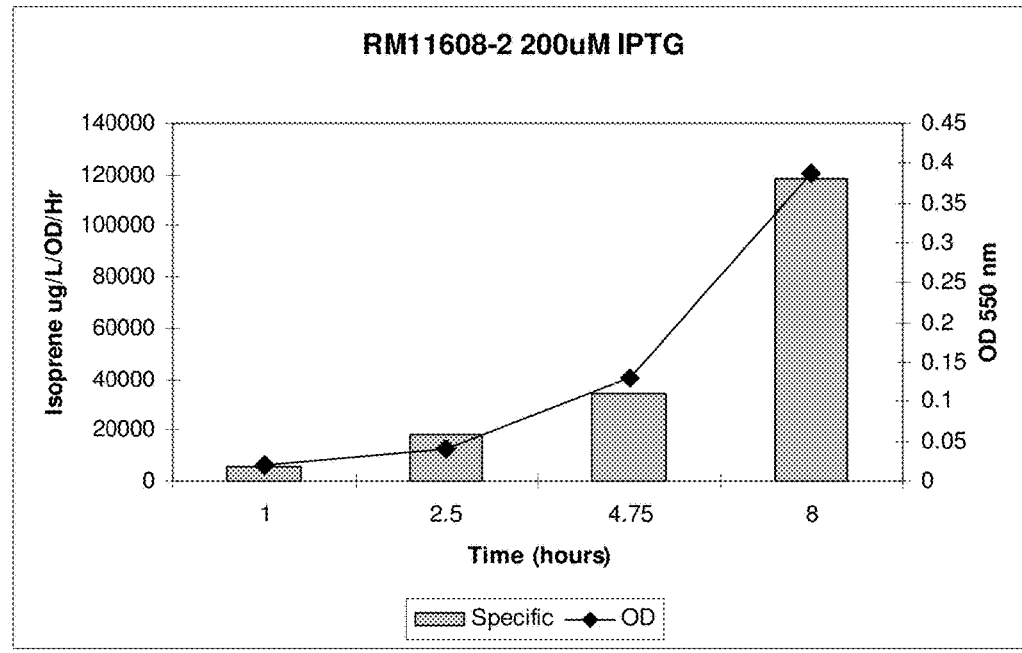
Figure 75C:
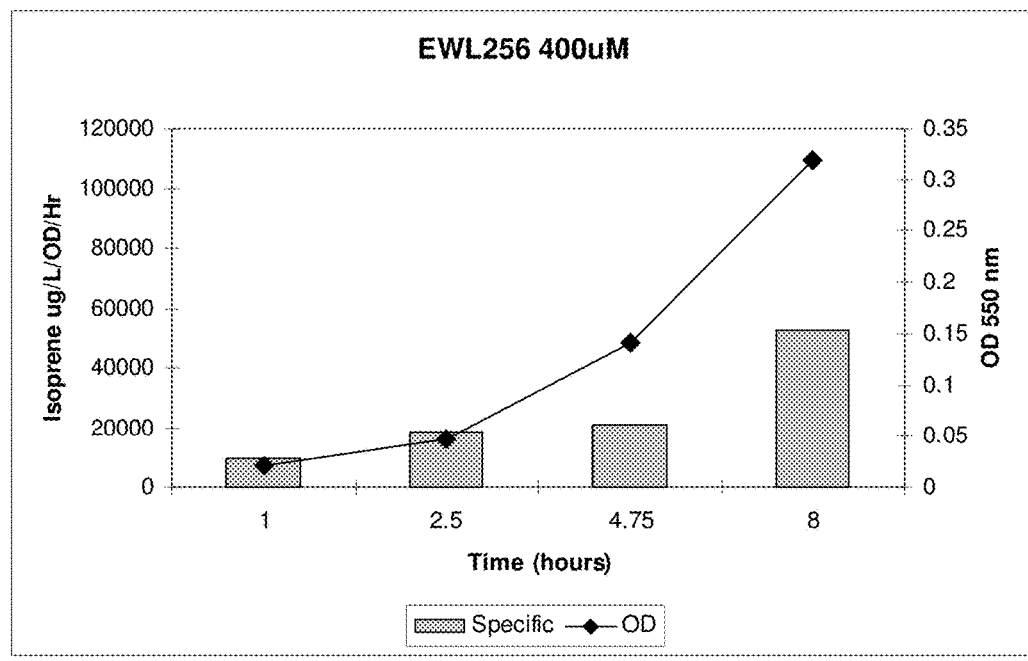
Figure 75D:
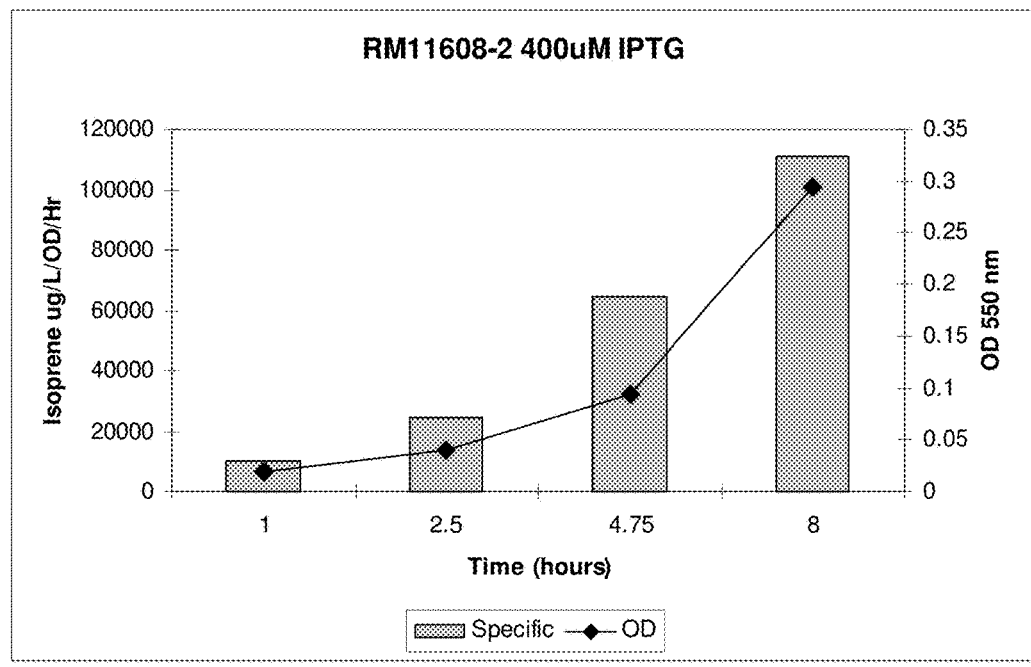

FIG. 74A is a map of MCM376-MVK from *M. mazei* archaeal Lowerin pET200D.

FIG. 74B(1) and FIG. 74B(2) are the nucleotide sequence of MCM376-MVK from *M. mazei* archaeal Lowerin pET200D (SEQ ID NO: 114).

FIG. 75A, FIG. 75B, FIG. 75C, and FIG. 75D show growth and specific productivity of isoprene production for EWL256 compared to RM11608-2. Growth (OD550) is represented by the white diamonds; specific productivity of isoprene is represented by the solid bars. The x-axis is time (hours) post-induction with either 200 (FIG. 75A and FIG. 75B) or 400 (FIG. 75C and FIG. 75D) uM IPTG. Y-1 axis is productivity of isoprene (ug/L/OD/hr) and Y-2 is arbitrary units of optical density at a wavelength of 550. These values for the OD550 must be multiplied by 6.66 to obtain the actual OD of the culture.

Figure 76:
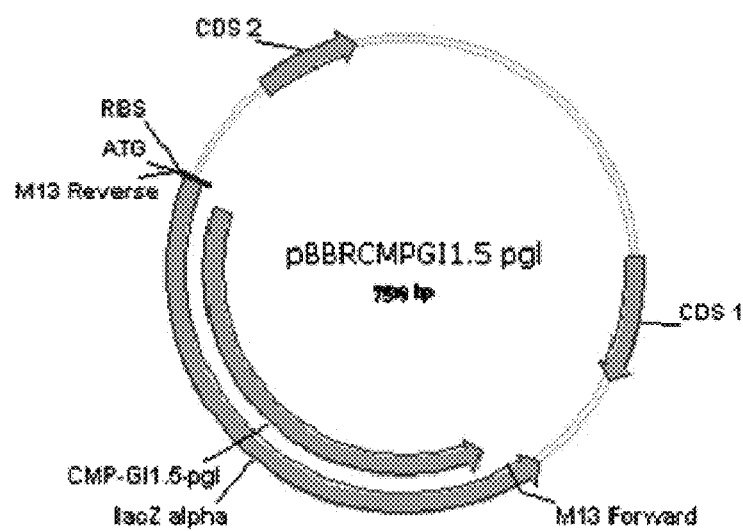

FIG. 76 is a map of plasmid pBBRCMPGI1.5-pgl.

FIG. 77A and FIG. 77B are the nucleotide sequence of plasmid pBBRCMPGI1.5-pgl (SEQ ID NO:122).

Figure 78A:
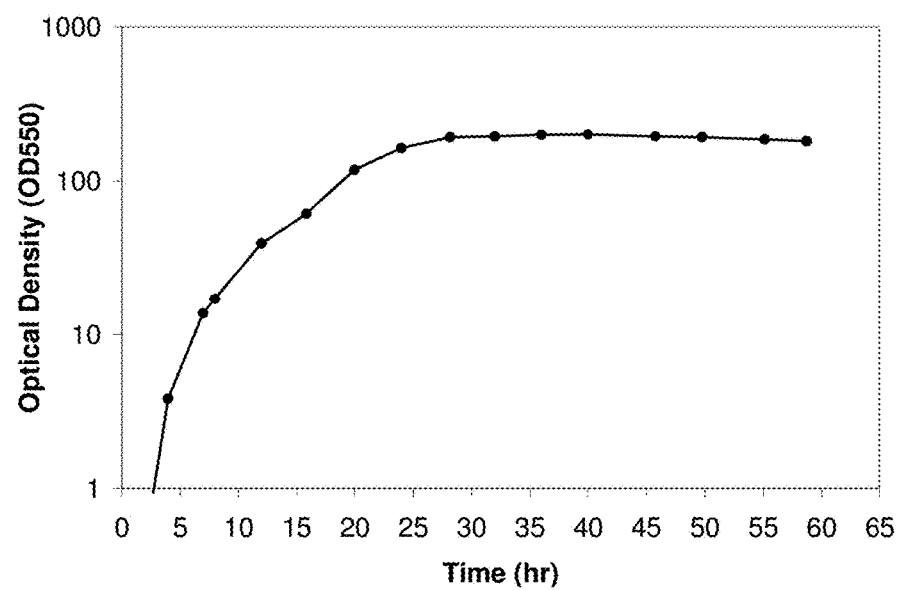
Figure 78B:
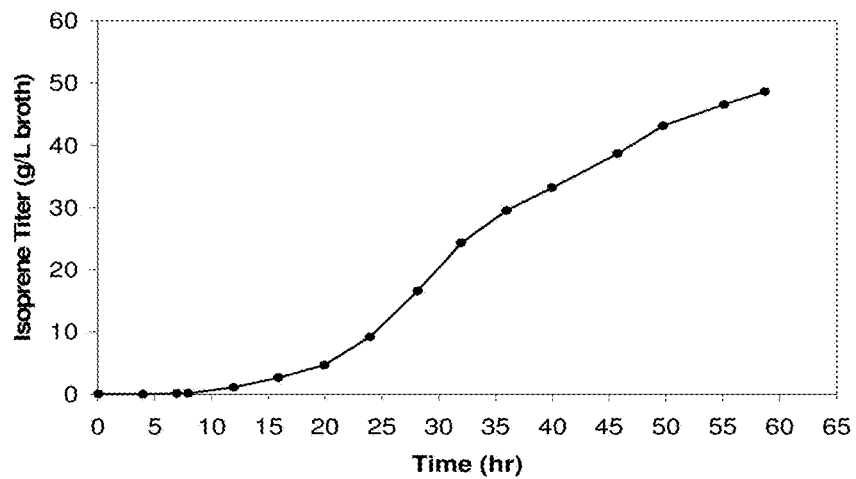
Figure 78C:
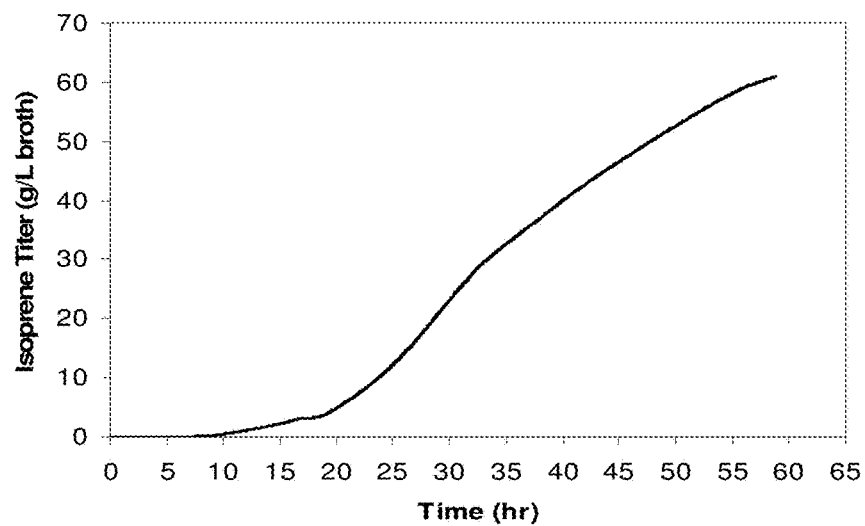
Figure 78D:
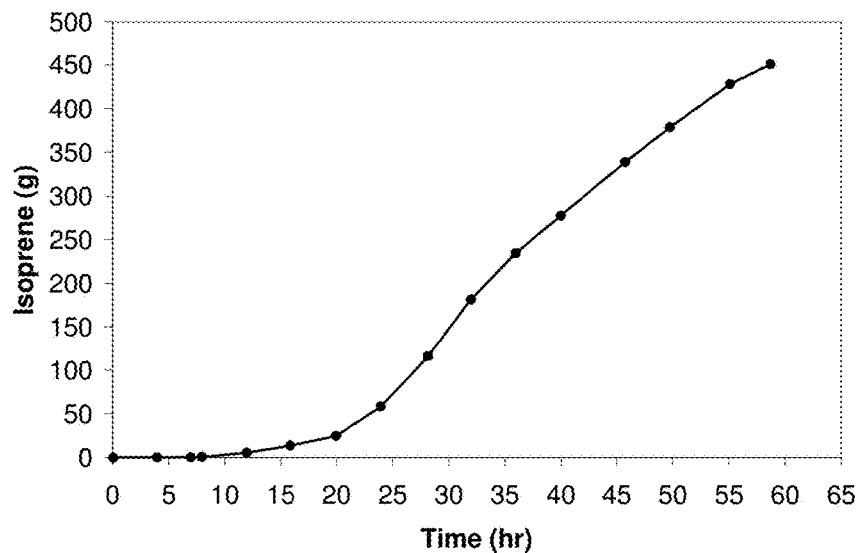
Figure 78E:
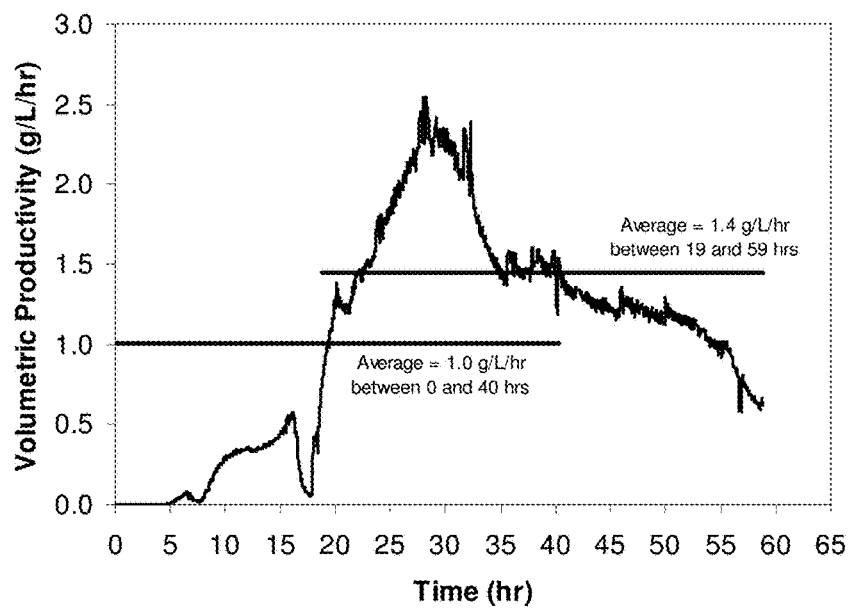
Figure 78F:
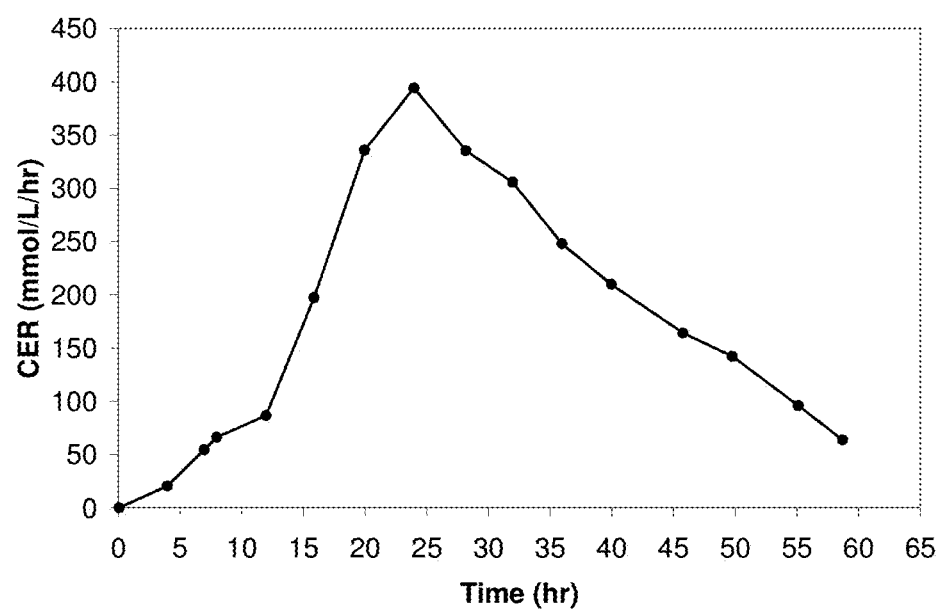

FIG. 78A, FIG. 78B, FIG. 78C, FIG. 78D, FIG. 78E, and FIG. 78F are graphs of isoprene production by *E. coli* strain expressing *M. mazei* mevalonate kinase, *P. alba* isoprene synthase, and pgl (RHM111608-2), and grown in fed-batch culture at the 15-L scale. FIG. 78A shows the time course of optical density within the 15-L bioreactor fed with glucose. FIG. 78B shows the time course of isoprene titer within the 15-L bioreactor fed with glucose. The titer is defined as the amount of isoprene produced per liter of fermentation broth. Method for calculating isoprene: cumulative isoprene produced in 59 hrs, g/Fermentor volume at 59 hrs, L [=]g/L broth. FIG. 78C also shows the time course of isoprene titer within the 15-L bioreactor fed with glucose. Method for calculating isoprene: ∫(Instantaneous isoprene production rate, g/L/hr)dt from t=0 to 59 hours [=]g/L broth. FIG. 78D shows the time course of total isoprene produced from the 15-L bioreactor fed with glucose. FIG. 78E shows volumetric productivity within the 15-L bioreactor fed with glucose. FIG. 78F shows carbon dioxide evolution rate (CER), or metabolic activity profile, within the 15-L bioreactor fed with glucose.

Figure 79A:
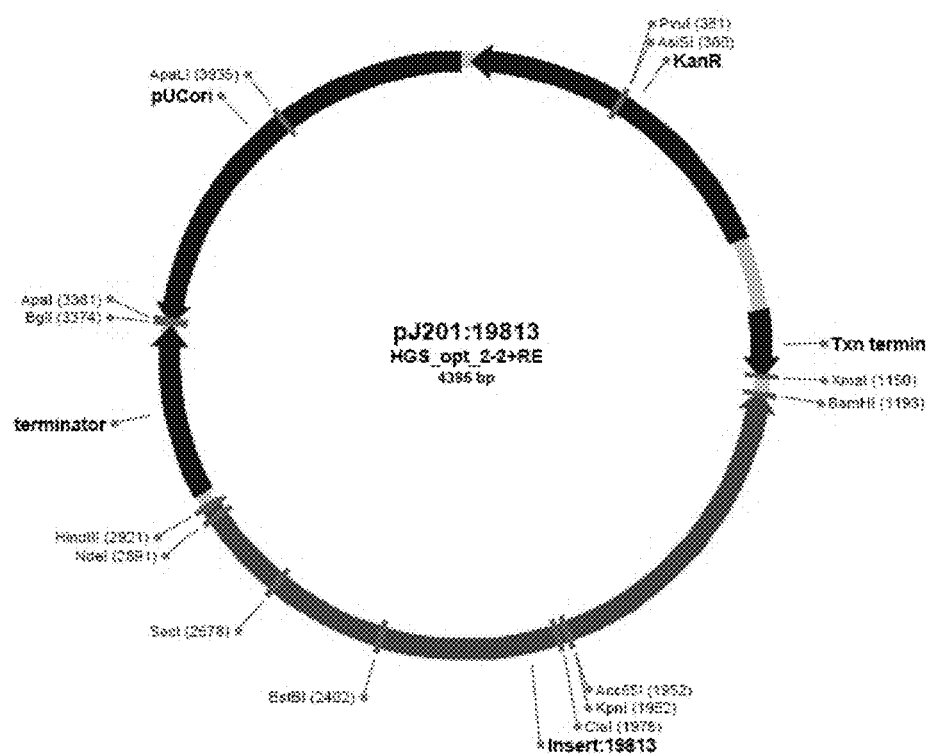

FIG. 79A is a map of plasmid pJ201:19813.

FIGS. 79B(1), FIG. 79B(2) and FIG. 79C are the nucleotide sequence of pJ201:19813 (SEQ ID NO:123).

DETAILED DESCRIPTION OF THE INVENTION

The invention features compositions and methods for the production of increased amounts of isoprene. In particular, these compositions and methods increase the rate of isoprene production and increase the total amount of isoprene that is produced. For example, cell culture systems that generate $4.8 \times 10^4$ nmole/$g_{wcm}$/hr of isoprene have been produced (Table 1). The efficiency of these systems is demonstrated by the conversion of ~23.6 molar % yield (10.7 weight % yield) of the carbon that the cells consume from a cell culture medium into isoprene (% carbon yield). As shown in the Examples and Table 2, approximately 60.5 g of isoprene per liter of broth was generated. Isoprene was produced at a peak specific rate of $1.88 \times 10^5$ nmol/OD/hr ($1.88 \times 10^5$ nmole/$g_{wcm}$/hr). If desired, even greater amounts of isoprene can be obtained using other conditions, such as those described herein. In some embodiments, a renewable carbon source is used for the production of isoprene. The compositions and methods of the present invention are desirable because they allow high isoprene yield per cell, high carbon yield, high isoprene purity, high productivity, low energy usage, low production cost and investment, and minimal side reactions. This efficient, large scale, biosynthetic process for isoprene production provides an isoprene source for synthetic isoprene-based rubber and provides a desirable, low-cost alternative to using natural rubber.

As discussed further below, the amount of isoprene produced by cells can be greatly increased by introducing a heterologous nucleic acid encoding an isoprene synthase polypeptide (e.g., a plant isoprene synthase polypeptide) into the cells. Isoprene synthase polypeptides convert dimethylallyl diphosphate (DMAPP) into isoprene. As shown in the Examples, a heterologous *Pueraria Montana* (kudzu) or *Populus alba* (Poplar) isoprene synthase polypeptide was expressed in a variety of host cells, such as *Escherichia coli*, *Panteoa citrea*, *Bacillus subtilis*, *Yarrowia lipolytica*, and *Trichoderma reesei*. As also shown in the Examples, a heterologous *Methanosarcina mazei* (*M. mazei*) mevalonate kinase (MVK) was expressed in host cells such as *Escherichia coli* to increase isoprene production. All of these cells produced more isoprene than the corresponding cells without the heterologous isoprene synthase polypeptide. As illustrated in Tables 1 and 2, large amounts of isoprene are produced using the methods described herein. For example, *B. subtilis* cells with a heterologous isoprene synthase nucleic acid produced approximately 10-fold more isoprene in a 14 liter fermentor than the corresponding control *B. subtilis* cells without the heterologous nucleic acid (Table 2). The production of 60.5 g of isoprene per liter of broth (mg/L, wherein the volume of broth includes both the volume of the cell medium and the volume of the cells) by *E. coli* and 30 mg/L by *B. subtilis* in fermentors indicates that significant amounts of isoprene can be generated (Table 2). If desired, isoprene can be produced on an even larger scale or other conditions described herein can be used to further increase the amount of isoprene. The vectors listed in Tables 1 and 2 and the experimental conditions are described in further detail below and in the Examples section.

TABLE 1

Exemplary yields of isoprene from a shake flask using the cell cultures and methods of the invention. The assay for measuring isoprene production is described in Example I, part II. For this assay, a sample was removed at one or more time points from the shake flask and cultured for 30 minutes. The amount of isoprene produced in this sample was then measured. The headspace concentration and specific rate of isoprene production are listed in Table 1 and described further herein.

| | Isoprene Production in a Headspace vial* | |
|---|---|---|
| Strain | Headspace concentration $\mu g/L_{gas}$ | Specific Rate $\mu g/L_{broth}$/hr/OD (nmol/$g_{wcm}$/hr) |
| E. coli BL21/pTrcKudzu IS | 1.40 | 53.2 (781.2) |
| E. coli BL21/Pcl DXS yidi Kudzu IS | 7.61 | 289.1 ($4.25 \times 10^3$) |
| E. coli BL21/MCM127 with kudzu IS and entire MVA pathway | 23.0 | 874.1 ($1.28 \times 10^4$) |
| E. coli BL21/Pet N-HisKudzu IS | 1.49 | 56.6 (831.1) |
| Pantoea citrea/pTrcKudzu IS | 0.66 | 25.1 (368.6) |
| E. coli w/Poplar IS [Miller (2001)] | — | 5.6 (82.2) |
| Bacillis licheniformis Fall U.S. Pat. No. 5,849,970 | — | 4.2 (61.4) |
| Yarrowia lipolytica with kudzu isoprene synthase | ~0.05 μg/L | ~2 (~30) |
| Trichoderma reesei with kudzu isoprene synthase | ~0.05 μg/L | ~2 (~30) |
| E. coli BL21/pTrcKKD$_y$I$_k$IS with kudzu IS and lower MVA pathway | 85.9 | $3.2 \times 10^3$ ($4.8 \times 10^4$) |

*Normalized to 1 mL of 1 OD$_{600}$, cultured for 1 hour in a sealed headspace vial with a liquid to headspace volume ratio of 1:19.

TABLE 2

Exemplary yields of isoprene in a fermentor using the cell cultures and methods of the invention. The assay for measuring isoprene production is described in Example I, part II. For this assay, a sample of the off-gas of the fermentor was taken and analyzed for the amount of isoprene. The peak headspace concentration (which is the highest headspace concentration during the fermentation), titer (which is the cumulative, total amount of isoprene produced per liter of broth), and peak specific rate of isoprene production (which is the highest specific rate during the fermentation) are listed in Table 2 and described further herein.

| | Isoprene Production in Fermentors | | |
|---|---|---|---|
| Strain | Peak Headspace concentration** (ug/$L_{gas}$) | Titer (mg/$L_{broth}$) | Peak Specific rate $\mu g/L_{broth}$/hr/OD (nmol/$g_{wcm}$/hr) |
| E. coli BL21/pTrcKudzu with Kudzu IS | 52 | 41.2 | 37 (543.3) |
| E. coli FM5/pTrcKudzu IS | 3 | 3.5 | 21.4 (308.1) |
| E. coli BL21/triple strain (DXS, yidi, IS) | 285 | 300 | 240 ($3.52 \times 10^3$) |
| E. coli FM5/triple strain (DXS, yidi, IS) | 50.8 | 29 | 180.8 ($2.65 \times 10^3$) |
| E. coli/MCM127 with Kudzu IS and entire MVA pathway | 1094 | 250 | 875 ($1.28 \times 10^4$) |
| Bacillus subtilis wild-type | 1.5 | 2.5 | 0.8 (11.7) |
| Bacillus pBS Kudzu IS | 16.6 | ~30 (over 100 hours) | 5 (73.4) |
| Bacillus Marburg 6051 [Wagner and Fall (1999)] | 2.04 | 0.61 | 24.5 (359.8) |
| Bacillus Marburg 6051 Fall U.S. Pat. No. 5,849,970 | 0.7 | 0.15 | 6.8 (100) |
| E. coli BL21/pCLPtrcUpper Pathway and gi1.2KKDyI and pTrcAlba-mMVK | $2.03 \times 10^4$ | $3.22 \times 10^4$ | $5.9 \times 10^3$ ($8.66 \times 10^4$) |
| E. coli BL21/pCLPtrcUpper Pathway and gi1.2KKDyI and pTrcAlba-mMVK plus pBBRCMPGI1.5pgl | $3.22 \times 10^4$ | $6.05 \times 10^4$ | $1.28 \times 10^4$ ($1.88 \times 10^5$) |

**Normalized to an off-gas flow rate of 1 vvm (1 volume off-gas per 1 $L_{broth}$ per minute).

Additionally, isoprene production by cells that contain a heterologous isoprene synthase nucleic acid can be enhanced by increasing the amount of a 1-deoxy-D-xylulose-5-phosphate synthase (DXS) polypeptide and/or an isopentenyl diphosphate isomerase (IDI) polypeptide expressed by the cells. For example, a DXS nucleic acid and/or an IDI nucleic acid can be introduced into the cells. The DXS nucleic acid may be a heterologous nucleic acid or a duplicate copy of an endogenous nucleic acid. Similarly, the IDI nucleic acid may be a heterologous nucleic acid or a duplicate copy of an endogenous nucleic acid. In some embodiments, the amount of DXS and/or IDI polypeptide is increased by replacing the endogenous DXS and/or IDI promoters or regulatory regions with other promoters and/or regulatory regions that result in greater transcription of the DXS and/or IDI nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

Figure 19A:
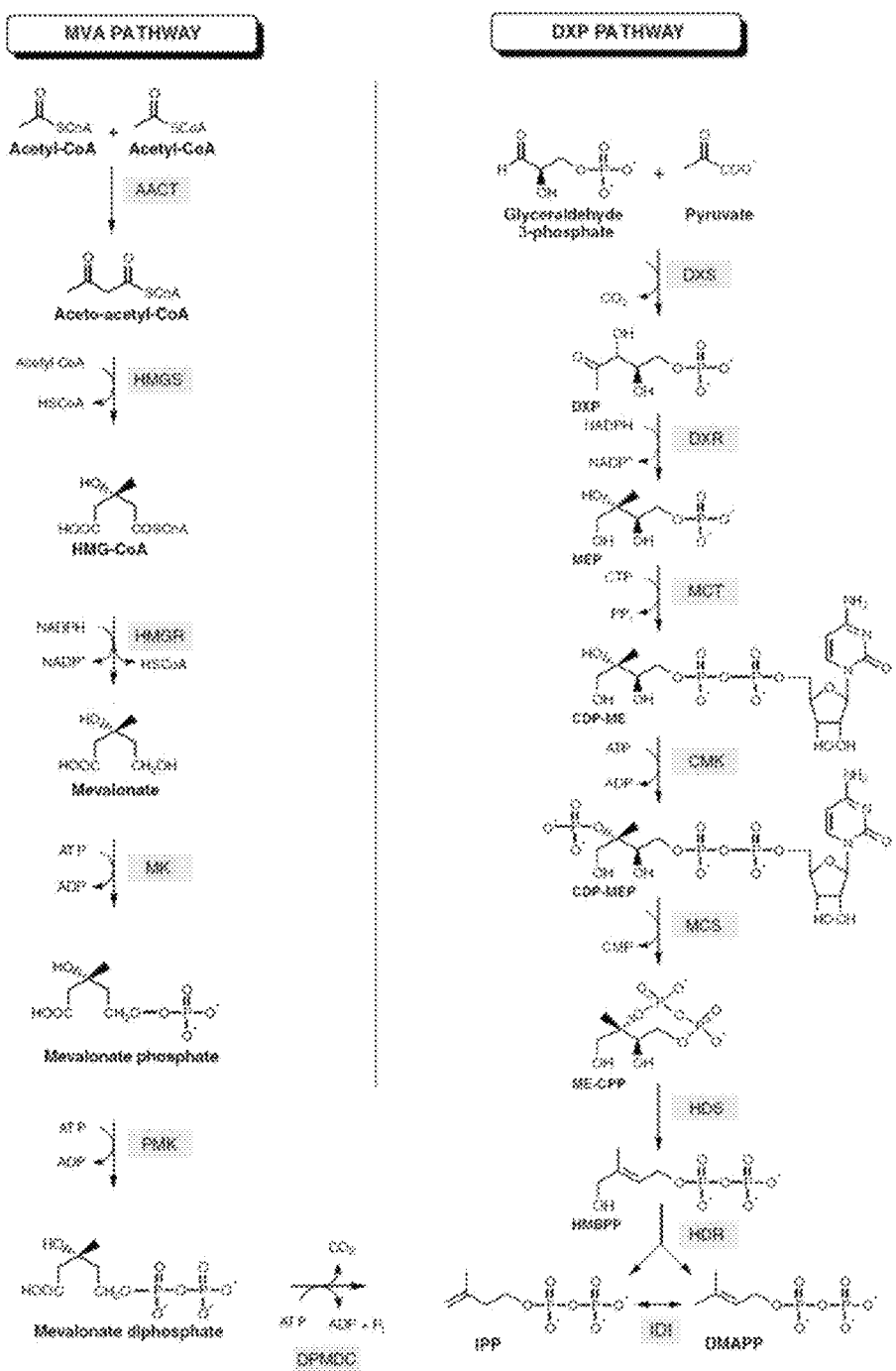
FIG. 19A shows the MVA and DXP metabolic pathways for isoprene (based on F. Bouvier et al., Progress in Lipid Res. 44: 357-429, 2005). The following description includes alternative names for each polypeptide in the pathways and a reference that discloses an assay for measuring the activity of the indicated polypeptide (each of these references are each hereby incorporated by reference in their entireties, particularly with respect to assays for polypeptide activity for polypeptides in the MVA and DXP pathways). Mevalonate Pathway: AACT; Acetyl-CoA acetyltransferase, MvaE, EC 2.3.1.9. Assay: *J. Bacteriol.*, 184: 2116-2122, 2002; HMGS; Hydroxymethylglutaryl-CoA synthase, MvaS, EC 2.3.3.10. Assay: *J. Bacteriol.*, 184: 4065-4070, 2002; HMGR; 3-Hydroxy-3-methylglutaryl-CoA reductase, MvaE, EC 1.1.1.34. Assay: *J. Bacteriol.*, 184: 2116-2122, 2002; MVK; Mevalonate kinase, ERG12, EC 2.7.1.36. Assay: *Curr Genet* 19:9-14, 1991. PMK; Phosphomevalonate kinase, ERG8, EC 2.7.4.2, Assay: *Mol Cell Biol.*, 11:620-631, 1991; DPMDC; Diphosphomevalonate decarboxylase, MVD1, EC 4.1.1.33. Assay: *Biochemistry*, 33:13355-13362, 1994; IDI; Isopentenyl-diphosphate delta-isomerase, IDI1, EC 5.3.3.2. Assay: *J. Biol. Chem.* 264: 19169-19175, 1989. DXP Pathway: DXS; 1-Deoxyxylulose-5-phosphate synthase, dxs, EC 2.2.1.7. Assay: *PNAS*, 94:12857-62, 1997; DXR; 1-Deoxy-D-xylulose 5-phosphate reductoisomerase, dxr, EC 2.2.1.7. Assay: *Eur. J. Biochem.* 269:4446-4457, 2002; MCT; 4-Diphosphocytidyl-2C-methyl-D-erythritol synthase, IspD, EC 2.7.7.60. Assay: *PNAS*, 97: 6451-6456, 2000; CMK; 4-Diphosphocytidyl-2-C-methyl-D-erythritol kinase, IspE, EC 2.7.1.148. Assay: *PNAS*, 97:1062-1067, 2000; MCS; 2C-Methyl-D-erythritol 2,4-cyclodiphosphate synthase, IspF, EC 4.6.1.12. Assay: *PNAS*, 96:11758-11763, 1999; HDS; 1-Hydroxy-2-methyl-2-(E)-butenyl 4-diphosphate synthase, ispG, EC 1.17.4.3. Assay: *J. Org. Chem.*, 70:9168-9174, 2005; HDR; 1-Hydroxy-2-methyl-2-(E)-butenyl 4-diphosphate reductase, IspH, EC 1.17.1.2. Assay: *JACS*, 126:12847-12855, 2004.

The encoded DXS and IDI polypeptides are part of the DXP pathway for the biosynthesis of isoprene (FIG. 19A). DXS polypeptides convert pyruvate and D-glyceraldehyde-3-phosphate into 1-deoxy-D-xylulose-5-phosphate. While not intending to be bound by any particular theory, it is believed that increasing the amount of DXS polypeptide increases the flow of carbon through the DXP pathway, leading to greater isoprene production. IDI polypeptides catalyze the interconversion of isopentenyl diphosphate (IPP) and dimethylallyl diphosphate (DMAPP). While not intending to be bound by any particular theory, it is believed that increasing the amount of IDI polypeptide in cells increases the amount of IPP that is converted into DMAPP, which in turn is converted into isoprene.

For example, fermentation of E. coli cells with a kudzu isoprene synthase, S. cerevisia IDI, and E. coli DXS nucleic acids was used to produce isoprene. The levels of isoprene varied from 50 to 300 µg/L over a time period of 15 hours (Example 7, part VII). As another example, fermentation of E. coli with M. mazei mevalonate kinase (MVK), P. alba isoprene synthase, the upper MVA pathway, and the integrated lower MVA pathway was used to produce isoprene. The levels of isoprene varied from 32 to 35.6 g/L over a time period of 67 hours (Example 10, part III).

In yet another example, fermentation of E. coli with M. mazei mevalonate kinase (MVK), P. alba isoprene synthase, pgl over-expression (RHM111608-2), the upper MVA pathway, and the integrated lower MVA pathway were used to produce isoprene. The levels of isoprene vary from 33.2 g/L to 40.0 g/L over a time period of 40 hours or 48.6 g/L to 60.5 g/L over a time period of 59 hours (Example 13, part (ii)).

In some embodiments, the presence of heterologous or extra endogenous isoprene synthase, IDI, and DXS nucleic acids causes cells to grow more reproducibly or remain viable for longer compared to the corresponding cell with only one or two of these heterologous or extra endogenous nucleic acids. For example, cells containing heterologous isoprene synthase, IDI, and DXS nucleic acids grew better than cells with only heterologous isoprene synthase and DXS nucleic acids or with only a heterologous isoprene synthase nucleic acid. Also, heterologous isoprene synthase, IDI, and DXS nucleic acids were successfully operably linked to a strong promoter on a high copy plasmid that was maintained by E. coli cells, suggesting that large amounts of these polypeptides could be expressed in the cells without causing an excessive amount of toxicity to the cells. While not intending to be bound to a particular theory, it is believed that the presence of heterologous or extra endogenous isoprene synthase and IDI nucleic acids may reduce the amount of one or more potentially toxic intermediates that would otherwise accumulate if only a heterologous or extra endogenous DXS nucleic acid was present in the cells.

Figure 19B:
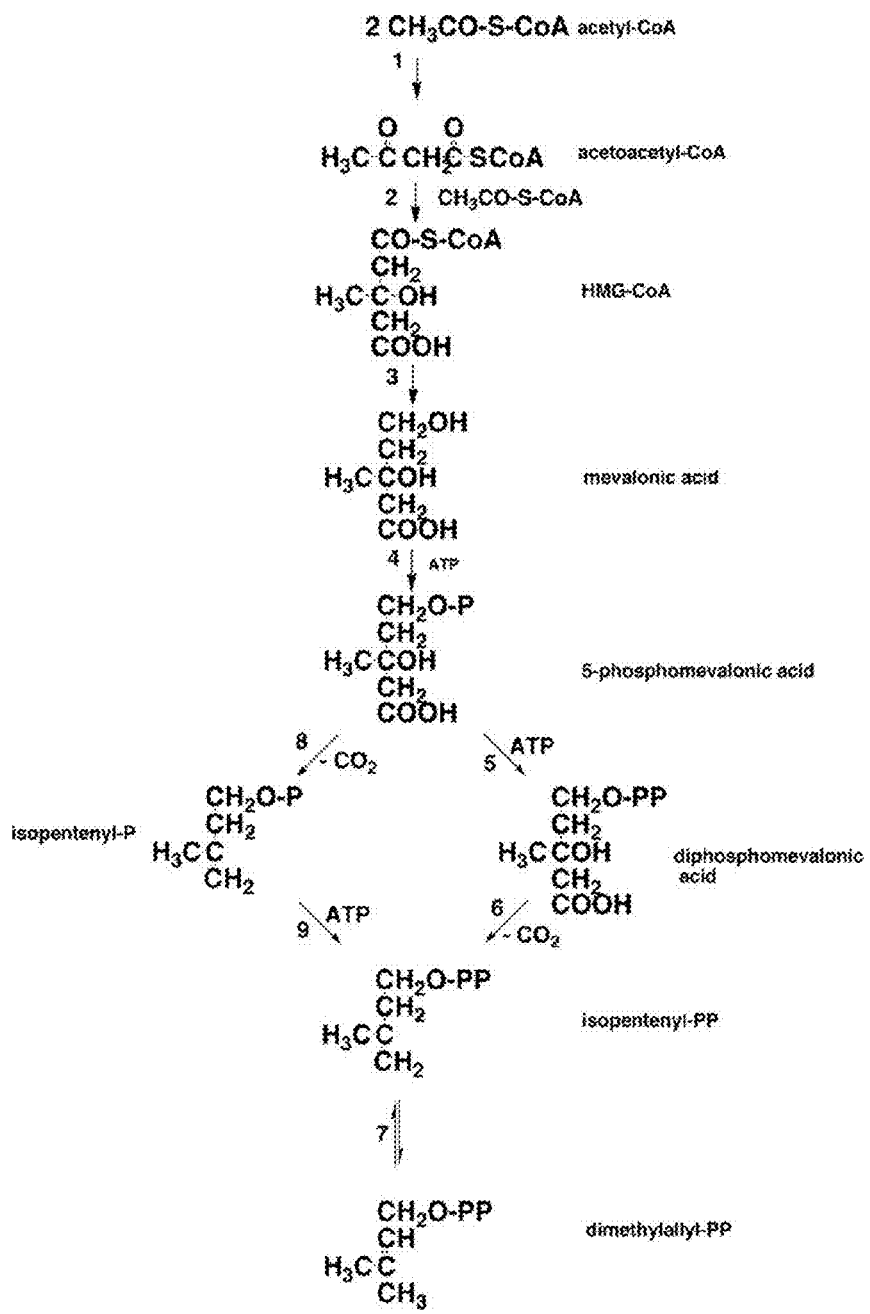
FIG. 19B illustrates the classical and modified MVA pathways. 1, acetyl-CoA acetyltransferase (AACT); 2, HMG-CoA synthase (HMGS); 3, HMG-CoA reductase (HMGR); 4, mevalonate kinase (MVK); 5, phosphomevalonate kinase (PMK); 6, diphosphomevalonate decarboxylase (MVD or DPMDC); 7, isopentenyl diphosphate isomerase (IDI); 8, phosphomevalonate decarboxylase (PMDC); 9, isopentenyl phosphate kinase (IPK). The classical MVA pathway proceeds from reaction 1 through reaction 7 via reactions 5 and 6, while a modified MVA pathway goes through reactions 8 and 9. P and PP in the structural formula are phosphate and pyrophosphate, respectively. This figure was taken from Koga and Morii, *Microbiology and Mol. Biology Reviews*, 71:97-120, 2007, which is incorporated by reference in its entirety, particularly with respect to nucleic acids and polypeptides of the modified MVA pathway. The modified MVA pathway is present, for example, in some archaeal organisms, such as *Methanosarcina mazei*.
Figure 21:
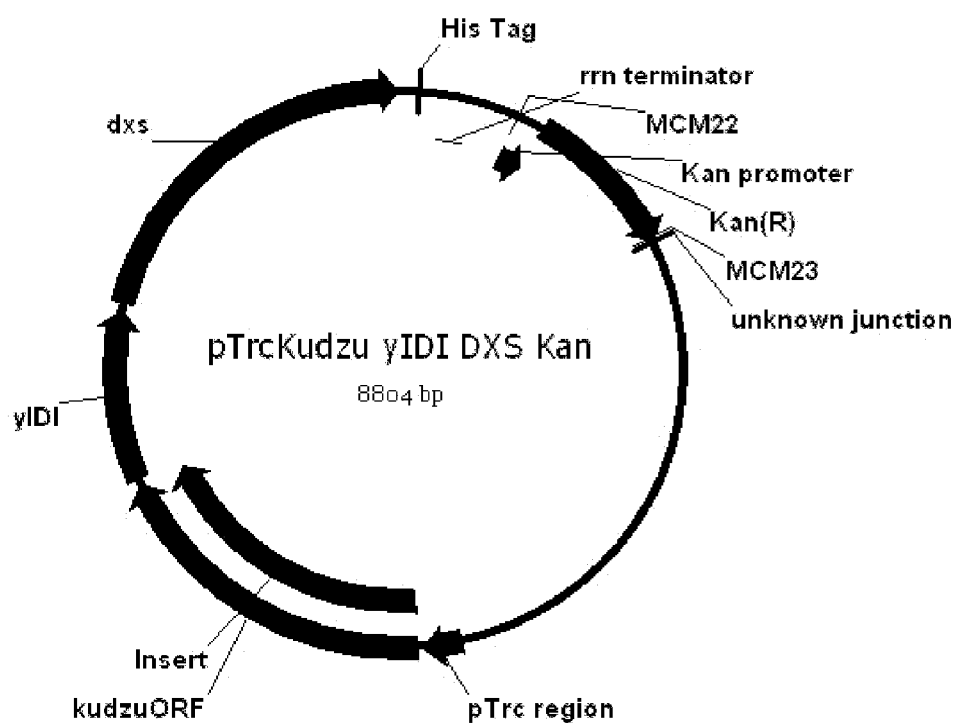
FIG. 21 is a map of pTrcKudzu yIDI DXS Kan.

In some embodiments, the production of isoprene by cells that contain a heterologous isoprene synthase nucleic acid is augmented by increasing the amount of a MVA polypeptide expressed by the cells (FIGS. 19A and 19B). Exemplary MVA pathways polypeptides include any of the following polypeptides: acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. For example, one or more MVA pathway nucleic acids can be introduced into the cells. In some embodiments, the cells contain the upper MVA pathway, which includes AA-CoA thiolase, HMG-CoA synthase, and HMG-CoA reductase nucleic acids. In some embodiments, the cells contain the lower MVA pathway, which includes MVK, PMK, MVD, and IDI nucleic acids. In some embodiments, the cells contain the entire MVA pathway, which includes AA-CoA thiolase, HMG-CoA synthase, HMG-CoA reductase, MVK, PMK, MVD, and IDI nucleic acids. In some embodiments, the cells contain an entire MVA pathway that includes AA-CoA thiolase, HMG-CoA synthase, HMG-CoA reductase, MVK, PMDC, IPK, and IDI nucleic acids. The MVA pathway nucleic acids may be heterologous nucleic acids or duplicate copies of endogenous nucleic acids. In some embodiments, the amount of one or more MVA pathway polypeptides is increased by replacing the endogenous promoters or regulatory regions for the MVA pathway nucleic acids with other promoters and/or regulatory regions that result in greater transcription of the MVA pathway nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

For example, E. coli cells containing a nucleic acid encoding a kudzu isoprene synthase polypeptide and nucleic acids encoding Saccharomyces cerevisia MVK, PMK, MVD, and IDI polypeptides generated isoprene at a rate of $6.67 \times 10^4$ nmol/$L_{broth}$/$OD_{600}$/hr (see Example 8). Additionally, a 14 liter fermentation of E. coli cells with nucleic acids encoding Enterococcus faecalis AA-CoA thiolase, HMG-CoA synthase, and HMG-CoA reductase polypeptides produced 22 grams of mevalonic acid (an intermediate of the MVA pathway). A shake flask of these cells produced 2-4 grams of mevalonic acid per liter. These results indicate that heterologous MVA pathways nucleic acids are active in E. coli. E. coli cells that contain nucleic acids for both the upper MVA pathway and the lower MVA pathway as well as a kudzu isoprene synthase (strain MCM 127) produced significantly more isoprene (874 ⊠ g/$L_{broth}$/hr/OD) compared to E. coli cells with nucleic acids for only the lower MVA pathway and the kudzu isoprene synthase (strain MCM 131) (see Table 3 and Example 8, part VIII).

As another example, E. coli cells containing a nucleic acid encoding a P. alba isoprene synthase polypeptide and a nucleic acid encoding M. mazei MVK polypeptide generated 320.6 g (at a peak specific rate of $9.54 \times 10^4$ nmol/$L_{broth}$/$OD_{600}$/hr (i.e. $9.5 \times 10^{-5}$ mol/$L_{broth}$/$OD_{600}$/hr)) of isoprene during a 67 hour fermentation in the absence of yeast extract feeding or 395.5 g (at a peak specific rate of $8.66 \times 10^4$ nmol/$L_{broth}$/$OD_{600}$/hr) during a 68 hour fermentation in the presence of yeast extract feeding (see Example 10).

In some embodiments, at least a portion of the cells maintain the heterologous isoprene synthase, DXS, IDI, and/or MVA pathway nucleic acid for at least about 5, 10, 20, 50, 75, 100, 200, 300, or more cell divisions in a continuous culture (such as a continuous culture without dilution). In some embodiments of any of the aspects of the invention, the nucleic acid comprising the heterologous or duplicate copy of an endogenous isoprene synthase, DXS, IDI, and/or MVA pathway nucleic acid also comprises a selective marker, such as a kanamycin, ampicillin, carbenicillin, gentamicin, hygromycin, phleomycin, bleomycin, neomycin, or chloramphenicol antibiotic resistance nucleic acid.

Figure 48A:
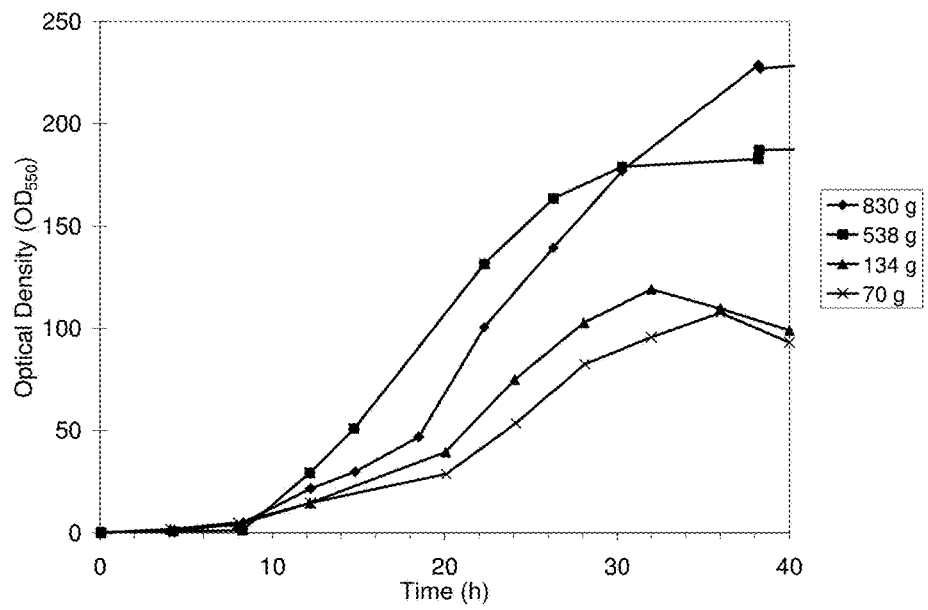
FIG. 48A, FIG. 48B, and FIG. 48C show graphs demonstrating the effect of yeast extract of isoprene production.
Figure 48B:
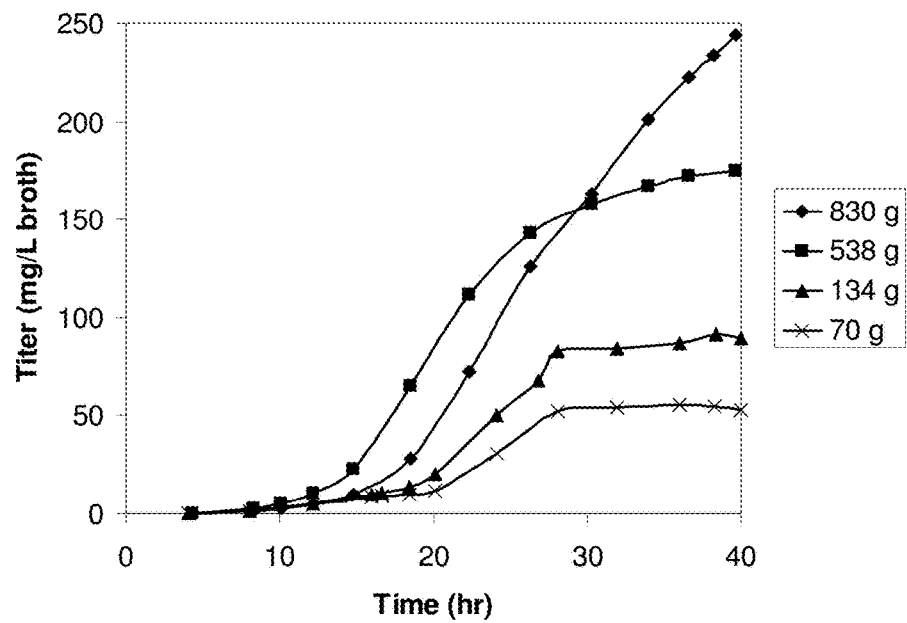
Figure 48C:
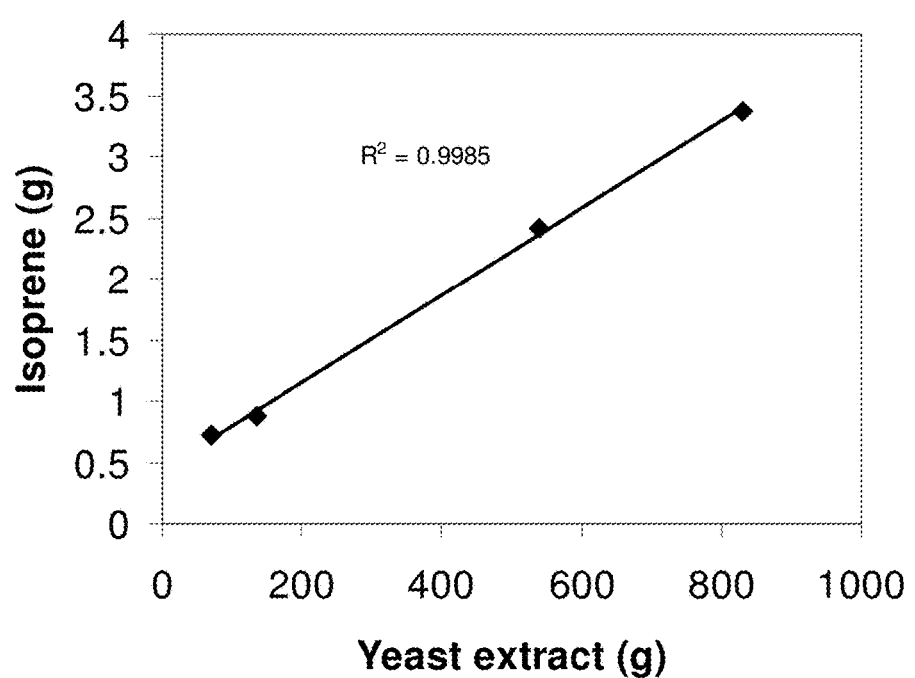

As indicated in Example 7, part VI, the amount of isoprene produced can be further increased by adding yeast extract to the cell culture medium using E. coli cells with kudzu isoprene synthase, S. cerevisia IDI, and E. coli DXS nucleic acids to produce isoprene. In particular, the amount of isoprene produced was linearly proportional to the amount of yeast extract in the cell medium for the concentrations tested (FIG. 48C). Additionally, approximately 0.11 grams of isoprene per liter of broth was produced from a cell medium with yeast extract and glucose (Example 7, part VIII). Increasing the amount of yeast extract in the presence of glucose resulted in more isoprene being produced than increasing the amount of glucose in the presence of yeast extract. Also, increasing the amount of yeast extract allowed the cells to produce a high level of isoprene for a longer length of time and improved the health of the cells.

Figure 69A:
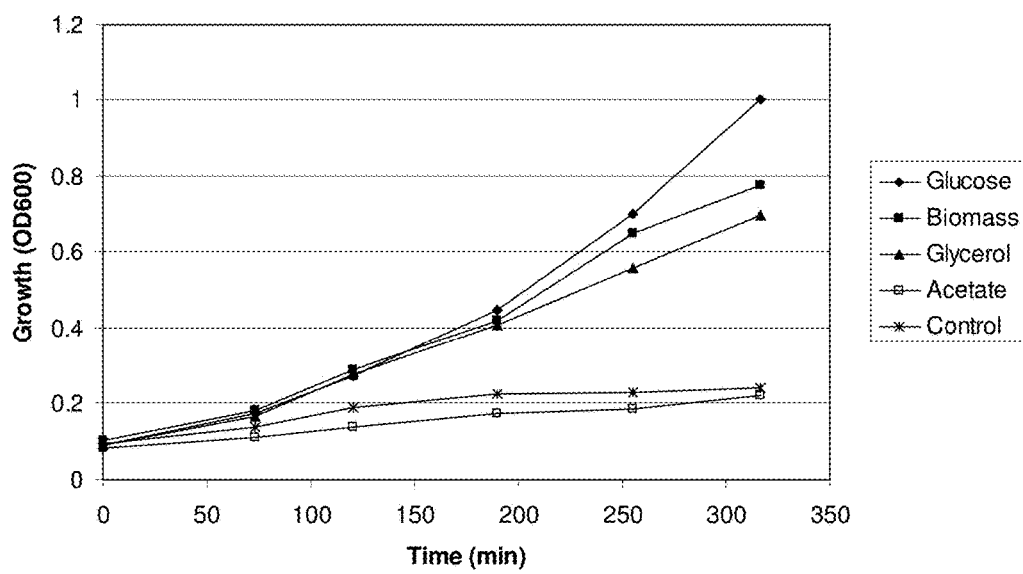
FIG. 69A, FIG. 69B, FIG. 69C, and FIG. 69D show production of isoprene from different carbon sources via the MVA (pathway).
Figure 69B:
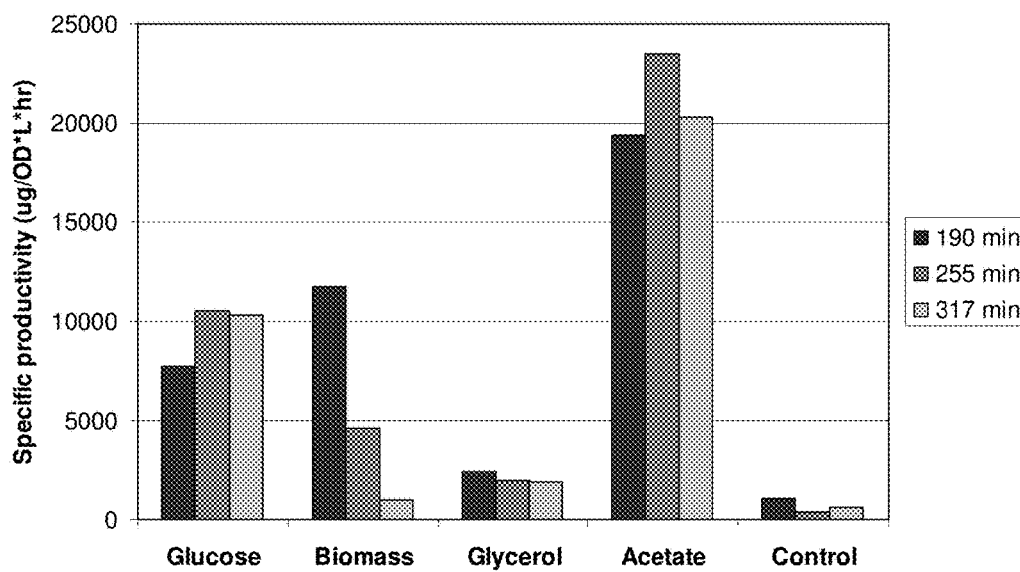
Figure 69C:
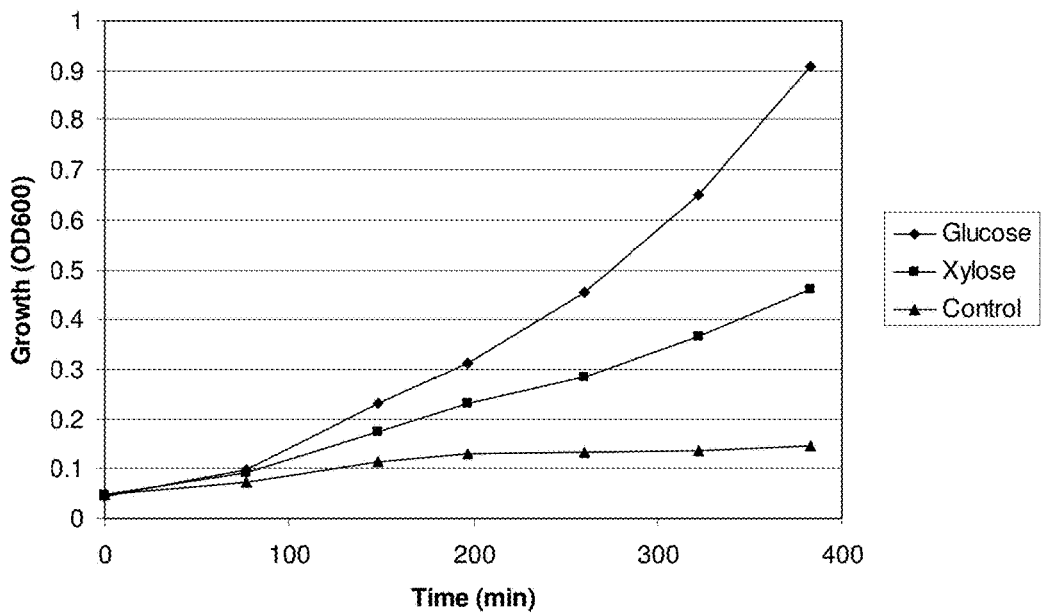

Isoprene production was also demonstrated using three types of hydrolyzed biomass (bagasse, corn stover, and soft wood pulp) as the carbon source (FIGS. 46A-C and FIGS. 69A and 69B). *E. coli* cells with kudzu isoprene synthase, *S. cerevisia* IDI, and *E. coli* DXS nucleic acids produced as much isoprene from these hydrolyzed biomass carbon sources as from the equivalent amount of glucose (e.g., 1% glucose, w/v). *E. coli* cells expressing *P. alba* isoprene synthase and the MVA pathway produced isoprene at a higher initial growth rate from ammonia fiber expansion (AFEX) pretreated corn stover than from the equivalent amount of glucose. (FIGS. 69A and 69B). If desired, any other biomass carbon source can be used in the compositions and methods of the invention. Biomass carbon sources are desirable because they are cheaper than many conventional cell mediums, thereby facilitating the economical production of isoprene.

Figure 47A:
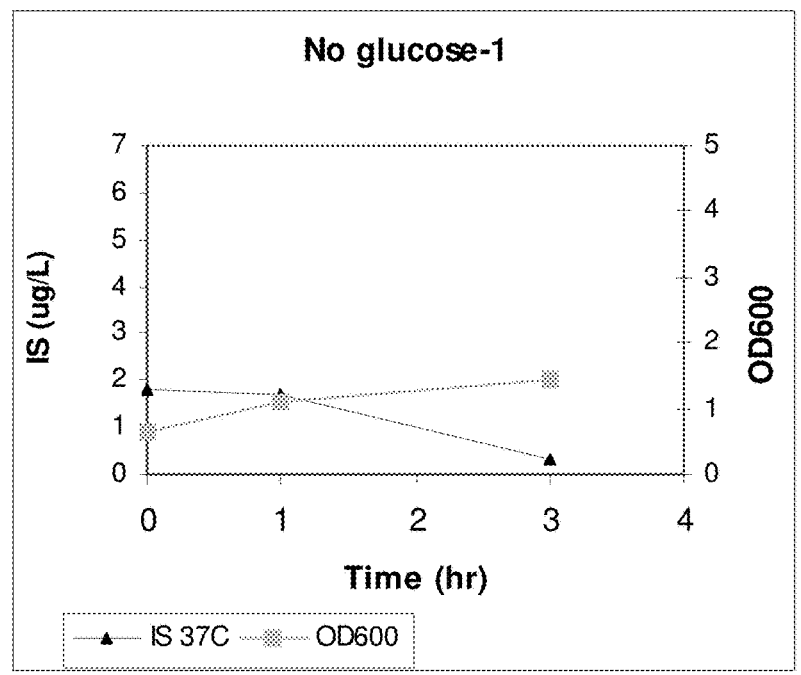
FIG. 47A shows a graph representing isoprene production by BL21 (λDE3) pTrcKudzu yIDI DXS (kan) in a culture with no glucose added. Squares represent OD$_{600}$, and triangles represent isoprene produced (μg/ml).
Figure 47B:
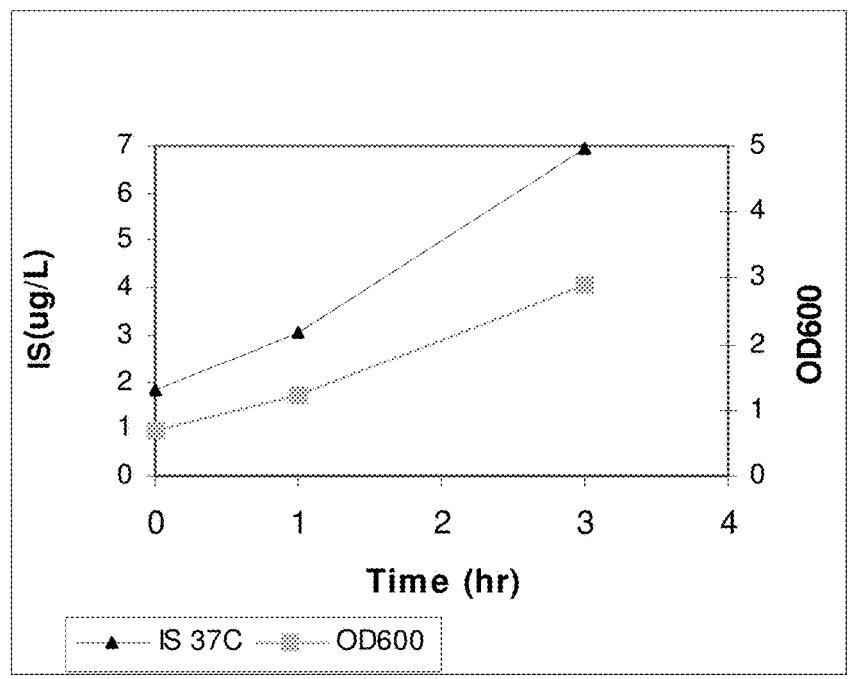
FIG. 47B shows a graph representing isoprene production from 1% glucose feedstock invert sugar by BL21 (λDE3) pTrcKudzu yIDI DXS (kan). Squares represent OD$_{600}$, and triangles represent isoprene produced (μg/ml).
Figure 47C:
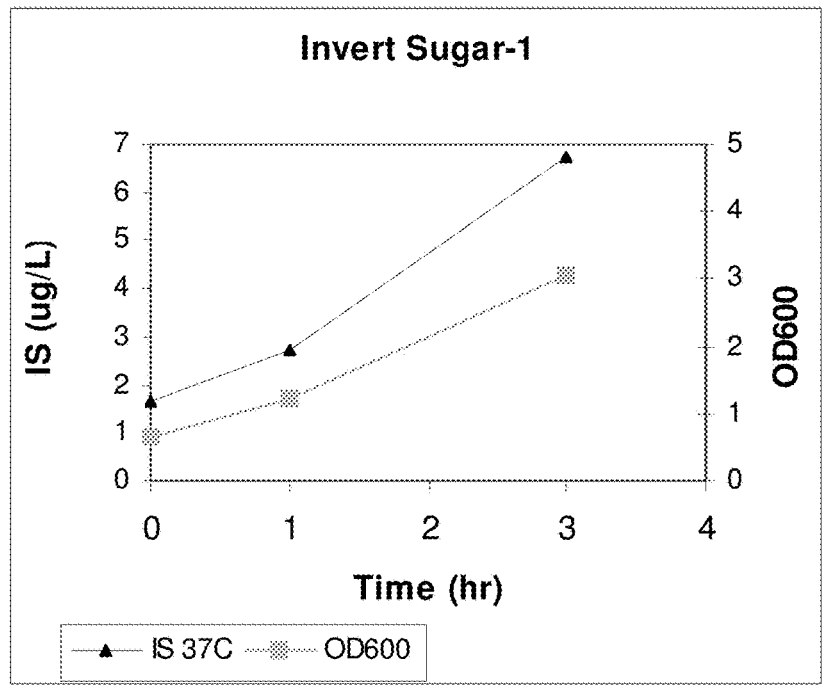
FIG. 47C shows a graph representing isoprene production from 1% invert sugar feedstock by BL21 (λDE3) pTrcKudzu yIDI DXS (kan). Squares represent OD$_{600}$, and triangles represent isoprene produced (μg/ml).
Figure 47D:
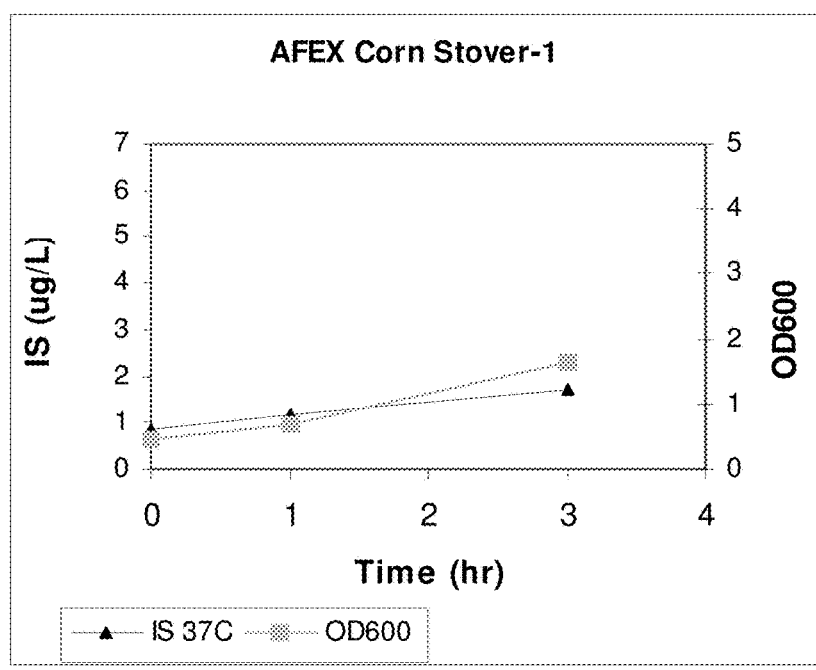
FIG. 47D shows a graph representing isoprene production from 1% AFEX corn stover feedstock by BL21 (λDE3) pTrcKudzu yIDI DXS (kan). Squares represent OD$_{600}$, and triangles represent isoprene produced (μg/ml).

Additionally, invert sugar was shown to function as a carbon source for the generation of isoprene (FIG. 47D).

Additionally, xylose, acetate, and glycerol were also shown to function as a carbon source for the generation of isoprene (FIGS. 69A-69D). For example, *E. coli* cells with *P. alba* isoprene synthase and the MVA pathway grown on acetate as the only carbon source had a specific productivity of isoprene about twice as high as during growth on glucose (Example 10, Part IV; FIGS. 69A and 69B).

In some embodiments, an oil is included in the cell medium. For example, *B. subtilis* cells containing a kudzu isoprene synthase nucleic acid produced isoprene when cultured in a cell medium containing an oil and a source of glucose (Example 4, part III). As another example, *E. coli* fadR atoC mutant cells containing the upper and lower MVA pathway plus kudzu isoprene synthase produced isoprene when cultured in a cell medium containing palm oil and a source of glucose (Example 12, part II). In some embodiments, more than one oil (such as 2, 3, 4, 5, or more oils) is included in the cell medium. While not intending to be bound to any particular theory, it is believed that (i) the oil may increase the amount of carbon in the cells that is available for conversion to isoprene, (ii) the oil may increase the amount of acetyl-CoA in the cells, thereby increasing the carbon flow through the MVA pathway, and/or (ii) the oil may provide extra nutrients to the cells, which is desirable since a lot of the carbon in the cells is converted to isoprene rather than other products. In some embodiments, cells that are cultured in a cell medium containing oil naturally use the MVA pathway to produce isoprene or are genetically modified to contain nucleic acids for the entire MVA pathway. In some embodiments, the oil is partially or completely hydrolyzed before being added to the cell culture medium to facilitate the use of the oil by the host cells.

Exemplary Polypeptides and Nucleic Acids

Various isoprene synthase, DXS, IDI, and/or MVA pathway polypeptides and nucleic acids can be used in the compositions and methods of the invention.

As used herein, "polypeptides" includes polypeptides, proteins, peptides, fragments of polypeptides, and fusion polypeptides that include part or all of a first polypeptide (e.g., an isoprene synthase, DXS, IDI, or MVA pathway polypeptide) and part or all of a second polypeptide (e.g., a peptide that facilitates purification or detection of the fusion polypeptide, such as a His-tag). In some embodiments, the fusion polypeptide has an activity of two or more MVA pathway polypeptides (such as AA-CoA thiolase and HMG-CoA reductase polypeptides). In some embodiments, the polypeptide is a naturally-occurring polypeptide (such as the polypeptide encoded by an *Enterococcus faecalis* mvaE nucleic acid) that has an activity of two or more MVA pathway polypeptides.

In various embodiments, a polypeptide has at least or about 50, 100, 150, 175, 200, 250, 300, 350, 400, or more amino acids. In some embodiments, the polypeptide fragment contains at least or about 25, 50, 75, 100, 150, 200, 300, or more contiguous amino acids from a full-length polypeptide and has at least or about 5%, 10%, 20%, 30%, 40%, 50%, 60%, 70%, 80%, 90%, 95%, or 100% of an activity of a corresponding full-length polypeptide. In particular embodiments, the polypeptide includes a segment of or the entire amino acid sequence of any naturally-occurring isoprene synthase, DXS, IDI, or MVA pathway polypeptide. In some embodiments, the polypeptide has one or more mutations compared to the sequence of a wild-type (i.e., a sequence occurring in nature) isoprene synthase, DXS, IDI, or MVA pathway polypeptide.

In some embodiments, the polypeptide is an isolated polypeptide. As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

In some embodiments, the polypeptide is a heterologous polypeptide. By "heterologous polypeptide" is meant a polypeptide whose amino acid sequence is not identical to that of another polypeptide naturally expressed in the same host cell.

As used herein, a "nucleic acid" refers to two or more deoxyribonucleotides and/or ribonucleotides in either single or double-stranded form. In some embodiments, the nucleic acid is a recombinant nucleic acid. By "recombinant nucleic acid" means a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences. In some embodiments, an isoprene synthase, DXS, IDI, or MVA pathway nucleic acid is operably linked to another nucleic acid encoding all or a portion of another polypeptide such that the recombinant nucleic acid encodes a fusion polypeptide that includes an isoprene synthase, DXS, IDI, or MVA pathway polypeptide and all or part of another polypeptide (e.g., a peptide that facilitates purification or detection of the fusion polypeptide, such as a His-tag). In some embodiments, part or all of a recombinant nucleic acid is chemically synthesized.

In some embodiments, the nucleic acid is a heterologous nucleic acid. By "heterologous nucleic acid" is meant a nucleic acid whose nucleic acid sequence is not identical to that of another nucleic acid naturally found in the same host cell.

In particular embodiments, the nucleic acid includes a segment of or the entire nucleic acid sequence of any naturally-occurring isoprene synthase, DXS, IDI, or MVA pathway nucleic acid.

In some embodiments, the nucleic acid includes at least or about 50, 100, 150, 200, 300, 400, 500, 600, 700, 800, or more contiguous nucleotides from a naturally-occurring isoprene synthase nucleic acid DXS, IDI, or MVA pathway nucleic acid. In some embodiments, the nucleic acid has one or more mutations compared to the sequence of a wild-type (i.e., a sequence occurring in nature) isoprene synthase, DXS, IDI, or MVA pathway nucleic acid. In some embodiments, the nucleic acid has one or more mutations (e.g., a silent mutation) that increase the transcription or translation of isoprene synthase, DXS, IDI, or MVA pathway nucleic acid. In some embodiments, the nucleic acid is a degenerate variant of any nucleic acid encoding an isoprene synthase, DXS, IDI, or MVA pathway polypeptide.

"Codon degeneracy" refers to divergence in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a nucleic acid for improved expression in a host cell, it is desirable in some embodiments to design the nucleic acid such that its frequency of codon usage approaches the frequency of preferred codon usage of the host cell.

The accession numbers of exemplary isoprene synthase, DXS, IDI, and/or MVA pathway polypeptides and nucleic acids are listed in Appendix 1 (the accession numbers of Appendix 1 and their corresponding sequences are herein incorporated by reference in their entireties, particularly with respect to the amino acid and nucleic acid sequences of isoprene synthase, DXS, IDI, and/or MVA pathway polypeptides and nucleic acids). The Kegg database also contains the amino acid and nucleic acid sequences of numerous exemplary isoprene synthase, DXS, IDI, and/or MVA pathway polypeptides and nucleic acids (see, for example, the world-wide web at "genome.jp/kegg/pathway/map/map00100.html" and the sequences therein, which are each hereby incorporated by reference in their entireties, particularly with respect to the amino acid and nucleic acid sequences of isoprene synthase, DXS, IDI, and/or MVA pathway polypeptides and nucleic acids). In some embodiments, one or more of the isoprene synthase, DXS, IDI, and/or MVA pathway polypeptides and/or nucleic acids have a sequence identical to a sequence publicly available on Dec. 12, 2007 or Dec. 11, 2008, such as any of the sequences that correspond to any of the accession numbers in Appendix 1 or any of the sequences present in the Kegg database. Additional exemplary isoprene synthase, DXS, IDI, and/or MVA pathway polypeptides and nucleic acids are described further below.

Exemplary Isoprene Synthase Polypeptides and Nucleic Acids

As noted above, isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Standard methods can be used to determine whether a polypeptide has isoprene synthase polypeptide activity by measuring the ability of the polypeptide to convert DMAPP into isoprene in vitro, in a cell extract, or in vivo. In an exemplary assay, cell extracts are prepared by growing a strain (e.g., the *E. coli*/pTrcKudzu strain described herein) in the shake flask method as described in Example 1. After induction is complete, approximately 10 mLs of cells are pelleted by centrifugation at 7000×g for 10 minutes and resuspended in 5 ml of PEB without glycerol. The cells are lysed using a French Pressure cell using standard procedures. Alternatively the cells are treated with lysozyme (Ready-Lyse lysozyme solution; EpiCentre) after a freeze/thaw at −80 C.

Isoprene synthase polypeptide activity in the cell extract can be measured, for example, as described in Silver et al., *J. Biol. Chem.* 270:13010-13016, 1995 and references therein, which are each hereby incorporated by reference in their entireties, particularly with respect to assays for isoprene synthase polypeptide activity. DMAPP (Sigma) is evaporated to dryness under a stream of nitrogen and rehydrated to a concentration of 100 mM in 100 mM potassium phosphate buffer pH 8.2 and stored at −20 0 C. To perform the assay, a solution of 5 µl of 1M $MgCl_2$, 1 mM (250 ⊠ g/ml) DMAPP, 65 ⊠ l of Plant Extract Buffer (PEB) (50 mM Tris-HCl, pH 8.0, 20 mM $MgCl_2$, 5% glycerol, and 2 mM DTT) is added to 25 ⊠ l of cell extract in a 20 ml Headspace vial with a metal screw cap and teflon coated silicon septum (Agilent Technologies) and cultured at 37 0 C for 15 minutes with shaking. The reaction is quenched by adding 200 ⊠ l of 250 mM EDTA and quantified by GC/MS as described in Example 1, part II.

Exemplary isoprene synthase nucleic acids include nucleic acids that encode a polypeptide, fragment of a polypeptide, peptide, or fusion polypeptide that has at least one activity of an isoprene synthase polypeptide. Exemplary isoprene synthase polypeptides and nucleic acids include naturally-occurring polypeptides and nucleic acids from any of the source organisms described herein as well as mutant polypeptides and nucleic acids derived from any of the source organisms described herein.

In some embodiments, the isoprene synthase polypeptide or nucleic acid is from the family Fabaceae, such as the Faboideae subfamily. In some embodiments, the isoprene synthase polypeptide or nucleic acid is a polypeptide or nucleic acid from *Pueraria montana* (kudzu) (Sharkey et al., Plant Physiology 137: 700-712, 2005), *Pueraria lobata*, poplar (such as *Populus alba, Populus nigra, Populus trichocarpa, Populus alba×tremula* (CAC35696), or *Populus alba*) (Sasaki et al., *FEBS Letters* 579(11): 2514-2518, 2005; Miller et al., *Planta* 213: 483-487, 2001), aspen (such as *Populus tremuloides*) (Silver et al., JBC 270(22): 13010-1316, 1995), or English Oak (*Quercus robur*) (Zimmer et al., WO 98/02550), which are each hereby incorporated by reference in their entireties, particularly with respect to isoprene synthase nucleic acids and the expression of isoprene synthase polypeptides. Suitable isoprene synthases include, but are not limited to, those identified by Genbank Accession Nos. AY341431, AY316691, AY279379, AJ457070, and AY182241, which are each hereby incorporated by reference in their entireties, particularly with respect to sequences of isoprene synthase nucleic acids and polypeptides. In some embodiments, the isoprene synthase polypeptide or nucleic acid is not a naturally-occurring polypeptide or nucleic acid from *Quercus robur* (i.e., the isoprene synthase polypeptide or nucleic acid is an isoprene synthase polypeptide or nucleic acid other than a naturally-occurring polypeptide or nucleic acid from *Quercus robur*). In some embodiments, the isoprene synthase nucleic acid or polypeptide is a naturally-occurring polypeptide or nucleic acid from poplar. In some embodiments, the isoprene synthase nucleic acid or polypeptide is not a naturally-occurring polypeptide or nucleic acid from poplar.

Exemplary DXS Polypeptides and Nucleic Acids

As noted above, 1-deoxy-D-xylulose-5-phosphate synthase (DXS) polypeptides convert pyruvate and D-glyceraldehyde-3-phosphate into 1-deoxy-D-xylulose-5-phosphate. Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS nucleic acids include nucleic acids that encode a polypeptide, fragment of a polypeptide, peptide, or fusion polypeptide that has at least one activity of a DXS polypeptide. Exemplary DXS polypeptides and nucleic acids include naturally-occurring polypeptides and nucleic acids from any of the source organisms described herein as well as mutant polypeptides and nucleic acids derived from any of the source organisms described herein.

Exemplary IDI Polypeptides and Nucleic Acids

Isopentenyl diphosphate isomerase polypeptides (isopentenyl-diphosphate delta-isomerase or IDI) catalyses the interconversion of isopentenyl diphosphate (IPP) and dimethylallyl diphosphate (DMAPP) (e.g., converting IPP into DMAPP and/or converting DMAPP into IPP).

Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Exemplary MVA Pathway Polypeptides and Nucleic Acids

Exemplary MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein as well as mutant polypeptides and nucleic acids derived from any of the source organisms described herein.

In particular, acetyl-CoA acetyltransferase polypeptides (AA-CoA thiolase or AACT) convert two molecules of acetyl-CoA into acetoacetyl-CoA. Standard methods (such as those described herein) can be used to determine whether a polypeptide has AA-CoA thiolase polypeptide activity by measuring the ability of the polypeptide to convert two molecules of acetyl-CoA into acetoacetyl-CoA in vitro, in a cell extract, or in vivo.

3-hydroxy-3-methylglutaryl-CoA synthase (HMG-CoA synthase or HMGS) polypeptides convert acetoacetyl-CoA into 3-hydroxy-3-methylglutaryl-CoA. Standard methods (such as those described herein) can be used to determine whether a polypeptide has HMG-CoA synthase polypeptide activity by measuring the ability of the polypeptide to convert acetoacetyl-CoA into 3-hydroxy-3-methylglutaryl-CoA in vitro, in a cell extract, or in vivo.

3-hydroxy-3-methylglutaryl-CoA reductase (HMG-CoA reductase or HMGR) polypeptides convert 3-hydroxy-3-methylglutaryl-CoA into mevalonate. Standard methods (such as those described herein) can be used to determine whether a polypeptide has HMG-CoA reductase polypeptide activity by measuring the ability of the polypeptide to convert 3-hydroxy-3-methylglutaryl-CoA into mevalonate in vitro, in a cell extract, or in vivo.

Mevalonate kinase (MVK) polypeptide phosphorylates mevalonate to form mevalonate-5-phosphate. Standard methods (such as those described herein) can be used to determine whether a polypeptide has MVK polypeptide activity by measuring the ability of the polypeptide to convert mevalonate into mevalonate-5-phosphate in vitro, in a cell extract, or in vivo.

Phosphomevalonate kinase (PMK) polypeptides phosphorylates mevalonate-5-phosphate to form mevalonate-5-diphosphate. Standard methods (such as those described herein) can be used to determine whether a polypeptide has PMK polypeptide activity by measuring the ability of the polypeptide to convert mevalonate-5-phosphate into mevalonate-5-diphosphate in vitro, in a cell extract, or in vivo.

Diphosphomevalonate decarboxylase (MVD or DPMDC) polypeptides convert mevalonate-5-diphosphate into isopentenyl diphosphate (IPP). Standard methods (such as those described herein) can be used to determine whether a polypeptide has MVD polypeptide activity by measuring the ability of the polypeptide to convert mevalonate-5-diphosphate into IPP in vitro, in a cell extract, or in vivo.

Phosphomevalonate decarboxylase (PMDC) polypeptides convert mevalonate-5-phosphate into isopentenyl phosphate (IP). Standard methods (such as those described herein) can be used to determine whether a polypeptide has PMDC polypeptide activity by measuring the ability of the polypeptide to convert mevalonate-5-phosphate into IP in vitro, in a cell extract, or in vivo.

Isopentenyl phosphate kinase (IPK) polypeptides phosphorylate isopentyl phosphate (IP) to form isopentenyl diphosphate (IPP). Standard methods (such as those described herein) can be used to determine whether a polypeptide has IPK polypeptide activity by measuring the ability of the polypeptide to convert IP into IPP in vitro, in a cell extract, or in vivo.

Exemplary IDI polypeptides and nucleic acids are described above.

Exemplary Methods for Isolating Nucleic Acids

Isoprene synthase, DXS, IDI, and/or MVA pathway nucleic acids can be isolated using standard methods. Methods of obtaining desired nucleic acids from a source organism of interest (such as a bacterial genome) are common and well known in the art of molecular biology (see, for example, WO 2004/033646 and references cited therein, which are each hereby incorporated by reference in their entireties, particularly with respect to the isolation of nucleic acids of interest). For example, if the sequence of the nucleic acid is known (such as any of the known nucleic acids described herein), suitable genomic libraries may be created by restriction endonuclease digestion and may be screened with probes complementary to the desired nucleic acid sequence. Once the sequence is isolated, the DNA may be amplified using standard primer directed amplification methods such as polymerase chain reaction (PCR) (U.S. Pat. No. 4,683,202, which is incorporated by reference in its entirety, particularly with respect to PCR methods) to obtain amounts of DNA suitable for transformation using appropriate vectors.

Alternatively, isoprene synthase, DXS, IDI, and/or MVA pathway nucleic acids (such as any isoprene synthase, DXS, IDI, and/or MVA pathway nucleic acids with a known nucleic acid sequence) can be chemically synthesized using standard methods.

Additional isoprene synthase, DXS, IDI, or MVA pathway polypeptides and nucleic acids which may be suitable for use in the compositions and methods described herein can be identified using standard methods. For example, cosmid libraries of the chromosomal DNA of organisms known to produce isoprene naturally can be constructed in organisms such as *E. coli*, and then screened for isoprene production. In particular, cosmid libraries may be created where large segments of genomic DNA (35-45 kb) are packaged into vectors and used to transform appropriate hosts. Cosmid vectors are unique in being able to accommodate large quantities of DNA. Generally cosmid vectors have at least one copy of the cos DNA sequence which is needed for packaging and subsequent circularization of the heterologous DNA. In addition to the cos sequence, these vectors also contain an origin of replication such as ColEI and drug resistance markers such as a nucleic acid resistant to ampicillin or neomycin. Methods of using cosmid vectors for the transformation of suitable bacterial hosts are well described in Sambrook et al., Molecular Cloning: A Laboratory Manual, 2$^{nd}$ ed., Cold Spring Harbor, 1989, which is hereby incorporated by reference in its entirety, particularly with respect to transformation methods.

Typically to clone cosmids, heterologous DNA is isolated using the appropriate restriction endonucleases and ligated adjacent to the cos region of the cosmid vector using the appropriate ligases. Cosmid vectors containing the linearized heterologous DNA are then reacted with a DNA packaging vehicle such as bacteriophage. During the packaging process, the cos sites are cleaved and the heterologous DNA is packaged into the head portion of the bacterial viral particle. These particles are then used to transfect suitable host cells such as *E. coli*. Once injected into the cell, the heterologous DNA circularizes under the influence of the cos sticky ends. In this manner, large segments of heterologous DNA can be introduced and expressed in host cells.

Additional methods for obtaining isoprene synthase, DXS, IDI, and/or MVA pathway nucleic acids include screening a metagenomic library by assay (such as the headspace assay described herein) or by PCR using primers directed against nucleotides encoding for a length of conserved amino acids (for example, at least 3 conserved amino acids). Conserved amino acids can be identified by aligning amino acid sequences of known isoprene synthase, DXS, IDI, and/or MVA pathway polypeptides. Conserved amino acids for isoprene synthase polypeptides can be identified based on aligned sequences of known isoprene synthase polypeptides. An organism found to produce isoprene naturally can be subjected to standard protein purification methods (which are well known in the art) and the resulting purified polypeptide can be sequenced using standard methods. Other methods are found in the literature (see, for example, Julsing et al., *Applied. Microbiol. Biotechnol.* 75: 1377-84, 2007; Withers et al., *Appl Environ Microbiol.* 73(19):6277-83, 2007, which are each hereby incorporated by reference in their entireties, particularly with respect to identification of nucleic acids involved in the synthesis of isoprene).

Additionally, standard sequence alignment and/or structure prediction programs can be used to identify additional DXS, IDI, or MVA pathway polypeptides and nucleic acids based on the similarity of their primary and/or predicted polypeptide secondary structure with that of known DXS, IDI, or MVA pathway polypeptides and nucleic acids. Standard databases such as the swissprot-trembl database (world-wide web at "expasy.org", Swiss Institute of Bioinformatics Swiss-Prot group CMU-1 rue Michel Servet CH-1211 Geneva 4, Switzerland) can also be used to identify isoprene synthase, DXS, IDI, or MVA pathway polypeptides and nucleic acids. The secondary and/or tertiary structure of an isoprene synthase, DXS, IDI, or MVA pathway polypeptide can be predicted using the default settings of standard structure prediction programs, such as PredictProtein (630 West, 168 Street, BB217, New York, N.Y. 10032, USA). Alternatively, the actual secondary and/or tertiary structure of an isoprene synthase, DXS, IDI, or MVA pathway polypeptide can be determined using standard methods. Additional isoprene synthase, DXS, IDI, or MVA pathway nucleic acids can also be identified by hybridization to probes generated from known isoprene synthase, DXS, IDI, or MVA pathway nucleic acids.

Exemplary Promoters and Vectors

Any of the isoprene synthase, DXS, IDI, or MVA pathway nucleic acid described herein can be included in one or more vectors. Accordingly, the invention also features vectors with one more nucleic acids encoding any of the isoprene synthase, DXS, IDI, or MVA pathway polypeptides that are described herein. As used herein, a "vector" means a construct that is capable of delivering, and desirably expressing one or more nucleic acids of interest in a host cell. Examples of vectors include, but are not limited to, plasmids, viral vectors, DNA or RNA expression vectors, cosmids, and phage vectors. In some embodiments, the vector contains a nucleic acid under the control of an expression control sequence.

As used herein, an "expression control sequence" means a nucleic acid sequence that directs transcription of a nucleic acid of interest. An expression control sequence can be a promoter, such as a constitutive or an inducible promoter, or an enhancer. An "inducible promoter" is a promoter that is active under environmental or developmental regulation. The expression control sequence is operably linked to the nucleic acid segment to be transcribed.

In some embodiments, the vector contains a selective marker. The term "selective marker" refers to a nucleic acid capable of expression in a host cell that allows for ease of selection of those host cells containing an introduced nucleic acid or vector. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. Exemplary nutritional selective markers include those markers known in the art as amdS, argB, and pyr4. Markers useful in vector systems for transformation of *Trichoderma* are known in the art (see, e.g., Finkelstein, Chapter 6 in Biotechnology of Filamentous Fungi, Finkelstein et al., Eds. Butterworth-Heinemann, Boston, Mass., Chap. 6, 1992; and Kinghorn et al., Applied Molecular Genetics of Filamentous Fungi, Blackie Academic and Professional, Chapman and Hall, London, 1992, which are each hereby incorporated by reference in their entireties, particularly with respect to selective markers). In some embodiments, the selective marker is the amdS nucleic acid, which encodes the enzyme acetamidase, allowing transformed cells to grow on acetamide as a nitrogen source. The use of an *A. nidulans* amdS nucleic acid as a selective marker is described in Kelley et al., *EMBO J.* 4:475-479, 1985 and Penttila et al., *Gene* 61:155-164, 1987 (which are each hereby incorporated by reference in their entireties, particularly with respect to selective markers). In some embodiments, an isoprene synthase, DXS, IDI, or MVA pathway nucleic acid integrates into a chromosome of the cells without a selective marker.

Suitable vectors are those which are compatible with the host cell employed. Suitable vectors can be derived, for example, from a bacterium, a virus (such as bacteriophage T7 or a M-13 derived phage), a cosmid, a yeast, or a plant. Protocols for obtaining and using such vectors are known to those in the art (see, for example, Sambrook et al., Molecular Cloning: A Laboratory Manual, $2^{nd}$ ed., Cold Spring Harbor, 1989, which is hereby incorporated by reference in its entirety, particularly with respect to the use of vectors).

Promoters are well known in the art. Any promoter that functions in the host cell can be used for expression of an isoprene synthase, DXS, IDI, or MVA pathway nucleic acid in the host cell. Initiation control regions or promoters, which are useful to drive expression of isoprene synthase, DXS, IDI, or MVA pathway nucleic acids in various host cells are numerous and familiar to those skilled in the art (see, for example, WO 2004/033646 and references cited therein, which are each hereby incorporated by reference in their entireties, particularly with respect to vectors for the expression of nucleic acids of interest). Virtually any promoter capable of driving these nucleic acids is suitable for the present invention including, but not limited to, CYC1, HIS3, GAL1, GAL10, ADH1, PGK, PHO5, GAPDH, ADCI, TRP1, URA3, LEU2, ENO, and TPI (useful for expression in *Saccharomyces*); AOX1 (useful for expression in *Pichia*); and lac, trp, ☒ $P_L$, ☒ $P_R$, T7, tac, and trc (useful for expression in *E. coli*).

In some embodiments, a glucose isomerase promoter is used (see, for example, U.S. Pat. No. 7,132,527 and references cited therein, which are each hereby incorporated by reference in their entireties, particularly with respect promoters and plasmid systems for expressing polypeptides of interest). Reported glucose isomerase promoter mutants can be used to vary the level of expression of the polypeptide encoded by a nucleic acid operably linked to the glucose isomerase promoter (U.S. Pat. No. 7,132,527). In various embodiments, the glucose isomerase promoter is contained in a low, medium, or high copy plasmid (U.S. Pat. No. 7,132,527).

In various embodiments, an isoprene synthase, DXS, IDI, and/or MVA pathway nucleic acid is contained in a low copy plasmid (e.g., a plasmid that is maintained at about 1 to about 4 copies per cell), medium copy plasmid (e.g., a plasmid that is maintained at about 10 to about 15 copies per cell), or high copy plasmid (e.g., a plasmid that is maintained at about 50 or more copies per cell). In some embodiments, the heterologous or extra endogenous isoprene synthase, DXS, IDI, or MVA pathway nucleic acid is operably linked to a T7 promoter. In some embodiments, the heterologous or extra endogenous isoprene synthase, DXS, IDI, or MVA pathway nucleic acid operably linked to a T7 promoter is contained in a medium or high copy plasmid. In some embodiments, the heterologous or extra endogenous isoprene synthase, DXS, IDI, or MVA pathway nucleic acid is operably linked to a Trc promoter. In some embodiments, the heterologous or extra endogenous isoprene synthase, DXS, IDI, or MVA pathway nucleic acid operably linked to a Trc promoter is contained in a medium or high copy plasmid. In some embodiments, the heterologous or extra endogenous isoprene synthase, DXS, IDI, or MVA pathway nucleic acid is operably linked to a Lac promoter. In some embodiments, the heterologous or extra endogenous isoprene synthase, DXS, IDI, or MVA pathway nucleic acid operably linked to a Lac promoter is contained in a low copy plasmid. In some embodiments, the heterologous or extra endogenous isoprene synthase, DXS, IDI, or MVA pathway nucleic acid is operably linked to an endogenous promoter, such as an endogenous *Escherichia*, *Panteoa*, *Bacillus*, *Yarrowia*, *Streptomyces*, or *Trichoderma* promoter or an endogenous alkaline serine protease, isoprene synthase, DXS, IDI, or MVA pathway promoter. In some embodiments, the heterologous or extra endogenous isoprene synthase, DXS, IDI, or MVA pathway nucleic acid operably linked to an endogenous promoter is contained in a high copy plasmid. In some embodiments, the vector is a replicating plasmid that does not integrate into a chromosome in the cells. In some embodiments, part or all of the vector integrates into a chromosome in the cells.

In some embodiments, the vector is any vector which when introduced into a fungal host cell is integrated into the host cell genome and is replicated. Reference is made to the Fungal Genetics Stock Center Catalogue of Strains (FGSC, the world-wide web at "fgsc.net" and the references cited therein, which are each hereby incorporated by reference in their entireties, particularly with respect to vectors) for a list of vectors. Additional examples of suitable expression and/or integration vectors are provided in Sambrook et al., Molecular Cloning: A Laboratory Manual, $2^{nd}$ ed., Cold Spring Harbor, 1989, Current Protocols in Molecular Biology (F. M. Ausubel et al. (eds) 1987, Supplement 30, section 7.7.18); van den Hondel et al. in Bennett and Lasure (Eds.) More Gene Manipulations in Fungi, Academic Press pp. 396-428, 1991; and U.S. Pat. No. 5,874,276, which are each hereby incorporated by reference in their entireties, particularly with respect to vectors. Particularly useful vectors include pFB6, pBR322, PUC 18, pUC100, and pENTR/D.

In some embodiments, an isoprene synthase, DXS, IDI, or MVA pathway nucleic acid is operably linked to a suitable promoter that shows transcriptional activity in a fungal host cell. The promoter may be derived from one or more nucleic acids encoding a polypeptide that is either endogenous or heterologous to the host cell. In some embodiments, the promoter is useful in a *Trichoderma* host. Suitable non-limiting examples of promoters include cbh1, cbh2, egl1, egl2, pepA, hfb1, hfb2, xyn1, and amy. In some embodiments, the promoter is one that is native to the host cell. For example, in some embodiments when *T. reesei* is the host, the promoter is a native *T. reesei* promoter. In some embodiments, the promoter is *T. reesei* cbh1, which is an inducible promoter and has been deposited in GenBank under Accession No. D86235, which is incorporated by reference in its entirety, particularly with respect to promoters. In some embodiments, the promoter is one that is heterologous to the fungal host cell. Other examples of useful promoters include promoters from the genes of *A. awamori* and *A. niger* glucoamylase (glaA) (Nunberg et al., *Mol. Cell Biol.* 4:2306-2315, 1984 and Boel et al., *EMBO J.* 3:1581-1585, 1984, which are each hereby incorporated by reference in their entireties, particularly with respect to promoters); *Aspergillus niger* alpha amylases, *Aspergillus oryzae* TAKA amylase, *T. reesei* xln1, and the *T. reesei* cellobiohydrolase 1 (EP 137280, which is incorporated by reference in its entirety, particularly with respect to promoters).

In some embodiments, the expression vector also includes a termination sequence. Termination control regions may also be derived from various genes native to the host cell. In some embodiments, the termination sequence and the promoter sequence are derived from the same source. In another embodiment, the termination sequence is endogenous to the host cell. A particularly suitable terminator sequence is cbh1 derived from a *Trichoderma* strain (such as *T. reesei*). Other useful fungal terminators include the terminator from an *A. niger* or *A. awamori* glucoamylase nucleic acid (Nunberg et al., *Mol. Cell Biol.* 4:2306-2315, 1984 and Boel et al., *EMBO J.* 3:1581-1585, 1984; which are each hereby incorporated by reference in their entireties, particularly with respect to fungal terminators). Optionally, a termination site may be included. For effective expression of the polypeptides, DNA encoding the polypeptide are linked operably through initiation codons to selected expression control regions such that expression results in the formation of the appropriate messenger RNA.

In some embodiments, the promoter, coding, region, and terminator all originate from the isoprene synthase, DXS, IDI, or MVA pathway nucleic acid to be expressed. In some embodiments, the coding region for an isoprene synthase, DXS, IDI, or MVA pathway nucleic acid is inserted into a general-purpose expression vector such that it is under the transcriptional control of the expression construct promoter and terminator sequences. In some embodiments, genes or part thereof are inserted downstream of the strong cbh1 promoter.

An isoprene synthase, DXS, IDI, or MVA pathway nucleic acid can be incorporated into a vector, such as an expression vector, using standard techniques (Sambrook et al., Molecular Cloning: A Laboratory Manual, Cold Spring Harbor, 1982, which is hereby incorporated by reference in its entirety, particularly with respect to the screening of appropriate DNA sequences and the construction of vectors). Methods used to ligate the DNA construct comprising a nucleic acid of interest (such as an isoprene synthase, DXS, IDI, or MVA pathway nucleic acid), a promoter, a terminator, and other sequences and to insert them into a suitable vector are well known in the art. For example, restriction enzymes can be used to cleave the isoprene synthase, DXS, IDI, or MVA pathway nucleic acid and the vector. Then, the compatible ends of the cleaved isoprene synthase, DXS, IDI, or MVA pathway nucleic acid and the cleaved vector can be ligated. Linking is generally accomplished by ligation at convenient restriction sites. If such sites do not exist, the synthetic oligonucleotide linkers are used in accordance with conventional practice (see, Sambrook et al., Molecular Cloning: A Laboratory Manual, $2^{nd}$ ed., Cold Spring Harbor, 1989, and Bennett and Lasure, More Gene Manipulations in Fungi, Academic Press, San Diego, pp 70-76, 1991, which are each hereby incorporated by reference in their entireties, particularly with respect to oligonucleotide linkers). Additionally, vectors can be constructed using known recombination techniques (e.g., Invitrogen Life Technologies, Gateway Technology).

In some embodiments, it may be desirable to over-express isoprene synthase, DXS, IDI, or MVA pathway nucleic acids at levels far higher than currently found in naturally-occurring cells. This result may be accomplished by the selective cloning of the nucleic acids encoding those polypeptides into multicopy plasmids or placing those nucleic acids under a strong inducible or constitutive promoter. Methods for over-expressing desired polypeptides are common and well known in the art of molecular biology and examples may be found in Sambrook et al., Molecular Cloning: A Laboratory Manual, $2^{nd}$ ed., Cold Spring Harbor, 1989, which is hereby incorporated by reference in its entirety, particularly with respect to cloning techniques.

The following resources include descriptions of additional general methodology useful in accordance with the invention: Kreigler, Gene Transfer and Expression; A Laboratory Manual, 1990 and Ausubel et al., Eds. Current Protocols in Molecular Biology, 1994, which are each hereby incorporated by reference in their entireties, particularly with respect to molecular biology and cloning techniques.

Exemplary Source Organisms

Isoprene synthase, DXS, IDI, or MVA pathway nucleic acids (and their encoded polypeptides) can be obtained from any organism that naturally contains isoprene synthase, DXS, IDI, and/or MVA pathway nucleic acids. As noted above, isoprene is formed naturally by a variety of organisms, such as bacteria, yeast, plants, and animals. Organisms contain the MVA pathway, DXP pathway, or both the MVA and DXP pathways for producing isoprene (FIG. 19). Thus, DXS nucleic acids can be obtained, e.g., from any organism that contains the DXP pathway or contains both the MVA and DXP pathways. IDI and isoprene synthase nucleic acids can be obtained, e.g., from any organism that contains the MVA pathway, DXP pathway, or both the MVA and DXP pathways. MVA pathway nucleic acids can be obtained, e.g., from any organism that contains the MVA pathway or contains both the MVA and DXP pathways.

In some embodiments, the nucleic acid sequence of the isoprene synthase, DXS, IDI, or MVA pathway nucleic is identical to the sequence of a nucleic acid that is produced by any of the following organisms in nature. In some embodiments, the amino acid sequence of the isoprene synthase, DXS, IDI, or MVA pathway polypeptide is identical to the sequence of a polypeptide that is produced by any of the following organisms in nature. In some embodiments, the isoprene synthase, DXS, IDI, or MVA pathway nucleic acid or polypeptide is a mutant nucleic acid or polypeptide derived from any of the organisms described herein. As used herein, "derived from" refers to the source of the nucleic acid or polypeptide into which one or more mutations is introduced. For example, a polypeptide that is "derived from a plant polypeptide" refers to polypeptide of interest that results from introducing one or more mutations into the sequence of a wild-type (i.e., a sequence occurring in nature) plant polypeptide.

In some embodiments, the source organism is a fungus, examples of which are species of *Aspergillus* such as *A. oryzae* and *A. niger*, species of *Saccharomyces* such as *S. cerevisiae*, species of *Schizosaccharomyces* such as *S. pombe*, and species of *Trichoderma* such as *T. reesei*. In some embodiments, the source organism is a filamentous fungal cell. The term "filamentous fungi" refers to all filamentous forms of the subdivision Eumycotina (see, Alexopoulos, C. J. (1962), Introductory Mycology, Wiley, New York). These fungi are characterized by a vegetative mycelium with a cell wall composed of chitin, cellulose, and other complex polysaccharides. The filamentous fungi are morphologically, physiologically, and genetically distinct from yeasts. Vegetative growth by filamentous fungi is by hyphal elongation and carbon catabolism is obligatory aerobic. The filamentous fungal parent cell may be a cell of a species of, but not limited to, *Trichoderma*, (e.g., *Trichoderma reesei*, the asexual morph of *Hypocrea jecorina*, previously classified as *T. longibrachiatum*, *Trichoderma viride*, *Trichoderma koningii*, *Trichoderma harzianum*) (Sheir-Neirs et al., Appl. Microbiol. Biotechnol 20: 46-53, 1984; ATCC No. 56765 and ATCC No. 26921); *Penicillium* sp., *Humicola* sp. (e.g., *H. insolens*, *H. lanuginose*, or *H. grisea*); *Chrysosporium* sp. (e.g., *C. lucknowense*), *Gliocladium* sp., *Aspergillus* sp. (e.g., *A. oryzae*, *A. niger*, *A sojae*, *A. japonicus*, *A. nidulans*, or *A. awamori*) (Ward et al., Appl. Microbiol. Biotechnol. 39: 7380743, 1993 and Goedegebuur et al., Genet 41: 89-98, 2002), *Fusarium* sp., (e.g., *F. roseum*, *F. graminum F. cerealis*, *F. oxysporuim*, or *F. venenatum*), *Neurospora* sp., (e.g., *N. crassa*), *Hypocrea* sp., *Mucor* sp., (e.g., *M. miehei*), *Rhizopus* sp. and *Emericella* sp. (see also, Innis et al., *Sci.* 228: 21-26, 1985). The term "*Trichoderma*" or "*Trichoderma* sp." or "*Trichoderma* spp." refer to any fungal genus previously or currently classified as *Trichoderma*.

In some embodiments, the fungus is *A. nidulans*, *A. awamori*, *A. oryzae*, *A. aculeatus*, *A. niger*, *A. japonicus*, *T. reesei*, *T. viride*, *F. oxysporum*, or *F. solani*. *Aspergillus* strains are disclosed in Ward et al., Appl. Microbiol. Biotechnol. 39:738-743, 1993 and Goedegebuur et al., Curr Gene 41:89-98, 2002, which are each hereby incorporated by reference in their entireties, particularly with respect to fungi. In particular embodiments, the fungus is a strain of *Trichoderma*, such as a strain of *T. reesei*. Strains of *T. reesei* are known and non-limiting examples include ATCC No. 13631, ATCC No. 26921, ATCC No. 56764, ATCC No. 56765, ATCC No. 56767, and NRRL 15709, which are each hereby incorporated by reference in their entireties, particularly with respect to strains of *T. reesei*. In some embodiments, the host strain is a derivative of RL-P37. RL-P37 is disclosed in Sheir-Neiss et al., Appl. Microbiol. Biotechnology 20:46-53, 1984, which is hereby incorporated by reference in its entirety, particularly with respect to strains of *T. reesei*.

In some embodiments, the source organism is a yeast, such as *Saccharomyces* sp., *Schizosaccharomyces* sp., *Pichia* sp., or *Candida* sp.

In some embodiments, the source organism is a bacterium, such as strains of *Bacillus* such as *B. lichenformis* or *B. subtilis*, strains of *Pantoea* such as *P. citrea*, strains of *Pseudomonas* such as *P. alcaligenes*, strains of *Streptomyces* such as *S. albus*, *S. lividans*, or *S. rubiginosus*, or strains of *Escherichia* such as *E. coli*.

As used herein, "the genus *Bacillus*" includes all species within the genus "*Bacillus*," as known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus*, *Amphibacillus*, *Aneurinibacillus*, *Anoxybacillus*, *Brevibacillus*, *Filobacillus*, *Gracilibacillus*, *Halobacillus*, *Paenibacillus*, *Salibacillus*, *Thermobacillus*, *Ureibacillus*, and *Virgibacillus*.

In some embodiments, the source organism is a gram-positive bacterium. Non-limiting examples include strains of *Streptomyces* (e.g., *S. albus*, *S. lividans*, *S. coelicolor*, or *S. griseus*) and *Bacillus*. In some embodiments, the source organism is a gram-negative bacterium, such as *E. coli* or *Pseudomonas* sp.

In some embodiments, the source organism is a plant, such as a plant from the family Fabaceae, such as the Faboideae subfamily. In some embodiments, the source organism is kudzu, poplar (such as *Populus alba×tremula* CAC35696 or *Populus alba*) (Sasaki et al., *FEBS Letters* 579(11): 2514-2518, 2005), aspen (such as *Populus tremuloides*), or *Quercus robur*.

In some embodiments, the source organism is an algae, such as a green algae, red algae, glaucophytes, chlorarachniophytes, euglenids, chromista, or dinoflagellates.

In some embodiments, the source organism is a cyanobacteria, such as cyanobacteria classified into any of the following groups based on morphology: Chroococcales, Pleurocapsales, Oscillatoriales, Nostocales, or Stigonematales.

Exemplary Host Cells

A variety of host cells can be used to express isoprene synthase, DXS, IDI, and/or MVA pathway polypeptides and to produce isoprene in the methods of the claimed invention. Exemplary host cells include cells from any of the organisms listed in the prior section under the heading "Exemplary Source Organisms." The host cell may be a cell that naturally produces isoprene or a cell that does not naturally produce isoprene. In some embodiments, the host cell naturally produces isoprene using the DXP pathway, and an isoprene synthase, DXS, and/or IDI nucleic acid is added to enhance production of isoprene using this pathway. In some embodiments, the host cell naturally produces isoprene using the MVA pathway, and an isoprene synthase and/or one or more MVA pathway nucleic acids are added to enhance production of isoprene using this pathway. In some embodiments, the host cell naturally produces isoprene using the DXP pathway and one or more MVA pathway nucleic acids are added to produce isoprene using part or all of the MVA pathway as well as the DXP pathway. In some embodiments, the host cell naturally produces isoprene using both the DXP and MVA pathways and one or more isoprene synthase, DXS, IDI, or MVA pathway nucleic acids are added to enhance production of isoprene by one or both of these pathways.

Exemplary Transformation Methods

Isoprene synthase, DXS, IDI, and/or MVA pathway nucleic acids or vectors containing them can be inserted into a host cell (e.g., a plant cell, a fungal cell, a yeast cell, or a bacterial cell described herein) using standard techniques for expression of the encoded isoprene synthase, DXS, IDI, and/or MVA pathway polypeptide. Introduction of a DNA construct or vector into a host cell can be performed using techniques such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (see, e.g., Current Protocols in Molecular Biology (F. M. Ausubel et al. (eds) Chapter 9, 1987; Sambrook et al., Molecular Cloning: A Laboratory Manual, $2^{nd}$ ed., Cold Spring Harbor, 1989; and Campbell et al., *Curr. Genet.*

16:53-56, 1989, which are each hereby incorporated by reference in their entireties, particularly with respect to transformation methods). The expression of heterologous polypeptide in *Trichoderma* is described in U.S. Pat. No. 6,022,725; U.S. Pat. No. 6,268,328; U.S. Pat. No. 7,262,041; WO 2005/001036; Harkki et al.; *Enzyme Microb. Technol.* 13:227-233, 1991; Harkki et al., *Bio Technol.* 7:596-603, 1989; EP 244,234; EP 215,594; and Nevalainen et al., "*The Molecular Biology of Trichoderma and its Application to the Expression of Both Homologous and Heterologous Genes,*" in Molecular Industrial Mycology, Eds. Leong and Berka, Marcel Dekker Inc., NY pp. 129-148, 1992, which are each hereby incorporated by reference in their entireties, particularly with respect to transformation and expression methods). Reference is also made to Cao et al., (*Sci.* 9:991-1001, 2000; EP 238023; and Yelton et al., *Proceedings. Natl. Acad Sci.* USA 81:1470-1474, 1984 (which are each hereby incorporated by reference in their entireties, particularly with respect to transformation methods) for transformation of *Aspergillus* strains. The introduced nucleic acids may be integrated into chromosomal DNA or maintained as extrachromosomal replicating sequences.

Any method known in the art may be used to select transformants. In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on a solid non-selective medium (e.g., a medium that lacks acetamide), harvesting spores from this culture medium, and determining the percentage of these spores which subsequently germinate and grow on selective medium containing acetamide.

In some embodiments, fungal cells are transformed by a process involving protoplast formation and transformation of the protoplasts followed by regeneration of the cell wall in a known manner. In one specific embodiment, the preparation of *Trichoderma* sp. for transformation involves the preparation of protoplasts from fungal mycelia (see, Campbell et al., *Curr. Genet.* 16:53-56, 1989, which is incorporated by reference in its entirety, particularly with respect to transformation methods). In some embodiments, the mycelia are obtained from germinated vegetative spores. The mycelia are treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate, and the like. Usually the concentration of these stabilizers varies between 0.8 M and 1.2 M. It is desirable to use about a 1.2 M solution of sorbitol in the suspension medium.

Uptake of DNA into the host *Trichoderma* sp. strain is dependent upon the calcium ion concentration. Generally, between about 10 mM $CaCl_2$ and 50 mM $CaCl_2$ is used in an uptake solution. In addition to the calcium ion in the uptake solution, other compounds generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). While not intending to be bound to any particular theory, it is believed that the polyethylene glycol acts to fuse the cell membranes, thus permitting the contents of the medium to be delivered into the cytoplasm of the *Trichoderma* sp. strain and the plasmid DNA to be transferred to the nucleus. This fusion frequently leaves multiple copies of the plasmid DNA integrated into the host chromosome.

Usually a suspension containing the *Trichoderma* sp. protoplasts or cells that have been subjected to a permeability treatment at a density of $10^5$ to $10^7$/mL (such as $2 \times 10^6$/mL) are used in the transformation. A volume of 100 μL of these protoplasts or cells in an appropriate solution (e.g., 1.2 M sorbitol and 50 mM $CaCl_2$) are mixed with the desired DNA. Generally, a high concentration of PEG is added to the uptake solution. From 0.1 to 1 volume of 25% PEG 4000 can be added to the protoplast suspension. In some embodiments, about 0.25 volumes are added to the protoplast suspension. Additives such as dimethyl sulfoxide, heparin, spermidine, potassium chloride, and the like may also be added to the uptake solution and aid in transformation. Similar procedures are available for other fungal host cells (see, e.g., U.S. Pat. Nos. 6,022,725 and 6,268,328, which are each hereby incorporated by reference in their entireties, particularly with respect to transformation methods).

Generally, the mixture is then cultured at approximately 0° C. for a period of between 10 to 30 minutes. Additional PEG is then added to the mixture to further enhance the uptake of the desired nucleic acid sequence. The 25% PEG 4000 is generally added in volumes of 5 to 15 times the volume of the transformation mixture; however, greater and lesser volumes may be suitable. The 25% PEG 4000 is desirably about 10 times the volume of the transformation mixture. After the PEG is added, the transformation mixture is then cultured either at room temperature or on ice before the addition of a sorbitol and $CaCl_2$ solution. The protoplast suspension is then further added to molten aliquots of a growth medium. When the growth medium includes a growth selection (e.g., acetamide or an antibiotic) it permits the growth of transformants only.

The transformation of bacterial cells may be performed according to conventional methods, e.g., as described in Sambrook et al., Molecular Cloning: A Laboratory Manual, Cold Spring Harbor, 1982, which is hereby incorporated by reference in its entirety, particularly with respect to transformation methods.

Exemplary Cell Culture Media

The invention also includes a cell or a population of cells in culture that produce isoprene. By "cells in culture" is meant two or more cells in a solution (e.g., a cell medium) that allows the cells to undergo one or more cell divisions. "Cells in culture" do not include plant cells that are part of a living, multicellular plant containing cells that have differentiated into plant tissues. In various embodiments, the cell culture includes at least or about 10, 20, 50, 100, 200, 500, 1,000, 5,000, 10,000 or more cells.

Any carbon source can be used to cultivate the host cells. The term "carbon source" refers to one or more carbon-containing compounds capable of being metabolized by a host cell or organism. For example, the cell medium used to cultivate the host cells may include any carbon source suitable for maintaining the viability or growing the host cells.

In some embodiments, the carbon source is a carbohydrate (such as monosaccharide, disaccharide, oligosaccharide, or polysaccharids), invert sugar (e.g., enzymatically treated sucrose syrup), glycerol, glycerine (e.g., a glycerine byproduct of a biodiesel or soap-making process), dihydroxyacetone, one-carbon source, oil (e.g., a plant or vegetable oil such as corn, palm, or soybean oil), acetate, animal fat, animal oil, fatty acid (e.g., a saturated fatty acid, unsaturated fatty acid, or polyunsaturated fatty acid), lipid, phospholipid, glycerolipid, monoglyceride, diglyceride, triglyceride, polypeptide (e.g., a microbial or plant protein or peptide), renewable carbon source (e.g., a biomass carbon source such as a hydrolyzed biomass carbon source), yeast extract, component from a yeast extract, polymer, acid, alcohol, aldehyde, ketone, amino acid, succinate, lactate, acetate, ethanol, or any combination of two or more of the foregoing. In some embodiments, the carbon source is a product of photosynthesis, including, but not limited to, glucose. In some embodiment, the carbohydrate is xylose or glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose). In some embodiments, the cell medium includes a carbohydrate as well as a carbon source other than a carbohydrate (e.g., glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, or a component from a yeast extract). In some embodiments, the cell medium includes a carbohydrate as well as a polypeptide (e.g., a microbial or plant protein or peptide). In some embodiments, the microbial polypeptide is a polypeptide from yeast or bacteria. In some embodiments, the plant polypeptide is a polypeptide from soy, corn, canola, jatropha, palm, peanut, sunflower, coconut, mustard, rapeseed, cottonseed, palm kernel, olive, safflower, sesame, or linseed.

In some embodiments, the concentration of the carbohydrate is at least or about 5 grams per liter of broth (g/L, wherein the volume of broth includes both the volume of the cell medium and the volume of the cells), such as at least or about 10, 15, 20, 30, 40, 50, 60, 80, 100, 150, 200, 300, 400, or more g/L. In some embodiments, the concentration of the carbohydrate is between about 50 and about 400 g/L, such as between about 100 and about 360 g/L, between about 120 and about 360 g/L, or between about 200 and about 300 g/L. In some embodiments, this concentration of carbohydrate includes the total amount of carbohydrate that is added before and/or during the culturing of the host cells.

Exemplary lipids are any substance containing one or more fatty acids that are C4 and above fatty acids that are saturated, unsaturated, or branched.

Exemplary oils are lipids that are liquid at room temperature. In some embodiments, the lipid contains one or more C4 or above fatty acids (e.g., contains one or more saturated, unsaturated, or branched fatty acid with four or more carbons). In some embodiments, the oil is obtained from soy, corn, canola, jatropha, palm, peanut, sunflower, coconut, mustard, rapeseed, cottonseed, palm kernel, olive, safflower, sesame, linseed, oleagineous microbial cells, Chinese tallow, or any combination of two or more of the foregoing.

Exemplary fatty acids include compounds of the formula RCOOH, where "R" is a hydrocarbon. Exemplary unsaturated fatty acids include compounds where "R" includes at least one carbon-carbon double bond. Exemplary unsaturated fatty acids include, but are not limited to, oleic acid, vaccenic acid, linoleic acid, palmitelaidic acid, and arachidonic acid. Exemplary polyunsaturated fatty acids include compounds where "R" includes a plurality of carbon-carbon double bonds. Exemplary saturated fatty acids include compounds where "R" is a saturated aliphatic group. In some embodiments, the carbon source includes one or more $C_{12}$-$C_{22}$ fatty acids, such as a $C_{12}$ saturated fatty acid, a $C_{14}$ saturated fatty acid, a $C_{16}$ saturated fatty acid, a $C_{18}$ saturated fatty acid, a $C_{20}$ saturated fatty acid, or a $C_{22}$ saturated fatty acid. In an exemplary embodiment, the fatty acid is palmitic acid. In some embodiments, the carbon source is a salt of a fatty acid (e.g., an unsaturated fatty acid), a derivative of a fatty acid (e.g., an unsaturated fatty acid), or a salt of a derivative of fatty acid (e.g., an unsaturated fatty acid). Suitable salts include, but are not limited to, lithium salts, potassium salts, sodium salts, and the like. Di- and triglycerols are fatty acid esters of glycerol.

In some embodiments, the concentration of the lipid, oil, fat, fatty acid, monoglyceride, diglyceride, or triglyceride is at least or about 1 gram per liter of broth (g/L, wherein the volume of broth includes both the volume of the cell medium and the volume of the cells), such as at least or about 5, 10, 15, 20, 30, 40, 50, 60, 80, 100, 150, 200, 300, 400, or more g/L. In some embodiments, the concentration of the lipid, oil, fat, fatty acid, monoglyceride, diglyceride, or triglyceride is between about 10 and about 400 g/L, such as between about 25 and about 300 g/L, between about 60 and about 180 g/L, or between about 75 and about 150 g/L. In some embodiments, the concentration includes the total amount of the lipid, oil, fat, fatty acid, monoglyceride, diglyceride, or triglyceride that is added before and/or during the culturing of the host cells. In some embodiments, the carbon source includes both (i) a lipid, oil, fat, fatty acid, monoglyceride, diglyceride, or triglyceride and (ii) a carbohydrate, such as glucose. In some embodiments, the ratio of the lipid, oil, fat, fatty acid, monoglyceride, diglyceride, or triglyceride to the carbohydrate is about 1:1 on a carbon basis (i.e., one carbon in the lipid, oil, fat, fatty acid, monoglyceride, diglyceride, or triglyceride per carbohydrate carbon). In particular embodiments, the amount of the lipid, oil, fat, fatty acid, monoglyceride, diglyceride, or triglyceride is between about 60 and 180 g/L, and the amount of the carbohydrate is between about 120 and 360 g/L.

Exemplary microbial polypeptide carbon sources include one or more polypeptides from yeast or bacteria. Exemplary plant polypeptide carbon sources include one or more polypeptides from soy, corn, canola, jatropha, palm, peanut, sunflower, coconut, mustard, rapeseed, cottonseed, palm kernel, olive, safflower, sesame, or linseed.

Exemplary renewable carbon sources include cheese whey permeate, cornsteep liquor, sugar beet molasses, barley malt, and components from any of the foregoing. Exemplary renewable carbon sources also include acetate, glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassava, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose.

In some embodiments, the renewable carbon source (such as biomass) is pretreated before it is added to the cell culture medium. In some embodiments, the pretreatment includes enzymatic pretreatment, chemical pretreatment, or a combination of both enzymatic and chemical pretreatment (see, for example, Farzaneh et al., *Bioresource Technology* 96 (18): 2014-2018, 2005; U.S. Pat. No. 6,176,176; U.S. Pat. No. 6,106,888; which are each hereby incorporated by reference in their entireties, particularly with respect to the pretreatment of renewable carbon sources). In some embodiments, the renewable carbon source is partially or completely hydrolyzed before it is added to the cell culture medium.

In some embodiments, the renewable carbon source (such as corn stover) undergoes ammonia fiber expansion (AFEX) pretreatment before it is added to the cell culture medium (see, for example, Farzaneh et al., *Bioresource Technology* 96 (18): 2014-2018, 2005). During AFEX pretreatment, a renewable carbon source is treated with liquid anhydrous ammonia at moderate temperatures (such as about 60 to about 100° C.) and high pressure (such as about 250 to about 300 psi) for about 5 minutes. Then, the pressure is rapidly released. In this process, the combined chemical and physical effects of lignin solubilization, hemicellulose hydrolysis, cellulose decrystallization, and increased surface area enables near complete enzymatic conversion of cellulose and hemicellulose to fermentable sugars. AFEX pretreatment has the advantage that nearly all of the ammonia can be recovered and reused, while the remaining serves as nitrogen source for microbes in downstream processes. Also, a wash stream is not required for AFEX pretreatment. Thus, dry matter recovery following the AFEX treatment is essentially 100%. AFEX is basically a dry to dry process. The treated renewable carbon source is stable for long periods and can be fed at very high solid loadings in enzymatic hydrolysis or fermentation processes. Cellulose and hemicellulose are well preserved in the AFEX process, with little or no degradation. There is no need for neutralization prior to the enzymatic hydrolysis of a renewable carbon source that has undergone AFEX pretreatment. Enzymatic hydrolysis of AFEX-treated carbon sources produces clean sugar streams for subsequent fermentation use.

In some embodiments, the concentration of the carbon source (e.g., a renewable carbon source) is equivalent to at least or about 0.1, 0.5, 1, 1.5 2, 3, 4, 5, 10, 15, 20, 30, 40, or 50% glucose (w/v). The equivalent amount of glucose can be determined by using standard HPLC methods with glucose as a reference to measure the amount of glucose generated from the carbon source. In some embodiments, the concentration of the carbon source (e.g., a renewable carbon source) is equivalent to between about 0.1 and about 20% glucose, such as between about 0.1 and about 10% glucose, between about 0.5 and about 10% glucose, between about 1 and about 10% glucose, between about 1 and about 5% glucose, or between about 1 and about 2% glucose.

In some embodiments, the carbon source includes yeast extract or one or more components of yeast extract. In some embodiments, the concentration of yeast extract is at least 1 gram of yeast extract per liter of broth (g/L, wherein the volume of broth includes both the volume of the cell medium and the volume of the cells), such at least or about 5, 10, 15, 20, 30, 40, 50, 60, 80, 100, 150, 200, 300, or more g/L. In some embodiments, the concentration of yeast extract is between about 1 and about 300 g/L, such as between about 1 and about 200 g/L, between about 5 and about 200 g/L, between about 5 and about 100 g/L, or between about 5 and about 60 g/L. In some embodiments, the concentration includes the total amount of yeast extract that is added before and/or during the culturing of the host cells. In some embodiments, the carbon source includes both yeast extract (or one or more components thereof) and another carbon source, such as glucose. In some embodiments, the ratio of yeast extract to the other carbon source is about 1:5, about 1:10, or about 1:20 (w/w).

Additionally the carbon source may also be one-carbon substrates such as carbon dioxide, or methanol. Glycerol production from single carbon sources (e.g., methanol, formaldehyde, or formate) has been reported in methylotrophic yeasts (Yamada et al., *Agric. Biol. Chem.*, 53(2) 541-543, 1989, which is hereby incorporated by reference in its entirety, particularly with respect to carbon sources) and in bacteria (Hunter et. al., *Biochemistry*, 24, 4148-4155, 1985, which is hereby incorporated by reference in its entirety, particularly with respect to carbon sources). These organisms can assimilate single carbon compounds, ranging in oxidation state from methane to formate, and produce glycerol. The pathway of carbon assimilation can be through ribulose monophosphate, through serine, or through xylulose-momophosphate (Gottschalk, Bacterial Metabolism, Second Edition, Springer-Verlag: New York, 1986, which is hereby incorporated by reference in its entirety, particularly with respect to carbon sources). The ribulose monophosphate pathway involves the condensation of formate with ribulose-5-phosphate to form a six carbon sugar that becomes fructose and eventually the three carbon product glyceraldehyde-3-phosphate. Likewise, the serine pathway assimilates the one-carbon compound into the glycolytic pathway via methylenetetrahydrofolate.

In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth Cl Compd.*, [Int. Symp.], 7$^{th}$ ed., 415-32. Editors: Murrell et al., Publisher: Intercept, Andover, UK, 1993, which is hereby incorporated by reference in its entirety, particularly with respect to carbon sources). Similarly, various species of *Candida* metabolize alanine or oleic acid (Sulter et al., *Arch. Microbiol.* 153(5), 485-9, 1990, which is hereby incorporated by reference in its entirety, particularly with respect to carbon sources).

In some embodiments, cells are cultured in a standard medium containing physiological salts and nutrients (see, e.g., Pourquie, J. et al., Biochemistry and Genetics of Cellulose Degradation, eds. Aubert et al., Academic Press, pp. 71-86, 1988 and Ilmen et al., *Appl. Environ. Microbiol.* 63:1298-1306, 1997, which are each hereby incorporated by reference in their entireties, particularly with respect to cell media). Exemplary growth media are common commercially prepared media such as Luria Bertani (LB) broth, Sabouraud Dextrose (SD) broth, or Yeast medium (YM) broth. Other defined or synthetic growth media may also be used, and the appropriate medium for growth of particular host cells are known by someone skilled in the art of microbiology or fermentation science.

In addition to an appropriate carbon source, the cell medium desirably contains suitable minerals, salts, cofactors, buffers, and other components known to those skilled in the art suitable for the growth of the cultures or the enhancement of isoprene production (see, for example, WO 2004/033646 and references cited therein and WO 96/35796 and references cited therein, which are each hereby incorporated by reference in their entireties, particularly with respect cell medias and cell culture conditions). In some embodiments where an isoprene synthase, DXS, IDI, and/or MVA pathway nucleic acid is under the control of an inducible promoter, the inducing agent (e.g., a sugar, metal salt or antimicrobial), is desirably added to the medium at a concentration effective to induce expression of an isoprene synthase, DXS, IDI, and/or MVA pathway polypeptide. In some embodiments, cell medium has an antibiotic (such as kanamycin) that corresponds to the antibiotic resistance nucleic acid (such as a kanamycin resistance nucleic acid) on a vector that has one or more DXS, IDI, or MVA pathway nucleic acids.

Exemplary Cell Culture Conditions

Materials and methods suitable for the maintenance and growth of bacterial cultures are well known in the art. Exemplary techniques may be found in Manual of Methods for General Bacteriology Gerhardt et al., eds), American Society for Microbiology, Washington, D.C. (1994) or Brock in Biotechnology: A Textbook of Industrial Microbiology, Second Edition (1989) Sinauer Associates, Inc., Sunderland, Mass., which are each hereby incorporated by reference in their entireties, particularly with respect to cell culture techniques. In some embodiments, the cells are cultured in a culture medium under conditions permitting the expression of one or more isoprene synthase, DXS, IDI, or MVA pathway polypeptides encoded by a nucleic acid inserted into the host cells.

Standard cell culture conditions can be used to culture the cells (see, for example, WO 2004/033646 and references cited therein, which are each hereby incorporated by reference in their entireties, particularly with respect to cell culture and fermentation conditions). Cells are grown and maintained at an appropriate temperature, gas mixture, and pH (such as at about 20 to about 37° C., at about 6% to about 84% $CO_2$, and at a pH between about 5 to about 9). In some embodiments, cells are grown at 35° C. in an appropriate cell medium. In some embodiments, e.g., cultures are cultured at approximately 28° C. in appropriate medium in shake cultures or fermentors until desired amount of isoprene production is achieved. In some embodiments, the pH ranges for fermentation are between about pH 5.0 to about pH 9.0 (such as about pH 6.0 to about pH 8.0 or about 6.5 to about 7.0). Reactions may be performed under aerobic, anoxic, or anaerobic conditions based on the requirements of the host cells. Exemplary culture conditions for a given filamentous fungus are known in the art and may be found in the scientific literature and/or from the source of the fungi such as the American Type Culture Collection and Fungal Genetics Stock Center.

In various embodiments, the cells are grown using any known mode of fermentation, such as batch, fed-batch, or continuous processes. In some embodiments, a batch method of fermentation is used. Classical batch fermentation is a closed system where the composition of the media is set at the beginning of the fermentation and is not subject to artificial alterations during the fermentation. Thus, at the beginning of the fermentation the cell medium is inoculated with the desired host cells and fermentation is permitted to occur adding nothing to the system. Typically, however, "batch" fermentation is batch with respect to the addition of carbon source and attempts are often made at controlling factors such as pH and oxygen concentration. In batch systems, the metabolite and biomass compositions of the system change constantly until the time the fermentation is stopped. Within batch cultures, cells moderate through a static lag phase to a high growth log phase and finally to a stationary phase where growth rate is diminished or halted.

In some embodiments, cells in log phase are responsible for the bulk of the isoprene production. In some embodiments, cells in stationary phase produce isoprene.

In some embodiments, a variation on the standard batch system is used, such as the Fed-Batch system. Fed-Batch fermentation processes comprise a typical batch system with the exception that the carbon source is added in increments as the fermentation progresses. Fed-Batch systems are useful when catabolite repression is apt to inhibit the metabolism of the cells and where it is desirable to have limited amounts of carbon source in the cell medium. Fed-batch fermentations may be performed with the carbon source (e.g., glucose) in a limited or excess amount. Measurement of the actual carbon source concentration in Fed-Batch systems is difficult and is therefore estimated on the basis of the changes of measurable factors such as pH, dissolved oxygen, and the partial pressure of waste gases such as $CO_2$. Batch and Fed-Batch fermentations are common and well known in the art and examples may be found in Brock, Biotechnology: A Textbook of Industrial Microbiology, Second Edition (1989) Sinauer Associates, Inc., which is hereby incorporated by reference in its entirety, particularly with respect to cell culture and fermentation conditions.

In some embodiments, continuous fermentation methods are used. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or isoprene production. For example, one method maintains a limiting nutrient such as the carbon source or nitrogen level at a fixed rate and allows all other parameters to moderate. In other systems, a number of factors affecting growth can be altered continuously while the cell concentration (e.g., the concentration measured by media turbidity) is kept constant. Continuous systems strive to maintain steady state growth conditions. Thus, the cell loss due to media being drawn off is balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, Biotechnology: A Textbook of Industrial Microbiology, Second Edition (1989) Sinauer Associates, Inc., which is hereby incorporated by reference in its entirety, particularly with respect to cell culture and fermentation conditions.

In some embodiments, cells are immobilized on a substrate as whole cell catalysts and subjected to fermentation conditions for isoprene production.

In some embodiments, bottles of liquid culture are placed in shakers in order to introduce oxygen to the liquid and maintain the uniformity of the culture. In some embodiments, an incubator is used to control the temperature, humidity, shake speed, and/or other conditions in which a culture is grown. The simplest incubators are insulated boxes with an adjustable heater, typically going up to ~65° C. More elaborate incubators can also include the ability to lower the temperature (via refrigeration), or the ability to control humidity or $CO_2$ levels. Most incubators include a timer; some can also be programmed to cycle through different temperatures, humidity levels, etc. Incubators can vary in size from tabletop to units the size of small rooms.

If desired, a portion or all of the cell medium can be changed to replenish nutrients and/or avoid the build up of potentially harmful metabolic byproducts and dead cells. In the case of suspension cultures, cells can be separated from the media by centrifuging or filtering the suspension culture and then resuspending the cells in fresh media. In the case of adherent cultures, the media can be removed directly by aspiration and replaced. In some embodiments, the cell medium allows at least a portion of the cells to divide for at least or about 5, 10, 20, 40, 50, 60, 65, or more cell divisions in a continuous culture (such as a continuous culture without dilution).

In some embodiments, a constitutive or leaky promoter (such as a Trc promoter) is used and a compound (such as IPTG) is not added to induce expression of the isoprene synthase, DXS, IDI, or MVA pathway nucleic acid(s) operably linked to the promoter. In some embodiments, a compound (such as IPTG) is added to induce expression of the isoprene synthase, DXS, IDI, or MVA pathway nucleic acid(s) operably linked to the promoter.

Exemplary Production of Isoprene

In some embodiments, the cells are cultured in a culture medium under conditions permitting the production of isoprene by the cells. By "peak absolute productivity" is meant the maximum absolute amount of isoprene in the off-gas during the culturing of cells for a particular period of time (e.g., the culturing of cells during a particular fermentation run). By "peak absolute productivity time point" is meant the time point during a fermentation run when the absolute amount of isoprene in the off-gas is at a maximum during the culturing of cells for a particular period of time (e.g., the culturing of cells during a particular fermentation run). In some embodiments, the isoprene amount is measured at the peak absolute productivity time point. In some embodiments, the peak absolute productivity for the cells is about any of the isoprene amounts disclosed herein.

By "peak specific productivity" is meant the maximum amount of isoprene produced per cell during the culturing of cells for a particular period of time (e.g., the culturing of cells during a particular fermentation run). By "peak specific productivity time point" is meant the time point during the culturing of cells for a particular period of time (e.g., the culturing of cells during a particular fermentation run) when the amount of isoprene produced per cell is at a maximum. The peak specific productivity is determined by dividing the total productivity by the amount of cells, as determined by optical density at 600 nm ($OD_{600}$). In some embodiments, the isoprene amount is measured at the peak specific productivity time point. In some embodiments, the peak specific productivity for the cells is about any of the isoprene amounts per cell disclosed herein.

By "peak volumetric productivity" is meant the maximum amount of isoprene produced per volume of broth (including the volume of the cells and the cell medium) during the culturing of cells for a particular period of time (e.g., the culturing of cells during a particular fermentation run). By "peak specific volumetric productivity time point" is meant the time point during the culturing of cells for a particular period of time (e.g., the culturing of cells during a particular fermentation run) when the amount of isoprene produced per volume of broth is at a maximum. The peak specific volumetric productivity is determined by dividing the total productivity by the volume of broth and amount of time. In some embodiments, the isoprene amount is measured at the peak specific volumetric productivity time point. In some embodiments, the peak specific volumetric productivity for the cells is about any of the isoprene amounts per volume per time disclosed herein.

By "peak concentration" is meant the maximum amount of isoprene produced during the culturing of cells for a particular period of time (e.g., the culturing of cells during a particular fermentation run). By "peak concentration time point" is meant the time point during the culturing of cells for a particular period of time (e.g., the culturing of cells during a particular fermentation run) when the amount of isoprene produced per cell is at a maximum. In some embodiments, the isoprene amount is measured at the peak concentration time point. In some embodiments, the peak concentration for the cells is about any of the isoprene amounts disclosed herein.

By "average volumetric productivity" is meant the average amount of isoprene produced per volume of broth (including the volume of the cells and the cell medium) during the culturing of cells for a particular period of time (e.g., the culturing of cells during a particular fermentation run). The average volumetric productivity is determined by dividing the total productivity by the volume of broth and amount of time. In some embodiments, the average specific volumetric productivity for the cells is about any of the isoprene amounts per volume per time disclosed herein.

By "cumulative total productivity" is meant the cumulative, total amount of isoprene produced during the culturing of cells for a particular period of time (e.g., the culturing of cells during a particular fermentation run). In some embodiments, the cumulative, total amount of isoprene is measured. In some embodiments, the cumulative total productivity for the cells is about any of the isoprene amounts disclosed herein.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 12,500, 20,000, 30,000, 40,000, 50,000, 75,000, 100,000, 125,000, 150,000, 188,000, or more nmole of isoprene/gram of cells for the wet weight of the cells/hour (nmole/$g_{wcm}$/hr). In some embodiments, the amount of isoprene is between about 2 to about 200,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, about 2,000 to about 5,000 nmole/$g_{wcm}$/hr, about 5,000 to about 10,000 nmole/$g_{wcm}$/hr, about 10,000 to about 50,000 nmole/$g_{wcm}$/hr, about 50,000 to about 100,000 nmole/$g_{wcm}$/hr, about 100,000 to about 150,000 nmole/$g_{wcm}$/hr, or about 150,000 to about 200,000 nmole/$g_{wcm}$/hr. In some embodiments, the amount of isoprene is between about 20 to about 200,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, about 400 to about 1,000 nmole/$g_{wcm}$/hr, about 1,000 to about 5,000 nmole/$g_{wcm}$/hr, about 2,000 to about 20,000 nmole/$g_{wcm}$/hr, about 5,000 to about 50,000 nmole/$g_{wcm}$/hr, about 10,000 to about 100,000 nmole/$g_{wcm}$/hr, about 20,000 to about 150,000 nmole/$g_{wcm}$/hr, or about 20,000 to about 200,000 nmole/$g_{wcm}$/hr.

The amount of isoprene in units of nmole/$g_{wcm}$/hr can be measured as disclosed in U.S. Pat. No. 5,849,970, which is hereby incorporated by reference in its entirety, particularly with respect to the measurement of isoprene production. For example, two mL of headspace (e.g., headspace from a culture such as 2 mL of culture cultured in sealed vials at 32

0 C with shaking at 200 rpm for approximately 3 hours) are analyzed for isoprene using a standard gas chromatography system, such as a system operated isothermally (85 0 C) with an n-octane/porasil C column (Alltech Associates, Inc., Deerfield, Ill.) and coupled to a RGD2 mercuric oxide reduction gas detector (Trace Analytical, Menlo Park, Calif.) (see, for example, Greenberg et al, *Atmos. Environ.* 27A: 2689-2692, 1993; Silver et al., *Plant Physiol.* 97:1588-1591, 1991, which are each hereby incorporated by reference in their entireties, particularly with respect to the measurement of isoprene production). The gas chromatography area units are converted to nmol isoprene via a standard isoprene concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr ($ng/g_{wcm}/h$). In some embodiments, the amount of isoprene is between about 2 to about 5,000 $ng/g_{wcm}/h$, such as between about 2 to about 100 $ng/g_{wcm}/h$, about 100 to about 500 $ng/g_{wcm}/h$, about 500 to about 1,000 $ng/g_{wcm}/h$, about 1,000 to about 2,000 $ng/g_{wcm}/h$, or about 2,000 to about 5,000 $ng/g_{wcm}/h$. In some embodiments, the amount of isoprene is between about 20 to about 5,000 $ng/g_{wcm}/h$, about 100 to about 5,000 $ng/g_{wcm}/h$, about 200 to about 2,000 $ng/g_{wcm}/h$, about 200 to about 1,000 $ng/g_{wcm}/h$, about 300 to about 1,000 $ng/g_{wcm}/h$, or about 400 to about 1,000 $ng/g_{wcm}/h$. The amount of isoprene in $ng/g_{wcm}/h$ can be calculated by multiplying the value for isoprene production in the units of $nmole/g_{wcm}/hr$ discussed above by 68.1 (as described in Equation 5 below).

In some embodiments, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth ($mg/L_{broth}$, wherein the volume of broth includes the volume of the cells and the cell medium). In some embodiments, the amount of isoprene is between about 2 to about 5,000 $mg/L_{broth}$, such as between about 2 to about 100 $mg/L_{broth}$, about 100 to about 500 $mg/L_{broth}$, about 500 to about 1,000 $mg/L_{broth}$, about 1,000 to about 2,000 $mg/L_{broth}$, or about 2,000 to about 5,000 $mg/L_{broth}$. In some embodiments, the amount of isoprene is between about 20 to about 5,000 $mg/L_{broth}$, about 100 to about 5,000 $mg/L_{broth}$, about 200 to about 2,000 $mg/L_{broth}$, about 200 to about 1,000 $mg/L_{broth}$, about 300 to about 1,000 $mg/L_{broth}$, or about 400 to about 1,000 $mg/L_{broth}$.

The specific productivity of isoprene in mg of isoprene/L of headspace from shake flask or similar cultures can be measured by taking a 1 ml sample from the cell culture at an $OD_{600}$ value of approximately 1.0, putting it in a 20 mL vial, incubating for 30 minutes, and then measuring the amount of isoprene in the headspace (as described, for example, in Example I, part II). If the $OD_{600}$ value is not 1.0, then the measurement can be normalized to an $OD_{600}$ value of 1.0 by dividing by the $OD_{600}$ value. The value of mg isoprene/L headspace can be converted to $mg/L_{broth}/hr/OD_{600}$ of culture broth by multiplying by a factor of 38. The value in units of $mg/L_{broth}/hr/OD_{600}$ can be multiplied by the number of hours and the $OD_{600}$ value to obtain the cumulative titer in units of mg of isoprene/L of broth.

In some embodiments, the cells in culture have an average volumetric productivity of isoprene at greater than or about 0.1, 1.0, 10, 25, 50, 100, 150, 200, 250, 300, 400, 500, 600, 700, 800, 900, 1,000, 1100, 1200, 1300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, or more mg of isoprene/L of broth/hr ($mg/L_{broth}/hr$, wherein the volume of broth includes the volume of the cells and the cell medium). In some embodiments, the average volumetric productivity of isoprene is between about 0.1 to about 3,500 $mg/L_{broth}/hr$, such as between about 0.1 to about 100 $mg/L_{broth}/hr$, about 100 to about 500 $mg/L_{broth}/hr$, about 500 to about 1,000 $mg/L_{broth}/hr$, about 1,000 to about 1,500 $mg/L_{broth}/hr$, about 1,500 to about 2,000 $mg/L_{broth}/hr$, about 2,000 to about 2,500 $mg/L_{broth}/hr$, about 2,500 to about 3,000 $mg/L_{broth}/hr$, or about 3,000 to about 3,500 $mg/L_{broth}/hr$. In some embodiments, the average volumetric productivity of isoprene is between about 10 to about 3,500 $mg/L_{broth}/hr$, about 100 to about 3,500 $mg/L_{broth}/hr$, about 200 to about 1,000 $mg/L_{broth}/hr$, about 200 to about 1,500 $mg/L_{broth}/hr$, about 1,000 to about 3,000 $mg/L_{broth}/hr$, or about 1,500 to about 3,000 $mg/L_{broth}/hr$.

In some embodiments, the cells in culture have a peak volumetric productivity of isoprene at greater than or about 0.5, 1.0, 10, 25, 50, 100, 150, 200, 250, 300, 400, 500, 600, 700, 800, 900, 1,000, 1100, 1200, 1300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,750, 4,000, 4,250, 4,500, 4,750, 5,000, 5,250, 5,500, 5,750, 6,000, 6,250, 6,500, 6,750, 7,000, 7,250, 7,500, 7,750, 8,000, 8,250, 8,500, 8,750, 9,000, 9,250, 9,500, 9,750, 10,000, 12,500, 15,000, or more mg of isoprene/L of broth/hr ($mg/L_{broth}/hr$, wherein the volume of broth includes the volume of the cells and the cell medium). In some embodiments, the peak volumetric productivity of isoprene is between about 0.5 to about 15,000 $mg/L_{broth}/hr$, such as between about 0.5 to about 10 $mg/L_{broth}/hr$, about 1.0 to about 100 $mg/L_{broth}/hr$, about 100 to about 500 $mg/L_{broth}/hr$, about 500 to about 1,000 $mg/L_{broth}/hr$, about 1,000 to about 1,500 $mg/L_{broth}/hr$, about 1,500 to about 2,000 $mg/L_{broth}/hr$, about 2,000 to about 2,500 $mg/L_{broth}/hr$, about 2,500 to about 3,000 $mg/L_{broth}/hr$, about 3,000 to about 3,500 $mg/L_{broth}/hr$, about 3,500 to about 5,000 $mg/L_{broth}/hr$, about 5,000 to about 7,500 $mg/L_{broth}/hr$, about 7,500 to about 10,000 $mg/L_{broth}/hr$, about 10,000 to about 12,500 $mg/L_{broth}/h$, or about 12,500 to about 15,000 $mg/L_{broth}/hr$. In some embodiments, the peak volumetric productivity of isoprene is between about 10 to about 15,000 $mg/L_{broth}/hr$, about 100 to about 2,500 $mg/L_{broth}/hr$, about 1,000 to about 5,000 $mg/L_{broth}/hr$, about 2,500 to about 7,500 $mg/L_{broth}/hr$, about 5,000 to about 10,000 $mg/L_{broth}/hr$, about 7,500 to about 12,500 $mg/L_{broth}/hr$, or about 10,000 to about 15,000 $mg/L_{broth}/hr$.

The instantaneous isoprene production rate in $mg/L_{broth}/hr$ in a fermentor can be measured by taking a sample of the fermentor off-gas, analyzing it for the amount of isoprene (in units such as mg of isoprene per $L_{gas}$) as described, for example, in Example I, part II and multiplying this value by the rate at which off-gas is passed though each liter of broth (e.g., at 1 vvm (volume of air/volume of broth/minute) this is 60 $L_{gas}$ per hour). Thus, an off-gas level of 1 mg/$L_{gas}$ corresponds to an instantaneous production rate of 60 mg/$L_{broth}$/hr at air flow of 1 vvm. If desired, the value in the units mg/$L_{broth}$/hr can be divided by the $OD_{600}$ value to obtain the specific rate in units of mg/$L_{broth}$/hr/OD. The average value of mg isoprene/$L_{gas}$ can be converted to the total product productivity (grams of isoprene per liter of fermentation broth, mg/$L_{broth}$) by multiplying this average off-gas isoprene concentration by the total amount of off-gas sparged per liter of fermentation broth during the fermentation. Thus, an average off-gas isoprene concentration of 0.5 mg/$L_{broth}$/hr over 10 hours at 1 vvm corresponds to a total product concentration of 300 mg isoprene/$L_{broth}$.

In some embodiments, the cells in culture convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 2.0, 2.2, 2.4, 2.6, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 23.2, 23.4, 23.6, 23.8, 24.0, 25.0, 30.0, 31.0, 32.0, 33.0, 35.0, 37.5, 40.0, 45.0, 47.5, 50.0, 55.0, 60.0, 65.0, 70.0, 75.0, 80.0, 85.0, or 90.0 molar % of the carbon in the cell culture medium into isoprene. In some embodiments, the percent conversion of carbon into isoprene is between about 0.002 to about 90.0 molar %, such as about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, about 1.0 to about 1.6%, about 1.6 to about 3.0%, about 3.0 to about 5.0%, about 5.0 to about 8.0%, about 8.0 to about 10.0%, about 10.0 to about 15.0%, about 15.0 to about 20.0%, about 20.0 to about 25.0%, about 25.0% to 30.0%, about 30.0% to 35.0%, about 35.0% to 40.0%, about 45.0% to 50.0%, about 50.0% to 55.0%, about 55.0% to 60.0%, about 60.0% to 65.0%, about 65.0% to 70.0%, about 75.0% to 80.0%, about 80.0% to 85.0%, or about 85.0% to 90.0%. In some embodiments, the percent conversion of carbon into isoprene is between about 0.002 to about 0.4 molar %, 0.002 to about 0.16 molar %, 0.04 to about 0.16 molar %, about 0.005 to about 0.3 molar %, about 0.01 to about 0.3 molar %, about 0.05 to about 0.3 molar %, about 0.1 to about 0.3 molar %, about 0.3 to about 1.0 molar %, about 1.0 to about 5.0 molar %, about 2 to about 5.0 molar %, about 5.0 to about 10.0 molar %, about 7 to about 10.0 molar %, about 10.0 to about 20.0 molar %, about 12 to about 20.0 molar %, about 16 to about 20.0 molar %, about 18 to about 20.0 molar %, about 18 to 23.2 molar %, about 18 to 23.6 molar %, about 18 to about 23.8 molar %, about 18 to about 24.0 molar %, about 18 to about 25.0 molar %, about 20 to about 30.0 molar %, about 30 to about 40.0 molar %, about 30 to about 50.0 molar %, about 30 to about 60.0 molar %, about 30 to about 70.0 molar %, about 30 to about 80.0 molar %, or about 30 to about 90.0 molar %

The percent conversion of carbon into isoprene (also referred to as "% carbon yield") can be measured by dividing the moles carbon in the isoprene produced by the moles carbon in the carbon source (such as the moles of carbon in batched and fed glucose and yeast extract). This number is multiplied by 100% to give a percentage value (as indicated in Equation 1).

$$\% \text{ Carbon Yield}=(\text{moles carbon in isoprene produced})/(\text{moles carbon in carbon source})*100 \qquad \text{Equation 1}$$

For this calculation, yeast extract can be assumed to contain 50% w/w carbon. As an example, for the 500 liter described in Example 7, part VIII, the percent conversion of carbon into isoprene can be calculated as shown in Equation 2.

$$\% \text{ Carbon Yield}=(39.1 \text{ g isoprene}*1/68.1 \text{ mol/g}*5 \text{ C/mol})/[(181221 \text{ g glucose}*1/180 \text{ mol/g}*6 \text{ C/mol})+(17780 \text{ g yeast extract}*0.5*1/12 \text{ mol/g})]* 100=0.042\% \qquad \text{Equation 2}$$

For the two 500 liter fermentations described herein (Example 7, parts VII and VIII), the percent conversion of carbon into isoprene was between 0.04-0.06%. A 0.11-0.16% carbon yield has been achieved using 14 liter systems as described herein.

One skilled in the art can readily convert the rates of isoprene production or amount of isoprene produced into any other units. Exemplary equations are listed below for interconverting between units.

Units for Rate of Isoprene Production (Total and Specific)

$$1 \text{ g isoprene}/L_{broth}/\text{hr}=14.7 \text{ mmol isoprene}/L_{broth}/\text{hr} \text{ (total volumetric rate)} \qquad \text{Equation 3}$$

$$1 \text{ nmol isoprene}/g_{wcm}/\text{hr}=1 \text{ nmol isoprene}/L_{broth}/\text{hr}/OD_{600} \text{ (This conversion assumes that one liter of broth with an } OD_{600} \text{ value of 1 has a wet cell weight of 1 gram.)} \qquad \text{Equation 4}$$

$$1 \text{ nmol isoprene}/g_{wcm}/\text{hr}=68.1 \text{ ng isoprene}/g_{wcm}/\text{hr} \text{ (given the molecular weight of isoprene)} \qquad \text{Equation 5}$$

$$1 \text{ nmol isoprene}/L_{gas} \text{ } O_2/\text{hr}=90 \text{ nmol isoprene}/L_{broth}/\text{hr(at an } O_2 \text{ flow rate of 90 L/hr per L of culture broth)} \qquad \text{Equation 6}$$

$$1 \text{ ug isoprene}/L_{gas} \text{ isoprene in off-gas}=60 \text{ ug isoprene}/L_{broth}/\text{hr at a flow rate of 60 } L_{gas} \text{ per } L_{broth} \text{ (1 vvm)} \qquad \text{Equation 7}$$

Units for Titer (Total and Specific)

$$1 \text{ nmol isoprene/mg cell protein}=150 \text{ nmol isoprene}/L_{broth}/OD_{600} \text{ (This conversion assumes that one liter of broth with an } OD_{600} \text{ value of 1 has a total cell protein of approximately 150 mg) (specific productivity)} \qquad \text{Equation 8}$$

$$1 \text{ g isoprene}/L_{broth}=14.7 \text{ mmol isoprene}/L_{broth} \text{ (total titer)} \qquad \text{Equation 9}$$

If desired, Equation 10 can be used to convert any of the units that include the wet weight of the cells into the corresponding units that include the dry weight of the cells.

$$\text{Dry weight of cells}=(\text{wet weight of cells})/3.3 \qquad \text{Equation 10}$$

In some embodiments encompassed by the invention, a cell comprising a heterologous nucleic acid encoding an isoprene synthase polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acid encoding the isoprene synthase polypeptide.

In some embodiments encompassed by the invention, a cell comprising a heterologous nucleic acid encoding an isoprene synthase polypeptide and one or more heterologous nucleic acids encoding a DXS, IDI, and/or MVA pathway polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acids.

Exemplary Isoprene Purification Methods

In some embodiments, any of the methods described herein further include recovering the isoprene. For example, the isoprene produced using the compositions and methods of the invention can be recovered using standard techniques such as gas stripping, fractionation, adsorption/desorption, pervaporation, thermal or vacuum desorption of isoprene from a solid phase, or extraction of isoprene immobilized or absorbed to a solid phase with a solvent (see, for example, U.S. Pat. Nos. 4,703,007 and 4,570,029, which are each hereby incorporated by reference in their entireties, particularly with respect to isoprene recovery and purification methods). In some embodiments, the recovery of isoprene involves the isolation of isoprene in a liquid form (such as a neat solution of isoprene or a solution of isoprene in a solvent). Gas stripping involves the removal of isoprene vapor from the fermentation off-gas stream in a continuous manner. Such removal can be achieved in several different ways including, but not limited to, adsorption to a solid phase, partition into a liquid phase, or direct condensation. In some embodiments, membrane enrichment of a dilute isoprene vapor stream above the dew point of the vapor resulting in the condensation of liquid isoprene.

The recovery of isoprene may involve one step or multiple steps. In some embodiments, the removal of isoprene vapor from the fermentation off-gas and the conversion of isoprene to a liquid phase are performed simultaneously. For example, isoprene can be directly condensed from the off-gas stream to form a liquid. In some embodiments, the removal of isoprene vapor from the fermentation off-gas and the conversion of isoprene to a liquid phase are performed sequentially. For example, isoprene may be adsorbed to a solid phase and then extracted from the solid phase with a solvent.

In some embodiments, any of the methods described herein further include purifying the isoprene. For example, the isoprene produced using the compositions and methods of the invention can be purified using standard techniques. Purification refers to a process through which isoprene is separated from one or more components that are present when the isoprene is produced. In some embodiments, the isoprene is obtained as a substantially pure liquid. Examples of purification methods include (i) distillation from a solution in a liquid extractant and (ii) chromatography. As used herein, "purified isoprene" means isoprene that has been separated from one or more components that are present when the isoprene is produced. In some embodiments, the isoprene is at least about 20%, by weight, free from other components that are present when the isoprene is produced. In various embodiments, the isoprene is at least or about 25%, 30%, 40%, 50%, 60%, 70%, 75%, 80%, 90%, 95%, or 99%, by weight, pure. Purity can be assayed by any appropriate method, e.g., by column chromatography, HPLC analysis, or GC-MS analysis.

In some embodiments, any of the methods described herein further include polymerizing the isoprene. For example, standard methods can be used to polymerize the purified isoprene to form cis-polyisoprene or other down stream products using standard methods.

Additional methods and compositions are described in U.S. Provisional patent application No. 61/097,186, filed on Sep. 15, 2008, U.S. Provisional patent application No. 61/097,189, filed on Sep. 15, 2008, and U.S. Provisional patent application No. 61/097,163, filed on Sep. 15, 2008, all of which are incorporated by reference in their entireties, particular with respect to compositions and methods for producing isoprene.

EXAMPLES

The examples, which are intended to be purely exemplary of the invention and should therefore not be considered to limit the invention in any way, also describe and detail aspects and embodiments of the invention discussed above. Unless indicated otherwise, temperature is in degrees Centigrade and pressure is at or near atmospheric. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Example 1: Production of Isoprene in *E. coli* Expressing Recombinant Kudzu Isoprene Synthase I. Construction of Vectors for Expression of the Kudzu Isoprene Synthase in *E. coli*

Figure 2:
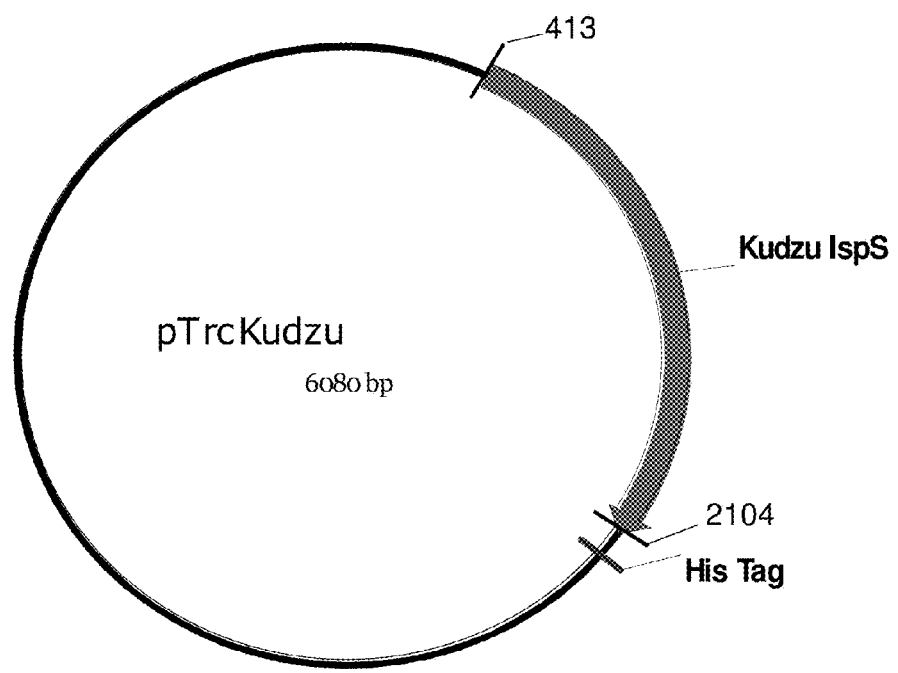
FIG. 2 is a map of pTrcKudzu.

The protein sequence for the kudzu (*Pueraria montana*) isoprene synthase gene (IspS) was obtained from GenBank (AAQ84170). A kudzu isoprene synthase gene, optimized for *E. coli* codon usage, was purchased from DNA2.0 (SEQ ID NO: 1). The isoprene synthase gene was removed from the supplied plasmid by restriction endonuclease digestion with BspLU11I/PstI, gel-purified, and ligated into pTrcHis2B (Invitrogen) that had been digested with NcoI/PstI. The construct was designed such that the stop codon in the isoprene synthase gene 5' to the PstI site. As a result, when the construct was expressed the His-Tag is not attached to the isoprene synthase protein. The resulting plasmid, pTrcKudzu, was verified by sequencing (FIGS. 2 and 3).

Figure 4:
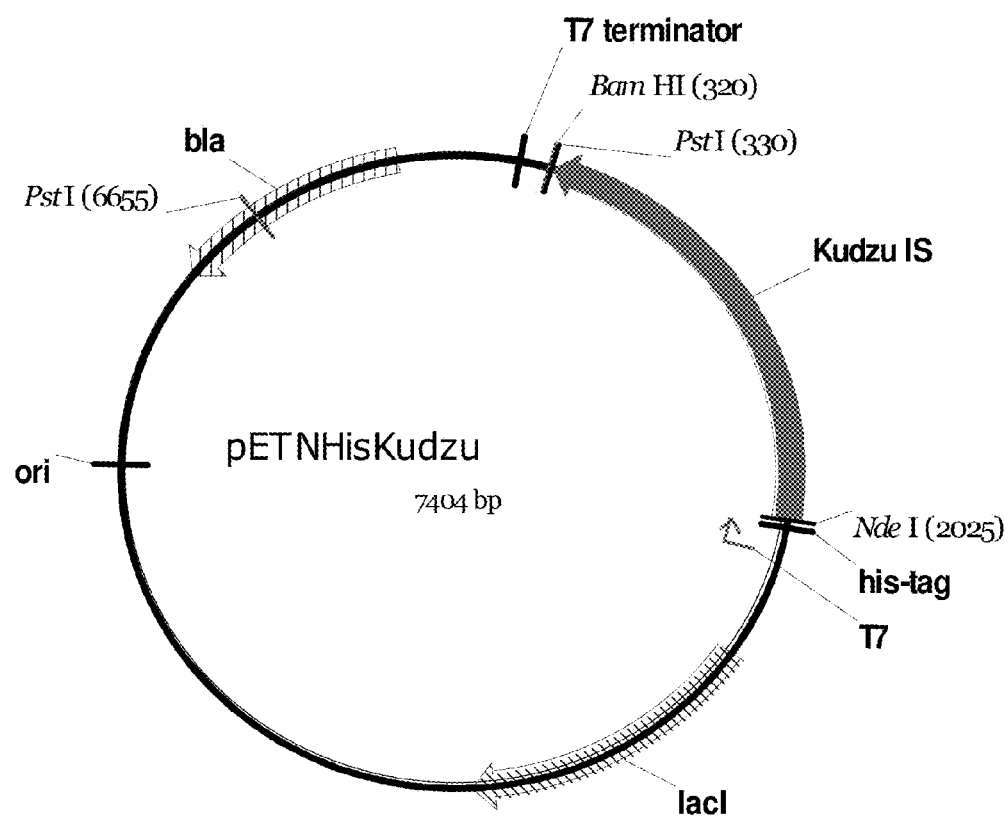
FIG. 4 is a map of pETNHisKudzu.

The isoprene synthase gene was also cloned into pET16b (Novagen). In this case, the isoprene synthase gene was inserted into pET16b such that the recombinant isoprene synthase protein contained the N-terminal His tag. The isoprene synthase gene was amplified from pTrcKudzu by PCR using the primer set pET-His-Kudzu-2F: 5'-CGT-GAGATCATATGTGTGCGACCTCTTCTCAATTTAC (SEQ ID NO:3) and pET-His-Kudzu-R: 5'-CGGTCGACG-GATCCCTGCAGTTAGACATACATCAGCTG (SEQ ID NO:4). These primers added an NdeI site at the 5'-end and a BamH1 site at the 3' end of the gene respectively. The plasmid pTrcKudzu, described above, was used as template DNA, Herculase polymerase (Stratagene) was used according to manufacture's directions, and primers were added at a concentration of 10 pMols. The PCR was carried out in a total volume of 25 al. The PCR product was digested with NdeI/BamH1 and cloned into pET16b digested with the same enzymes. The ligation mix was transformed into *E. coli* Top10 (Invitrogen) and the correct clone selected by sequencing. The resulting plasmid, in which the kudzu isoprene synthase gene was expressed from the T7 promoter, was designated pETNHisKudzu (FIGS. 4 and 5).

Figure 6:
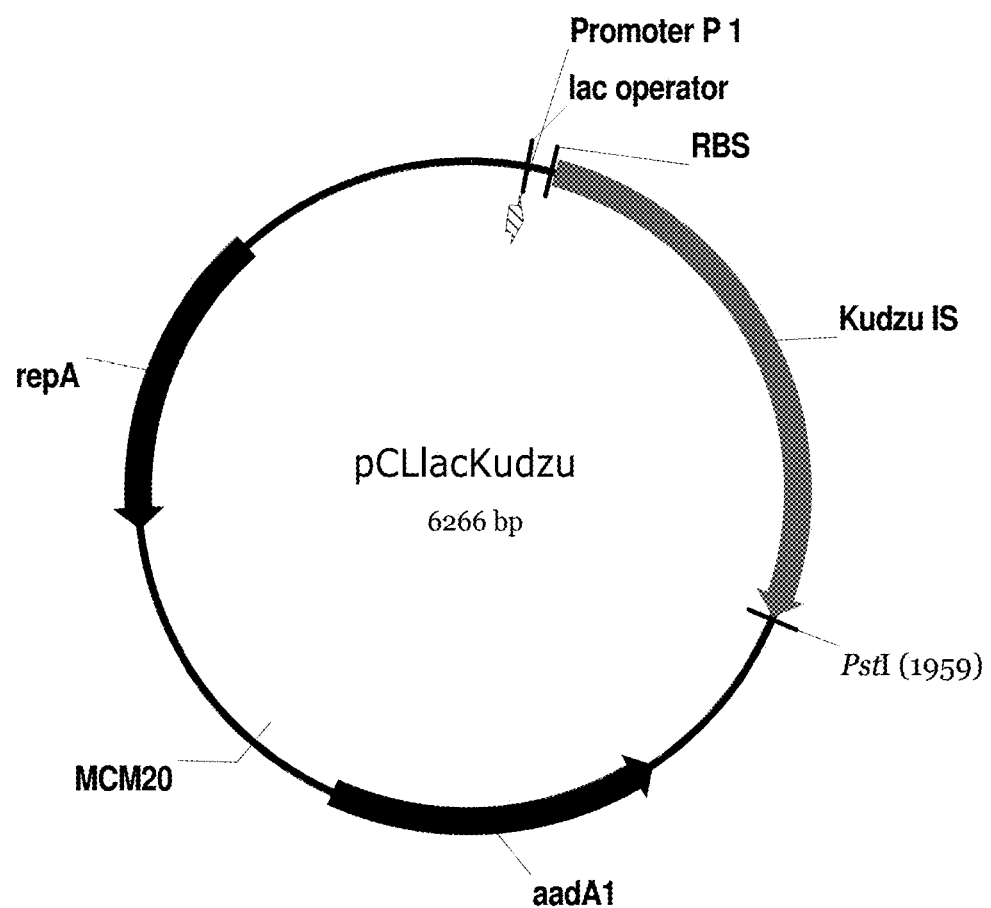
FIG. 6 is a map of pCL-lac-Kudzu.
Figure 8A:
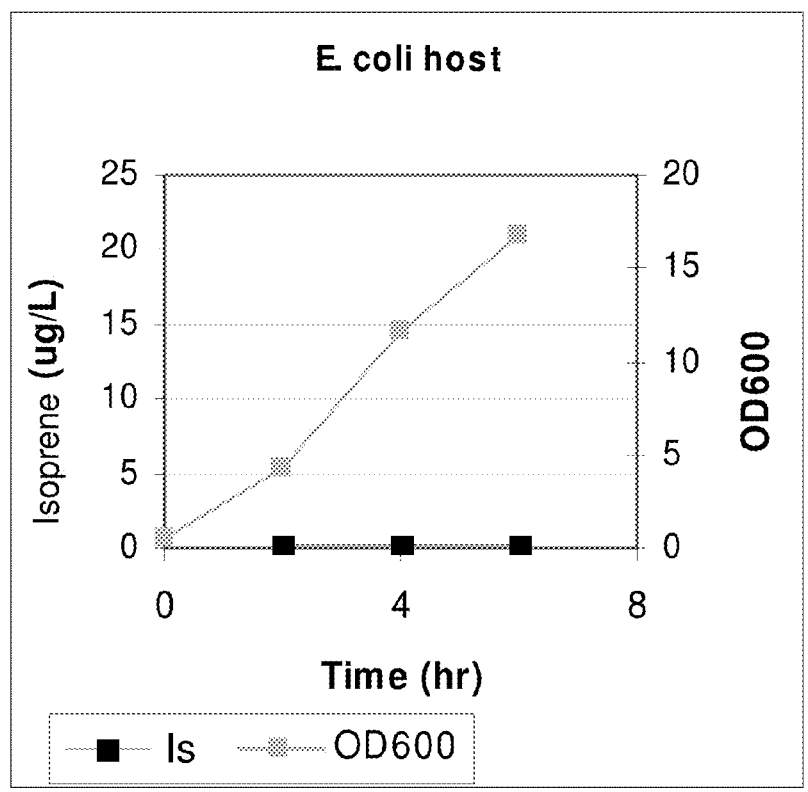
FIG. 8A is a graph showing the production of isoprene in *E. coli* BL21 cells with no vector.
Figure 8B:
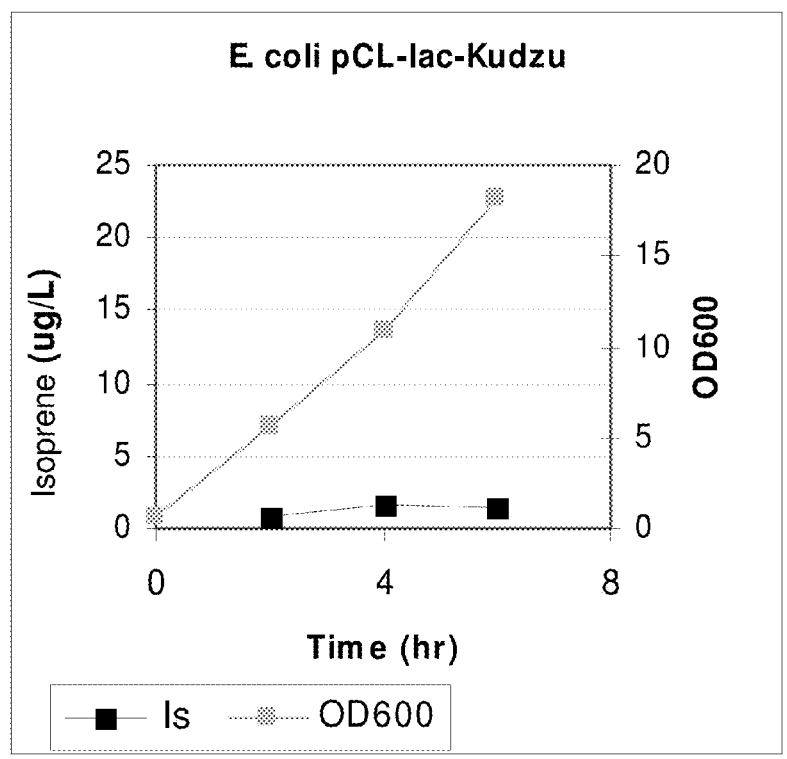
FIG. 8B is a graph showing the production of isoprene in *E. coli* BL21 cells with pCL-lac-Kudzu
Figure 8C:
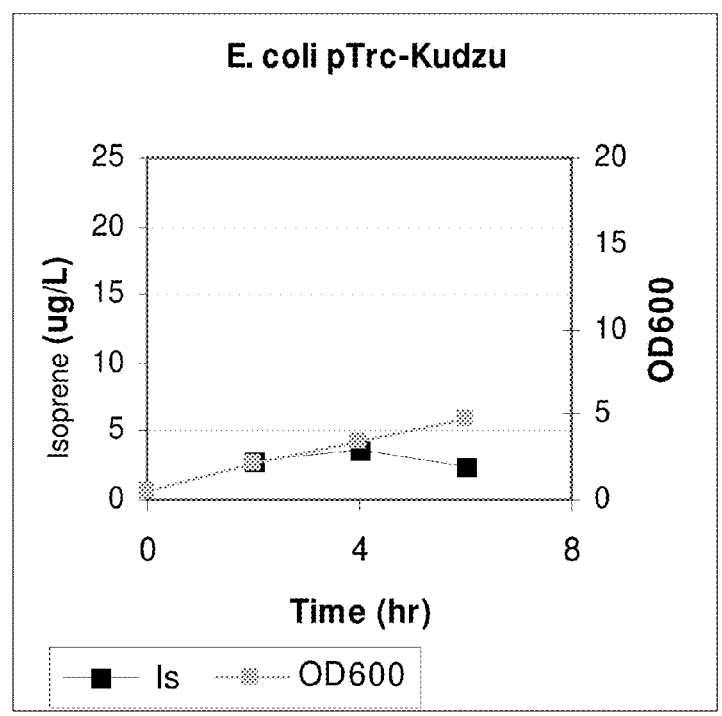
FIG. 8C is a graph showing the production of isoprene in *E. coli* BL21 cells with pTrcKudzu.
Figure 8D:
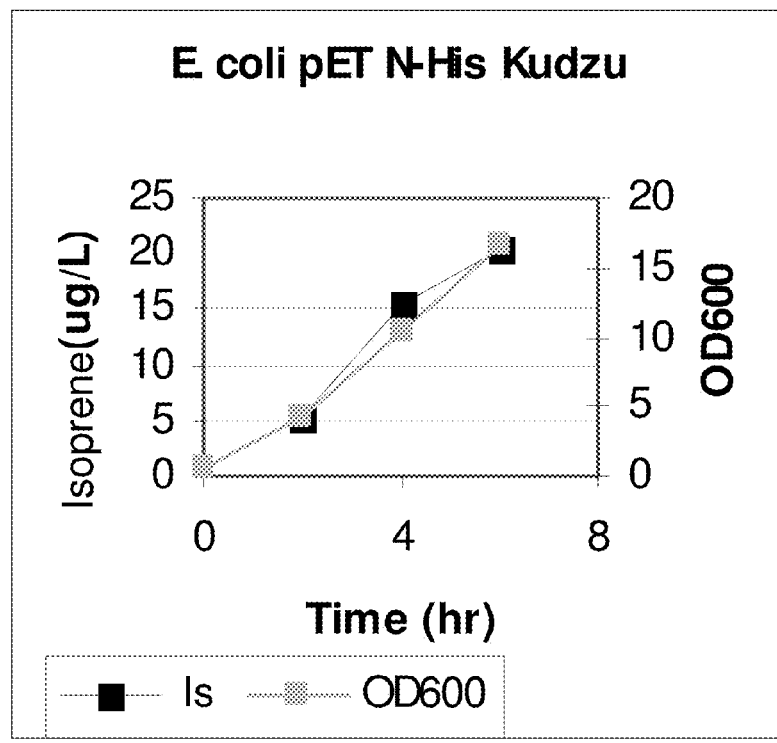
FIG. 8D is a graph showing the production of isoprene in *E. coli* BL21 cells with pETN-HisKudzu.

The kudzu isoprene synthase gene was also cloned into the low copy number plasmid pCL1920. Primers were used to amplify the kudzu isoprene synthase gene from pTrcKudzu described above. The forward primer added a HindIII site and an *E. coli* consensus RBS to the 5' end. The PstI cloning site was already present in pTrcKudzu just 3' of the stop codon so the reverse primer was constructed such that the final PCR product includes the PstI site. The sequences of the primers were: HindIII-rbs-Kudzu F: 5'-CATAT-GAAAGCTTGTATCGATTAAATAAGGAG-GAATAAACC (SEQ ID NO:6) and BamH1-Kudzu R: 5'-CGGTCGACGGATCCCTGCAGTTAGACATA-CATCAGCTG (SEQ ID NO:4). The PCR product was amplified using Herculase polymerase with primers at a concentration of 10 pmol and with 1 ng of template DNA (pTrcKudzu). The amplification protocol included 30 cycles of (95° C. for 1 minute, 60° C. for 1 minute, 72° C. for 2 minutes). The product was digested with HindIII and PstI and ligated into pCL1920 which had also been digested with HindIII and PstI. The ligation mix was transformed into *E. coli* Top10. Several transformants were checked by sequencing. The resulting plasmid was designated pCL-lac-Kudzu (FIGS. 6 and 7).

II. Determination of Isoprene Production

For the shake flask cultures, one ml of a culture was transferred from shake flasks to 20 ml CTC headspace vials (Agilent vial cat#5188 2753; cap cat#5188 2759). The cap was screwed on tightly and the vials incubated at the equivalent temperature with shaking at 250 rpm. After 30 minutes the vials were removed from the incubator and analyzed as described below (see Table 1 for some experimental values from this assay).

In cases where isoprene production in fermentors was determined, samples were taken from the off-gas of the fermentor and analyzed directly as described below (see Table 2 for some experimental values from this assay).

The analysis was performed using an Agilent 6890 GC/MS system interfaced with a CTC Analytics (Switzerland) CombiPAL autosampler operating in headspace mode. An Agilent HP-5MS GC/MS column (30 m×0.25 mm; 0.25 µm film thickness) was used for separation of analytes. The sampler was set up to inject 500 µL of headspace gas. The GC/MS method utilized helium as the carrier gas at a flow of 1 ml/minutes The injection port was held at 250° C. with a split ratio of 50:1. The oven temperature was held at 37° C. for the 2 minute duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene and was found to be linear from 1 µg/L to 200 µg/L. The limit of detection was estimated to be 50 to 100 ng/L using this method.

III. Production of Isoprene in Shake Flasks Containing *E. coli* Cells Expressing Recombinant Isoprene Synthase The vectors described above were introduced to *E. coli* strain BL21 (Novagen) to produce strains BL21/ptrcKudzu, BL21/pCL-lac-Kudzu and BL21/pETHisKudzu. The strains were spread for isolation onto LA (Luria agar) and carbenicillin (50 µg/ml) and incubated overnight at 37° C. Single colonies were inoculated into 250 ml baffled shake flasks containing 20 ml Luria Bertani broth (LB) and carbenicillin (100 µg/ml). Cultures were grown overnight at 20° C. with shaking at 200 rpm. The $OD_{600}$ of the overnight cultures were measured and the cultures were diluted into a 250 ml baffled shake flask containing 30 ml MagicMedia (Invitrogen) and carbenicillin (100 µg/ml) to an $OD_{600}$~0.05. The culture was incubated at 30° C. with shaking at 200 rpm. When the $OD_{600}$~0.5-0.8, 400 M IPTG was added and the cells were incubated for a further 6 hours at 30° C. with shaking at 200 rpm. At 0, 2, 4 and 6 hours after induction with IPTG, 1 ml aliquots of the cultures were collected, the $OD_{600}$ was determined and the amount of isoprene produced was measured as described above. Results are shown in FIG. 8.

IV. Production of Isoprene from BL21/ptrcKudzu in 14 Liter Fermentation

Large scale production of isoprene from *E. coli* containing the recombinant kudzu isoprene synthase gene was determined from a fed-batch culture. The recipe for the fermentation media (TM2) per liter of fermentation medium was as follows: $K_2HPO_4$ 13.6 g, $KH_2PO_4$ 13.6 g, MgSO4*7H$_2$O 2 g, citric acid monohydrate 2 g, ferric ammonium citrate 0.3 g, $(NH_4)_2SO_4$ 3.2 g, yeast extract 5 g, 1000× Modified Trace Metal Solution 1 ml. All of the components were added together and dissolved in diH$_2$O. The pH was adjusted to 6.8 with potassium hydroxide (KOH) and q.s. to volume. The final product was filter sterilized with 0.22µ filter (only, do not autoclave). The recipe for 1000× Modified Trace Metal Solution was as follows: Citric Acids*H$_2$O 40 g, $MnSO_4$*H$_2$O 30 g, NaCl 10 g, $FeSO_4$*7H$_2$O 1 g, $CoCl_2$*6H$_2$O 1 g, $ZnSO$*7H$_2$O 1 g, $CuSO_4$*5H$_2$O 100 mg, $H_3BO_3$ 100 mg, $NaMoO_4$*2H$_2$O 100 mg. Each component was dissolved one at a time in diH$_2$O, pH to 3.0 with HCl/NaOH, then q.s. to volume and filter sterilized with a 0.22µ filter.

Figure 9A:
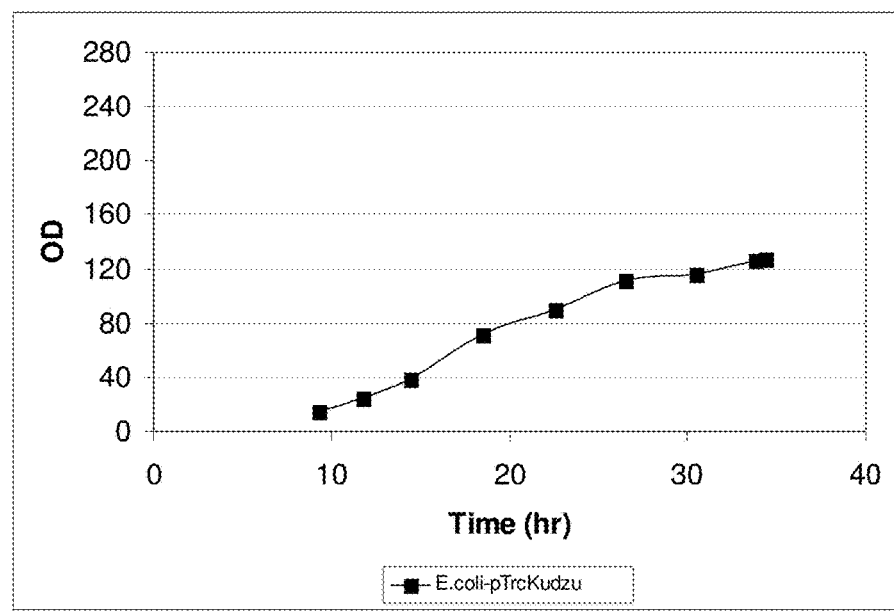
FIG. 9A is a graph showing OD over time of fermentation of *E. coli* BL21/pTrcKudzu in a 14 liter fed batch fermentation.
Figure 9B:
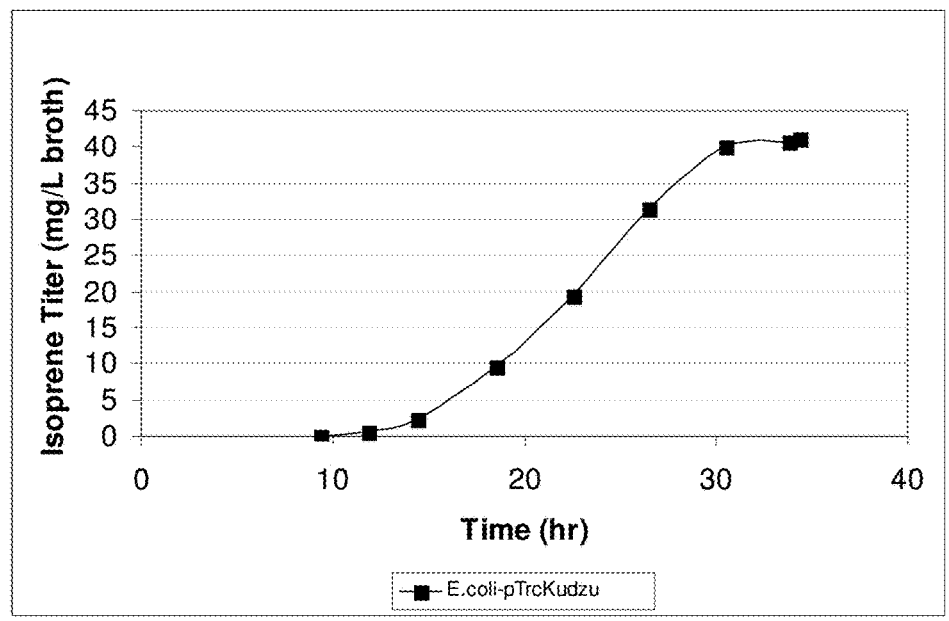
FIG. 9B is a graph showing isoprene production over time of fermentation of *E. coli* BL21/pTrcKudzu in a 14 liter fed batch fermentation.

This experiment was carried out in 14 L bioreactor to monitor isoprene formation from glucose at the desired fermentation, pH 6.7 and temperature 34° C. An inoculum of *E. coli* strain BL21/ptrcKudzu taken from a frozen vial was prepared in soytone-yeast extract-glucose medium. After the inoculum grew to $OD_{550}$=0.6, two 600 ml flasks were centrifuged and the contents resuspended in 70 ml supernatant to transfer the cell pellet (70 ml of OD 3.1 material) to the bioreactor. At various times after inoculation, samples were removed and the amount of isoprene produced was determined as described above. Results are shown in FIG. 9.

Figure 30:
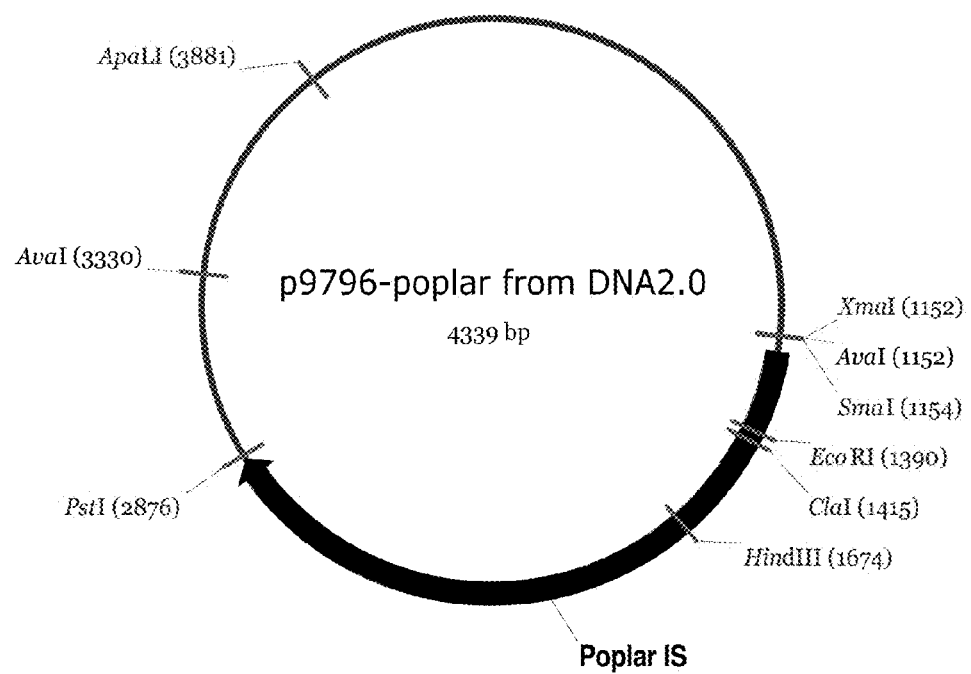
FIG. 30 is a map of p9796-poplar.
Figure 32:
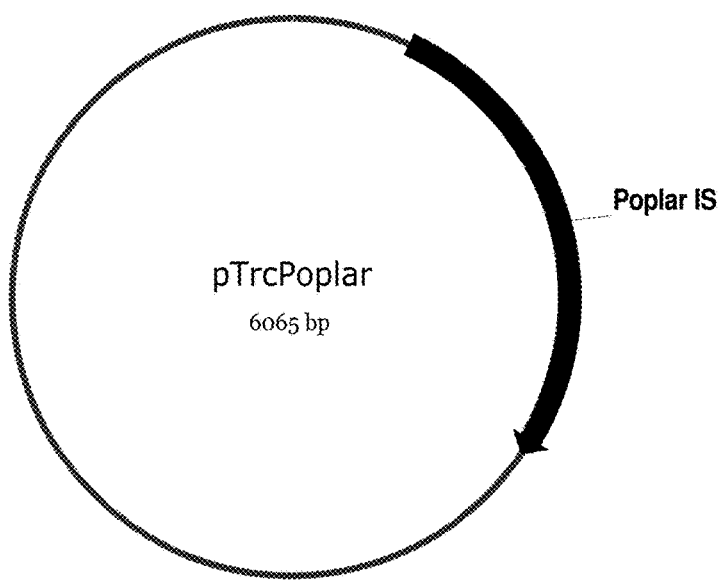
FIG. 32 is a map of pTrcPoplar.
Figure 34:
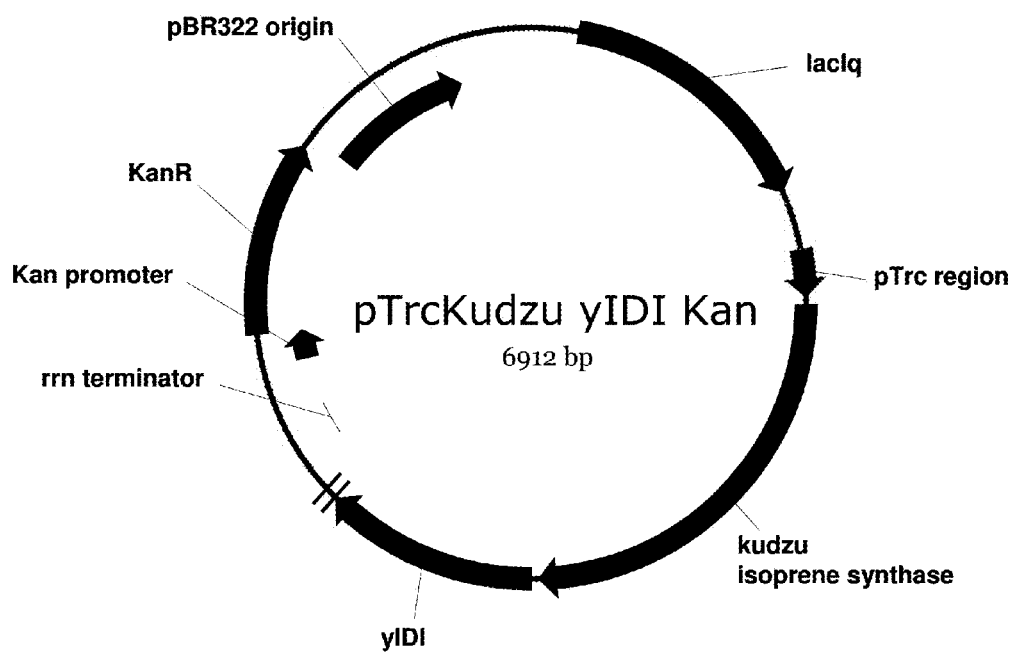
FIG. 34 is a map of pTrcKudzu yIDI Kan.
Figure 36:
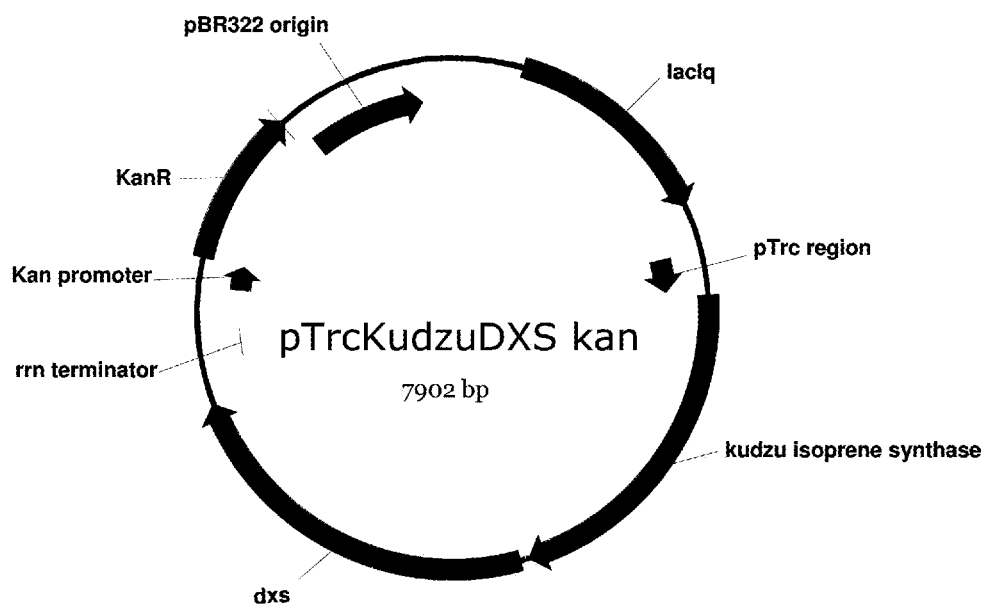
FIG. 36 is a map of pTrcKudzuDXS Kan.
Figure 38:
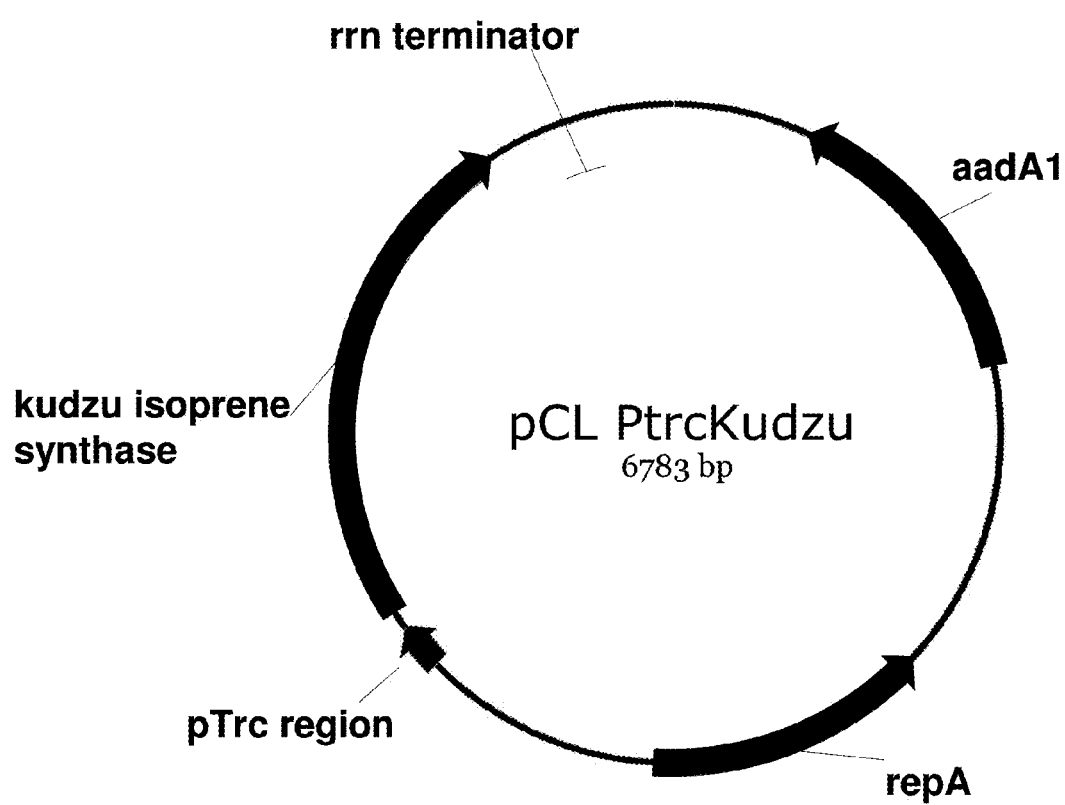
FIG. 38 is a map of pCL PtrcKudzu.
Figure 40:
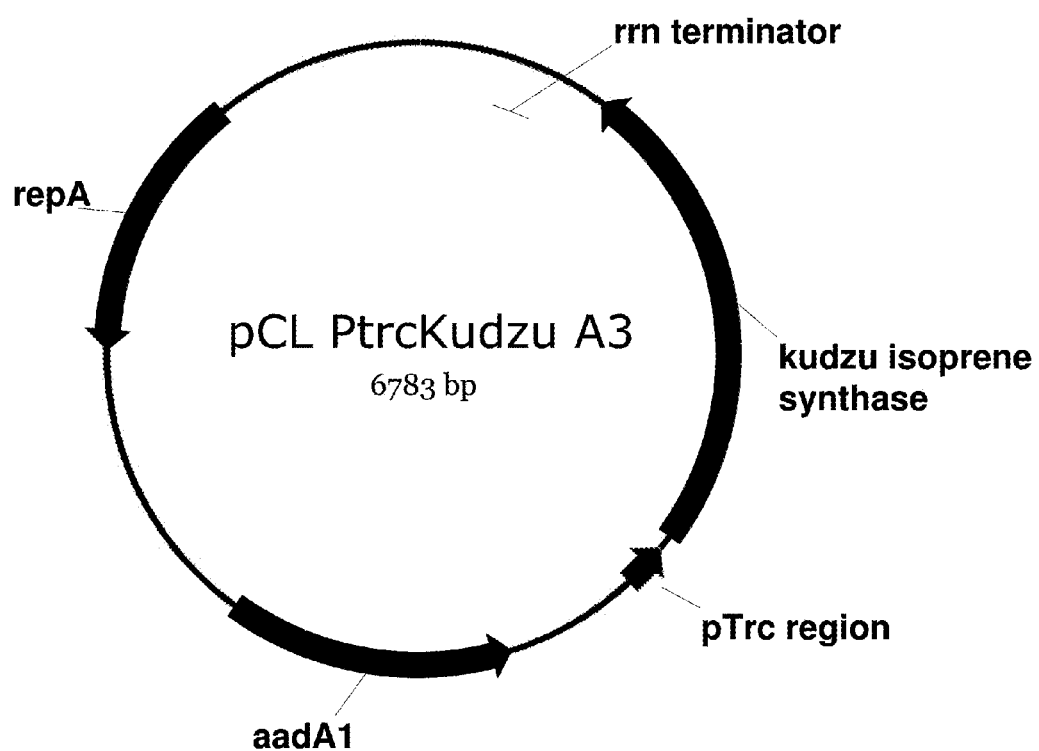
FIG. 40 is a map of pCL PtrcKudzu A3.
Figure 42:
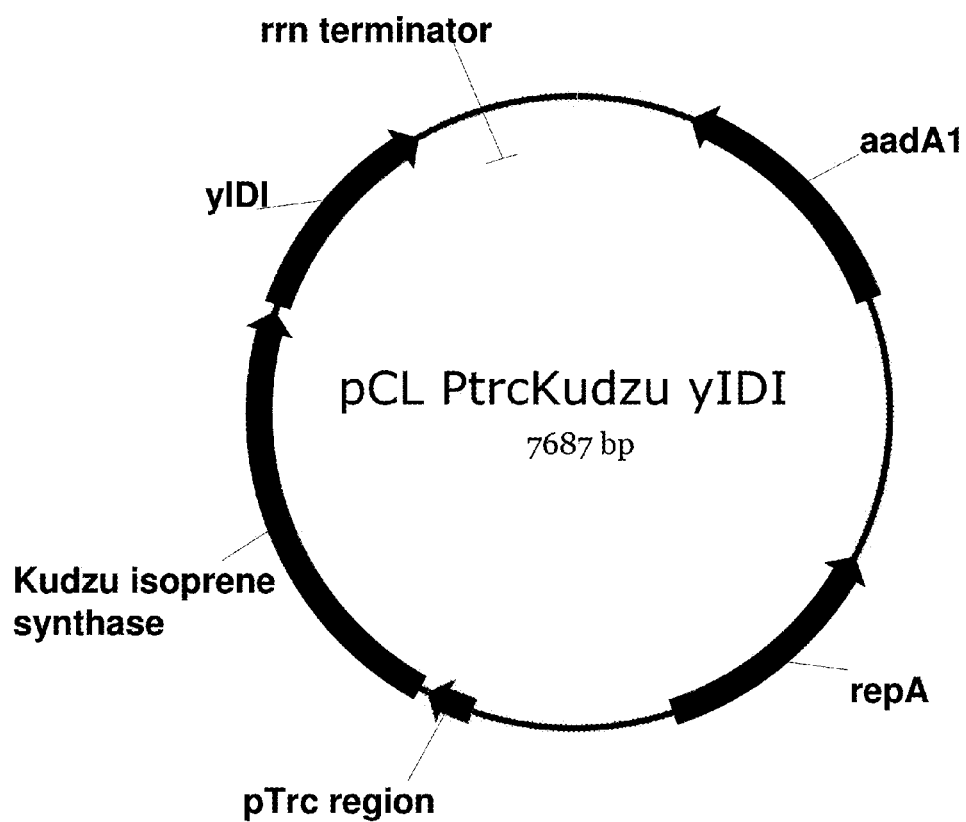
FIG. 42 is a map of pCL PtrcKudzu yIDI.
Figure 44:
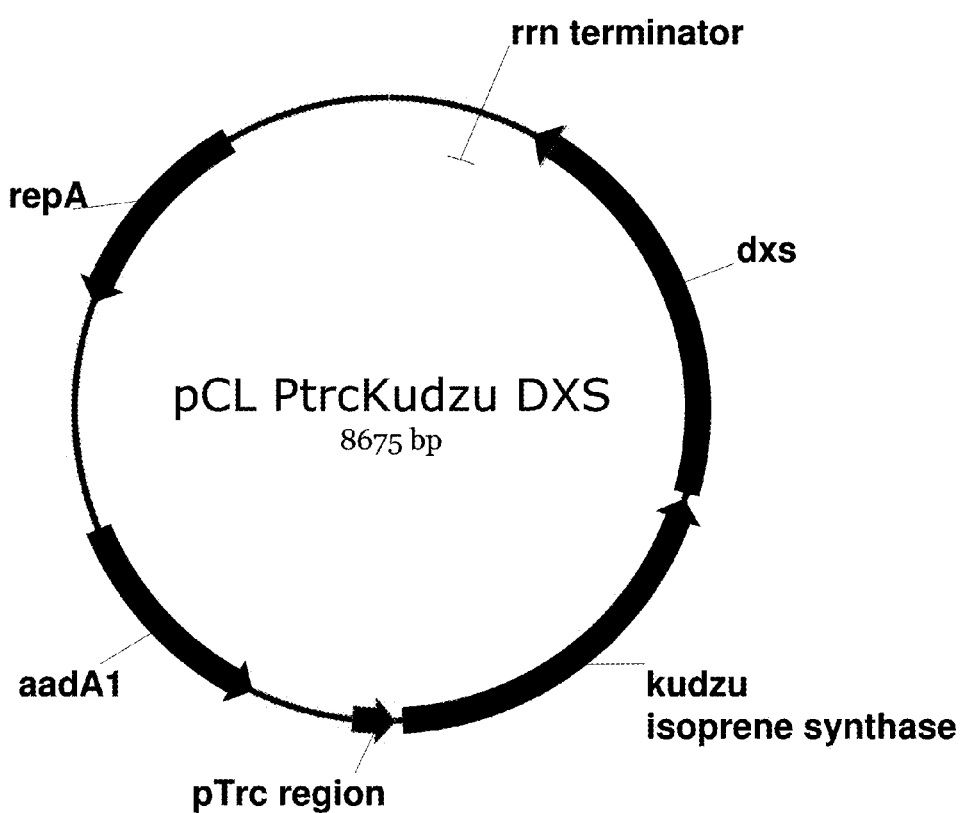
FIG. 44 is a map of pCL PtrcKudzu DXS.
Figure 46A:
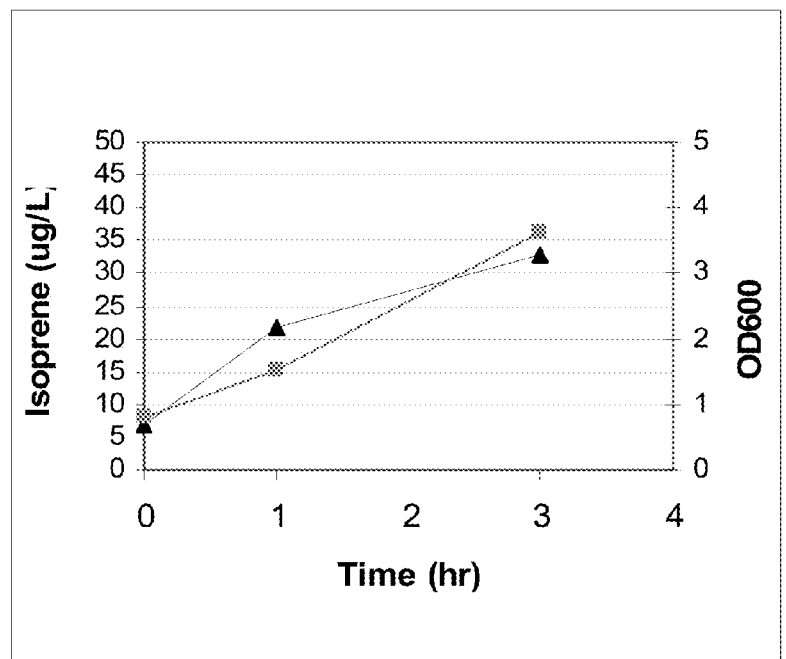
FIG. 46A, FIG. 46B, FIG. 46C, FIG. 46D, and FIG. 46E show graphs representing isoprene production from biomass feedstocks.
Figure 46B:
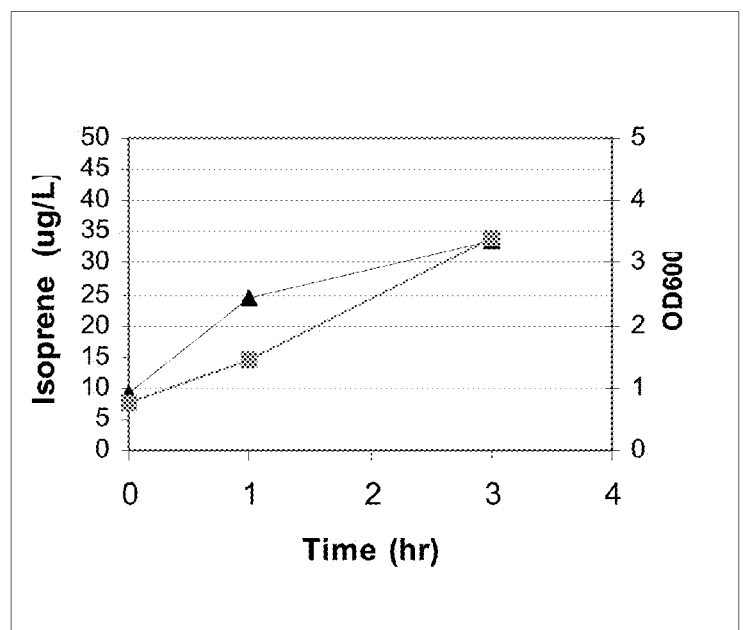
Figure 46C:
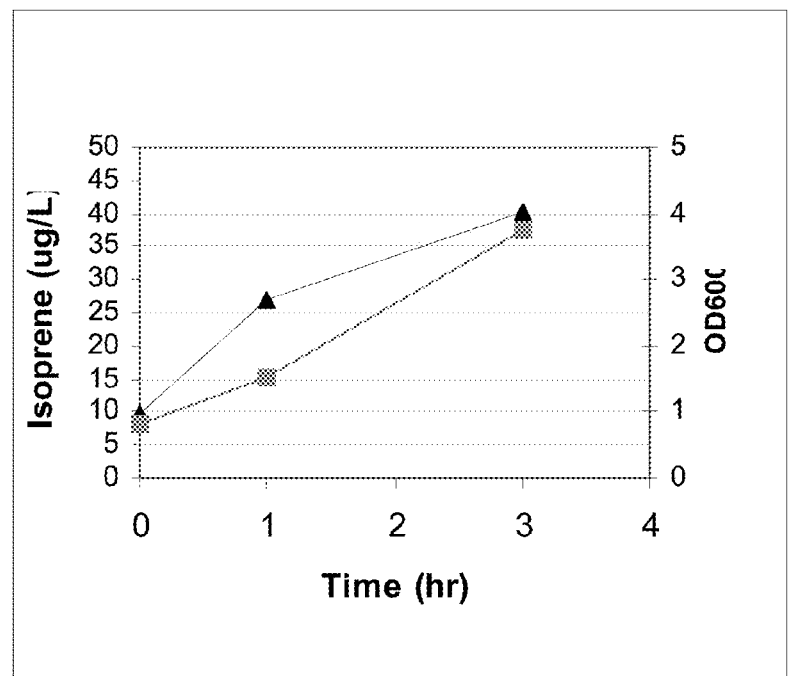
Figure 46D:
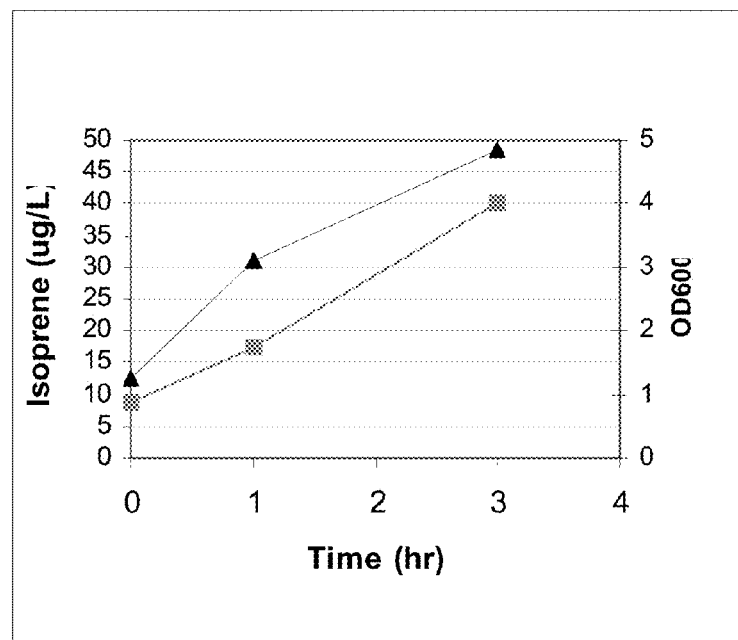
Figure 46E:
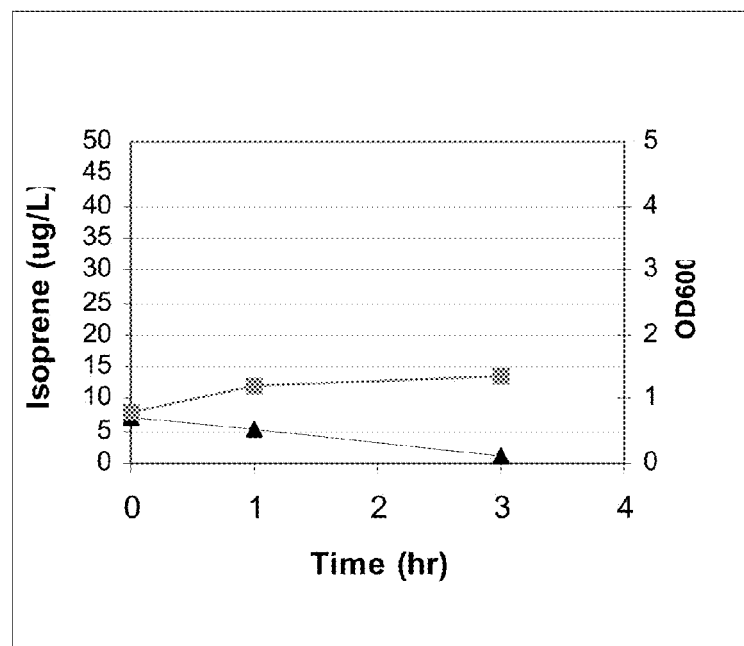

Example 2: Production of Isoprene in *E. coli* Expressing Recombinant Poplar Isoprene Synthase The protein sequence for the poplar (*Populus alba*× *Populus tremula*) isoprene synthase (Schnitzler, J-P, et al. (2005) *Planta* 222:777-786) was obtained from GenBank (CAC35696). A gene, codon optimized for *E. coli*, was purchased from DNA2.0 (p9796-poplar, FIG. 30, FIG. 31A and FIG. 31B). The isoprene synthase gene was removed from the supplied plasmid by restriction endonuclease digestion with BspLU11I/PstI, gel-purified, and ligated into pTrcHis2B that had been digested with NcoI/PstI. The construct is cloned such that the stop codon in the insert is before the PstI site, which results in a construct in which the His-Tag is not attached to the isoprene synthase protein. The resulting plasmid pTrcPoplar (FIG. 32, FIG. 33A, FIG. 33B and FIG. 33C), was verified by sequencing.

Example 3: Production of Isoprene in *Panteoa citrea* Expressing Recombinant Kudzu Isoprene Synthase The pTrcKudzu and pCL-lac Kudzu plasmids described in Example 1 were electroporated into *P. citrea* (U.S. Pat.

Figure 10A:
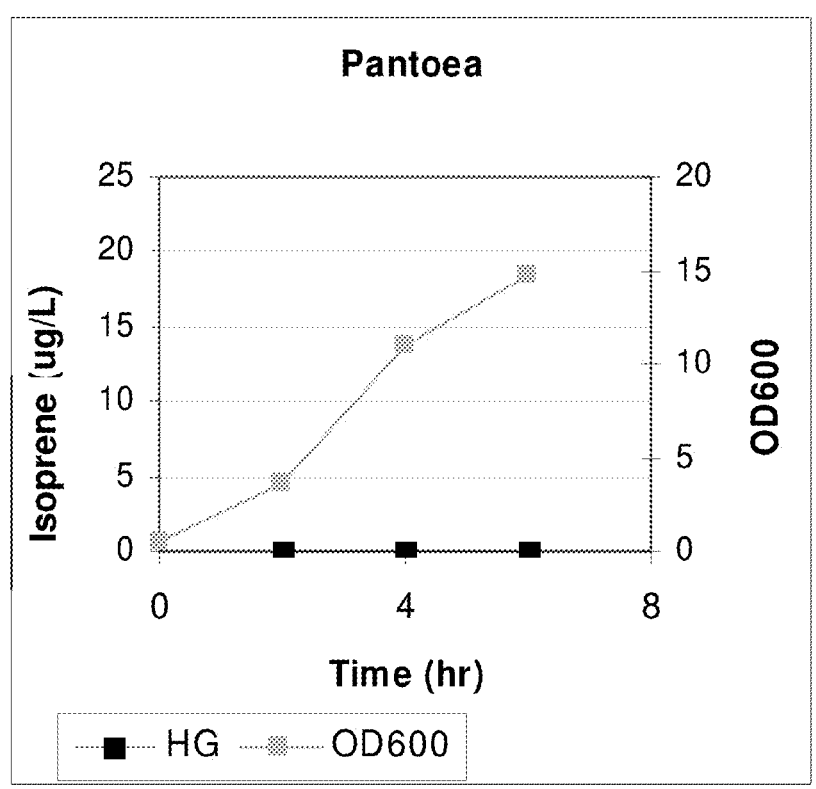
FIG. 10A is a graph showing the production of isoprene in *Panteoa citrea*. Control cells without recombinant kudzu isoprene synthase. Grey diamonds represent isoprene synthesis, black squares represent $OD_{600}$.
Figure 10B:
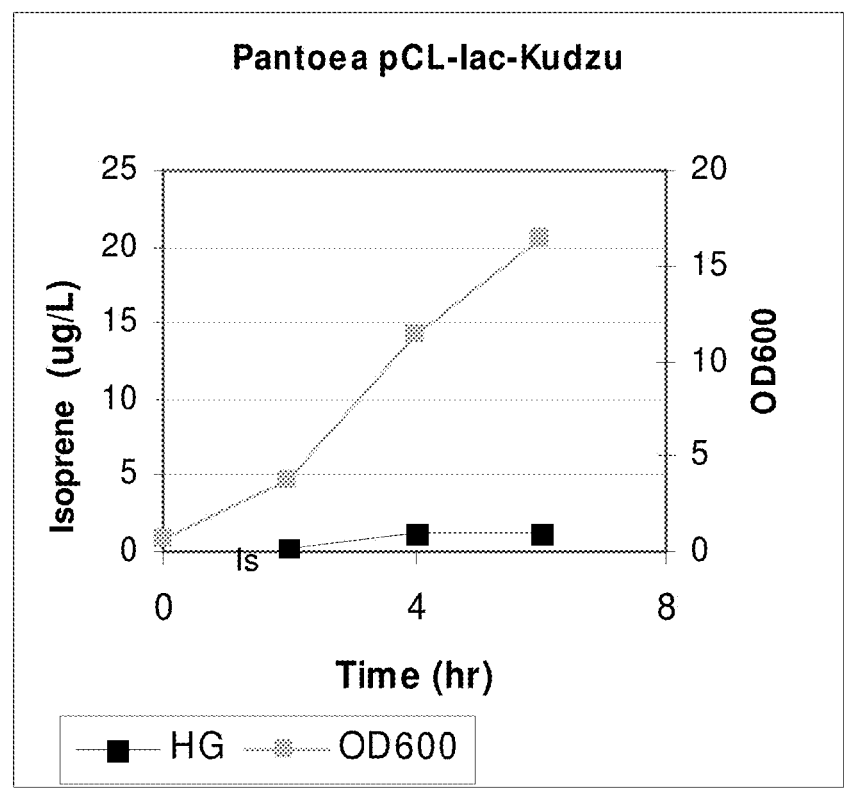
FIG. 10B is a graph showing the production of isoprene in *Panteoa citrea* expressing pCL-lac Kudzu. Grey diamonds represent isoprene synthesis, black squares represent $OD_{600}$.
Figure 10C:
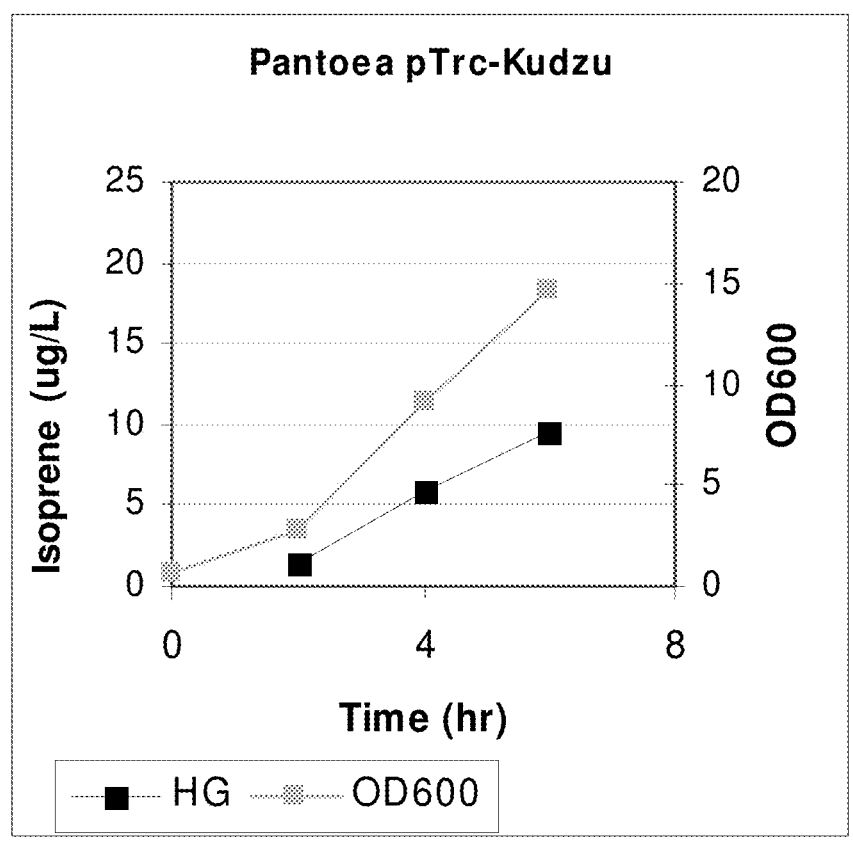
FIG. 10C is a graph showing the production of isoprene in *Panteoa citrea* expressing pTrcKudzu. Grey diamonds represent isoprene synthesis, black squares represent $OD_{600}$.

No. 7,241,587). Transformants were selected on LA containing carbenicillin (200 μg/ml) or spectinomycin (50 μg/ml) respectively. Production of isoprene from shake flasks and determination of the amount of isoprene produced was performed as described in Example 1 for *E. coli* strains expressing recombinant kudzu isoprene synthase. Results are shown in FIG. 10.

Example 4: Production of Isoprene in *Bacillus subtilis* Expressing Recombinant Kudzu Isoprene Synthase I. Construction of a *B. subtilis* Replicating Plasmid for the Expression of Kudzu Isoprene Synthase The kudzu isoprene synthase gene was expressed in *Bacillus subtilis* aprEnprE Pxyl-comK strain (BG3594comK) using a replicating plasmid (pBS19 with a chloramphenicol resistance cassette) under control of the aprE promoter. The isoprene synthase gene, the aprE promoter and the transcription terminator were amplified separately and fused using PCR. The construct was then cloned into pBS19 and transformed into *B. subtilis*.

a) Amplification of the aprE Promoter

The aprE promoter was amplified from chromosomal DNA from *Bacillus subtilis* using the following primers:

```
CF 797 (+) Start aprE promoter MfeI
                                      (SEQ ID NO: 58)
5'-GACATCAATTGCTCCATTTTCTTCTGCTATC CF 07-43 (-) Fuse aprE promoter to Kudzu ispS
                                      (SEQ ID NO: 59)
5'-ATTGAGAAGAGGTCGCACACACTCTTTACCCTCTCCTTTTA
``` b) Amplification of the Isoprene Synthase Gene

The kudzu isoprene synthase gene was amplified from plasmid pTrcKudzu (SEQ ID NO:2). The gene had been codon optimized for *E. coli* and synthesized by DNA 2.0. The following primers were used:

```
CF 07-42 (+) Fuse the aprE promoter to kudzu
isoprene synthase gene (GTG start codon)
                                      (SEQ ID NO: 60)
5'-TAAAAGGAGAGGGTAAAGAGTGTGTGCGACCTCTTCTCAAT CF 07-45 (-) Fuse the 3' end of kudzu isoprene
synthase gene to the terminator
                                      (SEQ ID NO: 61)
5'-CCAAGGCCGGTTTTTTTTAGACATACATCAGCTGGTTAATC
``` c) Amplification of the Transcription Terminator

The terminator from the alkaline serine protease of *Bacillus amyliquefaciens* was amplified from a previously sequenced plasmid pJHPms382 using the following primers:

```
CF 07-44 (+) Fuse the 3' end of kudzu isoprene
synthase to the terminator
                                      (SEQ ID NO: 62)
5'-GATTAACCAGCTGATGTATGTCTAAAAAAAACCGGCCTTGG CF 07-46 (-) End of B. amyliquefaciens
terminator (BamHI)
                                      (SEQ ID NO: 63)
5'-GACATGACGGATCCGATTACGAATGCCGTCTC
```

The kudzu fragment was fused to the terminator fragment using PCR with the following primers:

```
CF 07-42 (+) Fuse the aprE promoter to kudzu
isoprene synthase gene (GTG start codon)
                                      (SEQ ID NO: 61)
5'-TAAAAGGAGAGGGTAAAGAGTGTGTGCGACCTCTTCTCAAT CF 07-46 (-) End of B. amyliquefaciens
terminator (BamHI)
                                      (SEQ ID NO: 63)
5'-GACATGACGGATCCGATTACGAATGCCGTCTC
```

The kudzu-terminator fragment was fused to the promoter fragment using PCR with the following primers:

```
CF 797 (+) Start aprE promoter MfeI
                                      (SEQ ID NO: 64)
5'-GACATCAATTGCTCCATTTTCTTCTGCTATC CF 07-46 (-) End of B. amyliquefaciens
terminator (BamHI)
                                      (SEQ ID NO: 63)
5'-GACATGACGGATCCGATTACGAATGCCGTCTC
```

The fusion PCR fragment was purified using a Qiagen kit and digested with the restriction enzymes MfeI and BamHI. This digested DNA fragment was gel purified using a Qiagen kit and ligated to a vector known as pBS19, which had been digested with EcoRI and BamHI and gel purified.

The ligation mix was transformed into *E. coli* Top 10 cells and colonies were selected on LA and 50 carbenicillin plates. A total of six colonies were chosen and grown overnight in LB and 50 carbenicillin and then plasmids were isolated using a Qiagen kit. The plasmids were digested with EcoRI and BamHI to check for inserts and three of the correct plasmids were sent in for sequencing with the following primers:

```
CF 149 (+) EcoRI start of aprE promoter
                                      (SEQ ID NO: 65)
5'-GACATGAATTCCTCCATTTTCTTCTGC CF 847 (+) Sequence in pXX 049 (end of aprE
promoter)
                                      (SEQ ID NO: 66)
5'-AGGAGAGGGTAAAGAGTGAG CF 07-45 (-) Fuse the 3' end of kudzu isoprene
synthase to the terminator
                                      (SEQ ID NO: 61)
5'-CCAAGGCCGGTTTTTTTTAGACATACATCAGCTGGTTAATC CF 07-48 (+) Sequencing primer for kudzu
isoprene synthase
                                      (SEQ ID NO: 67)
5'-CTTTTCCATCACCCACCTGAAG CF 07-49 (+) Sequencing in kudzu isoprene
synthase
                                      (SEQ ID NO: 68)
5'-GGCGAAATGGTCCAACAACAAAATTATC
```

Figure 52:
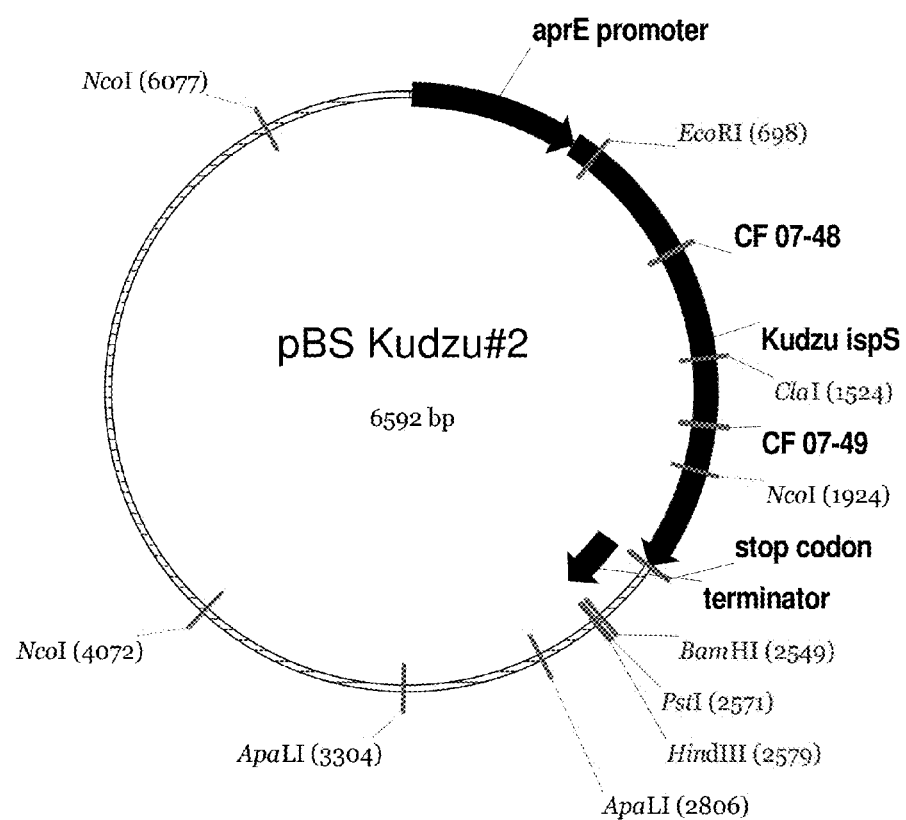
FIG. 52 is a map of pBS Kudzu #2.

The plasmid designated pBS Kudzu #2 (FIGS. 52 and 12) was correct by sequencing and was transformed into BG 3594 comK, a *Bacillus subtilis* host strain. Selection was done on LA and 5 chloramphenicol plates. A transformant was chosen and struck to single colonies on LA and 5 chloramphenicol, then grown in LB and 5 chloramphenicol until it reached an OD$_{600}$ of 1.5. It was stored frozen in a vial at −80° C. in the presence of glycerol. The resulting strain was designated CF 443.

Figure 11:
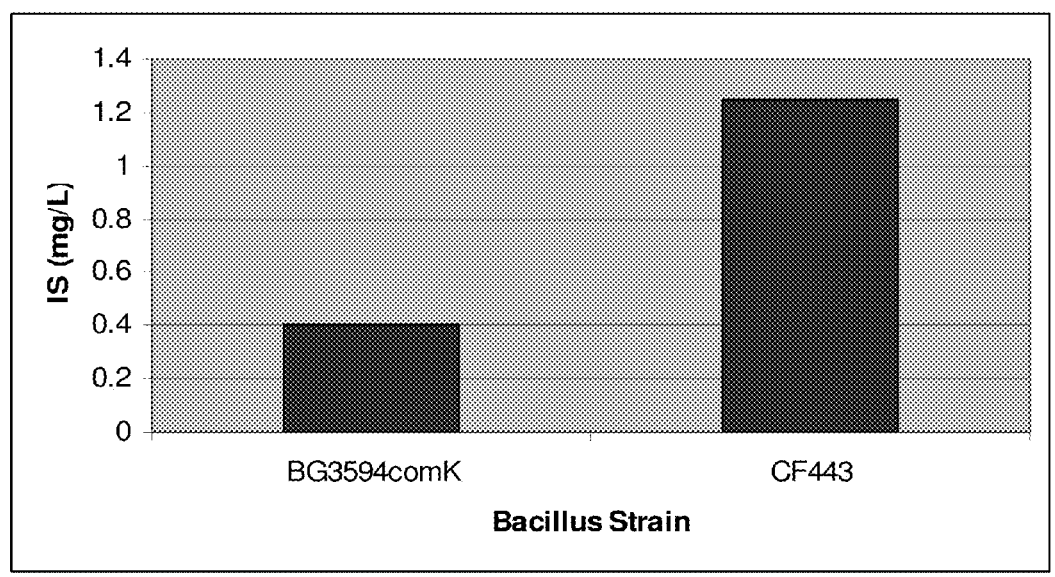
FIG. 11 is a graph showing the production of isoprene in *Bacillus subtilis* expressing recombinant isoprene synthase. BG3594comK is a *B. subtilis* strain without plasmid (native isoprene production). CF443-BG3594comK is a *B. subtilis* strain with pBSKudzu (recombinant isoprene production). IS on the y-axis indicates isoprene.

II. Production of Isoprene in Shake Flasks Containing *B. subtilis* Cells Expressing Recombinant Isoprene Synthase Overnight cultures were inoculated with a single colony of CF 443 from a LA and Chloramphenicol (Cm, 25 jag/ml). Cultures were grown in LB and Cm at 37° C. with shaking at 200 rpm. These overnight cultures (1 ml) were used to inoculate 250 ml baffled shake flasks containing 25 ml Grants II media and chloramphenicol at a final concentration of 25 jag/ml. Grants II Media recipe was 10 g soytone, 3 ml 1M $K_2HPO_4$, 75 g glucose, 3.6 g urea, 100 ml 10×MOPS, q.s. to 1 L with $H_2O$, pH 7.2; 10×MOPS recipe was 83.72 g MOPS, 7.17 g tricine, 12 g KOH pellets, 10 ml 0.276M $K_2SO_4$ solution, 10 ml 0.528M $MgCl_2$ solution, 29.22 g NaCl, 100 ml 100× micronutrients, q.s. to 1 L with $H_2O$; and 100× micronutrients recipe was 1.47 g $CaCl_2*2H_2O$, 0.4 g $FeSO_4*7H_2O$, 0.1 g $MnSO_4*H_2O$, 0.1 g $ZnSO_4*H_2O$, 0.05 g $CuCl_2*2H_2O$, 0.1 g $CoCl_2*6H_2O$, 0.1 g $Na_2MoO_4*2H_2O$, q.s. to 1 L with $H_2O$. Shake flasks were incubated at 37° C. and samples were taken at 18, 24, and 44 hours. At 18 hours the headspaces of CF443 and the control strain were sampled. This represented 18 hours of accumulation of isoprene. The amount of isoprene was determined by gas chromatography as described in Example 1. Production of isoprene was enhanced significantly by expressing recombinant isoprene synthase (FIG. 11).

III. Production of Isoprene by CF443 in 14 L Fermentation

Figure 53A:
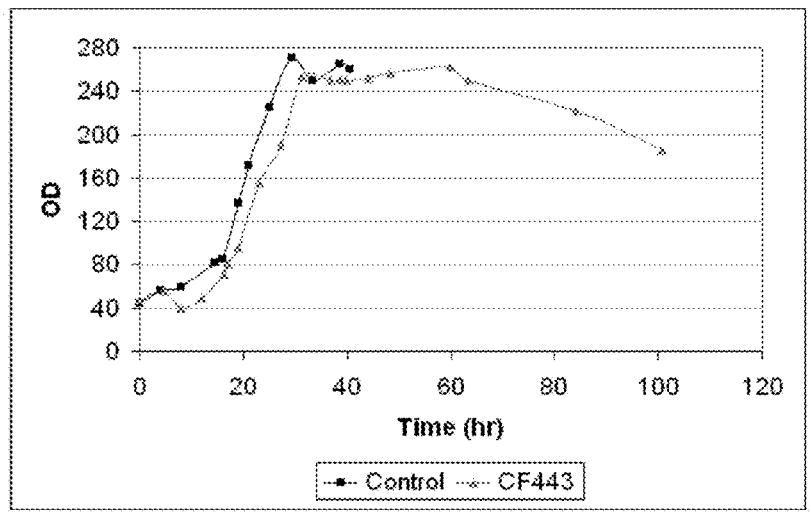
FIG. 53A is a graph showing growth during fermentation time of *Bacillus* expressing recombinant kudzu isoprene synthase in 14 liter fed batch fermentation. Black diamonds represent a control strain (BG3594comK) without recombinant isoprene synthase (native isoprene production) and grey triangles represent *Bacillus* with pBSKudzu (recombinant isoprene production).
Figure 53B:
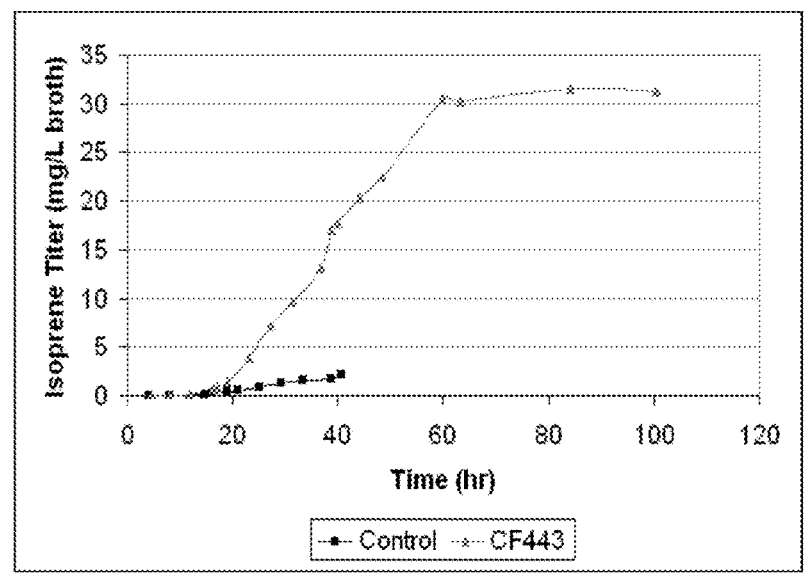
FIG. 53B is a graph showing isoprene production during fermentation time of *Bacillus* expressing recombinant kudzu isoprene synthase in 14 liter fed batch fermentation. Black diamonds represent a control strain (BG3594comK) without recombinant isoprene synthase (native isoprene production) and grey triangles represent *Bacillus* with pBSKudzu (recombinant isoprene production).

Large scale production of isoprene from *B. subtilis* containing the recombinant kudzu isoprene synthase gene on a replication plasmid was determined from a fed-batch culture. *Bacillus* strain CF 443, expressing a kudzu isoprene synthase gene, or control stain which does not express a kudzu isoprene synthase gene were cultivated by conventional fed-batch fermentation in a nutrient medium containing soy meal (Cargill), sodium and potassium phosphate, magnesium sulfate and a solution of citric acid, ferric chloride and manganese chloride. Prior to fermentation the media is macerated for 90 minutes using a mixture of enzymes including cellulases, hemicellulases and pectinases (see, WO95/04134). 14-L batch fermentations are fed with 60% wt/wt glucose (Cargill DE99 dextrose, ADM Versadex greens or Danisco invert sugar) and 99% wt/wt oil (Western Family soy oil, where the 99% wt/wt is the concentration of oil before it was added to the cell culture medium). Feed was started when glucose in the batch was non-detectable. The feed rate was ramped over several hours and was adjusted to add oil on an equal carbon basis. The pH was controlled at 6.8-7.4 using 28% w/v ammonium hydroxide. In case of foaming, antifoam agent was added to the media. The fermentation temperature was controlled at 37° C. and the fermentation culture was agitated at 750 rpm. Various other parameters such as pH, DO %, airflow, and pressure were monitored throughout the entire process. The DO % is maintained above 20. Samples were taken over the time course of 36 hours and analyzed for cell growth ($OD_{550}$) and isoprene production. Results of these experiments are presented in FIGS. 53A and 53B.

IV. Integration of the Kudzu Isoprene Synthase (ispS) in *B. subtilis*.

The kudzu isoprene synthase gene was cloned in an integrating plasmid (pJH101-cmpR) under the control of the aprE promoter. Under the conditions tested, no isoprene was detected.

Example 5: Production of Isoprene in *Trichoderma*

I. Construction of Vectors for Expression of the Kudzu Isoprene Synthase in *Trichoderma reesei*

The *Yarrowia lipolytica* codon-optimized kudzu IS gene was synthesized by DNA 2.0 (SEQ ID NO:8) (FIG. 13). This plasmid served as the template for the following PCR amplification reaction: 1 µl plasmid template (20 ng/ul), 1 µl Primer EL-945 (10 uM) 5'-GCTTATGGATCCTCTAGAC-TATTACACGTACATCAATTGG (SEQ ID NO:9), 1 µl Primer EL-965 (10 uM) 5'-CACCATGTGTGCAACCTC-CTCCCAGTTTAC (SEQ ID NO:10), 1 µl dNTP (10 mM), 5 µl 10× PfuUltra II Fusion HS DNA Polymerase Buffer, 1 µl PfuUltra II Fusion HS DNA Polymerase, 40 µl water in a total reaction volume of 50 µl. The forward primer contained an additional 4 nucleotides at the 5'-end that did not correspond to the *Y. lipolytica* codon-optimized kudzu isoprene synthase gene, but was required for cloning into the pENTR/D-TOPO vector. The reverse primer contained an additional 21 nucleotides at the 5'-end that did not correspond to the *Y. lipolytica* codon-optimized kudzu isoprene synthase gene, but were inserted for cloning into other vector backbones. Using the MJ Research PTC-200 Thermocycler, the PCR reaction was performed as follows: 95° C. for 2 minutes (first cycle only), 95° C. for 30 seconds, 55° C. for 30 seconds, 72° C. for 30 seconds (repeat for 27 cycles), 72° C. for 1 minute after the last cycle. The PCR product was analyzed on a 1.2% E-gel to confirm successful amplification of the *Y. lipolytica* codon-optimized kudzu isoprene synthase gene.

The PCR product was then cloned using the TOPO pENTR/D-TOPO Cloning Kit following manufacturer's protocol: 1 µl PCR reaction, 1 µl Salt solution, 1 µl TOPO pENTR/D-TOPO vector and 3 µl water in a total reaction volume of 6 al. The reaction was incubated at room temperature for 5 minutes. One microliter of TOPO reaction was transformed into TOP 10 chemically competent *E. coli* cells. The transformants were selected on LA and 50 µg/ml kanamycin plates. Several colonies were picked and each was inoculated into a 5 ml tube containing LB and 50 µg/ml kanamycin and the cultures grown overnight at 37° C. with shaking at 200 rpm. Plasmids were isolated from the overnight culture tubes using QIAprep Spin Miniprep Kit, following manufacturer's protocol. Several plasmids were sequenced to verify that the DNA sequence was correct.

A single pENTR/D-TOPO plasmid, encoding a *Y. lipolytica* codon-optimized kudzu isoprene synthase gene, was used for Gateway Cloning into a custom-made pTrex3g vector. Construction of pTrex3g is described in WO 2005/001036 A2. The reaction was performed following manufacturer's protocol for the Gateway LR Clonase II Enzyme Mix Kit (Invitrogen): 1 µl *Y. lipolytica* codon-optimized kudzu isoprene synthase gene pENTR/D-TOPO donor vector, 1 µl pTrex3g destination vector, 6 µl TE buffer, pH 8.0 in a total reaction volume of 8 al. The reaction was incubated at room temperature for 1 hour and then 1 µl proteinase K solution was added and the incubation continued at 37° C. for 10 minutes. Then 1 µl of reaction was transformed into TOP10 chemically competent *E. coli* cells. The transformants were selected on LA and 50 µg/ml carbenicillin plates. Several colonies were picked and each was inoculated into a 5 ml tube containing LB and 50 µlg/ml carbenicillin and the cultures were grown overnight at 37° C. with shaking at 200 rpm. Plasmids were isolated from the overnight culture tubes using QIAprep Spin Miniprep Kit (Qiagen, Inc.), following manufacturer's protocol. Several plasmids were sequenced to verify that the DNA sequence was correct.

Figure 14:
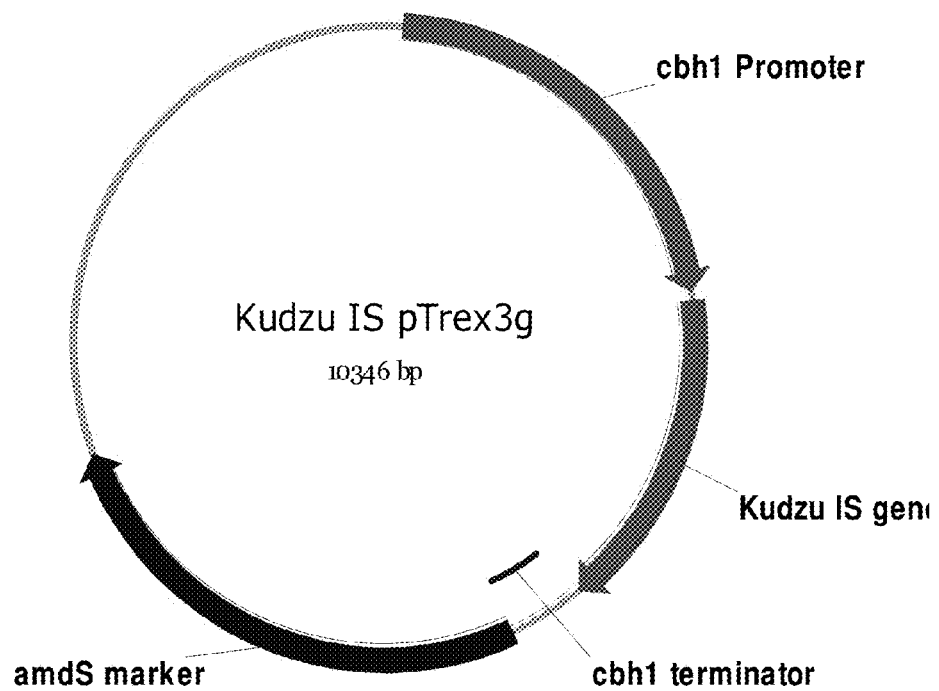
FIG. 14 is a map of pTrex3g comprising a kudzu isoprene synthase gene codon-optimized for expression in *Yarrowia*.

Biolistic transformation of *Y. lipolytica* codon-optimized kudzu isoprene synthase pTrex3g plasmid (FIG. 14) into a quad delete *Trichoderma reesei* strain was performed using the Biolistic PDS-1000/HE Particle Delivery System (see WO 2005/001036 A2). Isolation of stable transformants and shake flask evaluation was performed using protocol listed in Example 11 of patent publication WO 2005/001036 A2.

II. Production of Isoprene in Recombinant Strains of *T. reesei*

One ml of 15 and 36 hour old cultures of isoprene synthase transformants described above were transferred to head space vials. The vials were sealed and incubated for 5 hours at 30° C. Head space gas was measured and isoprene was identified by the method described in Example 1. Two of the transformants showed traces of isoprene. The amount of isoprene could be increased by a 14 hour incubation. The two positive samples showed isoprene at levels of about 0.5 µg/L for the 14 hour incubation. The untransformed control showed no detectable levels of isoprene. This experiment shows that *T. reesei* is capable of producing isoprene from endogenous precursor when supplied with an exogenous isoprene synthase.

Example 6: Production of Isoprene in *Yarrowia*

I. Construction of Vectors for Expression of the Kudzu Isoprene Synthase in *Yarrowia lipolytica*.

The starting point for the construction of vectors for the expression of the kudzu isoprene synthase gene in *Yarrowia lipolytica* was the vector pSPZ1(MAP29Spb). The complete sequence of this vector (SEQ ID No:11) is shown in FIG. 15A, FIG. 15B and FIG. 15C.

The following fragments were amplified by PCR using chromosomal DNA of a *Y. lipolytica* strain GICC 120285 as the template: a promotorless form of the URA3 gene, a fragment of 18S ribosomal RNA gene, a transcription terminator of the *Y. lipolytica* XPR2 gene and two DNA fragments containing the promoters of XPR2 and ICL1 genes. The following PCR primers were used:

ICL1 3
(SEQ ID NO: 69)
5'-GGTGAATTCAGTCTACTGGGGATTCCCAAATCTATATATA
CTGCAGGTGAC

ICL1 5
(SEQ ID NO: 70)
5'-GCAGGTGGGAAACTATGCACTCC

XPR 3
(SEQ ID NO: 71)
5'-CCTGAATTCTGTTGGATTGGAGGATTGGATAGTGGG

XPR 5
(SEQ ID NO: 72)
5'-GGTGTCGACGTACGGTCGAGCTTATTGACC

XPRT 3
(SEQ ID NO: 73)
5'-GGTGGGCCCGCATTTTGCCACCTACAAGCCAG

XPRT 5
(SEQ ID NO: 74)
5'-GGTGAATTCTAGAGGATCCCAACGCTGTTGCCTACAACGG

Y18S 3
(SEQ ID NO: 75)
5'-GGTGCGGCCGCTGTCTGGACCTGGTGAGTTTCCCCG

Y18S 5
(SEQ ID NO: 76)
5'-GGTGGGCCCATTAAATCAGTTATCGTTTATTTGATAG

YURA 3
(SEQ ID NO: 77)
5'-GGTGACCAGCAAGTCCATGGGTGGTTTGATCATGG

YURA 50
(SEQ ID NO: 78)
5'-GGTGCGGCCGCCTTTGGAGTACGACTCCAACTATG

YURA 51
(SEQ ID NO: 79)
5'-GCGGCCGCAGACTAAATTTATTTCAGTCTCC

For PCR amplification the PfuUltraII polymerase (Stratagene), supplier-provided buffer and dNTPs, 2.5 M primers and the indicated template DNA were used as per the manufacturer's instructions. The amplification was done using the following cycle: 95° C. for 1 min; 34× (95° C. for 30 sec; 55° C. for 30 sec; 72° C. for 3 min) and 10 min at 72° C. followed by a 4° C. incubation.

Figure 18B:
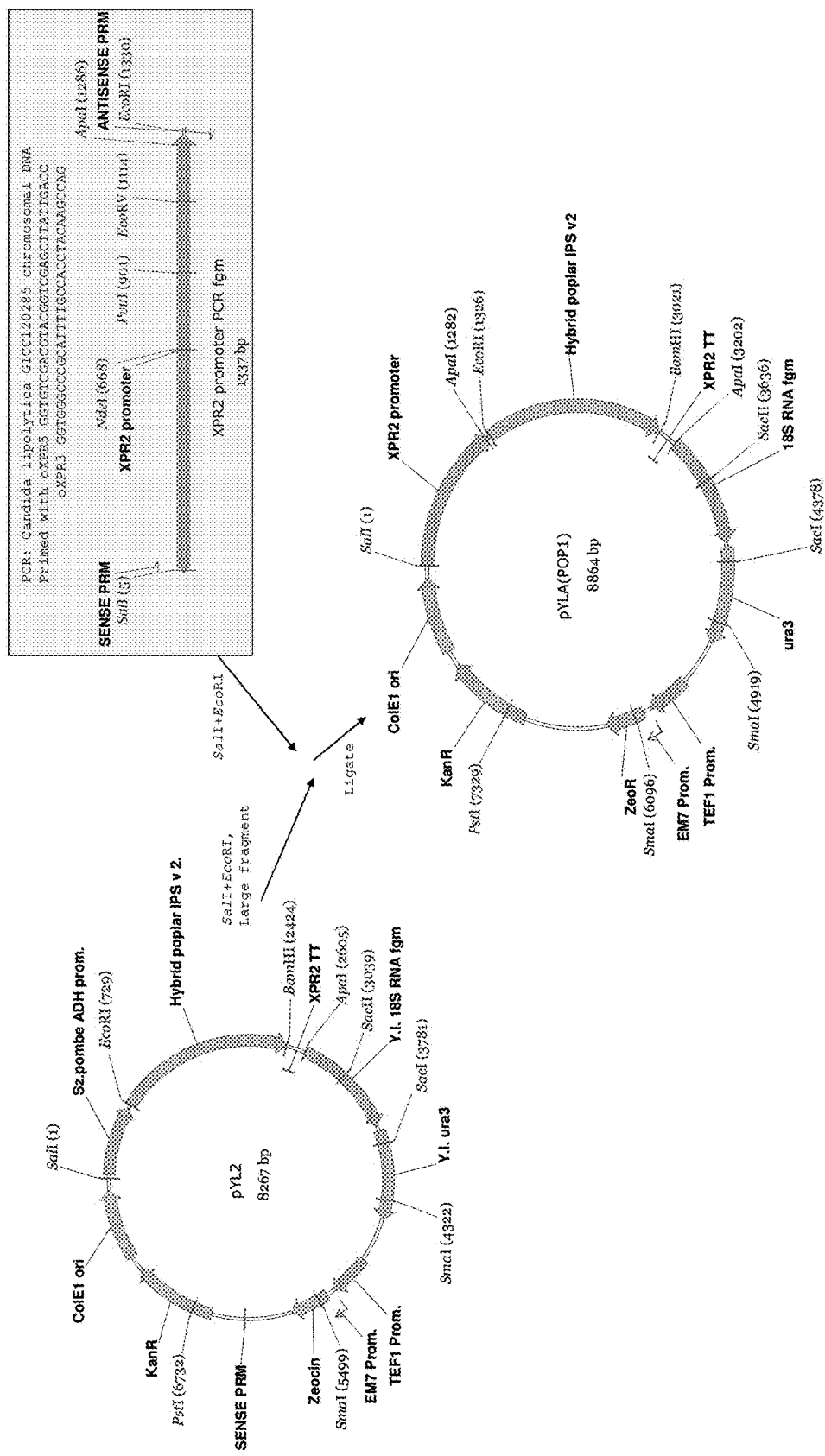
FIG. 18A(1) and FIG. 18A(2) show a schematic outlining construction of vectors pYLA 1, pYL1 and pYL2.
FIG. 18C shows a schematic outlining construction of the vector pYLA(KZ1)
FIG. 18D shows a schematic outlining construction of the vector pYLI(KZ1)
FIG. 18E shows a schematic outlining construction of the vector pYLI(MAP29)
FIG. 18F shows a schematic outlining construction of the vector pYLA(MAP29)
Figure 18C:
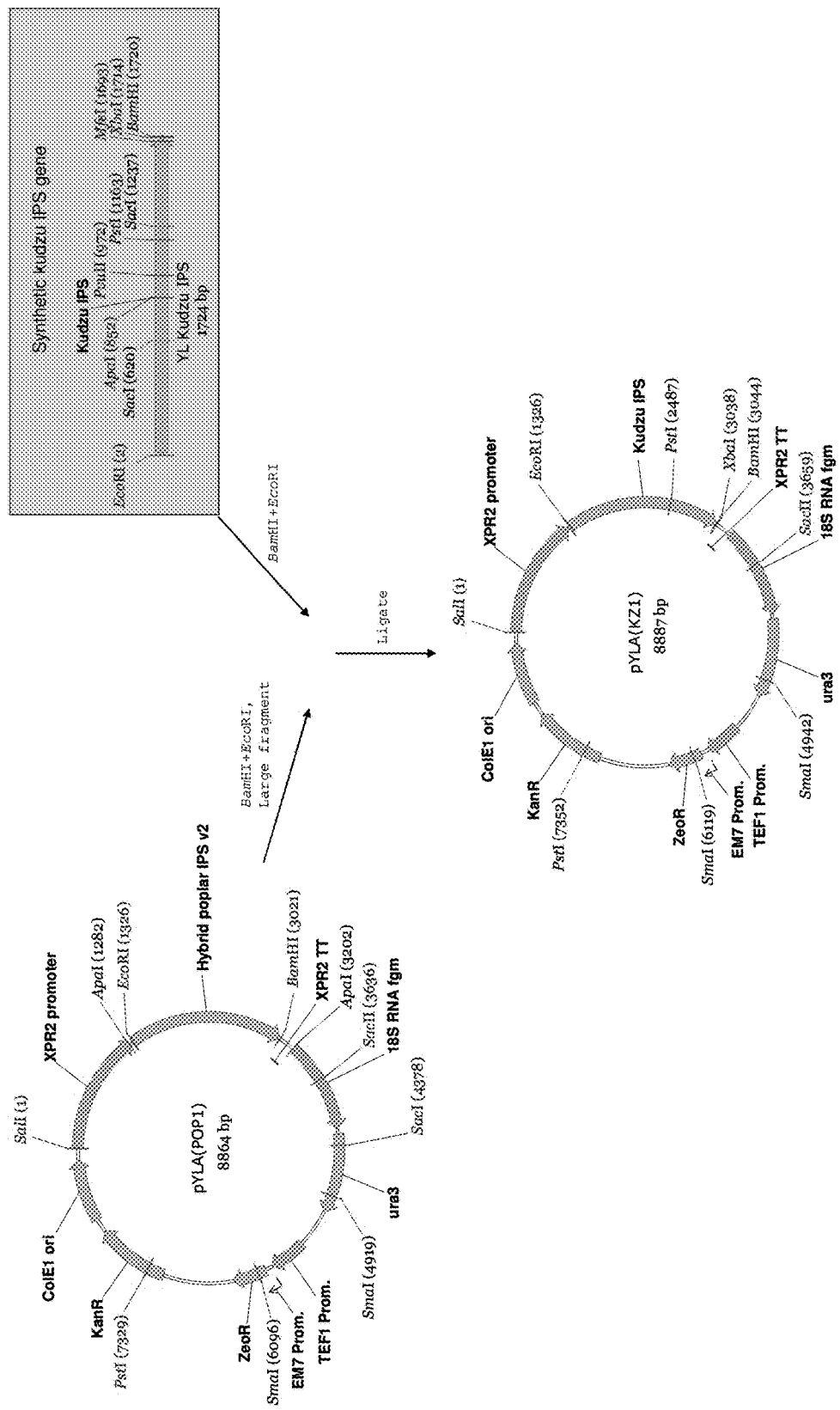
Figure 18D:
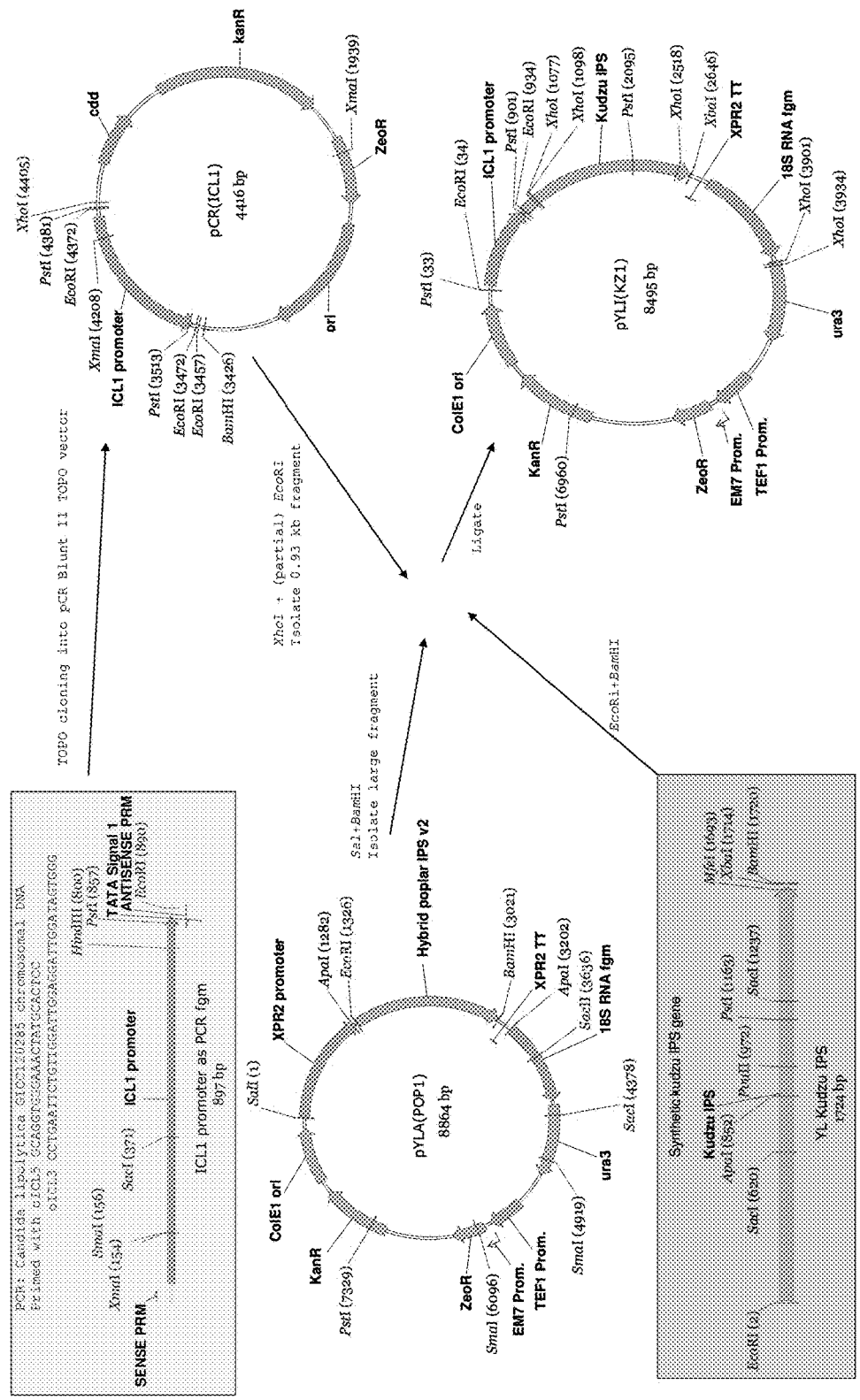
Figure 18E:
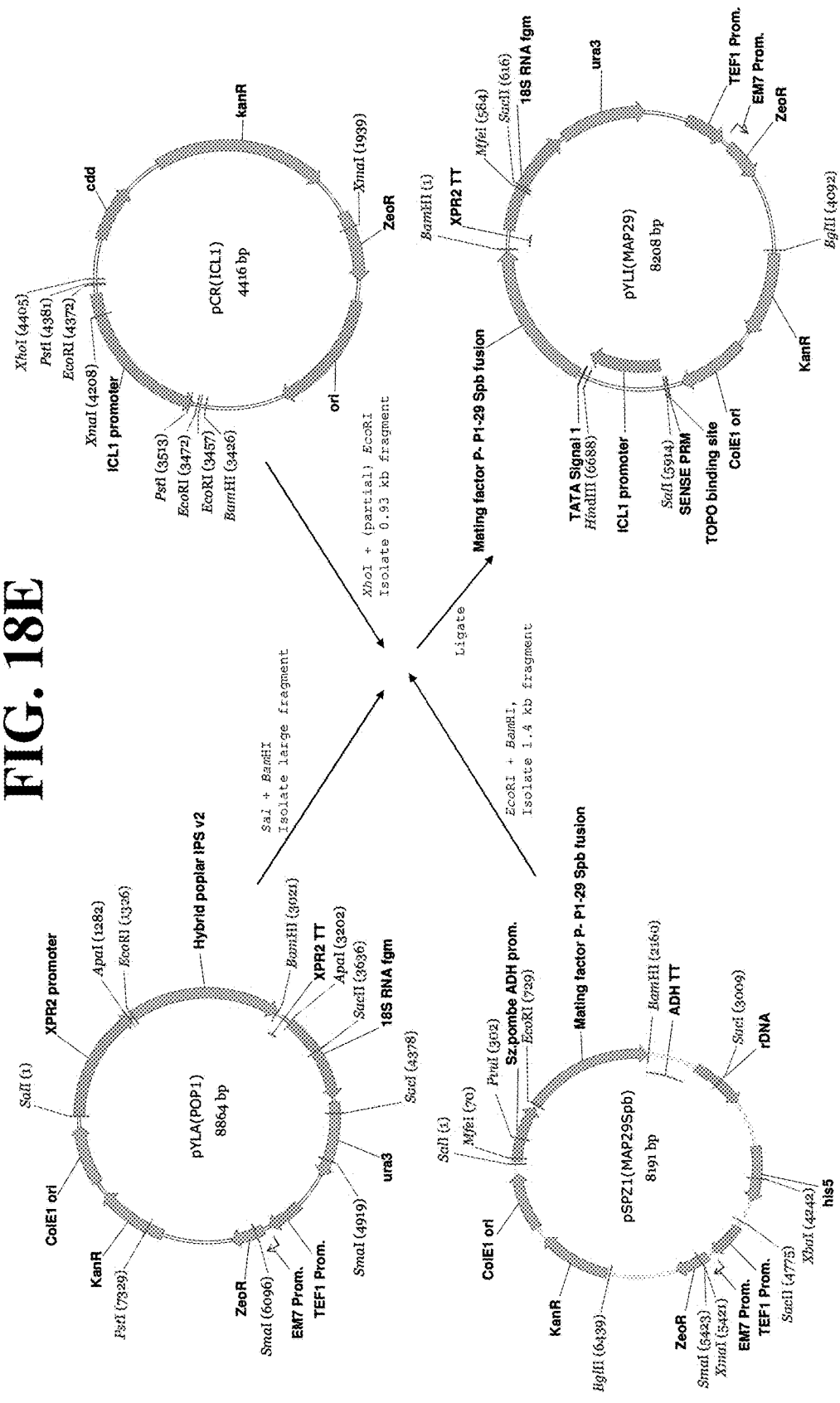
Figure 18F:
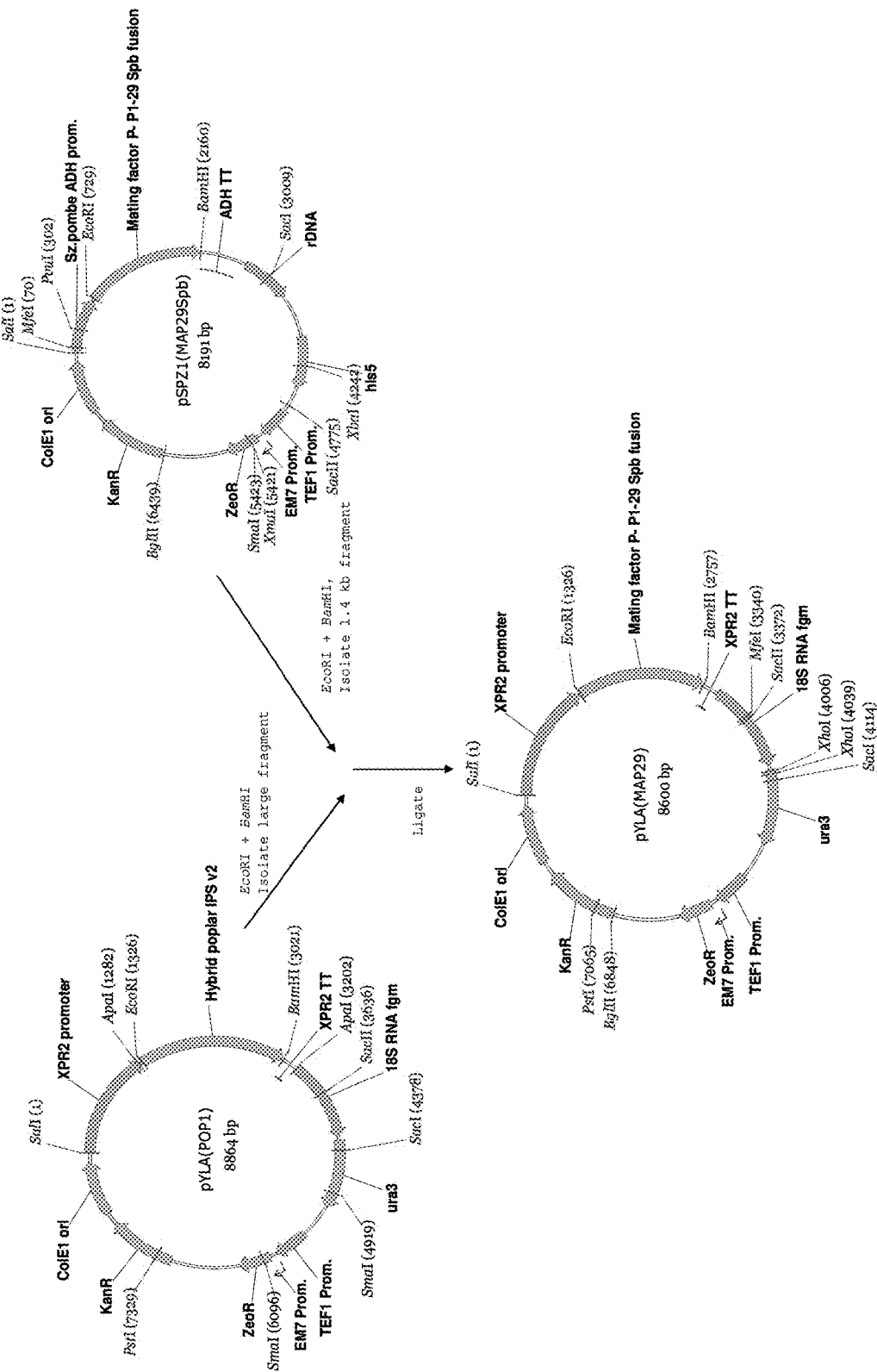

Synthetic DNA molecules encoding the kudzu isoprene synthase gene, codon-optimized for expression in *Yarrowia*, was obtained from DNA 2.0 (FIG. 16; SEQ ID NO: 12). Full detail of the construction scheme of the plasmids pYLA (KZ1) and pYLI(KZ1) carrying the synthetic kudzu isoprene synthase gene under control of XPR2 and ICL1 promoters respectively is presented in FIG. 18A(1) and FIG. 18A(2). Control plasmids in which a mating factor gene (MAP29) is inserted in place of an isoprene synthase gene were also constructed (FIGS. 18E and 18F).

A similar cloning procedure can be used to express a poplar (*Populus alba×Populus tremula*) isoprene synthase gene. The sequence of the poplar isoprene is described in Miller B. et al. (2001) *Planta* 213, 483-487 and shown in FIG. 17 (SEQ ID NO: 13). A construction scheme for the generation the plasmids pYLA(POP1) and pYLI(POP1) carrying synthetic poplar isoprene synthase gene under control of XPR2 and ICL1 promoters respectively is presented in FIG. 18A(1), FIG. 18A(2) and FIG. 18B.

II. Production of Isoprene by Recombinant Strains of *Y. lipolytica*.

Vectors pYLA(KZ1), pYLI(KZ1), pYLA(MAP29) and pYLI(MAP29) were digested with SacII and used to transform the strain *Y. lipolytica* CLIB 122 by a standard lithium acetate/polyethylene glycol procedure to uridine prototrophy. Briefly, the yeast cells grown in YEPD (1% yeast extract, 2% peptone, 2% glucose) overnight, were collected by centrifugation (4000 rpm, 10 min), washed once with sterile water and suspended in 0.1 M lithium acetate, pH 6.0. Two hundred µl aliquots of the cell suspension were mixed with linearized plasmid DNA solution (10-20 µg), incubated for 10 minutes at room temperature and mixed with 1 ml of 50% PEG 4000 in the same buffer. The suspensions were further incubated for 1 hour at room temperature followed by a 2 minutes heat shock at 42° C. Cells were then plated on SC his leu plates (0.67% yeast nitrogen base, 2% glucose, 100 mg/L each of leucine and histidine). Transformants appeared after 3-4 days of incubation at 30° C.

Three isolates from the pYLA(KZ1) transformation, three isolates from the pYLI(KZ1) transformation, two isolates from the pYLA(MAP29) transformation and two isolates from the pYLI(MAP29) transformation were grown for 24 hours in YEP7 medium (1% yeast extract, 2% peptone, pH 7.0) at 30° C. with shaking. Cells from 10 ml of culture were collected by centrifugation, resuspended in 3 ml of fresh YEP7 and placed into 15 ml screw cap vials. The vials were incubated overnight at room temperature with gentle (60 rpm) shaking. Isoprene content in the headspace of these vials was analyzed by gas chromatography using mass-spectrometric detector as described in Example 1. All transformants obtained with pYLA(KZ1) and pYLI(KZ1) produced readily detectable amounts of isoprene (0.5 µg/L to 1 µg/L, FIG. 20). No isoprene was detected in the headspace of the control strains carrying phytase gene instead of an isoprene synthase gene.

Example 7: Production of Isoprene in *E. coli* Expressing Kudzu Isoprene Synthase and idi, or dxs, or idi and dxs I. Construction of Vectors Encoding Kudzu Isoprene Synthase and idi, or dxs, or idi and dxs for the Production of Isoprene in *E. coli* i) Construction of pTrcKudzuKan

The bla gene of pTrcKudzu (described in Example 1) was replaced with the gene conferring kanamycin resistance. To remove the bla gene, pTrcKudzu was digested with BspHI, treated with Shrimp Alkaline Phosphatase (SAP), heat killed at 65° C., then end-filled with Klenow fragment and dNTPs. The 5 kbp large fragment was purified from an agarose gel and ligated to the kan$^r$ gene which had been PCR amplified from pCR-Blunt-II-TOPO using primers MCM22 5'-GAT-CAAGCTTAACCGGAATTGCCAGCTG (SEQ ID NO: 14) and MCM23 5'-GATCCGATCGTCA-GAAGAACTCGTCAAGAAGGC (SEQ ID NO:15), digested with HindIII and PvuI, and end-filled. A transformant carrying a plasmid conferring kanamycin resistance (pTrcKudzuKan) was selected on LA containing kanamycin 50 jag/ml.

ii) Construction of pTrcKudzu yIDI Kan pTrcKudzuKan was digested with PstI, treated with SAP, heat killed and gel purified. It was ligated to a PCR product encoding idi from *S. cerevisiae* with a synthetic RBS. The primers for PCR were NsiI-YIDI 1 F 5'-CATCAATG-CATCGCCCTTAGGAGGTAAAAAAAAATGAC (SEQ ID NO: 16) and PstI-YIDI 1 R 5'-CCTTCTGCAG-GACGCGTTGTTATAGC (SEQ ID NO: 17); and the template was *S. cerevisiae* genomic DNA. The PCR product was digested with NsiI and PstI and gel purified prior to ligation. The ligation mixture was transformed into chemically competent TOP10 cells and selected on LA containing 50 g/ml kanamycin. Several transformants were isolated and sequenced and the resulting plasmid was called pTrcKudzu-yIDI(kan) (FIG. 34, FIG. 35A, FIG. 35B and FIG. 35C).

iii) Construction of pTrcKudzu DXS Kan

Plasmid pTrcKudzuKan was digested with PstI, treated with SAP, heat killed and gel purified. It was ligated to a PCR product encoding dxs from *E. coli* with a synthetic RBS. The primers for PCR were MCM13 5'-GATCATG-CATTCGCCCTTAGGAGGTAAAAAAACATGAGTTTT-GATATTGCCAAATACCC G (SEQ ID NO:18) and MCM14 5'-CATGCTGCAGTTATGCCAGCCAGGCCTT-GAT (SEQ ID NO: 19); and the template was *E. coli* genomic DNA. The PCR product was digested with NsiI and PstI and gel purified prior to ligation. The resulting transformation reaction was transformed into TOP 10 cells and selected on LA with kanamycin 50 g/ml. Several transformants were isolated and sequenced and the resulting plasmid was called pTrcKudzu-DXS(kan) (FIG. 36, FIG. 37A, FIG. 37B and FIG. 37C).

iv) Construction of pTrcKudzu-yIDI-dxs (kan)

pTrcKudzu-yIDI(kan) was digested with PstI, treated with SAP, heat killed and gel purified. It was ligated to a PCR product encoding *E. coli* dxs with a synthetic RBS (primers MCM13 5'-GATCATGCATTCGCCCTTAGGAG-GTAAAAAAACATGAGTTTTGATATTGCCAAATACCC G (SEQ ID NO:18) and MCM14 5'-CATGCTGCAGTTAT-GCCAGCCAGGCCTTGAT (SEQ ID NO: 19); template TOP10 cells) which had been digested with NsiI and PstI and gel purified. The final plasmid was called pTrcKudzu-yIDI-dxs (kan) (FIG. 21, FIG. 22A, FIG. 22B, FIG. 22C and FIG. 22D).

v) Construction of pCL PtrcKudzu

A fragment of DNA containing the promoter, structural gene and terminator from Example 1 above was digested from pTrcKudzu using SspI and gel purified. It was ligated to pCL1920 which had been digested with PvuII, treated with SAP and heat killed. The resulting ligation mixture was transformed into TOP 10 cells and selected in LA containing spectinomycin 50 µg/ml. Several clones were isolated and sequenced and two were selected. pCL PtrcKudzu and pCL PtrcKudzu (A3) have the insert in opposite orientations (FIG. 38, FIG. 39A, FIG. 39B, FIG. 39C, FIG. 40, FIG. 41A, FIG. 41B, FIG. 41C).

vi) Construction of pCL PtrcKudzu yIDI

The NsiI-PstI digested, gel purified, IDI PCR amplicon from (ii) above was ligated into pCL PtrcKudzu which had been digested with PstI, treated with SAP, and heat killed. The ligation mixture was transformed into TOP 10 cells and selected in LA containing spectinomycin 50 µg/ml. Several clones were isolated and sequenced and the resulting plasmid is called pCL PtrcKudzu yIDI (FIG. 42, FIG. 43A, FIG. 43B and FIG. 43C).

vii) Construction of pCL PtrcKudzu DXS

The NsiI-PstI digested, gel purified, DXS PCR amplicon from (iii) above was ligated into pCL PtrcKudzu (A3) which had been digested with PstI, treated with SAP, and heat killed. The ligation mixture was transformed into TOP 10 cells and selected in LA containing spectinomycin 50 jag/ml. Several clones were isolated and sequenced and the resulting plasmid is called pCL PtrcKudzu DXS (FIG. 44, FIG. 45A, FIG. 45B, FIG. 45C and FIG. 45D).

II. Measurement of Isoprene in Headspace from Cultures Expressing Kudzu Isoprene Synthase, idi, and/or dxs at Different Copy Numbers.

Cultures of *E. coli* BL21(λDE3) previously transformed with plasmids pTrcKudzu(kan) (A), pTrcKudzu-yIDI kan (B), pTrcKudzu-DXS kan (C), pTrcKudzu-yIDI-DXS kan (D) were grown in LB kanamycin 50 jag/mL. Cultures of pCL PtrcKudzu (E), pCL PtrcKudzu, pCL PtrcKudzu-yIDI (F) and pCL PtrcKudzu-DXS (G) were grown in LB spectinomycin 50 jag/mL. Cultures were induced with 400 µM IPTG at time 0 ($OD_{600}$ approximately 0.5) and samples taken for isoprene headspace measurement (see Example 1). Results are shown in FIG. 23A, FIG. 23B, FIG. 23C, FIG. 23D, FIG. 23E, FIG. 23F and FIG. 23G.

Figure 23A:
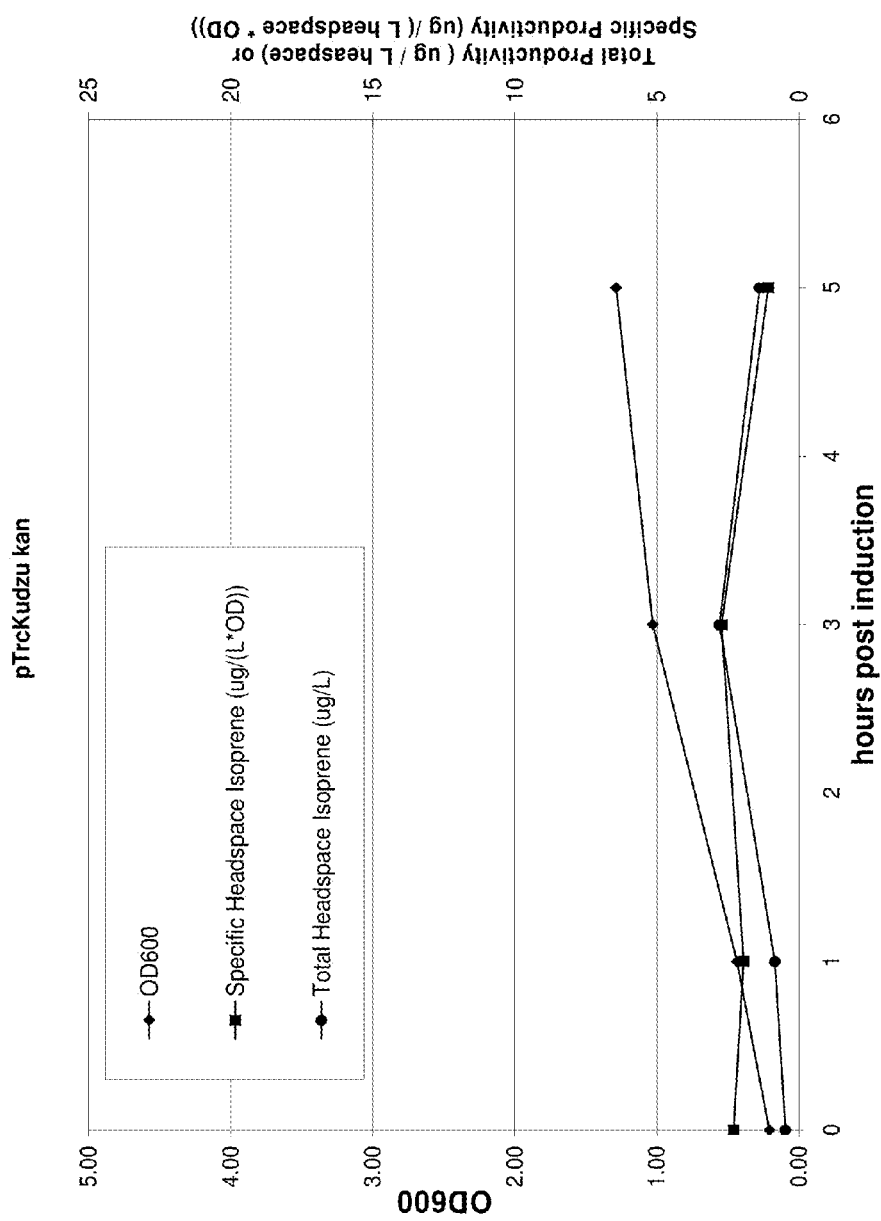
FIG. 23A is a graph showing production of isoprene from glucose in BL21/pTrcKudzukan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23B:
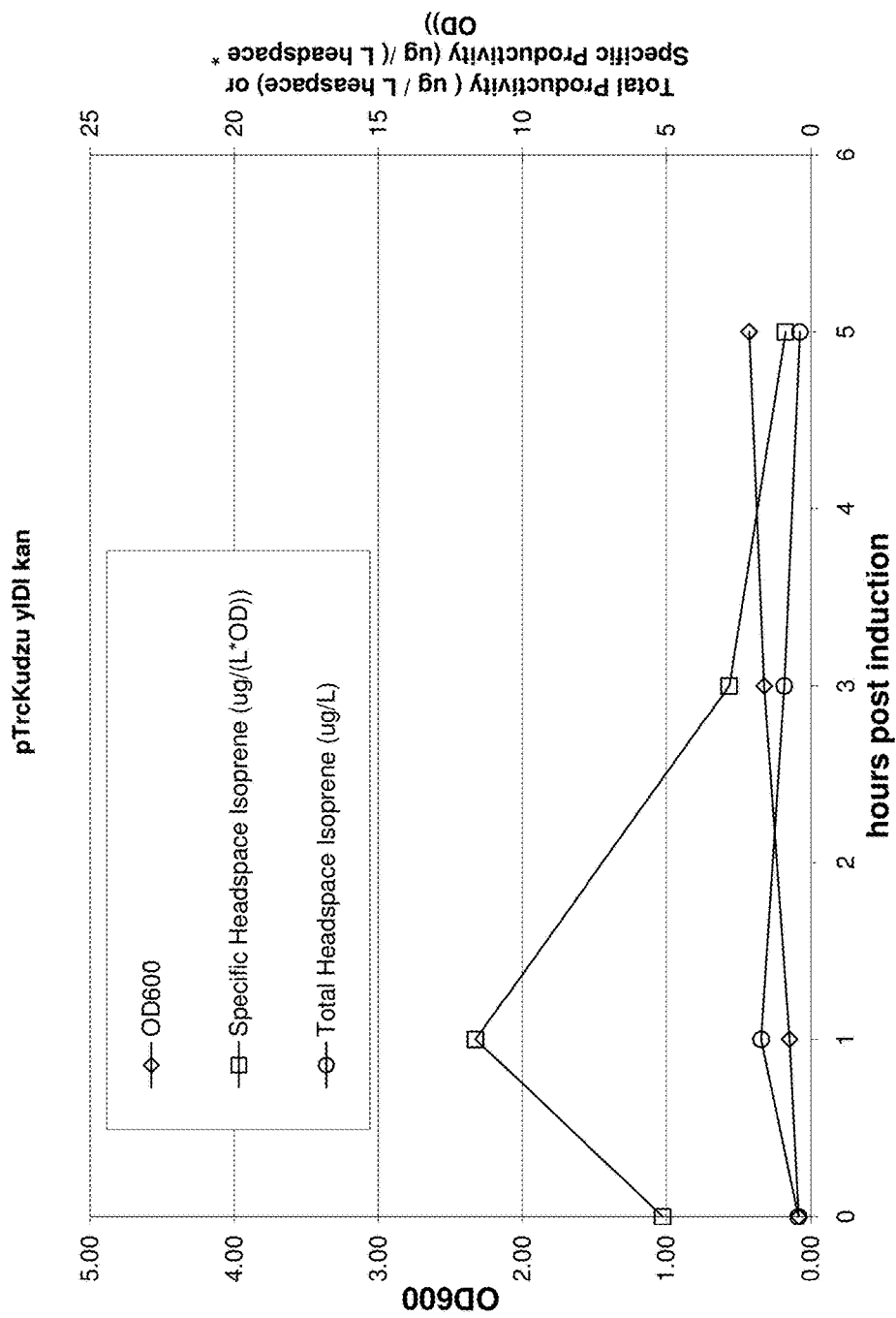
FIG. 23B is a graph showing production of isoprene from glucose in BL21/pTrcKudzu yIDI kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23C:
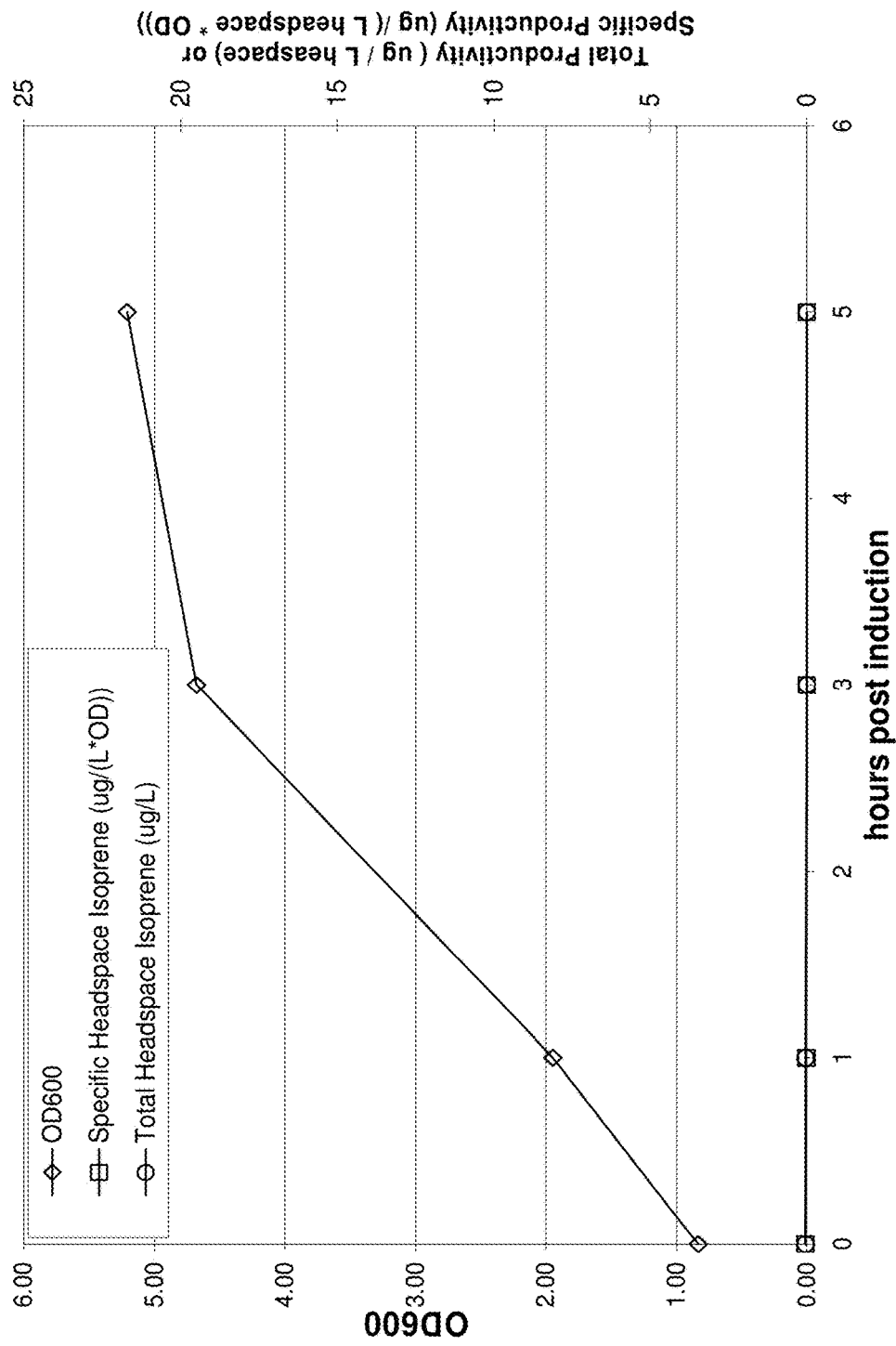
FIG. 23C is a graph showing production of isoprene from glucose in BL21/pTrcKudzu DXS kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23D:
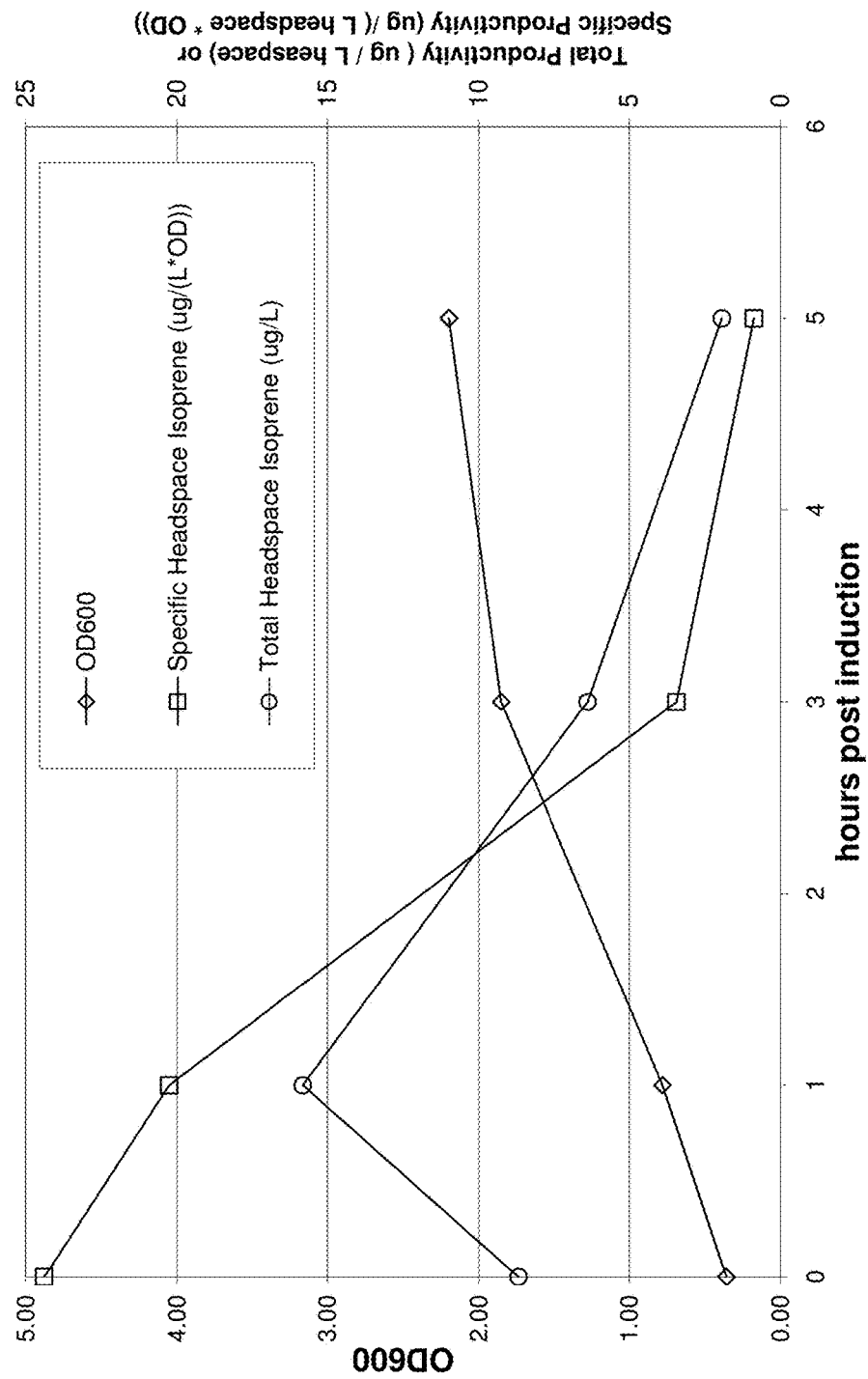
FIG. 23D is a graph showing production of isoprene from glucose in BL21/pTrcKudzu yIDI DXS kan. Time 0 is the time of induction with IPTG (400 μmol). The x-axis is time after induction; the y-axis is OD$_{600}$ and the y2-axis is total productivity of isoprene (μg/L headspace or specific productivity (μg/L headspace/OD). Diamonds represent OD$_{600}$, circles represent total isoprene productivity (μg/L) and squares represent specific productivity of isoprene (μg/L/OD).
Figure 23E:
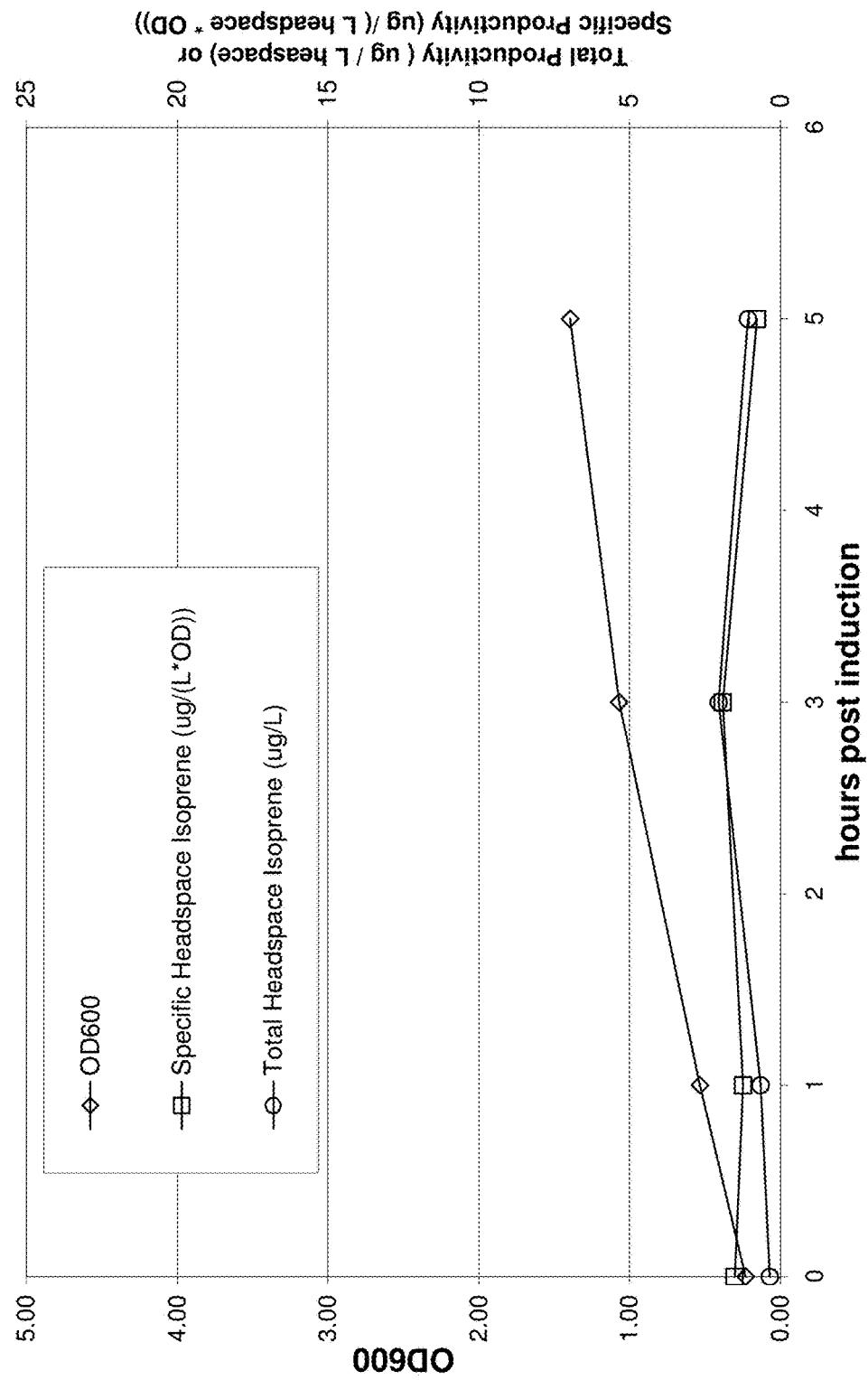
FIG. 23E is a graph showing production of isoprene from glucose in BL21/pCL PtrcKudzu. Time 0 is the time of induction with IPTG (400 μmol). The x-axis is time after induction; the y-axis is OD$_{600}$ and the y2-axis is total productivity of isoprene (μg/L headspace or specific productivity (μg/L headspace/OD). Diamonds represent OD$_{600}$, circles represent total isoprene productivity (μg/L) and squares represent specific productivity of isoprene (μg/L/OD).
Figure 23F:
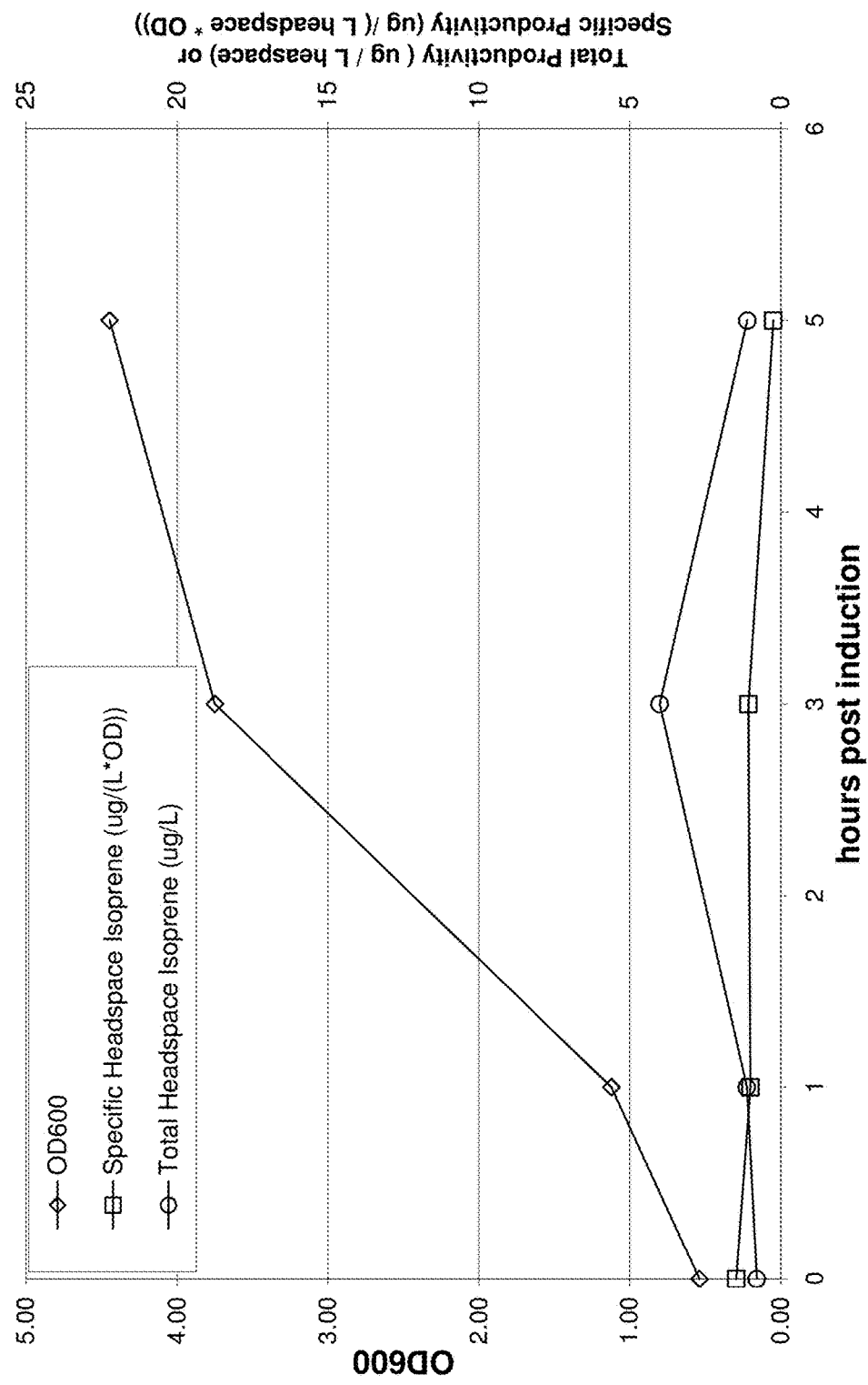
FIG. 23F is a graph showing production of isoprene from glucose in BL21/pCL PtrcKudzu yIDI. Time 0 is the time of induction with IPTG (400 μmol). The x-axis is time after induction; the y-axis is OD$_{600}$ and the y2-axis is total productivity of isoprene (μg/L headspace or specific productivity (μg/L headspace/OD). Diamonds represent OD$_{600}$, circles represent total isoprene productivity (μg/L) and squares represent specific productivity of isoprene (μg/L/OD).
Figure 23G:
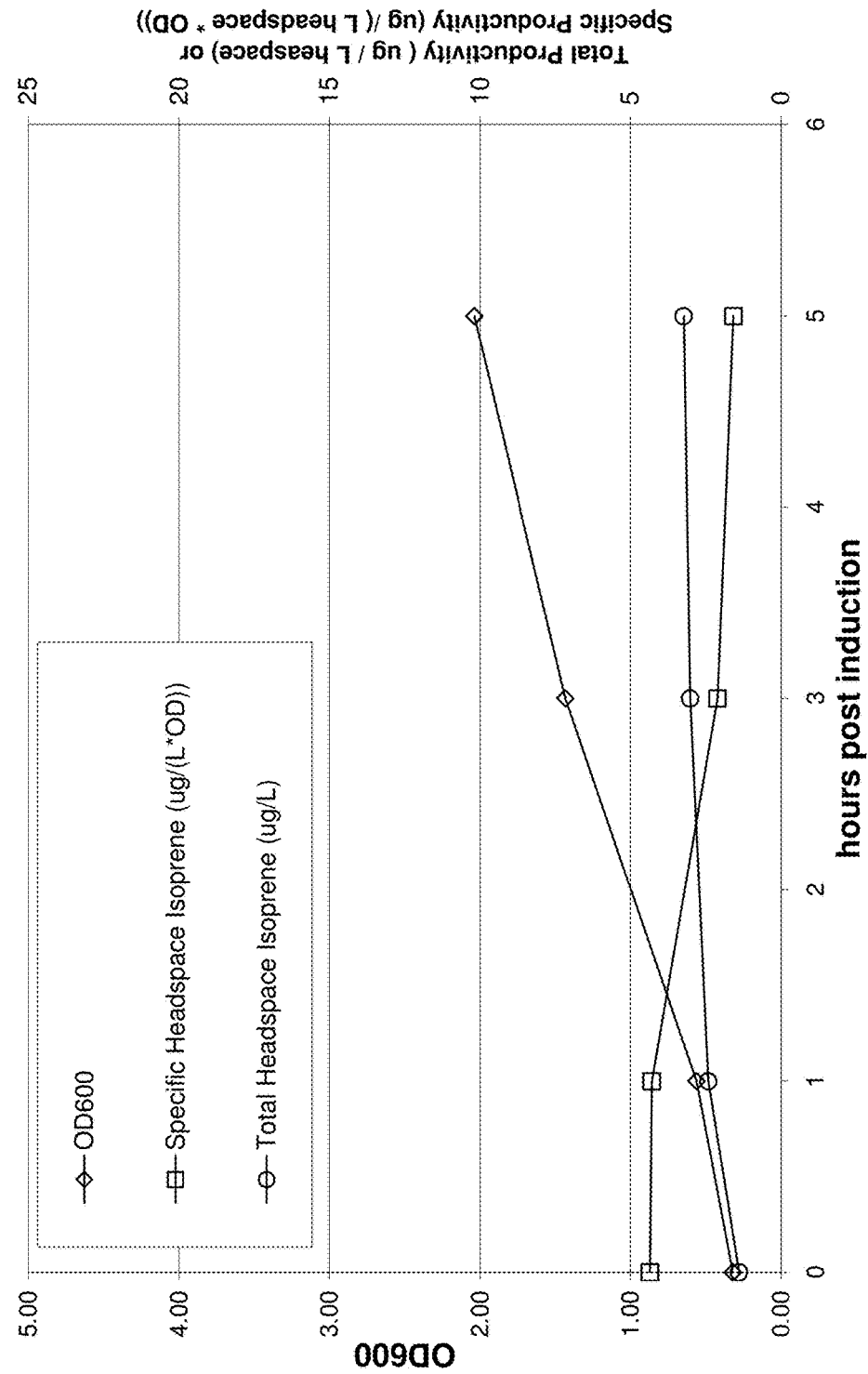
FIG. 23G is a graph showing production of isoprene from glucose in BL21/pCL PtrcKudzu DXS. Time 0 is the time of induction with IPTG (400 μmol). The x-axis is time after induction; the y-axis is OD$_{600}$ and the y2-axis is total productivity of isoprene (μg/L headspace or specific productivity (μg/L headspace/OD). Diamonds represent OD$_{600}$, circles represent total isoprene productivity (μg/L) and squares represent specific productivity of isoprene (μg/L/OD).
Figure 23H:
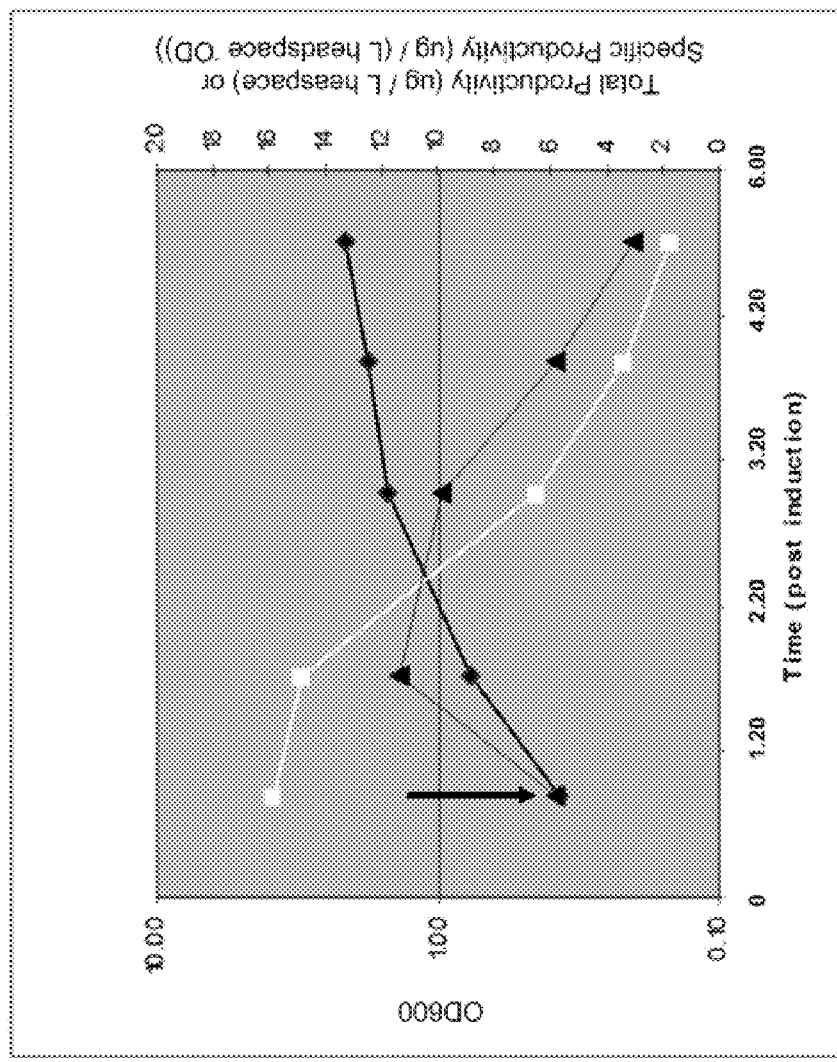
FIG. 23H is a graph showing production of isoprene from glucose in BL21/pTrcKudzuIDIDXSkan. The arrow indicates the time of induction with IPTG (400 μmol). The x-axis is time after induction; the y-axis is OD$_{600}$ and the y2-axis is total productivity of isoprene (μg/L headspace or specific productivity (μg/L headspace/OD). Black diamonds represent OD$_{600}$, black triangles represent isoprene productivity (μg/L) and white squares represent specific productivity of isoprene (μg/L/OD).
Figure 24:
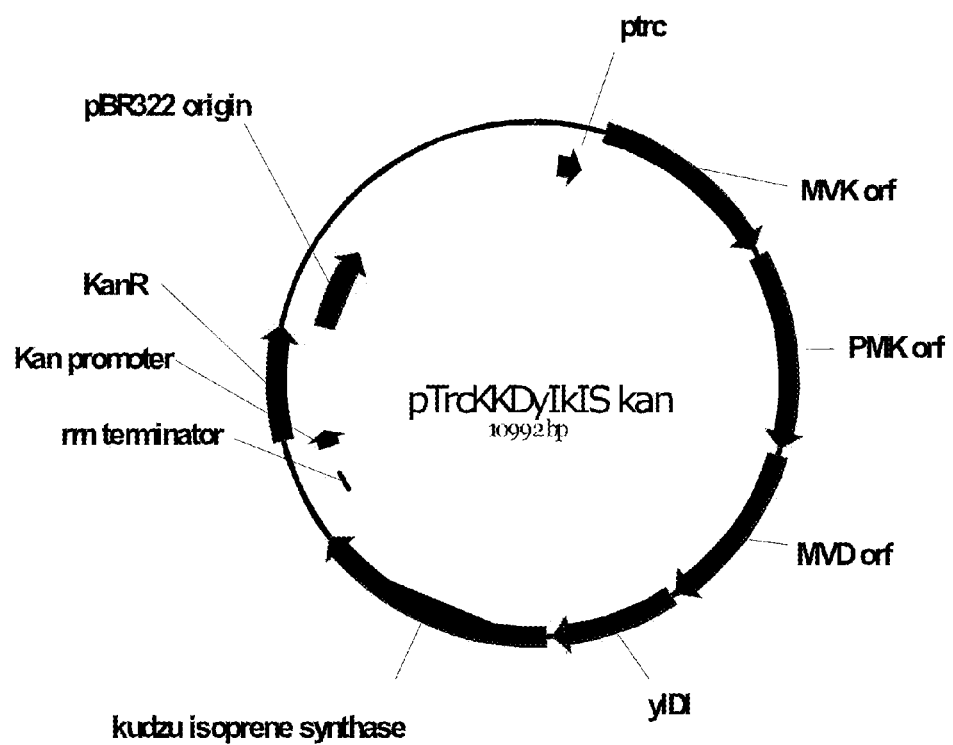
FIG. 24 is a map of pTrcKKDyIkIS kan.
Figure 26:
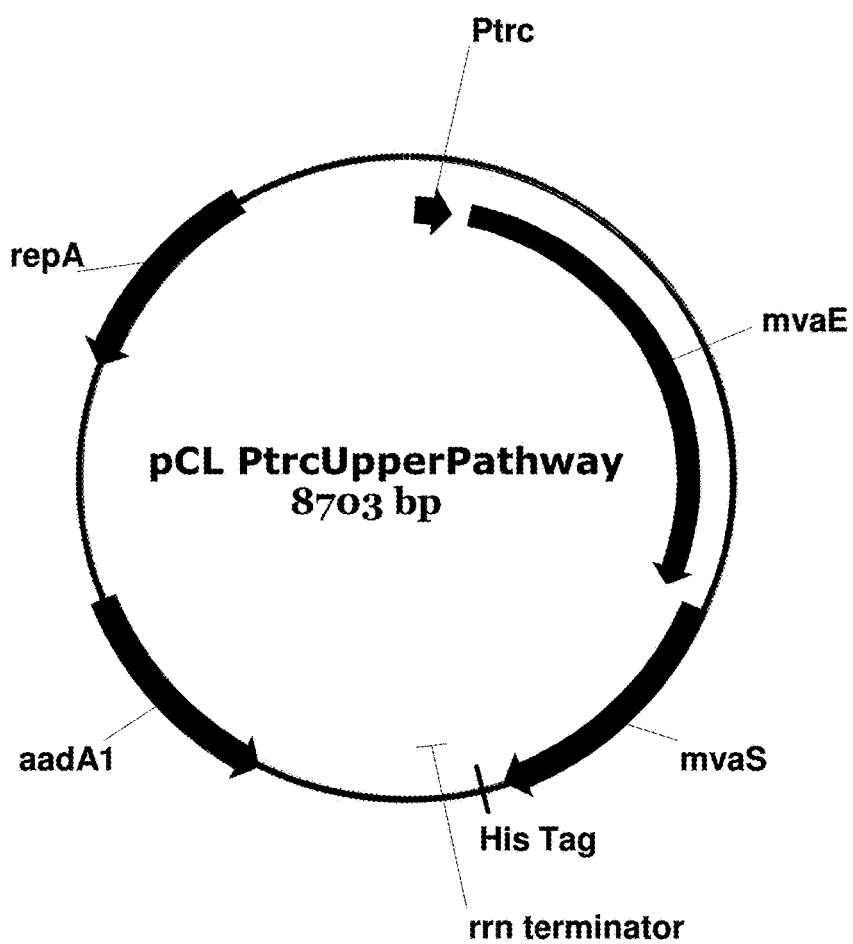
FIG. 26 is a map of pCL PtrcUpperPathway.
Figure 28:
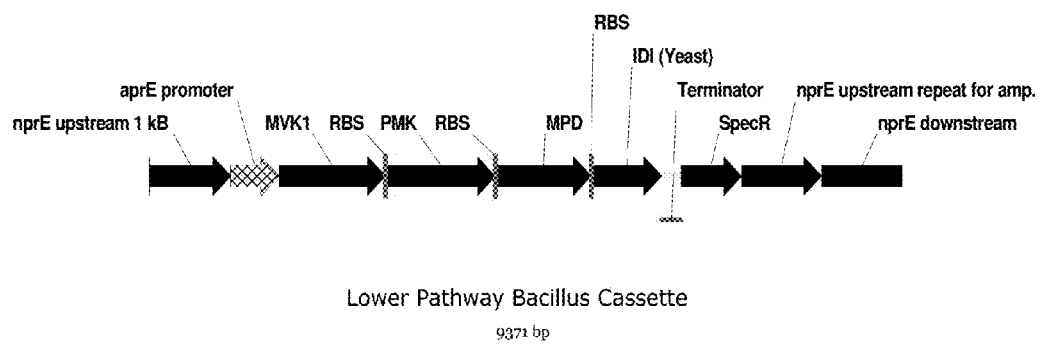
FIG. 28 shows a map of the cassette containing the lower MVA pathway and yeast idi for integration into the *B. subtilis* chromosome at the nprE locus. nprE upstream/downstream indicates 1 kb each of sequence from the nprE locus for integration. aprE promoter (alkaline serine protease promoter) indicates the promoter (−35, −10, +1 transcription start site, RBS) of the aprE gene. MVK1 indicates the yeast mevalonate kinase gene. RBS-PMK indicates the yeast phosphomevalonte kinase gene with a *Bacillus* RBS upstream of the start site. RBS-MPD indicates the yeast diphosphomevalonate decarboxylase gene with a *Bacillus* RBS upstream of the start site. RBS-IDI indicates the yeast idi gene with a *Bacillus* RBS upstream of the start site. Terminator indicates the terminator alkaline serine protease transcription terminator from *B. amyliquefaciens*. SpecR indicates the spectinomycin resistance marker. "nprE upstream repeat for amp." indicates a direct repeat of the upstream region used for amplification.

Plasmid pTrcKudzu-yIDI-dxs (kan) was introduced into *E. coli* strain BL21 by transformation. The resulting strain BL21/pTrc Kudzu IDI DXS was grown overnight in LB containing kanamycin (50 µg/ml) at 20° C. and used to inoculate shake flasks of TM3 (13.6 g $K_2PO_4$, 13.6 g $KH_2PO_4$, 2.0 g $MgSO_4*7H_2O$), 2.0 g citric acid monohydrate, 0.3 g ferric ammonium citrate, 3.2 g $(NH_4)_2SO_4$, 0.2 g yeast extract, 1.0 ml 1000× Modified Trace Metal Solution, adjusted to pH 6.8 and q.s. to $H_2O$, and filter sterilized) containing 1% glucose. Flasks were incubated at 30° C. until an $OD_{600}$ of 0.8 was reached, and then induced with 400 µM IPTG. Samples were taken at various times after induction and the amount of isoprene in the head space was measured as described in Example 1. Results are shown in FIG. 23H.

III. Production of Isoprene from Biomass in *E. coli*/pTrcKudzu yIDI DXS

The strain BL21 pTrcKudzuIDIDXS was tested for the ability to generate isoprene from three types of biomass; bagasse, corn stover and soft wood pulp with glucose as a control. Hydrolysates of the biomass were prepared by enzymatic hydrolysis (Brown, L and Torget, R., 1996, NREL standard assay method Lap-009 "Enzymatic Saccharification of Lignocellulosic Biomass") and used at a dilution based upon glucose equivalents. In this example, glucose equivalents were equal to 1% glucose. A single colony from a plate freshly transformed cells of BL21 (DE3) pTrcKudzu yIDI DXS (kan) was used to inoculate 5 ml of LB plus kanamycin (50 µg/ml). The culture was incubated overnight at 25° C. with shaking. The following day the overnight culture was diluted to an $OD_{600}$ of 0.05 in 25 ml of TM3 and 0.2% YE and 1% feedstock. The feedstock was corn stover, bagasse, or softwood pulp. Glucose was used as a positive control and no glucose was used as a negative control. Cultures were incubated at 30° C. with shaking at 180 rpm. The culture was monitored for $OD_{600}$ and when it reached an $OD_{600}$ of ~0.8, cultures were analyzed at 1 and 3 hours for isoprene production as described in Example 1. Cultures are not induced. All cultures containing added feedstock produce isoprene equivalent to those of the glucose positive control. Experiments were done in duplicate and are shown in FIG. 46.

IV. Production of Isoprene from Invert Sugar in *E. coli*/pTrcKudzuIDIDXS

A single colony from a plate freshly transformed cells of BL21 (λDE3)/pTrcKudzu yIDI DXS (kan) was used to inoculate 5 mL of LB and kanamycin (50 jag/ml). The culture was incubated overnight at 25° C. with shaking. The following day the overnight culture was diluted to an $OD_{600}$ of 0.05 in 25 ml of TM3 and 0.2% YE and 1% feedstock. Feedstock was glucose, inverted glucose or corn stover. The invert sugar feedstock (Danisco Invert Sugar) was prepared by enzymatically treating sucrose syrup. AFEX corn stover was prepared as described below (Part V). The cells were grown at 30° C. and the first sample was measured when the cultures reached an $OD_{600}$~0.8-1.0 (0 hour). The cultures were analyzed for growth as measured by $OD_{600}$ and for isoprene production as in Example 1 at 0, 1 and 3 hours. Results are shown in FIG. 47.

V. Preparation of Hydrolysate from AFEX Pretreated Corn Stover

AFEX pretreated corn stover was obtained from Michigan Biotechnology Institute. The pretreatment conditions were 60% moisture, 1:1 ammonia loading, and 90° C. for 30 minutes, then air dried. The moisture content in the AFEX pretreated corn stover was 21.27%. The contents of glucan and xylan in the AFEX pretreated corn stover were 31.7% and 19.1% (dry basis), respectively. The saccharification process was as follows; 20 g of AFEX pretreated corn stover was added into a 500 ml flask with 5 ml of 1 M sodium citrate buffer pH 4.8, 2.25 ml of Accellerase 1000, 0.1 ml of Grindamyl H121 (Danisco xylanase product from *Aspergillus niger* for bread-making industry), and 72.65 ml of DI water. The flask was put in an orbital shaker and incubated at 50° C. for 96 hours. One sample was taken from the shaker and analyzed using HPLC. The hydrolysate contained 38.5 g/l of glucose, 21.8 g/l of xylose, and 10.3 g/l of oligomers of glucose and/or xylose.

VI. The Effect of Yeast Extract on Isoprene Production in *E. coli* Grown in Fed-Batch Culture Fermentation was performed at the 14-L scale as previously described with *E. coli* cells containing the pTrcKudzu yIDI DXS plasmid described above. Yeast extract (Bio Springer, Montreal, Quebec, Canada) was fed at an exponential rate. The total amount of yeast extract delivered to the fermentor was varied between 70-830 g during the 40 hour fermentation. Optical density of the fermentation broth was measured at a wavelength of 550 nm. The final optical density within the fermentors was proportional to the amount of yeast extract added (FIG. 48A). The isoprene level in the off-gas from the fermentor was determined as previously described. The isoprene titer increased over the course of the fermentation (FIG. 48B). The amount of isoprene produced was linearly proportional to the amount of fed yeast extract (FIG. 48C).

VII. Production of Isoprene in 500 L Fermentation of pTrcKudzu DXS yIDI

A 500 liter fermentation of *E. coli* cells with a kudzu isoprene synthase, *S. cerevisiae* IDI, and *E. coli* DXS nucleic acids (*E. coli* BL21 (λDE3) pTrc Kudzu dxs yidi) was used to produce isoprene. The levels of isoprene varied from 50 to 300 µg/L over a time period of 15 hours. On the basis of the average isoprene concentrations, the average flow through the device and the extent of isoprene breakthrough, the amount of isoprene collected was calculated to be approximately 17 g.

VIII. Production of Isoprene in 500 L Fermentation of *E. coli* Grown in Fed-Batch Culture Medium Recipe (Per Liter Fermentation Medium):

$K_2HPO_4$ 7.5 g, $MgSO_4*7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in $diH_2O$. This solution was autoclaved. The pH was adjusted to 7.0 with ammonium gas ($NH_3$) and q.s. to volume. Glucose 10 g, thiamine*HCl 0.1 g, and antibiotic were added after sterilization and pH adjustment.

1000× Modified Trace Metal Solution:

Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in DI $H_2O$, pH to 3.0 with HCl/NaOH, then q.s. to volume and filter sterilized with 0.22 micron filter.

Fermentation was performed in a 500-L bioreactor with *E. coli* cells containing the pTrcKudzu yIDI DXS plasmid. This experiment was carried out to monitor isoprene formation from glucose and yeast extract at the desired fermentation pH 7.0 and temperature 30° C. An inoculum of *E. coli* strain taken from a frozen vial was prepared in soytone-yeast extract-glucose medium. After the inoculum grew to OD 0.15, measured at 550 nm, 20 ml was used to inoculate a bioreactor containing 2.5-L soytone-yeast extract-glucose medium. The 2.5-L bioreactor was grown at 30° C. to OD 1.0 and 2.0-L was transferred to the 500-L bioreactor.

Figure 49A:
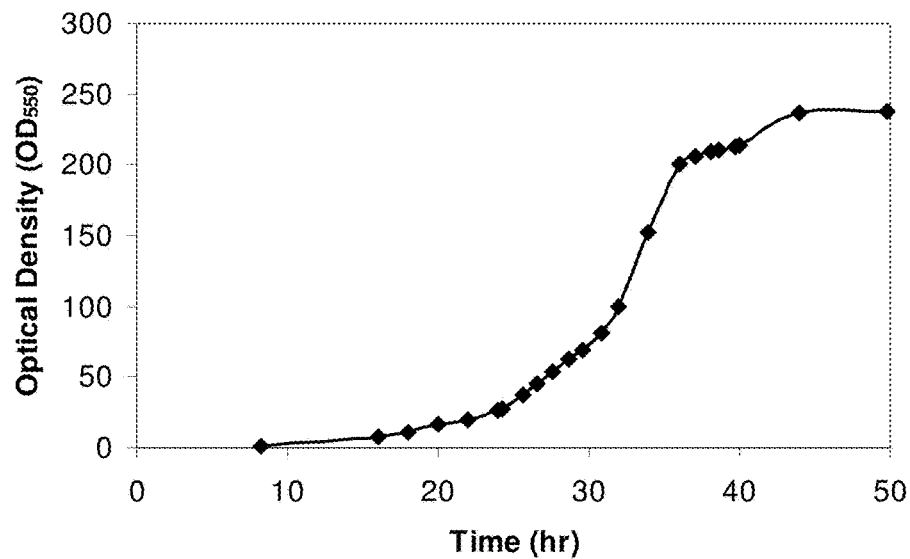
FIG. 49A, FIG. 49B, and FIG. 49C show graphs demonstrating isoprene production from a 500 L bioreactor with *E. coli* cells containing the pTrcKudzu and yIDI and DXS plasmid.

Yeast extract (Bio Springer, Montreal, Quebec, Canada) and glucose were fed at exponential rates. The total amount of glucose and yeast extract delivered to the bioreactor during the 50 hour fermentation was 181.2 kg and 17.6 kg, respectively. The optical density within the bioreactor over time is shown in FIG. 49A. The isoprene level in the off-gas from the bioreactor was determined as previously described.

Figure 49B:
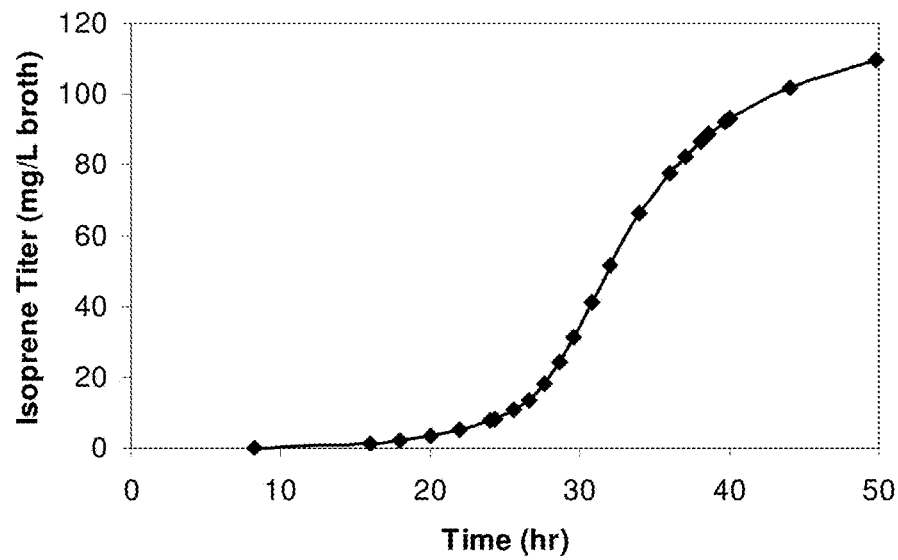
Figure 49C:
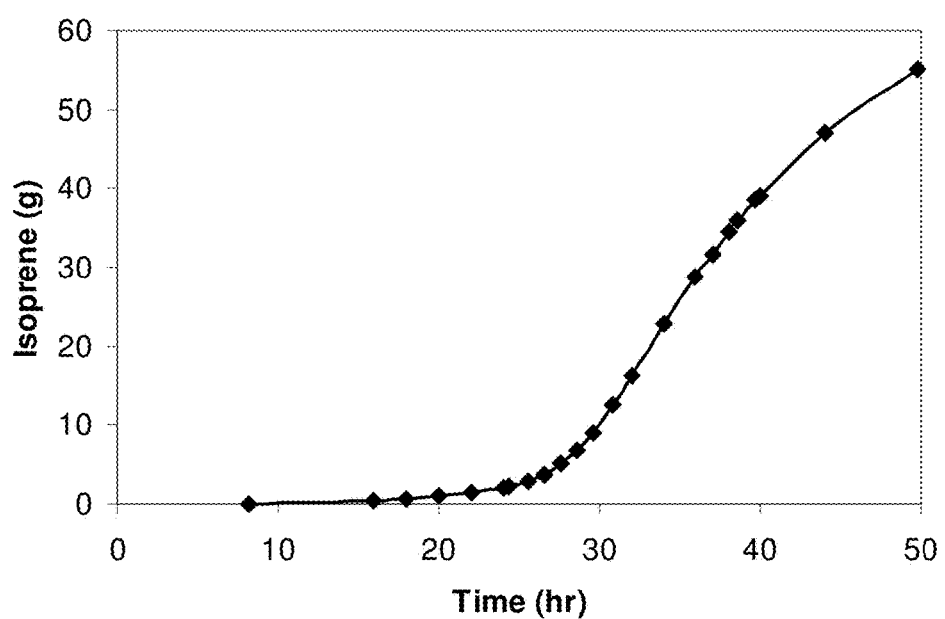
Figure 50:
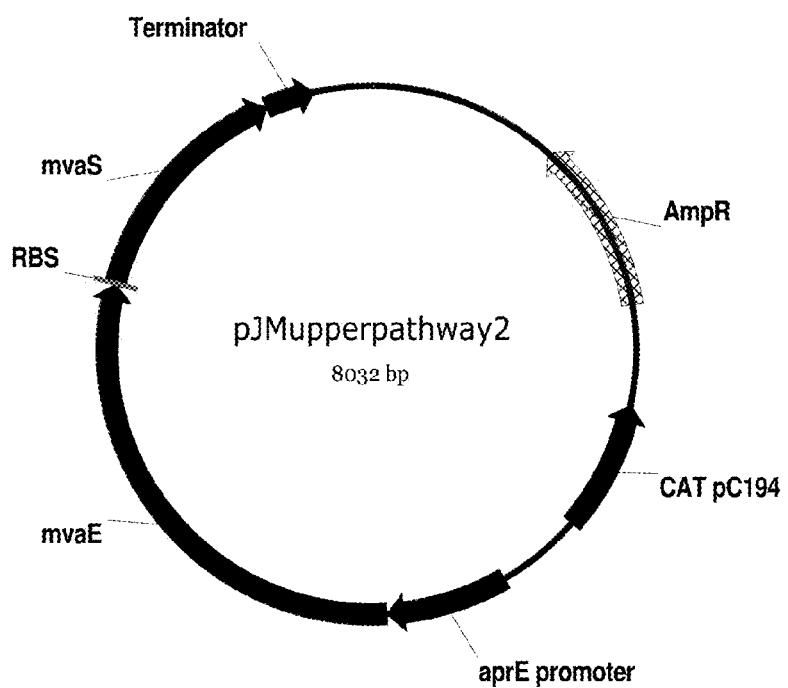
FIG. 50 is a map of pJMupperpathway2.

The isoprene titer increased over the course of the fermentation (FIG. 49B). The total amount of isoprene produced during the 50 hour fermentation was 55.1 g and the time course of production is shown in FIG. 49C.

Example 8: Production of Isoprene in E. coli Expressing Kudzu Isoprene Synthase and Recombinant Mevalonic Acid Pathway Genes I. Cloning the Lower MVA Pathway The strategy for cloning the lower mevalonic pathway was as follows. Four genes of the mevalonic acid biosynthesis pathway; mevalonate kinase (MVK), phosphomevalonate kinase (PMK), diphosphomevalonte decarboxylase (MVD) and isopentenyl diphosphate isomerase genes were amplified by PCR from S. cerevisiae chromosomal DNA and cloned individually into the pCR BluntII TOPO plasmid (Invitrogen). In some cases, the idi gene was amplified from E. coli chromosomal DNA. The primers were designed such that an E. coli consensus RBS (AGGAGGT (SEQ ID NO:80) or AAGGAGG (SEQ ID NO:81)) was inserted at the 5' end, 8 bp upstream of the start codon and a PstI site was added at the 3' end. The genes were then cloned one by one into the pTrcHis2B vector until the entire pathway was assembled.

Chromosomal DNA from S. cerevisiae S288C was obtained from ATCC (ATCC 204508D). The MVK gene was amplified from the chromosome of S. cerevisiae using primers MVKF (5'-AGGAGGTAAAAAAACATGTCATTACCGTTCTTAACTTCTGC, SEQ ID NO:21) and MVK-Pst1-R (5'-ATGGCTGCAGGCCTATCGCAAATTAGCT-TATGAAGTCCATGGTAAATTCGTG, SEQ ID NO:22) using PfuTurbo as per manufacturer's instructions. The correct sized PCR product (1370 bp) was identified by electrophoresis through a 1.2% E-gel (Invitrogen) and cloned into pZeroBLUNT TOPO. The resulting plasmid was designated pMVK1. The plasmid pMVK1 was digested with SacI and Taq1 restriction endonucleases and the fragment was gel purified and ligated into pTrcHis2B digested with SacI and BstBI. The resulting plasmid was named pTrcMVK1.

The second gene in the mevalonic acid biosynthesis pathway, PMK, was amplified by PCR using primers: PstI-PMK1 R (5'-GAATTCGCCCTTCTGCAGCTACC, SEQ ID NO:23) and BsiHKA I-PMK1 F (5'-CGACTGGTGCAC-CCTTAAGGAGGAAAAAAACATGTCAG, SEQ ID NO:24). The PCR reaction was performed using Pfu Turbo polymerase (Stratagene) as per manufacturer's instructions. The correct sized product (1387 bp) was digested with PstI and BsiHKI and ligated into pTrcMVK1 digested with PstI. The resulting plasmid was named pTrcKK. The MVD and the idi genes were cloned in the same manner. PCR was carried out using the primer pairs PstI-MVD 1 R (5'-GTGCTGGAATTCGCCCTTCTGCAGC, SEQ ID NO:25) and NsiI-MVD 1 F (5'-GTAGATGCATGCAGAATTCGC-CCTTAAGGAGG, SEQ ID NO:26) to amplify the MVD gene and PstI-YIDI 1 R (5'-CCTTCTGCAGGACGCGTT-GTTATAGC, SEQ ID NO:27) and NsiI-YIDI 1 F (5'-CATCAATGCATCGCCCTTAGGAGGTAAAAAAAAAT-GAC, SEQ ID NO:28) to amplify the yIDI gene. In some cases the IPP isomerase gene, idi from E. coli was used. To amplify idi from E. coli chromosomal DNA, the following primer set was used: PstI-CIDI 1 R (5'-GTGTGATGGA-TATCTGCAGAATTCG, SEQ ID NO:29) and NsiI-CIDI 1 F (5'-CATCAATGCATCGCCCTTAGGAGG-TAAAAAAACATG, SEQ ID NO:30). Template DNA was chromosomal DNA isolated by standard methods from E. coli FM5 (WO 96/35796 and WO 2004/033646, which are each hereby incorporated by reference in their entireties, particularly with respect to isolation of nucleic acids). The final plasmids were named pKKDIy for the construct encoding the yeast idi gene or pKKDIc for the construct encoding the E. coli idi gene. The plasmids were transformed into E. coli hosts BL21 for subsequent analysis. In some cases the isoprene synthase from kudzu was cloned into pKKDIy yielding plasmid pKKDIyIS.

The lower MVA pathway was also cloned into pTrc containing a kanamycin antibiotic resistance marker. The plasmid pTrcKKDIy was digested with restriction endonucleases ApaI and PstI, the 5930 bp fragment was separated on a 1.2% agarose E-gel and purified using the Qiagen Gel Purification kit according to the manufacturer's instructions. The plasmid pTrcKudzuKan, described in Example 7, was digested with restriction endonucleases ApaI and PstI, and the 3338 bp fragment containing the vector was purified from a 1.2% E-gel using the Qiagen Gel Purification kit. The 3338 bp vector fragment and the 5930 bp lower MVA pathway fragment were ligated using the Roche Quick Ligation kit. The ligation mix was transformed into E. coli TOP10 cells and tranformants were grown at 37° C. overnight with selection on LA containing kanamycin (50 jag/ml). The transformants were verified by restriction enzyme digestion and one was frozen as a stock. The plasmid was designated pTrcKanKKDIy.

II. Cloning a Kudzu Isoprene Synthase Gene into pTrcKanKKDIy

The kudzu isoprene synthase gene was amplified by PCR from pTrcKudzu, described in Example 1, using primers MCM50 5'-GATCATGCATTCGCCCTTAGGAGG-TAAAAAAACATGTGTGCGACCTCTTCTCAATTTAC T (SEQ ID NO:31) and MCM53 5'-CGGTCGACGGATC-CCTGCAGTTAGACATACATCAGCTG (SEQ ID NO:32). The resulting PCR fragment was cloned into pCR2.1 and transformed into E. coli TOP10. This fragment contains the coding sequence for kudzu isoprene synthase and an upstream region containing a RBS from E. coli. Transformants were incubated overnight at 37° C. with selection on LA containing carbenicillin (50 jag/ml). The correct insertion of the fragment was verified by sequencing and this strain was designated MCM93.

The plasmid from strain MCM93 was digested with restriction endonucleases NsiI and PstI to liberate a 1724 bp insert containing the RBS and kudzu isoprene synthase. The 1724 bp fragment was separated on a 1.2% agarose E-gel and purified using the Qiagen Gel Purification kit according to the manufacturer's instructions. Plasmid pTrcKanKKDIy was digested with the restriction endonuclease PstI, treated with SAP for 30 minutes at 37° C. and purified using the Qiagen PCR cleanup kit. The plasmid and kudzu isoprene synthase encoding DNA fragment were ligated using the Roche Quick Ligation kit. The ligation mix was transformed into E. coli TOP10 cells and transformants were grown overnight at 37° C. with selection on LA containing Kanamycin at 50 jag/ml. The correct transformant was verified by restriction digestion and the plasmid was designated pTrcKKDyIkISKan (FIG. 24, FIG. 25A, FIG. 25B, FIG. 25C and FIG. 25D). This plasmid was transformed into BL21(λDE3) cells (Invitrogen).

III. Isoprene Production from Mevalonate in E. coli Expressing the Recombinant Lower Mevalonate Pathway and Isoprene Synthase from Kudzu.

Strain BL21/pTrcKKDyIkISKan was cultured in MOPS medium (Neidhardt et al., (1974) J. Bacteriology 119:736-747) adjusted to pH 7.1 and supplemented with 0.5% glucose and 0.5% mevalonic acid. A control culture was also set up using identical conditions but without the addition of 0.5% mevalonic acid. The culture was started from an overnight seed culture with a 1% inoculum and induced with 500 μM IPTG when the culture had reached an $OD_{600}$ of 0.3 to 0.5. The cultures were grown at 30° C. with shaking at 250 rpm. The production of isoprene was analyzed 3 hours after induction by using the head space assay described in Example 1. Maximum production of isoprene was $6.67\times10^4$ nmol/$L_{broth}$/$OD_{600}$/hr where $L_{broth}$ is the volume of broth and includes both the volume of the cell medium and the volume of the cells. The control culture not supplemented with mevalonic acid did not produce measurable isoprene.

IV. Cloning the Upper MVA Pathway

The upper mevalonate biosynthetic pathway, comprising two genes encoding three enzymatic activities, was cloned from *Enterococcus faecalis*. The mvaE gene encodes a protein with the enzymatic activities of both acetyl-CoA acetyltransferase and 3-hydroxy-3-methylglutaryl-CoA (HMG-CoA) reductase, the first and third proteins in the pathway, and the mvaS gene encodes second enzyme in the pathway, HMG-CoA synthase. The mvaE gene was amplified from *E. faecalis* genomic DNA (ATCC 700802D-5) with an *E. coli* ribosome binding site and a spacer in front using the following primers:

```
CF 07-60 (+) Start of mvaE w/RBS + ATG start codon
SacI
                                       (SEQ ID NO: 34)
5'-GAGACATGAGCTCAGGAGGTAAAAAAACATGAAAACAGTAGTTATTA

TTG

CF 07-62 (-) Fuse mvaE to mvaS with RBS in between
                                       (SEQ ID NO: 35)
5'-TTTATCAATCCCAATTGTCATGTTTTTTTACCTCCTTTATTGTTTTC

TTAAATC
```

The mvaS gene was amplified from *E. faecalis* genomic DNA (ATCC 700802D-5) with a RBS and spacer from *E. coli* in front using the following primers:

```
CF 07-61 (+) Fuse mvaE to mvaS with RBS in between
                                       (SEQ ID NO: 36)
5'-GATTTAAGAAAACAATAAAGGAGGTAAAAAAACATGACAATTGGGAT

TGATAAA (SEQ ID NO: 37)
CF 07-102 (-) End of mvaS gene BglII
5'-GACATGACATAGATCTTTAGTTTCGATAAGAACGAACGGT
```

The PCR fragments were fused together with PCR using the following primers:

```
CF 07-60 (+) Start of mvaE w/RBS + ATG start codon
SacI
                                       (SEQ ID NO: 34)
5'-GAGACATGAGCTCAGGAGGTAAAAAAACATGAAAACAGTAGTTATTA

TTG

CF 07-102 (-) End of mvaS gene BglII
                                       (SEQ ID NO: 37)
5'-GACATGACATAGATCTTTAGTTTCGATAAGAACGAACGGT
```

The fusion PCR fragment was purified using a Qiagen kit and digested with the restriction enzymes SacI and BglII. This digested DNA fragment was gel purified using a Qiagen kit and ligated into the commercially available vector pTrcHis2A, which had been digested with SacI and BglII and gel purified.

The ligation mix was transformed into *E. coli* Top 10 cells and colonies were selected on LA and 50 g/ml carbenicillin plates. A total of six colonies were chosen and grown overnight in LB and 50 g/ml carbenicillin and plasmids were isolated using a Qiagen kit. The plasmids were digested with SacI and BglII to check for inserts and one correct plasmid was sequenced with the following primers:

```
CF 07-58 (+) Start of mvaE gene
                                       (SEQ ID NO: 38)
5'-ATGAAAACAGTAGTTATTATTGATGC CF 07-59 (-) End of mvaE gene
                                       (SEQ ID NO: 39)
5'-ATGTTATTGTTTTCTTAAATCATTTAAAATAGC CF 07-82 (+) Start of mvaS gene
                                       (SEQ ID NO: 40)
5'-ATGACAATTGGGATTGATAAAATTAG CF 07-83 (-) End of mvaS gene
                                       (SEQ ID NO: 41)
5'-TTAGTTTCGATAAGAACGAACGGT CF 07-86 (+) Sequence in mvaE
                                       (SEQ ID NO: 42)
5'-GAAATAGCCCCATTAGAAGTATC CF 07-87 (+) Sequence in mvaE
                                       (SEQ ID NO: 43)
5'-TTGCCAATCATATGATTGAAAATC CF 07-88 (+) Sequence in mvaE
                                       (SEQ ID NO: 44)
5'-GCTATGCTTCATTAGATCCTTATCG CF 07-89 (+) Sequence mvaS
                                       (SEQ ID NO: 45)
5'-GAAACCTACATCCAATCTTTTGCCC
```

The plasmid called pTrcHis2AUpperPathway#1 was correct by sequencing and was transformed into the commercially available *E. coli* strain BL21. Selection was done on LA and 50 g/ml carbenicillin. Two transformants were chosen and grown in LB and 50 g/ml carbenicillin until they reached an $OD_{600}$ of 1.5. Both strains were frozen in a vial at −80° C. in the presence of glycerol. Strains were designated CF 449 for pTrcHis2AUpperPathway#1 in BL21, isolate #1 and CF 450 for pTrcHis2AUpperPathway#1 in BL21, isolate #2. Both clones were found to behave identically when analyzed.

V. Cloning of UpperMVA Pathway into pCL1920

The plasmid pTrcHis2AUpperPathway was digested with the restriction endonuclease SspI to release a fragment containing pTrc-mvaE-mvaS-(His tag)-terminator. In this fragment, the his-tag was not translated. This blunt ended 4.5 kbp fragment was purified from a 1.2% E-gel using the Qiagen Gel Purification kit. A dephosphorylated, blunt ended 4.2 kbp fragment from pCL1920 was prepared by digesting the vector with the restriction endonuclease PvuII, treating with SAP and gel purifying from a 1.2% E-gel using the Qiagen Gel Purification kit. The two fragments were ligated using the Roche Quick Ligation Kit and transformed into TOP 10 chemically competent cells. Transformants were selected on LA containing spectinomycin (50 jag/ml). A correct colony was identified by screening for the presence of the insert by PCR. The plasmid was designated pCL PtrcUpperPathway (FIG. 26, FIG. 27A, FIG. 27B, FIG. 27C and FIG. 27D).

VI. Strains Expressing the Combined Upper and Lower Mevalonic Acid Pathways

To obtain a strain with a complete mevalonic acid pathway plus kudzu isoprene synthase, plasmids pTrcKKDyIkI-Skan and pCLpTrcUpperPathway were both transformed into BL21(λDE3) competent cells (Invitrogen) and transformants were selected on LA containing kanamycin (50 μg/ml) and Spectinomycin (50 jag/ml). The transformants were checked by plasmid prep to ensure that both plasmids were retained in the host. The strain was designated MCM127.

VII. Production of Mevalonic Acid from Glucose in *E. coli*/pUpperpathway

Single colonies of the BL21/pTrcHis2A-mvaE/mvaS or FM5/p pTrcHis2A-mvaE/mvaS are inoculated into LB and carbenicillin (100 μg/ml) and are grown overnight at 37° C. with shaking at 200 rpm. These cultures were diluted into 50 ml medium in 250 ml baffled flasks to an $OD_{600}$ of 0.1. The medium was TM3, 1 or 2% glucose, carbenicillin (100 ug/ml) or TM3, 1% glucose. hydrolyzed soy oil, and carbenicillin (100 ug/ml) or TM3 and biomass (prepared bagasse, corn stover or switchgrass). Cultures were grown at 30° C. with shaking at 200 rpm for approximately 2-3 hours until an $OD_{600}$ of 0.4 was reached. At this point the expression from the mvaE mvaS construct was induced by the addition of IPTG (400 μM). Cultures were incubated for a further 20 or 40 hours with samples taken at 2 hour intervals to 6 hour post induction and then at 24, 36 and 48 hours as needed. Sampling was done by removing 1 ml of culture, measuring the $OD_{600}$, pelleting the cells in a microfuge, removing the supernatant and analyzing it for mevalonic acid.

A 14 liter fermentation of *E. coli* cells with nucleic acids encoding *Enterococcus faecalis* AA-CoA thiolase, HMG-CoA synthase, and HMG-CoA reductase polypeptides produced 22 grams of mevalonic acid with TM3 medium and 2% glucose as the cell medium. A shake flask of these cells produced 2-4 grams of mevalonic acid per liter with LB medium and 1% glucose as the cell culture medium. The production of mevalonic acid in these strains indicated that the MVA pathway was functional in *E. coli*.

VIII. Production of Isoprene from *E. coli* BL21 Containing the Upper and Lower MVA Pathway Plus Kudzu Isoprene Synthase.

The following strains were created by transforming in various combinations of plasmids containing the upper and lower MVA pathway and the kudzu isoprene synthase gene as described above and the plasmids containing the idi, dxs, and dxr and isoprene synthase genes described in Example 7. The host cells used were chemically competent BL21 (λDE3) and the transformations were done by standard methods. Transformants were selected on L agar containing kanamycin (50 μg/ml) or kanamycin plus spectinomycin (both at a concentration of 50 jag/ml). Plates were grown at 37° C. The resulting strains were designated as follows:

Grown on Kanamycin plus Spectinomycin (50 μg/ml each)
MCM127-pCL Upper MVA and pTrcKKDyIkIS (kan) in BL21(λDE3)
MCM131-pCL1920 and pTrcKKDyIkIS (kan) in BL21 (λDE3)
MCM125-pCL Upper MVA and pTrcHis2B (kan) in BL21 (λDE3)
Grown on Kanamycin (50 μg/ml)
MCM64-pTrcKudzu yIDI DXS (kan) in BL21(λDE3)
MCM50-pTrcKudzu (kan) in BL21(λDE3)
MCM123-pTrcKudzu yIDI DXS DXR (kan) in BL21 (λDE3)

The above strains were streaked from freezer stocks to LA and appropriate antibiotic and grown overnight at 37° C. A single colony from each plate was used to inoculate shake flasks (25 ml LB and the appropriate antibiotic). The flasks were incubated at 22° C. overnight with shaking at 200 rpm. The next morning the flasks were transferred to a 37° C. incubator and grown for a further 4.5 hours with shaking at 200 rpm. The 25 ml cultures were centrifuged to pellet the cells and the cells were resuspended in 5 ml LB and the appropriate antibiotic. The cultures were then diluted into 25 ml LB, % glucose, and the appropriate antibiotic to an $OD_{600}$ of 0.1. Two flasks for each strain were set up, one set for induction with IPTG (800 μM) the second set was not induced. The cultures were incubated at 37° C. with shaking at 250 rpm. One set of the cultures were induced after 1.50 hours (immediately following sampling time point 1). At each sampling time point, the $OD_{600}$ was measured and the amount of isoprene determined as described in Example 1. Results are presented in Table 3. The amount of isoprene made is presented as the amount at the peak production for the particular strain.

TABLE 3

| Production of isoprene in *E. coli* strains | |
|---|---|
| Strain | Isoprene ($\mu g/L_{broth}$/hr/OD) |
| MCM50 | 23.8 |
| MCM64 | 289 |
| MCM125 | ND |
| MCM131 | Trace |
| MCM127 | 874 |

ND: not detected
Trace: peak present but not integrable.

IX. Analysis of Mevalonic Acid

Mevalonolactone (1.0 g, 7.7 mmol) (CAS#503-48-0) was supplied from Sigma-Aldrich (WI, USA) as a syrup that was dissolved in water (7.7 mL) and was treated with potassium hydroxide (7.7 mmol) in order to generate the potassium salt of mevalonic acid. The conversion to mevalonic acid was confirmed by $^1$H NMR analysis. Samples for HPLC analysis were prepared by centrifugation at 14,000 rpm for 5 minutes to remove cells, followed by the addition of a 300 μl aliquot of supernatant to 900 μl of $H_2O$. Perchloric acid (36 μl of a 70% solution) was then added followed by mixing and cooling on ice for 5 minutes. The samples were then centrifuged again (14,000 rpm for 5 min) and the supernatant transferred to HPLC. Mevalonic acid standards (20, 10, 5, 1 and 0.5 g/L) were prepared in the same fashion. Analysis of mevalonic acid (20 uL injection volume) was performed by HPLC using a BioRad Aminex 87-H+ column (300 mm by 7.0 mm) eluted with 5 mM sulfuric acid at 0.6 mL/min with refractive index (RI) detection. Under these conditions mevalonic acid eluted as the lactone form at 18.5 minutes.

Example 9: Construction of the Upper and Lower MVA Pathway for Integration into *Bacillus subtilis*

I. Construction of the Upper MVA Pathway in *Bacillus subtilis*

The upper pathway from *Enterococcus faecalis* is integrated into *B. subtilis* under control of the aprE promoter. The upper pathway consists of two genes; mvaE, which encodes for AACT and HMGR, and mvaS, which encodes for HMGS. The two genes are fused together with a stop codon in between, an RB S site in front of mvaS, and are under the control of the aprE promoter. A terminator is situated after the mvaE gene. The chloramphenicol resistance marker is cloned after the mvaE gene and the construct is integrated at the aprE locus by double cross over using flanking regions of homology.

Four DNA fragments are amplified by PCR such that they contain overhangs that will allow them to be fused together by a PCR reaction. PCR amplifications are carried out using Herculase polymerase according to manufacturer's instructions.

1: PaprE

```
CF 07-134 (+) Start of aprE promoter PstI
                                              (SEQ ID NO: 82)
  5'-GACATCTGCAGCTCCATTTTCTTCTGC CF 07-94 (-) Fuse PaprE to mvaE
                                              (SEQ ID NO: 83)
  5'-CAATAATAACTACTGTTTTCACTCTTTACCCTCTCCTTTTAA
```

Template: *Bacillus subtilis* chromosomal DNA

2: mvaE

```
CF 07-93 (+) fuse mvaE to the aprE promoter
(GTG start codon)
                                              (SEQ ID NO: 84)
5'-TTAAAAGGAGAGGGTAAAGAGTGAAAACAGTAGTTATTATTG CF 07-62 (-) Fuse mvaE to mvaS with RBS in between
                                              (SEQ ID NO: 35)
5'-TTTATCAATCCCAATTGTCATGTTTTTTTACCTCCTTTATTGTTTTC
TTAAATC
```

Template: *Enterococcus faecalis* chromosomal DNA (from ATCC)

3. mvaS

```
CF 07-61(+) Fuse mvaE to mvaS with RBS in between
                                              (SEQ ID NO: 36)
5'-GATTTAAGAAAACAATAAAGGAGGTAAAAAAACATGACAATTGGGAT
TGATAAA CF 07-124 (-) Fuse the end of mvaS to the
terminator
                                              (SEQ ID NO: 85)
5'-CGGGGCCAAGGCCGGTTTTTTTTAGTTTCGATAAGAACGAACGGT
```

Template: *Enterococcus faecalis* chromosomal DNA

4. *B. amyliquefaciens* alkaline serine protease terminator

```
CF 07-123 (+) Fuse the end of mvaS to the
terminator
                                              (SEQ ID NO: 86)
5'-ACCGTTCGTTCTTATCGAAACTAAAAAAAACCGGCCTTGGCCCCG CF 07-46(-) End of B. amyliquefaciens terminator
BamHI
                                              (SEQ ID NO: 63)
5'-GACATGACGGATCCGATTACGAATGCCGTCTC
```

Template: *Bacillus* amyliquefaciens chromosomal DNA

PCR Fusion Reactions

5. Fuse mvaE to mvaS

```
CF 07-93 (+) fuse mvaE to the aprE promoter
(GTG start codon)
                                              (SEQ ID NO: 84)
5'-TTAAAAGGAGAGGGTAAAGAGTGAAAACAGTAGTTATTATTG CF 07-124 (-) Fuse the end of mvaS to the
terminator
                                              (SEQ ID NO: 85)
5'-CGGGGCCAAGGCCGGTTTTTTTTAGTTTCGATAAGAACGAACGGT
```

Template: #2 and 3 from above

6. Fuse mvaE-mvaS to aprE promoter

```
CF 07-134 (+) Start of aprE promoter PstI
                                              (SEQ ID NO: 82)
5'-GACATCTGCAGCTCCATTTTCTTCTGC CF 07-124 (-) Fuse the end of mvaS to the
terminator
                                              (SEQ ID NO: 85)
5'-CGGGGCCAAGGCCGGTTTTTTTTAGTTTCGATAAGAACGAACGGT
```

Template #1 and #4 from above

7. Fuse PaprE-mvaE-mvaS to terminator

```
CF 07-134 (+) Start of aprE promoter PstI
                                              (SEQ ID NO: 82)
5'-GACATCTGCAGCTCCATTTTCTTCTGC CF 07-46 (-) End of B. amyliquefaciens terminator
BamHI
                                              (SEQ ID NO: 63)
5'-GACATGACGGATCCGATTACGAATGCCGTCTC
```

Template: #4 and #6

The product is digested with restriction endonucleases PstI/BamHI and ligated to pJM102 (Perego, M. 1993. Integrational vectors for genetic manipulation in *Bacillus subtilis*, p. 615-624. In A. L. Sonenshein, J. A. Hoch, and R. Losick (ed.), *Bacillus subtilis* and other gram-positive bacteria: biochemistry, physiology, and molecular genetics. American Society for Microbiology, Washington, D.C.) which is digested with PstI/BamHI. The ligation is transformed into *E. coli* TOP 10 chemically competent cells and transformants are selected on LA containing carbenicillin (50 μg/ml). The correct plasmid is identified by sequencing and is designated pJMUpperpathway2 (FIG. 50, FIG. 51A, FIG. 51B and FIG. 51C). Purified plasmid DNA is transformed into *Bacillus subtilis* aprEnprE Pxyl-comK and transformants are selected on L agar containing chloramphenicol (5 μg/ml). A correct colony is selected and is plated sequentially on L agar containing chloramphenicol 10, 15 and 25 μg/ml to amplify the number of copies of the cassette containing the upper pathway.

The resulting strain is tested for mevalonic acid production by growing in LB containing 1% glucose and 1%. Cultures are analyzed by GC for the production of mevalonic acid.

This strain is used subsequently as a host for the integration of the lower mevalonic acid pathway.

The following primers are used to sequence the various constructs above.

Sequencing Primers:

```
CF 07-134 (+) Start of aprE promoter PstI
                                      (SEQ ID NO: 82)
5'-GACATCTGCAGCTCCATTTTCTTCTGC CF 07-58 (+) Start of mvaE gene
                                      (SEQ ID NO: 38)
5'-ATGAAAACAGTAGTTATTATTGATGC CF 07-59 (-) End of mvaE gene
                                      (SEQ ID NO: 39)
5'-ATGTTATTGTTTTCTTAAATCATTTAAAATAGC CF 07-82 (+) Start of mvaS gene
                                      (SEQ ID NO: 40)
5'-ATGACAATTGGGATTGATAAAATTAG CF 07-83 (-) End of mvaS gene
                                      (SEQ ID NO: 41)
5'-TTAGTTTCGATAAGAACGAACGGT CF 07-86 (+) Sequence in mvaE
                                      (SEQ ID NO: 42)
5'-GAAATAGCCCCATTAGAAGTATC CF 07-87 (+) Sequence in mvaE
                                      (SEQ ID NO: 43)
5'-TTGCCAATCATATGATTGAAAATC CF 07-88 (+) Sequence in mvaE
                                      (SEQ ID NO: 44)
5'-GCTATGCTTCATTAGATCCTTATCG CF 07-89 (+) Sequence mvaS
                                      (SEQ ID NO: 45)
5'-GAAACCTACATCCAATCTTTTGCCC
```

Transformants are selected on LA containing chloramphenicol at a concentration of 5 µg/ml. One colony is confirmed to have the correct integration by sequencing and is plated on LA containing increasing concentrations of chloramphenicol over several days, to a final level of 25 g/ml. This results in amplification of the cassette containing the genes of interest. The resulting strain is designated CF 455: pJMupperpathway#1× *Bacillus subtilis* aprEnprE Pxyl comK (amplified to grow on LA containing chloramphenicol 25 g/ml).

II. Construction of the Lower MVA Pathway in *Bacillus subtilis*

The lower MVA pathway, consisting of the genes mvk1, pmk, mpd and idi are combined in a cassette consisting of flanking DNA regions from the nprE region of the *B. subtilis* chromosome (site of integration), the aprE promoter, and the spectinomycin resistance marker (see FIG. 28, FIG. 29A, FIG. 29B, FIG. 29C and FIG. 29D). This cassette is synthesized by DNA2.0 and is integrated into the chromosome of *B. subtilis* containing the upper MVA pathway integrated at the aprE locus. The kudzu isoprene synthase gene is expressed from the replicating plasmid described in Example 4 and is transformed into the strain with both upper and lower pathways integrated.

Example 10: Production of Isoprene in *E. coli* Expressing *M. mazei* Mevalonate Kinase and *P. alba* Isoprene Synthase I. Construction of Vectors and Strains Encoding *M. mazei* Mevalonate Kinase (MVK) and *P. alba* Isoprene Synthase (i) Construction of Strain EWL201 (BL21, Cm-GI1.2-KKDyI)

*E. coli* BL21 (Novagen brand, EMD Biosciences, Inc.) was a recipient strain, transduced with MCM331 P1 µlysate (lysate prepared according to the method described in Ausubel, et al., *Current Protocols in Molecular Biology*. John Wiley and Sons, Inc.). Transductants were selected for by spreading cells onto L Agar and 20 µg/µl chloramphenicol. The plates were incubated overnight at 30° C. Analysis of transductants showed no colonies on control plates (water+ cells control plate for reversion and water and P1 µlysate control plate for lysate contamination.

Four transductants were picked and used to inoculate 5 mL L Broth and 20 µg/µl chloramphenicol. The cultures were grown overnight at 30° C. with shaking at 200 rpm. To make genomic DNA preps of each transductant for PCR analysis, 1.5 mL of overnight cell culture were centrifuged. The cell pellet was resuspended with 400 µl Resuspension Buffer (20 mM Tris, 1 mM EDTA, 50 mM NaCl, pH 7.5) and 4 µl RNase, DNase-free (Roche) was added. The tubes were incubated at 37° C. for 30 minutes followed by the addition of 4 µl 10% SDS and 4 µl of 10 mg/ml Proteinase K stock solution (Sigma-Aldrich). The tubes were incubated at 37° C. for 1 hour. The cell lysate was transferred into 2 ml Phase Lock Light Gel tubes (Eppendorf) and 200 µl each of saturated phenol pH7.9 (Ambion Inc.) and chloroform were added. The tubes were mixed well and microcentrifuged for 5 minutes. A second extraction was done with 400 µl chloroform and the aqueous layer was transferred to a new eppendorf tube. The genomic DNA was precipitated by the addition of 1 ml of 100% ethanol and centrifugation for 5 minutes. The genomic DNA pellet was washed with 1 ml 70% ethanol. The ethanol was removed and the genomic DNA pellet was allowed to air dry briefly. The genomic DNA pellet was resuspended with 200 µl TE.

Using Pfu Ultra II DNA polymerase (Stratagene) and 200 ng/µl of genomic DNA as template, 2 different sets of PCR reaction tubes were prepared according to manufacturer's protocol. For set 1, primers MCM130 and GB Cm-Rev (Table 4) were used to ensure transductants were successfully integrated into the attTn7 µlocus. PCR parameters for set 1 were 95° C. for 2 minutes (first cycle only), 95° C. for 25 seconds, 55° C. for 25 seconds, 72° C. for 25 seconds (repeat steps 2-4 for 28 cycles), 72° C. for 1 minute. For set 2, primers MVD For and MVD Rev (Table 4) were used to ensure that the gi1.2-KKDyI operon integrated properly. PCR parameters for set 2 were 95° C. for 2 minutes (first cycle only), 95° C. for 25 seconds, 55° C. for 25 seconds, 72° C. for 10 seconds (repeat steps 2-4 for 28 cycles), 72° C. for 1 minute. Analysis of PCR amplicons on a 1.2% E-gel (Invitrogen Corp.) showed that all 4 transductant clones were correct (picked one and designated as strain EWL201).

ii) Construction of Strain EWL204 (BL21, Loopout-GI1.2-KKDyI)

The chloramphenicol marker was looped out of strain EWL201 using plasmid pCP20 as described by Datsenko and Wanner (2000) (Datsenko et al., *Proc Natl. Acad. Sci USA* 97:6640-6645, 2000). One-step inactivation of chromosomal genes in *Escherichia coli* K-12 using PCR products. (Datsenko et al., *PNAS*, 97: 6640-6645, 2000).

EWL201 cells were grown in L Broth to midlog phase and then washed three times in ice-cold, sterile water. An aliquot of 50 µl of cell suspension was mixed with 1 µl of pCP20 and the cell suspension mixture was electroporated in a 2 mm cuvette (Invitrogen Corp.) at 2.5 Volts and 25uFd using a Gene Pulser Electroporator (Bio-Rad Inc.). 1 ml of LB was immediately added to the cells, then transferred to a 14 ml polypropylene tube (Sarstedt) with a metal cap. Cells were allowed to recover by growing for 1 hour at 30° C. Transformants were selected on L Agar and 20 µg/µl chloramphenicol and 50 µg/µl carbenicillin and incubated at 30° C. overnight. The next day, a single clone was grown in 10 ml L Broth and 50 µg/µl carbenicillin at 30° C. until early log phase. The temperature of the growing culture was then shifted to 42° C. for 2 hours. Serial dilutions were made, the cells were then spread onto LA plates (no antibiotic selection), and incubated overnight at 30° C. The next day, 20 colonies were picked and patched onto L Agar (no antibiotics) and LA and 20 µg/µl chloramphenicol plates. Plates were then incubated overnight at 30° C. Cells able to grow on LA plates, but not LA and 20 µg/µl chloramphenicol plates, were deemed to have the chloramphenicol marker looped out (picked one and designated as strain EWL204).

iii) Construction of Plasmid pEWL230 (pTrc *P. alba*)

Figure 54:
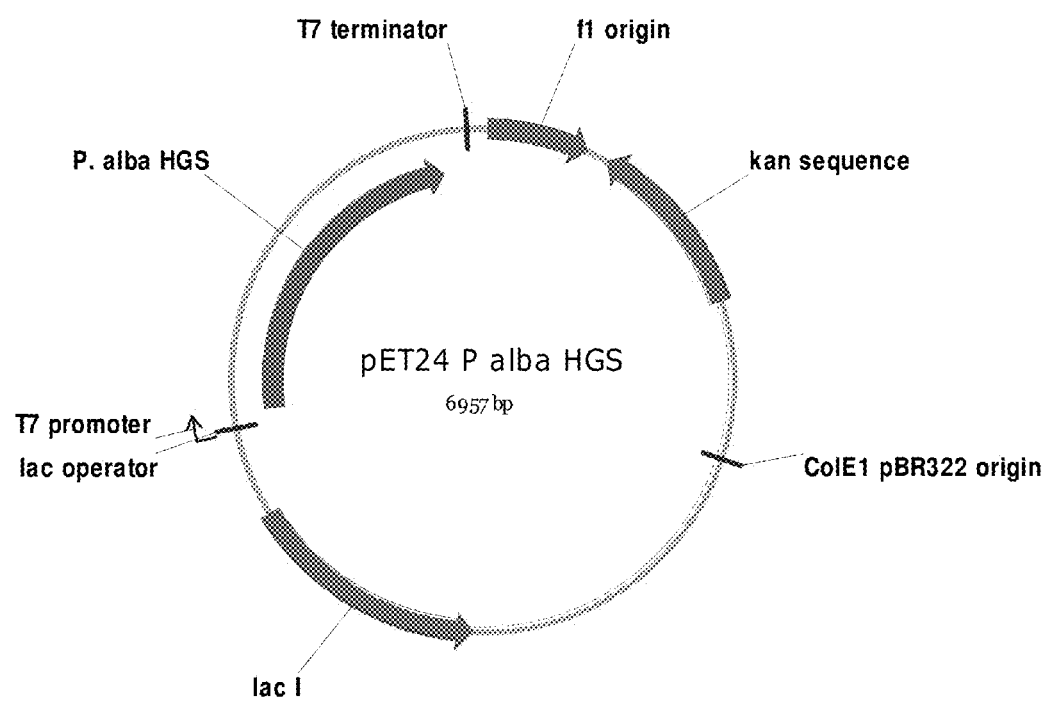
FIG. 54 is a map of plasmid pET24 *P. alba* HGS.

Generation of a synthetic gene encoding *Populus alba* isoprene synthase (*P. alba* HGS) was outsourced to DNA2.0 Inc. (Menlo Park, Calif.) based on their codon optimization method for *E. coli* expression. The synthetic gene was custom cloned into plasmid pET24a (Novagen brand, EMD Biosciences, Inc.) and delivered lyophilized (FIG. 54, FIG. 55A and FIG. 55B).

A PCR reaction was performed to amplify the *P. alba* isoprene synthase (*P. alba* HGS) gene using pET24 *P. alba* HGS as the template, primers MCM182 and MCM192, and Herculase II Fusion DNA polymerase (Stratagene) according to manufacturer's protocol. PCR conditions were as follows: 95° C. for 2 minutes (first cycle only), 95° C. for 25 seconds, 55° C. for 20 seconds, 72° C. for 1 minute, repeat for 25 cycles, with final extension at 72° C. for 3 minutes. The *P. alba* isoprene synthase PCR product was purified using QIAquick PCR Purification Kit (Qiagen Inc.).

Figure 56:
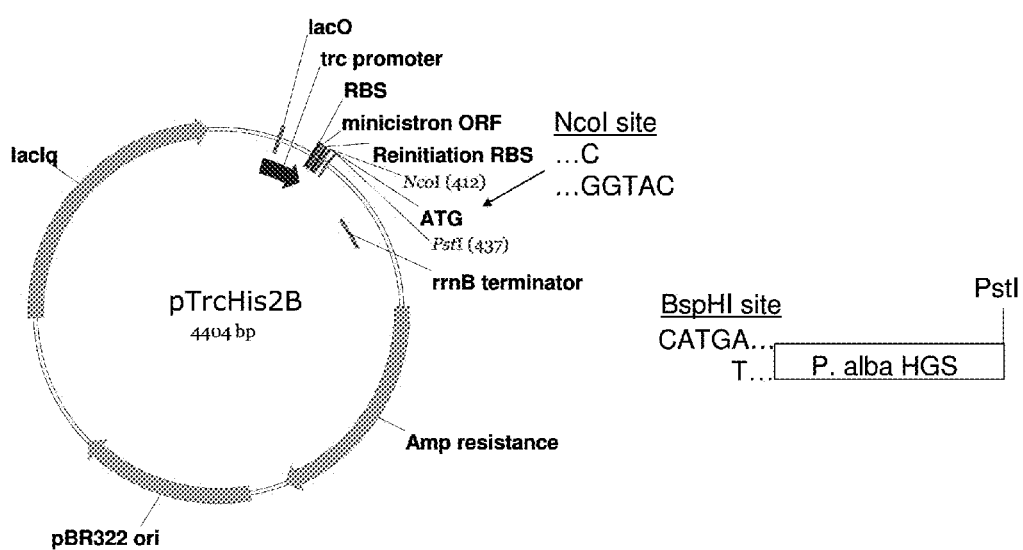
FIG. 56 is a schematic diagram showing restriction sites used for endonuclease digestion to construct plasmid EWL230 and compatible cohesive ends between BspHI and NcoI sites.

*P. alba* isoprene synthase PCR product was then digested in a 20 µl reaction containing 1 µl BspHI endonuclease (New England Biolabs) with 2 µl 10×NEB Buffer 4. The reaction was incubated for 2 hours at 37° C. The digested PCR fragment was then purified using the QIAquick PCR Purification Kit. A secondary restriction digest was performed in a 20 µl reaction containing 1 µl PstI endonuclease (Roche) with 2 µl 10× Buffer H. The reaction was incubated for 2 hours at 37° C. The digested PCR fragment was then purified using the QIAquick PCR Purification Kit. Plasmid pTrcHis2B (Invitrogen Corp.) was digested in a 20 µl reaction containing 1 µl NcoI endonuclease (Roche), 1 µl PstI endonuclease, and 2 µl 10× Buffer H. The reaction was incubated for 2 hours at 37° C. The digested pTrcHis2B vector was gel purified using a 1.2% E-gel (Invitrogen Corp.) and extracted using the QIAquick Gel Extraction Kit (Qiagen) (FIG. 56). Using the compatible cohesive ends of BspHI and NcoI sites, a 20 µl ligation reaction was prepared containing 5 µl *P. alba* isoprene synthase insert, 2 µl pTrc vector, 1 µl T4 DNA ligase (New England Biolabs), 2 µl 10× ligase buffer, and 10 µl ddH$_2$O. The ligation mixture was incubated at room temperature for 40 minutes. The ligation mixture was desalted by floating a 0.025 µm nitrocellulose membrane filter (Millipore) in a petri dish of ddH$_2$O and applying the ligation mixture gently on top of the nitrocellulose membrane filter for 30 minutes at room temperature.

Figure 57:
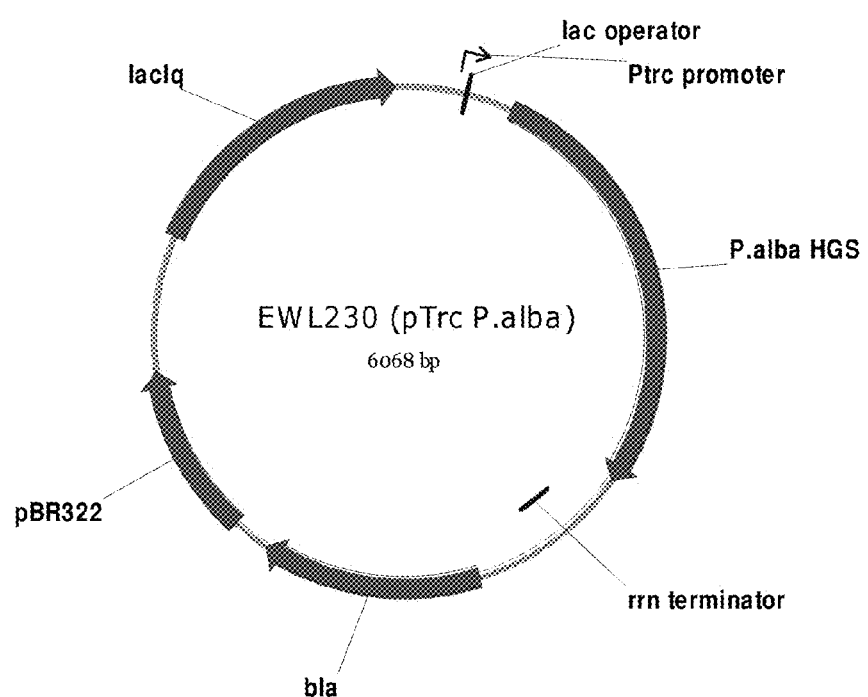
FIG. 57 is a map of plasmid EWL230.

MCM446 cells (See section II) were grown in LB to midlog phase and then washed three times in ice-cold, sterile water. An aliquot of 50 µl of cell suspension was mixed with 5 µl of desalted pTrc *P. alba* HGS ligation mix. The cell suspension mixture was electroporated in a 2 mm cuvette at 2.5 Volts and 25uFd using a Gene Pulser Electroporator. 1 ml of LB is immediately added to the cells, then transferred to a 14 ml polypropylene tube (Sarstedt) with a metal cap. Cells were allowed to recover by growing for 2 hour at 30° C. Transformants were selected on L Agar and 50 µg/µl carbenicillin and 10 mM mevalonic acid and incubated at 30° C. The next day, 6 transformants were picked and grown in 5 ml L Broth and 50 µg/µl carbenicillin tubes overnight at 30° C. Plasmid preps were performed on the overnight cultures using QIAquick Spin Miniprep Kit (Qiagen). Due to the use of BL21 cells for propagating plasmids, a modification of washing the spin columns with PB Buffer 5× and PE Buffer 3× was incorporated to the standard manufacturer's protocol for achieving high quality plasmid DNA. Plasmids were digested with PstI in a 20 µl reaction to ensure the correct sized linear fragment. All 6 plasmids were the correct size and shipped to Quintara Biosciences (Berkeley, Calif.) for sequencing with primers MCM65, MCM66, EL1000 (Table 4). DNA sequencing results showed all 6 plasmids were correct. Picked one and designated plasmid as EWL230 (FIGS. 57, 58A and 58B).

iv) Construction of Plasmid pEWL244 (pTrc *P. alba*-mMVK)

A PCR reaction was performed to amplify the *Methanosarcina mazei* (*M. mazei*) MVK gene using MCM376 as the template (see section v), primers MCM165 and MCM177 (see Table 4), and Pfu Ultra II Fusion DNA polymerase (Stratagene) according to manufacturer's protocol. PCR conditions were as follows: 95° C. for 2 minutes (first cycle only), 95° C. for 25 seconds, 55° C. for 25 seconds, 72° C. for 18 seconds, repeat for 28 cycles, with final extension at 72° C. for 1 minute. The *M. mazei* MVK PCR product was purified using QIAquick PCR Purification Kit (Qiagen Inc.,)

Figure 59:
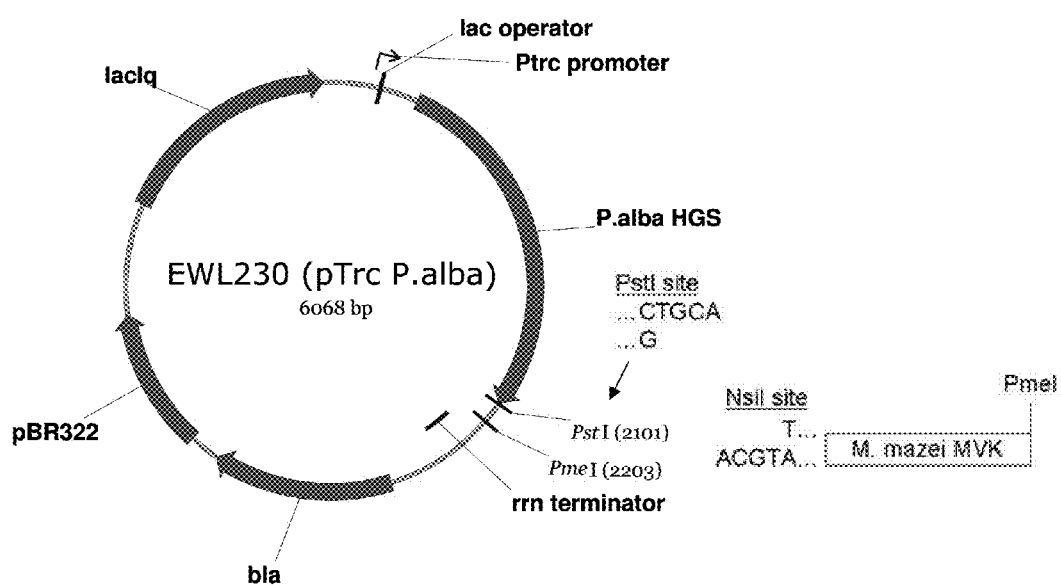
FIG. 59 is a schematic diagram showing restriction sites used for endonuclease digestion to construct plasmid EWL244 and compatible cohesive ends between NsiI and PstI sites.
Figure 60:
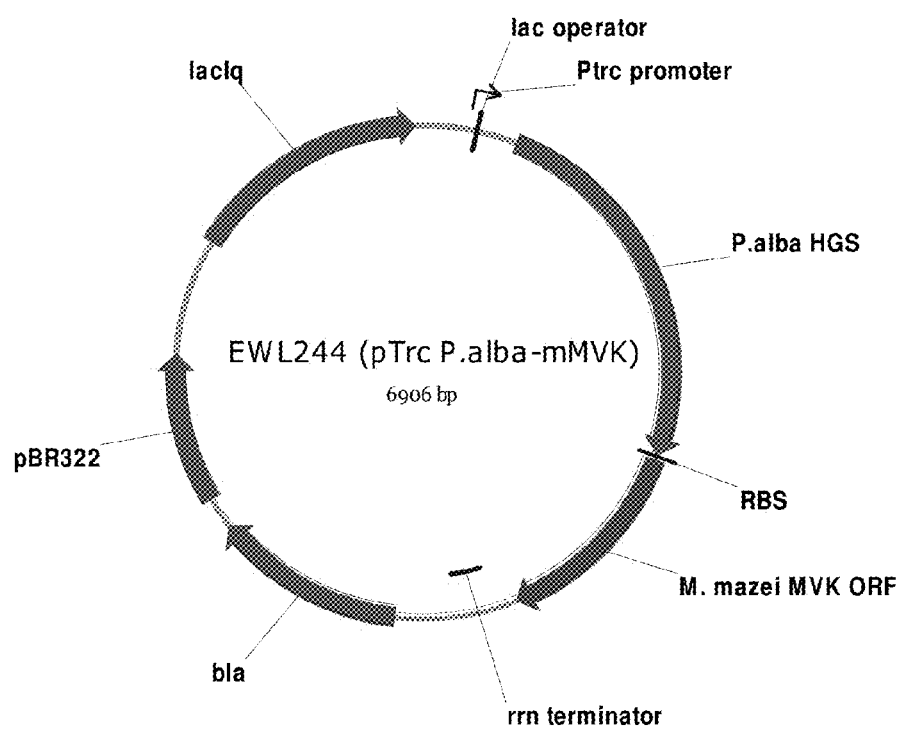
FIG. 60 is a map of EWL244.
Figure 62:
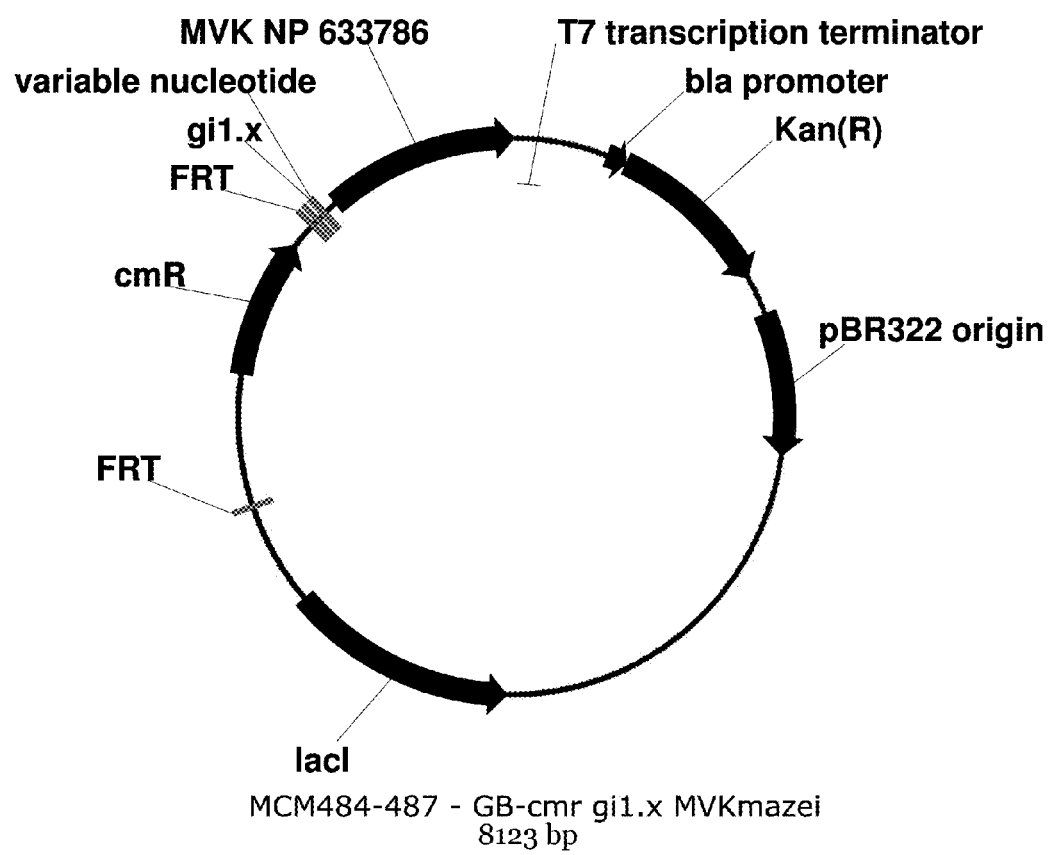
FIG. 62 is a map of plasmids MCM484-487.

The *M. mazei* MVK PCR product was then digested in a 40 µl reaction containing 8 µl PCR product, 2 µl PmeI endonuclease (New England Biolabs), 4 µl 10×NEB Buffer 4, 4 µl 10× NEB BSA, and 22 µl of ddH$_2$O. The reaction was incubated for 3 hours at 37° C. The digested PCR fragment was then purified using the QIAquick PCR Purification Kit. A secondary restriction digest was performed in a 47 µl reaction containing 2 µl NsiI endonuclease (Roche), 4.7 µl 10× Buffer H, and 40 µl of PmeI digested *M. mazei* MVK fragment. The reaction was incubated for 3 hours at 37° C. The digested PCR fragment was then gel purified using a 1.2% E-gel and extracted using the QIAquick Gel Extraction Kit. Plasmid EWL230 was digested in a 40 µl reaction containing 10 µl plasmid, 2 µl PmeI endonuclease, 4 µl 10×NEB Buffer 4, 4 µl 10×NEB BSA, and 20 µl of ddH$_2$O. The reaction was incubated for 3 hours at 37° C. The digested PCR fragment was then purified using the QIAquick PCR Purification Kit. A secondary restriction digest was performed in a 47 µl reaction containing 2 µl PstI endonuclease, 4.7 µl 10× Buffer H, and 40 µl of PmeI digested EWL230 µlinear fragment. The reaction was incubated for 3 hours at 37° C. The digested PCR fragment was then gel purified using a 1.2% E-gel and extracted using the QIAquick Gel Extraction Kit (FIG. 59). Using the compatible cohesive ends of NsiI and PstI sites, a 20 µl ligation reaction was prepared containing 8 µl *M. mazei* MVK insert, 3 µl EWL230 plasmid, 1 µl T4 DNA ligase, 2 µl 10× ligase buffer, and 6 µl ddH$_2$O. The ligation mixture was incubated at overnight at 16° C. The next day, the ligation mixture was desalted by floating a 0.025 µm nitrocellulose membrane filter in a petri dish of ddH$_2$O and applying the ligation mixture gently on top of the nitrocellulose membrane filter for 30 minutes at room temperature. MCM446 cells were grown in LB to midlog phase and then washed three times in ice-cold, sterile water. An aliquot of 50 µl of cell suspension was mixed with 5 µl of desalted pTrc P. alba-mMVK ligation mix. The cell suspension mixture was electroporated in a 2 mm cuvette at 2.5 Volts and 25uFd using a Gene Pulser Electroporator. 1 ml of LB is immediately added to the cells, then the cells are transferred to a 14 ml polypropylene tube with a metal cap. Cells were allowed to recover by growing for 2 hour at 30° C. Transformants were selected on LA and 50 µg/µl carbenicillin and 5 mM mevalonic acid plates and incubated at 30° C. The next day, 6 transformants were picked and grown in 5 ml LB and 50 µg/µl carbenicillin tubes overnight at 30° C. Plasmid preps were performed on the overnight cultures using QIAquick Spin Miniprep Kit. Due to the use of BL21 cells for propagating plasmids, a modification of washing the spin columns with PB Buffer 5× and PE Buffer 3× was incorporated to the standard manufacturer's protocol for achieving high quality plasmid DNA. Plasmids were digested with PstI in a 20 µl reaction to ensure the correct sized linear fragment. Three of the 6 plasmids were the correct size and shipped to Quintara Biosciences for sequencing with primers MCM65, MCM66, EL1000, EL1003, and EL1006 (Table 4). DNA sequencing results showed all 3 plasmids were correct. Picked one and designated plasmid as EWL244 (FIG. 60, FIG. 61A and FIG. 61B).

v) Construction of Plasmid MCM376-MVK from *M. mazei* Archaeal Lower in pET200D.

The MVK ORF from the *M. mazei* archaeal Lower Pathway operon (FIG. 73A, FIG. 73B(1) and FIG. 73B(2)) was PCR amplified using primers MCM161 and MCM162 (Table 4) using the Invitrogen Platinum HiFi PCR mix. 45 uL of PCR mix was combined with 1 uL template, 1 uL of each primer at 10 uM, and 2 uL water. The reaction was cycled as follows: 94 0 C for 2:00 minutes; 30 cycles of 94 0 C for 0:30 minutes, 55 0 C for 0:30 minutes and 68 0 C for 1:15 minutes; and then 72 0 C for 7:00 minutes, and 4 0 C until cool. 3 uL of this PCR reaction was ligated to Invitrogen pET200D plasmid according to the manufacturer's protocol. 3 uL of this ligation was introduced into Invitrogen TOP10 cells, and transformants were selected on LA/kan50. A plasmid from a transformant was isolated and the insert sequenced, resulting in MCM376 (FIG. 74A, FIG. 74(1) and FIG. 74B(2)).

vi) Construction of strain EWL251 (BL21(DE3), Cm-GI1.2-KKDyI, pTrc P. alba-mMVK)

MCM331 cells (which contain chromosomal construct gi1.2KKDyI encoding *S. cerevisiae* mevalonate kinase, mevalonate phosphate kinase, mevalonate pyrophosphate decarboxylase, and IPP isomerase) were grown in LB to midlog phase and then washed three times in ice-cold, sterile water. Mixed 50 µl of cell suspension with 1 µl of plasmid EWL244. The cell suspension mixture was electroporated in a 2 mm cuvette at 2.5 Volts and 25uFd using a Gene Pulser Electroporator. 1 ml of LB is immediately added to the cells, then the cells were transferred to a 14 ml polypropylene tube with a metal cap. Cells were allowed to recover by growing for 2 hours at 30° C. Transformants were selected on LA and 50 µg/µl carbenicillin and 5 mM mevalonic acid plates and incubated at 37° C. One colony was selected and designated as strain EWL251.

vii) Construction of Strain EWL256 (BL21(DE3), Cm-GI1.2-KKDyI, pTrc P. alba-mMVK, pCL Upper MVA)

EWL251 cells were grown in LB to midlog phase and then washed three times in ice-cold, sterile water. Mixed 50 µl of cell suspension with 1 µl of plasmid MCM82 (which is pCL PtrcUpperPathway encoding *E. faecalis* mvaE and mvaS). The cell suspension mixture was electroporated in a 2 mm cuvette at 2.5 Volts and 25uFd using a Gene Pulser Electroporator. 1 ml of LB was immediately added to the cells, then transferred to a 14 ml polypropylene tube with a metal cap. Cells were allowed to recover by growing for 2 hour at 30° C. Transformants were selected on LA and 50 µg/µl carbenicillin and 50 µg/µl spectinomycin plates and incubated at 37° C. Picked one colony and designated as strain EWL256.

TABLE 4

Primer Sequences

| Primer name | Primer sequence |
|---|---|
| MCM130 | ACCAATTGCACCCGGCAGA (SEQ ID NO: 94) |
| GB Cm Rev | GCTAAAGCGCATGCTCCAGAC (SEQ ID NO: 95) |
| MVD For | GACTGGCCTCAGATGAAAGC (SEQ ID NO: 96) |
| MVD Rev | CAAACATGTGGCATGGAAAG (SEQ ID NO: 97) |
| MCM182 | GGGCCCGTTTAAACTTTAACTAGACTCTGCAGTTAGCGTTC AAACGGCAGAA (SEQ ID NO: 98) |
| MCM192 | CGCATGCATGTCATGAGATGTAGCGTGTCCACCGAAAA (SEQ ID NO: 99) |
| MCM65 | ACAATTTCACACAGGAAACAGC (SEQ ID NO: 100) |
| MCM66 | CCAGGCAAATTCTGTTTTATCAG (SEQ ID NO: 101) |
| EL1000 | GCACTGTCTTTCCGTCTGCTGC (SEQ ID NO: 102) |
| MCM165 | GCGAACGATGCATAAAGGAGGTAAAAAAACATGGTATCCTG TTCTGCGCCGGGTAAGATTTACCTG (SEQ ID NO: 103) |
| MCM177 | GGGCCCGTTTAAACTTTAACTAGACTTTAATCTACTTTCAG ACCTTGC (SEQ ID NO: 104) |
| EL1003 | GATAGTAACGGCTGCGCTGCTACC (SEQ ID NO: 105) |
| EL1006 | GACAGCTTATCATCGACTGCACG (SEQ ID NO: 106) |
| MCM161 | CACCATGGTATCCTGTTCTGCG (SEQ ID NO: 107) |
| MCM162 | TTAATCTACTTTCAGACCTTGC (SEQ ID NO: 108) |

II. Construction of MCM442-449: BL21 and BL21(DE3) with FRT-cmR-FRT-gi1.x-mKKDyI i) Construction of Template for Recombination FRT-based recombination cassettes, and plasmids for Red/ET-mediated integration and antibiotic marker loopout were obtained from Gene Bridges GmbH (Germany). Procedures using these materials were carried out according to Gene Bridges protocols. Primers MCM193 and MCM195 were used to amplify the resistance cassette from the FRT-gb2-Cm-FRT template using Stratagene Herculase II Fusion kit according to the manufacturer's protocol. The 50 uL reaction was cycled as follows: 95° C., 2 minutes; (95° C., 20 seconds, 55° C., 20 seconds, 72° C., 1 minute)×5, (95° C., 20 seconds, 60° C., 20 seconds, 72° C., 1 minute)×25; 72° C., 3 minutes; 4° C. until cool. The amplicon was purified by a Qiagen PCR column according to the manufacturer's protocol and eluted in 30 uL EB (Elution Buffer). DNA was digested with NdeI and PciI in a 20 uL reaction with 1× Roche H buffer and 0.5 uL BSA. Plasmid MCM376 was digested in a 10 uL reaction containing 1 uL each of NdeI, NcoI, and Roche H buffer. Reactions proceeded overnight at 37° C., and then cut DNA was purified on Qiagen PCR columns and eluted in 30 uL EB. The PCR product was ligated into MCM376 in a reaction containing 1 uL vector, 3 uL PCR product, 1 uL Roche Quick Ligase Buffer 2, 5 uL Buffer1, and 1 uL Ligase. The reaction proceeded at room temperature for 3 hours and then 5 uL was transformed into Invitrogen TOP 10 cells according to the manufacturer's protocol. Transformants were selected on L agar (LA) and chloramphenicol (10 ug/mLO) at 37° C. overnight.

Transformant colonies were patched onto LA containing chloramphenicol (30 ug/mL) and kanamycin (50 ug/ml) for storage and sent to Quintara (Berkeley, Calif.) for sequencing. Four clones, one each with the four different nucleotides at the "N" in primer MCM195, were found to have the correct sequence for the inserted promoter. Clones were grown in 5 mL LB containing chloramphenicol (30 ug/mL) and kanamycin (50 ug/mL) and used for the preparation of plasmid DNA. This plasmid was retransformed into TOP10 cells and strains were frozen as:

TABLE 5

MCM484-487

| | |
|---|---|
| MCM484 | cmR-gi1.6-MVK(mazei) in pET (clone A1-3, variable nt A) |
| MCM485 | cmR-gi1.0-MVK(mazei) in pET (clone B4-6, variable nt C) |
| MCM486 | cmR-gi1.2-MVK(mazei) in pET (clone C1-5, variable nt G) |
| MCM487 | cmR-gi1.5-MVK(mazei) in pET (clone C3-3, variable nt T) | ii) Creation of Recombination Target Strains MCM349 and MCM441

The chloramphenicol resistance (cmR) marker was looped out of strain MCM331 using plasmid pGB706 (GeneBridges) according to Manufacturer's instructions. MCM331 cells were grown to mid-log in LB and washed three times in iced, sterile water. A 1 uL aliquot of pGB706 DNA was added to 50 uL of cell suspension and this mixture was electroporated in a 2 mm cuvette at 2.5 volts, 25uFd followed immediately by recovery in 500 uL LB for one hour at 30 C. Transformants were selected on LB containing tetracycline (5 ug/ml) at 30° C. The following day, a clone was grown up at 30° C. in LB containing tetracycline (5 ug/ml) until visibly turbid (OD600-0.5-0.8). This culture was streaked onto LB and grown overnight at 37° C. A clone that was unable to grow on LB containing chloramphenicol (10 ug/mL) or LB containing tetracycline (5 ug/mL) was frozen as MCM348. Plasmid MCM356 (pRedET carbencillin; GeneBridges) was electroporated in as described above and transformants were selected on LB containing carbenicillin (50 ug/mL) at 30° C. A clone was grown in LB carbenicillin (50 ug/mL) at 30° C. and frozen as MCM349.

Strain MCM441 was created by electrotransforming plasmid MCM356 into EWL204 as above.

iii) Recombination of FRT-cmR-FRT-gi1.x-mMVK into MCM349 and MCM441

Plasmids MCM484-487 were used as template for PCR amplification with primers MCM120 and MCM196 and Herculase II Fusion kit, according to the manufacturer's protocol. Three reactions per template were carried out, with 0, 1, or 3 uL DMSO. The 50 uL reactions were cycled as follows: 95° C., 2 minutes; (95° C., 20 seconds; 55° C. 20 seconds; 72° C., 1.5 minutes) for five cycles; (95° C., 20 seconds; 60° C. 20 seconds; 72° C., 1.5 minutes) for 25 cycles; 72° C. for 3 minutes; 4° C., overnight.] The three reactions from a given template were pooled and purified on Qiagen PCR columns and eluted with 30 uL EB at 60° C. 5 uL DNA was digested with 1 uL DpnI in 1× Roche Buffer A for 3 hours at 37° C. This DNA was then microdialyzed against excess water for 30 minutes.

Strains were grown in 5 mL LB containing carbenicillin (50 ug/mL) from fresh streaks at 30 C to an OD600 of ~0.5. 40 mM L-arabinose was added and cultures were incubated at 37 C for 1.5 hours. Cells were harvested and electroporated with 3 uL dialyzed amplicons above, and then recovered in 500 uL SOC at 37 C for 1.5-3 hours. Transformants were selected on LA plates containing chloramphenicol (5 ug/mL) at 37° C.

Kanamycin sensitive clones were screened by PCR for insertion of the amplicon. PCR products from positive clones were sequenced to verify the sequence of inserted DNA. Amplicons were consistent with the FRT-gi 1.2-yKKDyI at attTn7 in MCM441 and 348 being replaced by FRT-cmR-FRT-gi1.x-mKKDyI (The yK and mK designations refer to the mevalonate kinase from *Saccharomyces cerevisiae* and *Methanosarcina mazei* respectively).

TABLE 6A

The following strains were grown in LB containing chloramphenicol (5 ug/mL) and frozen.

| Strain ID | Name | Parent | Recombination Amplicon Template |
|---|---|---|---|
| MCM442 | BL21(DE3) cmR-gi1.6mKKDyI A1, clone37 (A) | MCM349 | MCM484 |
| MCM443 | BL21(DE3) cmR-gi1.0mKKDyI B4, clone27 (C) | MCM349 | MCM485 |
| MCM444 | BL21(DE3) cmR-gi1.2mKKDyI C1, clone16 (G) | MCM349 | MCM486 |
| MCM445 | BL21(DE3) cmR-gi1.5mKKDyI C3, clone7 (T) | MCM349 | MCM487 |
| MCM446 | BL21 cmR-gi1.6mKKDyI A1-3 (A) | MCM441 | MCM484 |
| MCM447 | BL21 cmR-gi1.0mKKDyI B4-6 (C) | MCM441 | MCM485 |
| MCM448 | BL21 cmR-gi1.2mKKDyI C1-5 (G) | MCM441 | MCM486 |
| MCM449 | BL21 cmR-gi1.5mKKDyI C3-3 (T) | MCM441 | MCM487 |

TABLE 6B

Primers

MCM120 AAAGTAGCCGAAGATGACGGTTTGTCACATGGAGTTGGCAGGA
TGTTTGATTAAAAGCAATTAACCCTCACTAAAGGGCGG
(SEQ ID NO: 109)

MCM193 GATATACATATGAATTAACCCTCACTAAAGG
(SEQ ID NO: 110)

MCM195 GCATGCATGACATGTTTTTTACCTCCTTTGTTATCCGCTCAC
AATTAGTGGTTGAATTATTTGCTCAGGATGTGGCATNGTCAAG
GGCGCGGCCGCGATCTAATACGACTCACTATAGGGCTCG
(SEQ ID NO: 111)

TABLE 6B-continued

Primers

MCM196 AGGCTCTCAACTCTGACATGTTTTTTTCCTCCTTAAGGGTGCA
GGCCTATCGCAAATTAGCTTAATCTACTTTCAGACCTTGCTCG
G
(SEQ ID NO: 112)

III. The Effect of Yeast Extract on Isoprene Production in *E. coli* Expressing Genes from the Mevalonic Acid Pathway and Grown in Fed-Batch Culture at the 15-L Scale Medium Recipe (Per Liter Fermentation Medium):

$K_2HPO_4$ 7.5 g, $MgSO_4*7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in Di $H_2O$, pH to 3.0 with HCl/NaOH, then q.s. to volume and filter sterilized with a 0.22 micron filter.

Figure 67A:
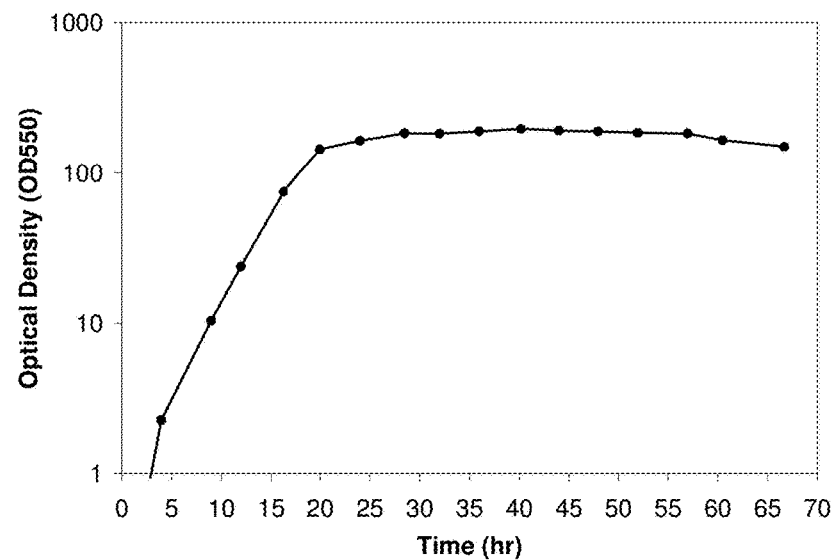
FIG. 67A, FIG. 67B, FIG. 67C, and FIG. 67D are graphs of isoprene production by *E. coli* strain (EWL256) expressing genes from the MVA pathway and grown in fed-batch culture at the 15-L scale without yeast extract feeding.
Figure 67B:
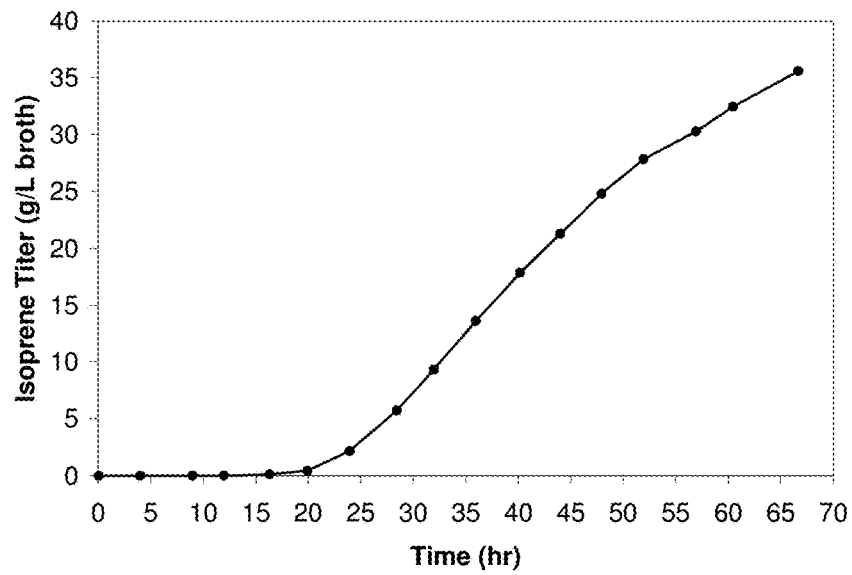
Figure 67C:
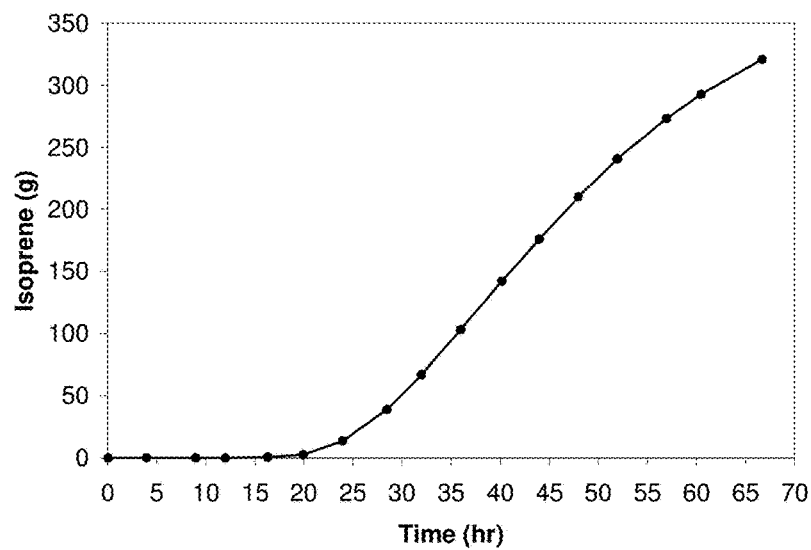
Figure 67D:
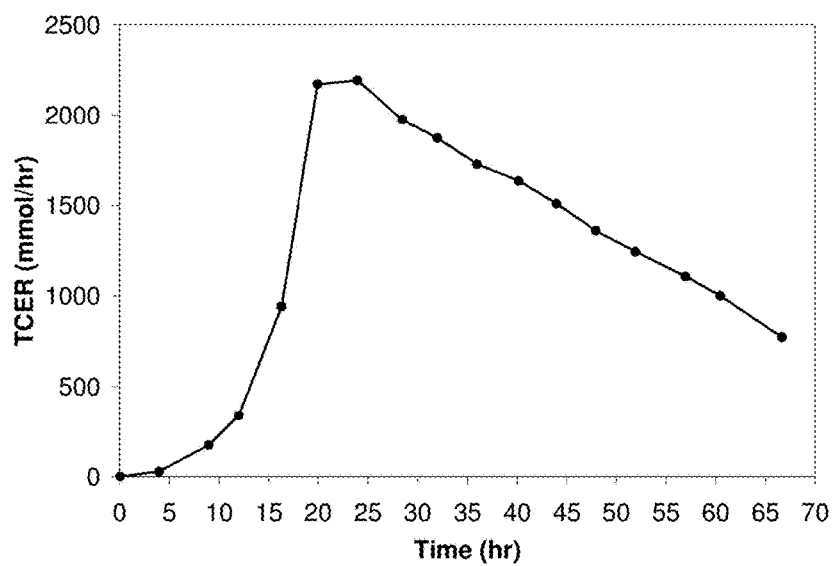

Fermentation was performed in a 15-L bioreactor with BL21 (DE3) *E. coli* cells containing the upper mevalonic acid (MVA) pathway (pCL Upper), the integrated lower MVA pathway (gi1.2KKDyI), and high expression of mevalonate kinase from *M. mazei* and isoprene synthase from *P. alba* (pTrcAlba-mMVK). This experiment was carried out to monitor isoprene formation from glucose at the desired fermentation pH 7.0 and temperature 30° C. A frozen vial of the *E. coli* strain was thawed and inoculated into tryptone-yeast extract medium. After the inoculum grew to OD 1.0, measured at 550 nm, 500 mL was used to inoculate a 15-L bioreactor bringing the initial volume to 5-L.

i) Production of Isoprene in *E. coli* Cells (EL256) Grown in Fed-Batch Culture without Yeast Extract Feeding Glucose was fed at an exponential rate until cells reached the stationary phase. After this time the glucose feed was decreased to meet metabolic demands. The total amount of glucose delivered to the bioreactor during the 67 hour fermentation was 3.9 kg. Induction was achieved by adding isopropyl-beta-D-1-thiogalactopyranoside (IPTG). The IPTG concentration was brought to 102 uM when the optical density at 550 nm ($OD_{550}$) reached a value of 9. The IPTG concentration was raised to 192 uM when $OD_{550}$ reached 140. The $OD_{550}$ profile within the bioreactor over time is shown in FIG. 67A. The isoprene level in the off gas from the bioreactor was determined using a Hiden mass spectrometer. The isoprene titer increased over the course of the fermentation to a final value of 35.6 g/L (FIG. 67B). The total amount of isoprene produced during the 67 hour fermentation was 320.6 g and the time course of production is shown in FIG. 67C. The metabolic activity profile, as measured by TCER, is shown in FIG. 67D. The molar yield of utilized carbon that went into producing isoprene during fermentation was 17.9%. The weight percent yield of isoprene from glucose was 8.1%.

Figure 68A:
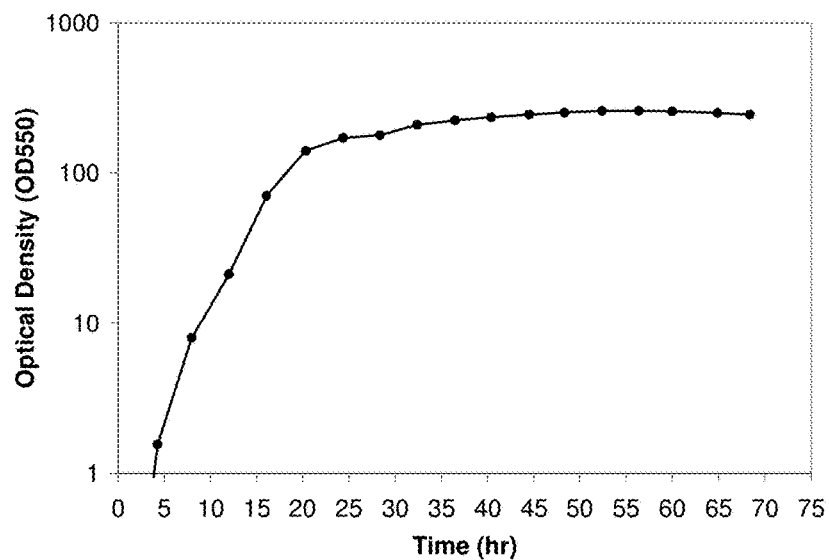
FIG. 68A, FIG. 68B, FIG. 68C, FIG. 68D, and FIG. 68E are graphs of isoprene production by *E. coli* strain (EWL256) expressing genes from the MVA pathway and grown in fed-batch culture at the 15-L scale with yeast extract feeding.
Figure 68B:
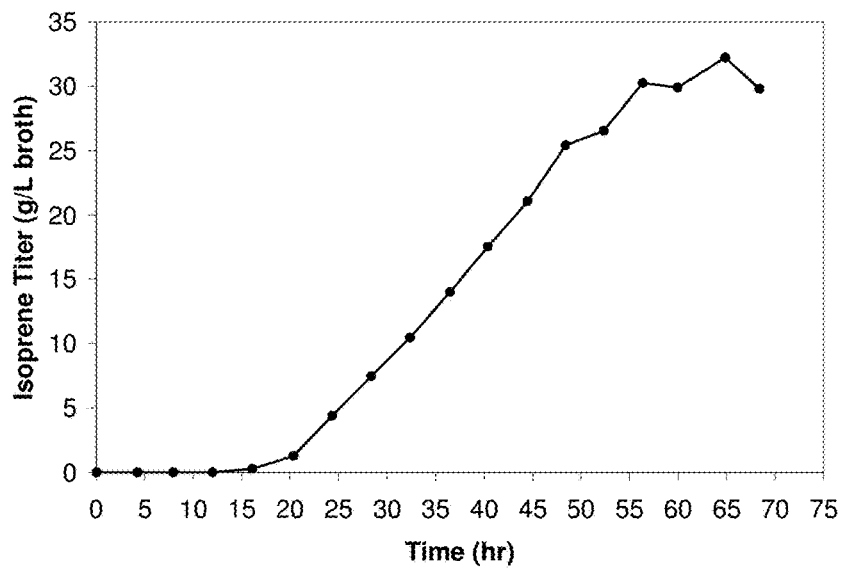
Figure 68C:
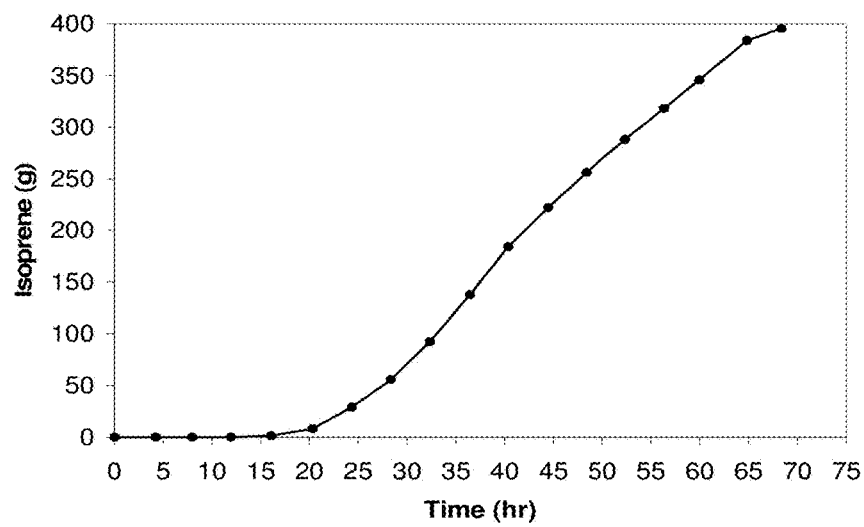
Figure 68D:
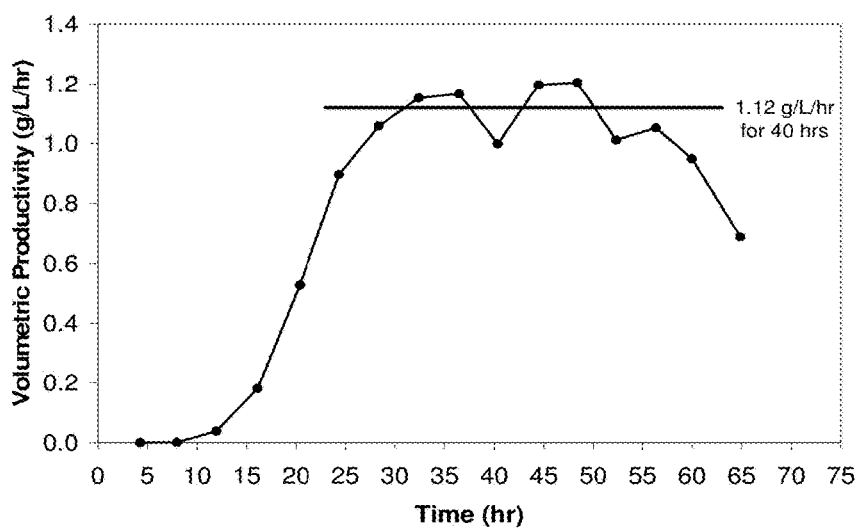
Figure 68E:
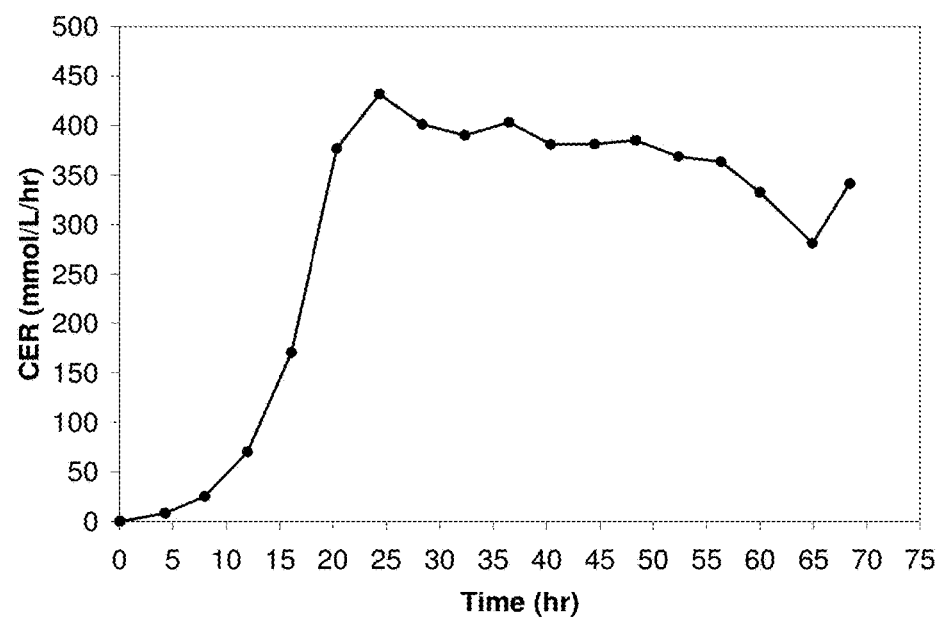

Production of Isoprene in *E. coli* Cells (EL256) Grown in Fed-Batch Culture with Yeast Extract Feeding Glucose was fed at an exponential rate until cells reached the stationary phase. After this time the glucose feed was decreased to meet metabolic demands. The total amount of glucose delivered to the bioreactor during the 68 hour fermentation was 7.1 kg. A total of 1.06 kg of yeast extract was also fed during the fermentation. Induction was achieved by adding IPTG. The IPTG concentration was brought to 208 uM when the optical density at 550 nm ($OD_{550}$) reached a value of 7. The IPTG concentration was raised to 193 uM when $OD_{550}$ reached 180. The $OD_{550}$ profile within the bioreactor over time is shown in FIG. 68A. The isoprene level in the off gas from the bioreactor was determined using a Hiden mass spectrometer. The isoprene titer increased over the course of the fermentation to a maximum value of 32.2 g/L (FIG. 68B). The total amount of isoprene produced during the 68 hour fermentation was 395.5 g and the time course of production is shown in FIG. 68C. The time course of volumetric productivity is shown in FIG. 68D and shows that an average rate of 1.1 g/L/hr was maintained for between 23 and 63 hours. The metabolic activity profile, as measured by CER, is shown in FIG. 68E The molar yield of utilized carbon that went into producing isoprene during fermentation was 10.3%. The weight percent yield of isoprene from glucose was 5.2%.

IV. Production of Isoprene from Different Carbon Sources in *E. coli* Harboring the Mevalonic Acid (MVA) Pathway and Isoprene Synthase (EWL256)

Media Recipe (Per Liter Fermentation Media):

$K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 0.2 g, 1000× Modified Trace Metal Solution 1 ml. All of the components were dissolved sequentially in $diH_2O$. The pH was adjusted to 6.8 with ammonium hydroxide (30%) and brought to volume. Media was filter sterilized with a 0.22 micron filter. Carbon source was added to a final concentration of 1%. Required antibiotics were added after sterilization and pH adjustment.

1000× Trace Metal Solution (Per Liter Fermentation Media):

Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component was dissolved one at a time in $diH_2O$, pH to 3.0 with HCl/NaOH, and then brought to volume and filter sterilized with a 0.22 micron filter.

i) Preparation of AFEX Biomass Hydrolysate

AFEX pretreated corn stover was hydrolyzed to prepare biomass hydrolysate containing both xylose, glucose and acetate.

AFEX pretreated corn stover, received from Michigan Biotechnology Institute, was used. The pretreatment conditions were, 60% moisture, 1:1 ammonia loading, and 90° C. for 30 minutes, then air dried. The moisture content in the AFEX pretreated corn stover was 21.27%. Content of glucan and xylan in the AFEX pretreated corn stover were 31.7% and 19.1% (dry basis) respectively. The enzyme used was accellerase 1000, Grindamyl H121 (Danisco xylanase product from *Aspergillus niger* for bread-making industry).

For saccharification, 20 g of AFEX pretreated corn stover was added into a 500 ml flask, together with 5 ml of 1 M pH 4.8 sodium citrate buffer, 2.25 ml of Accellerase 1000, 0.1 ml of Grindamyl H121, and 72.65 ml of DI water. The flask was put in an orbital shaker, and incubated at 50° C. for 96 hours.

For analysis, one sample was taken from the shaker, and analyzed using HPLC. The hydrolysate contained 37.2 g/l of glucose and 24.3 g/L of xylose, and 7.6 g/L of oligomers of glucose and/or xylose. Additionally, the hydrolysate also contains 1.17 g/L acetate.

ii) Experimental Procedure

An inoculum of the *E. coli* strain EWL256 containing the MVA pathway and isoprene synthase was taken from a frozen vial and streaked onto an LB broth agar plate containing spectinomycin (50 ug/mL) and carbinicllin (50 ug/mL) and incubated at 30° C. overnight. A single colony was inoculated into TM3 media containing glucose, xylose, glycerol, acetate or biomass as only carbon source and grown overnight at 30° C. Cells grow on acetate reached a significantly lower optical density. Cells grown on glucose, glycerol, biomass hydrolysate or acetate were diluted into 20 mL of TM3 media containing the respective carbon sources to reach an optical density of between 0.1 measured at 600 nM. A negative control not containing any carbon source was prepared from the glucose overnight culture. A separate experiment was performed with glucose and xylose, where the cultures were diluted to an optical density of 0.05. All culture conditions (except for acetate and glycerol) were tested in duplicates and the presented results are averaged between these cultures. Production of isoprene was induced with 200 µM IPTG from the beginning of the experiment. The flasks were incubated at 30° C. in an orbital shaker (200 rpm) and growth was followed by measuring optical density. After the glucose fed cultures had reached an optical density of approximately 0.4, samples were analyzed for isoprene production from all the tested carbon sources every hour for three hours. Samples of 100 µL were transferred in duplicates to 2 mL glass vials, sealed and incubated for 30 min at 30° C. The bacteria were then heat killed by incubation at 80° C. for 8 minutes. The amount of produced isoprene was measured using GC-MS and specific productivity (µg/L*hr) was calculated.

iii) Results

Significant production of isoprene could be demonstrated during growth on all the tested carbon sources. These carbon sources are examples of common alcohols, organic acids, sugars containing 5 or 6 carbon units (C5 or C6), and biomass hydrolysate.

Figure 69D:
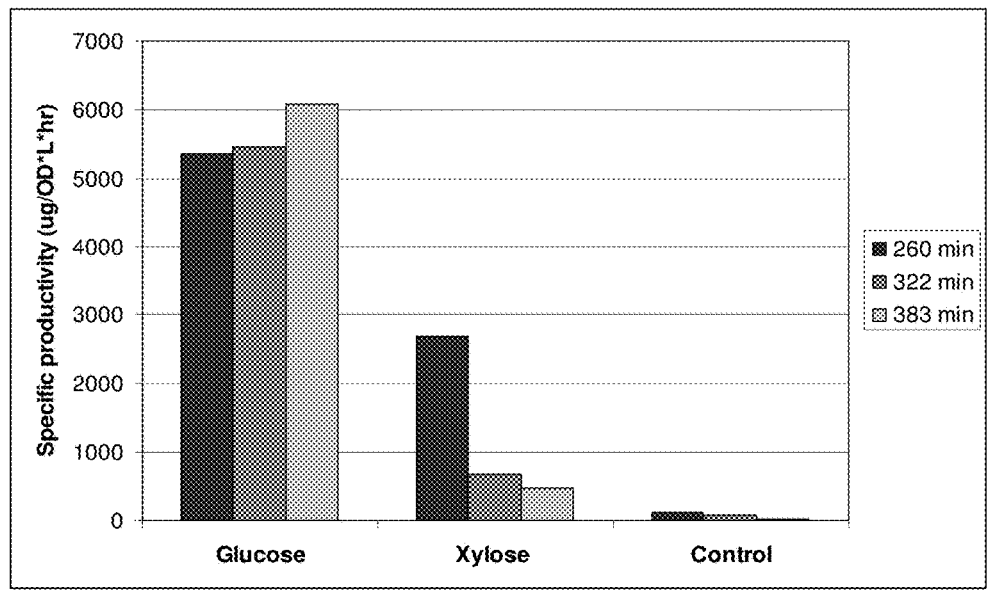

The initial growth rate on biomass hydrolysate was comparable to the growth rate on glucose (FIG. 69A). The initial specific productivity during growth on biomass hydrolysate was significantly higher than during growth on glucose. This demonstrates that biomass hydrolysate can be used as an efficient source of carbon for the production of isoprene. The specific productivity declined after 255 minutes of growth on biomass hydrolysate (FIG. 69B). The bacteria had a slower growth rate with xylose as only carbon source when compared to glucose (FIG. 69C), but a significant specific isoprene productivity was measured (FIG. 69D). This shows that both C5 and C6 sugars can be utilized for the production of isoprene via the mevalonate acid pathway.

Suprisingly, bacteria grown on acetate as the only carbon source had a specific productivity of isoprene approximately twice as high as during growth on glucose (FIG. 69A). The bacteria grew slower on acetate when compared to glucose (FIG. 69B), but the performed experiment demonstrates that acetate can also be used as a carbon source for the production of isoprene. Acetate was also present in the biomass hydrolysate as measured by HPLC.

The bacteria grew well with glycerol as only carbon source (FIG. 69A) and significant production of isoprene was demonstrated (FIG. 69B). This shows that common alcohols may also be used as carbon sources for production of isoprene via the mevalonate acid pathway.

Example 11: Expression of Isoprene-Synthase from Plant in *Streptomyces* sp.

The gene for isoprene synthase Kudzu was obtained from plasmid pJ201:19813. Plasmid pJ201:19813 encodes isoprene synthase from *Pueraia lobata* (Kudzu plant) and was codon-optimized for *Pseudomonas fluorescens*, *Pseudomonas putida*, *Rhodopseudomonas palustris* and *Corynebacterium* (FIGS. 79A-79C (SEQ ID NO:123)). Digestion of plasmid pJ201:19813 with restriction enzymes NdeI and BamHI liberated gene iso19813 that was ligated into the *Streptomyces-E. coli* shuttle vector pUWL201PW (Doumith et al., *Mol. Gen. Genet.* 264: 477-485, 2000; FIG. 71) to generate pUWL201_iso. Successful cloning was verified by restriction analysis of pUWL201_iso. Expression of isoprene synthase iso19813 was under control of the erm-promoter which allows for constitutive expression in *Streptomycetes* species, but not for expression in *E. coli*.

PUWL201PW (no insert) and pUWL201_iso were introduced in *Streptomyces albus* J1074 (Sanchez et al., *Chem. Biol.* 9:519-531, 2002) by transformation of protoplasts as described by Hopwood et al., *The John innes foundation*, Norwich, 1985.

A 200 µl aliquot of protoplast suspensions was transformed with 1.9 g pUWL201PW or 2.9 g pUWL201_iso. After incubation overnight at 28° C. on non-selective R5-agarplates, positive transformants were selected by further incubation for 4 days in R3-overlay agar containing thiostrepton (250 µg/ml). Thiostrepton resistant transformants were examined for presence of the pUWL-plasmids by plasmid preparation using Plasmid Mini Kit (Qiagen). Prepared plasmid DNA was reintroduced in *E. coli* DH5α to generate sufficient amounts of plasmid DNA to be analyzed by restriction analysis. Positive transformants were selected on ampicillin-containing L-agar plates and insert analysis was done by digestion of plasmid DNA with NdeI and BamHI endonucleases. Isoprene synthase was identified as a 1.7 kb fragment in positive pUWL201 iso clones while in the control strains (pUWL201PW) no such fragment was observed.

Wild type strain and transformants of *S. albus* containing control plasmid pUWL201PW or isoprene synthase encoding pUWL201_iso were analyzed for isoprene formation. Strains were cultivated in duplicate on solid media (tryptic soy broth agar, TSB; 2.5 ml) in presence or absence of thiostrepton (200 µg/ml) and incubated for 4 days at 28° C. in sealed head-space vials (total volume 20 ml). 500 µl head-space samples (end point measurements) were analyzed by GC-MS in SIM-mode and isoprene was identified according to reference retention times and molecular masses (67 m/z). Isoprene present in head-space samples was quantified by previously generated calibration curves. While wild-type *S. albus* and control strains harboring pUWL201PW produced isoprene in concentrations slightly higher than the detection limit (0.04-0.07 ppm), *S. albus* harboring pUWL201_iso produced isoprene in at least ten-fold excess compared to controls (0.75 ppm; FIG. 72). The results demonstrate successful expression of plant-derived isoprene synthase in a prokaryotic organism of the Actinomycetes group.

Example 12: Production of Isoprene or Mevalonate from Fatty Acid or Palm Oil in *E. coli* fadR atoC LS5218 Containing the Upper or Upper and Lower Mevalonic Acid Pathway Plus Kudzu Isoprene Synthase

*Escherichia coli* fadR atoC strain LS5218 (#6966) was obtained from the *Coli* Genetic Stock Center. FadR encodes a transcription repressor that negatively regulates expression of the genes encoding fatty acid degradation enzymes (Campbell et al., *J. Bacteriol.* 183: 5982-5990, 2001). AtoC is a response regulator in a two-component regulatory system with AtoS, regulates acetolactate metabolism. The fadR atoC strain allows constitutive expression of the fatty acid degradation genes and incorporates long chain fatty acids into long-chain-length polyhydroxyalkanoates. When palm oil is used as a carbon source for either mevalonate or isoprene production, the palm oil was converted to glycerol plus fatty acid. Methods for this are well known in the art, and it can be done either enzymatically by incubation with a lipase (for example Porcine pancreatic lipase, *Candida rugosa* lipase, or other similar lipases) or chemically by saponification with a base such as sodium hydroxide.

i) *E. coli* fadR atoC Strain Expressing the Upper Mevalonic Acid Pathway

Strain WW4 was created by electroporating pCLPtrcUpperPathway into LS5218 using standard methods (Sambrooke et al., Molecular Cloning: A Laboratory Manual, 2$^{nd}$ ed., Cold Spring Harbor, 1989). Incorporation of the plasmid was demonstrated by the production of mevalonic acid (MVA) when cells were cultured in TM3 medium supplemented with either C12 fatty acid (FA) or palm oil as the carbon source. To demonstrate production of MVA by WW4 from fatty acid, cells from an overnight culture were diluted 1 to 100 into 5 mL of modified TM3 medium (TM3 without yeast extract) supplemented with 0.25% C12 FA (Sigma cat #L9755). The first sign of MVA production (24 mg/L) was apparent after overnight incubation at 30° C. of the IPTG induced culture. Production increased over three days with the final level of 194 mg/L of MVA produced. To demonstrate production of MVA by WW4 from oil, cells from an overnight culture were diluted 1 to 100 into modified TM3 medium supplemented with 200 mg of digested palm oil per 5 mL of TM3 medium. The first sign of MVA production (50 mg/L) was apparent after overnight incubation of the IPTG induced culture at 30° C. Production increased over three days with a final level of 500 mg/L of MVA produced.

ii) *E. coli* fadR atoC Strain Expressing the Upper and Lower MVA Pathway Plus Kudzu Isoprene Synthase

Figure 70A:
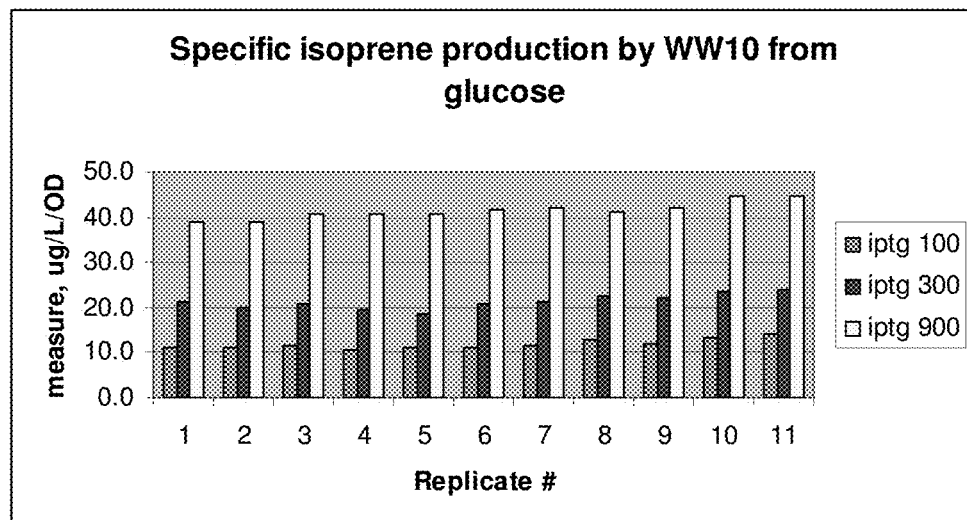
FIG. 70A and FIG. 70B show the production of isoprene by *E. coli* strains from glucose and from fatty acid, respectively. For FIG. 70A, eleven colonies from the transformation of WW4 with pMCM118, the plasmid bearing the lower mevalonic acid pathway, were picked to verify the presence of the lower pathway. Cell from the colonies were cultured in TM3 medium containing 0.1% yeast extract and 2% glucose. Aliquots of induced culture were assayed for isoprene production after 4 hours of induction. All colonies showed the production of isoprene. The inducer IPTG had a strong growth inhibitory effect as was evident from the 3 to 4.6-fold reduced cell density in going from 50 to 900 uM concentration of the inducer (data not shown). The graph shows that higher induction, yields a higher specific titer of isoprene. For FIG. 70B, the production culture was inoculated from a washed overnight culture at 1 to 10 dilution.

*Escherichia coli* strain WW4 (LS5218 fadR atoC pCLPtrcUpperPathway) was transformed with pMCM118 [pTrcKKDyIkIS] to yield WW10. The incorporation of the plasmid was demonstrated by evidence of production of isoprene when the strain was cultured in TM3 and glucose and induced with IPTG (100, 300, or 900 uM). The strain was relatively sensitive to IPTG and showed a significant growth defect even at 100 uM IPTG. These results are shown in FIG. 70A.

To test isoprene production from dodecanoic acid, WW10 was cultured overnight in L broth containing spectinomycin (50 ug/ml), and kanamycin (50 ug/ml) at 37 C with shaking at 200 rpm. The cells were washed with modified TM3 medium by centrifugation and resuspension in their original culture volume with this medium. The washed and resuspended cells from this starter culture were diluted 1 to 100 and 1 to 10 into 5 mL of modified TM3 medium containing 0.125% C12 Fatty Acid (Sigma cat #L9755).

To demonstrate production of mevalonate from palm oil, the oil was predigested with lipase at 37° C. and 250 rpm for several days to release the fatty acids (evidence of hydrolysis was judged by the foam formed when tubes were shaken).

Figure 70B:
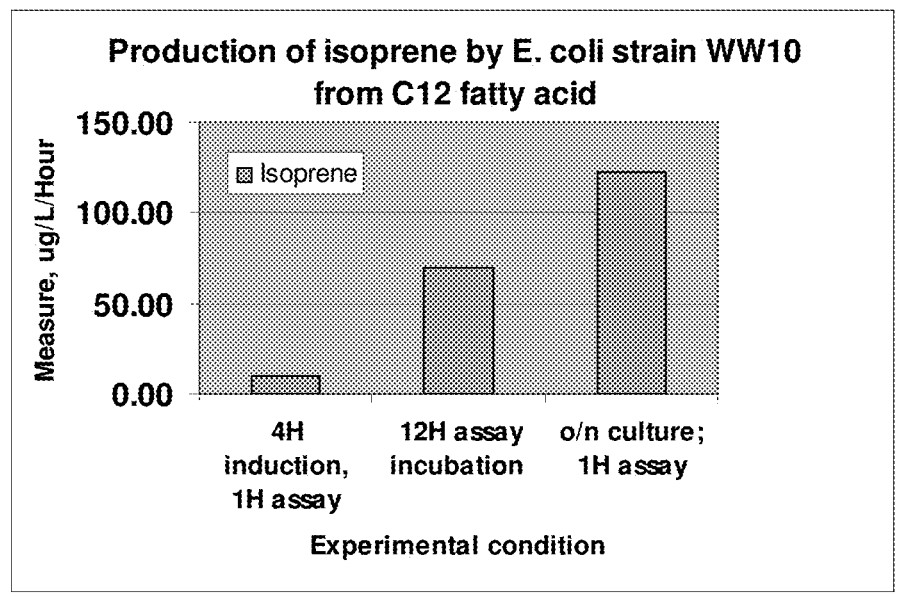

In addition, a culture was set up by diluting the washed cells at 1 to 10 into modified TM3 medium contained in test tubes with palm oil. A further tube was set up by the addition of 0.125% C12FA to the remainder (2.5 mL) of the washed cells without further dilution (bioconversion). After 3.75 hours of growth at 30° C. with shaking at 250 rpm all of the cultures were induced by the addition of 50 uM IPTG. Incubation was continued for 4 hours after which time 200 uL of each of the cultures was assayed for isoprene accumulation with a modified head space assay (1 hour accumulation at 30° C. with shaking at 500 rpm). An additional isoprene assay was conducted by a 12 hour incubation of the assay glass block prior to GCMS analysis. Incubation of the induced cultures was continued overnight and 200 uL aliquots were again assayed for isoprene production (1 hour, 30 deg, 500 rpm Shel-Lab shaker) the following morning. Analysis of these cultures showed the production of significant levels of isoprene. The highest levels of isoprene were observed in the culture which was seeded at 1/10 dilution from the overnight starter culture after it had been incubated and induced overnight. This result suggests that this culture continued to grow and increase in cell density. These results are shown in FIG. 70B. Cell density could not be measured directly because the fatty acid suspension had a turbid appearance. Cell density of this culture was therefore determined by plating an aliquot of the culture and showed 8×10$^7$ colony forming units. This corresponds approximately to an OD$_{600}$ of 0.1. Nevertheless, this culture provided significant isoprene production; no isoprene is observed for similar strains without the pathway described in this example.

Example 13: Improvement of Isoprene Production by Constitutive Expression of ybhE in *E. coli*

This example shows production of isoprene in a strain constitutively expressing ybhE (pgl) compared to a control strain with wild type ybhE. The gene ybhE (pgl) encodes a 6-phosphogluconolactonase that suppresses posttranslational gluconylation of heterologously expressed proteins and improves product solubility and yield while also improving biomass yield and flux through the pentose phosphate pathway (Aon et al. *Applied and Environmental Microbiology*, 74(4): 950-958, 2008).

The BL21 strain of *E. coli* producing isoprene (EWL256) was constructed with constitutive expression of the ybhE gene on a replicating plasmid pBBR1MCS5 (Gentamycin) (obtained from Dr. K. Peterson, Louisiana State University).

FRT-based recombination cassettes, and plasmids for Red/ET-mediated integration and antibiotic marker loopout were obtained from Gene Bridges GmbH (Germany). Procedures using these materials were carried out according to Gene Bridges protocols. Primers Pgl-F and PglGl1.5-R were used to amplify the resistance cassette from the FRT-gb2-Cm-FRT template using Stratagene Herculase II Fusion kit according to the manufacturer's protocol. The PCR reaction (50 uL final volume) contained: 5 uL buffer, 1 uL template DNA (FRT-gb2-Cm-F from Gene Bridges), 10 pmols of each primer, and 1.5 uL 25 mM dNTP mix, made to 50 uL with dH$_2$O. The reaction was cycled as follows: 1×2 minutes, 95° C. then 30 cycles of (30 seconds at 95° C.; 30 seconds at 63° C.; 3 minutes at 72° C.).

The resulting PCR product was purified using the QiaQick PCR purification kit (Qiagen) and electroporated into electrocompetent MG1655 cells harboring the pRed-ET recombinase-containing plasmid as follows. Cells were prepared by growing in 5 mLs of L broth to and OD600~0.6 at 30° C. The cells were induced for recombinase expression by the addition of 4% arabinose and allowed to grow for 30 minutes at 30° C. followed by 30 minutes of growth at 37° C. An aliquot of 1.5 mLs of the cells was washed 3-4 times in ice cold dH$_2$O. The final cell pellet was resuspended in 40 uL of ice cold dH$_2$O and 2-5 uL of the PCR product was added. The electroporation was carried out in 1-mm gap cuvettes, at 1.3 kV in a Gene Pulser Electroporator (Bio-Rad Inc.). Cells were recovered for 1-2 hours at 30° C. and plated on L agar containing chloramphenicol (5 ug/mL). Five transformants were analyzed by PCR and sequencing using primers flanking the integration site (2 primer sets: pgl and 49 rev and 3' EcoRV-pglstop; Bottom Pgb2 and Top GB's CMP (946)). A correct transformant was selected and this strain was designated MG1655 GI1.5-pgl::CMP.

The chromosomal DNA of MG1655 GI1.5-pgl::CMP was used as template to generate a PCR fragment containing the FRT-CMP-FRT-GI1.5-ybhE construct. This construct was cloned into pBBR1MCS5 (Gentamycin) as follows. The fragment, here on referred to as CMP-GI1.5-pgl, was amplified using the 5' primer Pglconfirm-F and 3' primer 3' EcoRV-pglstop. The resulting fragment was cloned using the Invitrogen TOPO-Blunt cloning kit into the plasmid vector pCR-Blunt II-TOPO as suggested from the manufacturer. The NsiI fragment harboring the CMP-GI1.5-pgl fragment was cloned into the PstI site of pBBR1MCS5 (Gentamycin). A 20 µl ligation reaction was prepared containing 5 µl CMP-GI1.5-pgl insert, 2 µl pBBR1MCS5 (Gentamycin) vector, 1 µl T4 DNA ligase (New England Biolabs), 2 µl 10× ligase buffer, and 10 µl ddH$_2$O. The ligation mixture was incubated at room temperature for 40 minutes then 2-4 uL were electroporated into electrocompetent Top 10 cells (Invitrogen) using the parameters disclosed above. Transformants were selected on L agar containing 10 ug/ml chloramphenicol and 5 ug/ml Gentamycin. The sequence of the selected clone was determined using a number of the primers described above as well as with the in-house T3 and Reverse primers provided by Sequetech, CA. This plasmid was designated pBBRCMPGI1.5-pgl (FIG. 77A and FIG. 77B and SEQ ID NO: 122).

Plasmid pBBRCMPGI1.5-pgl was electroporated into EWL256, as described above in Example 10 and transformants were plated on L agar containing Chloramphenicol (10 ug/mL), Gentamycin (5 ug/mL), spectinomycin (50 ug/mL), and carbenicillin (50 ug/mL). One transformant was selected and designated RM11608-2.

Primers:

Pgl-F
(SEQ ID NO: 115)
5'-ACCGCCAAAAGCGACTAATTTTAGCTGTTACAGTCAGTTGAATTAA
CCCTCACTAAAGGGCGGCCGC-3'

PglGI1.5-R
(SEQ ID NO: 116)
5'-GCTGGCGATATAAACTGTTTGCTTCATGAATGCTCCTTTGGGTTAC
CTCCGGGAAACGCGGTTGATTTGTTTAGTGGTTGAATTATTTGCTCAGG

ATGTGGCATAGTCAAGGGCGTGACGGCTCGCTAATACGACTCACTATAG
GGCTCGAG-3'

3' EcoRV-pglstop:
(SEQ ID NO: 117)
5'-CTT GAT ATC TTA GTG TGC GTT AAC CAC CAC pgl +49 rev:
(SEQ ID NO: 118)
CGTGAATTTGCTGGCTCTCAG Bottom Pgb2:
(SEQ ID NO: 119)
GGTTTAGTTCCTCACCTTGTC Top GB's CMP(946):
(SEQ ID NO: 120)
ACTGAAACGTTTTCATCGCTC Pglconfirm-F
(SEQ ID NO: 121)
5'-ACCGCCAAAAGCGACTAATTTTAGCT-3' i) Small Scale Analysis

Media Recipe (Per Liter Fermentation Media):

K$_2$HPO$_4$ 13.6 g, KH$_2$PO$_4$ 13.6 g, MgSO$_4$*7H$_2$O 2 g, citric acid monohydrate 2 g, ferric ammonium citrate 0.3 g, (NH$_4$)$_2$SO$_4$ 3.2 g, yeast extract 1 g, 1000× Trace Metals Solution 1 ml. All of the components were added together and dissolved in diH$_2$O. The pH was adjusted to 6.8 with ammonium hydroxide (30%) and brought to volume. Media was filter-sterilized with a 0.22 micron filter. Glucose 5.0 g and antibiotics were added after sterilization and pH adjustment.

1000× Trace Metal Solution (Per Liter Fermentation Media):

Citric Acid*H$_2$O 40 g, MnSO$_4$*H$_2$O 30 g, NaCl 10 g, FeSO$_4$*7H$_2$O 1 g, CoCl$_2$*6H$_2$O 1 g, ZnSO$_4$*7H$_2$O 1 g, CuSO$_4$*5H$_2$O 100 mg, H$_3$BO$_3$ 100 mg, NaMoO$_4$*2H$_2$O 100 mg. Each component is dissolved one at a time in diH$_2$O. The pH is adjusted to 3.0 with HCl/NaOH, and then the solution is brought to volume and filter-sterilized with a 0.22 micron filter.

a) Experimental Procedure

Isoprene production was analyzed by growing the strains in a Cellerator™ from MicroReactor Technologies, Inc. The working volume in each of the 24 wells was 4.5 mL. The temperature was maintained at 30° C., the pH setpoint was 7.0, the oxygen flow setpoint was 20 sccm and the agitation rate was 800 rpm. An inoculum of E. coli strain taken from a frozen vial was streaked onto an LB broth agar plate (with antibiotics) and incubated at 30° C. A single colony was inoculated into media with antibiotics and grown overnight. The bacteria were diluted into 4.5 mL of media with antibiotics to reach an optical density of 0.05 measured at 550 nm.

Off-gas analysis of isoprene was performed using a gas chromatograph-mass spectrometer (GC-MS) (Agilent) headspace assay. Sample preparation was as follows: 100 pL of whole broth was placed in a sealed GC vial and incubated at 30° C. for a fixed time of 30 minutes. Following a heat kill step, consisting of incubation at 70° C. for 5 minutes, the sample was loaded on the GC.

Optical density (OD) at a wavelength of 550 nm was obtained using a microplate reader (Spectramax) during the course of the run. Specific productivity was obtained by dividing the isoprene concentration (µg/L) by the OD reading and the time (hour).

The two strains EWL256 and RM11608-2 were assessed at 200 and 400 uM IPTG induction levels. Samples were analyzed for isoprene production and cell growth (OD550) at 1, 2.5, 4.75, and 8 hours post-induction. Samples were done in duplicate.

b) Results

The experiment demonstrated that at 2 different concentrations of IPTG the strain expressing the ybhE (pgl) had a dramatic 2-3 fold increase in specific productivity of isoprene compared to the control strain.

ii) Isoprene Fermentation from *E. coli* Expressing *M. mazei* Mevalonate Kinase, *P. alba* Isoprene Synthase, and Pgl Over-Expression (RHM111608-2) and Grown in Fed-Batch Culture at the 15-L Scale Medium Recipe (Per Liter Fermentation Medium)

$K_2HPO_4$ 7.5 g, $MgSO_4*7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in Di $H_2O$, pH to 3.0 with HCl/NaOH, then q.s. to volume and filter sterilized with a 0.22 micron filter Fermentation was performed in a 15-L bioreactor with BL21 (DE3) *E. coli* cells containing the upper mevalonic acid (MVA) pathway (pCL Upper), the integrated lower MVA pathway (gi1.2KKDyI), high expression of mevalonate kinase from *M. mazei* and isoprene synthase from *P. alba* (pTrcAlba-mMVK), and high expression of pgl (pBBR-pgl). This experiment was carried out to monitor isoprene formation from glucose at the desired fermentation pH 7.0 and temperature 34° C. A frozen vial of the *E. coli* strain was thawed and inoculated into tryptone-yeast extract medium. After the inoculum grew to OD 1.0, measured at 550 nm, 500 mL was used to inoculate a 15-L bioreactor bringing the initial volume to 5-L.

Glucose was fed at an exponential rate until cells reached the stationary phase. After this time the glucose feed was decreased to meet metabolic demands. The total amount of glucose delivered to the bioreactor during the 40 hour (59 hour) fermentation was 3.1 kg (4.2 kg at 59 hour). Induction was achieved by adding IPTG. The IPTG concentration was brought to 110 uM when the optical density at 550 nm ($OD_{550}$) reached a value of 4. The IPTG concentration was raised to 192 uM when $OD_{550}$ reached 150. The $OD_{550}$ profile within the bioreactor over time is shown in FIG. 78A. The isoprene level in the off gas from the bioreactor was determined using a Hiden mass spectrometer. The isoprene titer increased over the course of the fermentation to a maximum value of 33.2 g/L at 40 hours (48.6 g/L at 59 hours) (FIG. 78B). The isoprene titer increased over the course of the fermentation to a maximum value of 40.0 g/L at 40 hours (60.5 g/L at 59 hours) (FIG. 78C). The total amount of isoprene produced during the 40-hour (59-hour) fermentation was 281.3 g (451.0 g at 59 hours) and the time course of production is shown in FIG. 78D. The time course of volumetric productivity is shown in FIG. 78E and shows that an average rate of 1.0 g/L/hr was maintained between 0 and 40 hours (1.4 g/L/hour between 19 and 59 hour). The metabolic activity profile, as measured by CER, is shown in FIG. 78F. The molar yield of utilized carbon that went into producing isoprene during fermentation was 19.6% at 40 hours (23.6% at 59 hours). The weight percent yield of isoprene from glucose was 8.9% at 40 hours (10.7% at 59 hours).

Unless defined otherwise, the meanings of all technical and scientific terms used herein are those commonly understood by one of skill in the art to which this invention belongs. Singleton, et al., Dictionary of Microbiology and Molecular Biology, 2nd ed., John Wiley and Sons, New York (1994), and Hale & Marham, The Harper Collins Dictionary of Biology, Harper Perennial, N.Y. (1991) provide one of skill with a general dictionary of many of the terms used in this invention. It is to be understood that this invention is not limited to the particular methodology, protocols, and reagents described, as these may vary. One of skill in the art will also appreciate that any methods and materials similar or equivalent to those described herein can also be used to practice or test the invention.

The headings provided herein are not limitations of the various aspects or embodiments of the invention which can be had by reference to the specification as a whole.

For use herein, unless clearly indicated otherwise, use of the terms "a", "an," and the like refers to one or more.

Reference to "about" a value or parameter herein includes (and describes) embodiments that are directed to that value or parameter per se. For example, description referring to "about X" includes description of "X." Numeric ranges are inclusive of the numbers defining the range.

It is understood that aspects and embodiments of the invention described herein include "comprising," "consisting," and "consisting essentially of" aspects and embodiments.

APPENDIX 1

Exemplary 1-deoxy-D-xylulose-5-phosphate synthase nucleic acids and polypeptides ATH: AT3G21500(DXPS1) AT4G15560(CLA1) AT5G11380(DXPS3)
OSA: 4338768 4340090 4342614
CME: CMFO89C
PFA: MAL13P1.186
TAN: TA20470
TPV: TP01_0516
ECO: b0420(dxs)
ECJ: JW0410(dxs)
ECE: Z0523(dxs)
ECS: ECs0474
ECC: c0531(dxs)
ECI: UTI89_C0443(dxs)
ECP: ECP_0479
ECV: APECO1_1590(dxs)
ECW: EcE24377A_0451(dxs)
ECX: EcHS_A0491
STY: STY0461(dxs)
STT: t2441(dxs)
SPT: SPA2301(dxs)
SEC: SC0463(dxs)
STM: STM0422(dxs)
YPE: YPO3177(dxs)
YPK: y1008(dxs)
YPM: YP_0754(dxs)
YPA: YPA_2671
YPN: YPN_0911
YPP: YPDSF_2812

YPS: YPTB0939(dxs)
YPI: YpsIP31758_3112(dxs)
SFL: SF0357(dxs)
SFX: S0365(dxs)
SFV: SFV_0385(dxs)
SSN: SSON_0397(dxs)
SBO: SBO_0314(dxs)
SDY: SDY_0310(dxs)
ECA: ECA1131(dxs)
PLU: plu3887(dxs)
BUC: BU464(dxs)
BAS: BUsg448(dxs)
WBR: WGLp144(dxs)
SGL: SG0656
KPN: KPN_00372(dxs)
BFL: Bfl238(dxs)
BPN: BPEN_244(dxs)
HIN: HI1439(dxs)
HIT: NTHI1691(dxs)
HIP: CGSHiEE_04795
HIQ: CGSHiGG_01080
HDU: HD0441(dxs)
HSO: HS_0905(dxs)
PMU: PM0532(dxs)
MSU: MS 1059(dxs)
APL: APL_0207(dxs)
XFA: XF2249
XFT: PD1293(dxs)
XCC: XCC2434(dxs)
XCB: XC_1678
XCV: XCV2764(dxs)
XAC: XAC2565(dxs)
XOO: XOO2017(dxs)
XOM: XOO_1900(XOO1900)
VCH: VC0889
VVU: VV1_0315
VVY: VV0868
VPA: VP0686
VFI: VF0711
PPR: PBPRA0805
PAE: PA4044(dxs)
PAU: PA14_11550(dxs)
PAP: PSPA7_1057(dxs)
PPU: PP_0527(dxs)
PST: PSPTO_0698(dxs)
PSB: Psyr_0604
PSP: PSPPH_0599(dxs)
PFL: PFL_5510(dxs)
PFO: Pfl_5007
PEN: PSEEN0600(dxs)
PMY: Pmen_3844
PAR: Psyc_0221(dxs)
PCR: Pcryo_0245
ACI: ACIAD3247(dxs)
SON: SO_1525(dxs)
SDN: Sden_2571
SFR: Sfri_2790
SAZ: Sama_2436
SBL: Sbal_1357
SLO: Shew_2771
SHE: Shewmr4_2731
SHM: Shewmr7_2804
SHN: Shewana3_2901
SHW: Sputw3181_2831
ILO: IL2138(dxs)
CPS: CPS_1088(dxs)
PHA: PSHAa2366(dxs)
PAT: Patl_1319
SDE: Sde_3381
PIN: Ping_2240
MAQ: Maqu_2438
MCA: MCA0817(dxs)
FTU: FTT1018c(dxs)
FTF: FTF1018c(dxs)
FTW: FTW_0925(dxs)
FTL: FTL_1072
FTH: FTH_1047(dxs)
FTA: FTA_1131(dxs)
FTN: FTN_0896(dxs)
NOC: Noc_1743
AEH: Mlg_1381
HCH: HCH_05866(dxs)
CSA: Csal_0099
ABO: ABO_2166(dxs)
AHA: AHA_3321(dxs)
BCI: BCI_0275(dxs)
RMA: Rmag_0386
VOK: COSY_0360(dxs)
NME: NMB1867
NMA: NMA0589(dxs)
NMC: NMC0352(dxs)
NGO: NGO0036
CVI: CV_2692(dxs)
RSO: RSc2221(dxs)
REU: Reut_A0882
REH: H16_A2732(dxs)
RME: Rmet_2615
BMA: BMAA0330(dxs)
BMV: BMASAVP1_1512(dxs)
BML: BMA10299_1706(dxs)
BMN: BMA10247_A0364(dxs)
BXE: Bxe_B2827
BUR: Bcep18194_B2211
BCN: Bcen_4486
BCH: Bcen2424_3879
BAM: Bamb_3250
BPS: BPSS1762(dxs)
BPM: BURPS1710b_A0842(dxs)
BPL: BURPS1106A_A2392(dxs)
BPD: BURPS668_A2534(dxs)
BTE: BTH_II0614(dxs)
BPE: BP2798(dxs)
BPA: BPP2464(dxs)
BBR: BB1912(dxs)
RFR: Rfer_2875
POL: Bpro_1747
PNA: Pnap_1501
AJS: Ajs_1038
MPT: Mpe_A2631
HAR: HEAR0279(dxs)
MMS: mma_0331
NEU: NE1161(dxs)
NET: Neut_1501
NMU: Nmul_A0236
EBA: ebA4439(dxs)
AZO: azol 198(dxs)
DAR: Daro_3061
TBD: Tbd_0879
MFA: Mfla_2133
HPY: HP0354(dxs)
HPJ: jhp0328(dxs)
HPA: HPAG1_0349
HHE: HH0608(dxs)
HAC: Hac_0968(dxs)

WSU: WS1996
TDN: Tmden_0475
CJE: Cj0321(dxs)
CJR: CJE0366(dxs)
CJJ: CJJ81176_0343(dxs)
CJU: C8J_0298(dxs)
CJD: JJD26997_1642(dxs)
CFF: CFF8240_0264(dxs)
CCV: CCV52592_1671(dxs) CCV52592_1722
CHA: CHAB381_1297(dxs)
CCO: CCC13826_1594(dxs)
ABU: Abu_2139(dxs)
NIS: NIS_0391(dxs)
SUN: SUN_2055(dxs)
GSU: GSU0686(dxs-1) GSU1764(dxs-2)
GME: Gmet_1934 Gmet_2822
PCA: Pcar_1667
PPD: Ppro_1191 Ppro_2403
DVU: DVU1350(dxs)
DVL: Dvul_1718
DDE: Dde_2200
LIP: LI0408(dsx)
DPS: DP2700
ADE: Adeh_1097
MXA: MXAN_4643(dxs)
SAT: SYN_02456
SFU: Sfum_1418
PUB: SAR11_0611(dxs)
MLO: mlr7474
MES: Meso_0735
SME: SMc00972(dxs)
ATU: Atu0745(dxs)
ATC: AGR_C_1351
RET: RHE_CH00913(dxs)
RLE: RL0973(dxs)
BME: BMEI1498
BMF: BAB1_0462(dxs)
BMS: BR0436(dxs)
BMB: BruAb1_0458(dxs)
BOV: BOV_0443(dxs)
BJA: bll2651(dxs)
BRA: BRADO2161(dxs)
BBT: BBta_2479(dxs)
RPA: RPA0952(dxs)
RPB: RPB_4460
RPC: RPC_1149
RPD: RPD_4305
RPE: RPE_1067
NWI: Nwi_0633
NHA: Nham_0778
BHE: BH04350(dxs)
BQU: BQ03540(dxs)
BBK: BARBAKC583_0400(dxs)
CCR: CC_2068
SIL: SPO0247(dxs)
SIT: TM1040 2920
RSP: RSP_0254(dxsA) RSP_1134(dxs)
JAN: Jann_0088 Jann_0170
RDE: RD1_0101(dxs) RD1_0548(dxs)
MMR: Mmar10_0849
HNE: HNE_1838(dxs)
ZMO: ZMO1234(dxs) ZMO1598(dxs)
NAR: Saro_0161
SAL: Sala_2354
ELI: ELI_12520
GOX: GOX0252
GBE: GbCGDNIH1_0221 GbCGDNIH1_2404
RRU: Rru_A0054 Rru_A2619
MAG: amb2904
MGM: Mmc1_1048
SUS: Acid_1783
BSU: BG11715(dxs)
BHA: BH2779
BAN: BA4400(dxs)
BAR: GBAA4400(dxs)
BAA: BA_4853
BAT: BAS4081
BCE: BC4176(dxs)
BCA: BCE_4249(dxs)
BCZ: BCZK3930(dxs)
BTK: BT9727_3919(dxs)
BTL: BALH_3785(dxs)
BLI: BL01523(dxs)
BLD: BLi02598(dxs)
BCL: ABC2462(dxs)
BAY: RBAM_022600
BPU: BPUM_2159
GKA: GK2392
GTN: GTNG_2322
LMO: lmo1365(tktB)
LMF: LMOf2365_1382(dxs)
LIN: lin1402(tktB)
LWE: lwe1380(tktB)
LLA: L108911(dxsA) L123365(dxsB)
LLC: LACR_1572 LACR_1843
LLM: llmg_0749(dxsB)
SAK: SAK_0263
LPL: lp_2610(dxs)
LJO: LJ0406
LAC: LBA0356
LSL: LSL_0209(dxs)
LGA: LGAS_0350
STH: STH1842
CAC: CAC2077 CA_P0106(dxs)
CPE: CPE1819
CPF: CPF_2073(dxs)
CPR: CPR_1787(dxs)
CTC: CTC01575
CNO: NT01CX_1983
CTH: Cthe_0828
CDF: CD1207(dxs)
CBO: CBO1881(dxs)
CBA: CLB_1818(dxs)
CBH: CLC_1825(dxs)
CBF: CLI_1945(dxs)
CKL: CKL_1231(dxs)
CHY: CHY_1985(dxs)
DSY: DSY2348
DRM: Dred_1078
PTH: PTH_1196(dxs)
SWO: Swol_0582
CSC: Csac_1853
TTE: TTE1298(dxs)
MTA: Moth_1511
MPE: MYPE730
MGA: MGA_1268(dxs)
MTU: Rv2682c(dxs1) Rv3379c(dxs2)
MTC: MT2756(dxs)
MBO: Mb2701c(dxs1) Mb3413c(dxs2)
MLE: ML1038(dxs)
MPA: MAP2803c(dxs)
MAV: MAV_3577(dxs)
MSM: MSMEG_2776(dxs)
MMC: Mmcs_2208

CGL: NCgl1827(cgl 1902)
CGB: cg2083(dxs)
CEF: CE1796
CDI: DIP1397(dxs)
CJK: jk1078(dxs)
NFA: nfa37410(dxs)
RHA: RHA1_ro06843
SCO: SCO6013(SC1C3.01) SCO6768(SC6A5.17)
SMA: SAV1646(dxs1) SAV2244(dxs2)
TWH: TWT484
TWS: TW280(Dxs)
LXX: Lxx10450(dxs)
CMI: CMM_1660(dxsA)
AAU: AAur_1790(dxs)
PAC: PPA1062
TFU: Tfu_1917
FRA: Francci3_1326
FAL: FRAAL2088(dxs)
ACE: Acel_1393
SEN: SACE_1815(dxs) SACE_4351
BLO: BL1132(dxs)
BAD: BAD_0513(dxs)
FNU: FN1208 FN1464
RBA: RB2143(dxs)
CTR: CT331(dxs)
CTA: CTA_0359(dxs)
CMU: TC0608
CPN: CPn1060(tktB_2)
CPA: CP0790
CPJ: CPj 1060(tktB_2)
CPT: CpB1102
CCA: CCA00304(dxs)
CAB: CAB301(dxs)
CFE: CF0699(dxs)
PCU: pc0619(dxs)
TPA: TP0824
TDE: TDE1910(dxs)
LIL: LA3285(dxs)
LIC: LIC10863(dxs)
LBJ: LBJ_0917(dxs)
LBL: LBL_0932(dxs)
SYN: sll1945(dxs)
SYW: SYNW1292(Dxs)
SYC: sycl087_c(dxs)
SYF: Synpcc7942_0430
SYD: Syncc9605_1430
SYE: Syncc9902_1069
SYG: sync_1410(dxs)
SYR: SynRCC307_1390(dxs)
SYX: SynWH7803_1223(dxs)
CYA: CYA_1701(dxs)
CYB: CYB_1983(dxs)
TEL: tll0623
GVI: gll0194
ANA: alr0599
AVA: Ava_4532
PMA: Pro0928(dxs)
PMM: PMM0907(Dxs)
PMT: PMT0685(dxs)
PMN: PMN2A_0300
PMI: PMT9312_0893
PMB: A9601_09541(dxs)
PMC: P9515_09901(dxs)
PMF: P9303_15371(dxs)
PMG: P9301_09521(dxs)
PMH: P9215_09851
PMJ: P9211_08521

PME: NATL1_09721(dxs)
TER: Tery_3042
BTH: BT_1403 BT_4099
BFR: BF0873 BF4306
BFS: BF0796(dxs) BF4114
PGI: PG2217(dxs)
CHU: CHU_3643(dxs)
GFO: GFO_3470(dxs)
FPS: FP0279(dxs)
CTE: CT0337(dxs)
CPH: Cpha266_0671
PVI: Cvib_0498
PLT: Plut_0450
DET: DET0745(dxs)
DEH: cbdb_A720(dxs)
DRA: DR_1475
DGE: Dgeo_0994
TTH: TTC1614
TTJ: TTHA0006
AAE: aq_881
TMA: TM1770
PMO: Pmob_1001

Exemplary Acetyl-CoA-Acetyltransferase Nucleic Acids and Polypeptides

HSA: 38(ACAT1) 39(ACAT2)
PTR: 451528(ACAT1)
MCC: 707653(ACAT1) 708750(ACAT2)
MMU: 110446(Acat1) 110460(Acat2)
RNO: 25014(Acat1)
CFA: 484063(ACAT2) 489421(ACAT1)
GGA: 418968(ACAT1) 421587(RCJMB04_34i5)
XLA: 379569(MGC69098) 414622(MGC81403) 414639 (MGC81256) 444457(MGC83664)
XTR: 394562(acat2)
DRE: 30643(acat2)
SPU: 759502(LOC759502)
DME: Dmel_CG10932 Dmel_CG9149
CEL: T02G5.4 T02G5.7 T02G5.8(kat-1)
ATH: AT5G48230(ACAT2/EMB 1276)
OSA: 4326136 4346520
CME: CMA042C CME087C
SCE: YPL028W(ERG10)
AGO: AGOS_ADR165C
PIC: PICST_31707(ERG10)
CAL: CaO19.1591(erg10)
CGR: CAGL0L12364g
SPO: SPBC215.09c
MGR: MGG_01755 MGG_13499
ANI: AN1409.2
AFM: AFUA_6G14200 AFUA_8G04000
AOR: AO090103000012 AO090103000406
CNE: CNC05280
UMA: UM03571.1
DDI: DDB_0231621
PFA: PF14_0484
TET: TTHERM_00091590 TTHERM_00277470 TTHERM_00926980
TCR: 511003.60
ECO: b2224(atoB)
ECJ: JW2218(atoB) JW5453(yqeF)
ECE: Z4164(yqeF)
ECS: ECs3701
ECC: c2767(atoB) c3441(yqeF)
ECI: UTI89_C2506(atoB) UTI89_C3247(yqeF)
ECP: ECP_2268 ECP_2857

ECV: APECO1_3662(yqeF) APECO1_4335(atoB) APECO1_43352(atoB)
ECX: EcHS_A2365
STY: STY3164(yqeF)
STT: t2929(yqeF)
SPT: SPA2886(yqeF)
SEC: SC2958(yqeF)
STM: STM3019(yqeF)
SFL: SF2854(yqeF)
SFX: S3052(yqeF)
SFV: SFV_2922(yqeF)
SSN: SSON_2283(atoB) SSON_3004(yqeF)
SBO: SBO_2736(yqeF)
ECA: ECA1282(atoB)
ENT: Ent638_3299
SPE: Spro_0592
HIT: NTHI0932(atoB)
XCC: XCC1297(atoB)
XCB: XC_2943
XCV: XCV1401(thlA)
XAC: XAC1348(atoB)
XOO: XOO1881(atoB)
XOM: XOO_1778(XOO1778)
VCH: VCA0690
VCO: VC0395_0630
VVU: VV2_0494 VV2_0741
VVY: VVA1043 VVA1210
VPA: VPA0620 VPA1123 VPA1204
PPR: PBPRB1112 PBPRB1840
PAE: PA2001(atoB) PA2553 PA3454 PA3589 PA3925
PAU: PA14_38630(atoB)
PPU: PP_2051(atoB) PP_2215(fadAx) PP_3754 PP_4636
PPF: Pput_2009 Pput_2403 Pput_3523 Pput_4498
PST: PSPTO_0957(phbA-1) PSPTO_3164(phbA-2)
PSB: Psyr_0824 Psyr_3031
PSP: PSPPH_0850(phbA1) PSPPH_2209(phbA2)
PFL: PFL_1478(atoB-2) PFL_2321 PFL_3066 PFL_4330 (atoB-2) PFL_5283
PFO: Pfl_1269 Pfl_1739 Pfl_2074 Pfl_2868
PEN: PSEEN3197 PSEEN3547(fadAx) PSEEN4635(phbA)
PMY: Pmen_1138 Pmen_2036 Pmen_3597 Pmen_3662 Pmen_3820
PAR: Psyc_0252 Psyc_1169
PCR: Pcryo_0278 Pcryo_1236 Pcryo_1260
PRW: PsycPRwf_2011
ACI: ACIAD0694 ACIAD1612 ACIAD2516(atoB)
SON: SO_1677(atoB)
SDN: Sden_1943
SFR: Sfri_1338 Sfri_2063
SAZ: Sama_1375
SBL: Sbal_1495
SBM: Shew185_1489
SBN: Sbal195_1525
SLO: Shew_1667 Shew_2858
SPC: Sputcn32_1397
SSE: Ssed_1473 Ssed_3533
SPL: Spea_2783
SHE: Shewmr4_2597
SHM: Shewmr7_2664
SHN: Shewana3_2771
SHW: Sputw3181_2704
ILO: IL0872
CPS: CPS_1605 CPS_2626
PHA: PSHAa0908 PSHAa1454(atoB) PSHAa1586(atoB)
PAT: Patl_2923
SDE: Sde_3149
PIN: Ping_0659 Ping_2401
MAQ: Maqu_2117 Maqu_2489 Maqu_2696 Maqu_3162
CBU: CBU_0974
LPN: lpg1825(atoB)
LPF: lpl1789
LPP: lpp1788
NOC: Noc_1891
AEH: Mlg_0688 Mlg_2706
HHA: Hhal_1685
HCH: HCH_05299
CSA: Csal_0301 Csal_3068
ABO: ABO_0648(fadAx)
MMW: Mmwyl1_0073 Mmwyl1_3021 Mmwyl1_3053 Mmwyl1_3097 Mmwyl1_4182
AHA: AHA_2143(atoB)
CVI: CV_2088(atoB) CV_2790(phaA)
RSO: RSc0276(atoB) RSc1632(phbA) RSc1637(bktB) RSc1761(RS02948)
REU: Reut_A0138 Reut_A1348 Reut_A1353 Reut_B4561 Reut_B4738 Reut_B5587 Reut_C5943 Reut_C6062
REH: H16_A0170 H16_A0867 H16_A0868 H16_A0872 H16_A1297 H16_A1438(phaA) H16_A1445(bktB) H16_A1528 H16_A1713 H16_A1720 H16_A1887 H16_A2148 H16_B0380 H16_B0381 H16_B0406 H16_B0662 H16_B0668 H16_B0759 H16_B1369 H16_B1771
RME: Rmet_0106 Rmet_1357 Rmet_1362 Rmet_5156
BMA: BMA1316 BMA1321(phbA) BMA1436
BMV: BMASAVP1_A1805(bktB) BMASAVP1_A1810 (phbA)
BML: BMA10299_A0086(phbA) BMA10299_A0091
BMN: BMA10247_1076(bktB) BMA10247_1081(phbA)
BXE: Bxe_A2273 Bxe_A2335 Bxe_A2342 Bxe_A4255 Bxe_B0377 Bxe_B0739 Bxe_C0332 Bxe_C0574 Bxe_C0915
BVI: Bcep1808_0519 Bcep1808_1717 Bcep1808_2877 Bcep1808_3594 Bcep1808_4015 Bcep1808_5507 Bcep1808_5644
BUR: Bcep18194_A3629 Bcep18194_A5080 Bcep18194_A5091 Bcep18194_A6102 Bcep18194_B0263 Bcep18194_B1439 Bcep18194_C6652 Bcep18194_C6802 Bcep18194_C6874 Bcep18194_C7118 Bcep18194_C7151 Bcep18194_C7332
BCN: Bcen_1553 Bcen_1599 Bcen_2158 Bcen_2563 Bcen_2998 Bcen_6289
BCH: Bcen2424_0542 Bcen2424_1790 Bcen2424_2772 Bcen2424_5368 Bcen2424_6232 Bcen2424_6276
BAM: Bamb_0447 Bamb_1728 Bamb_2824 Bamb_4717 Bamb_5771 Bamb_5969
BPS: BPSL1426 BPSL1535(phbA) BPSL1540
BPM: BURPS1710b_2325(bktB) BURPS1710b_2330 (phbA) BURPS1710b_2453 (atoB-2)
BPL: BURPS1106A_2197(bktB) BURPS1106A_2202 (phbA)
BPD: BURPS668_2160(bktB) BURPS668_2165(phbA)
BTE: BTH_12144 BTH_12256 BTH_12261
PNU: Pnuc_0927
BPE: BP0447 BP0668 BP2059
BPA: BPP0608 BPP1744 BPP3805 BPP4216 BPP4361
BBR: BB0614 BB3364 BB4250 BB4804 BB4947
RFR: Rfer_0272 Rfer_1000 Rfer_1871 Rfer_2273 Rfer_2561 Rfer_2594 Rfer_3839
POL: Bpro_1577 Bpro_2140 Bpro_3113 Bpro_4187
PNA: Pnap_0060 Pnap_0458 Pnap_0867 Pnap_1159 Pnap_2136 Pnap_2804

AAV: Aave_0031 Aave_2478 Aave_3944 Aave_4368
AJS: Ajs_0014 Ajs_0124 Ajs_1931 Ajs_2073 Ajs_2317 Ajs_3548 Ajs_3738 Ajs_3776
VEI: Veis_1331 Veis_3818 Veis_4193
DAC: Daci_0025 Daci_0192 Daci_3601 Daci_5988
MPT: Mpe_A1536 Mpe_A1776 Mpe_A1869 Mpe_A3367
HAR: HEAR0577(phbA)
MMS: mma_0555
NEU: NE2262(bktB)
NET: Neut_0610
EBA: ebA5202 p2A409(tioL)
AZO: azo0464(fadA1) azo0469(fadA2) azo2172(thlA)
DAR: Daro_0098 Daro_3022
HPA: HPAG1_0675
HAC: Hac_0958(atoB)
GME: Gmet_1719 Gmet_2074 Gmet_2213 Gmet_2268 Gmet_3302
GUR: Gura_3043
BBA: Bd0404(atoB) Bd2095
DOL: Dole_0671 Dole_1778 Dole_2160 Dole_2187
ADE: Adeh_0062 Adeh_2365
AFW: Anae109_0064 Anae109_1504
MXA: MXAN_3791
SAT: SYN_02642
SFU: Sfum_2280 Sfum_3582
RPR: RP737
RCO: RC1134 RC1135
RFE: RF_0163(paaJ)
RBE: RBE_0139(paaJ)
RAK: A1C_05820
RBO: A1I_07215
RCM: A1E_04760
PUB: SAR11_0428(thlA)
MLO: mlr3847
MES: Meso_3374
PLA: Plav_1573 Plav_2783
SME: SMa1450 SMc03879(phbA)
SMD: Smed_0499 Smed_3117 Smed_5094 Smed_5096
ATU: Atu2769(atoB) Atu3475
ATC: AGR_C_5022(phbA) AGR_L_2713
RET: RHE_CH04018(phbAch) RHE_PC00068(ypc00040) RHE_PF00014(phbAf)
RLE: RL4621(phaA) pRL100301 pRL120369
BME: BMEI0274 BMEII0817
BMF: BAB1_1783(phbA-1) BAB2_0790(phbA-2)
BMS: BR1772(phbA-1) BRA0448(phbA-2)
BMB: BruAb1_1756(phbA-1) BruAb2_0774(phbA-2)
BOV: BOV_1707(phbA-1)
OAN: Oant_1130 Oant_3107 Oant_3718 Oant_4020
BJA: b110226(atoB) b113949 b117400 b117819 blr3724(phbA)
BRA: BRADO0562(phbA) BRADOO0983(pimB) BRADO3110 BRADO3134(atoB)
BBT: BBta_3558 BBta_3575(atoB) BBta_5147(pimB) BBta_7072(pimB) BBta_7614(phbA)
RPA: RPA0513(pcaF) RPA0531 RPA3715(pimB)
RPB: RPB_0509 RPB_0525 RPB_1748
RPC: RPC_0504 RPC_0636 RPC_0641 RPC_0832 RPC_1050 RPC_2005 RPC_2194 RPC_2228
RPD: RPD_0306 RPD_0320 RPD_3105 RPD_3306
RPE: RPE_0168 RPE_0248 RPE_3827
NWI: Nwi_3060
XAU: Xaut_3108 Xaut_4665
CCR: CC_0510 CC_0894 CC_3462
SIL: SPO0142(bktB) SPO0326(phbA) SPO0773 SPO3408
SIT: TM1040_0067 TM1040_2790 TM1040_3026 TM1040_3735
RSP: RSP_0745 RSP_1354 RSP_3184
RSH: Rsph17029_0022 Rsph17029_2401 Rsph17029_3179 Rsph17029_3921
RSQ: Rsph17025_0012 Rsph17025_2466 Rsph17025_2833
JAN: Jann_0262 Jann_0493 Jann_4050
RDE: RD1_0025 RD1_0201(bktB) RD1_3394(phbA)
PDE: Pden_2026 Pden_2663 Pden_2870 Pden_2907 Pden_4811 Pden_5022
DSH: Dshi_0074 Dshi_3066 Dshi_3331
MMR: Mmar10_0697
HNE: HNE_2706 HNE_3065 HNE_3133
NAR: Saro_0809 Saro_1069 Saro_1222 Saro_2306 Saro_2349
SAL: Sala_0781 Sala_1244 Sala_2896 Sala_3158
SWI: Swit_0632 Swit_0752 Swit_2893 Swit_3602 Swit_4887 Swit_5019 Swit_5309
ELI: ELI_01475 ELI_06705 ELI_12035
GBE: GbCGDNIH1_0447
ACR: Acry_1847 Acry_2256
RRU: Rru_A0274 Rru_A1380 Rru_A1469 Rru_A1946 Rru_A3387
MAG: amb0842
MGM: Mmc1_1165
ABA: Acid345_3239
BSU: BG11319(mmgA) BG13063(yhfS)
BHA: BH1997 BH2029 BH3801(mmgA)
BAN: BA3687 BA4240 BA5589
BAR: GBAA3687 GBAA4240 GBAA5589
BAA: BA_0445 BA_4172 BA_4700
BAT: BAS3418 BAS3932 BAS5193
BCE: BC3627 BC4023 BC5344
BCA: BCE_3646 BCE_4076 BCE_5475
BCZ: BCZK3329(mmgA) BCZK3780(thl) BCZK5044(atoB)
BCY: Bcer98_2722 Bcer98_3865
BTK: BT9727_3379(mmgA) BT9727_3765(thl) BT9727_5028(atoB)
BTL: BALH_3262(mmgA) BALH_3642(fadA) BALH_4843(atoB)
BLI: BL03925(mmgA)
BLD: BLi03968(mmgA)
BCL: ABC0345 ABC2989 ABC3617 ABC3891(mmgA)
BAY: RBAM_022450
BPU: BPUM_2374(yhfS) BPUM_2941 BPUM_3373
OIH: OB0676 OB0689 OB2632 OB3013
GKA: GK1658 GK3397
SAU: SA0342 SA0534(vraB)
SAV: SAV0354 SAV0576(vraB)
SAM: MW0330 MW0531(vraB)
SAR: SAR0351(thl) SAR0581
SAS: SAS0330 SAS0534
SAC: SACOL0426 SACOL0622(atoB)
SAB: SAB0304(thl) SAB0526
SAA: SAUSA300_0355 SAUSA300_0560(vraB)
SAO: SAOUHSC_00336 SAOUHSC_00558
SAJ: SaurJH9_0402
SAH: SaurJH1_0412
SEP: SE0346 SE2384
SER: SERP0032 SERP0220
SHA: SH0510(mvaC) SH2417
SSP: SSP0325 SSP2145
LMO: lmo1414
LMF: LMOf2365_1433
LIN: lin1453
LWE: lwe1431
LLA: L11745(thiL) L25946(fadA)
LLC: LACR_1665 LACR_1956

LLM: llmg_0930(thiL)
SPY: SPy_0140 SPy_1637(atoB)
SPZ: M5005_Spy_0119 M5005_Spy_0432 M5005_Spy_1344(atoB)
SPM: spyM18_0136 spyM18_1645(atoB)
SPG: SpyM3_0108 SpyM3_1378(atoB)
SPS: SPs0110 SPs0484
SPH: MGAS10270_Spy0121 MGAS10270_Spy0433 MGAS10270_Spy1461(atoB)
SPI: MGAS10750_Spy0124 MGAS10750_Spy0452 MGAS10750_Spy1453(atoB)
SPJ: MGAS2096_Spy0123 MGAS2096_Spy0451 MGAS2096_Spy1365(atoB)
SPK: MGAS9429_Spy0121 MGAS9429_Spy0431 MGAS9429_Spy1339(atoB)
SPF: SpyM50447(atoB2)
SPA: M6_Spy0166 M6_Spy0466 M6_Spy1390
SPB: M28_Spy0117 M28_Spy0420 M28_Spy1385(atoB)
SAK: SAK_0568
LJO: LJ1609
LAC: LBA0626(thiL)
LSA: LSA1486
LDB: Ldb0879
LBU: LBUL_0804
LBR: LVIS_2218
LCA: LSEI_1787
LGA: LGAS_1374
LRE: Lreu_0052
EFA: EF1364
OOE: OEOE_0529
STH: STH2913 STH725 STH804
CAC: CAC2873 CA_P0078(thiL)
CPE: CPE2195(atoB)
CPF: CPF_2460
CPR: CPR_2170
CTC: CTC00312
CNO: NT01CX_0538 NT01CX_0603
CDF: CD1059(thlA1) CD2676(thlA2)
CBO: CB03200(thl)
CBE: Cbei_0411 Cbei_3630
CKL: CKL_3696(thlA1) CKL_3697(thlA2) CKL_3698(thlA3)
AMT: Amet_4630
AOE: Clos_0084 Clos_0258
CHY: CHY_1288 CHY_1355(atoB) CHY_1604 CHY_1738
DSY: DSY0632 DSY0639 DSY1567 DSY1710 DSY2402 DSY3302
DRM: Dred_0400 Dred_1491 Dred_1784 Dred_1892
SWO: Swol_0308 Swol_0675 Swol_0789 Swol_1486 Swol_1934 Swol_2051
TTE: TTE0549(paaJ)
MTA: Moth_1260
MTU: Rv1l135A Rv1323(fadA4) Rv3546(fadA5)
MTC: MT1365(phbA)
MBO: Mb1167 Mb1358(fadA4) Mb3576(fadA5) Mb3586c(fadA6)
MBB: BCG_1197 BCG_1385(fadA4) BCG_3610(fadA5) BCG_3620c(fadA6)
MLE: ML1158(fadA4)
MPA: MAP2407c(fadA3) MAP2436c(fadA4)
MAV: MAV_1544 MAV_1573 MAV_1863 MAV_5081
MSM: MSMEG_2224 MSMEG_4920
MUL: MUL_0357
MVA: Mvan_1976 Mvan_1988 Mvan_4305 Mvan_4677 Mvan_4891
MGI: Mflv_1347 Mflv_1484 Mflv_2040 Mflv_2340 Mflv_4356 Mflv_4368
MMC: Mmcs_1758 Mmcs_1769 Mmcs_3796 Mmcs_3864
MKM: Mkms_0251 Mkms_1540 Mkms_1805 Mkms_1816 Mkms_2836 Mkms_3159 Mkms_3286 Mkms_3869 Mkms_3938 Mkms_4227 Mkms_4411 Mkms_4580 Mkms_4724 Mkms_4764 Mkms_4776
MJL: Mjls_0231 Mjls_1739 Mjls_1750 Mjls_2819 Mjls_3119 Mjls_3235 Mjls_3800 Mjls_3850 Mjls_4110 Mjls_4383 Mjls_4705 Mjls_4876 Mjls_5018 Mjls_5063 Mjls_5075
CGL: NCgl2309(cgl2392)
CGB: cg2625(pcaF)
CEF: CE0731 CE2295
CJK: jk1543(fadA3)
NFA: nfa10750(fadA4)
RHA: RHA1_ro01455 RHA1_ro01623 RHA1_ro01876 RHA1_ro02517(catF) RHA1_ro03022 RHA1_ro03024 RHA1_ro03391 RHA1_ro03892 RHA1_ro04599 RHA1_ro05257 RHA1_ro08871
SCO: SC05399(SC8F4.03)
SMA: SAV1384(fadA5) SAV2856(fadA1)
ART: Arth_1160 Arth_2986 Arth_3268 Arth_4073
NCA: Noca_1371 Noca_1797 Noca_1828 Noca_2764 Noca_4142
TFU: Tfu_1520 Tfu_2394
FRA: Francci3_3687
FRE: Franean1_1044 Franean1_2711 Franean1_2726 Franean1_3929 Franean1_4037 Franean1_4577
FAL: FRAAL2514 FRAAL2618 FRAAL5910(atoB)
ACE: Acel_0626 Acel_0672
SEN: SACE_1192(mmgA) SACE_2736(fadA6) SACE_4011(catF) SACE_6236(fadA4)
STP: Strop_3610
SAQ: Sare_1316 Sare_3991
RXY: Rxyl_1582 Rxyl_1842 Rxyl_2389 Rxyl_2530
FNU: FN0495
BGA: BG0110(fadA)
BAF: BAPKO_0110(fadA)
LIL: LA0457(thiL1) LA0828(thiL2) LA4139(fadA)
LIC: LIC10396(phbA)
LBJ: LBJ_2862(paaJ-4)
LBL: LBL_0209(paaJ-4)
SYN: slr1993(phaA)
SRU: SRU_1211(atoB) SRU_1547
CHU: CHU_1910(atoB)
GFO: GFO_1507(atoB)
FJO: Fjoh_4612
FPS: FP0770 FP1586 FP1725
RRS: RoseRS_3911 RoseRS_4348
RCA: Rcas_0702 Rcas_3206
HAU: Haur_0522
DRA: DR_1072 DR_1428 DR_1960 DR_2480 DR_A0053
DGE: Dgeo_0755 Dgeo_1305 Dgeo_1441 Dgeo_1883
TTH: TTC0191 TTC0330
TTJ: TTHA0559
TME: Tmel_1134
FNO: Fnod_0314
PMO: Pmob_0515
HMA: rrnAC0896(acaB3) rrnAC2815(aca2) rrnAC3497(yqeF) rrnB0240(aca1) rrnB0242(acaB2) rrnB0309(acaB1)
TAC: Ta0582
TVO: TVN0649
PTO: PTO1505
APE: APE_2108
SSO: SSO2377(acaB-4)

STO: ST0514
SAI: Saci_0963 Saci_1361(acaB1)
MSE: Msed_0656
PAI: PAE1220
PIS: Pisl_0029 Pisl_1301
PCL: Pcal_0781
PAS: Pars_0309 Pars_1071
CMA: Cmaq_1941

Exemplary HMG-CoA Synthase Nucleic Acids and Polypeptides

HSA: 3157(HMGCS1) 3158(HMGCS2)
PTR: 457169(HMGCS2) 461892(HMGCS1)
MCC: 702553(HMGCS1) 713541(HMGCS2)
MMU: 15360(Hmgcs2) 208715(Hmgcs1)
RNO: 24450(Hmgcs2) 29637(Hmgcs1)
CFA: 479344(HMGCS1) 607923(HMGCS2)
BTA: 407767(HMGCS1)
SSC: 397673(CH242-38B5.1)
GGA: 396379(HMGCS1)
XLA: 380091(hmgcs1) 447204(MGC80816)
DRE: 394060(hmgcs1)
SPU: 578259(LOC578259)
DME: Dmel_CG4311(Hmgs)
CEL: F25B4.6
ATH: AT4G11820(BAP 1)
OSA: 4331418 4347614
CME: CMM189C
SCE: YML126C(ERG13)
AGO: AGOS_ADL356C
PIC: PICST_83020
CAL: CaO19_7312(CaO19.7312)
CGR: CAGL0H04081g
SPO: SPAC4F8.14c(hcs)
MGR: MGG_01026
ANI: AN4923.2
AFM: AFUA_3G10660 AFUA_8G07210
AOR: AO090003000611 AO090010000487
CNE: CNC05080 CNG02670
UMA: UM05362.1
ECU: ECU10_0510
DDI: DDBDRAFT_0217522 DDB_0219924(hgsA)
TET: TTHERM_00691190
TBR: Tb927.8.6110
YPE: YPO1457
YPK: y2712(pksG)
YPM: YP_1349(pksG)
YPA: YPA_0750
YPN: YPN_2521
YPP: YPDSF_1517
YPS: YPTB1475
CBD: COXBU7E912_1931
TCX: Tcr_1719
DNO: DNO_0799
BMA: BMAA1212
BPS: BPSS1002
BPM: BURPS1710b_A2613
BPL: BURPS1106A_A1384
BPD: BURPS668_A1470
BTE: BTH_II1670
MXA: MXAN_3948(tac) MXAN_4267(mvaS)
BSU: BG10926(pksG)
OIH: OB2248
SAU: SA2334(mvaS)
SAV: SAV2546(mvaS)
SAM: MW2467(mvaS)
SAR: SAR2626(mvaS)
SAS: SAS2432
SAC: SACOL2561
SAB: SAB2420(mvaS)
SAA: SAUSA300_2484
SAO: SAOUHSC_02860
SAJ: SaurJH9_2569
SAH: SaurJH1_2622
SEP: SE2110
SER: SERP2122
SHA: SH0508(mvaS)
SSP: SSP0324
LMO: lmo1415
LMF: LMOf2365_1434(mvaS)
LIN: lin1454
LWE: lwe1432(mvaS)
LLA: L13187(hmcM)
LLC: LACR_1666
LLM: llmg_0929(hmcM)
SPY: SPy_0881(mvaS.2)
SPZ: M5005_Spy_0687(mvaS.1)
SPM: spyM18_0942(mvaS2)
SPG: SpyM3_0600(mvaS.2)
SPS: SPs1253
SPH: MGAS10270_Spy0745(mvaS1)
SPI: MGAS10750_Spy0779(mvaS1)
SPJ: MGAS2096_Spy0759(mvaS1)
SPK: MGAS9429_Spy0743(mvaS1)
SPF: SpyM51121(mvaS)
SPA: M6_Spy0704
SPB: M28_Spy0667(mvaS.1)
SPN: SP_1727
SPR: spr1571(mvaS)
SPD: SPD_1537(mvaS)
SAG: SAG1316
SAN: gbs1386
SAK: SAK_1347
SMU: SMU.943c
STC: str0577(mvaS)
STL: stu0577(mvaS)
STE: STER_0621
SSA: SSA_0338(mvaS)
SSU: SSU05_1641
SSV: SSU98_1652
SGO: SGO_0244
LPL: lp_2067(mvaS)
LJO: LJ1607
LAC: LBA0628(hmcS)
LSA: LSA1484(mvaS)
LSL: LSL_0526
LDB: Ldb0881(mvaS)
LBU: LBUL_0806
LBR: LVIS_1363
LCA: LSEI_1785
LGA: LGAS_1372
LRE: Lreu_0676
PPE: PEPE_0868
EFA: EF1363
OOE: OEOE_0968
LME: LEUM_1184
NFA: nfa22120
SEN: SACE_4570(pksG)
BBU: BB0683
BGA: BG0706
BAF: BAPKO_0727
FJO: Fjoh_0678
HAL: VNG1615G(mvaB)

HMA: rrnAC1740(mvaS)
HWA: HQ2868A(mvaB)
NPH: NP2608A(mvaB_1) NP4836A(mvaB_2)

Exemplary Hydroxymethylglutaryl-CoA Reductase
Nucleic Acids and Polypeptides

HSA: 3156(HMGCR)
PTR: 471516(HMGCR)
MCC: 705479(HMGCR)
MMU: 15357(Hmgcr)
RNO: 25675(Hmgcr)
CFA: 479182(HMGCR)
BTA: 407159(HMGCR)
GGA: 395145(RCJMB04_14m24)
SPU: 373355(LOC373355)
DME: Dmel_CG10367(Hmgcr)
CEL: F08F8.2
OSA: 4347443
SCE: YLR450W(HMG2) YML075C(HMG1)
AGO: AGOS_AER152W
CGR: CAGL0L11506g
SPO: SPCC162.09c(hmg1)
ANI: AN3817.2
AFM: AFUA_1G11230 AFUA_2G03700
AOR: AO090103000311 AO090120000217
CNE: CNF04830
UMA: UM03014.1
ECU: ECU10_1720
DDI: DDB_0191125(hmgA) DDB_0215357(hmgB)
TBR: Tb927.6.4540
TCR: 506831.40 509167.20
LMA: LmjF30.3190
VCH: VCA0723
VCO: VC0395_0662
VVU: VV2_0117
VVY: VVA0625
VPA: VPA0968
VFI: VFA0841
PAT: Patl_0427
CBU: CBU_0030 CBU_0610
CBD: COXBU7E912_0151 COXBU7E912_0622(hmgA)
TCX: Tcr_1717
DNO: DNO_0797
CVI: CV_1806
SUS: Acid_5728 Acid_6132
SAU: SA2333(mvaA)
SAV: SAV2545(mvaA)
SAM: MW2466(mvaA)
SAB: SAB2419c(mvaA)
SEP: SE2109
LWE: lwe0819(mvaA)
LLA: L10433(mvaA)
LLC: LACR_1664
LLM: llmg_0931(mvaA)
SPY: SPy_0880(mvaS.1)
SPM: spyM18_0941(mvaS1)
SPG: SpyM3_0599(mvaS.1)
SPS: SPs1254
SPH: MGAS10270_Spy0744
SPI: MGAS10750_Spy0778
SPJ: MGAS2096_Spy0758
SPK: MGAS9429_Spy0742
SPA: M6_Spy0703
SPN: SP_1726
SAG: SAG1317
SAN: gbs1387

STC: str0576(mvaA)
STL: stu0576(mvaA)
STE: STER_0620
SSA: SSA_0337(mvaA)
LPL: lp_0447(mvaA)
LJO: LJ1608
LSL: LSL_0224
LBR: LVIS_0450
LGA: LGAS_1373
EFA: EF1364
NFA: nfa22110
BGA: BG0708(mvaA)
SRU: SRU_2422
FPS: FP2341
MMP: MMP0087(hmgA)
MMQ: MmarC5_1589
MAC: MA3073(hmgA)
MBA: Mbar_A1972
MMA: MM_0335
MBU: Mbur_1098
MHU: Mhun_3004
MEM: Memar_2365
MBN: Mboo_0137
MTH: MTH562
MST: Msp_0584(hmgA)
MSI: Msm_0227
MKA: MK0355(HMG1)
AFU: AF1736(mvaA)
HAL: VNG1875G(mvaA)
HMA: rrnAC3412(mvaA)
HWA: HQ3215A(hmgR)
NPH: NP0368A(mvaA_2) NP2422A(mvaA_1)
TAC: Ta0406m
TVO: TVN1168
PTO: PTO1143
PAB: PAB2106(mvaA)
PFU: PF1848
TKO: TK0914
RCI: RCIX1027(hmgA) RCIX376(hmgA)
APE: APE_1869
IHO: Igni_0476
HBU: Hbut_1531
SSO: SSO0531
STO: ST1352
SAI: Saci_1359
PAI: PAE2182
PIS: Pisl_0814
PCL: Pcal_1085
PAS: Pars_0796

Exemplary Mevalonate Kinase Nucleic Acids and
Polypeptides

HSA: 4598(MVK)
MCC: 707645(MVK)
MMU: 17855(Mvk)
RNO: 81727(Mvk)
CFA: 486309(MVK)
BTA: 505792(MVK)
GGA: 768555(MVK)
DRE: 492477(zgc: 103473)
SPU: 585785(LOC585785)
DME: Dmel_CG33671
OSA: 4348331
SCE: YMR208W(ERG12)
AGO: AGOS_AER335W
PIC: PICST_40742(ERG12)

CGR: CAGL0F03861g
SPO: SPAC13G6.11c
MGR: MGG_06946
ANI: AN3869.2
AFM: AFUA_4G07780
AOR: AO090023000793
CNE: CNK01740
ECU: ECU09_1780
DDI: DDBDRAFT_0168621
TET: TTHERM_00637680
TBR: Tb927.4.4070
TCR: 436521.9 509237.10
LMA: LmjF31.0560
CBU: CBU_0608 CBU_0609
CBD: COXBU7E912_0620(mvk)
LPN: lpg2039
LPF: lpl2017
LPP: lpp2022
BBA: Bd1027(lmbP) Bd1630(mvk)
MXA: MXAN_5019(mvk)
OIH: OB0225
SAU: SA0547(mvaK1)
SAV: SAV0590(mvaK1)
SAM: MW0545(mvaK1)
SAR: SAR0596(mvaK1)
SAS: SAS0549
SAC: SACOL0636(mvk)
SAB: SAB0540(mvaK1)
SAA: SAUSA300_0572(mvk)
SAO: SAOUHSC_00577
SEP: SE0361
SER: SERP0238(mvk)
SHA: SH2402(mvaK1)
SSP: SSP2122
LMO: lmo0010
LMF: LMOf2365_0011
LIN: lin0010
LWE: lwe0011(mvk)
LLA: L7866(yeaG)
LLC: LACR_0454
LLM: llmg_0425(mvk)
SPY: SPy_0876(mvaK1)
SPZ: M5005_Spy_0682(mvaK1)
SPM: spyM18_0937(mvaK1)
SPG: SpyM3_0595(mvaK1)
SPS: SPs1258
SPH: MGAS10270_Spy0740(mvaK1)
SPI: MGAS10750_Spy0774(mvaK1)
SPJ: MGAS2096_Spy0753(mvaK1)
SPK: MGAS9429_Spy0737(mvaK1)
SPF: SpyM51126(mvaK1)
SPA: M6_Spy0699
SPB: M28_Spy0662(mvaK1)
SPN: SP 0381
SPR: spr0338(mvk)
SPD: SPD_0346(mvk)
SAG: SAG1326
SAN: gbs1396
SAK: SAK_1357(mvk)
SMU: SMU.181
STC: str0559(mvaK1)
STL: stu0559(mvaK1)
STE: STER_0598
SSA: SSA_0333(mvaK1)
SSU: SSU05_0289
SSV: SSU98_0285
SGO: SGO_0239(mvk)
LPL: lp_1735(mvaK1)
LJO: LJ1205
LAC: LBA1167(mvaK)
LSA: LSA0908(mvaK1)
LSL: LSL_0685(eRG)
LDB: Ldb0999(mvk)
LBU: LBUL_0906
LBR: LVIS_0858
LCA: LSEI_1491
LGA: LGAS_1033
LRE: Lreu_0915
PPE: PEPE_0927
EFA: EF0904(mvk)
OOE: OEOE_1100
LME: LEUM_1385
NFA: nfa22070
BGA: BG0711
BAF: BAPKO_0732
FPS: FP0313
MMP: MMP1335
MAE: Maeo_0775
MAC: MA0602(mvk)
MBA: Mbar_A1421
MMA: MM_1762
MBU: Mbur_2395
MHU: Mhun_2890
MEM: Memar_1812
MBN: Mboo_2213
MST: Msp_0858(mvk)
MSI: Msm_1439
MKA: MK0993(ERG12)
HAL: VNG1145G(mvk)
HMA: rrnACOO77(mvk)
HWA: HQ2925A(mvk)
NPH: NP2850A(mvk)
PTO: PTO1352
PHO: PH1625
PAB: PAB0372(mvk)
PFU: PF1637(mvk)
TKO: TK1474
RCI: LRC399(mvk)
APE: APE_2439
HBU: Hbut_0877
SSO: SS00383
STO: ST2185
SAI: Saci_2365(mvk)
MSE: Msed_1602
PAI: PAE3108
PIS: Pisl_0467
PCL: Pcal_1835

Exemplary Phosphomevalonate Kinase Nucleic
Acids and Polypeptides

HSA: 10654(PMVK)
PTR: 457350(PMVK)
MCC: 717014(PMVK)
MMU: 68603(Pmvk)
CFA: 612251(PMVK)
BTA: 513533(PMVK)
DME: Dmel_CG10268
ATH: AT1G31910
OSA: 4332275
SCE: YMR220W(ERG8)
AGO: AGOS_AER354W
PIC: PICST_52257(ERG8)
CGR: CAGL0F03993g SPO: SPAC343.01c
MGR: MGG_05812
ANI: AN2311.2
AFM: AFUA_5G10680
AOR: AO090010000471
CNE: CNM00100
UMA: UM00760.1
DDI: DDBDRAFT_0184512
TBR: Tb09.160.3690
TCR: 507913.20 508277.140
LMA: LmjF15.1460
MXA: MXAN_5017
OIH: OB0227
SAU: SA0549(mvaK2)
SAV: SAV0592(mvaK2)
SAM: MW0547(mvaK2)
SAR: SAR0598(mvaK2)
SAS: SAS0551
SAC: SACOL0638
SAB: SAB0542(mvaK2)
SAA: SAUSA300_0574
SAO: SAOUHSC_00579
SAJ: SaurJH9_0615
SEP: SE0363
SER: SERP0240
SHA: SH2400(mvaK2)
SSP: SSP2120
LMO: lmo0012
LMF: LMOf2365_0013
LIN: lin0012
LWE: lwe0013
LLA: L10014(yebA)
LLC: LACR_0456
LLM: llmg_0427
SPY: SPy_0878(mvaK2)
SPZ: M5005_Spy_0684(mvaK2)
SPM: spyM18_0939
SPG: SpyM3_0597(mvaK2)
SPS: SPs1256
SPH: MGAS10270_Spy0742(mvaK2)
SPI: MGAS10750_Spy0776(mvaK2)
SPJ: MGAS2096_Spy0755(mvaK2)
SPK: MGAS9429_Spy0739(mvaK2)
SPF: SpyM51124(mvaK2)
SPA: M6_Spy0701
SPB: M28_Spy0664(mvaK2)
SPN: SP_0383
SPR: spr0340(mvaK2)
SPD: SPD_0348(mvaK2)
SAG: SAG1324
SAN: gbs1394
SAK: SAK_1355
SMU: SMU.938
STC: str0561(mvaK2)
STL: stu0561(mvaK2)
STE: STER_0600
SSA: SSA_0335(mvaK2)
SSU: SSU05_0291
SSV: SSU98_0287
SGO: SGO_0241
LPL: lp_1733(mvaK2)
LJO: LJ1207
LAC: LBA1169
LSA: LSA0906(mvaK2)
LSL: LSL_0683
LDB: Ldb0997(mvaK)
LBU: LBUL_0904

LBR: LVIS_0860
LCA: LSEI_1092
LGA: LGAS_1035
LRE: Lreu_0913
PPE: PEPE_0925
EFA: EF0902
NFA: nfa22090
BGA: BG0710
BAF: BAPKO_0731
NPH: NP2852A
SSO: SSO2988
STO: ST0978
SAI: Saci_1244

Exemplary Diphosphomevalonate Decarboxylase
Nucleic Acids and Polypeptides

HSA: 4597(MVD)
PTR: 468069(MVD)
MCC: 696865(MVD)
MMU: 192156(Mvd)
RNO: 81726(Mvd)
CFA: 489663(MVD)
GGA: 425359(MVD)
DME: Dmel_CG8239
SCE: YNR043W(MVD1)
AGO: AGOS_AGL232C
PIC: PICST_90752
CGR: CAGL0C03630g
SPO: SPAC24C9.03
MGR: MGG_09750
ANI: AN4414.2
AFM: AFUA_4G07130
AOR: AO090023000862
CNE: CNL04950
UMA: UM05179.1
DDI: DDBDRAFT_0218058
TET: TTHERM_00849200
TBR: Tb10.05.0010 Tb10.61.2745
TCR: 507993.330 511281.40
LMA: LmjF18.0020
CBU: CBU_0607(mvaD)
CBD: COXBU7E912_0619(mvaD)
LPN: lpg2040
LPF: lpl2018
LPP: lpp2023
TCX: Tcr_1734
DNO: DNO_0504(mvaD)
BBA: Bd1629
MXA: MXAN_5018(mvaD)
OIH: OB0226
SAU: SA0548(mvaD)
SAV: SAV0591(mvaD)
SAM: MW0546(mvaD)
SAR: SAR0597(mvaD)
SAS: SAS0550
SAC: SACOL0637(mvaD)
SAB: SAB0541(mvaD)
SAA: SAUSA300_0573(mvaD)
SAO: SAOUHSC_00578
SAJ: SaurJH9_0614
SAH: SaurJH1_0629
SEP: SE0362
SER: SERP0239(mvaD)
SHA: SH2401(mvaD)
SSP: SSP2121
LMO: lmo0011

LMF: LMOf2365_0012(mvaD)
LIN: lin0011
LWE: lwe0012(mvaD)
LLA: L9089(yeaH)
LLC: LACR_0455
LLM: llmg_0426(mvaD)
SPY: SPy_0877(mvaD)
SPZ: M5005_Spy_0683(mvaD)
SPM: spyM18_0938(mvd)
SPG: SpyM3_0596(mvaD)
SPS: SPs1257
SPH: MGAS10270_Spy0741(mvaD)
SPI: MGAS10750_Spy0775(mvaD)
SPJ: MGAS2096_Spy0754(mvaD)
SPK: MGAS9429_Spy0738(mvaD)
SPF: SpyM51125(mvaD)
SPA: M6_Spy0700
SPB: M28_Spy0663(mvaD)
SPN: SP_0382
SPR: spr0339(mvdl)
SPD: SPD_0347(mvaD)
SAG: SAG1325(mvaD)
SAN: gbs1395
SAK: SAK_1356(mvaD)
SMU: SMU.937
STC: str0560(mvaD)
STL: stu0560(mvaD)
STE: STER_0599
SSA: SSA_0334(mvaD)
SSU: SSU05_0290
SSV: SSU98_0286
SGO: SGO_0240(mvaD)
LPL: lp_1734(mvaD)
LJO: LJ1206
LAC: LBA1168(mvaD)
LSA: LSA0907(mvaD)
LSL: LSL_0684
LDB: Ldb0998(mvaD)
LBU: LBUL_0905
LBR: LVIS_0859
LCA: LSEI_1492
LGA: LGAS_1034
LRE: Lreu_0914
PPE: PEPE_0926
EFA: EF0903(mvaD)
LME: LEUM_1386
NFA: nfa22080
BBU: BB0686
BGA: BG0709
BAF: BAPKO_0730
GFO: GFO_3632
FPS: FP0310(mvaD)
HAU: Haur_1612
HAL: VNG0593G(dmd)
HMA: rrnAC1489(dmd)
HWA: HQ1525A(mvaD)
NPH: NP1580A(mvaD)
PTO: PT00478 PT01356
SSO: SSO2989
STO: ST0977
SAI: Saci_1245(mvd)
MSE: Msed_1576

Exemplary Isopentenyl Phosphate Kinases (IPK)
Nucleic Acids and Polypeptides

*Methanobacterium thermoautotrophicum* gi|2621082
*Methanococcus jannaschii* DSM2661 gi|1590842;
*Methanocaldococcus jannaschii* gi|1590842
*Methanothermobacter thermautotrophicus* gi|2621082
*Picrophilus torridus* DSM9790 (IG-57) gi|48477569
*Pyrococcus abyssi* gi|14520758
*Pyrococcus horikoshii* OT3 gi|3258052
*Archaeoglobus fulgidus* DSM4304 gi|2648231

Exemplary Isopentenyl-Diphosphate
Delta-Isomerase (IDI) Nucleic Acids and
Polypeptides HSA: 3422(IDI1) 91734(IDI2)
PTR: 450262(IDI2) 450263(IDI1)
MCC: 710052(LOC710052) 721730(LOC721730)
MMU: 319554(Idi1)
RNO: 89784(Idi1)
GGA: 420459(IDI1)
XLA: 494671(LOC494671)
XTR: 496783(idi2)
SPU: 586184(LOC586184)
CEL: K06H7.9(idi-1)
ATH: AT3G02780(IPP2)
OSA: 4338791 4343523
CME: CMB062C
SCE: YPL117C(IDI1)
AGO: AGOS_ADL268C
PIC: PICST_68990(IDI1)
CGR: CAGL0J06952g
SPO: SPBC106.15(idi1)
ANI: AN0579.2
AFM: AFUA_6G11160
AOR: AO090023000500
CNE: CNA02550
UMA: UM04838.1
ECU: ECU02_0230
DDI: DDB_0191342(ipi)
TET: TTHERM 00237280 TTHERM 00438860
TBR: Tb09.211.0700
TCR: 408799.19 510431.10
LMA: LmjF35.5330
EHI: 46.t00025
ECO: b2889(idi)
ECJ: JW2857(idi)
ECE: Z4227
ECS: ECs3761
ECC: c3467
ECI: UTI89_C3274
ECP: ECP_2882
ECV: APECO1_3638
ECW: EcE24377A_3215(idi)
ECX: EcHS_A3048
STY: STY3195
STT: t2957
SPT: SPA2907(idi)
SEC: SC2979(idi)
STM: STM3039(idi)
SFL: SF2875(idi)
SFX: S3074
SFV: SFV_2937
SSN: SSON_3042 SSON_3489(yhfK)
SBO: SBO_3103
SDY: SDY_3193
ECA: ECA2789
PLU: plu3987
ENT: Ent638_3307
SPE: Spro_2201
VPA: VPA0278

VFI: VF0403
PPR: PBPRA0469(mvaD)
PEN: PSEEN4850
CBU: CBU_0607(mvaD)
CBD: COXBU7E912_0619(mvaD)
LPN: lpg2051
LPF: lpl2029
LPP: lpp2034
TCX: Tcr_1718
HHA: Hhal_1623
DNO: DNO_0798
EBA: ebA5678 p2A143
DVU: DVU1679(idi)
DDE: Dde_1991
LIP: LI1134
BBA: Bd1626
AFW: Anae109_4082
MXA: MXAN_5021(fni)
RPR: RP452
RTY: RT0439(idi)
RCO: RC0744
RFE: RF_0785(fni)
RBE: RBE_0731(fni)
RAK: A1C_04190
RBO: A1I_04755
RCM: A1E_02555
RRI: A1G_04195
MLO: mlr6371
RET: RHE_PD00245(ypd00046)
XAU: Xaut_4134
SIL: SPO0131
SIT: TM1040_3442
RSP: RSP_0276
RSH: Rsph17029_1919
RSQ: Rsph17025_1019
JAN: Jann_0168
RDE: RD1_0147(idi)
DSH: Dshi_3527
BSU: BG11440(ypgA)
BAN: BA1520
BAR: GBAA1520
BAA: BA_2041
BAT: BAS1409
BCE: BC1499
BCA: BCE_1626
BCZ: BCZK1380(fni)
BCY: Bcer98_1222
BTK: BT9727_1381(fni)
BTL: BALH_1354
BLI: BL02217(fni)
BLD: BLi02426
BAY: RBAM_021020(fni)
BPU: BPUM_2020(fni)
OIH: OB0537
SAU: SA2136(fni)
SAV: SAV2346(fni)
SAM: MW2267(fni)
SAR: SAR2431(fni)
SAS: SAS2237
SAC: SACOL2341(fni)
SAB: SAB2225c(fni)
SAA: SAUSA300_2292(fni)
SAO: SAOUHSC_02623
SEP: SE1925
SER: SERP1937(fni-2)
SHA: SH0712(fni)
SSP: SSP0556
LMO: lmo1383
LMF: LMOf2365_1402(fni)
LIN: lin1420
LWE: lwe1399(fni)
LLA: L11083(yebB)
LLC: LACR_0457
LLM: llmg_0428(fni)
SPY: SPy_0879
SPZ: M5005_Spy_0685
SPM: spyM18_0940
SPG: SpyM3_0598
SPS: SPs1255
SPH: MGAS10270_Spy0743
SPI: MGAS10750_Spy0777
SPJ: MGAS2096_Spy0756
SPK: MGAS9429_Spy0740
SPF: SpyM51123(fni)
SPA: M6_Spy0702
SPB: M28_Spy0665
SPN: SP_0384
SPR: spr0341(fni)
SPD: SPD_0349(fni)
SAG: SAG1323
SAN: gbs1393
SAK: SAK_1354(fni)
SMU: SMU.939
STC: str0562(idi)
STL: stu0562(idi)
STE: STER_0601
SSA: SSA_0336
SGO: SGO_0242
LPL: lp_1732(idi1)
LJO: LJ1208
LAC: LBA1171
LSA: LSA0905(idi)
LSL: LSL_0682
LDB: Ldb0996(fni)
LBU: LBUL_0903
LBR: LVIS_0861
LCA: LSEI_1493
LGA: LGAS_1036
LRE: Lreu_0912
EFA: EF0901
OOE: OEOE_1103
STH: STH1674
CBE: Cbei_3081
DRM: Dred_0474
SWO: Swol_1341
MTA: Moth_1328
MTU: Rv1745c(idi)
MTC: MT1787(idi)
MBO: Mb1774c(idi)
MBB: BCG_1784c(idi)
MPA: MAP3079c
MAV: MAV_3894(fni)
MSM: MSMEG_1057(fni) MSMEG_2337(fni)
MUL: MUL_0380(idi2)
MVA: Mvan_1582 Mvan_2176
MGI: Mflv_1842 Mflv_4187
MMC: Mmcs_1954
MKM: Mkms_2000
MJL: Mjls_1934
CGL: NCg12223(cg12305)
CGB: cg2531(idi)
CEF: CE2207
CDI: DIP1730(idi)
NFA: nfa19790 nfa22100

RHA: RHA1_ro00239
SCO: SCO6750(SC5F2A.33c)
SMA: SAV1663(idi)
LXX: Lxx23810(idi)
CMI: CMM_2889(idiA)
AAU: AAur_0321(idi)
PAC: PPA2115
FRA: Francci3_4188
FRE: Franean1_5570
FAL: FRAAL6504(idi)
KRA: Krad_3991
SEN: SACE_2627(idiB_2) SACE_5210(idi)
STP: Strop_4438
SAQ: Sare_4564 Sare_4928
RXY: Rxyl_0400
BBU: BB0684
BGA: BG0707
SYN: sll1556
SYC: syc2161_c
SYF: Synpcc7942_1933
CYA: CYA_2395(fni)
CYB: CYB_2691(fni)
TEL: tll1403
ANA: all4591
AVA: Ava_2461 Ava_B0346
TER: Tery_1589
SRU: SRU_1900(idi)
CHU: CHU_0674(idi)
GFO: GFO_2363(idi)
FJO: Fjoh_0269
FPS: FP1792(idi)
CTE: CT0257
CCH: Cag_1445
CPH: Cpha266_0385
PVI: Cvib 1545
PLT: Plut 1764
RRS: RoseRS_2437
RCA: Rcas_2215
HAU: Haur 4687
DRA: DR_1087
DGE: Dgeo_1381
TTH: TT_P0067
TTJ: TTHB110
MJA: MJ0862
MMP: MMP0043
MMQ: MmarC5_1637
MMX: MmarC6_0906
MMZ: MmarC7_1040
MAE: Maeo_1184
MVN: Mevan_1058
MAC: MA0604(idi)
MBA: Mbar_A1419
MMA: MM_1764
MBU: Mbur_2397
MTP: Mthe_0474
MHU: Mhun_2888
MLA: Mlab_1665
MEM: Memar_1814
MBN: Mboo_2211
MTH: MTH48
MST: Msp_0856(fni)
MSI: Msm_1441
MKA: MK0776(lldD)
AFU: AF2287
HAL: VNG1818G(idi) VNG6081G(crt_1) VNG6445G (crt_2) VNG7060 VNG7149
HMA: rrnAC3484(idi)
HWA: HQ2772A(idiA) HQ2847A(idiB)
NPH: NP0360A(idiB_1) NP4826A(idiA) NP5124A (idiB_2)
TAC: Ta0102
TVO: TVN0179
PTO: PTO0496
PHO: PH1202
PAB: PAB1662
PFU: PF0856
TKO: TK1470
RCI: LRC397(fni)
APE: APE_1765.1
SMR: Smar_0822
IHO: Igni_0804
HBU: Hbut_0539
SSO: SSO0063
STO: ST2059
SAI: Saci_0091
MSE: Msed_2136
PAI: PAE0801
PIS: Pisl_1093
PCL: Pcal_0017
PAS: Pars_0051
TPE: Tpen_0272

Exemplary Isoprene Synthase Nucleic Acids and Polypeptides

Genbank Accession Nos.
AY341431
AY316691
AY279379
AJ457070
AY182241

What is claimed as new and desired to be protected by Letters Patent of the United States is:

1. Recombinant cells capable of producing isoprene, the cells comprising (a) heterologous nucleic acid encoding an isoprene synthase polypeptide and (b) two or more heterologous mevalonate (MVA) pathway polypeptides and wherein the cells (i) produce greater than about 400 nmole/$g_{wcm}$/hr of isoprene, (ii) convert more than about 0.002 molar percent of the carbon that the cells consume from a cell culture medium into isoprene, or (iii) have an average volumetric productivity of isoprene greater than about 0.1 mg/$L_{broth}$/hr.

2. The cells of claim 1, wherein the heterologous nucleic acid encoding an isoprene synthase polypeptide is operably linked to a promoter.

3. The cells of claim 1, wherein the isoprene synthase polypeptide is a plant isoprene synthase polypeptide.

4. The cells of claim 3, wherein the plant isoprene synthase polypeptide is a poplar isoprene synthase polypeptide or a kudzu isoprene synthase polypeptide.

5. The cells of claim 1, wherein the heterologous nucleic acid encoding an isoprene synthase polypeptide is in a vector or is integrated into a chromosome of the cells.

6. The cells of claim 1, further comprising nucleic acids encoding: (a) an isopentenyl-diphosphate delta-isomerase (IDI) polypeptide or (b) a 1-Deoxyxylulose-5-phosphate synthase (DXS) polypeptide.

7. The cells of claim 1, wherein at least one of the nucleic acids encoding one or more MVA pathway polypeptides is a heterologous nucleic acid or a copy of an endogenous nucleic acid.

8. The cells of claim 1, wherein the cells comprise polypeptides of the entire MVA pathway.

9. The cells of claim 1, wherein at least one of the nucleic acids encoding the isoprene synthase polypeptide and two or more heterologous mevalonate (MVA) pathway polypeptides is over-expressed.

10. The cells of claim 9, wherein the over-expressed nucleic acid is cloned into a multicopy plasmid.

11. The cells of claim 9, wherein the over-expressed nucleic acid is placed under an inducible promoter or a constitutive promoter.

12. The cells of claim 1, wherein the cells are gram-positive bacterial cells or gram-negative bacterial cells.

13. The cells of claim 12, wherein the cells are selected from the group consisting of *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells.

14. The cells of claim 1, wherein the cells are fungal cells.

15. The cells of claim 14, wherein the fungal cells are *Aspergillus*, yeast, *Trichoderma*, or *Yarrowia* cells.

16. The cells of claim 15, where the yeast cells are *Saccharomyces* sp., *Schizosaccharomyces* sp., *Pichia* sp., or *Candida* sp. cells.

17. The cells of claim 14, where the fungal cells are selected from the group consisting of *A. oryzae, A. niger, S. cerevisiae, S. pombe, T. reesei, H. insolens, H. lanuginose, H. grisea, C. lucknowense, A. oryzae, A. niger, A sojae, A. japonicus, A. nidulans, A. aculeatus, A. awamori, F. roseum, F. graminum F. cerealis, F. oxysporuim, F. venenatum, N. crassa, M. miehei, T. viride, F. oxysporum,* and *F. solan* cells.

18. The cells of claim 1, wherein the cells are algal cells.

19. The cells of claim 18, wherein the algal cells are selected from the group consisting of: green algae, red algae, glaucophytes, chlorarachniophytes, euglenids, chromista, and dinoflagellates.

20. The cells of claim 1, wherein the cells produce greater than about 400 nmole/$g_{wcm}$/hr of isoprene.

21. The cells of claim 1, wherein the cells convert more than about 0.002 molar percent of the carbon that the cells consume from a cell culture medium into isoprene.

22. The cells of claim 1, wherein the cells have an average volumetric productivity of isoprene greater than about 0.1 mg/$L_{broth}$/hr.

23. A method for producing isoprene, the method comprising (a) culturing the recombinant cells of claim 1 under suitable conditions for the production of isoprene; and (b) producing isoprene.

24. The method of claim 23, further comprising (c) recovering the isoprene.

* * * * *